US012522617B2

(12) United States Patent
Mo et al.

(10) Patent No.: US 12,522,617 B2
(45) Date of Patent: Jan. 13, 2026

(54) POLYCYCLIC COMPOUND AND ORGANIC LIGHT EMITTING DEVICE COMPRISING SAME

(71) Applicant: LT MATERIALS CO., LTD., Yongin-Si (KR)

(72) Inventors: Jun-Tae Mo, Yongin-si (KR); Mi-Jin Kim, Yongin-si (KR); Ji-Yoon Byun, Yongin-si (KR); Yong-Hui Lee, Yongin-si (KR); Jong-Su Lee, Yongin-si (KR); Dong-Jun Kim, Yongin-si (KR)

(73) Assignee: LT MATERIALS CO., LTD., Yongin-Si (KR)

( * ) Notice: Subject to any disclaimer, the term of this patent is extended or adjusted under 35 U.S.C. 154(b) by 1004 days.

(21) Appl. No.: 17/418,306

(22) PCT Filed: Dec. 26, 2019

(86) PCT No.: PCT/KR2019/018453

§ 371 (c)(1),
(2) Date: Jun. 25, 2021

(87) PCT Pub. No.: WO2020/138944

PCT Pub. Date: Jul. 2, 2020

(65) Prior Publication Data

US 2022/0089610 A1 Mar. 24, 2022

(30) Foreign Application Priority Data

Dec. 27, 2018 (KR) ........................ 10-2018-0170110

(51) Int. Cl.

| | |
|---|---|
| ***H01L 51/54*** | (2006.01) |
| ***C07D 493/00*** | (2006.01) |
| ***C07D 495/00*** | (2006.01) |
| ***C07D 519/00*** | (2006.01) |
| ***H10K 85/60*** | (2023.01) |
| *H10K 50/11* | (2023.01) |
| *H10K 101/00* | (2023.01) |
| *H10K 101/10* | (2023.01) |

(52) U.S. Cl.

CPC ......... *C07D 519/00* (2013.01); *C07D 493/00* (2013.01); *C07D 495/00* (2013.01); *H10K 85/622* (2023.02); *H10K 85/624* (2023.02); *H10K 85/626* (2023.02); *H10K 85/633* (2023.02); *H10K 85/636* (2023.02); *H10K 85/654* (2023.02); *H10K 85/6572* (2023.02); *H10K 85/6574* (2023.02); *H10K 85/6576* (2023.02); *H10K 50/11* (2023.02); *H10K 2101/10* (2023.02); *H10K 2101/90* (2023.02)

(58) Field of Classification Search

None

See application file for complete search history.

(56) References Cited

U.S. PATENT DOCUMENTS

| | | | | |
|---|---|---|---|---|
| 2011/0168992 | A1 | 7/2011 | Bae et al. | |
| 2014/0001442 | A1 | 1/2014 | Lee et al. | |
| 2014/0124764 | A1 * | 5/2014 | Kitano ............... | H10K 85/6574 257/40 |
| 2014/0323723 | A1 | 10/2014 | Ahn et al. | |
| 2016/0118598 | A1 | 4/2016 | Baba et al. | |
| 2016/0336518 | A1 | 11/2016 | Chun et al. | |
| 2017/0213977 | A1 * | 7/2017 | Shin ..................... | H10K 85/622 |
| 2018/0037546 | A1 * | 2/2018 | Sugino ................. | C07D 409/14 |
| 2018/0072695 | A1 | 3/2018 | Byun et al. | |
| 2018/0123048 | A1 | 5/2018 | So et al. | |
| 2019/0047992 | A1 | 2/2019 | Park et al. | |
| 2019/0241548 | A1 | 8/2019 | Park et al. | |
| 2020/0111969 | A1 | 4/2020 | No et al. | |
| 2022/0089610 | A1 | 3/2022 | Mo et al. | |

FOREIGN PATENT DOCUMENTS

| | | | |
|---|---|---|---|
| CN | 102224148 | A | 10/2011 |
| CN | 104761535 | A | 7/2015 |
| CN | 106565705 | A | 4/2017 |
| CN | 107880058 | A | 4/2018 |
| CN | 110818675 | A | 2/2020 |
| CN | 111808085 | A | 10/2020 |
| EP | 2 332 831 | A2 | 6/2011 |
| JP | 2022-515619 | A | 2/2022 |
| KR | 10-2013-0055198 | A | 5/2013 |
| KR | 10-2015-0004099 | A | 1/2015 |
| KR | 10-2016-0022768 | A | 3/2016 |
| KR | 10-2016-0027940 | A | 3/2016 |
| KR | 10-2016-0080262 | A | 7/2016 |
| KR | 10-2016-0121946 | A | 10/2016 |
| KR | 10-2018-0053121 | A | 5/2018 |
| KR | 10-2018-0096444 | A | 8/2018 |
| KR | 10-2018-0108428 | A | 10/2018 |
| WO | WO 2011/068204 | A1 | 6/2011 |
| WO | WO 2012/036482 | A1 | 3/2012 |

(Continued)

OTHER PUBLICATIONS

European Communication pursuant to Article 94(3) EPC for European Application No. 19906362.9; dated Dec. 18, 2023.
International Search Report (PCT/ISA/210) issued in PCT/KR2019/018453 mailed on Apr. 8, 2020.
Extended European Search Report for European Application No. 19906362.9, dated Jul. 14, 2022.

*Primary Examiner* — Andrew K Bohaty

(74) *Attorney, Agent, or Firm* — NKL Law; Jae Youn Kim

(57) ABSTRACT

The present specification relates to a multicyclic compound represented by Chemical Formula 1, and an organic light emitting device including the same.

13 Claims, 1 Drawing Sheet

(56) References Cited

FOREIGN PATENT DOCUMENTS

| | | | | | |
|---|---|---|---|---|---|
| WO | WO 2012/073541 | A1 | | 6/2012 | |
| WO | WO 2013/032297 | A1 | | 3/2013 | |
| WO | WO 2013/191404 | A1 | | 12/2013 | |
| WO | WO 2014/163173 | A1 | | 10/2014 | |
| WO | WO-2016129672 | A1 | * | 8/2016 | ........... C07D 209/82 |
| WO | WO 2016/148425 | A2 | | 9/2016 | |
| WO | WO 2017/090918 | A1 | | 6/2017 | |
| WO | WO 2017/090919 | A1 | | 6/2017 | |

* cited by examiner

【FIG. 1】
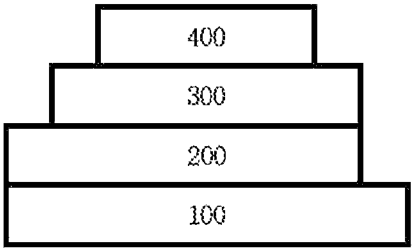
【FIG. 2】
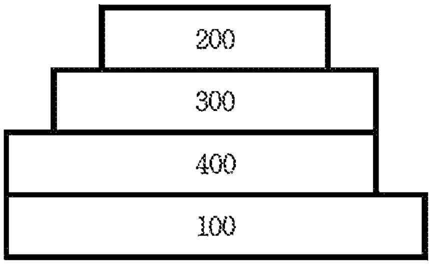
【FIG. 3】
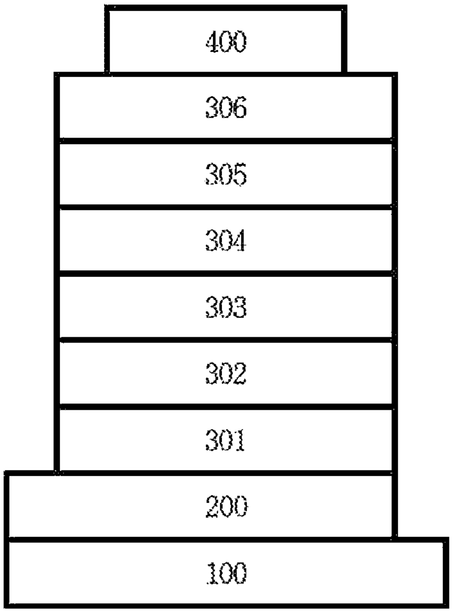

POLYCYCLIC COMPOUND AND ORGANIC LIGHT EMITTING DEVICE COMPRISING SAME

TECHNICAL FIELD

The present specification relates to a multicyclic compound, and an organic light emitting device including the same.

The present specification claims priority to and the benefits of Korean Patent Application No. 10-2018-0170110, filed with the Korean Intellectual Property Office on Dec. 27, 2018, the entire contents of which are incorporated herein by reference.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present specification is directed to providing a multicyclic compound, and an organic light emitting device including the same.

Technical Solution

One embodiment of the present specification provides a multicyclic compound represented by the following Chemical Formula 1.

[Chemical Formula 1]

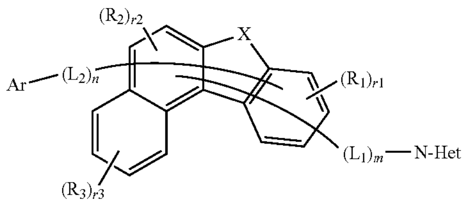

In Chemical Formula 1,

X is O; S; or $NR_{21}$, $L_1$ and $L_2$ are the same as or different from each other, and each independently a direct bond; or a substituted or unsubstituted arylene group, Ar is a substituted or unsubstituted aryl group; a substituted or unsubstituted heteroaryl group; or a substituted or unsubstituted amine group, N-Het is a monocyclic or multicyclic heteroaryl group substituted or unsubstituted and including one or more Ns, and when $L_1$ is a direct bond, the N-Het is a tricyclic or lower heteroaryl group substituted or unsubstituted and including one or more Ns, $R_1$ to $R_3$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring, $R_{21}$ is a phenyl group; or a naphthyl group, m and n are each an integer of 1 to 5, r1 is an integer of 1 to 4, r2 is an integer of 0 to 2, r3 is an integer of 1 to 4, and when r2 is 2 and m, n, r1 and r3 are an integer of 2 or greater, substituents in the parentheses are the same as or different from each other.

Another embodiment of the present application provides an organic light emitting device including a first electrode; a second electrode provided opposite to the first electrode; and one or more organic material layers provided between the first electrode and the second electrode, wherein one or more layers of the organic material layers include one or more types of the multicyclic compound represented by Chemical Formula 1.

Advantageous Effects

A compound described in the present specification can be used as a material of an organic material layer of an organic light emitting device. The compound is capable of performing a role of a hole injection material, a hole transfer material, a light emitting material, an electron transfer material, an electron injection material and the like. Particularly, the compound can be used as a light emitting layer material of an organic light emitting device. For example, the compound can be used alone as a light emitting material, or can be used as a host material of a light emitting layer.

Particularly, by introducing naphthobenzofuran, naphthobenzothiophene or benzocarbazole structure between an electron accepting substituent containing Nitrogen and an electron donating substituent, Chemical Formula 1 has a proper band gap (2.7 eV to 3.3 eV) suitable for an application as a host, and has a structure inducing a decrease in the $T_1$ energy caused by an expansion of conjugation and an expansion of planarity of the molecular structure. The value of $T_1$ energy decreased as above is identified to be between 2.18 eV to 2.48 eV from a measurement result, which is between $T_1$ energy (2.0 eV to 2.10 eV) of a generally used red dopant and $T_1$ energy (2.5 eV to 2.7 eV) of a host adjacent layer (electron blocking layer, hole transfer layer) enabling efficient energy transfer to a dopant. In addition, the increase in the planarity of the molecular structure increases intermolecular overlap, which is important in lowering a driving voltage by facilitating electron inflow and transfer.

Specifically, when using the multicyclic compound represented by Chemical Formula 1 in an organic material layer, a device driving voltage can be lowered, light efficiency can be enhanced, and device lifetime properties can be enhanced.

DESCRIPTION OF DRAWINGS

FIG. 1 to FIG. 3 are diagrams each illustrating a lamination structure of an organic light emitting device according to one embodiment of the present specification.

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present specification will be described in more detail.

In the present specification, a certain part "including" certain constituents means capable of further including other constituents, and does not exclude other constituents unless particularly stated on the contrary.

In the present specification, $T_1$ energy, means an energy level value in a triple state.

In the present specification, * of a structural formula means a bonding position.

A term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group includes linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group includes linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group includes linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group includes monocyclic or multicyclic having 3 to 60 carbon atoms, and may be further substituted with other substituents. Herein, the multicyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group includes O, S, Se, N or Si as a heteroatom, includes monocyclic or multicyclic having 2 to 60 carbon atoms, and may be further substituted with other substituents. Herein, the multicyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group.

The number of carbon atoms of the heterocycloalkyl group may be from 2 to 60, specifically from 2 to 40 and more specifically from 3 to 20.

In the present specification, the aryl group includes monocyclic or multicyclic having 6 to 60 carbon atoms, and may be further substituted with other substituents. Herein, the multicyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group includes a spiro group. The number of carbon atoms of the aryl group may be from 6 to 60, specifically from 6 to 40 and more specifically from 6 to 25. Specific examples of the aryl group may include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the fluorenyl group may be substituted, and adjacent substituents may bond to each other to form a ring.

When the fluorenyl group is substituted,

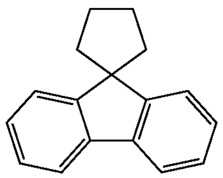
,
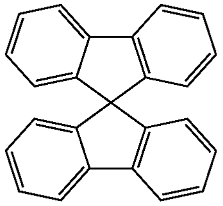
,
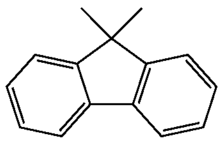
,
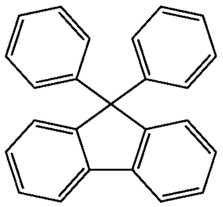
,
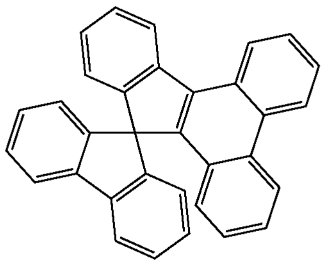
,

-continued

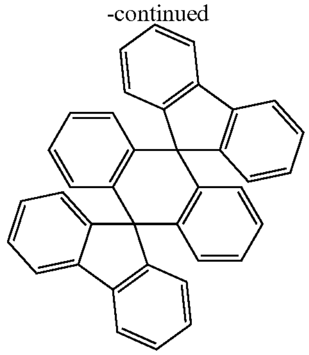

and the like may be included, however, the structure is not limited thereto.

In the present specification, the heteroaryl group includes O, S, Se, N or Si as a heteroatom, includes monocyclic or multicyclic having 2 to 60 carbon atoms, and may be further substituted with other substituents. Herein, the multicyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 2,3-dihydrobenzo[b]thiophene group, a 2,3-dihydrobenzofuran group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the phosphine oxide group may be specifically substituted with an aryl group, and as the aryl group, examples described above may be used. Examples of the phosphine oxide group may include a diphenylphosphine oxide group, a dinaphthylphosphine oxide group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

As the aliphatic hydrocarbon ring, the aromatic hydrocarbon ring, the aliphatic heteroring or the aromatic heteroring that the adjacent groups may form, the structures illustrated above as the cycloalkyl group, the aryl group, the heterocycloalkyl group and the heteroaryl group may be used except for those that are not monovalent.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or multicyclic cycloalkyl; C2 to C60 monocyclic or multicyclic heterocycloalkyl; C6 to C60 monocyclic or multicyclic aryl; C2 to C60 monocyclic or multicyclic heteroaryl; —SiRR'R"; —P(═O)RR'; C1 to C20 alkylamine; C6 to C60 monocyclic or multicyclic arylamine; and C2 to C60 monocyclic or multicyclic heteroarylamine, or being unsubstituted, or being substituted with a substituent linking two or more substituents selected from among the substituents illustrated above, or being unsubstituted. R, R' and R" are the same as or different from each other, and each independently hydrogen; deuterium; a cyano group; a substituted or unsubstituted alkyl group; a substituted or unsubstituted cycloalkyl group; a substituted or unsubstituted aryl group; or a substituted or unsubstituted heteroaryl group.

One embodiment of the present specification provides a multicyclic compound represented by Chemical Formula 1.

Particularly, by introducing naphthobenzofuran, naphthobenzothiophene or benzocarbazole structure between an electron accepting substituent containing Nitrogen and an electron donating substituent, Chemical Formula 1 has a proper band gap (2.7 eV to 3.3 eV) suitable for an application as a host, and has a structure inducing a decrease in the $T_1$ energy caused by an expansion of conjugation and an expansion of planarity of the molecular structure. The value of $T_1$ energy decreased as above is identified to be between 2.18 eV to 2.48 eV from a measurement result, which is between $T_1$ energy (2.0 eV to 2.10 eV) of a generally used red dopant and $T_1$ energy (2.5 eV to 2.7 eV) of a host adjacent layer (electron blocking layer, hole transfer layer) enabling efficient energy transfer to a dopant. In addition, the increase in the planarity of the molecular structure increases intermolecular overlap, which is important in lowering a driving voltage by facilitating electron inflow and transfer.

In one embodiment of the present specification, $L_1$ and $L_2$ are the same as or different from each other, and each independently a direct bond; or a substituted or unsubstituted arylene group.

In another embodiment, $L_1$ and $L_2$ are the same as or different from each other, and may be each independently a direct bond; or a substituted or unsubstituted C6 to C60 arylene group.

In another embodiment, $L_1$ and $L_2$ are the same as or different from each other, and may be each independently a direct bond; or a substituted or unsubstituted C6 to C40 arylene group.

In another embodiment, $L_1$ and $L_2$ are the same as or different from each other, and may be each independently a direct bond; or a substituted or unsubstituted C6 to C20 arylene group.

In another embodiment, $L_1$ and $L_2$ are the same as or different from each other, and may be each independently a direct bond; or a C6 to C20 arylene group.

In another embodiment, $L_1$ and $L_2$ are the same as or different from each other, and may be each independently a direct bond; a phenylene group; a biphenylene group; or a naphthylene group.

In one embodiment of the present specification, Ar is a substituted or unsubstituted aryl group; a substituted or unsubstituted heteroaryl group; or a substituted or unsubstituted amine group.

In another embodiment, Ar may be a substituted or unsubstituted C6 to C60 aryl group; a substituted or unsubstituted C2 to C60 heteroaryl group; or a substituted or unsubstituted C1 to C30 amine group.

In another embodiment, Ar may be a substituted or unsubstituted C6 to C60 aryl group; a substituted or unsubstituted C2 to C60 heteroaryl group; or a C1 to C30 amine group unsubstituted or substituted with an aryl group.

In another embodiment, Ar may be a substituted or unsubstituted C6 to C40 aryl group; a substituted or unsubstituted C2 to C40 heteroaryl group; or a substituted or unsubstituted C1 to C30 arylamine group.

In one embodiment of the present specification, Ar may be selected from among the following structural formulae.

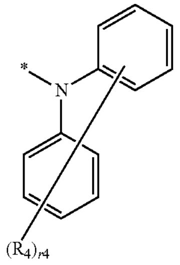

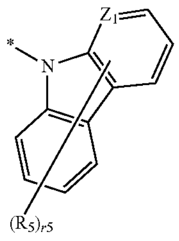

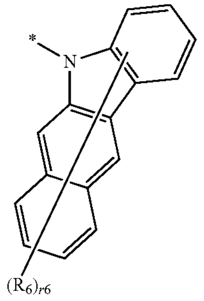

-continued

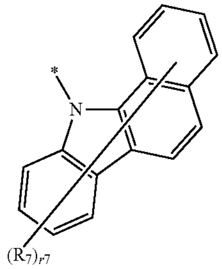

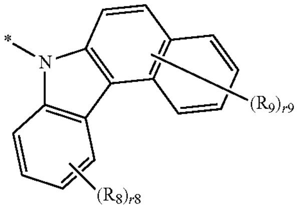

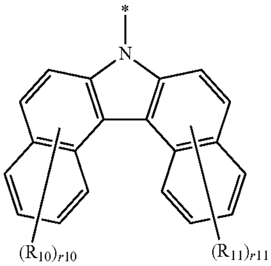

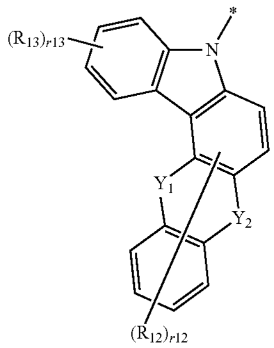

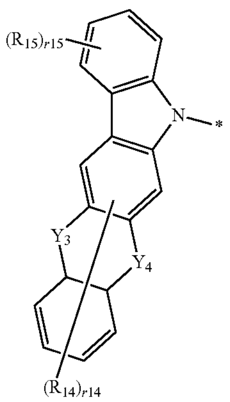

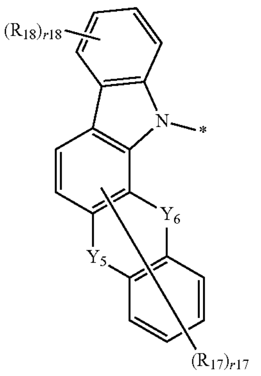

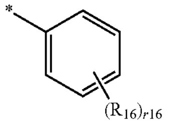

In the structural formulae, $Y_1$ to $Y_6$ are the same as or different from each other, and each independently a direct bond; O; S; or $NR_{22}$, $Z_1$ is N or $CR_{31}$, $R_5$ to $R_{15}$, $R_{18}$ and $R_{31}$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, $R_4$, $R_{16}$ and $R_{17}$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or bond to adjacent groups to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring, $R_{22}$ is a substituted or unsubstituted aryl group, r4, r6 and r7 are each an integer of 1 to 10, r5 is an integer of 1 to 7, r8, r13, r15 and r18 are each an integer of 1 to 4, r9 to r12, r14 and r17 are each an integer of 1 to 6, r16 is an integer of 1 to 5, and when r4 to r18 are an integer of 2 or greater, substituents in the parentheses are the same as or different from each other.

In one embodiment of the present specification, any one of $Y_1$ and $Y_2$ is a direct bond, and the other one may be O; S; or $NR_{22}$.

In one embodiment of the present specification, any one of $Y_3$ and $Y_4$ is a direct bond, and the other one may be O; S; or $NR_{22}$.

In one embodiment of the present specification, any one of $Y_5$ and $Y_6$ is a direct bond, and the other one may be O; S; or $NR_{22}$.

In one embodiment of the present specification, $R_5$ to $R_{15}$ and $R_{18}$ are the same as or different from each other, and may be each independently selected from the group consisting of hydrogen; deuterium; and a substituted or unsubstituted aryl group.

In another embodiment, $R_5$ to $R_{15}$ and $R_{18}$ are the same as or different from each other, and may be each independently selected from the group consisting of hydrogen; deuterium; and a substituted or unsubstituted C6 to C40 aryl group.

In another embodiment, $R_5$ to $R_{15}$ and $R_{18}$ are the same as or different from each other, and may be each independently selected from the group consisting of hydrogen; deuterium; and a substituted or unsubstituted C6 to C20 aryl group.

In another embodiment, $R_5$ to $R_{15}$ and $R_{18}$ are the same as or different from each other, and may be each independently selected from the group consisting of hydrogen; deuterium; a substituted or unsubstituted phenyl group; a substituted or unsubstituted biphenyl group; and a substituted or unsubstituted naphthyl group.

In another embodiment, $R_5$ to $R_{15}$ and $R_{18}$ are the same as or different from each other, and may be each independently selected from the group consisting of hydrogen; deuterium; a phenyl group; a biphenyl group; and a naphthyl group.

In one embodiment of the present specification, $R_5$ and $R_7$ to $R_9$ may be hydrogen; or a phenyl group.

In one embodiment of the present specification, $R_6$, $R_{10}$ to $R_{15}$ and $R_{18}$ may be hydrogen.

In one embodiment of the present specification, $R_4$, $R_{16}$ and $R_{17}$ are the same as or different from each other, and each independently selected from the group consisting of hydrogen; deuterium; a substituted or unsubstituted aryl group; and a substituted or unsubstituted heteroaryl group, or may bond to adjacent groups to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring.

In one embodiment of the present specification, $R_4$, $R_{16}$ and $R_{17}$ are the same as or different from each other, and may be each independently selected from the group consisting of hydrogen; deuterium; a substituted or unsubstituted aryl group; and a substituted or unsubstituted heteroaryl group.

In one embodiment of the present specification, $R_4$, $R_{16}$ and $R_{17}$ are the same as or different from each other, and may be each independently selected from the group consisting of hydrogen; deuterium; a substituted or unsubstituted C6 to C60 aryl group; and a substituted or unsubstituted C2 to C60 heteroaryl group.

In one embodiment of the present specification, $R_4$, $R_{16}$ and $R_{17}$ are the same as or different from each other, and may be each independently selected from the group consisting of hydrogen; deuterium; a substituted or unsubstituted C6 to C40 aryl group; and a substituted or unsubstituted C2 to C40 heteroaryl group.

In one embodiment of the present specification, $R_4$, $R_{16}$ and $R_{17}$ are the same as or different from each other, and may be each independently selected from the group consisting of hydrogen; deuterium; a substituted or unsubstituted phenyl group; a substituted or unsubstituted biphenyl group; a substituted or unsubstituted naphthyl group; a substituted or unsubstituted fluorenyl group; a substituted or unsubstituted carbazole group; a substituted or unsubstituted benzocarbazole group; a substituted or unsubstituted dibenzofuran group; and a substituted or unsubstituted dibenzothiophene group.

In another embodiment, $R_4$, $R_{16}$ and $R_{17}$ may bond to adjacent groups to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring.

In one embodiment of the present specification, $R_4$, $R_{16}$ and $R_{17}$ may bond to each other to form a ring of the following structures.

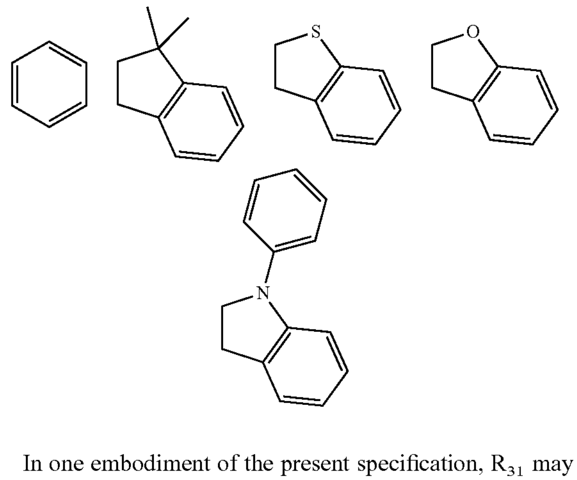

In one embodiment of the present specification, $R_{31}$ may be hydrogen.

In one embodiment of the present specification, the N-Het is a monocyclic or multicyclic heteroaryl group substituted or unsubstituted and including one or more Ns, and when $L_1$ is a direct bond, the N-Het is a tricyclic or lower heteroaryl group substituted or unsubstituted and including one or more Ns.

In one embodiment of the present specification, the N-Het may be selected from among the following structural formulae.

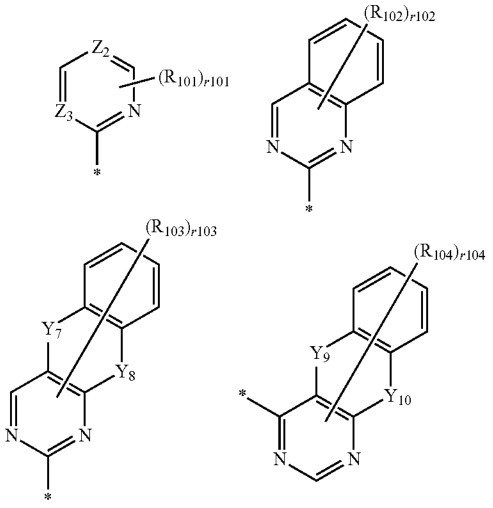

In the structural formulae, $Y_7$ to $Y_{10}$ are the same as or different from each other, and each a direct bond; O; S; or $NR_{23}$, $Z_2$ and $Z_3$ are each N or $CR_{32}$, $R_{101}$ to $R_{104}$ and $R_{32}$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring, $R_{23}$ is a substituted or unsubstituted aryl group, r101 is 1 or 2, r102 to r104 are each an integer of 1 to 5, and when r101 is 2 and r102 to r104 are an integer of 2 or greater, substituents in the parentheses are the same as or different from each other.

In one embodiment of the present specification, any one of $Y_7$ and $Y_8$ is a direct bond, and the other one may be O; S; or $NR_{23}$.

In one embodiment of the present specification, any one of $Y_9$ and $Y_{10}$ is a direct bond, and the other one may be O; S; or $NR_{23}$.

In one embodiment of the present specification, $Z_2$ and $Z_3$ are each N or $CR_{32}$, and at least one thereof may be N.

In another embodiment, $Z_2$ and $Z_3$ may be N.

In one embodiment of the present specification, $R_{101}$ to $R_{104}$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other may bond to each other to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring.

In another embodiment, $R_{101}$ to $R_{104}$ are the same as or different from each other, and each independently selected from the group consisting of hydrogen; deuterium; a substituted or unsubstituted aryl group; and a substituted or unsubstituted heteroaryl group, or two or more groups adjacent to each other may bond to each other to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring.

In another embodiment, $R_{101}$ to $R_{104}$ are the same as or different from each other, and each independently selected from the group consisting of hydrogen; deuterium; a substituted or unsubstituted C6 to C60 aryl group; and a substituted or unsubstituted C2 to C60 heteroaryl group, or two or more groups adjacent to each other may bond to each other to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring.

In another embodiment, $R_{101}$ to $R_{104}$ are the same as or different from each other, and each independently selected from the group consisting of hydrogen; deuterium; a substituted or unsubstituted C6 to C40 aryl group; and a substituted or unsubstituted C2 to C40 heteroaryl group, or two or more groups adjacent to each other may bond to each other to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring.

In another embodiment, $R_{101}$ to $R_{104}$ are the same as or different from each other, and each independently selected from the group consisting of hydrogen; deuterium; a substituted or unsubstituted C6 to C20 aryl group; and a substituted or unsubstituted C2 to C20 heteroaryl group, or two or more groups adjacent to each other may bond to each other to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring.

In another embodiment, $R_{101}$ to $R_{104}$ are the same as or different from each other, and each independently selected from the group consisting of hydrogen; deuterium; a substituted or unsubstituted C6 to C60 aryl group; and a substituted or unsubstituted C6 to C60 heteroaryl group, or two or more groups adjacent to each other may bond to each other to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring.

In another embodiment, $R_{101}$ to $R_{104}$ are the same as or different from each other, and each independently selected from the group consisting of hydrogen; deuterium; a substituted or unsubstituted C6 to C40 aryl group; and a substituted or unsubstituted C6 to C40 heteroaryl group, or two or more groups adjacent to each other may bond to each other to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring.

In another embodiment, $R_{101}$ to $R_{104}$ are the same as or different from each other, and each independently selected from the group consisting of hydrogen; deuterium; a substituted or unsubstituted C6 to C20 aryl group; and a substituted or unsubstituted C6 to C20 heteroaryl group, or two or more groups adjacent to each other may bond to each other to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring.

In another embodiment, $R_{101}$ to $R_{104}$ are the same as or different from each other, and each independently selected from the group consisting of hydrogen; deuterium; a substituted or unsubstituted phenyl group; a substituted or unsubstituted biphenyl group; a substituted or unsubstituted terphenyl group; a substituted or unsubstituted naphthyl group; a substituted or unsubstituted dibenzofuran group; a substituted or unsubstituted dibenzothiophene group; a substituted or unsubstituted carbazole group; a substituted or unsubstituted benzocarbazole group; and a substituted or unsubstituted fluorene group, or two or more groups adjacent to each other may bond to each other to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring.

In another embodiment, $R_{101}$ to $R_{104}$ are the same as or different from each other, and each independently selected from the group consisting of hydrogen; deuterium; a phenyl group unsubstituted or substituted with an aryl group or a heteroaryl group; a biphenyl group; a naphthyl group unsubstituted or substituted with an aryl group; a dibenzofuran group; a dibenzothiophene group; a carbazole group unsubstituted or substituted with an aryl group; a benzocarbazole group; a dimethylfluorene group; a diphenylfluorene group; and 9,9'-spirobi[fluorene], or two or more groups adjacent to each other may bond to each other to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring.

In one embodiment of the present specification, $R_{101}$ to $R_{104}$ are the same as or different from each other, and may be each independently selected from the group consisting of hydrogen; deuterium; a phenyl group unsubstituted or substituted with an aryl group or a heteroaryl group; a biphenyl group; a naphthyl group unsubstituted or substituted with an aryl group; a dibenzofuran group; a dibenzothiophene group; a carbazole group unsubstituted or substituted with an aryl group; a benzocarbazole group; a dimethylfluorene group; a diphenylfluorene group; and 9,9'-spirobi[fluorene].

In one embodiment of the present specification, when the substituent is a substituted or unsubstituted carbazole group; or a substituted or unsubstituted benzocarbazole group, the bonding position may be N of the pyrrole ring, or C of the benzene ring.

In one embodiment of the present specification, $R_{32}$ may be hydrogen.

In one embodiment of the present specification, $R_1$ to $R_3$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other may bond to each other to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring.

In one embodiment of the present specification, $R_1$ to $R_3$ are the same as or different from each other, and each independently hydrogen; deuterium; or a substituted or unsubstituted aryl group.

In one embodiment of the present specification, $R_1$ to $R_3$ are the same as or different from each other, and each independently hydrogen; deuterium; a substituted or unsubstituted phenyl group; a substituted or unsubstituted biphenyl group; or a substituted or unsubstituted naphthyl group.

In another embodiment, $R_1$ to $R_3$ are hydrogen; a phenyl group; a biphenyl group; or a naphthyl group.

In one embodiment of the present specification, $R_{21}$ is a phenyl group; or a naphthyl group.

In one embodiment of the present specification, $R_{21}$ is a phenyl group.

In the multicyclic compound provided in one embodiment of the present specification, Chemical Formula 1 is represented by the following Chemical Formula 2 or 3.

[Chemical Formula 2]

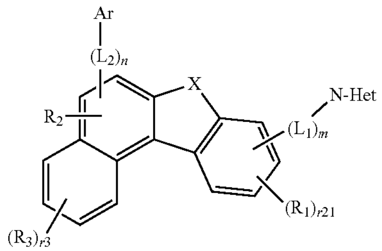

[Chemical Formula 3]

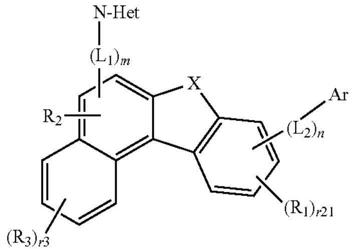

In Chemical Formulae 2 and 3, r21 is an integer of 1 to 3, when r21 is an integer of 2 or greater, substituents in the parentheses are the same as or different from each other, and the remaining substituents have the same definitions as in Chemical Formula 1.

In one embodiment of the present specification, Chemical Formula 1 may be represented by any one of the following compounds, but is not limited thereto.

F1

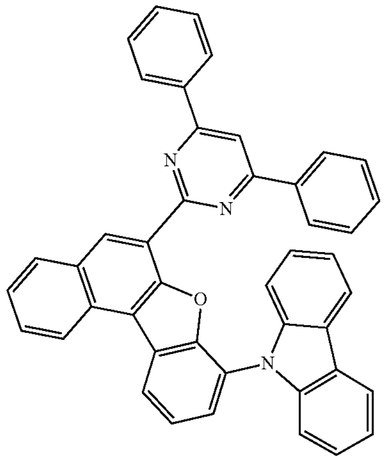

F2

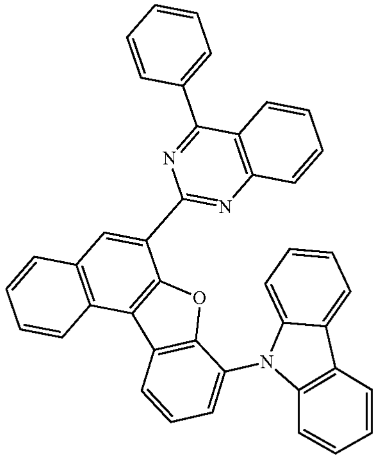

F3

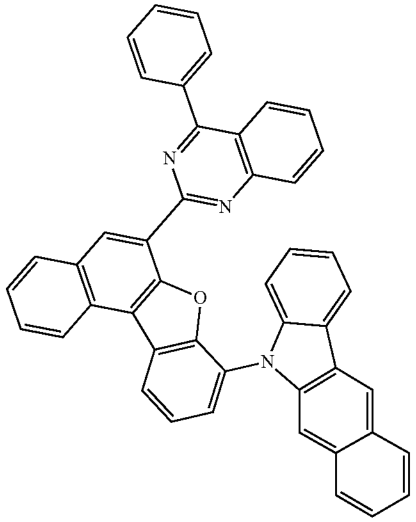

-continued
F4
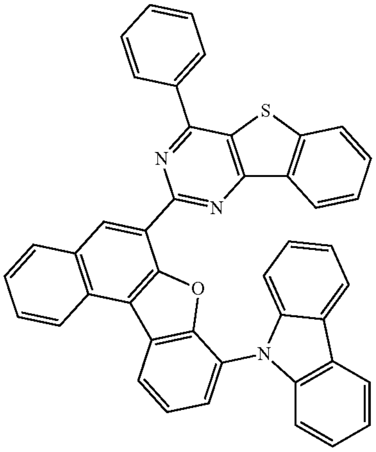
F5
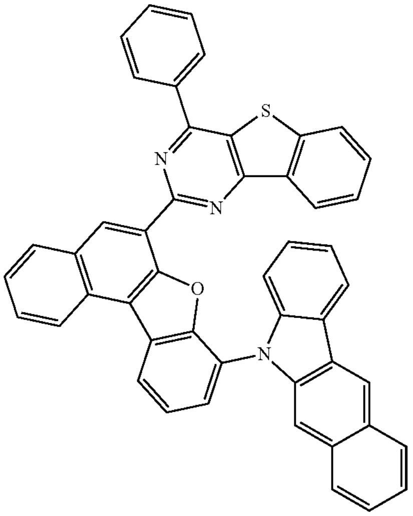
F6
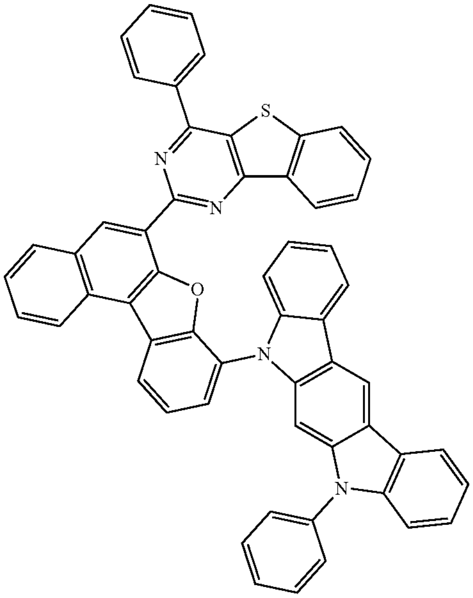
-continued
F7
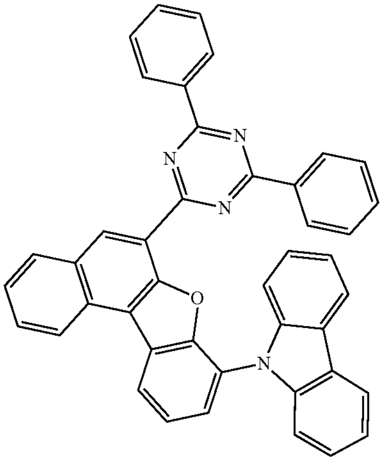
F8
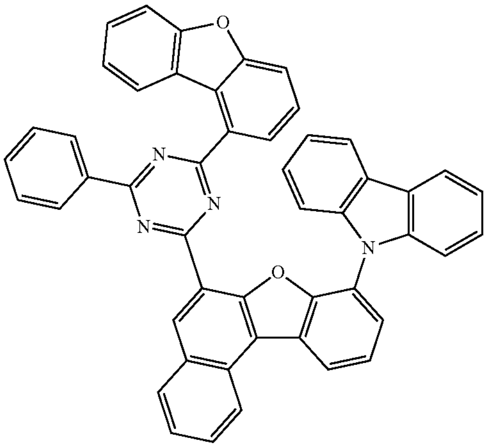
F9
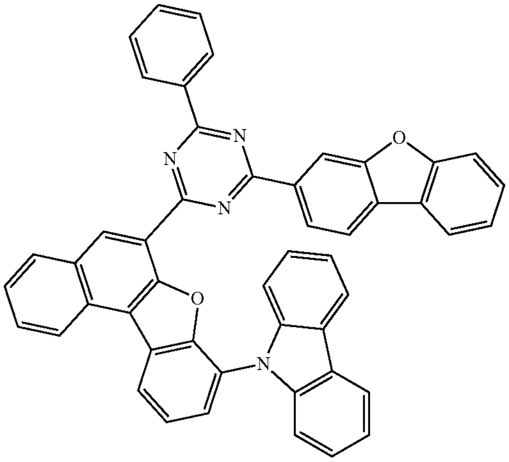

-continued
F10
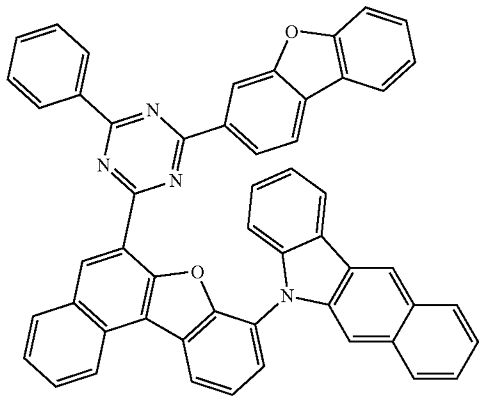
F11
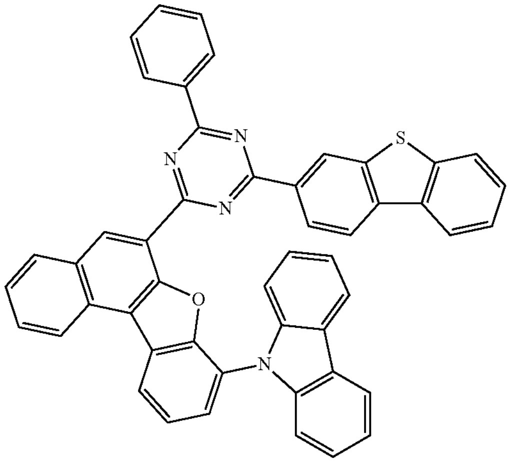
F12
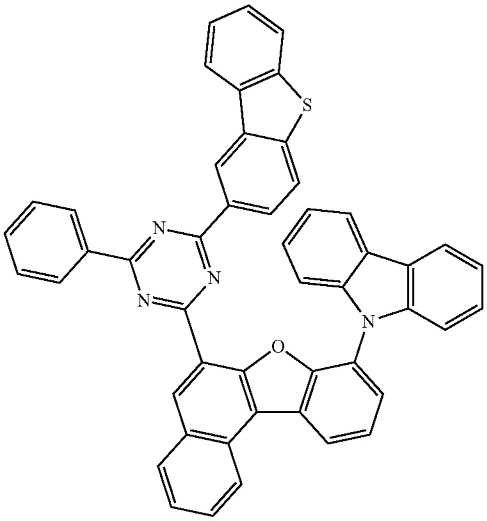
-continued
F13
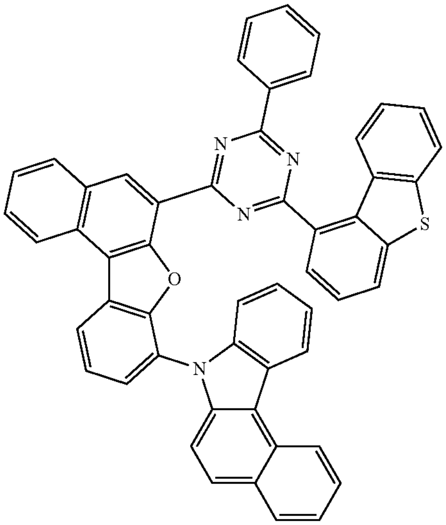
F14
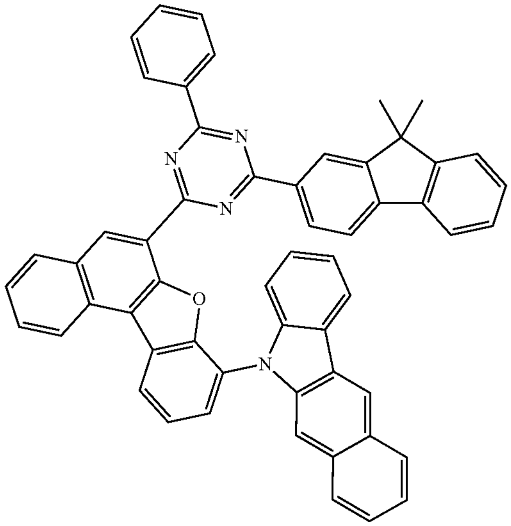
F15
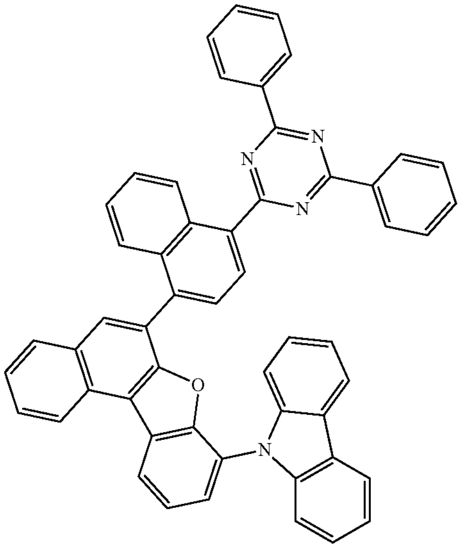

-continued
F16
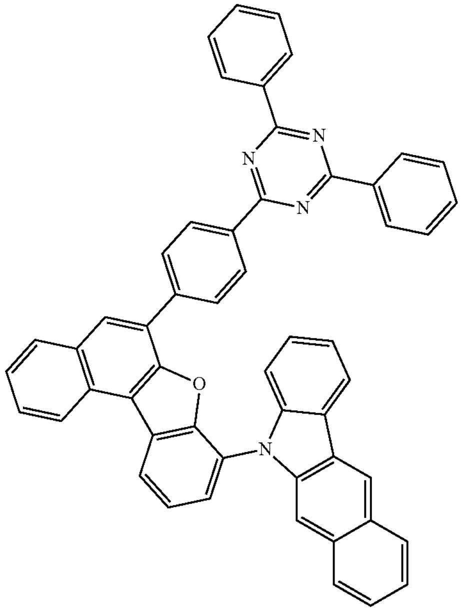
F17
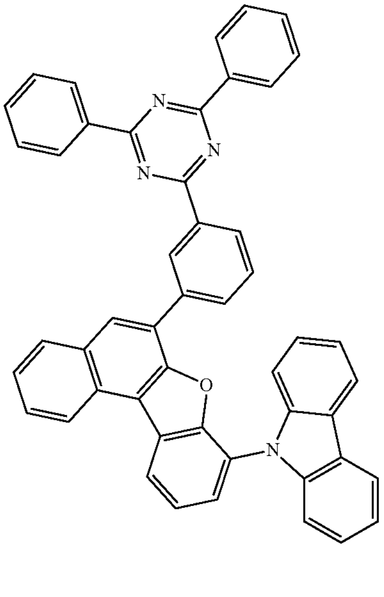
-continued
F18
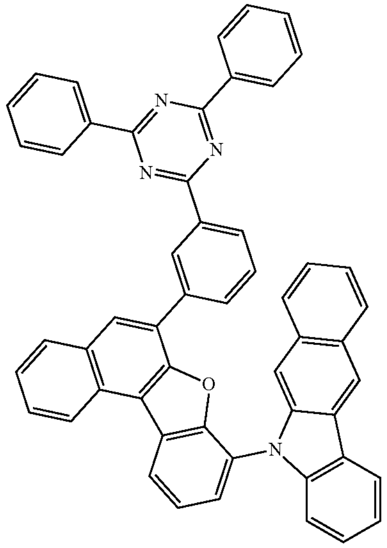
F19
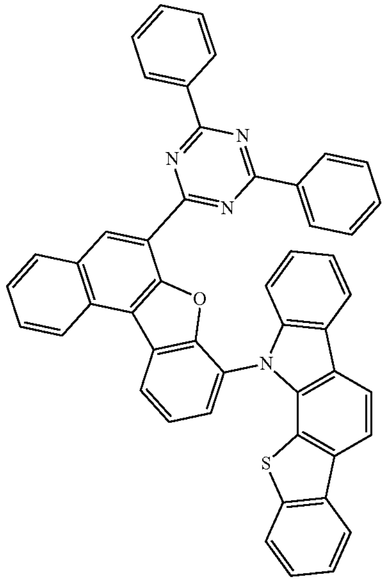

-continued
F20
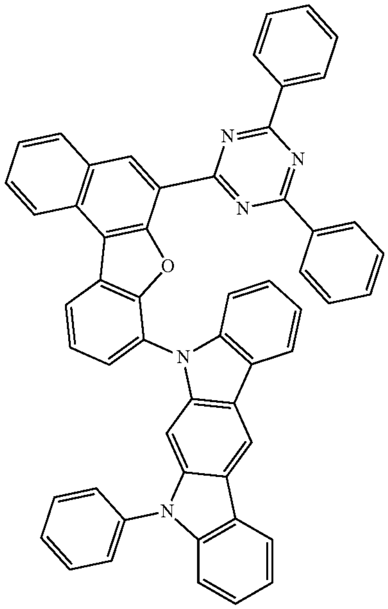
F21
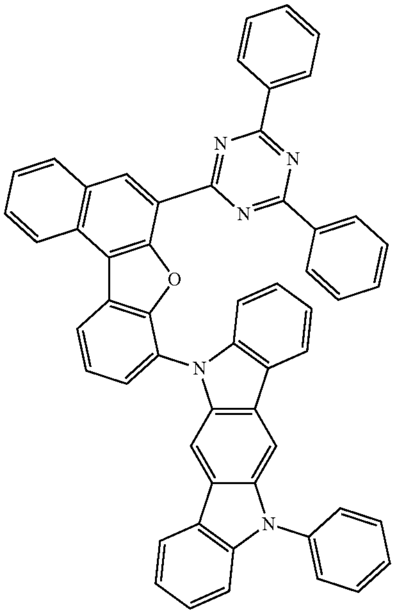
-continued
F22
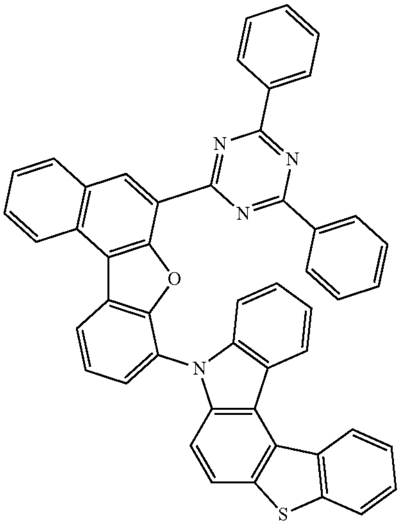
F23
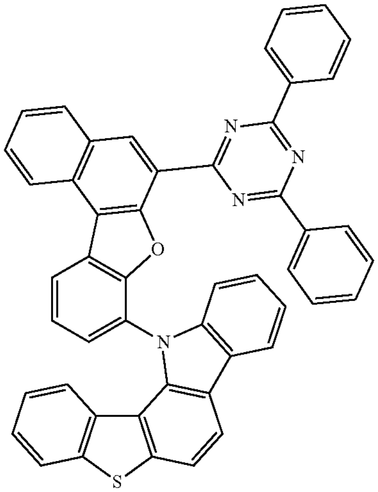
F24
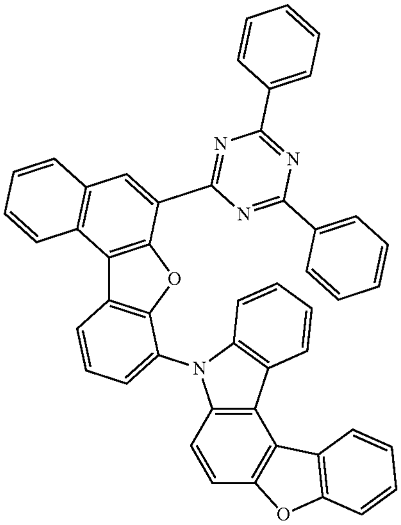

-continued
F25
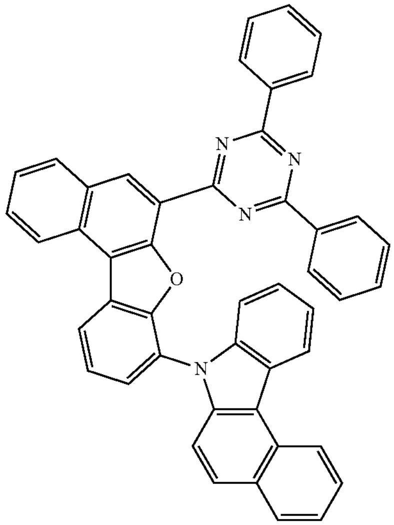
F26
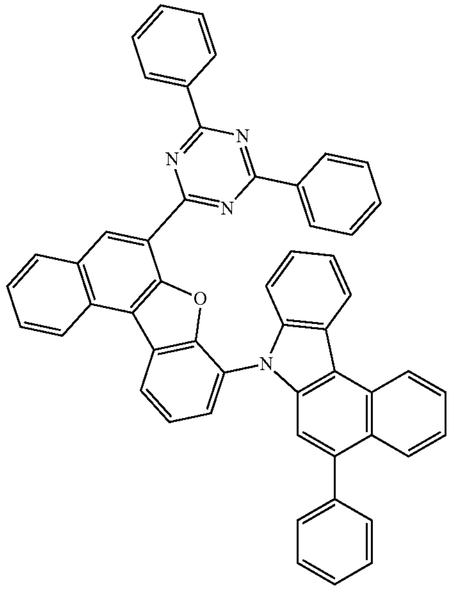
-continued
F27
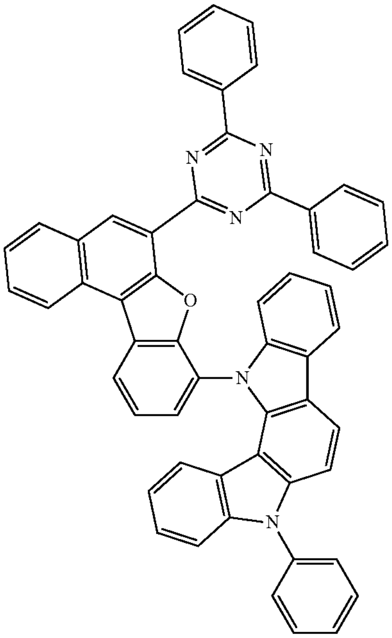
F28
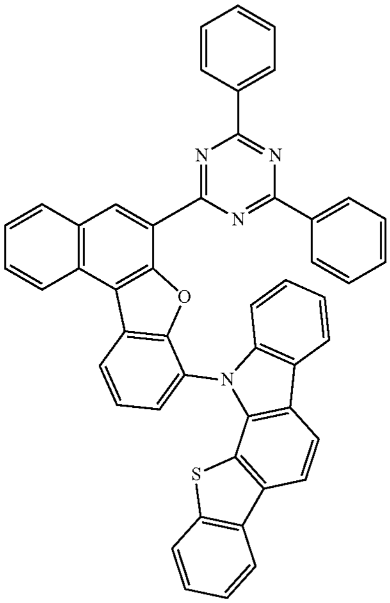

-continued
F29
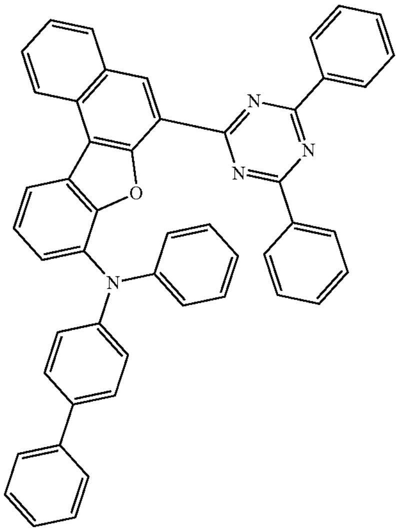
F30
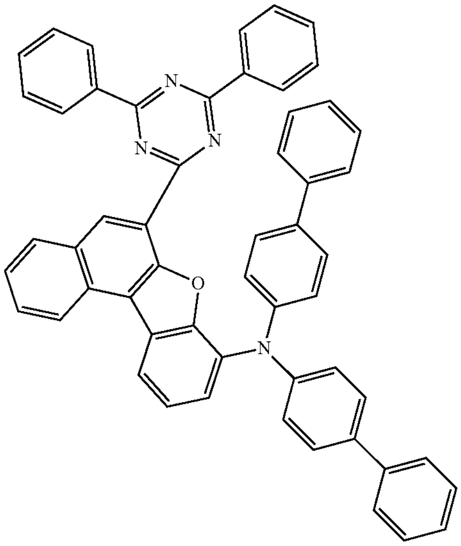
F31
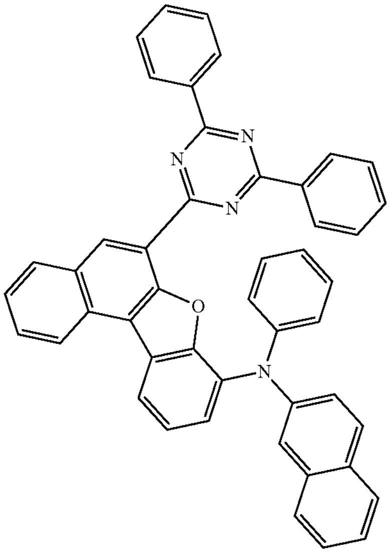
-continued
F32
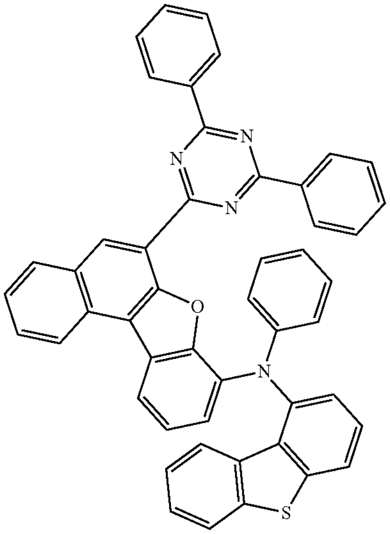
F33
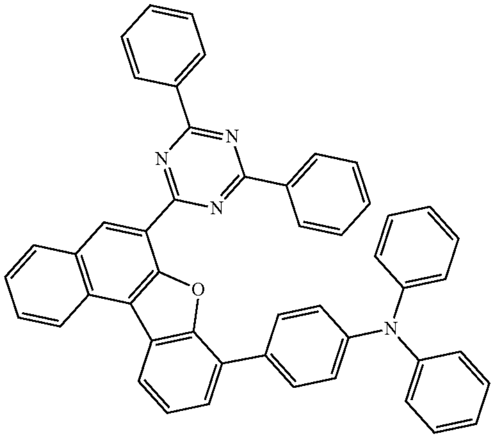
F34
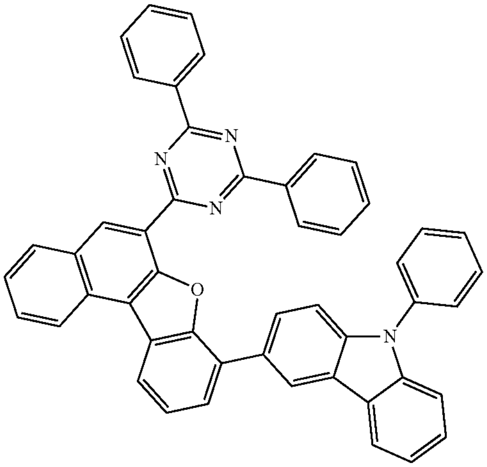

-continued
F35
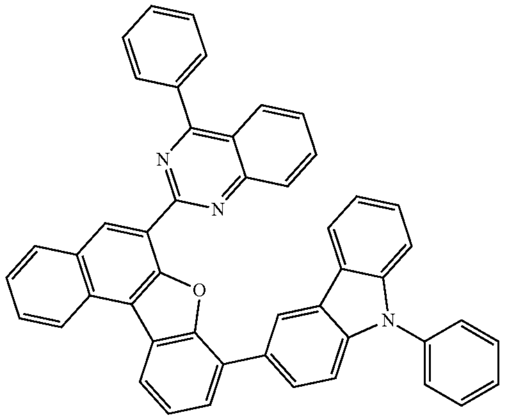
F36
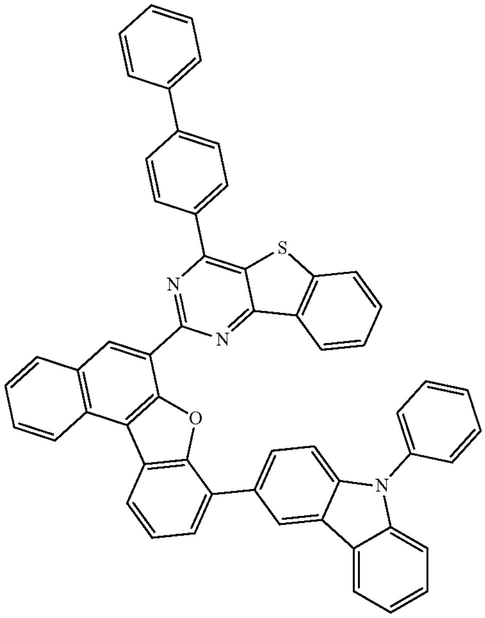
F37
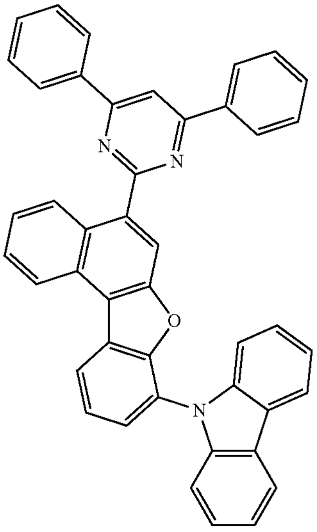
-continued
F38
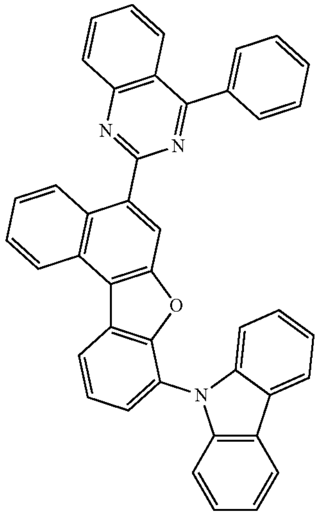
F39
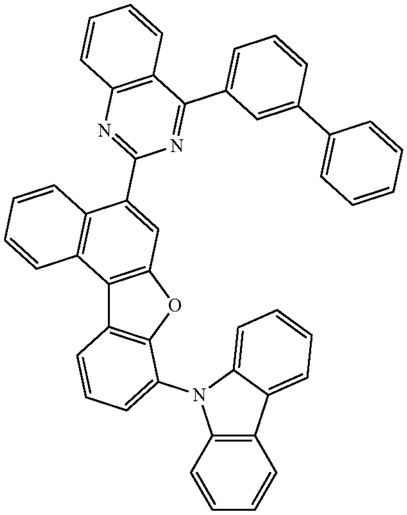
F40
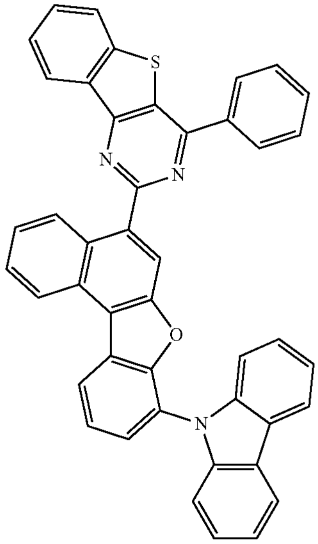

-continued
F41
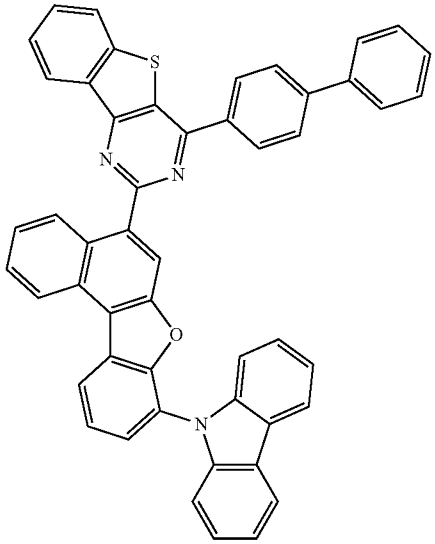
F42
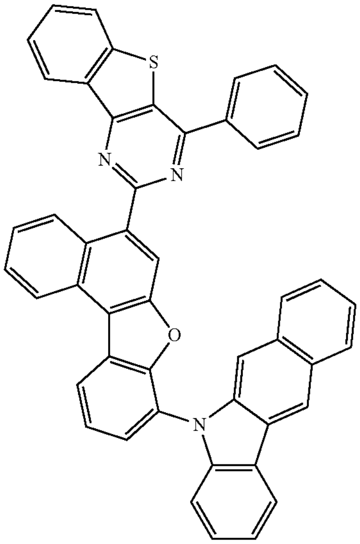
F43
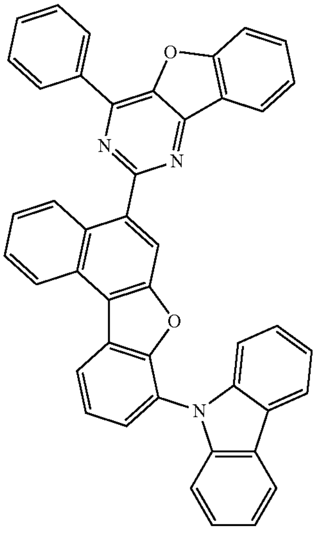
-continued
F44
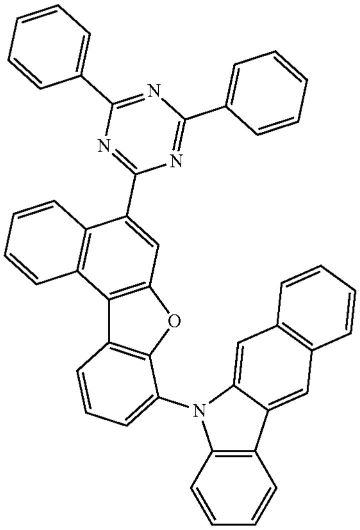
F45
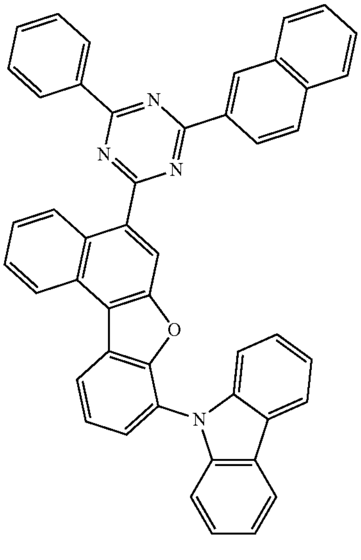

-continued
F46
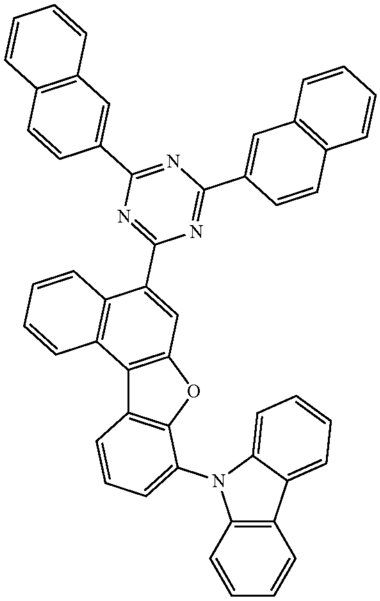
F47
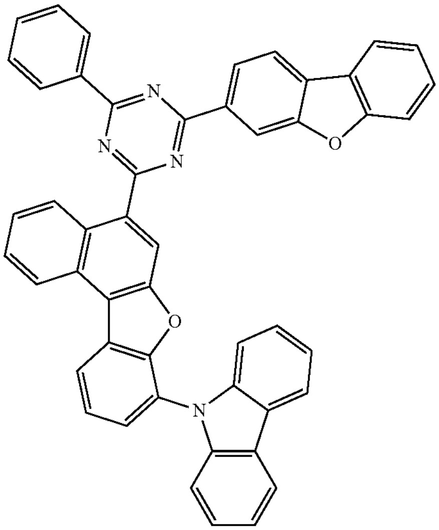
-continued
F48
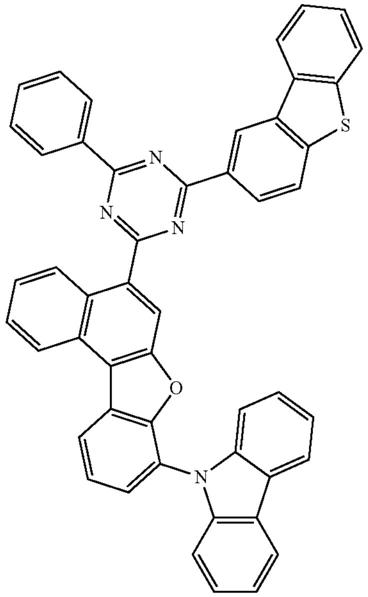
F49
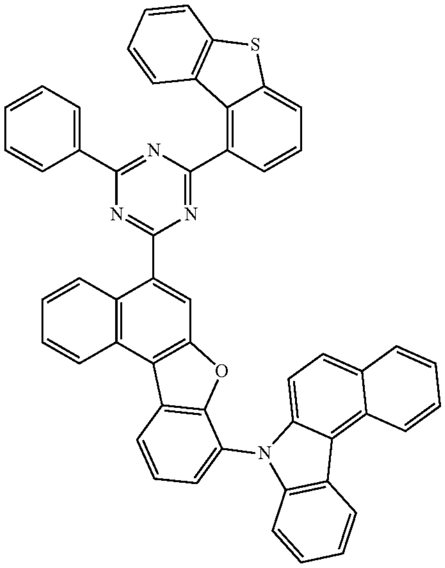

-continued
F50
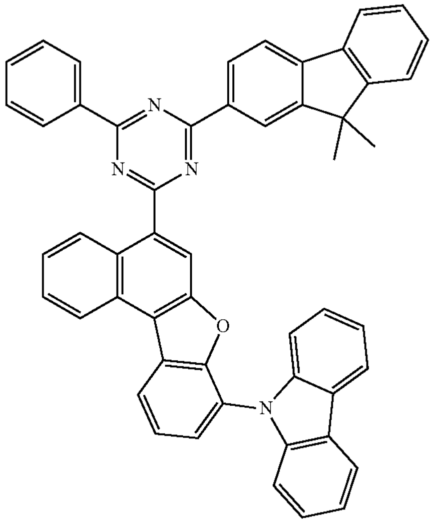
F51
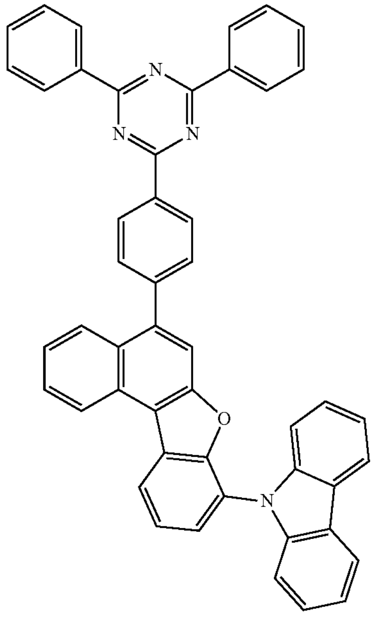
-continued
F52
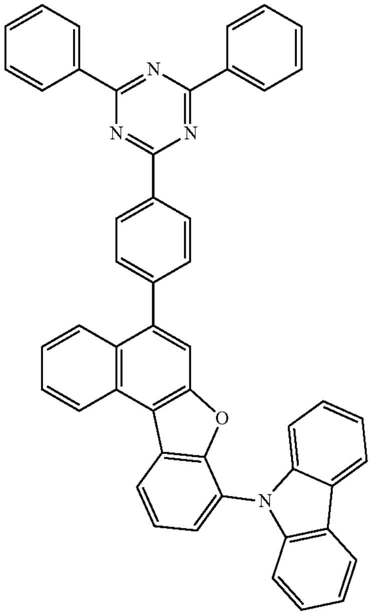
F53
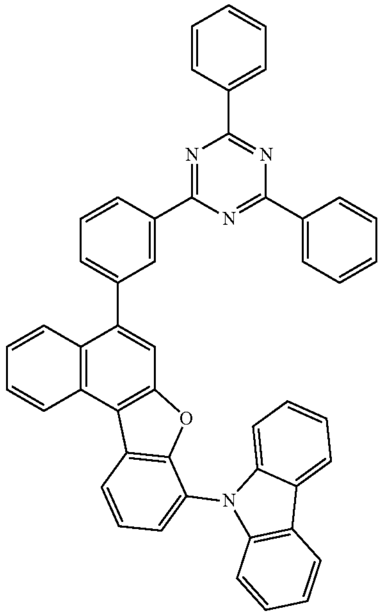

-continued
F54
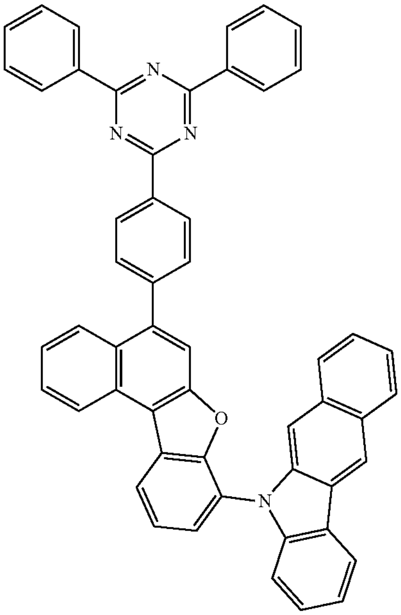
F55
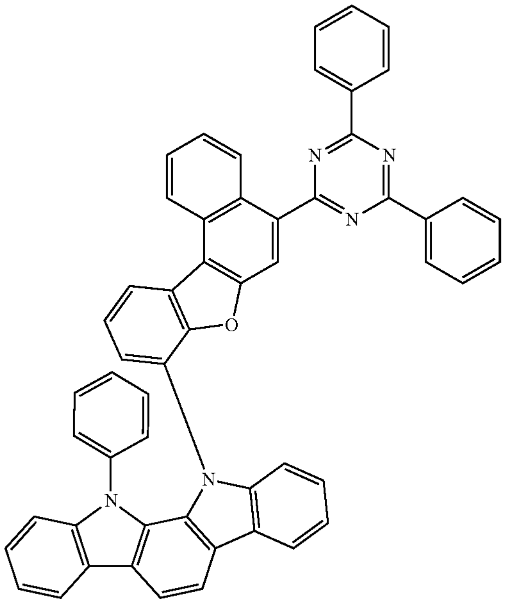
-continued
F56
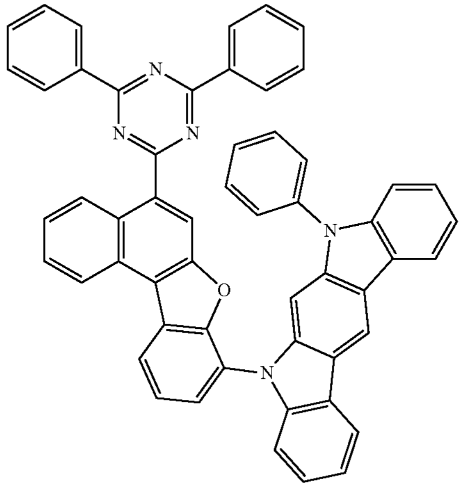
F57
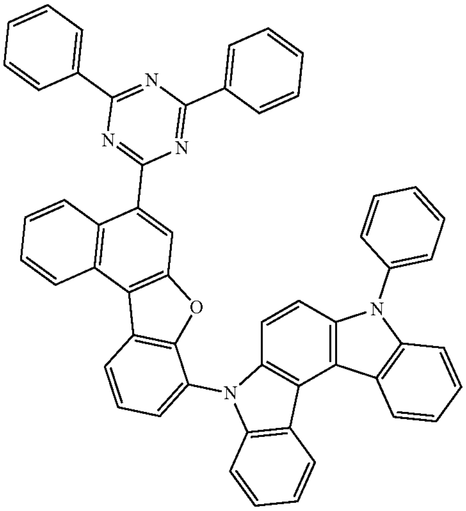
F58
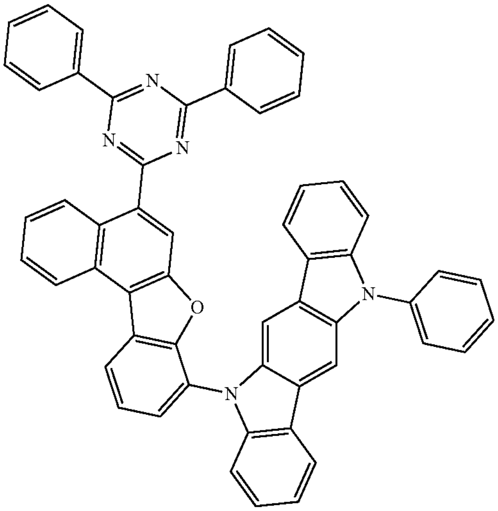

-continued
F59
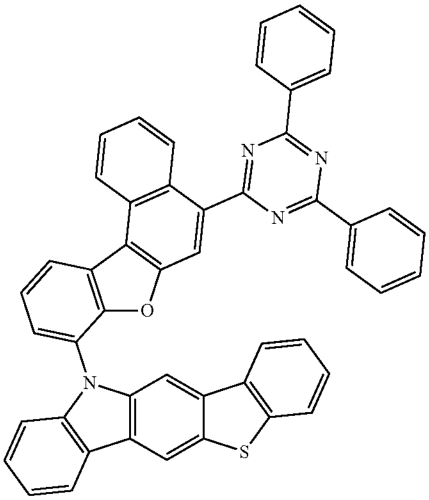
F60
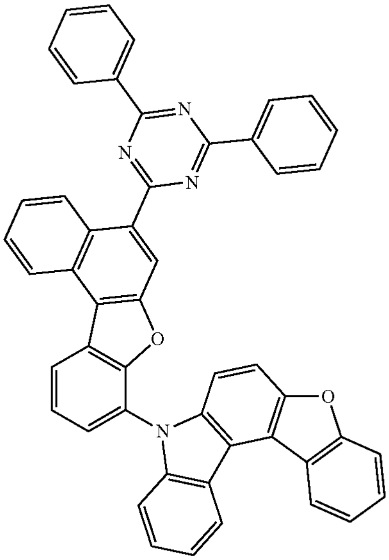
F61
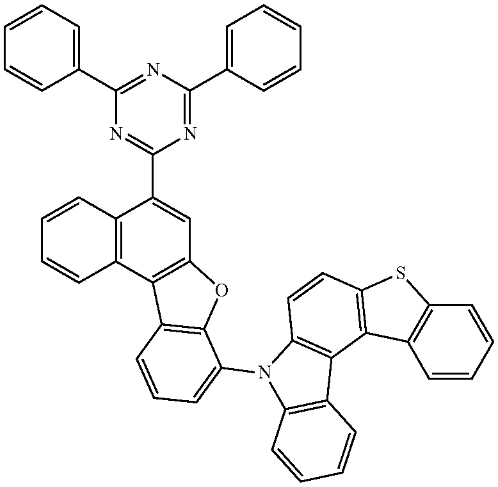
-continued
F62
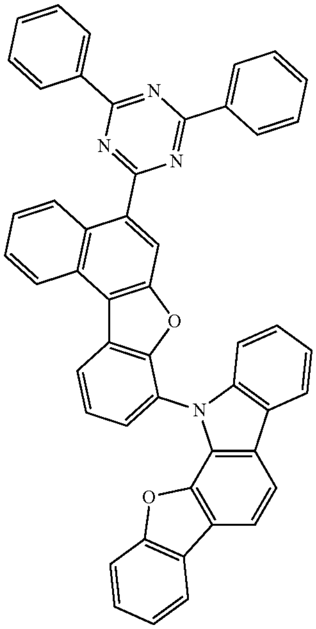
F63
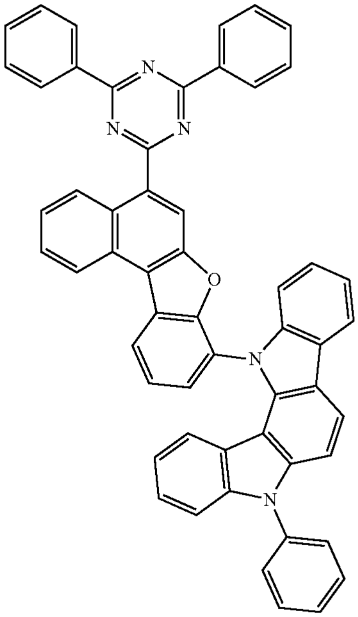

-continued
F64
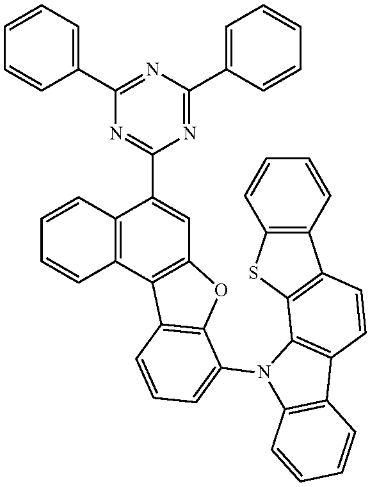
F65
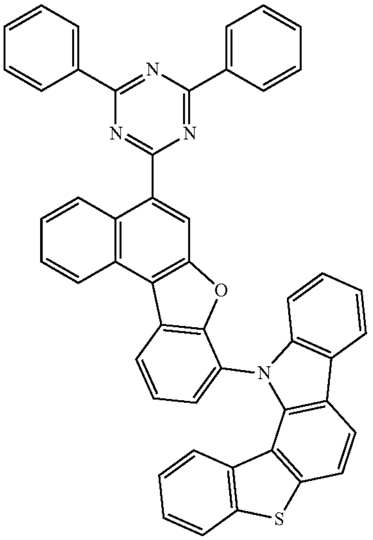
F66
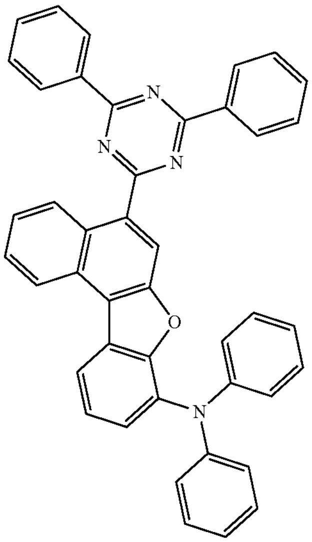
-continued
F67
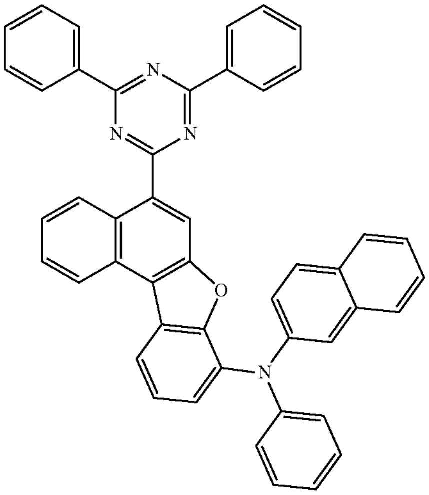
F68
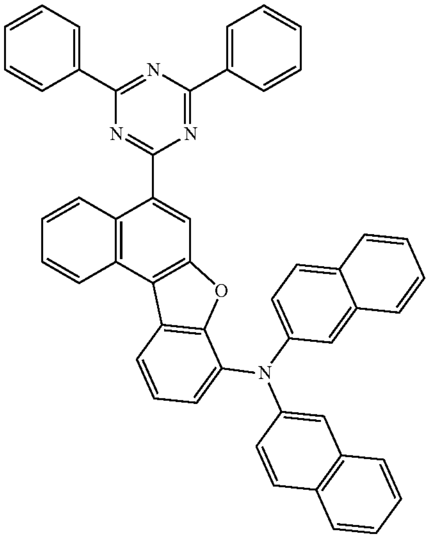
F69
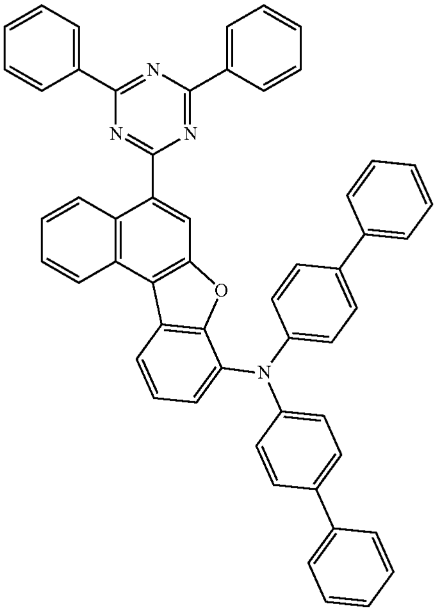

-continued
F70
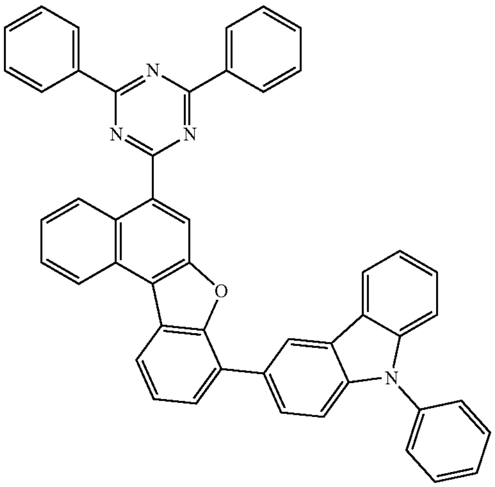
F71
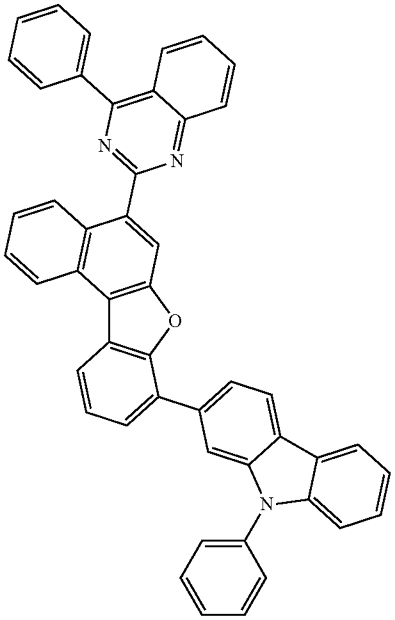
-continued
F72
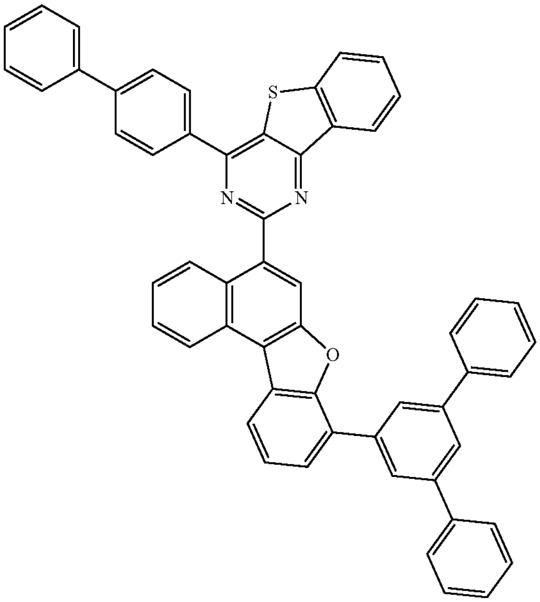
F73
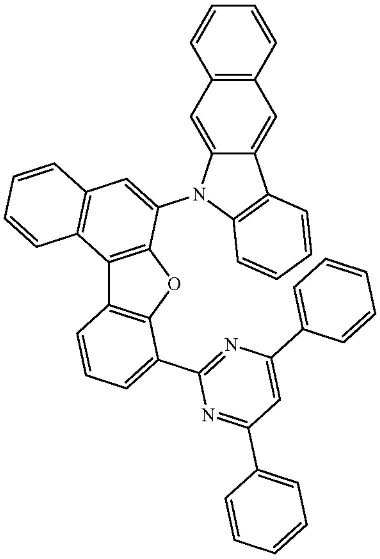

-continued
F74
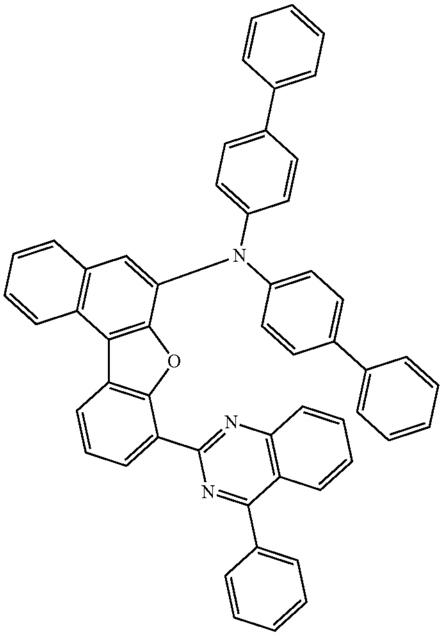
F75
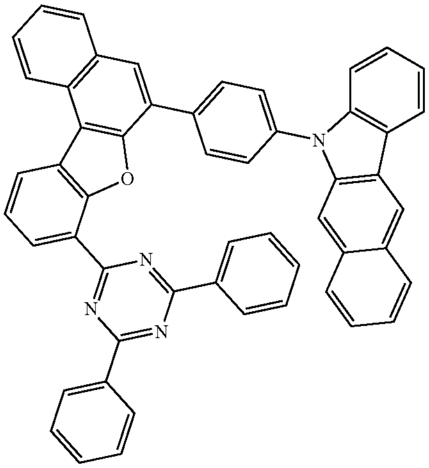
F76
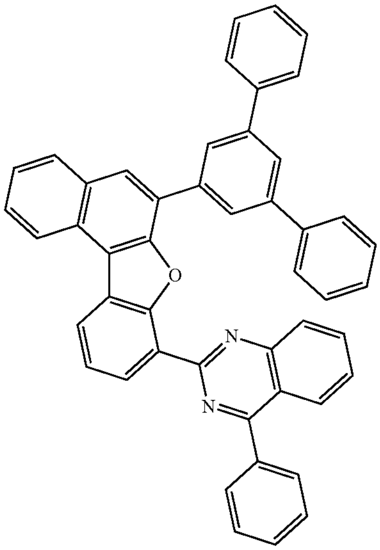
-continued
F77
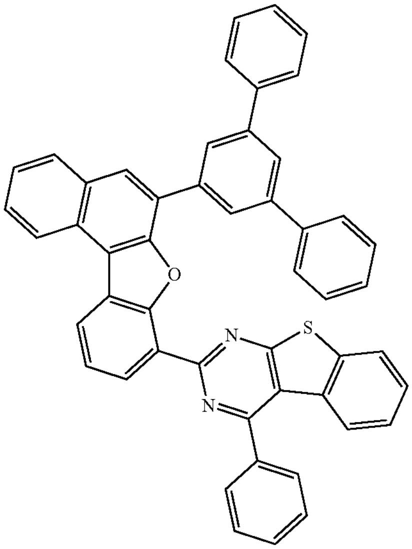
F78
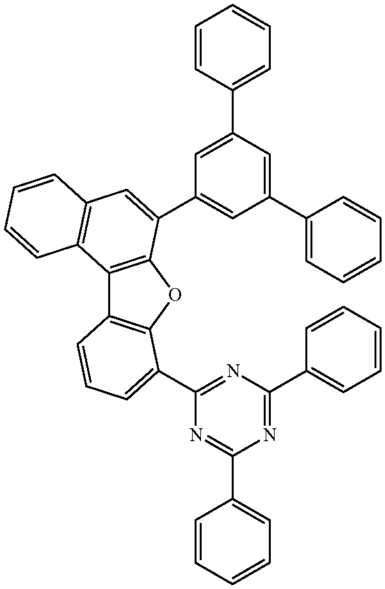
F79
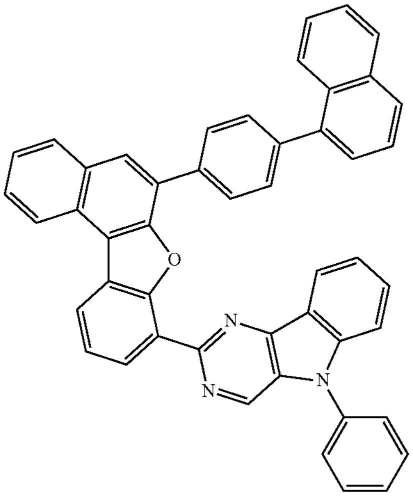

-continued
F80
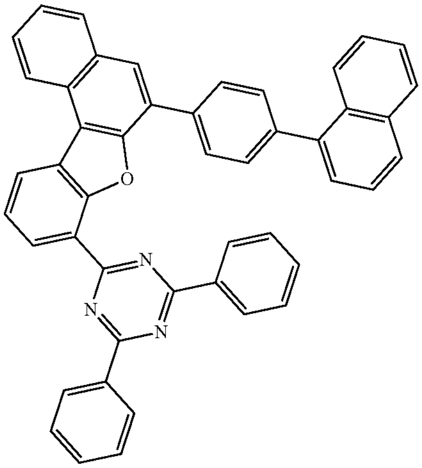
F81
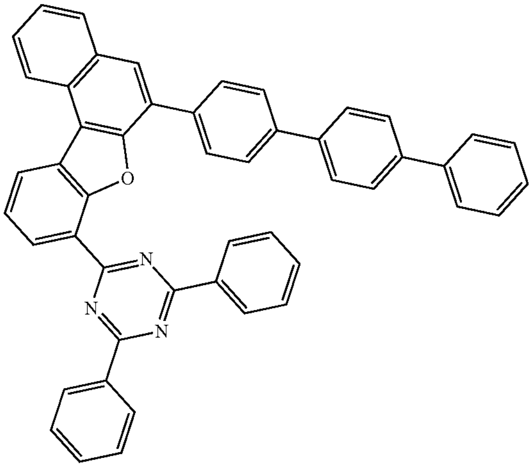
F82
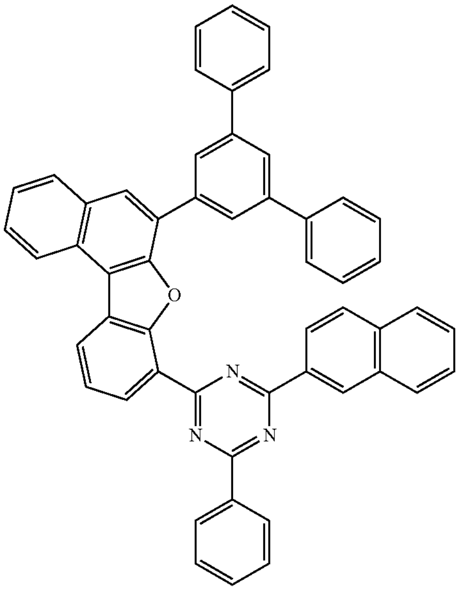
-continued
F83
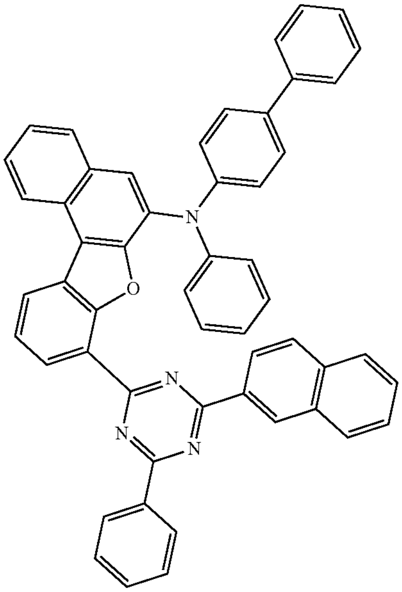
F84
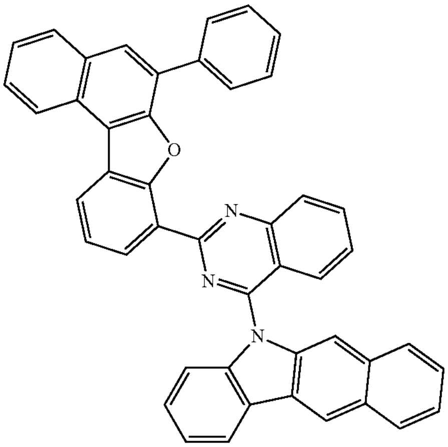
F85
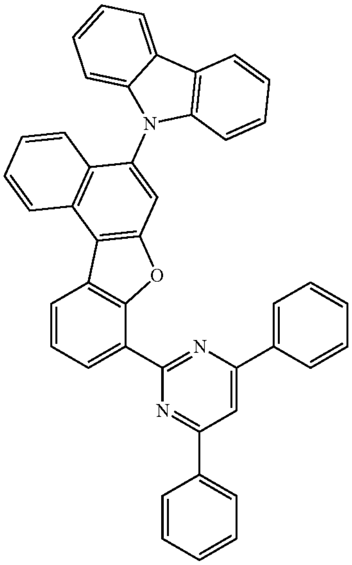

-continued
F86
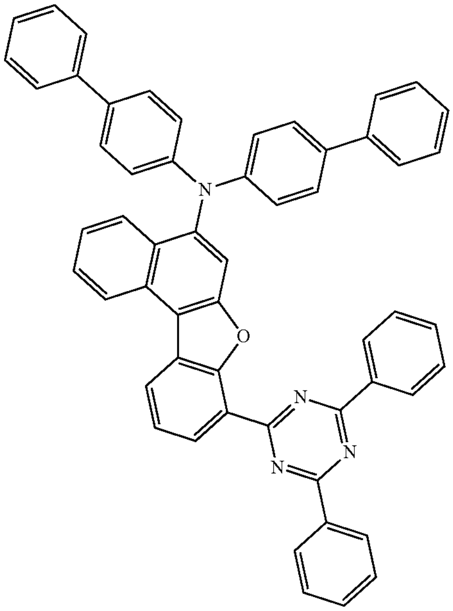
F88
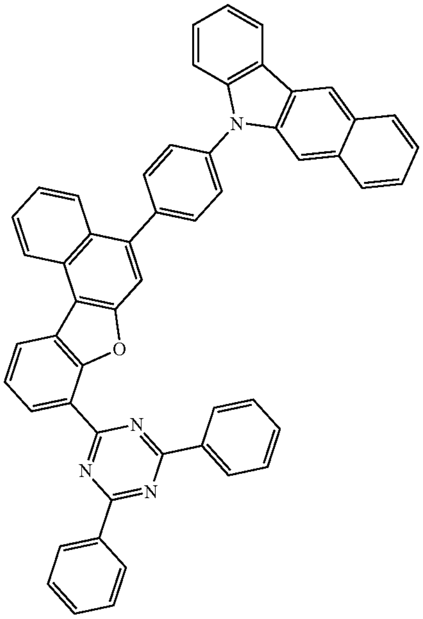
F87
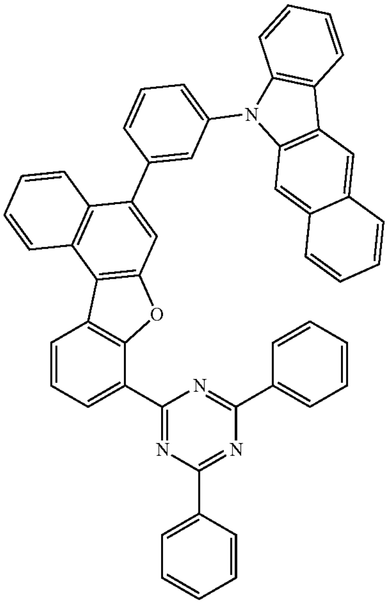
F89
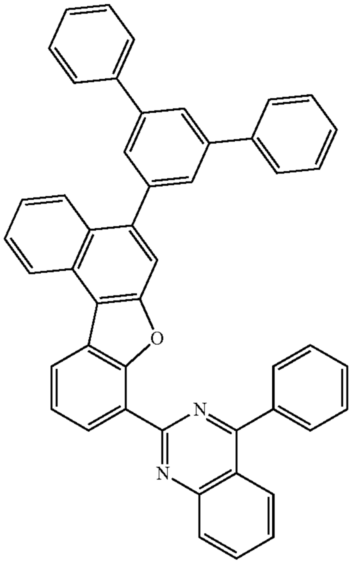
-continued -continued
F90
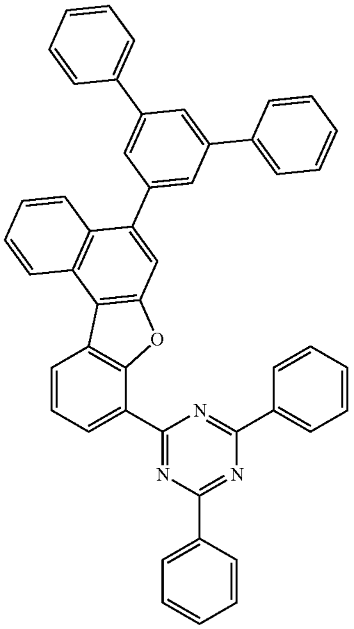
F91
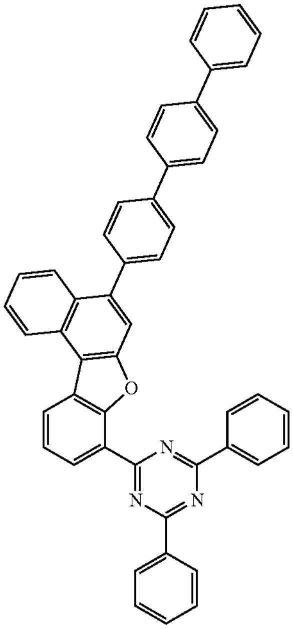
-continued
F92
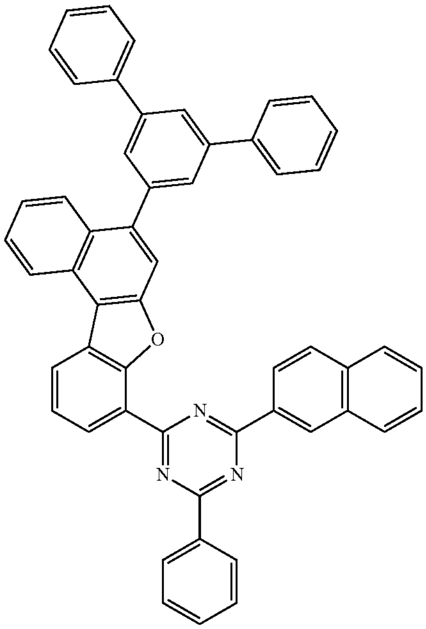
F93
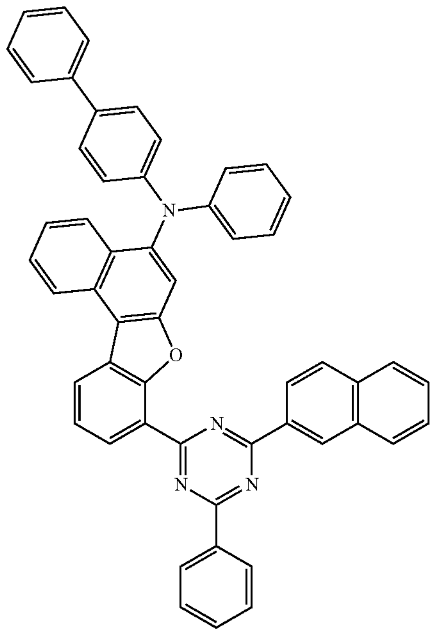

-continued
F94
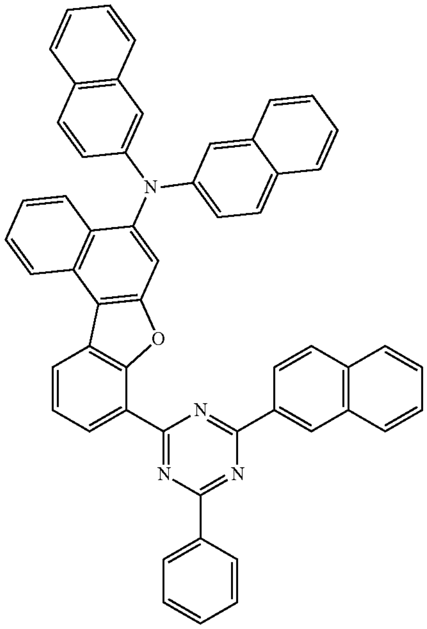
F95
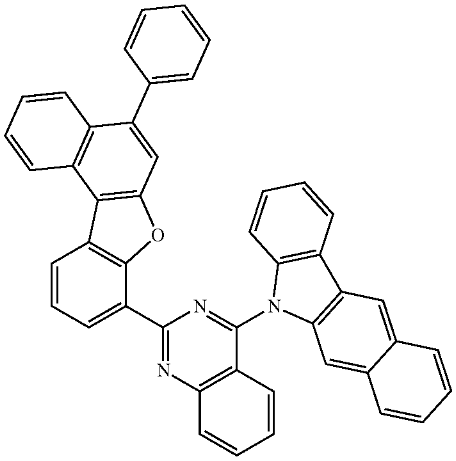
F96
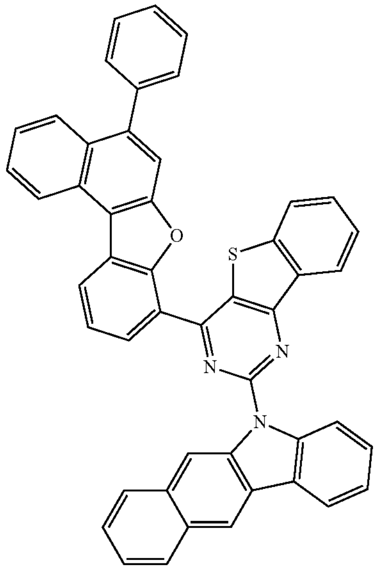
-continued
F97
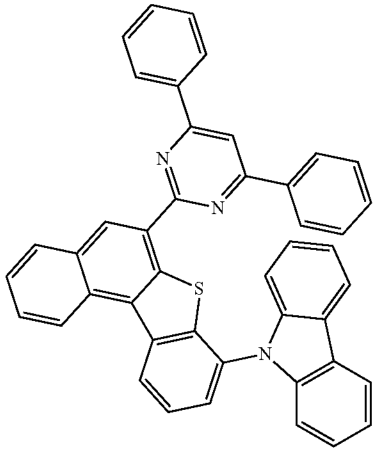
F98
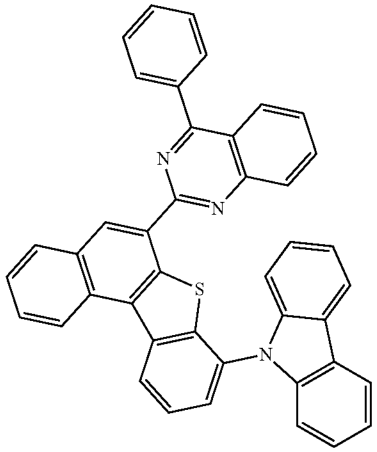
F99
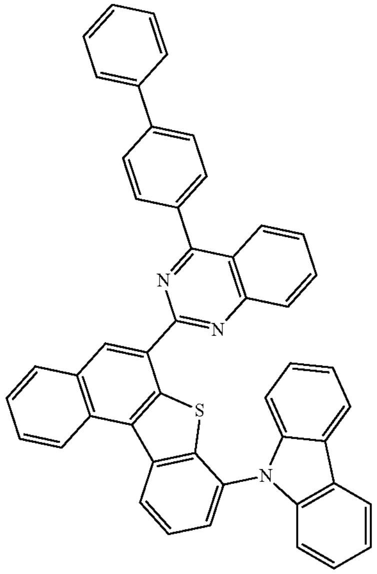

-continued
F100
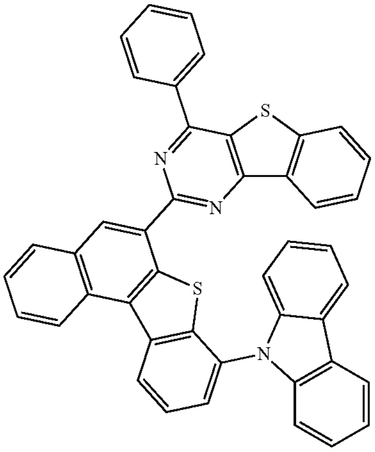
F101
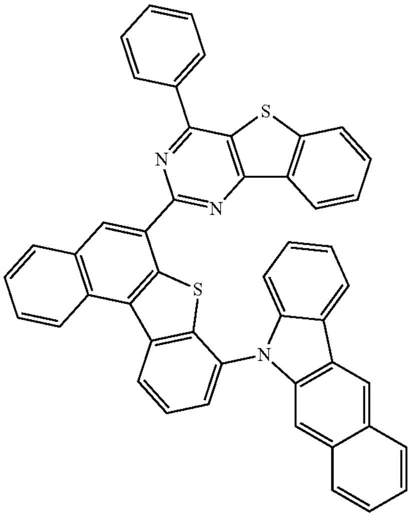
F102
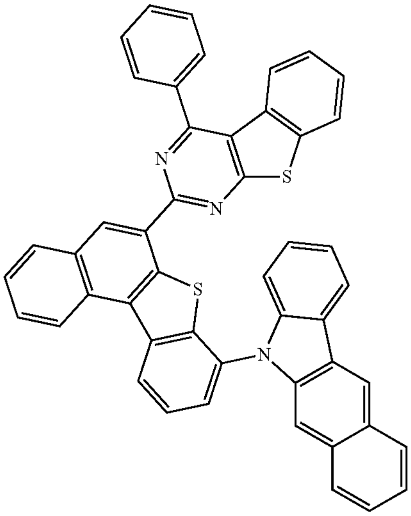
-continued
F103
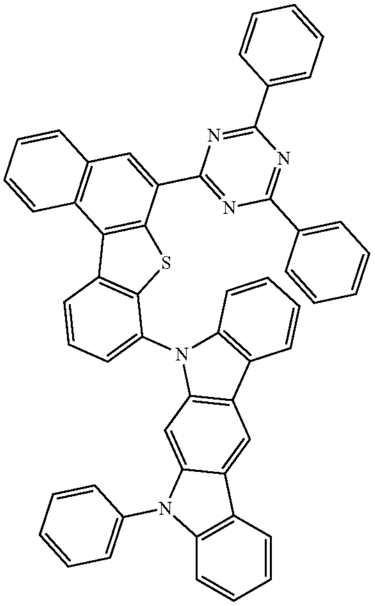
F104
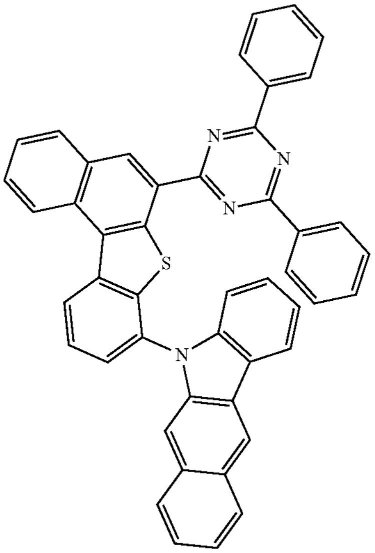

-continued
F105
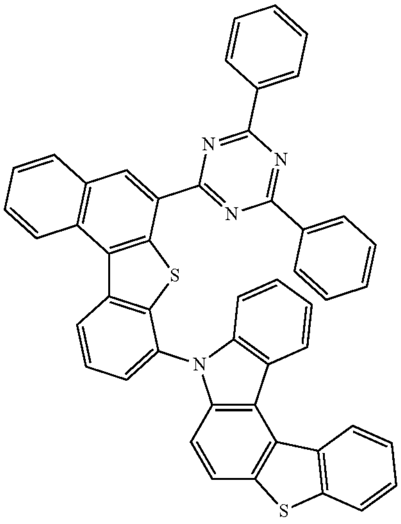
F106
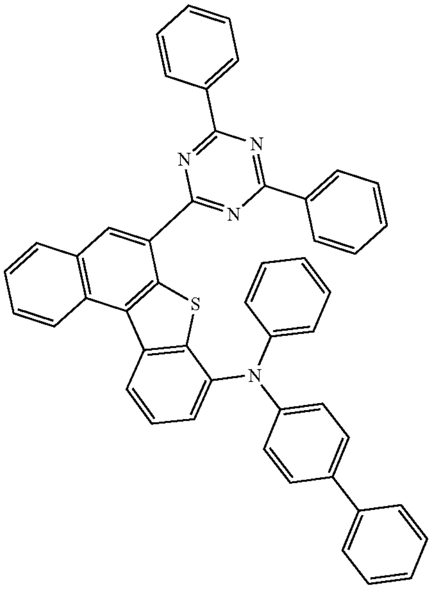
-continued
F107
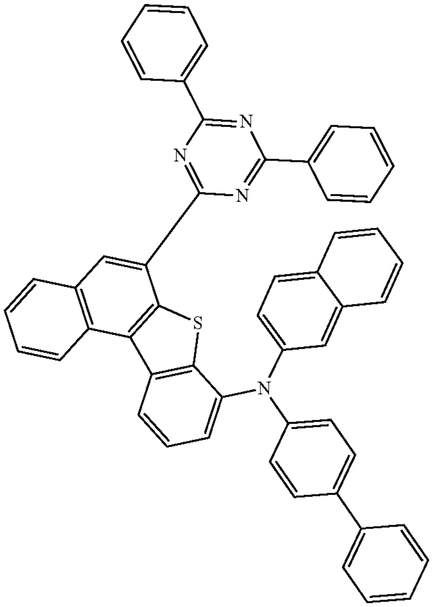
F108
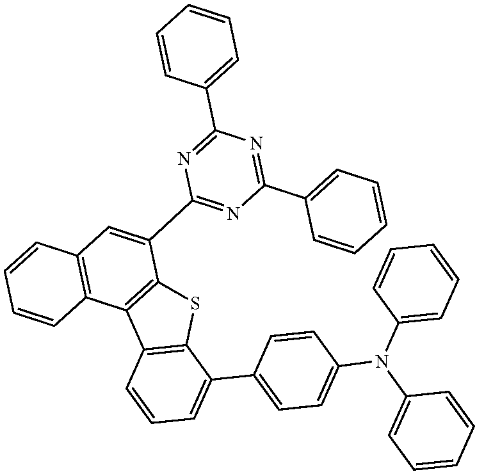
F109
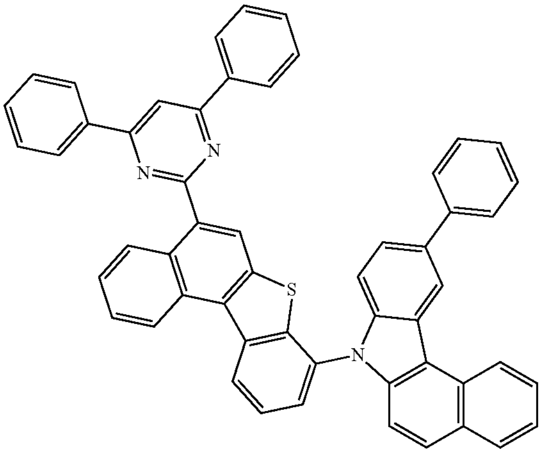

-continued
F110
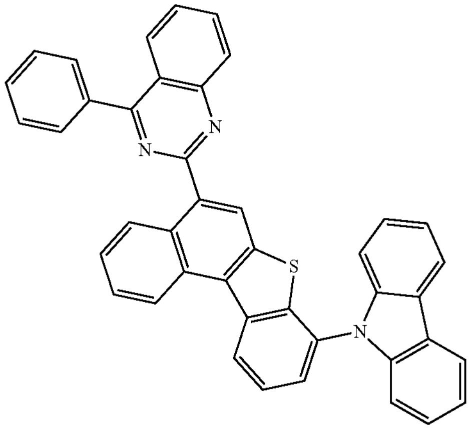
F111
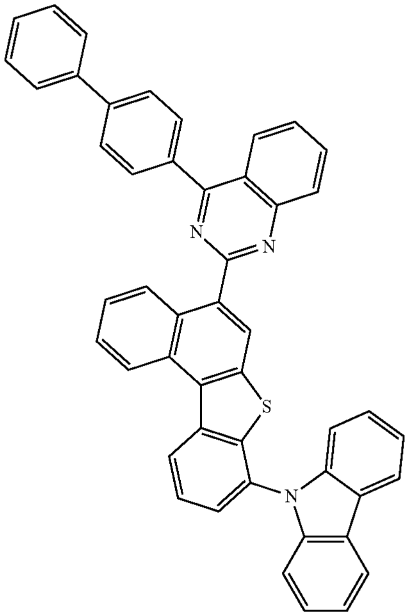
F112
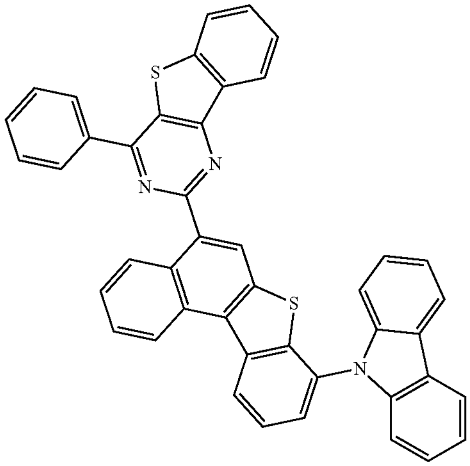
-continued
F113
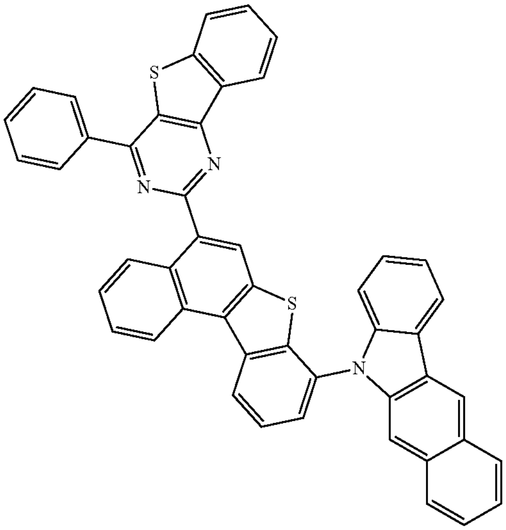
F114
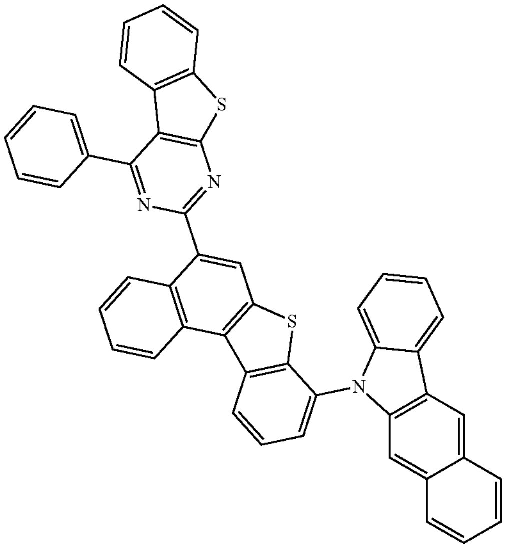

-continued
F115
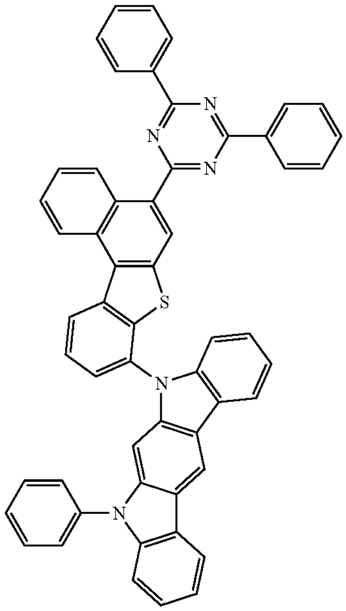
F116
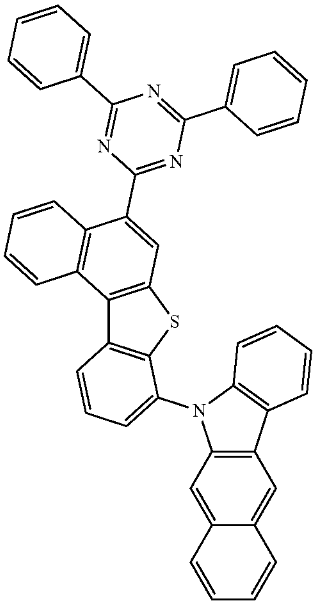
-continued
F117
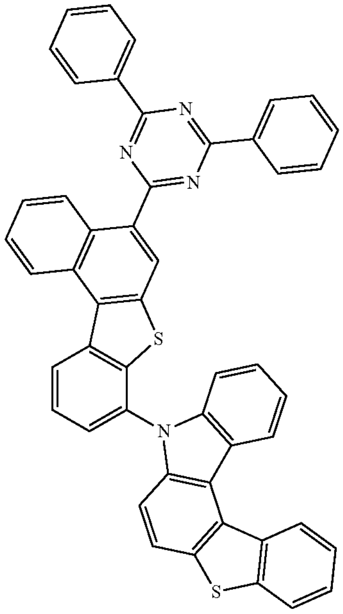
F118
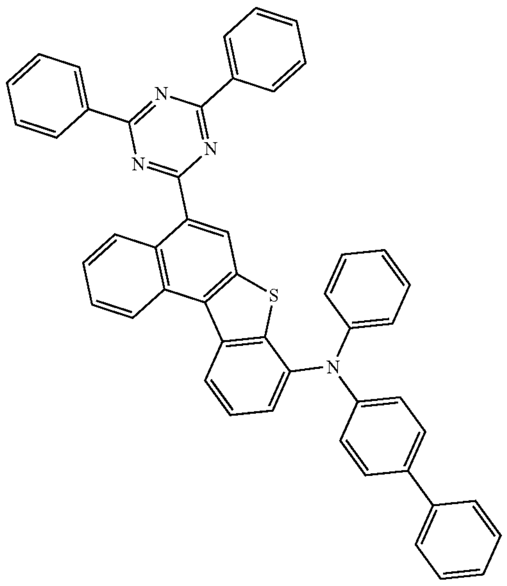

-continued
F119
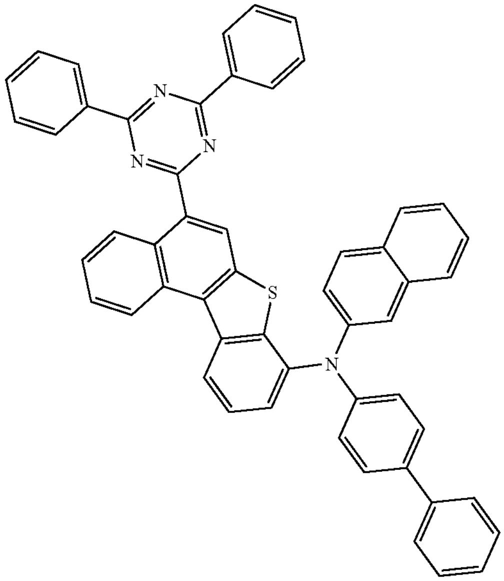
F120
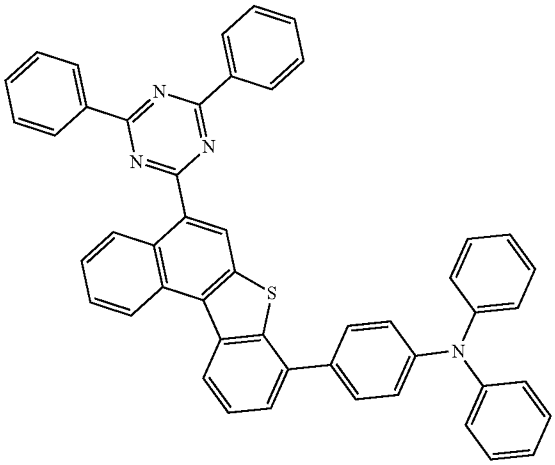
F121
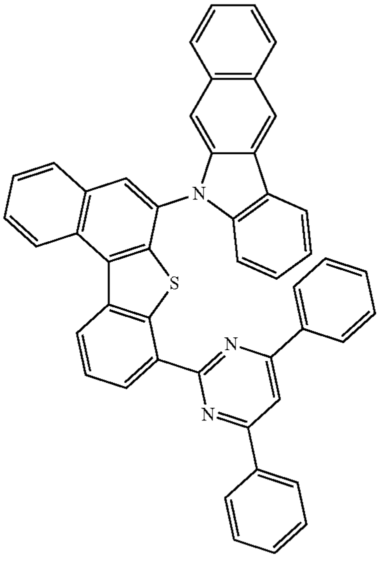
-continued
F122
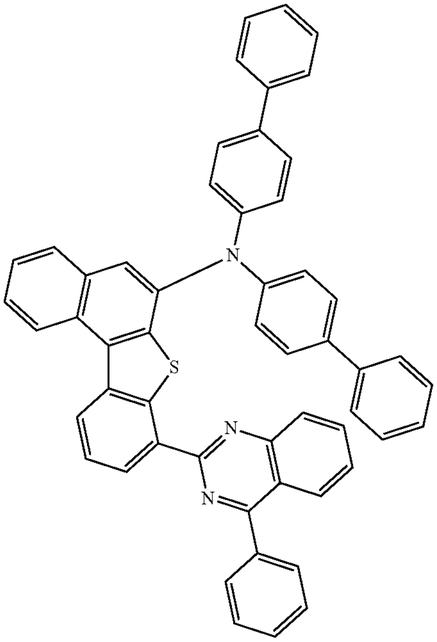
F123
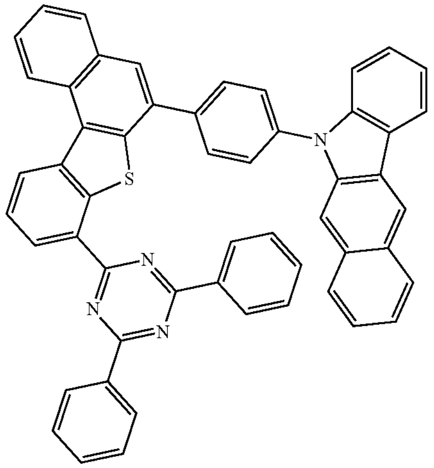
F124
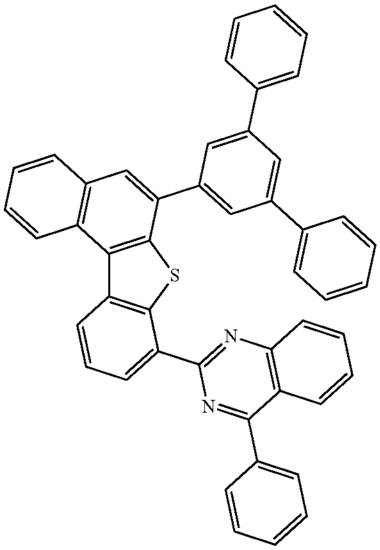

-continued
F125
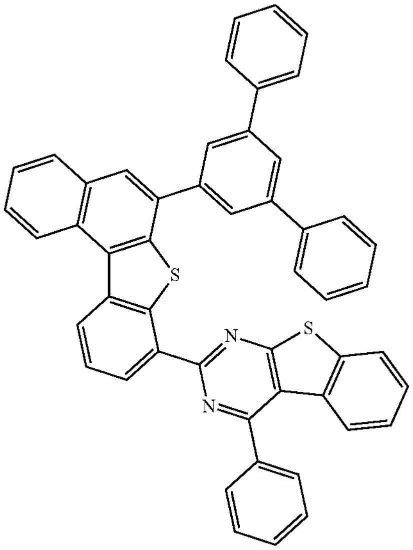
F126
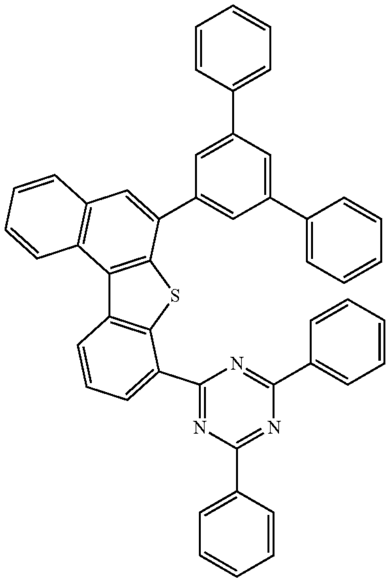
F127
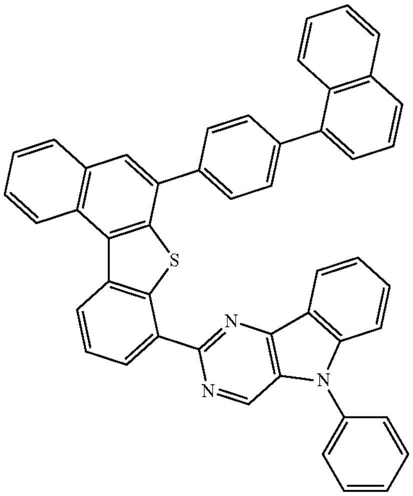
-continued
F128
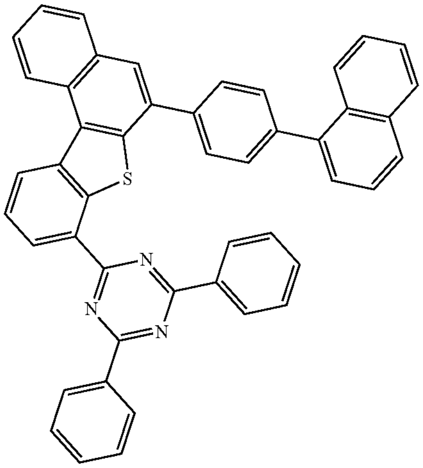
F129
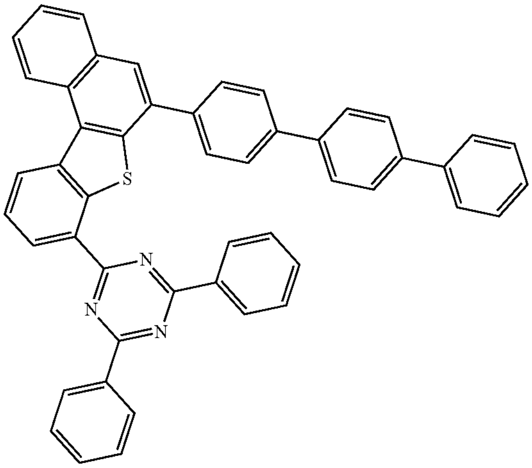
F130
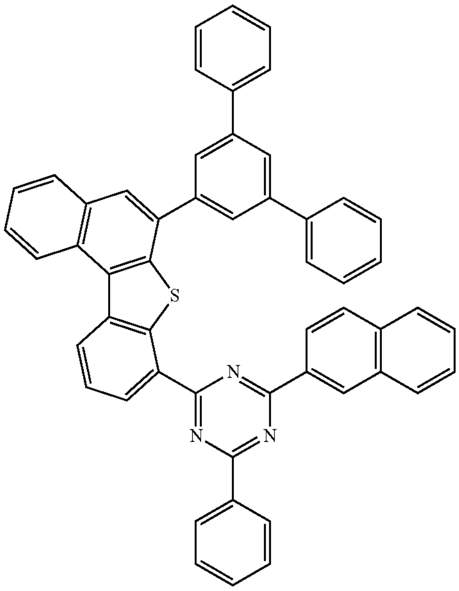

-continued
F131
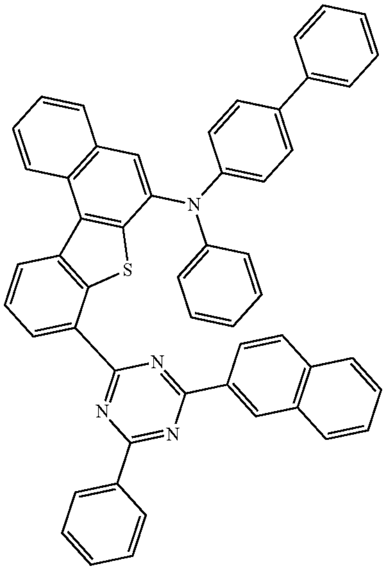
F132
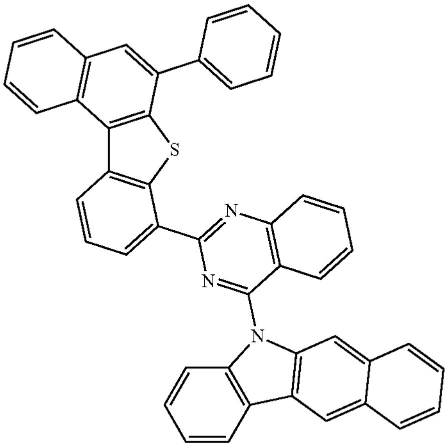
F133
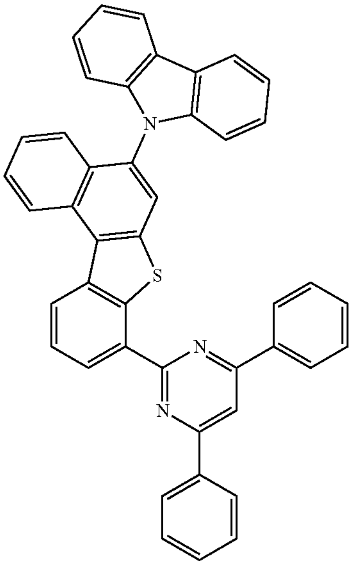
-continued
F134
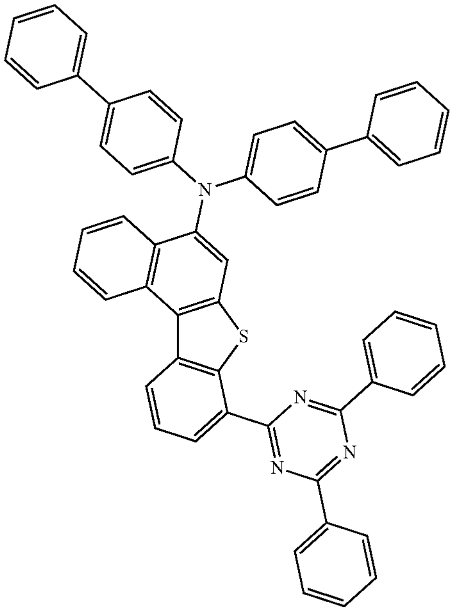
F135
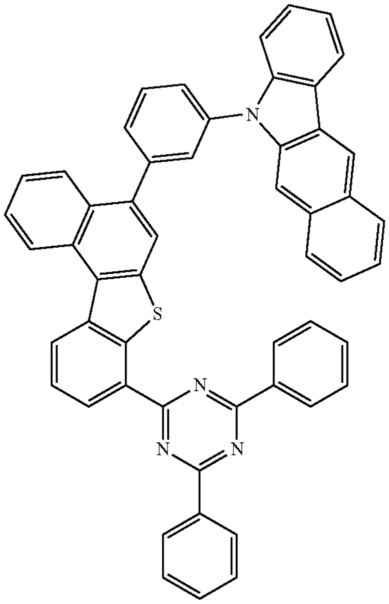

-continued
F136
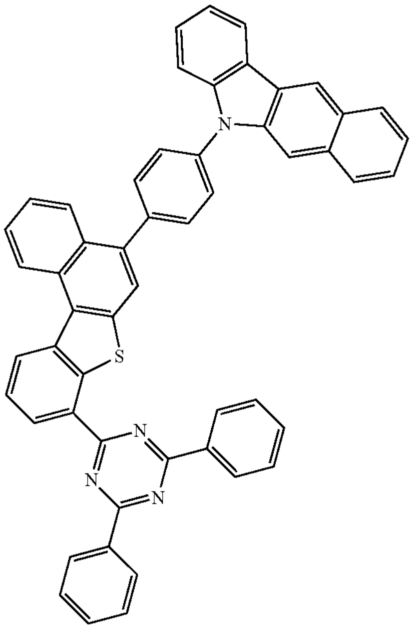
F137
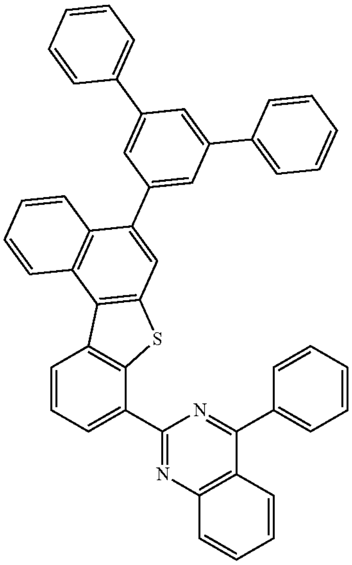
-continued
F138
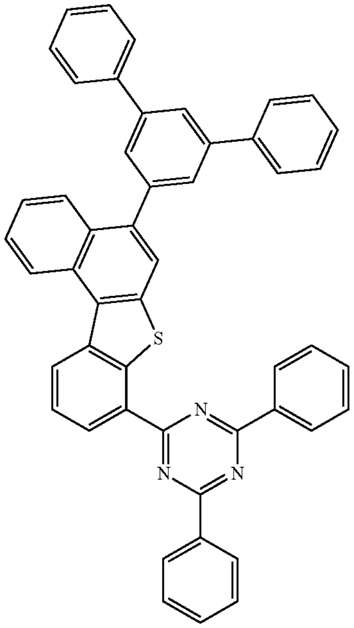
F139
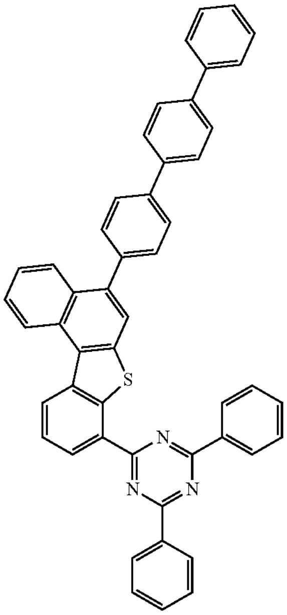

-continued
F140
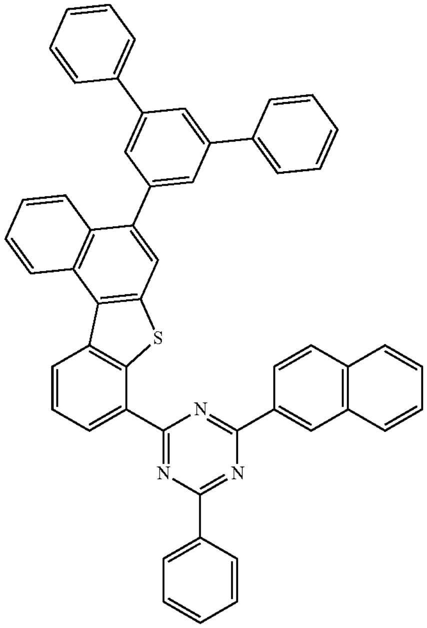
F141
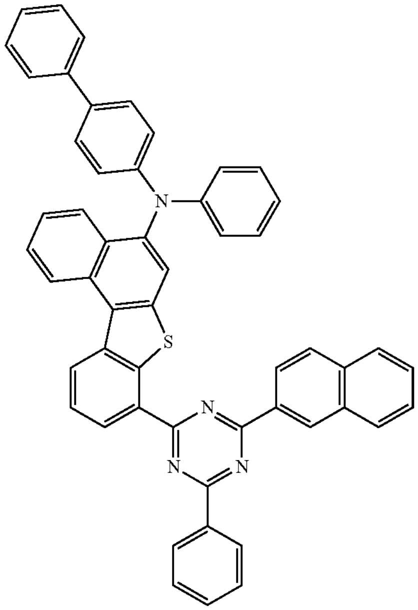
-continued
F142
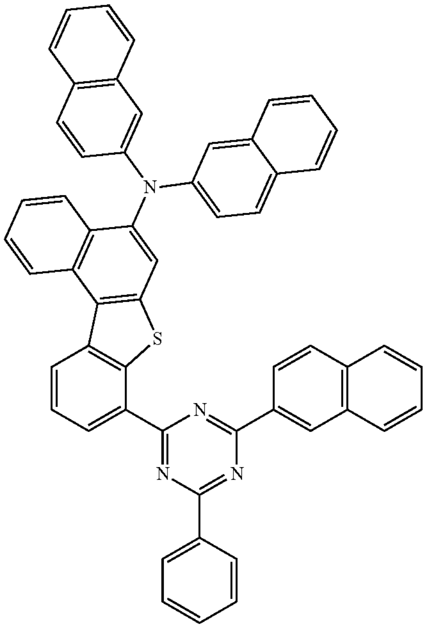
F143
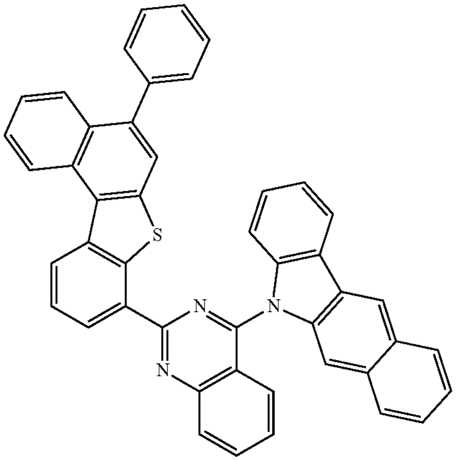

-continued
F144
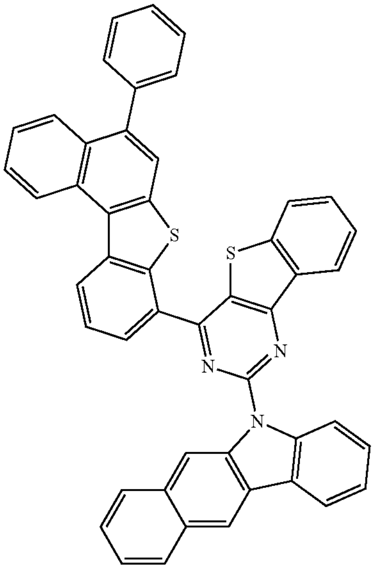
F145
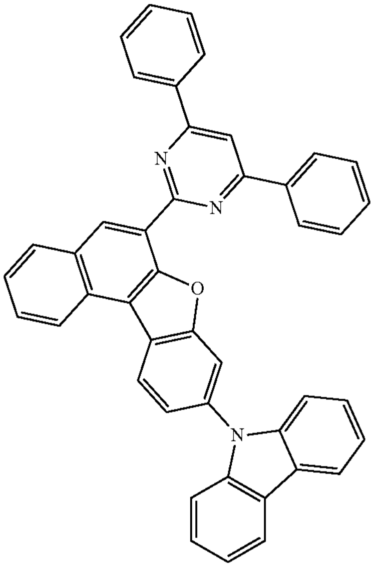
-continued
F146
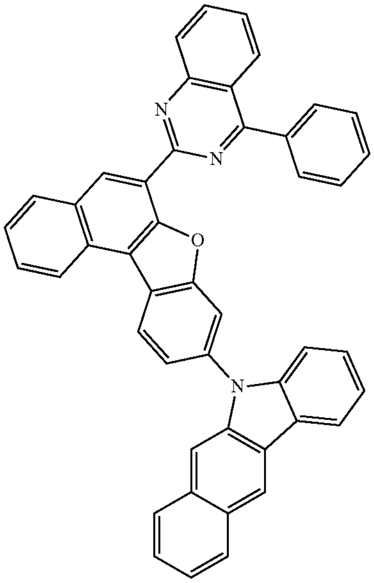
F147
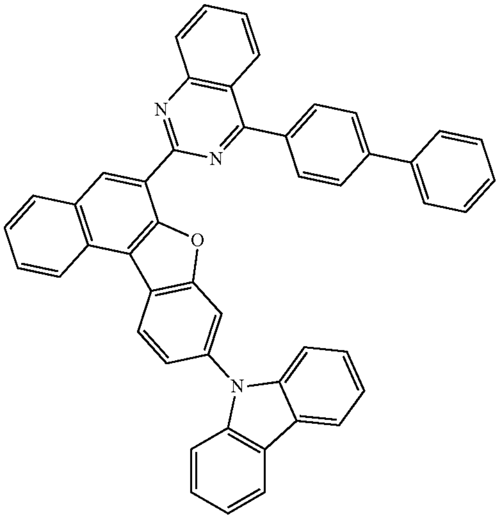

-continued
F148
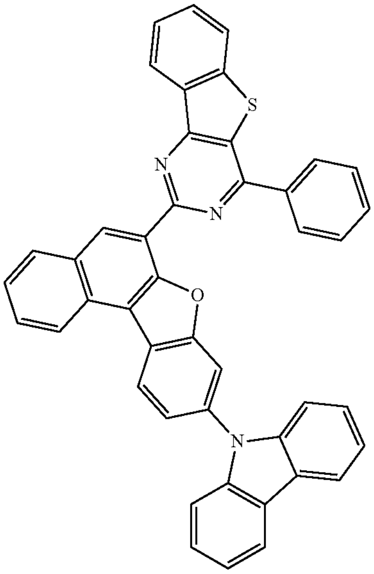
F149
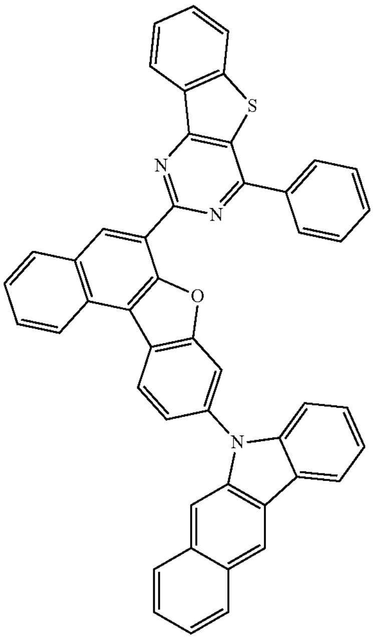
-continued
F150
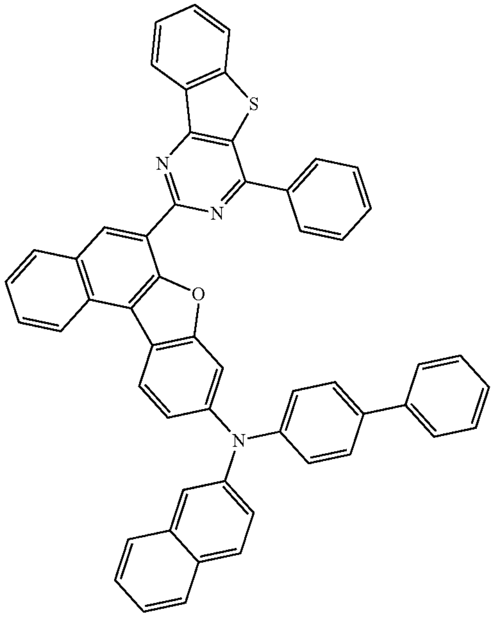
F151
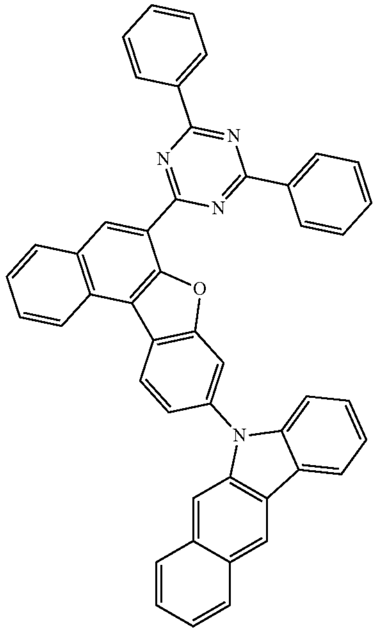

-continued
F152
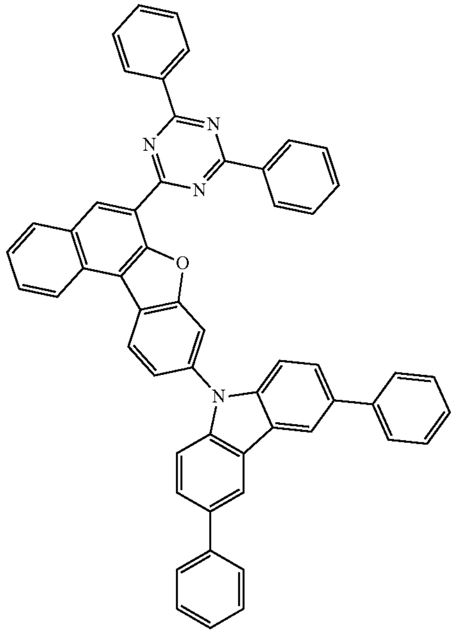
-continued
F154
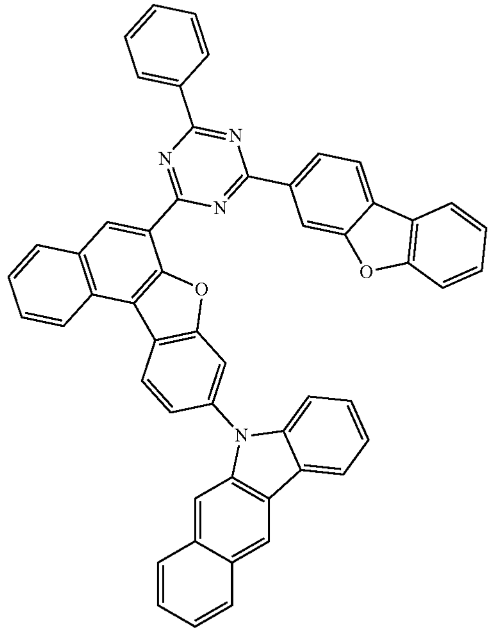
F153
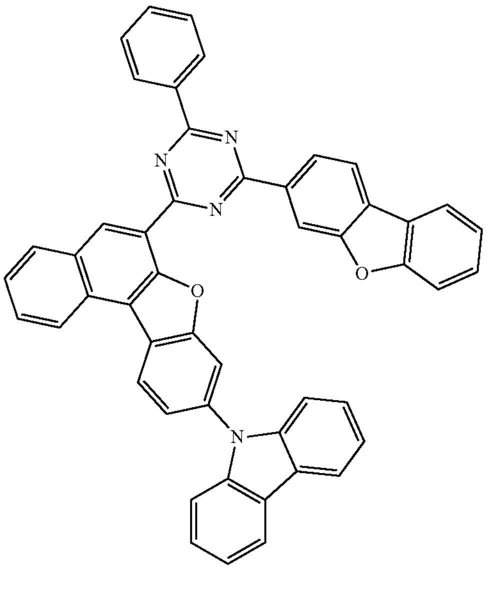
F155
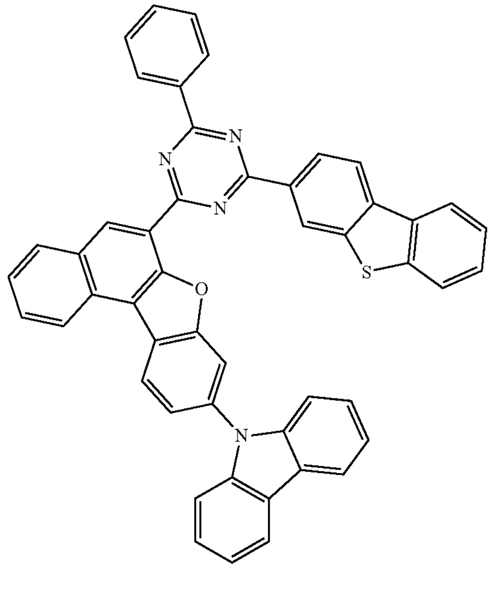

-continued
F156
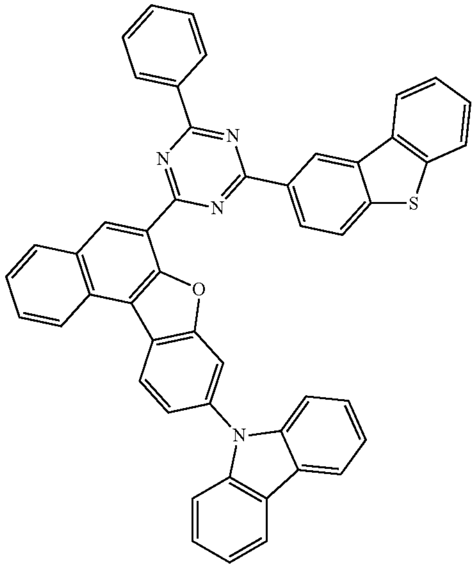
F157
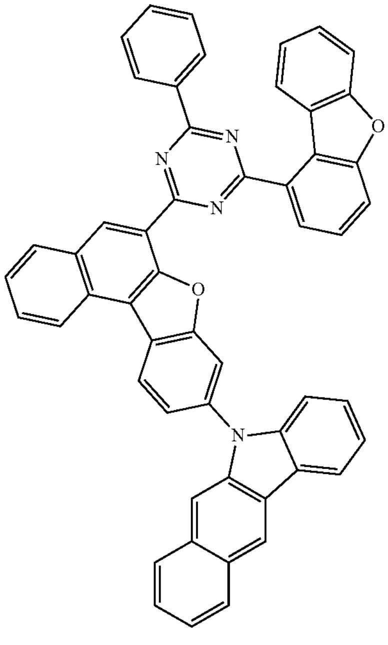
-continued
F158
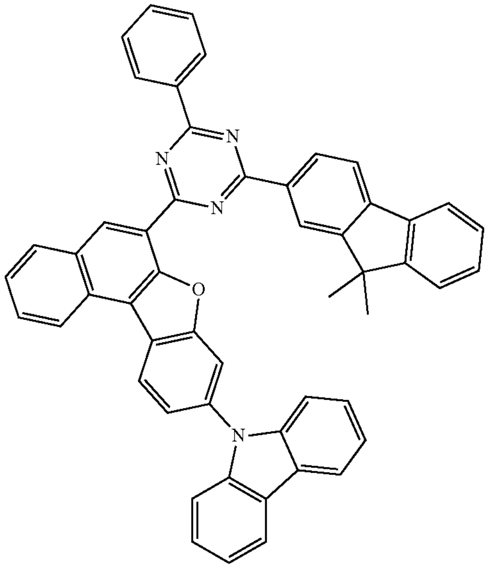
F159
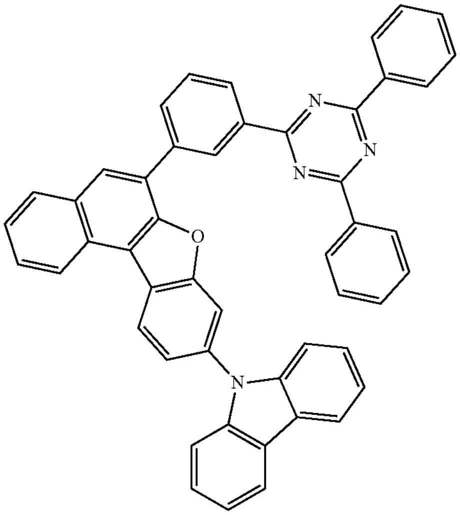

-continued
F160
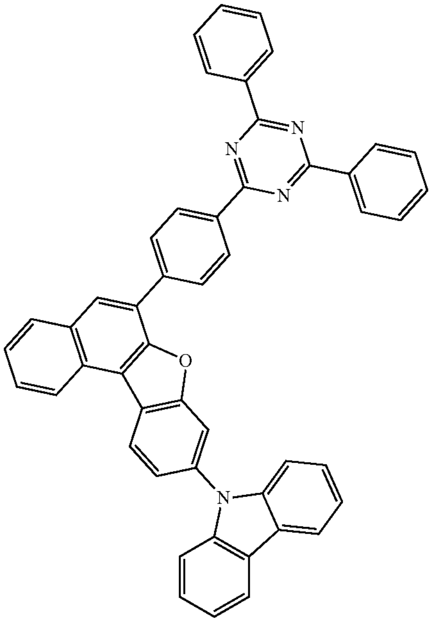
F161
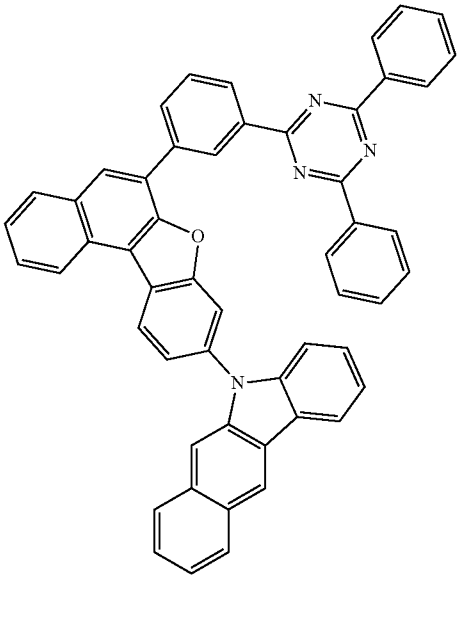
-continued
F162
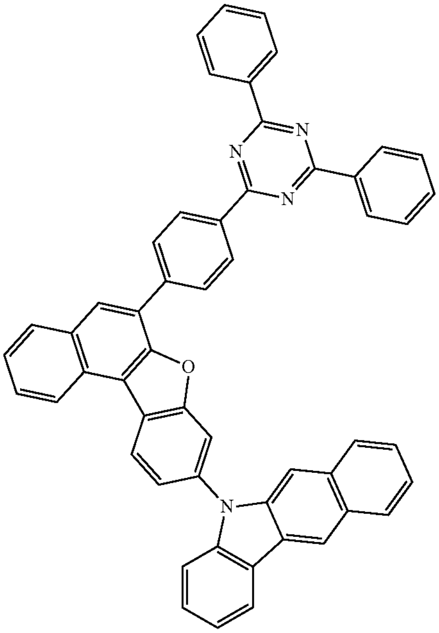
F163
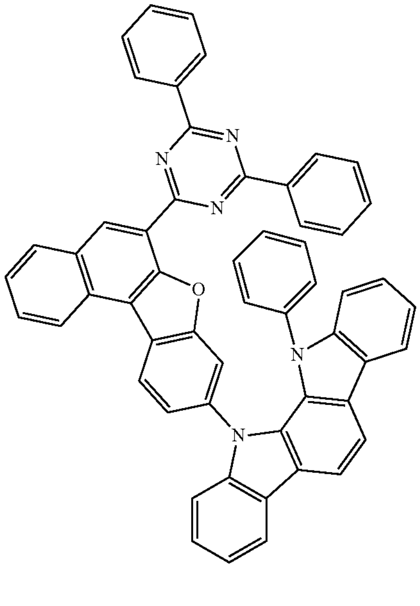

-continued
F164
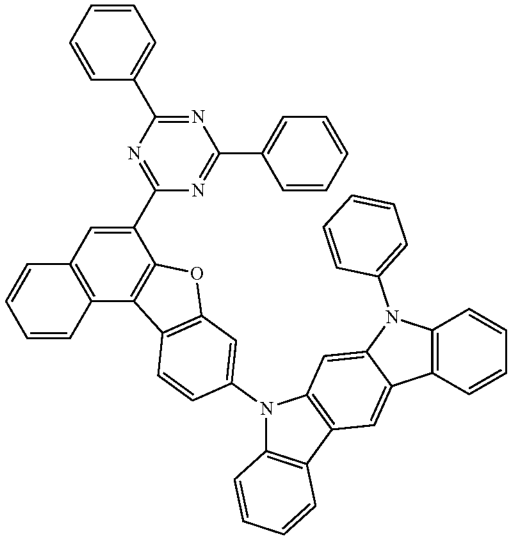
F165
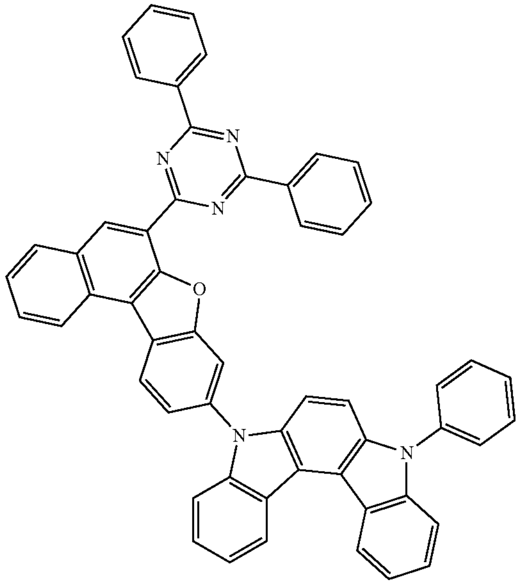
-continued
F166
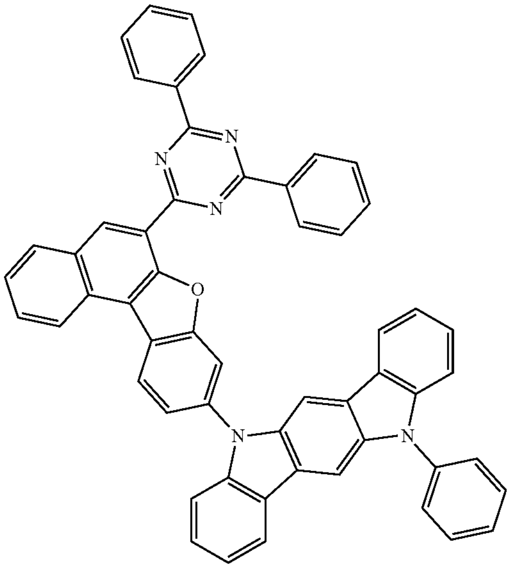
F167
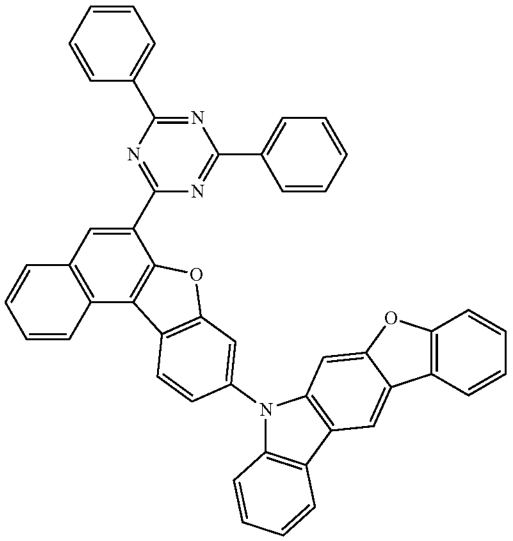

-continued
F168
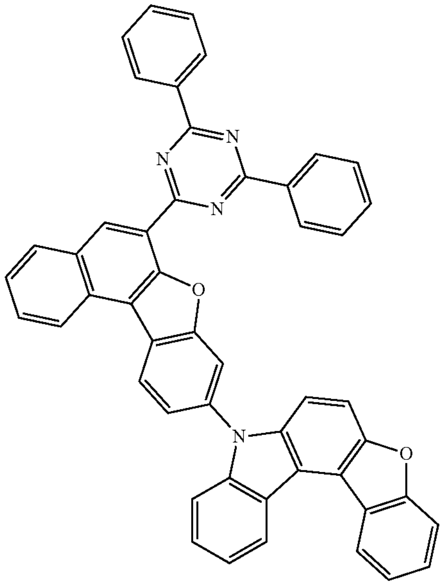
F169
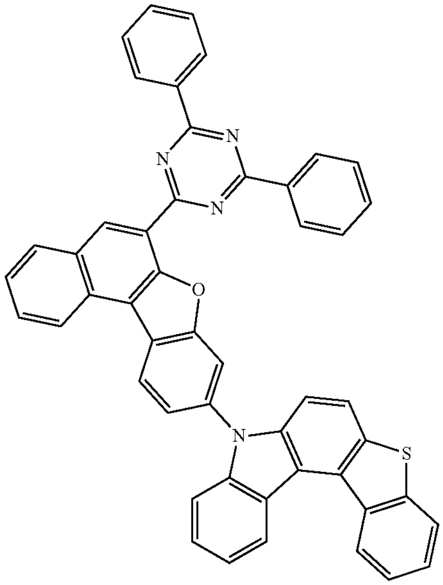
-continued
F170
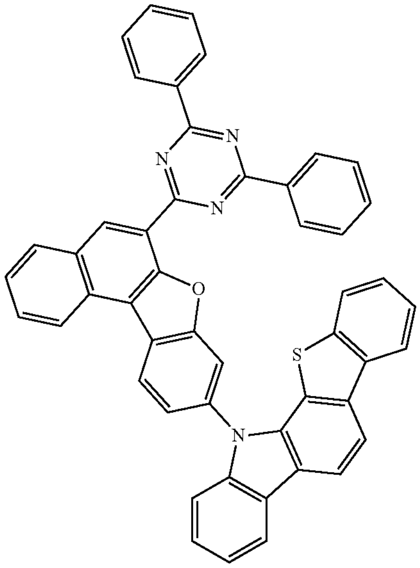
F171
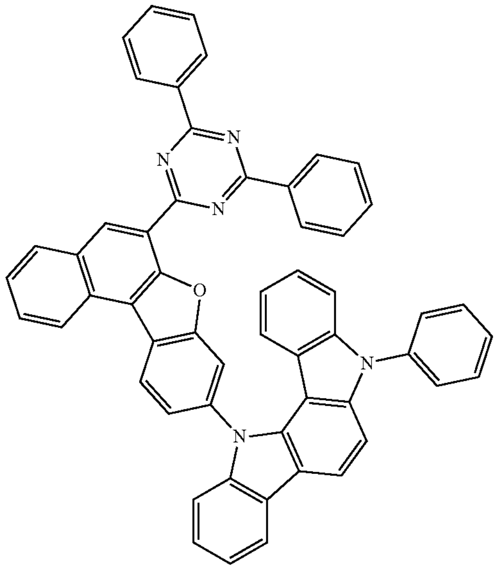

-continued
F172
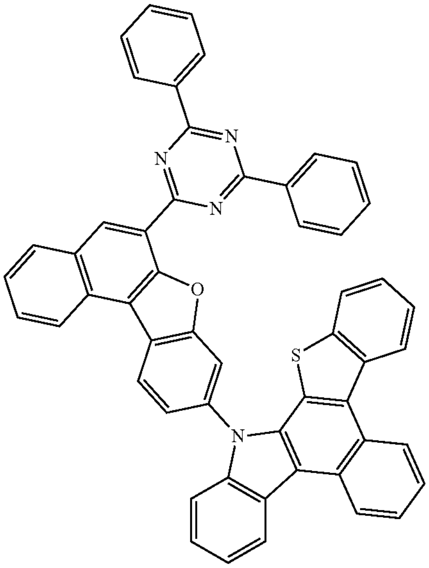
F173
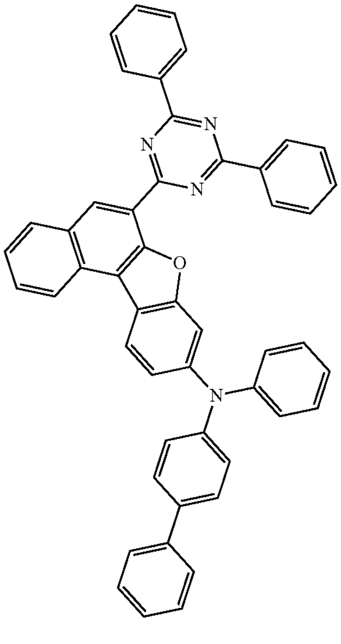
-continued
F174
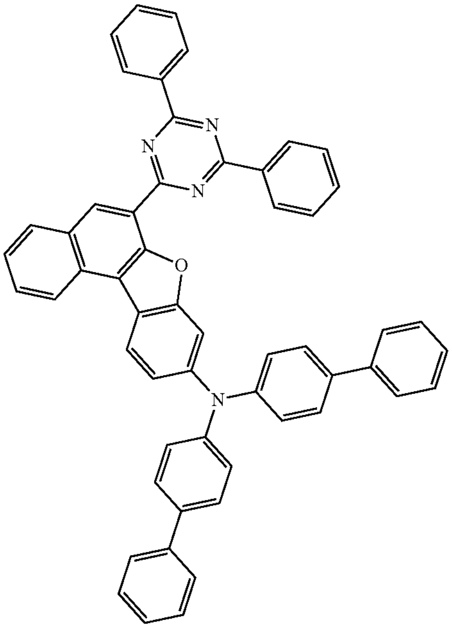
F175
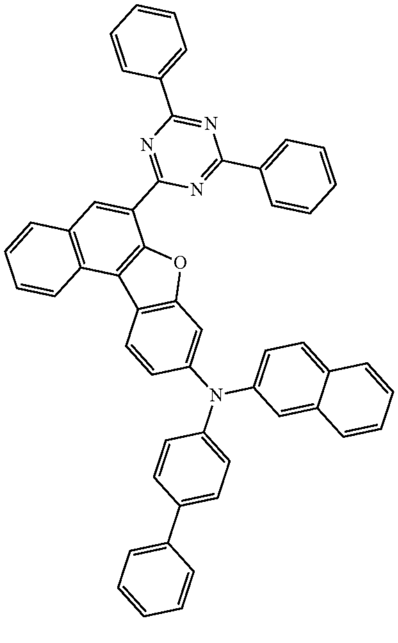

-continued
F176
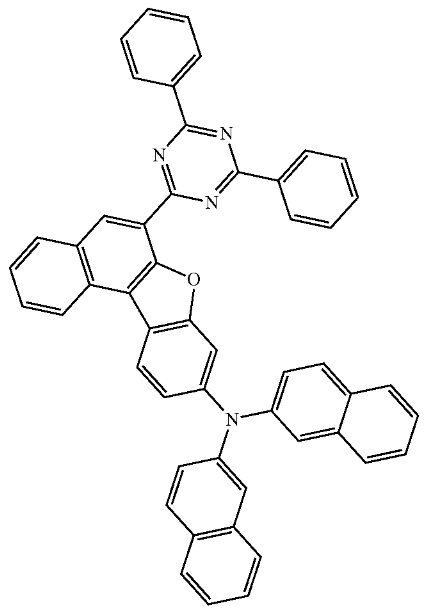
F177
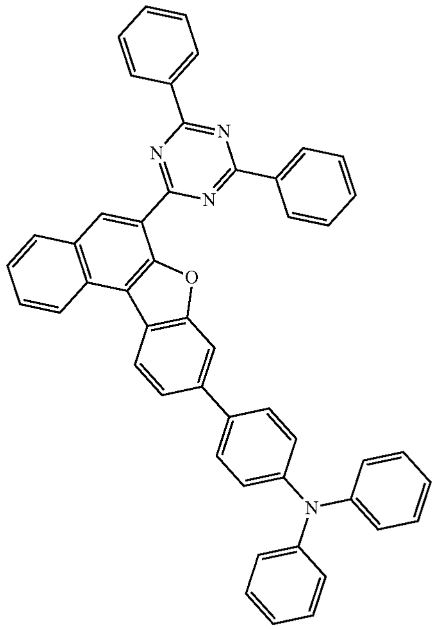
-continued
F178
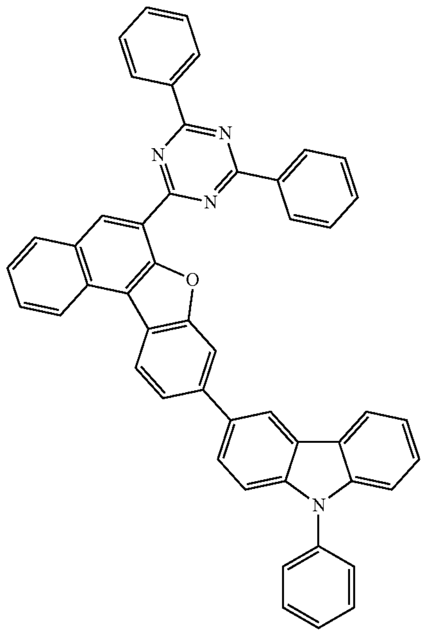
F179
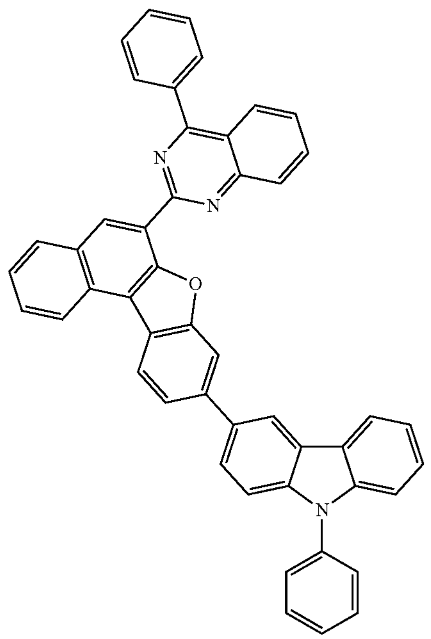

-continued
F180
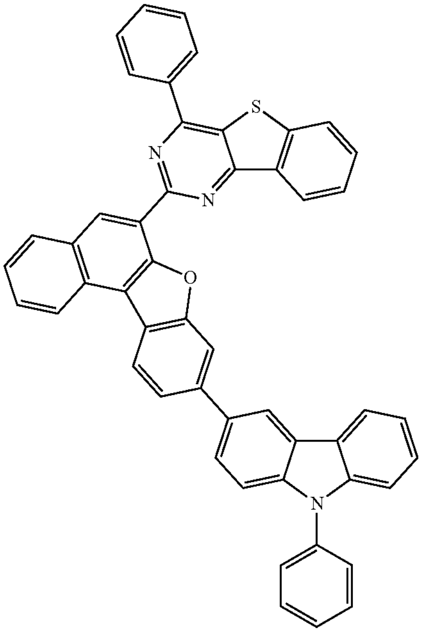
F181
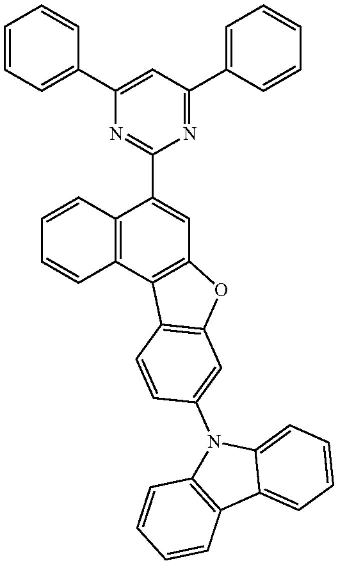
-continued
F182
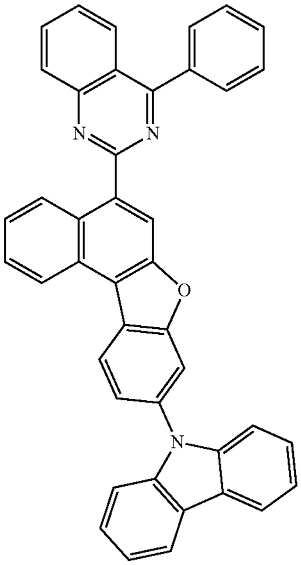
F183
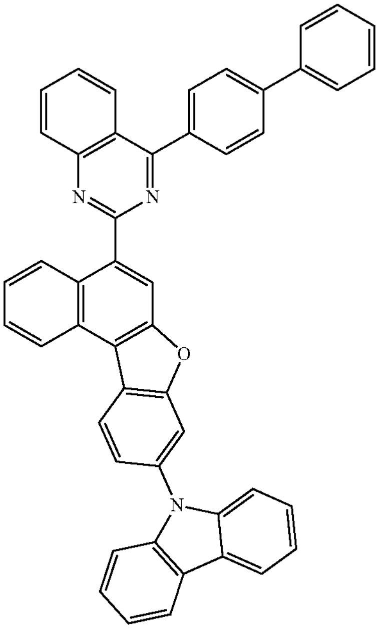

-continued
F184
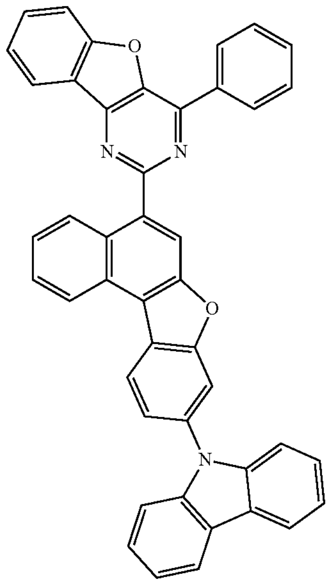
F185
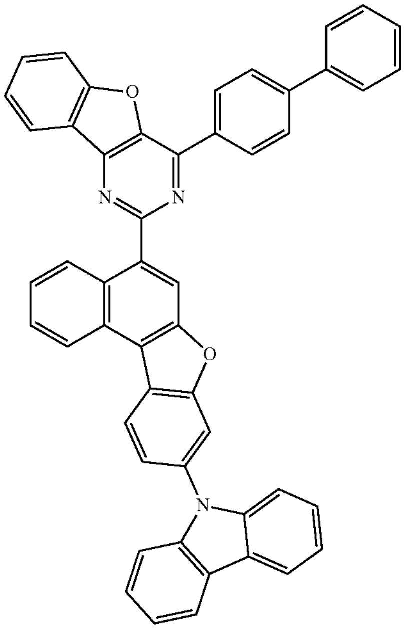
-continued
F186
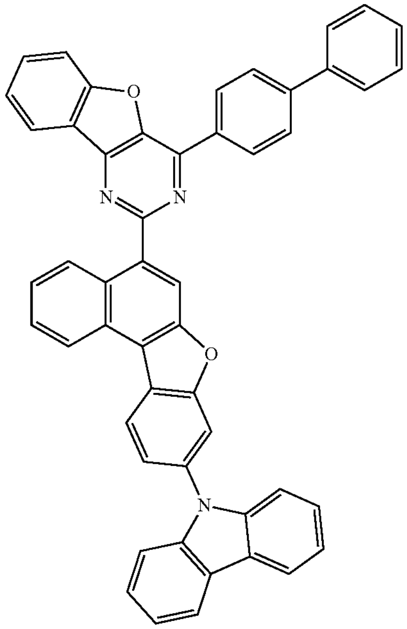
F187
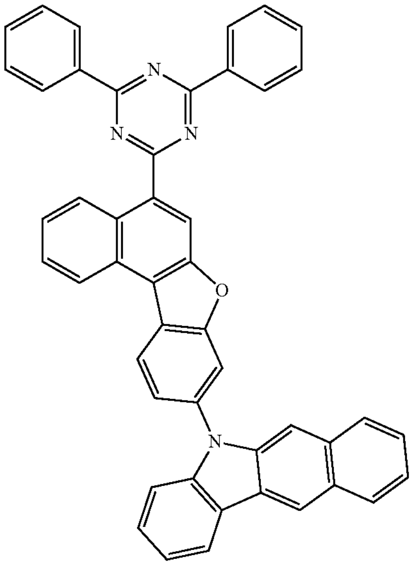

-continued
F188
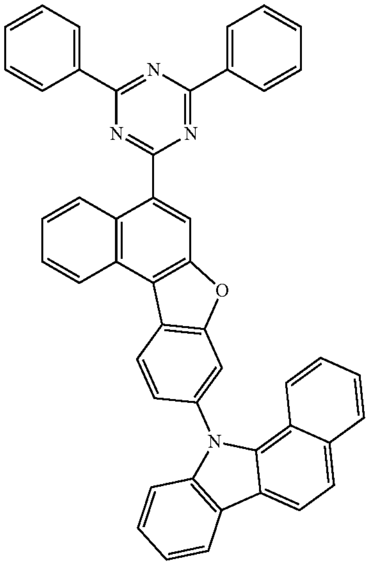
F189
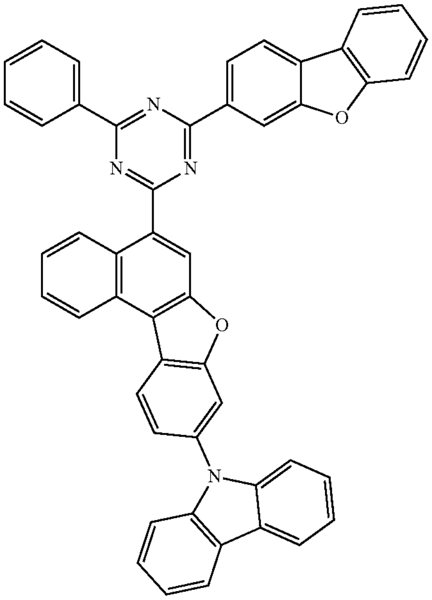
-continued
F190
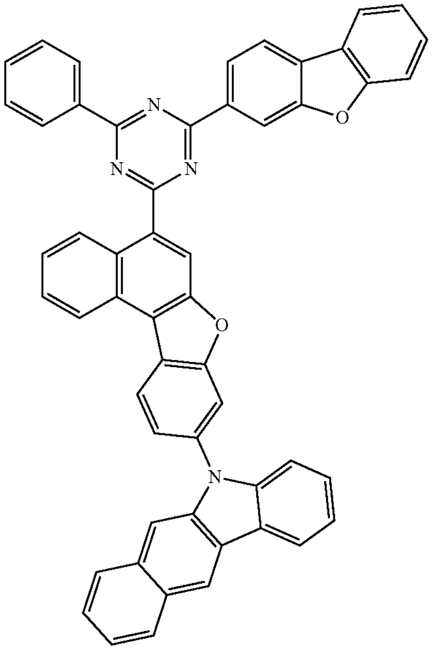
F191
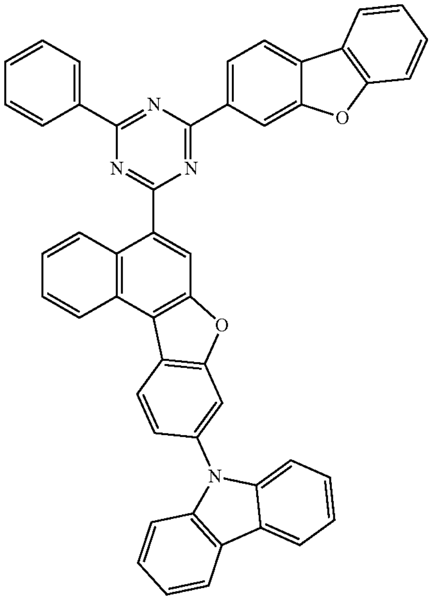

-continued
F192
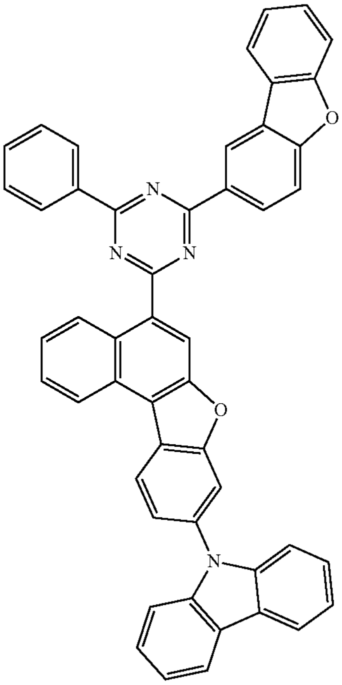
F193
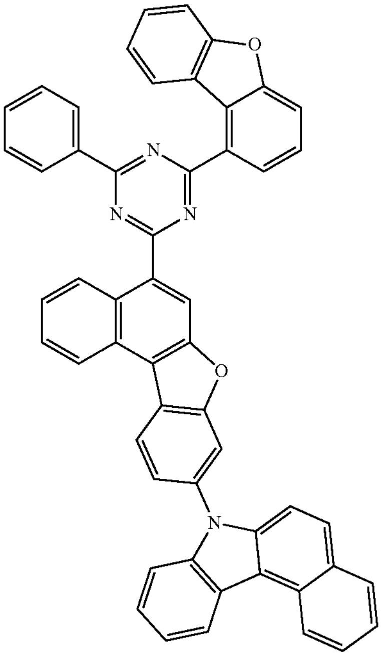
-continued
F194
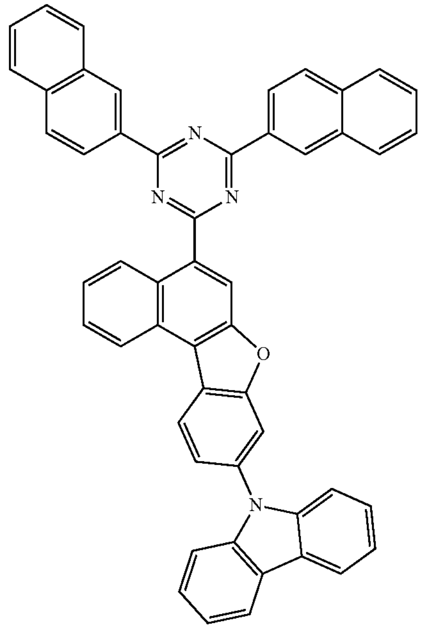
F195
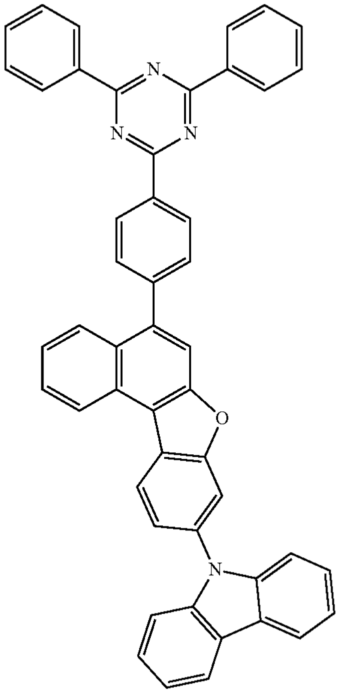

-continued
F196
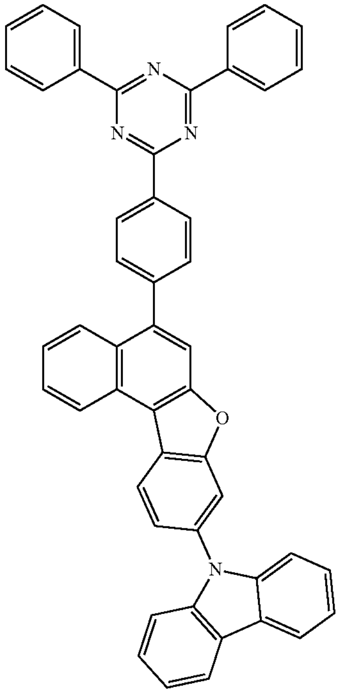
F197
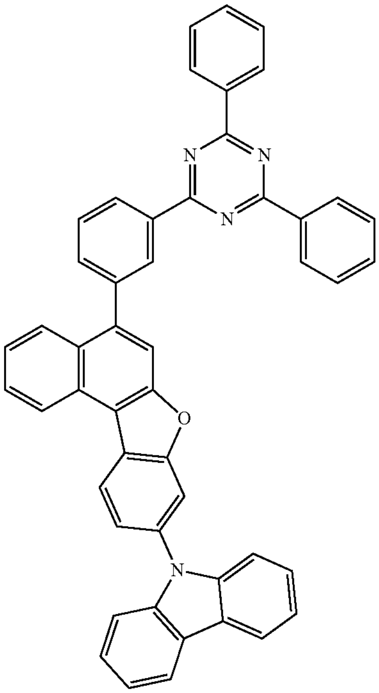
-continued
F198
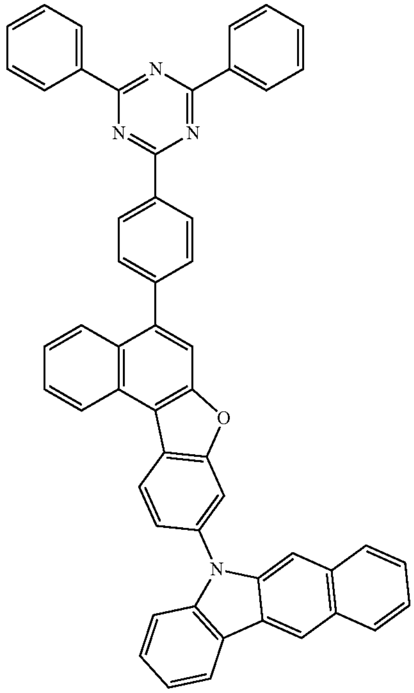
F199
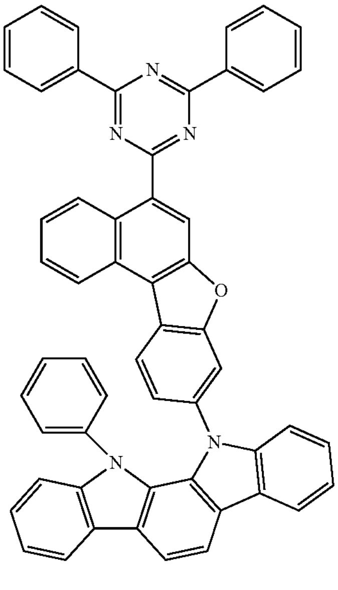

-continued
F200
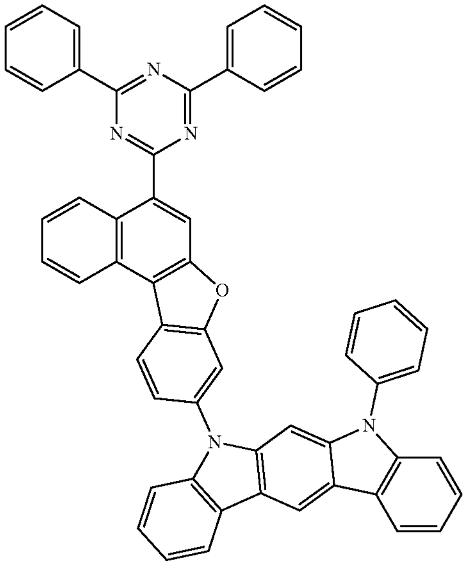
F201
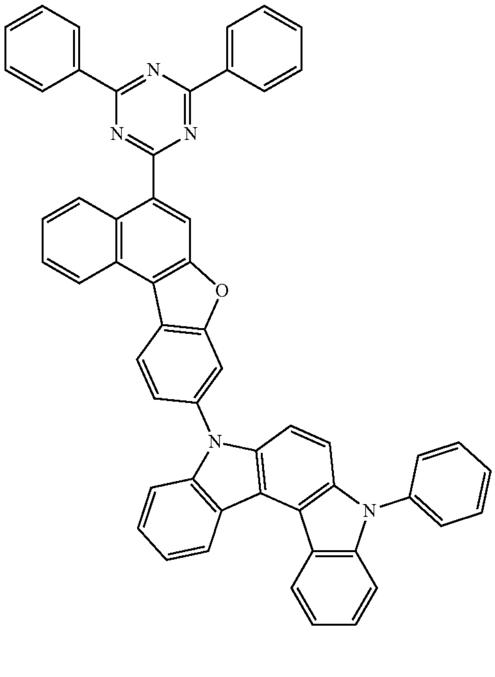
-continued
F202
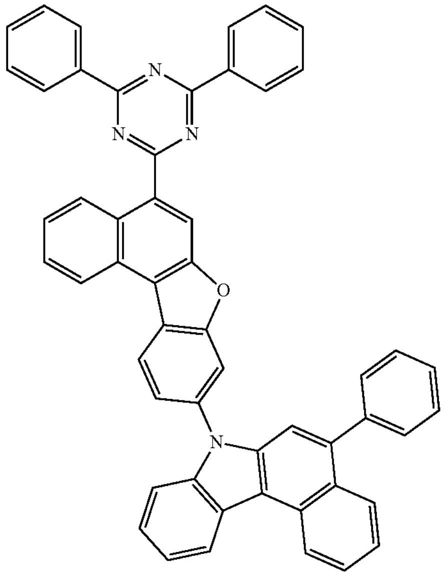
F203
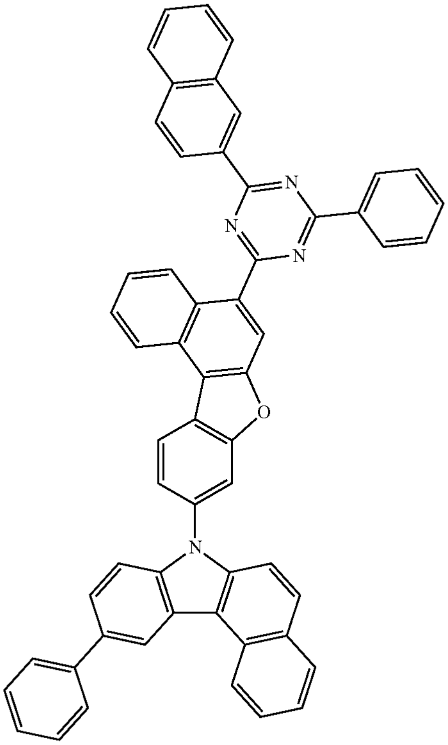

-continued
F204
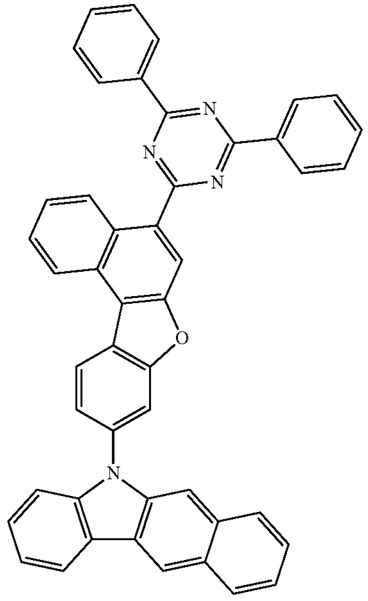
F205
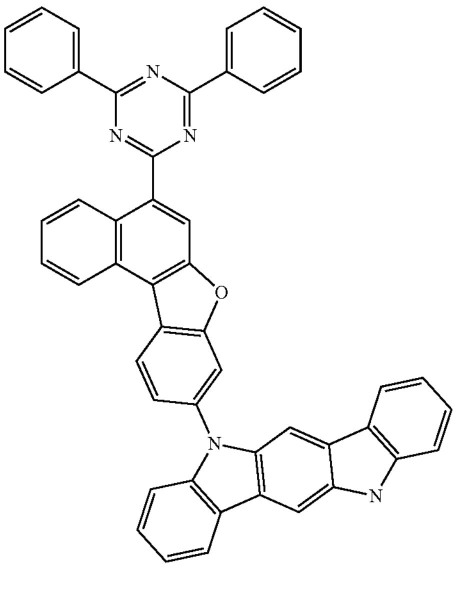
-continued
F206
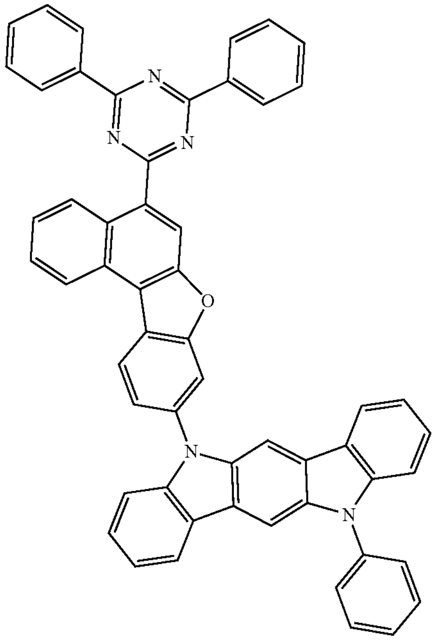
F207
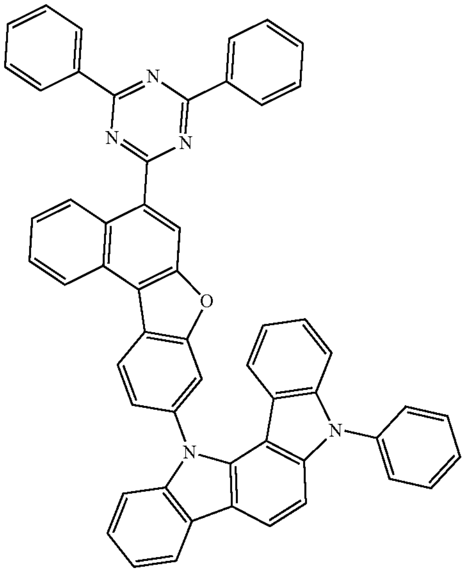

-continued
F208
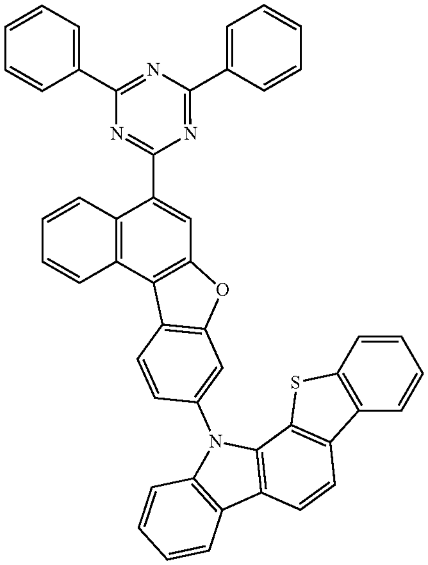
F209
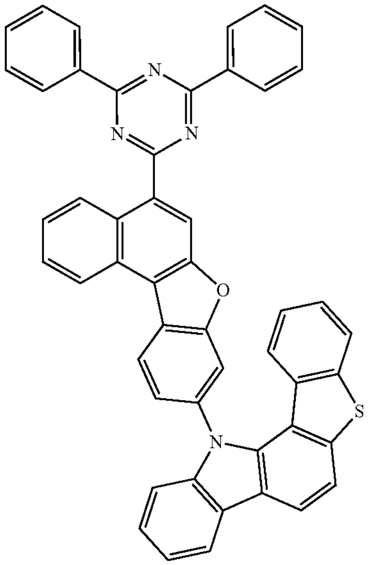
-continued
F210
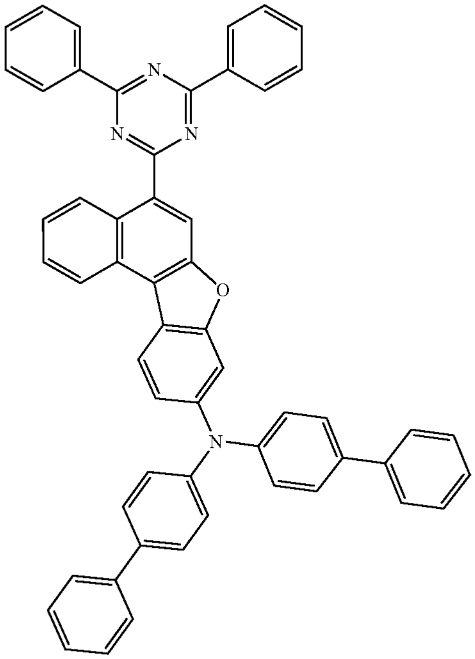
F211
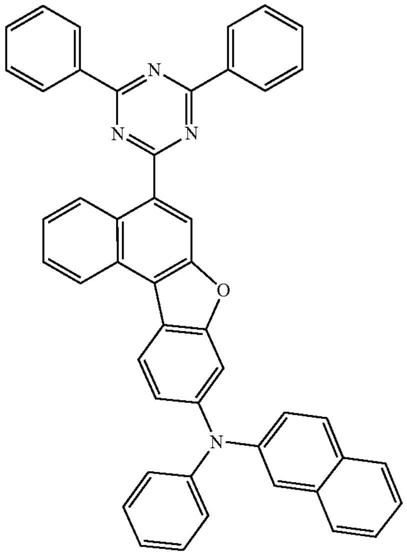

F212
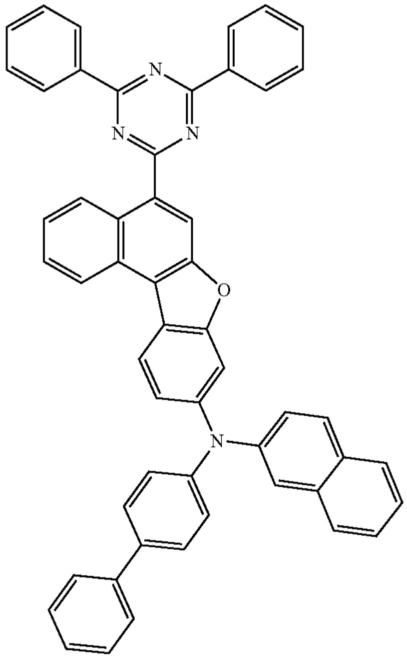
F213
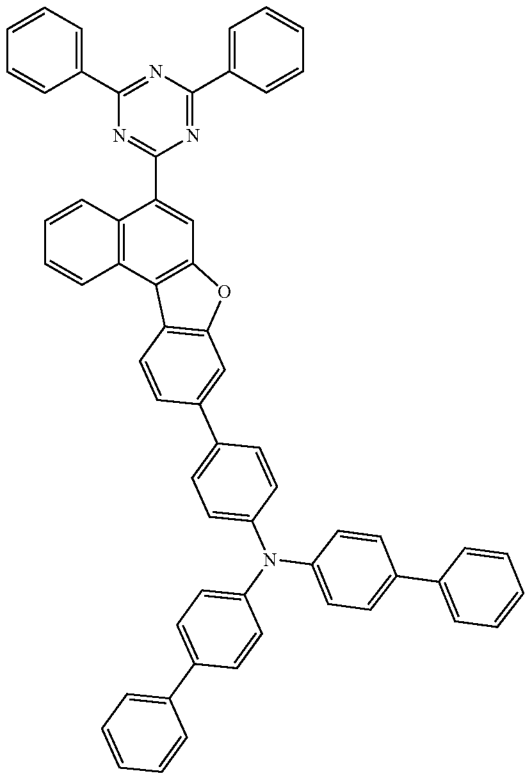
F214
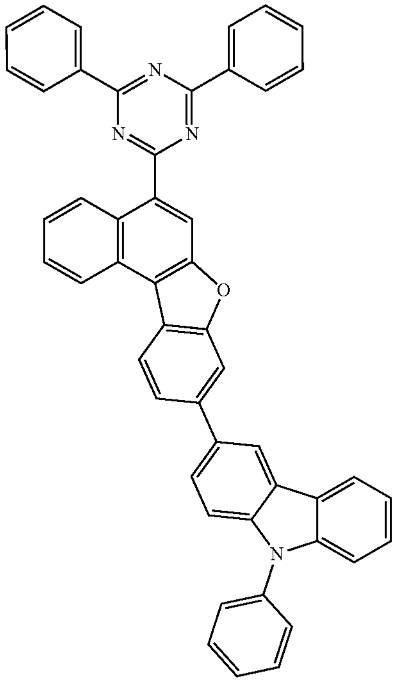
F215
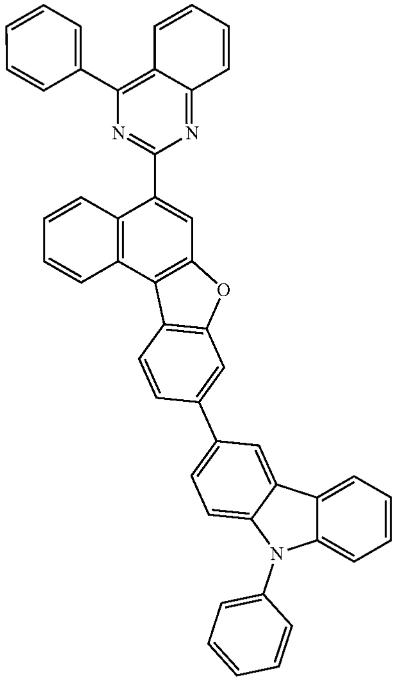

-continued
F216
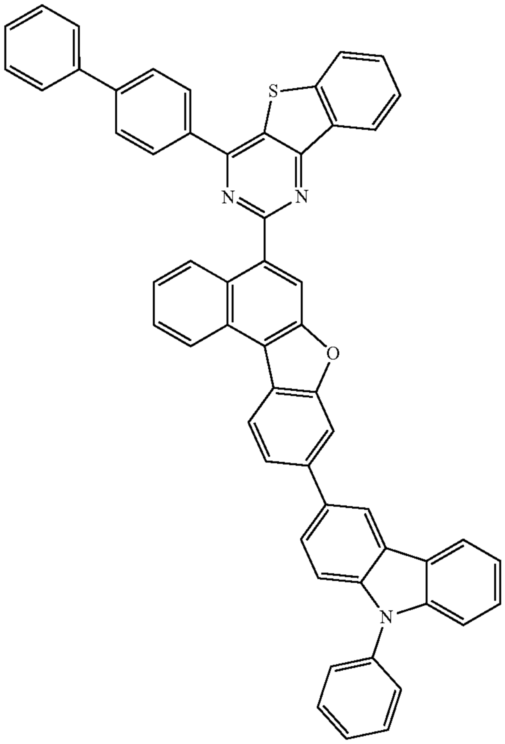
F217
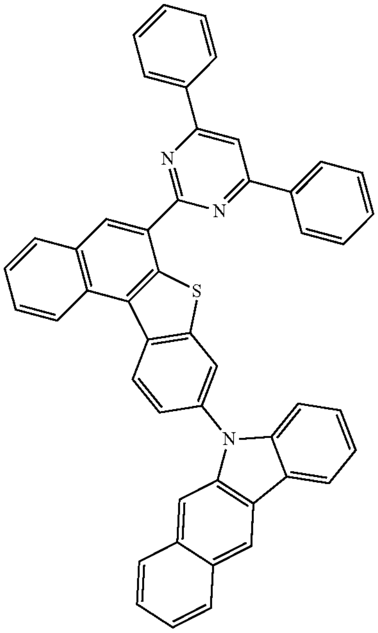
-continued
F218
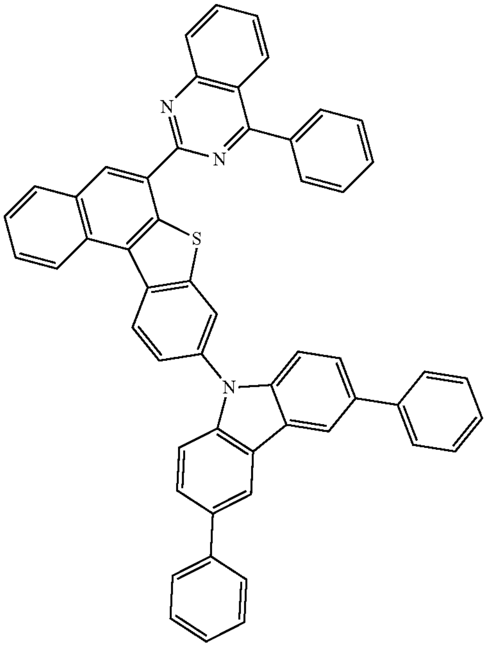
F219
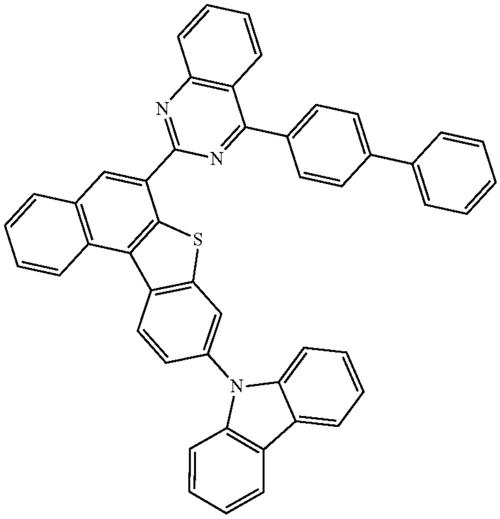

-continued
F220
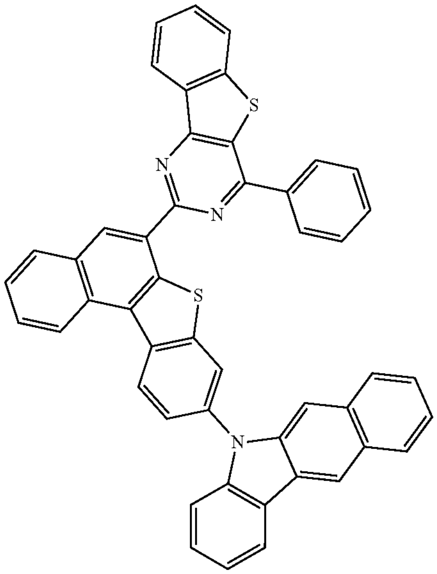
F221
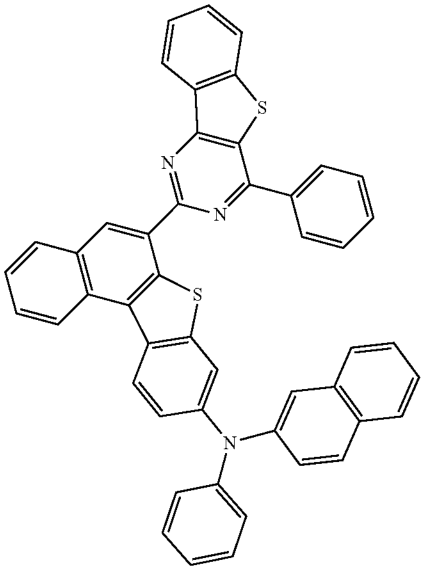
-continued
F222
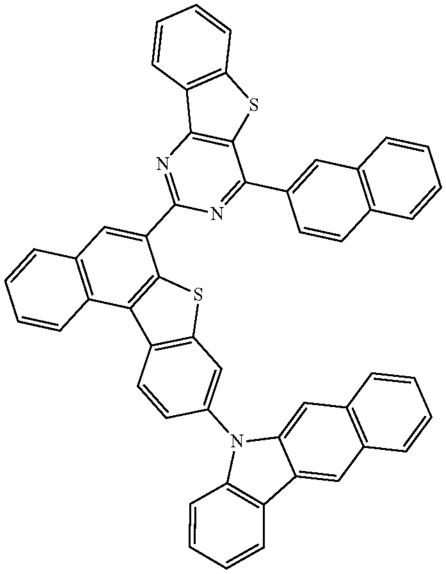
F223
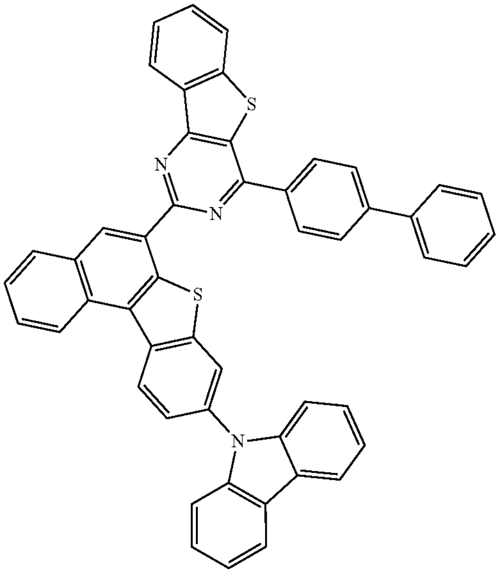

-continued
F224
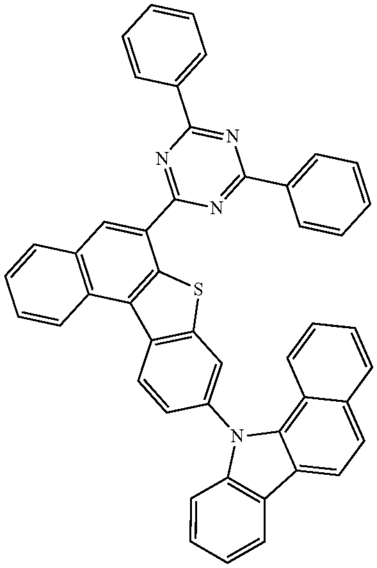
F225
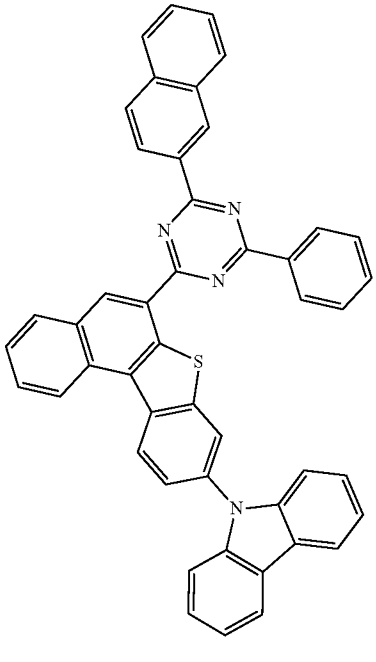
-continued
F226
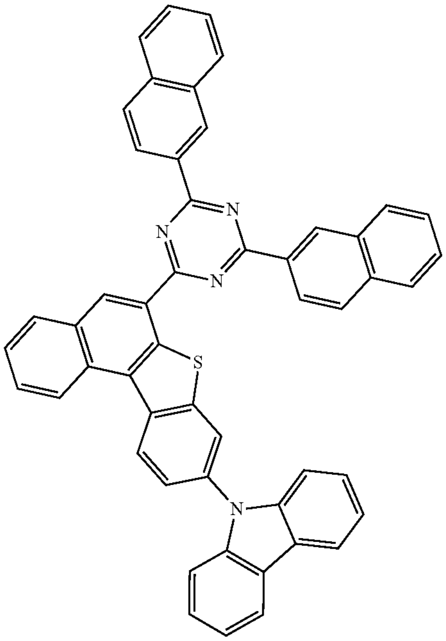
F227
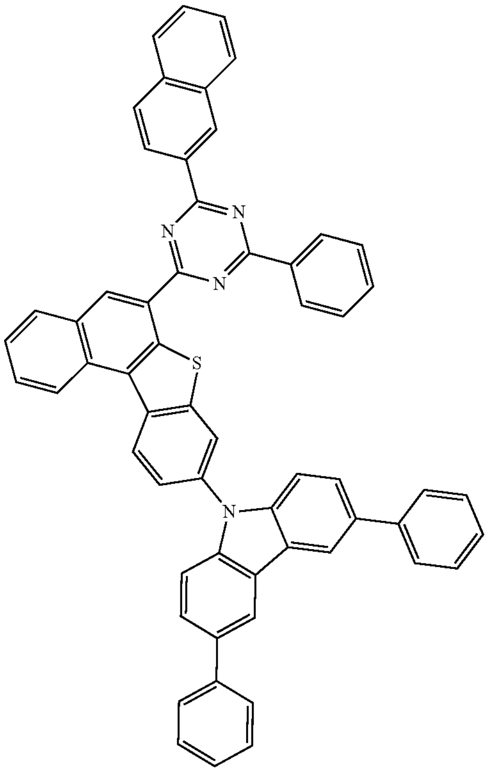

-continued
F228
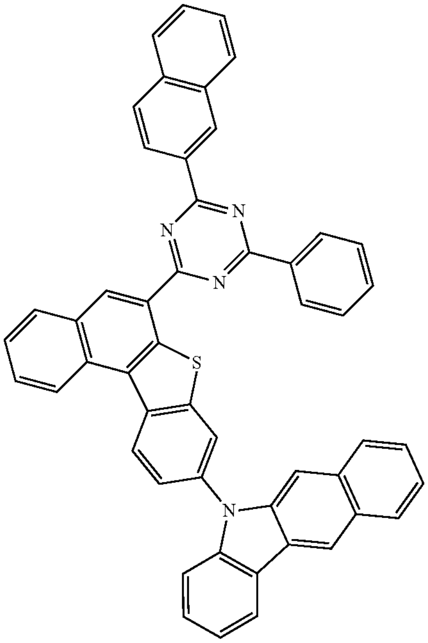
F229
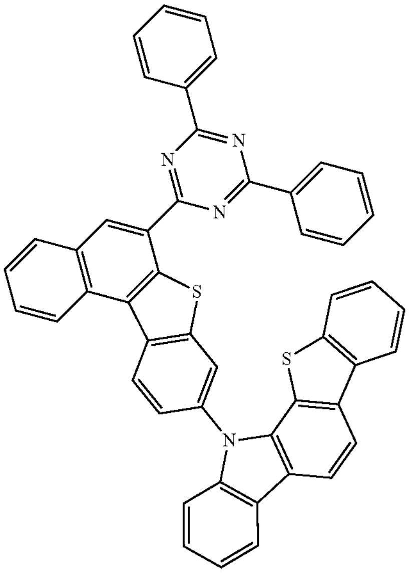
-continued
F230
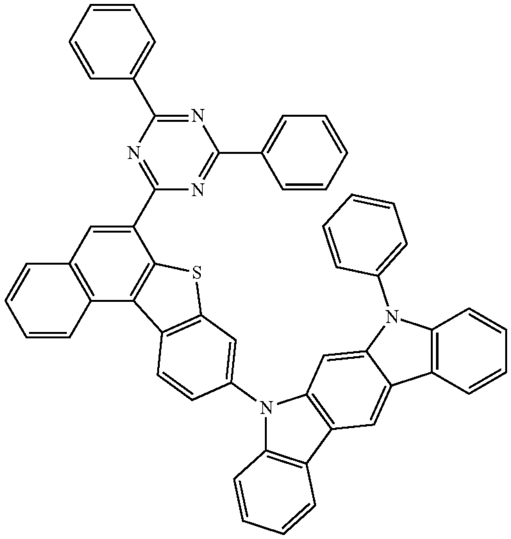
F231
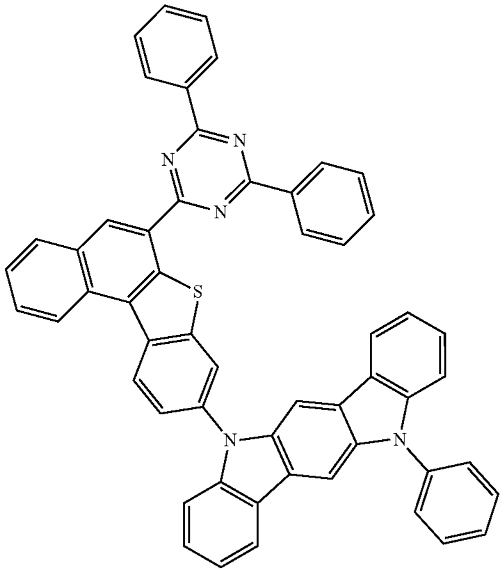

-continued
F232
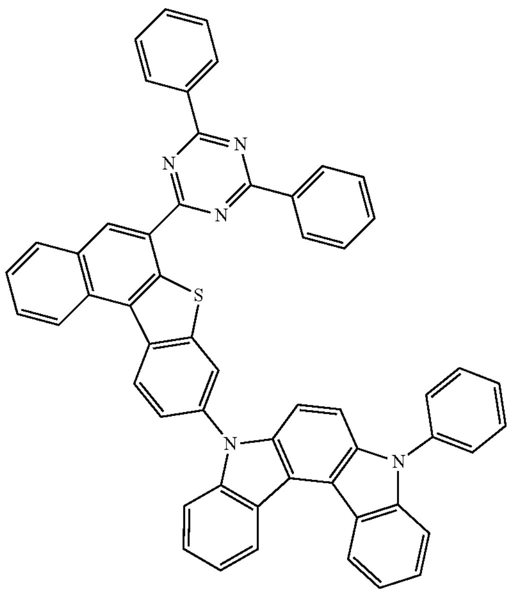
F233
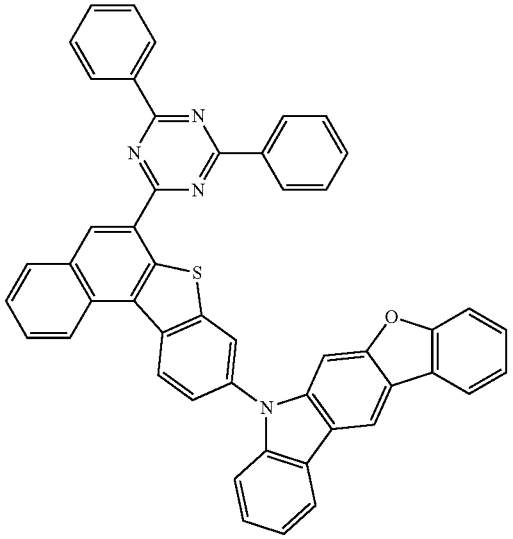
-continued
F234
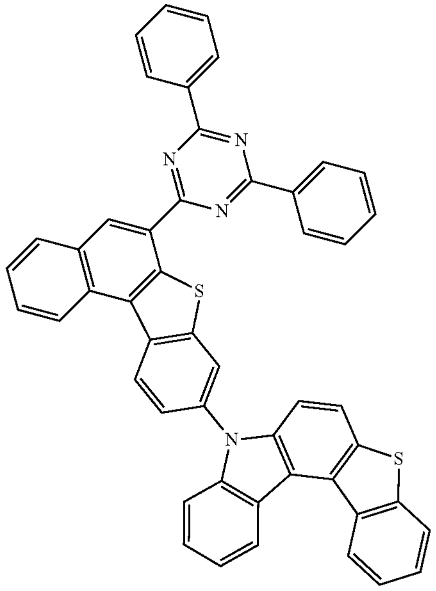
F235
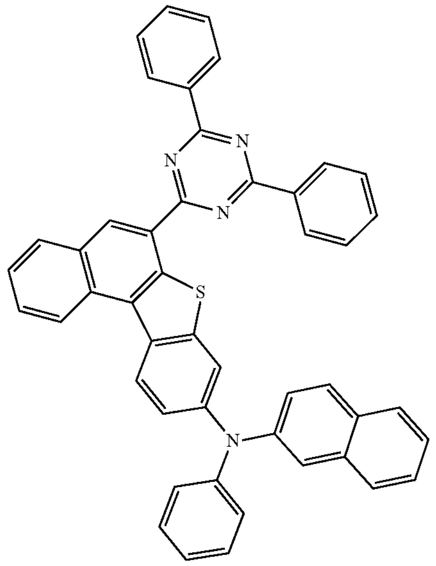

-continued
F236
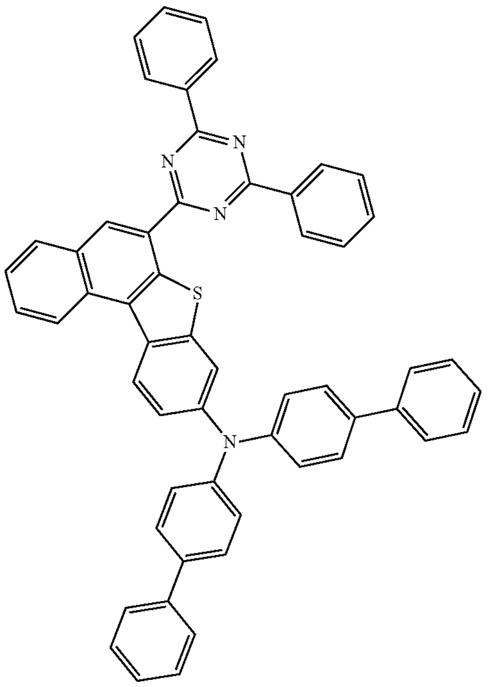
F237
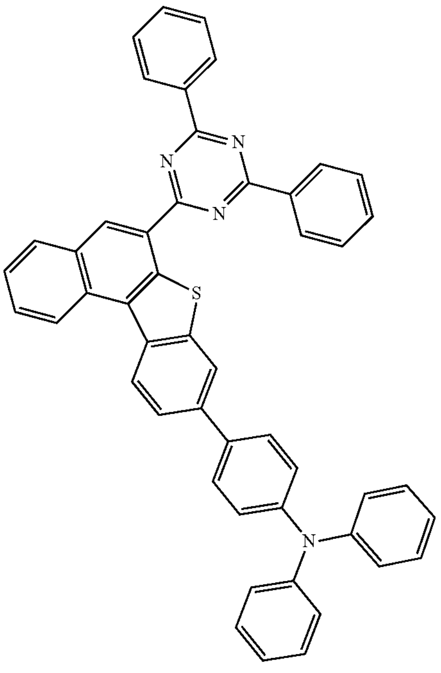
-continued
F238
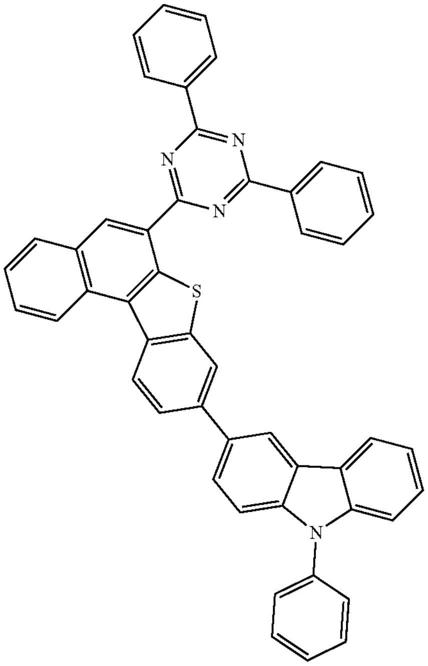
F239
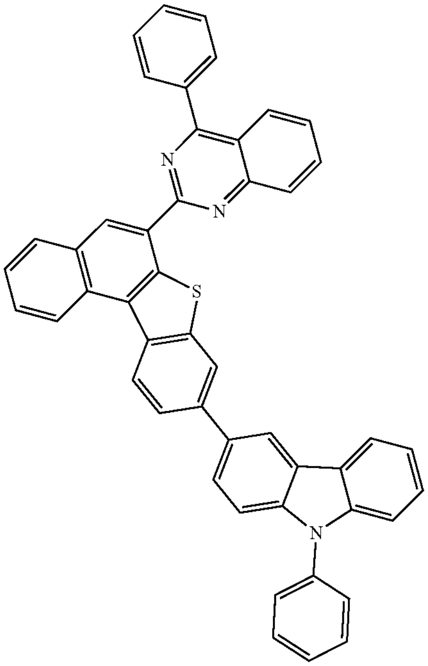

F240
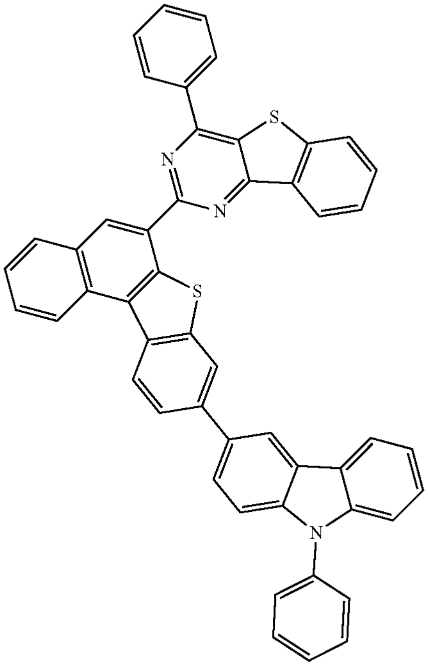
F241
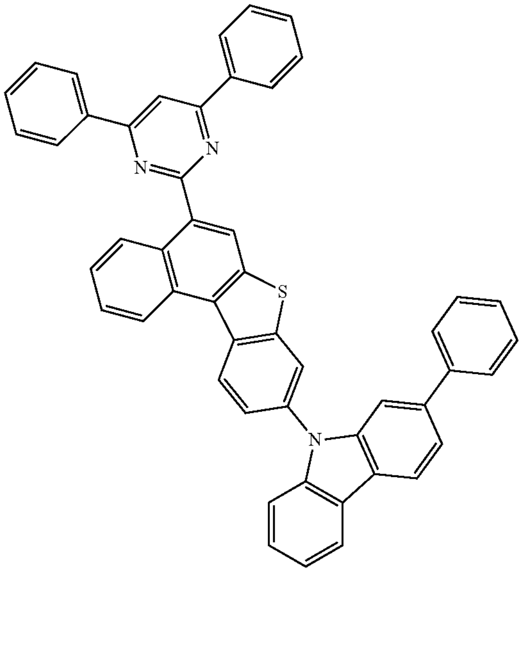
F242
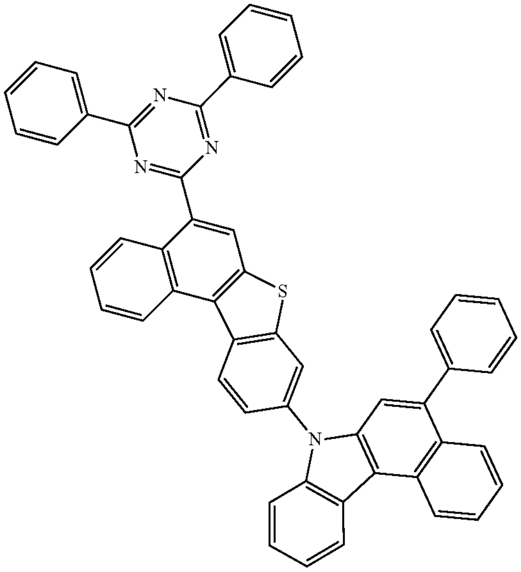
F243
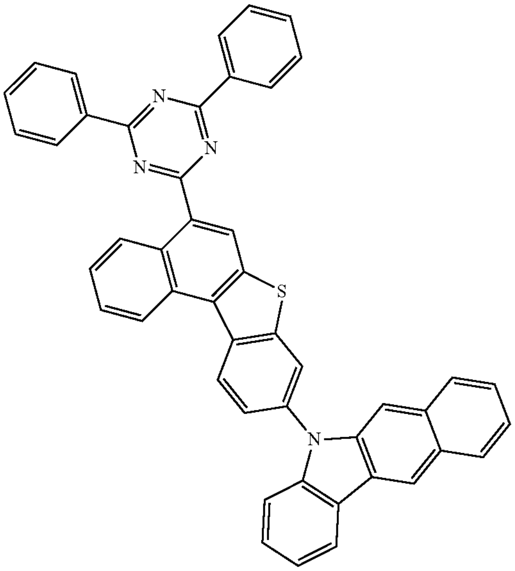

-continued
F244
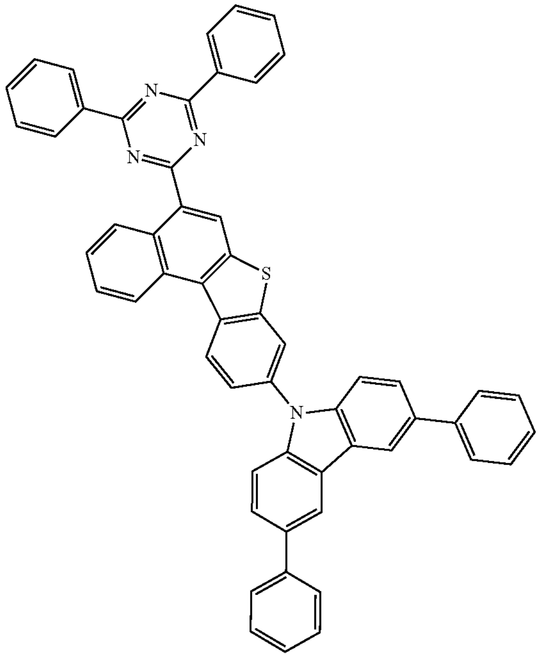
F245
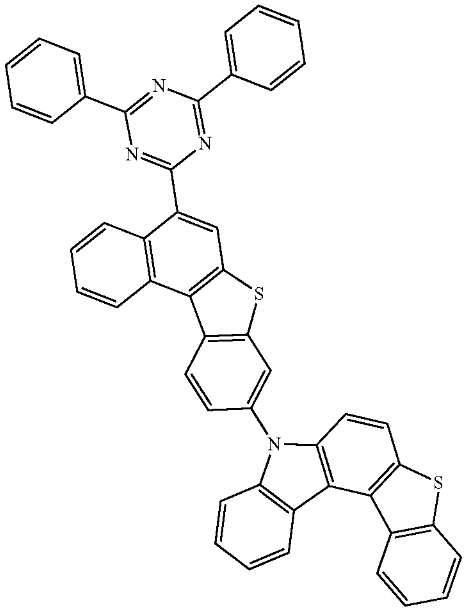
-continued
F246
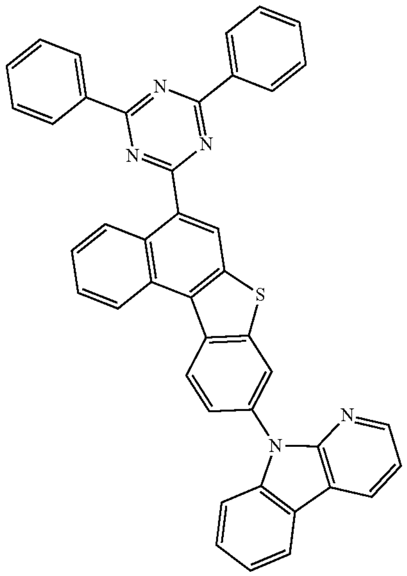
F247
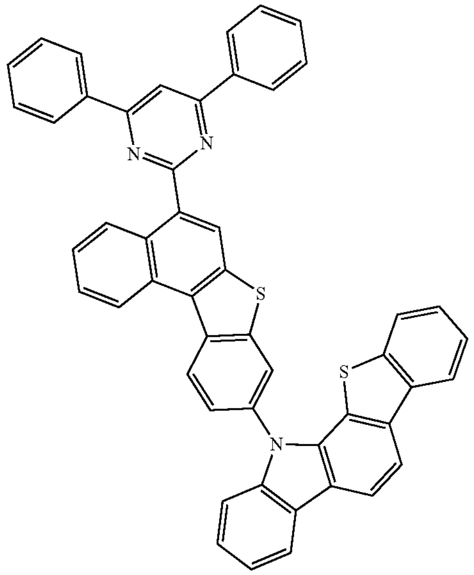

-continued
F248
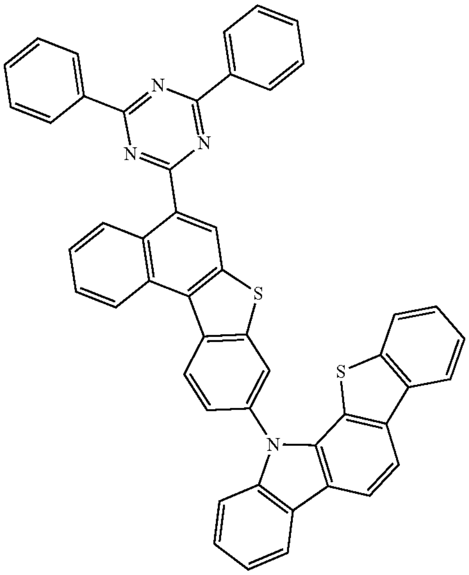
F249
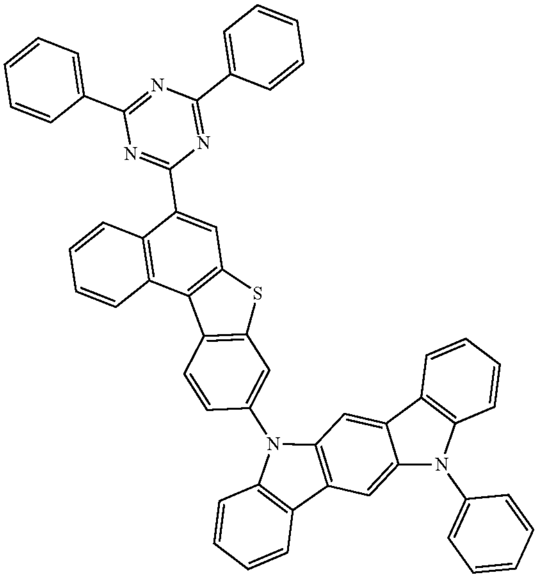
-continued
F250
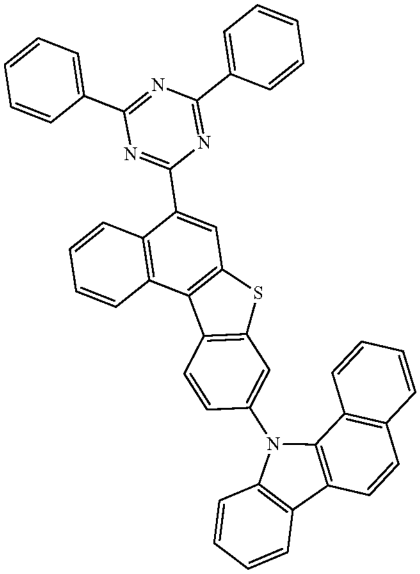
F251
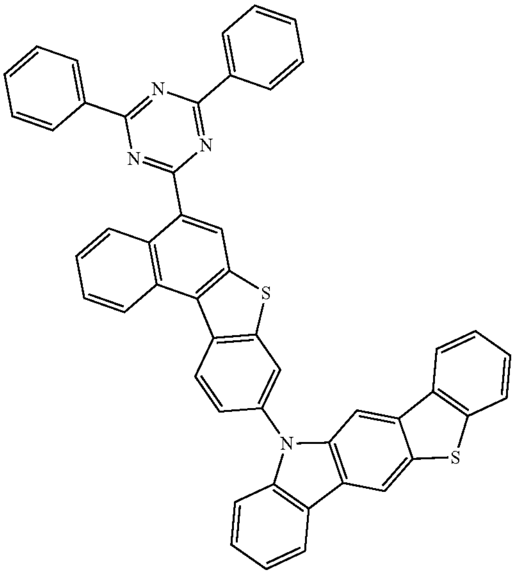

-continued
F252
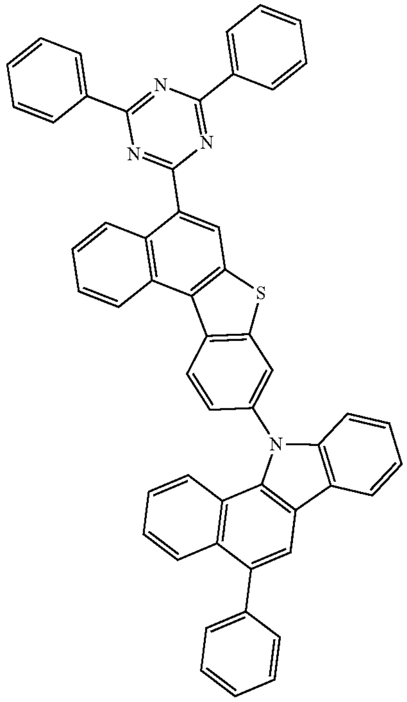
F253
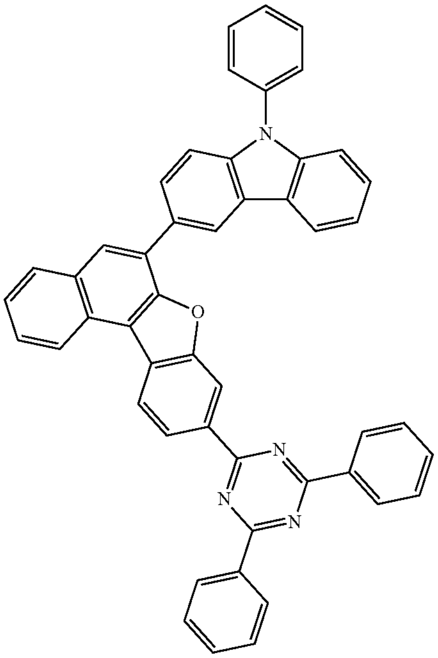
-continued
F254
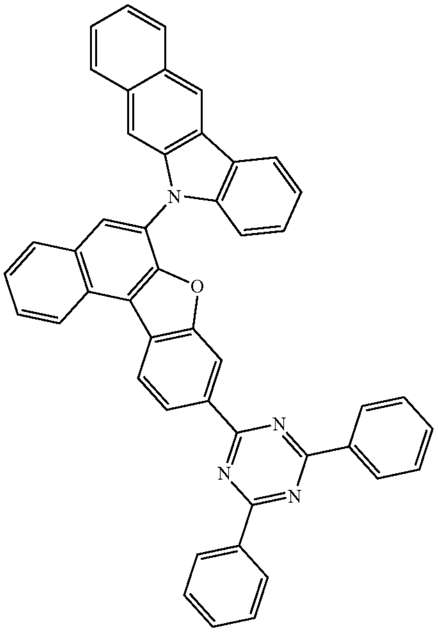
F255
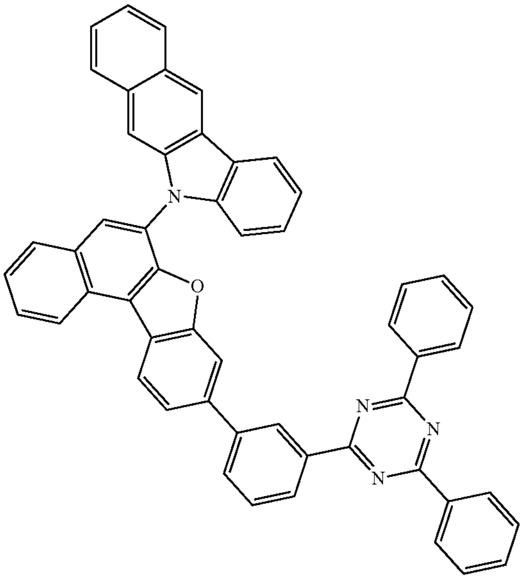

-continued
F256
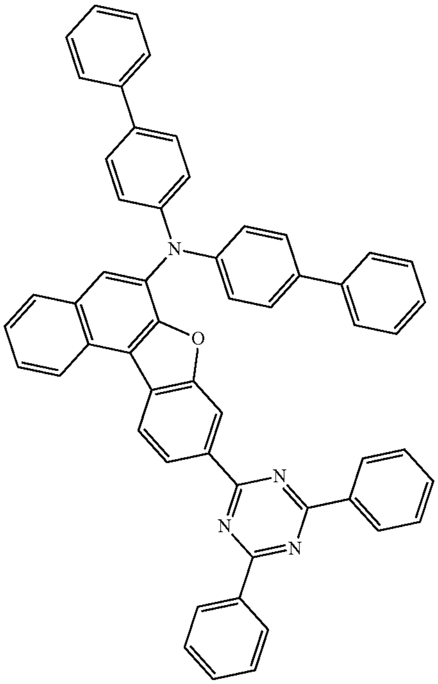
F257
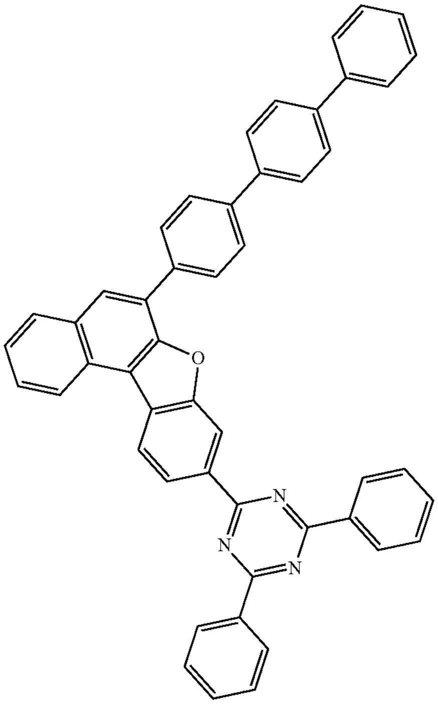
-continued
F258
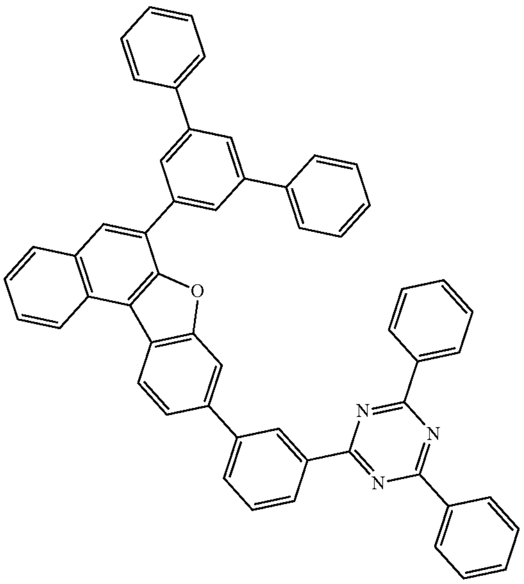
F259
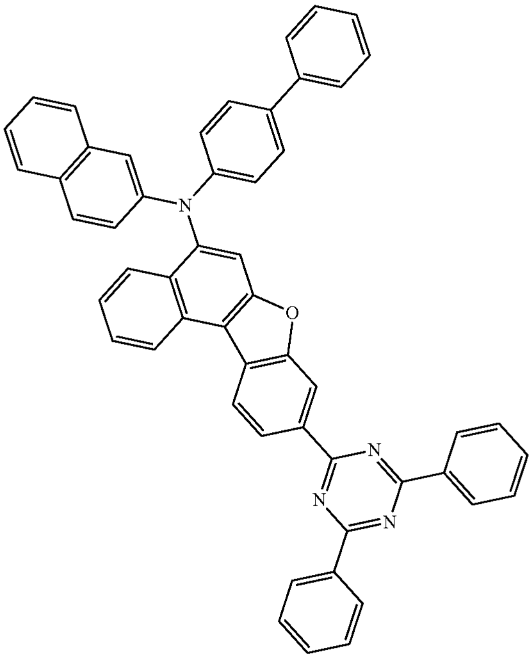

F260
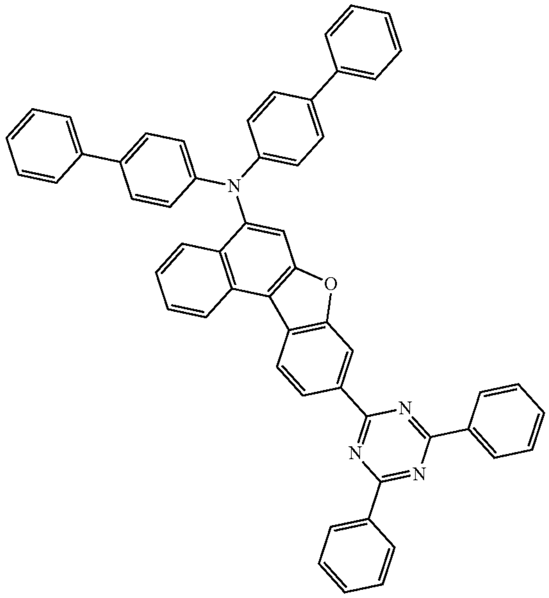
F261
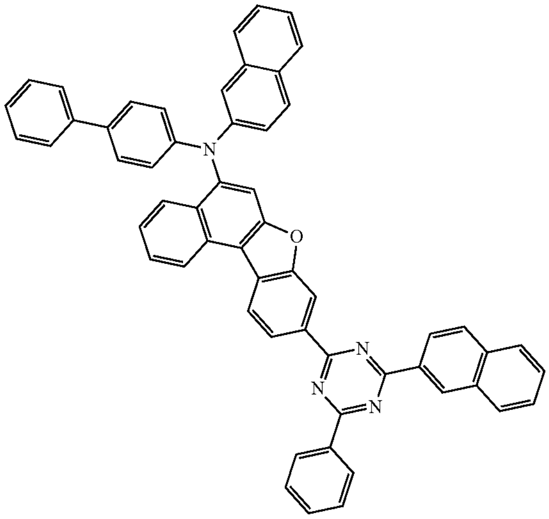
F262
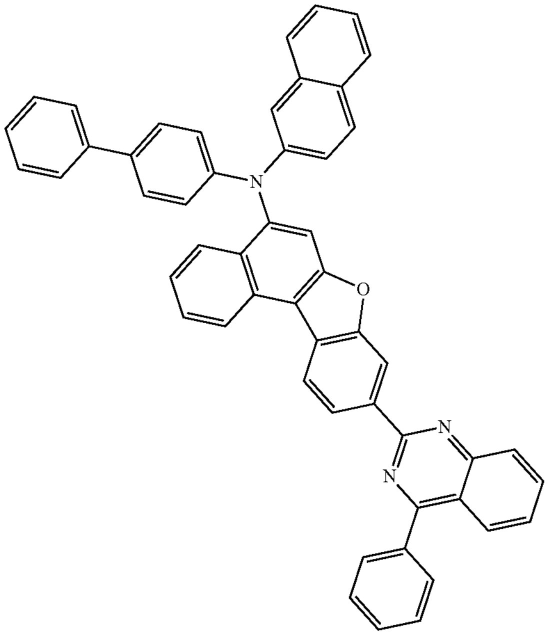
F263
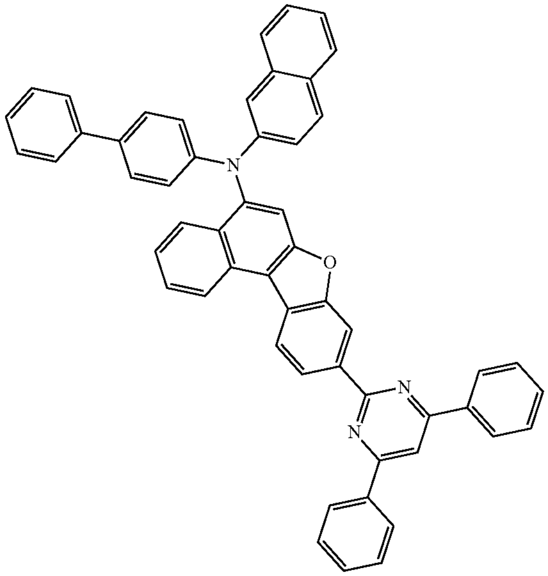

-continued
F264
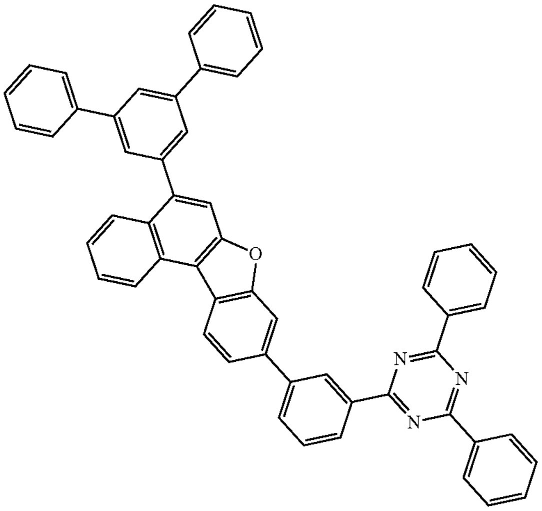
F265
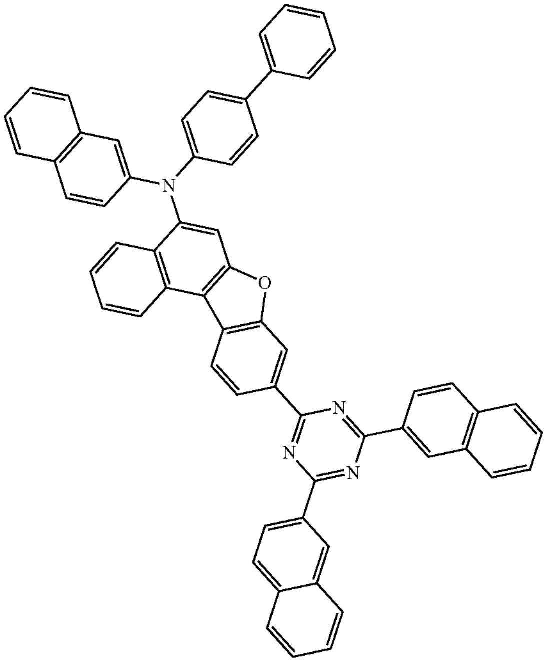
-continued
F266
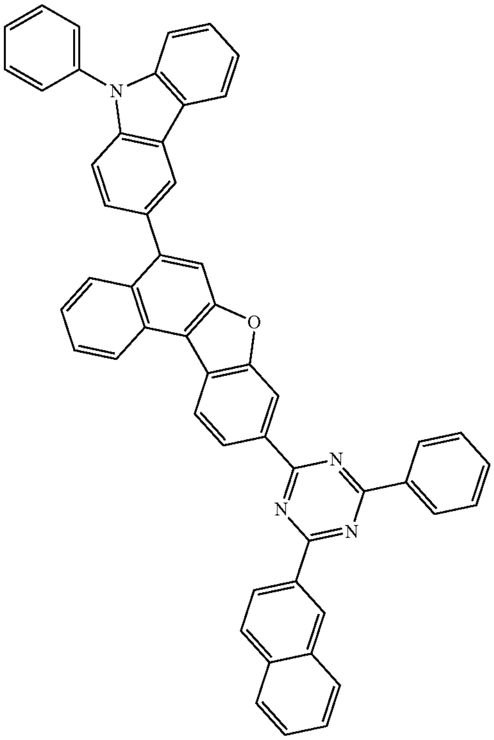
F267
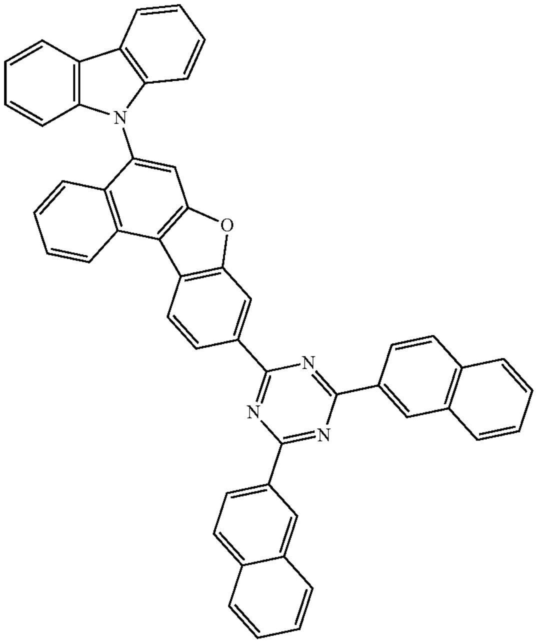

-continued
F268
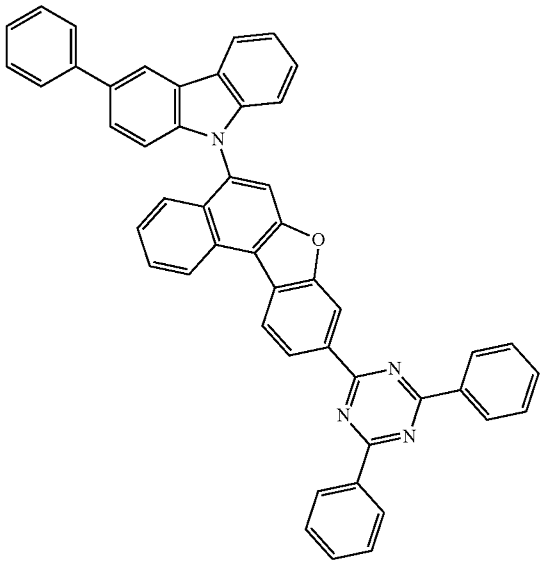
F269
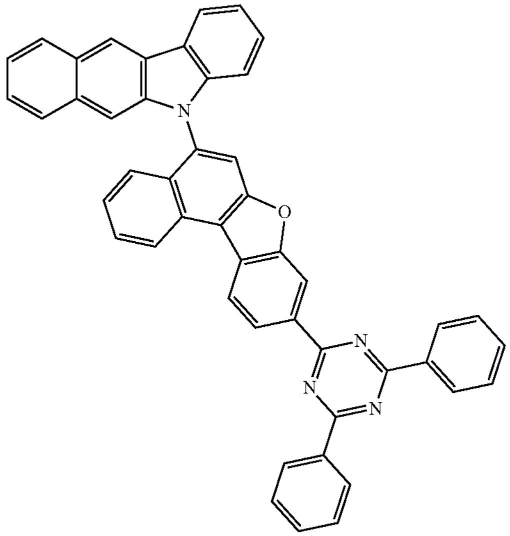
-continued
F270
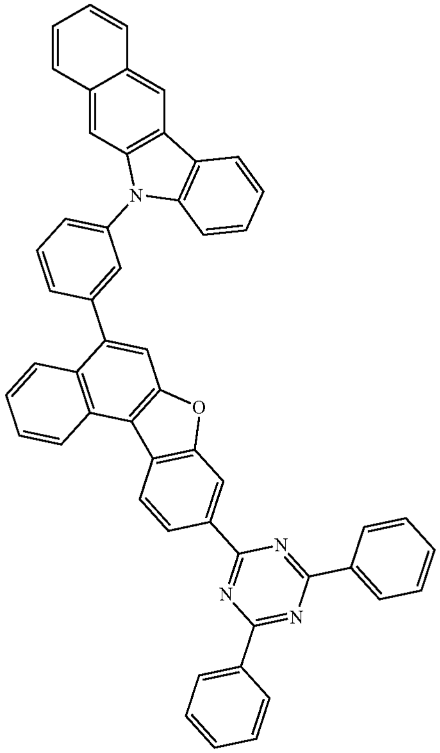
F271
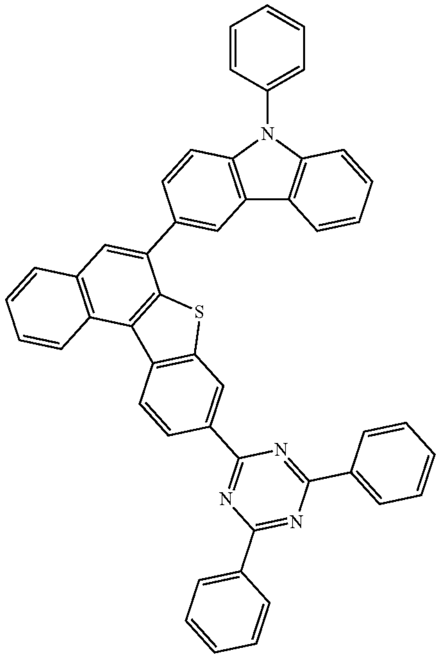

-continued
F272
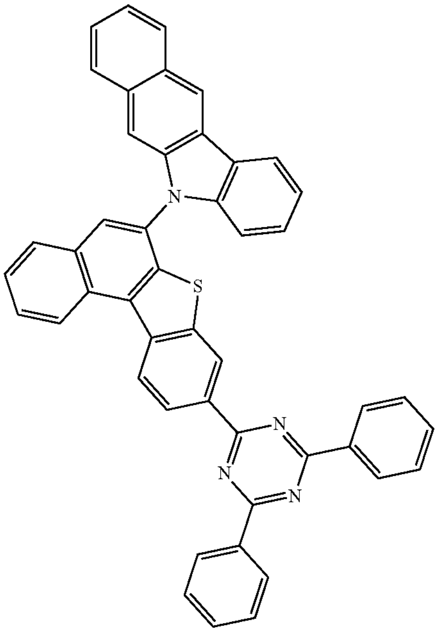
F273
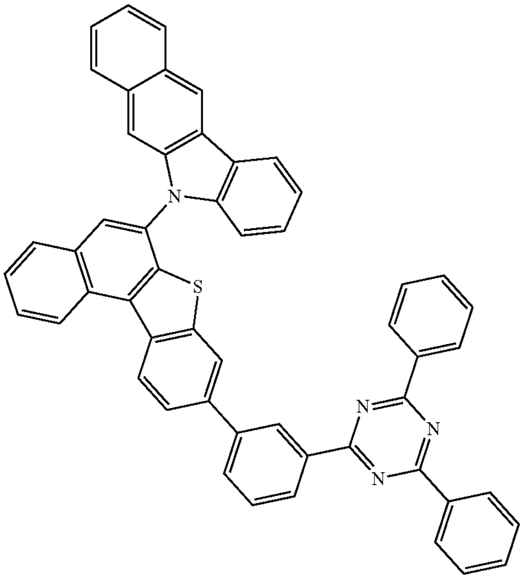
-continued
F274
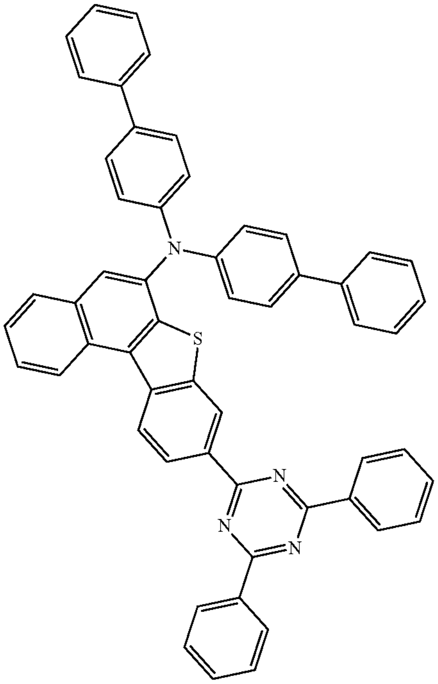
F275
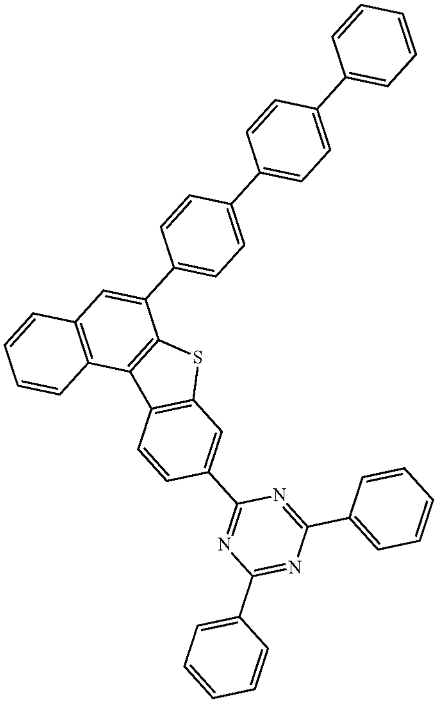

-continued
F276
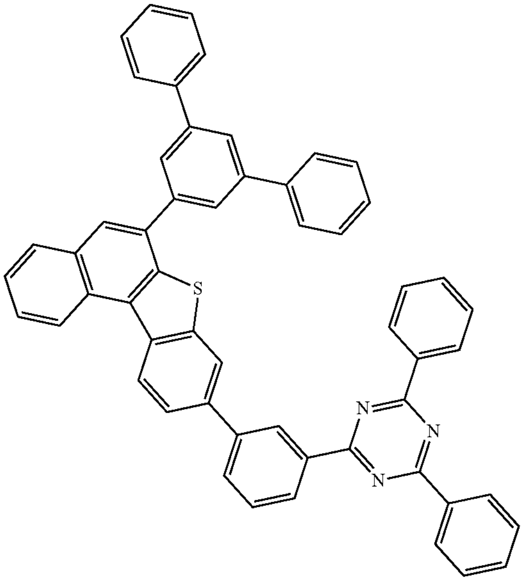
F277
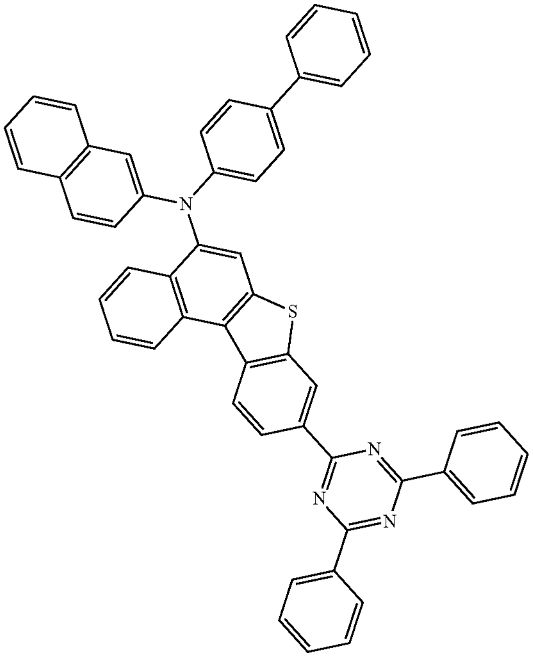
-continued
F278
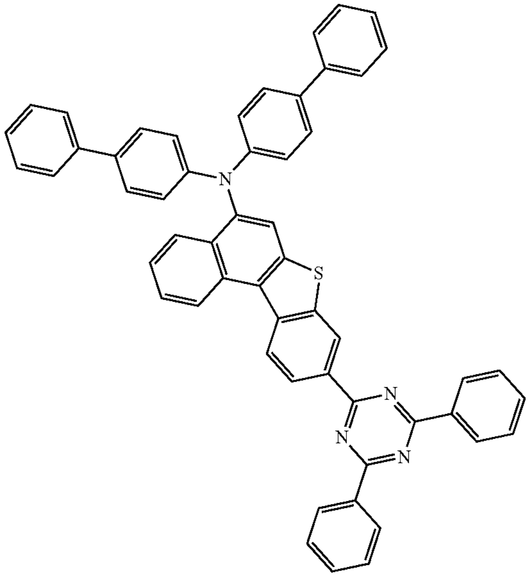
F279
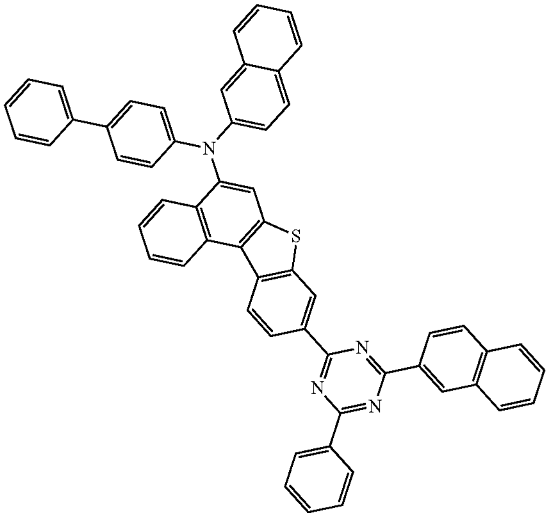

-continued
F280
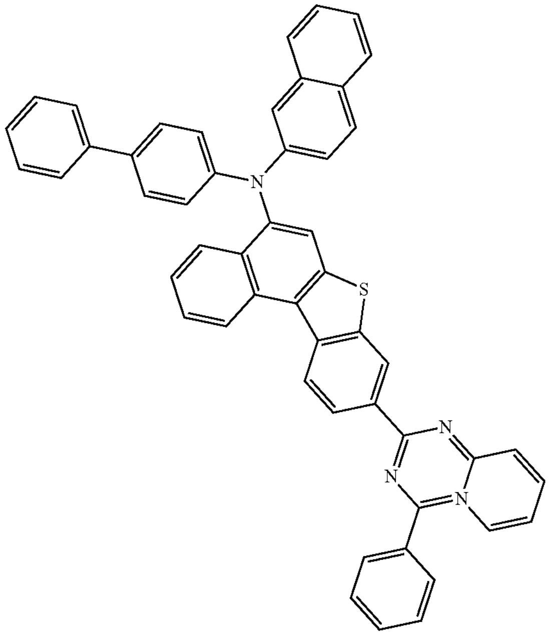
-continued
F282
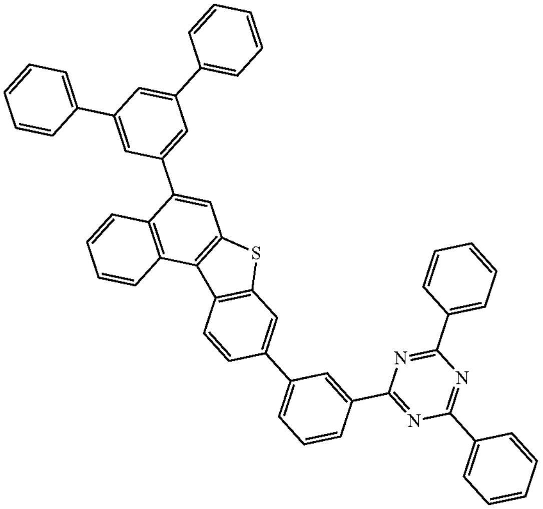
F281
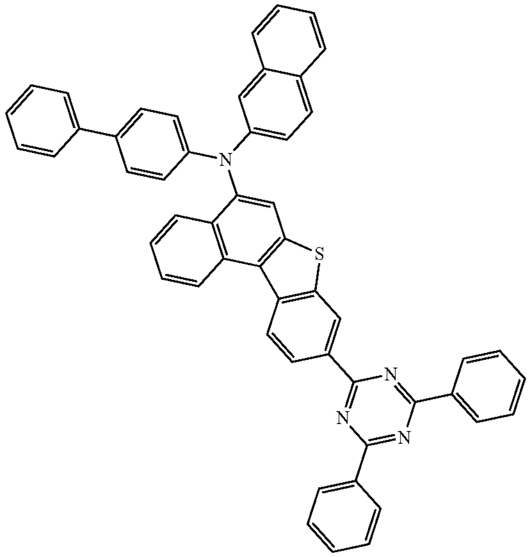
F283
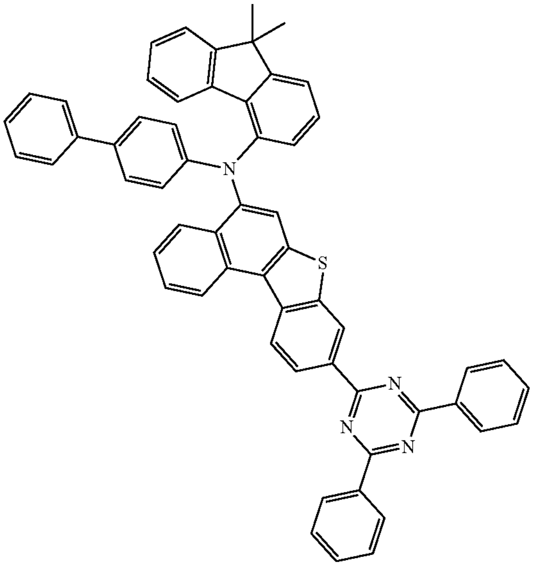

-continued
F284
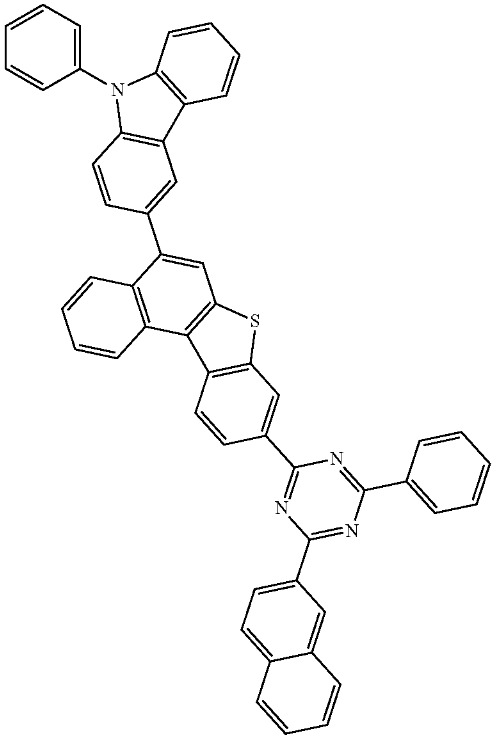
F285
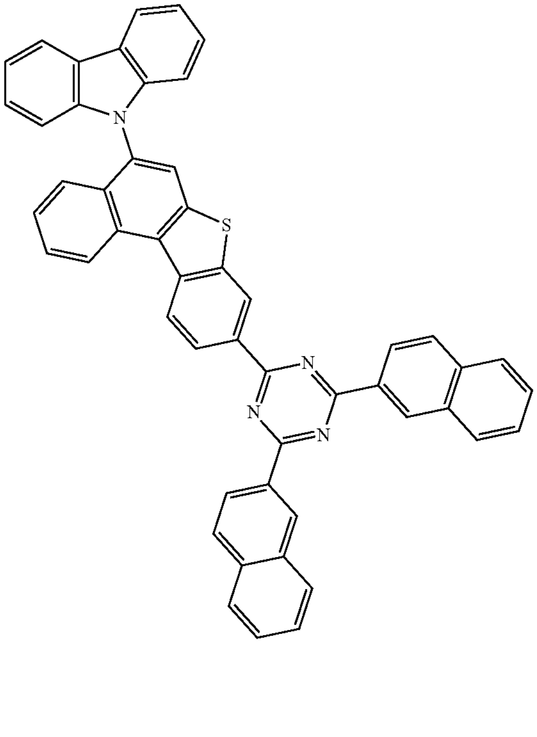
-continued
F286
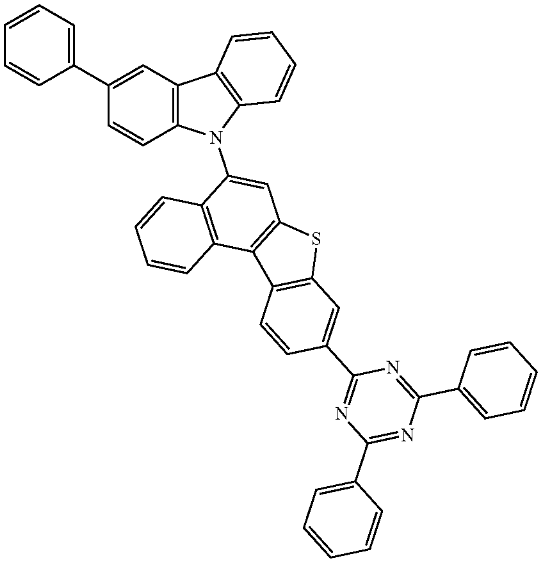
F287
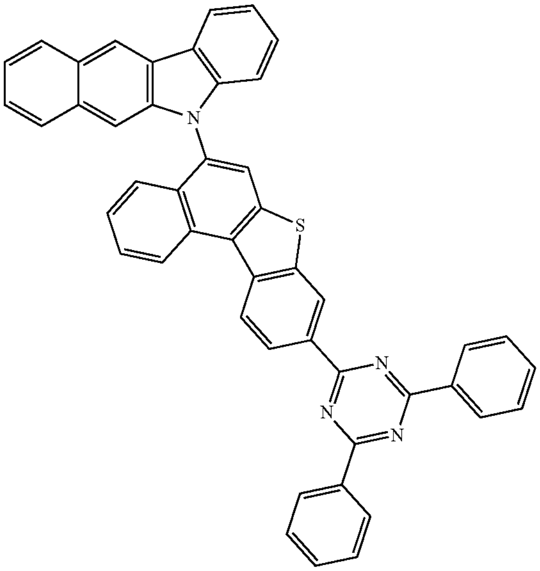

F288
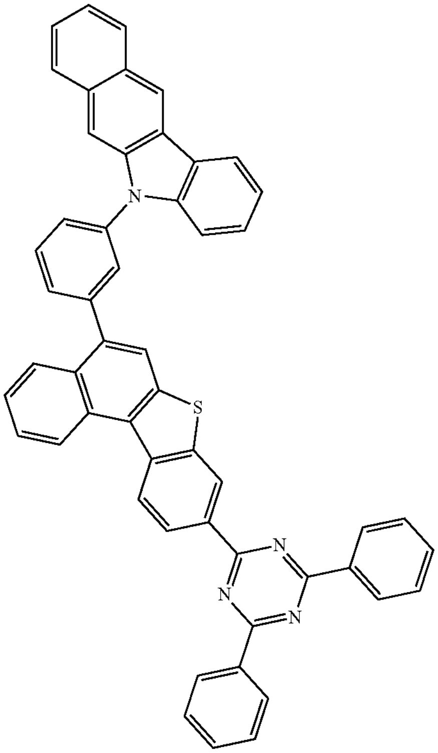
F289
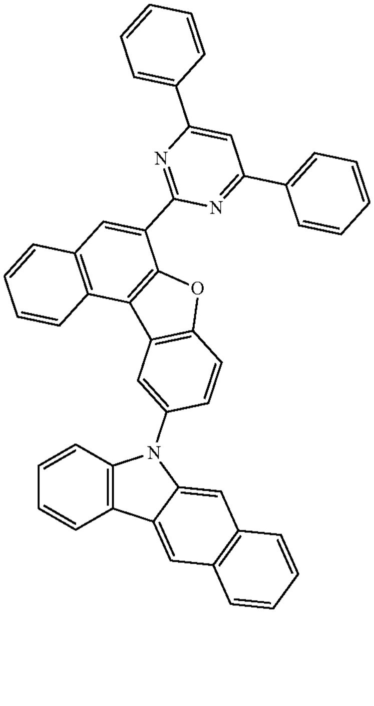
F290
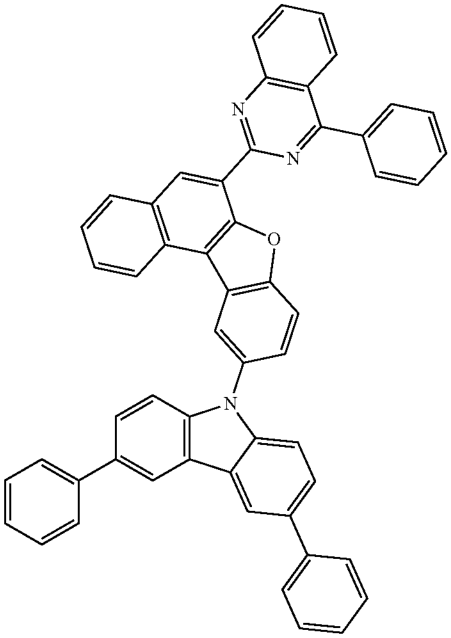
F291
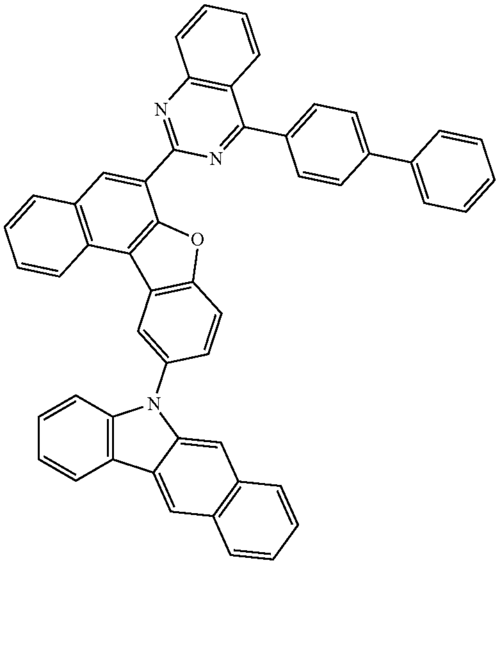

-continued
F292
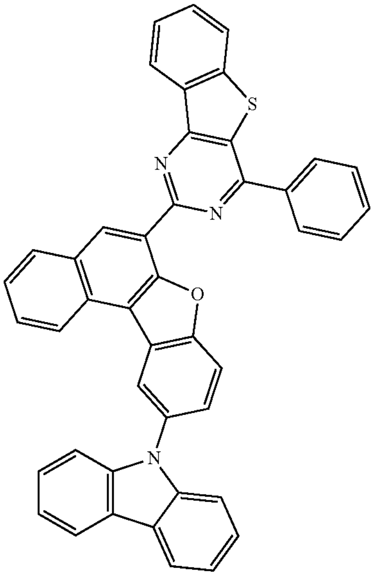
F293
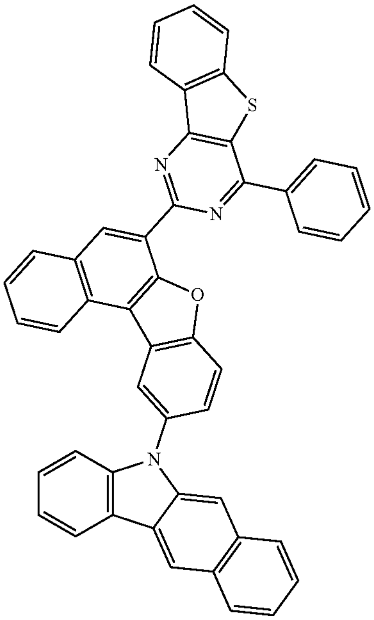
-continued
F294
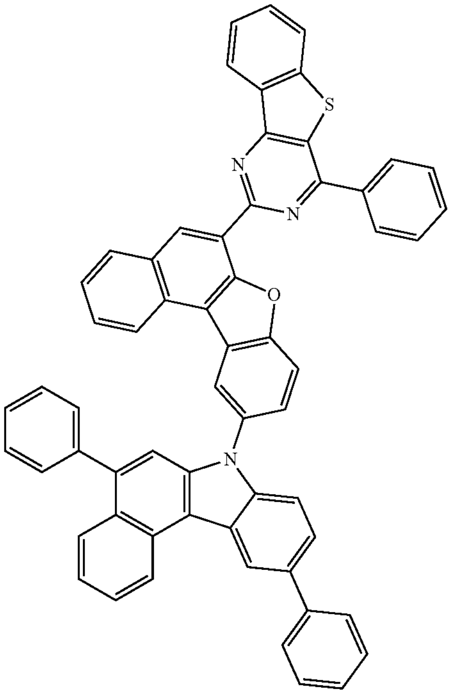
F295
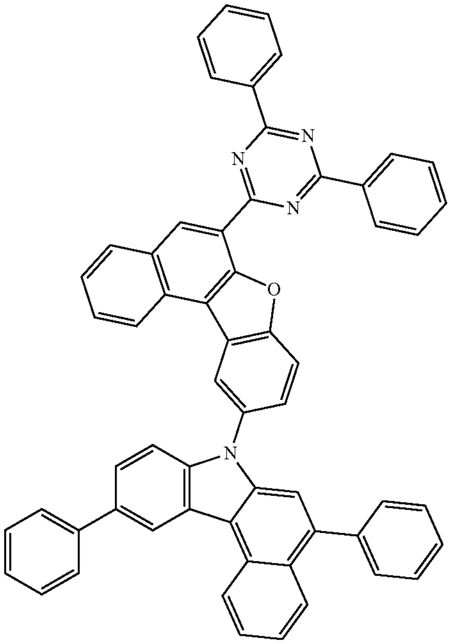

-continued
F296
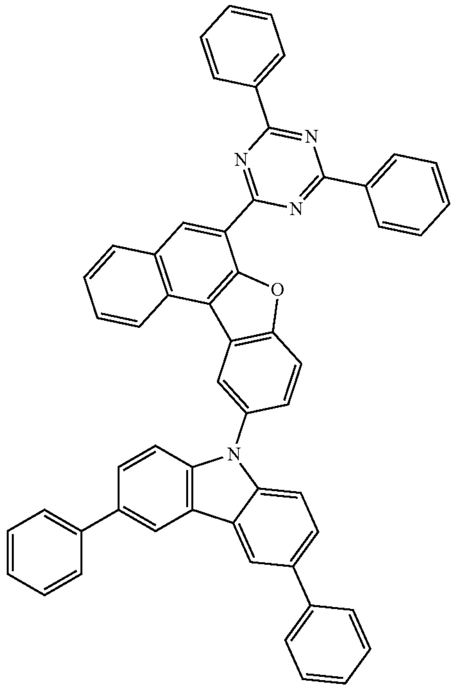
F297
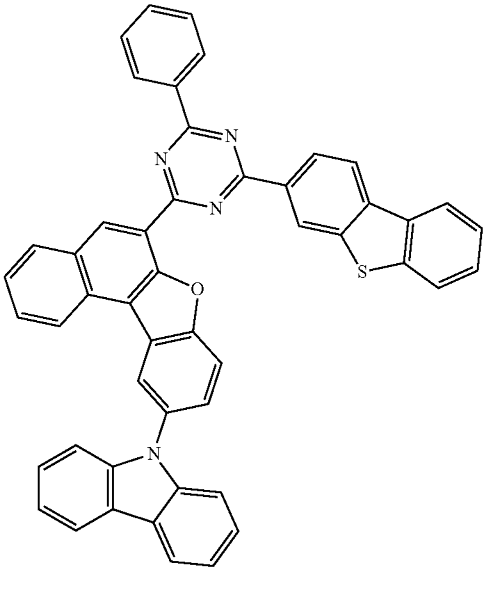
-continued
F298
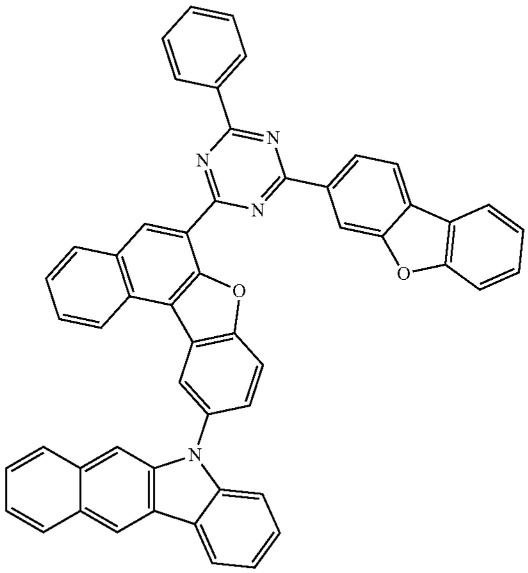
F299
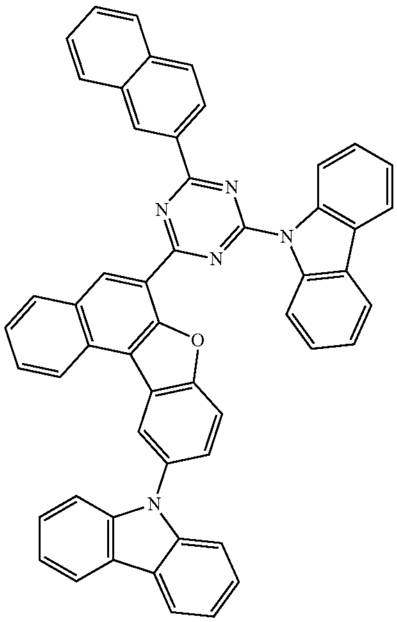

-continued
F300
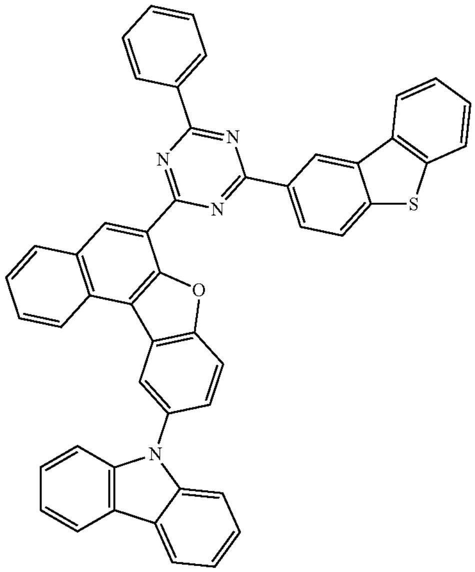
F301
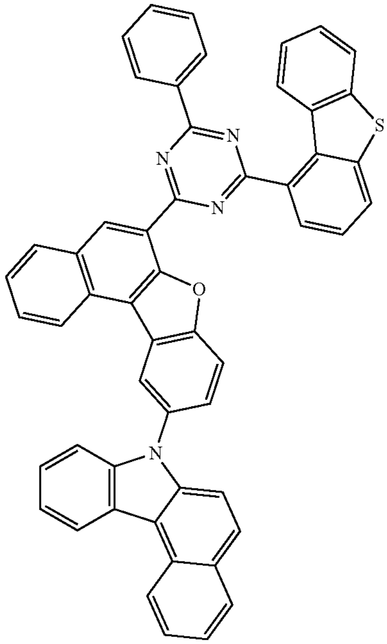
-continued
F302
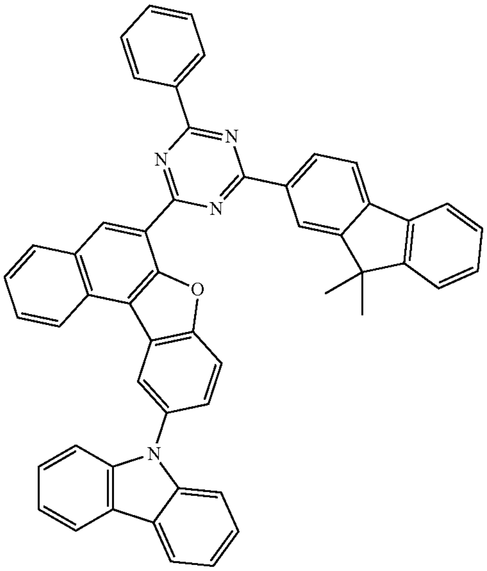
F303
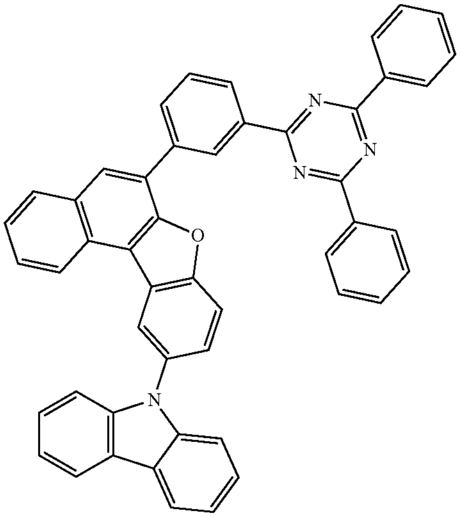

-continued
F304
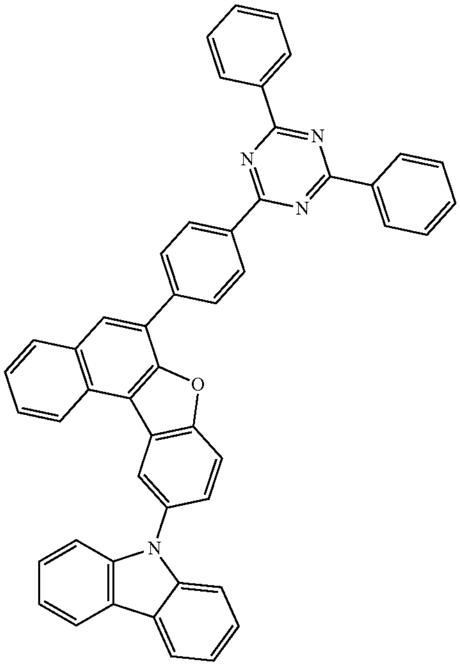
F305
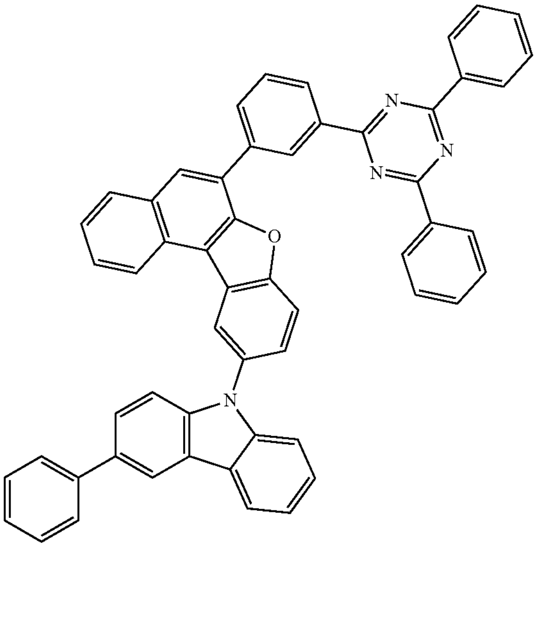
-continued
F306
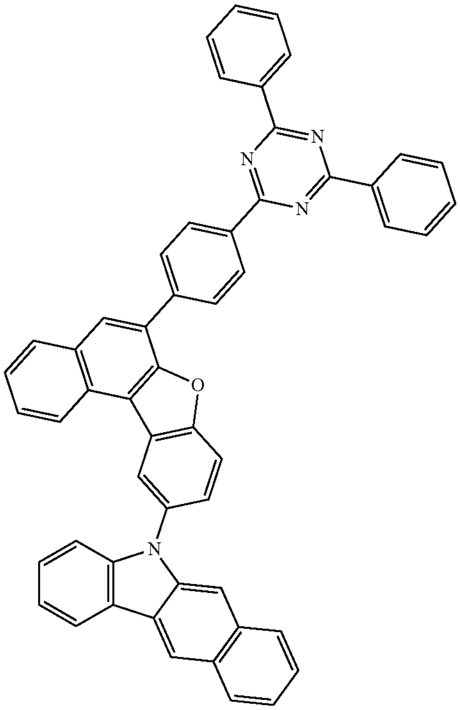
F307
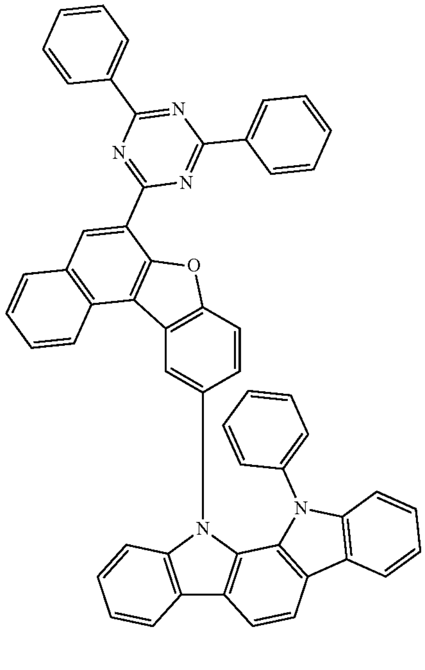

-continued
F308
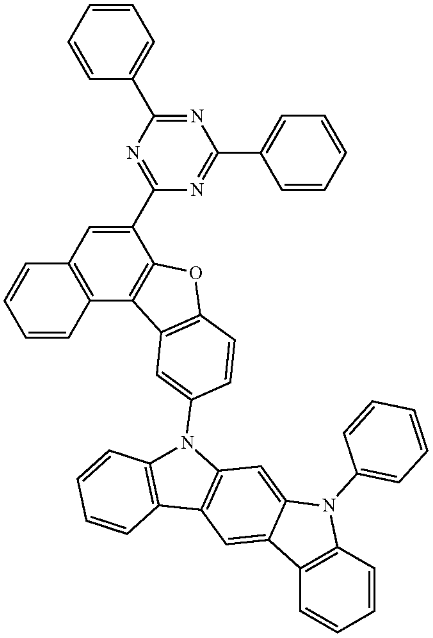
F309
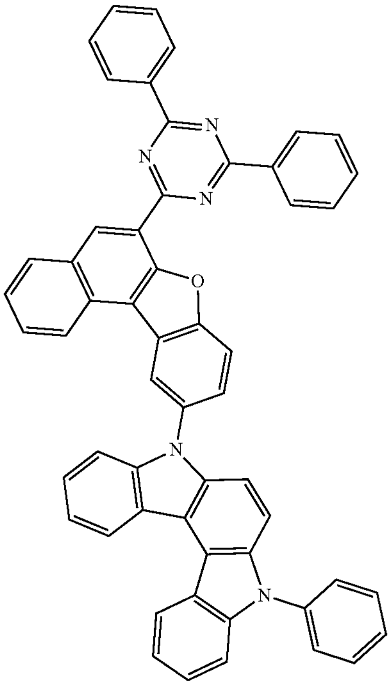
-continued
F310
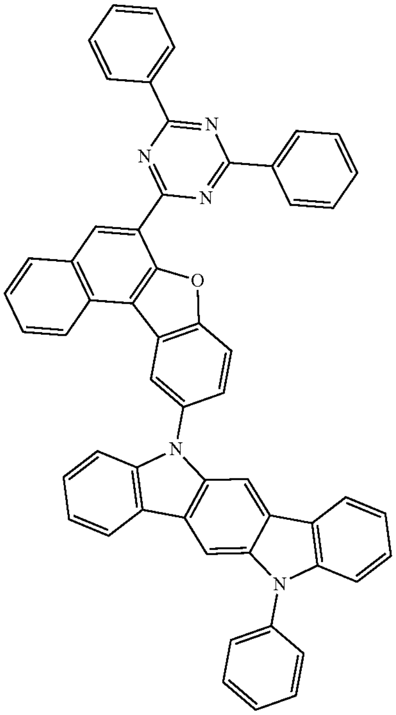
F311
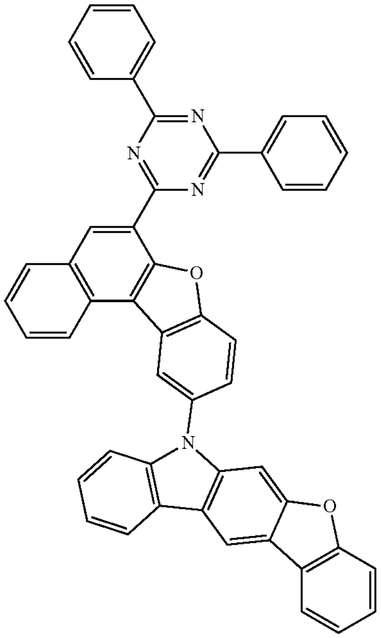

-continued
F312
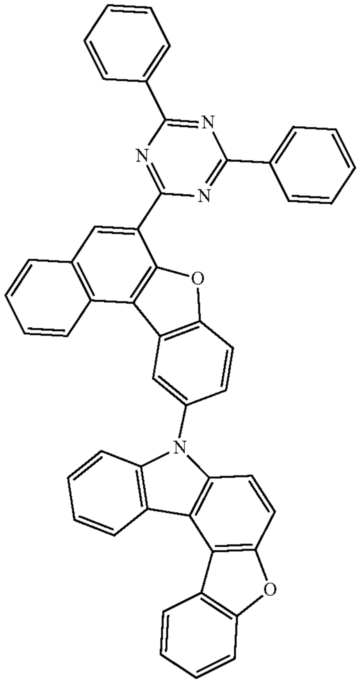
F313
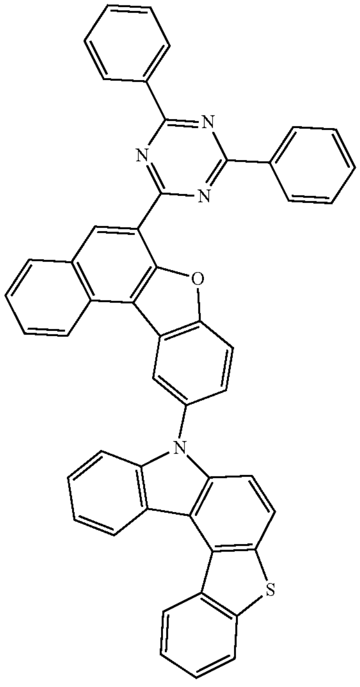
-continued
F314
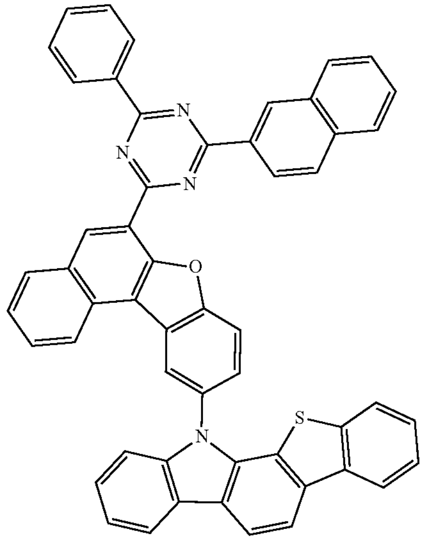
F315
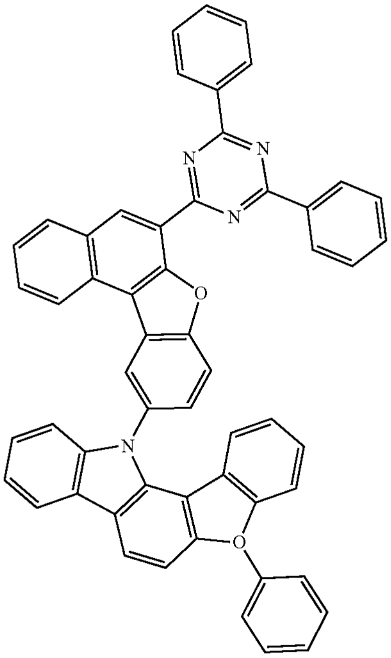

-continued
F316
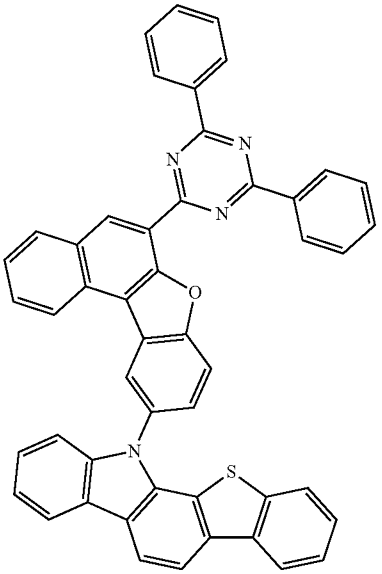
F317
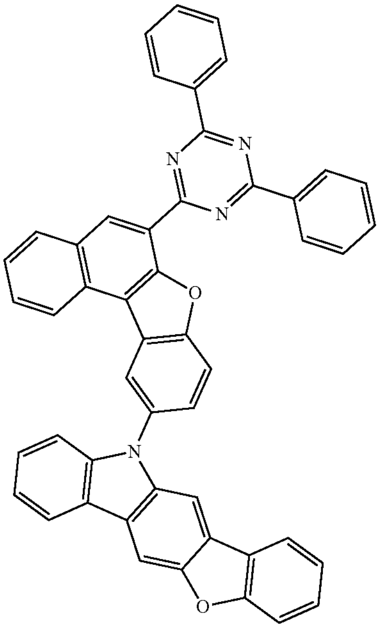
-continued
F318
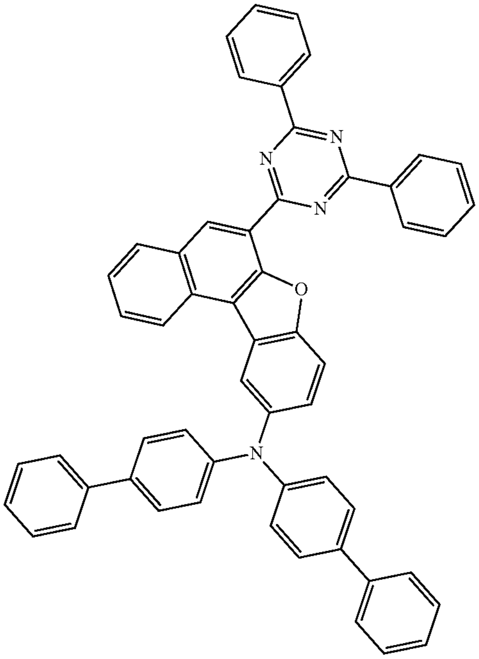
F319
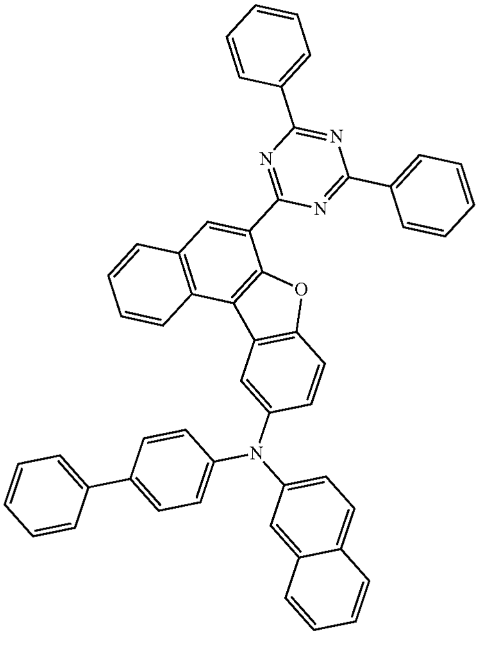

-continued
F320
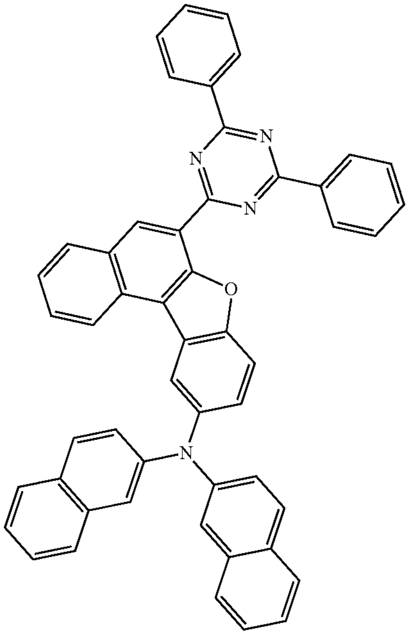
F321
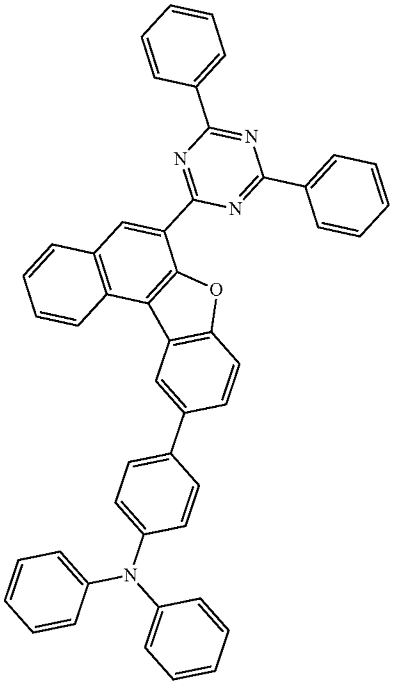
-continued
F322
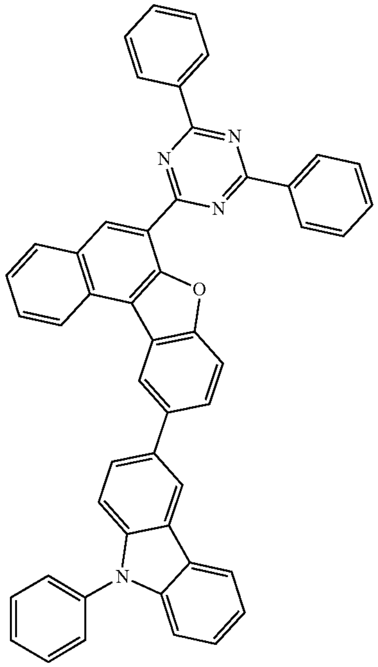
F323
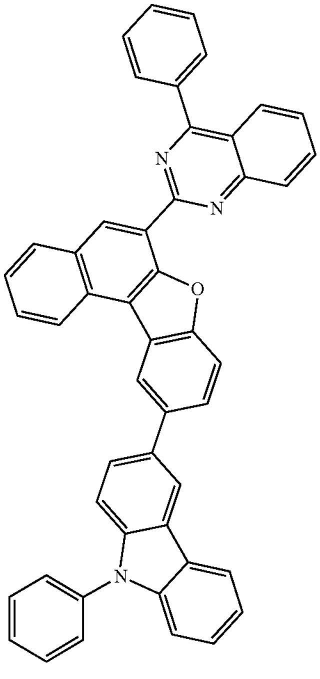

-continued
F324
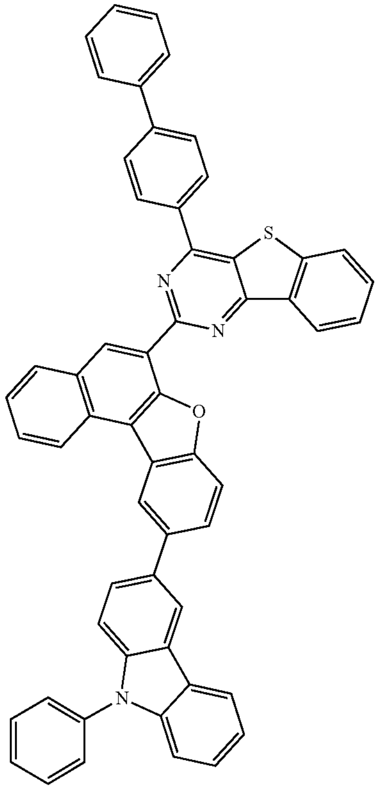
F325
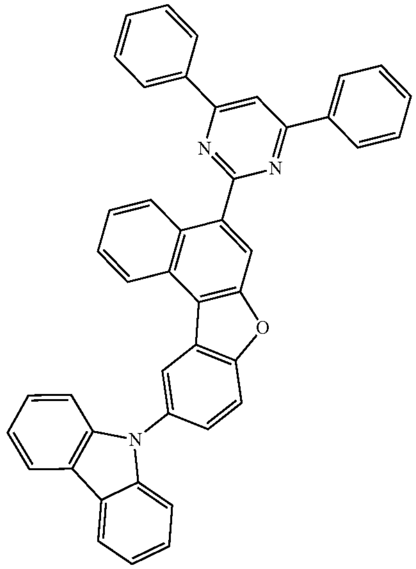
-continued
F326
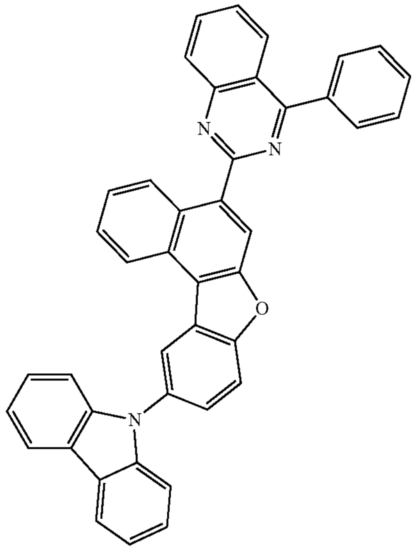
F327
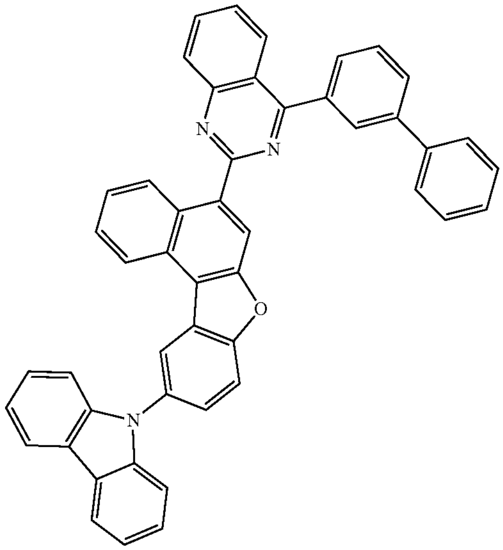

-continued
F328
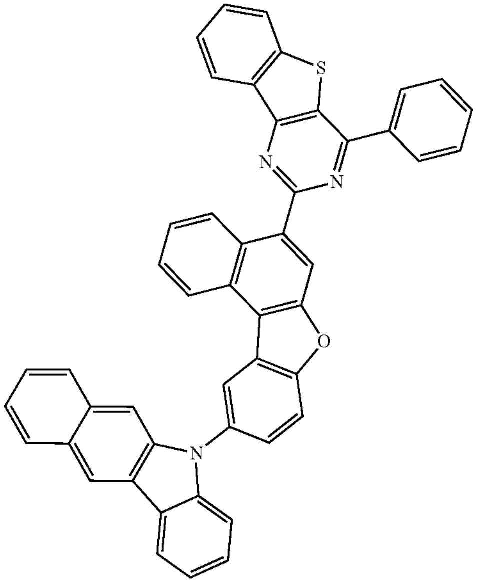
F329
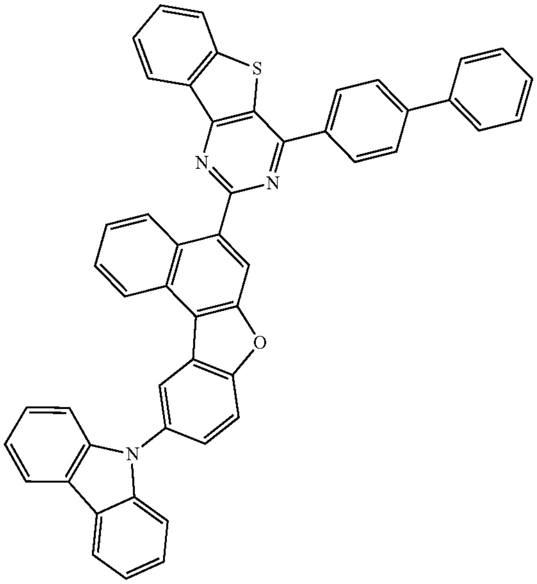
-continued
F330
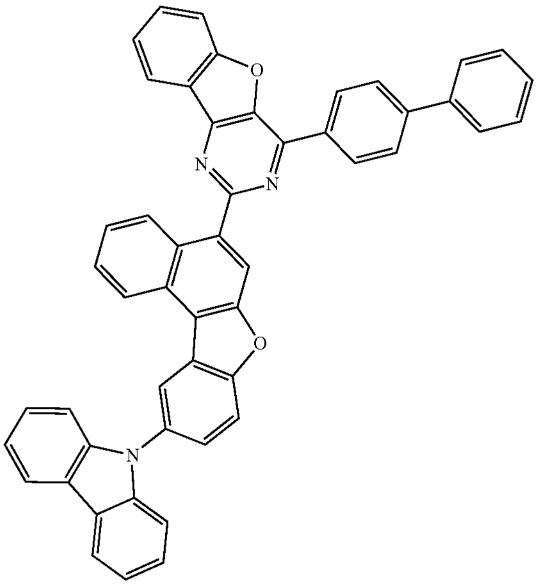
F331
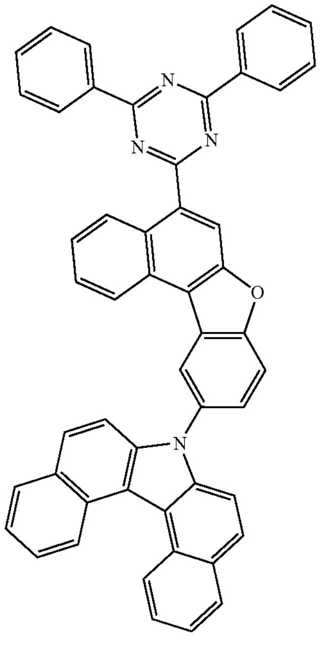

-continued
F332
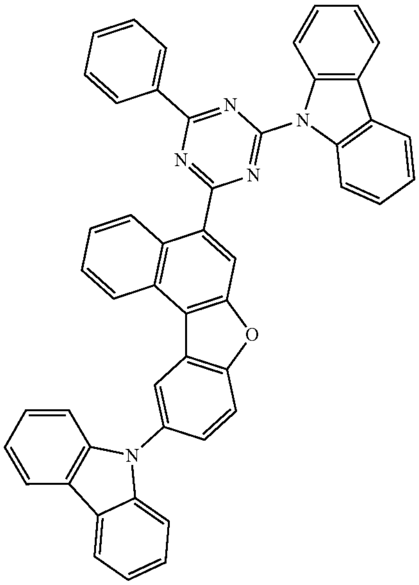
F333
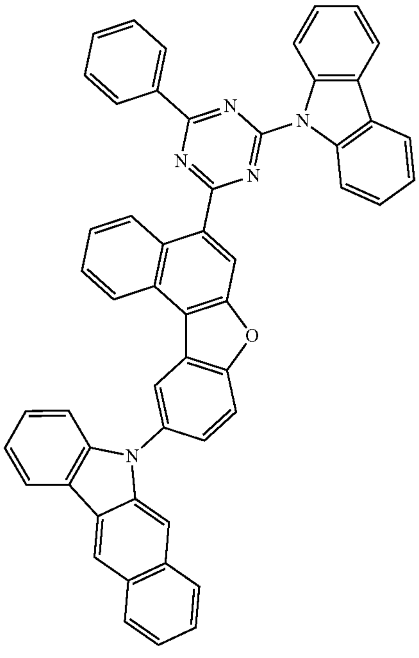
-continued
F334
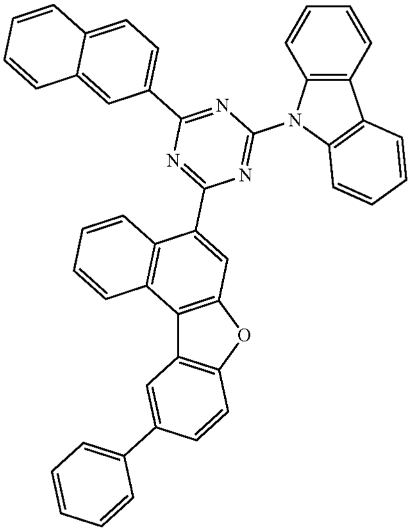
F335
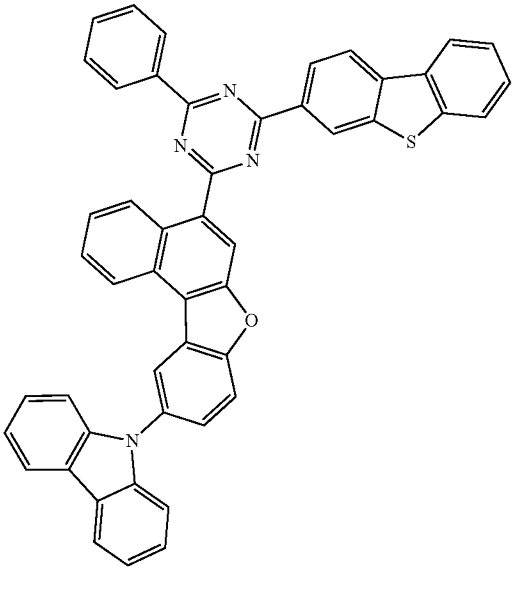

-continued
F336
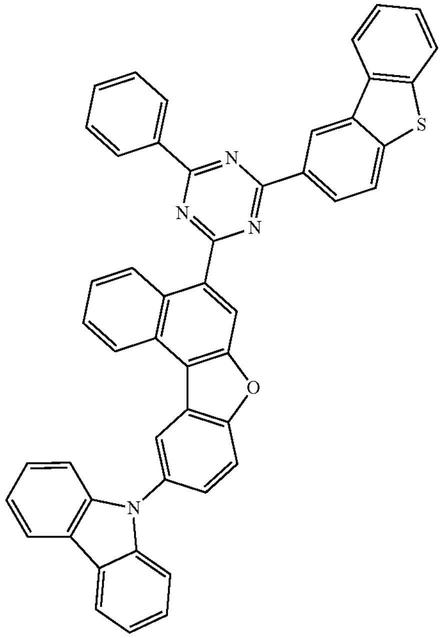
F337
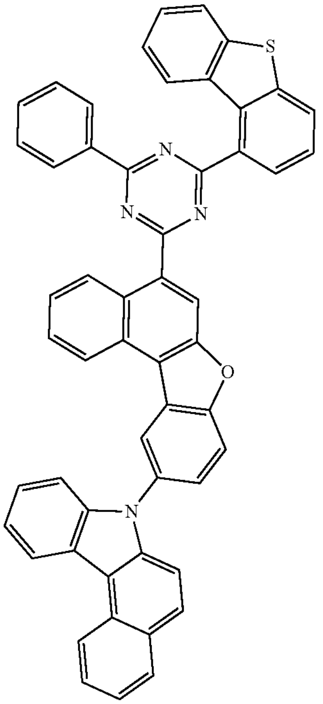
-continued
F338
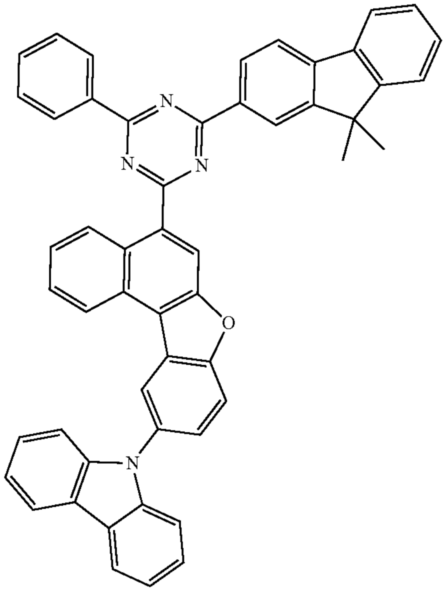
F339
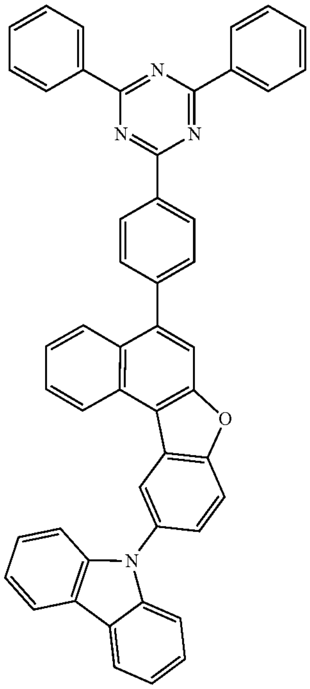

-continued
F340
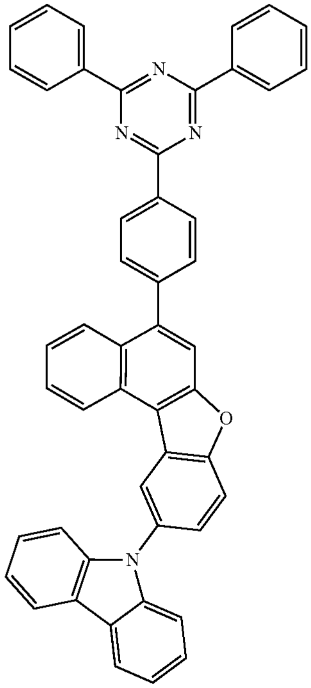
F341
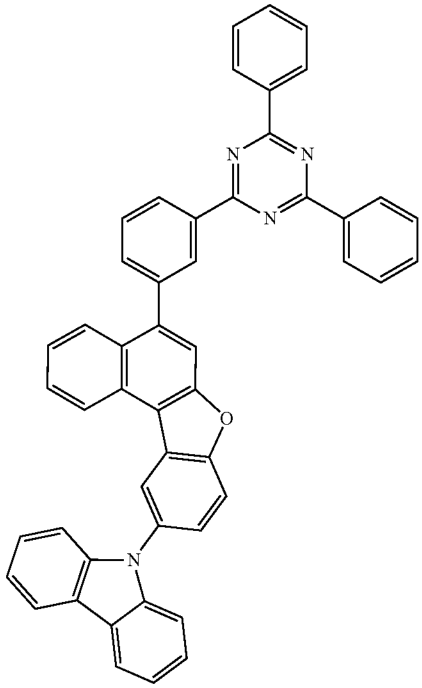
-continued
F342
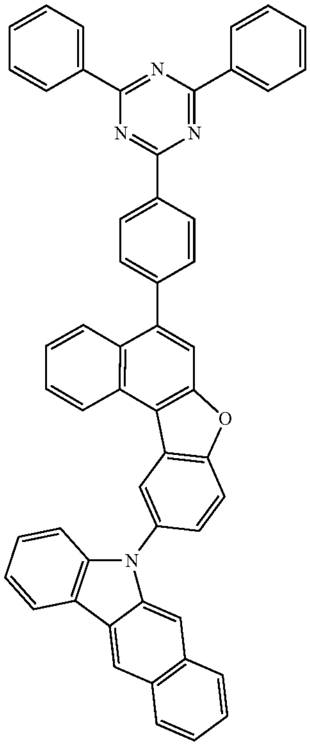
F343
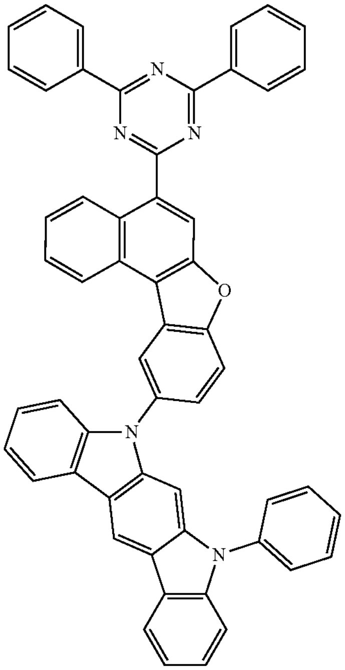

-continued
F344
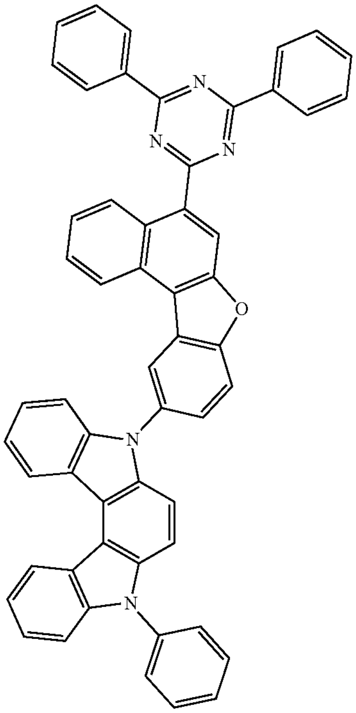
F345
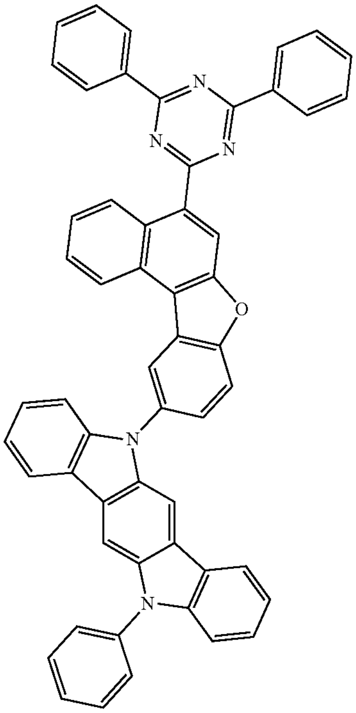
-continued
F346
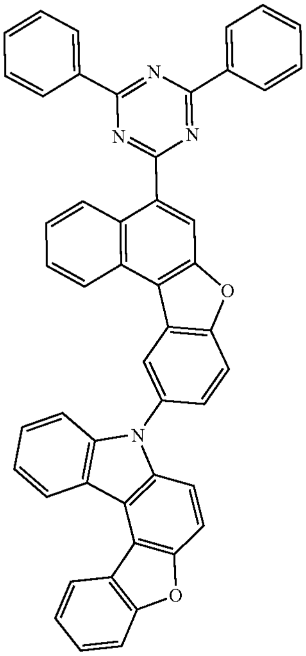
F347
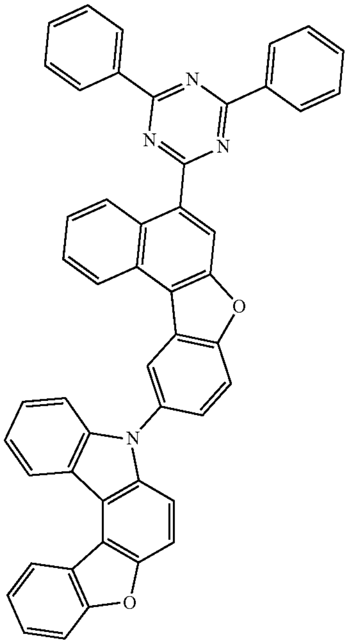

-continued
F348
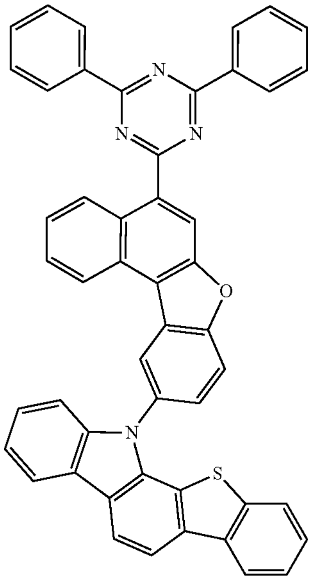
F349
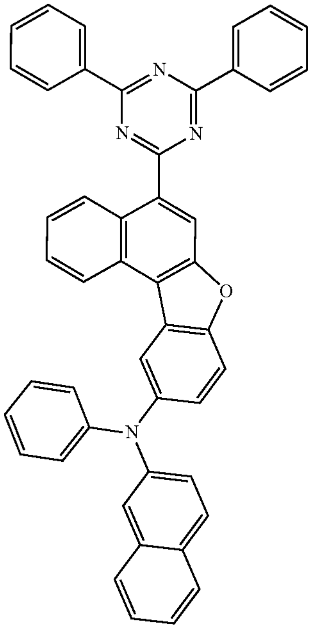
-continued
F350
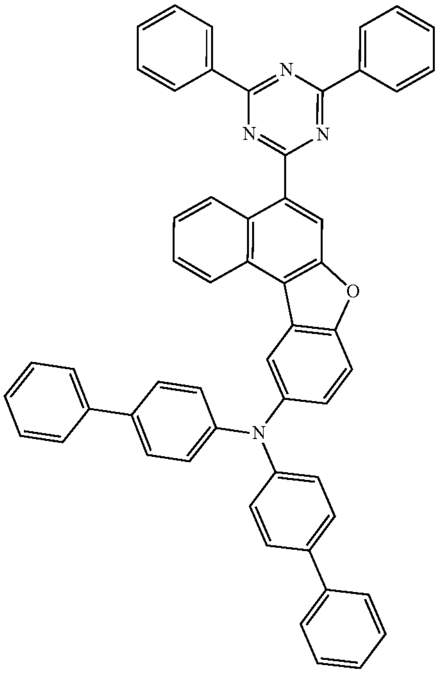
F351
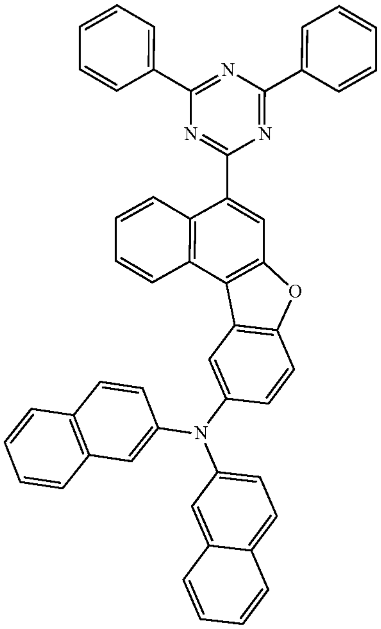

-continued
F352
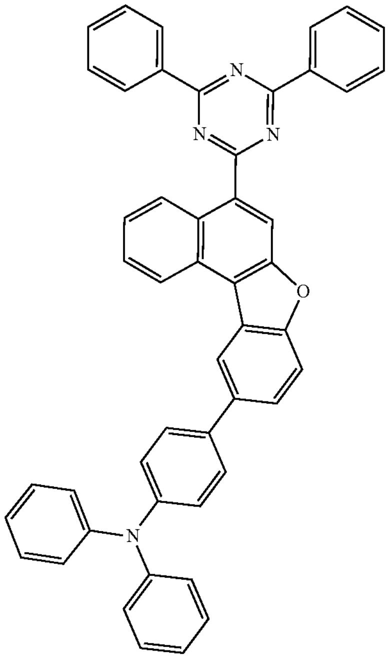
F353
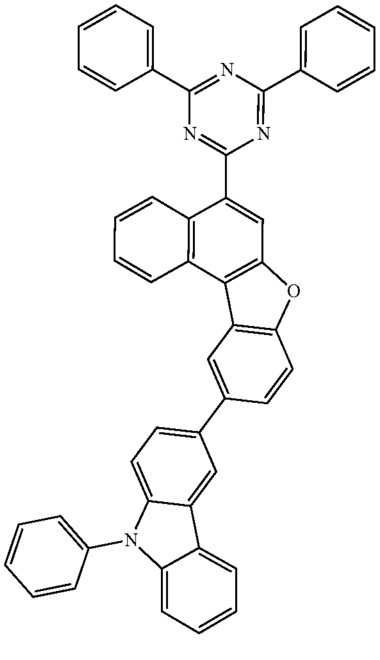
-continued
F354
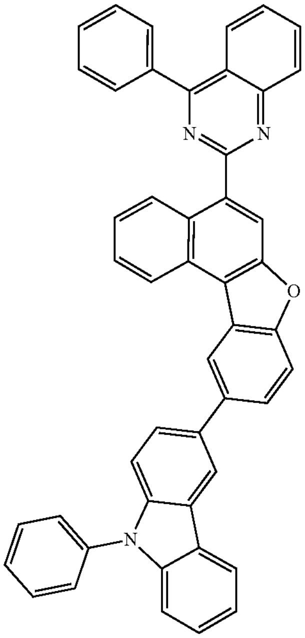
F355
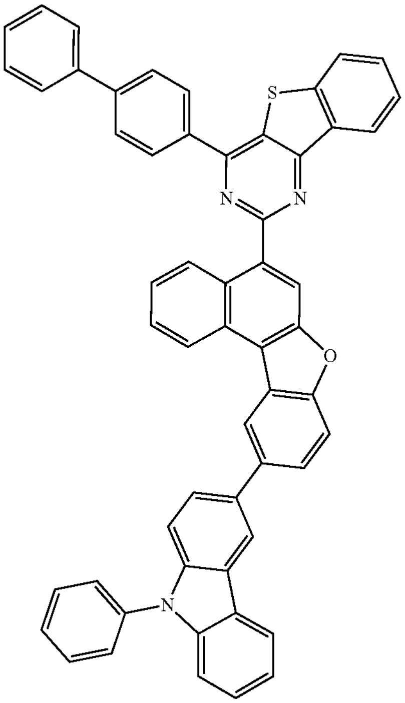

F356
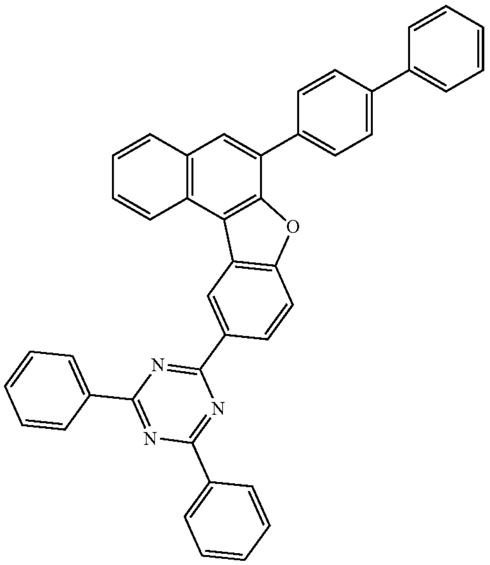
F357
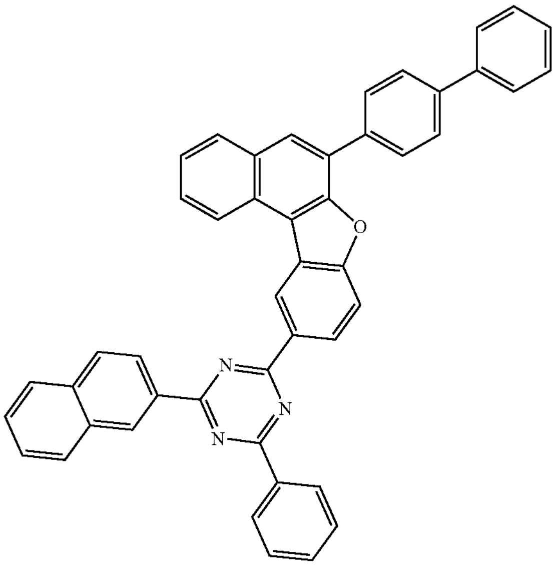
F358
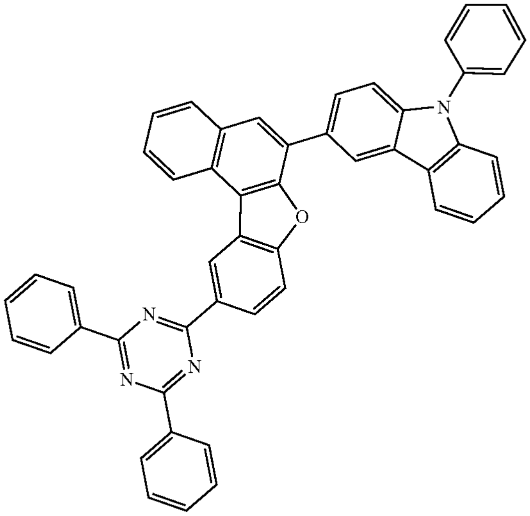
F359
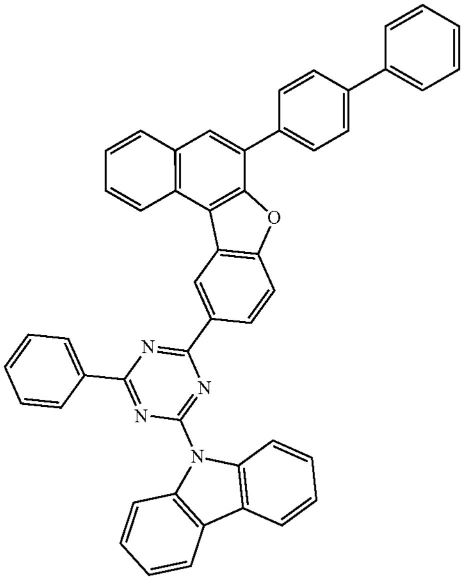

-continued
F360
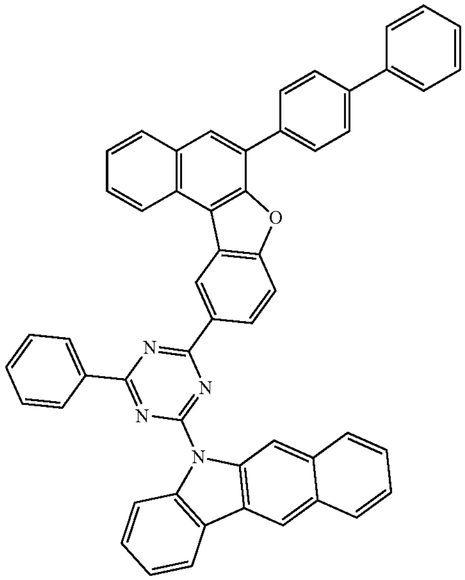
F361
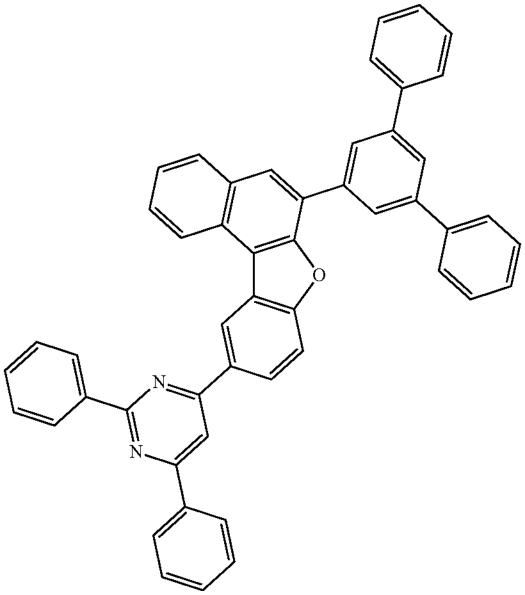
F362
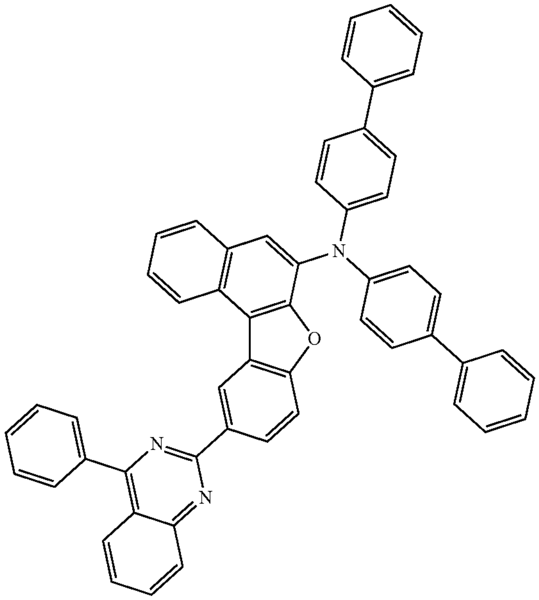

-continued
F363
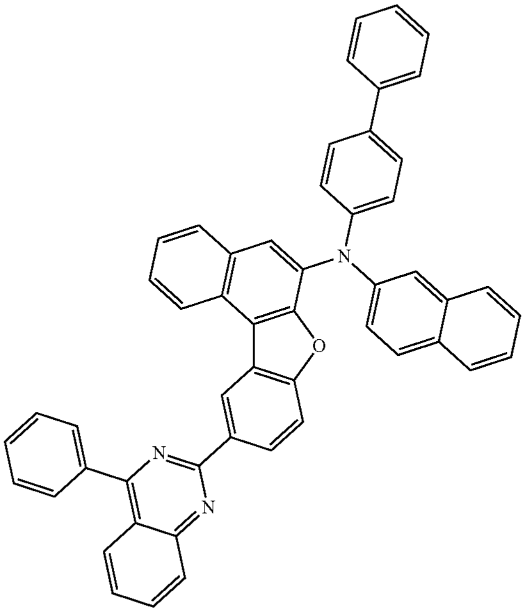
F364
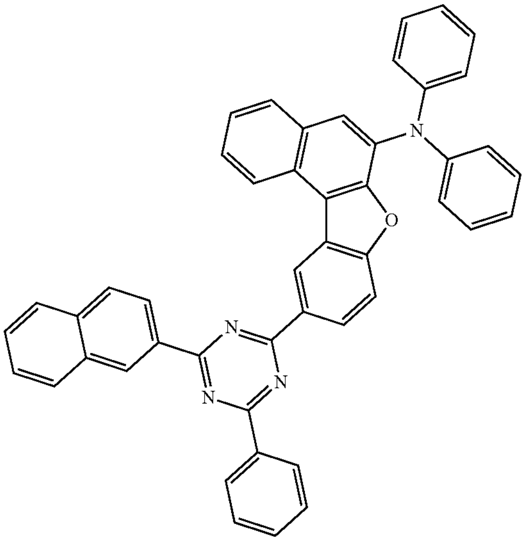
F365
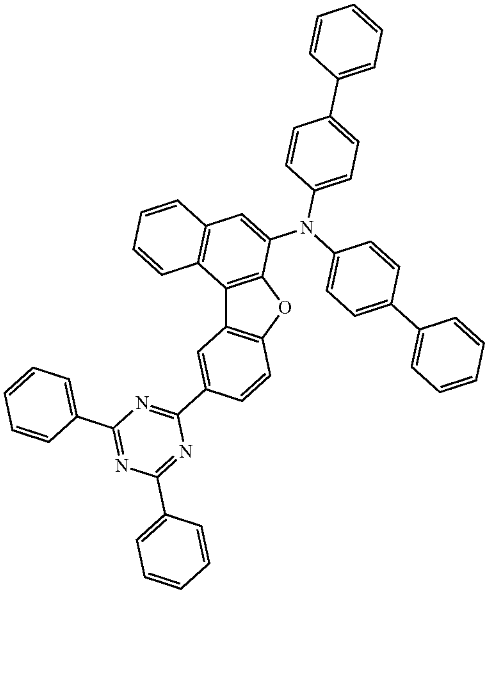
F366
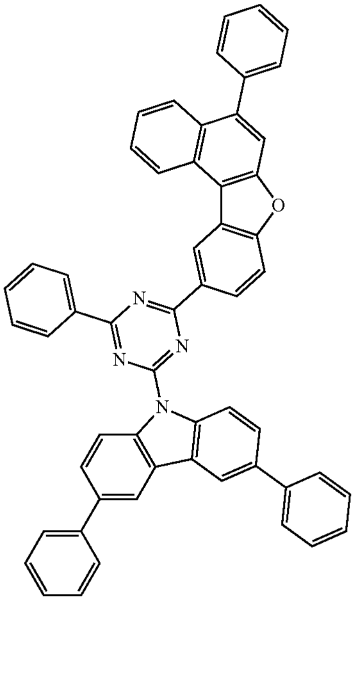

-continued
F367
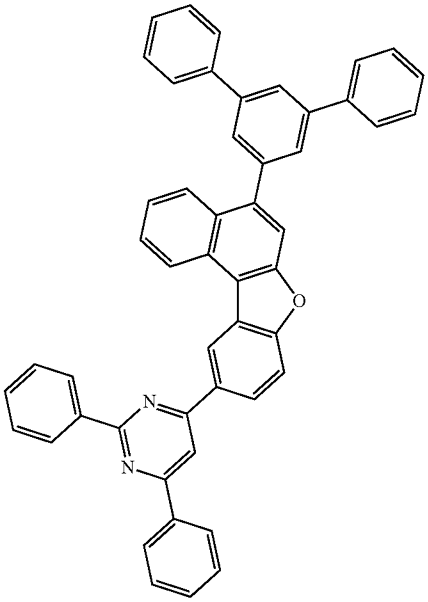
F368
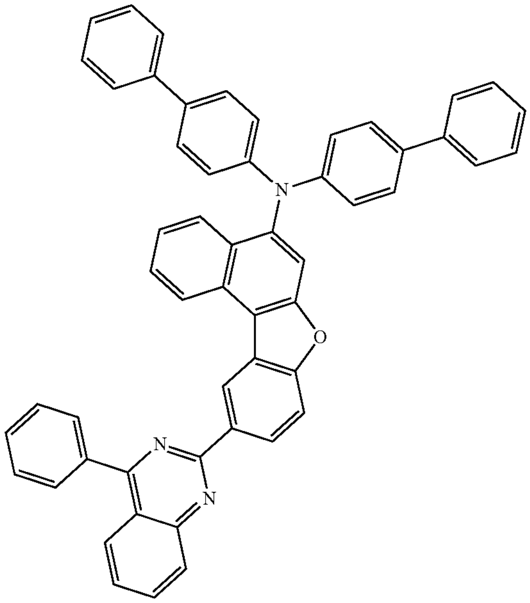
F369
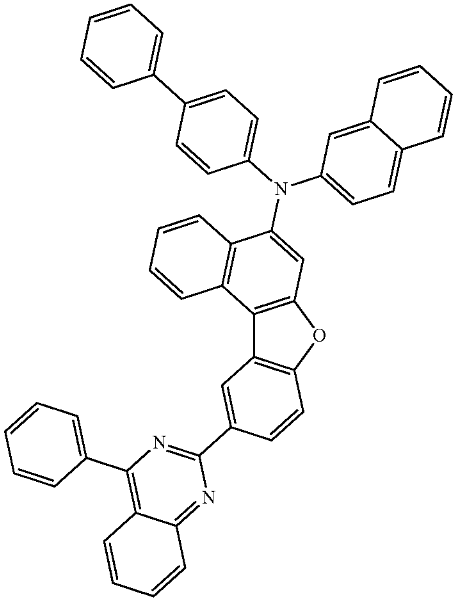
F370
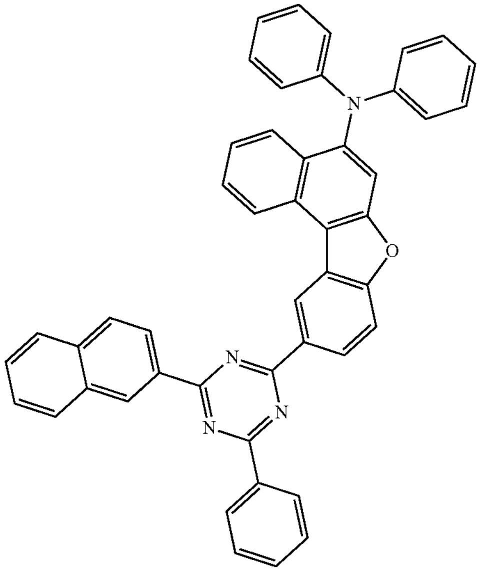

-continued
F371
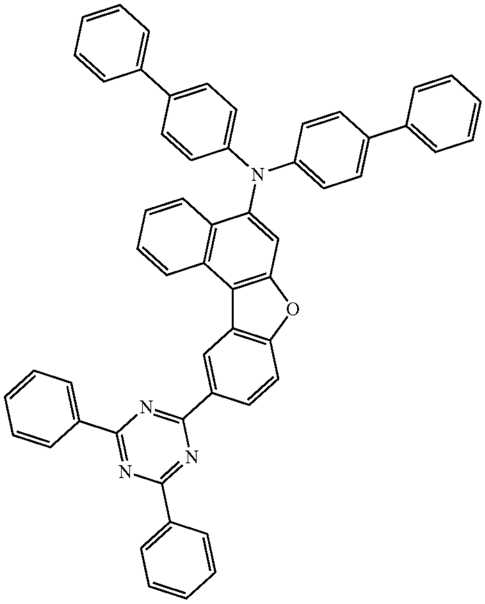
F372
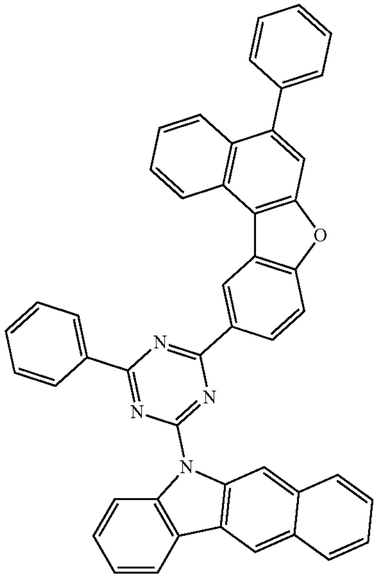
F373
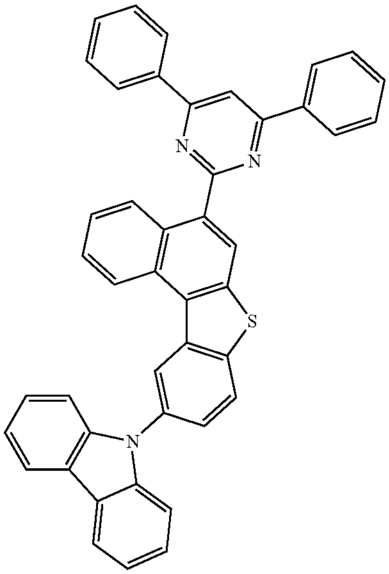
F374
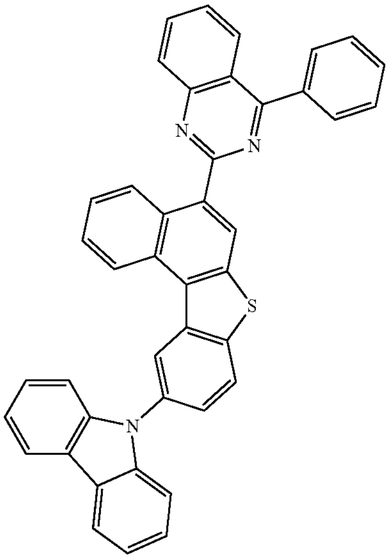

-continued
F375
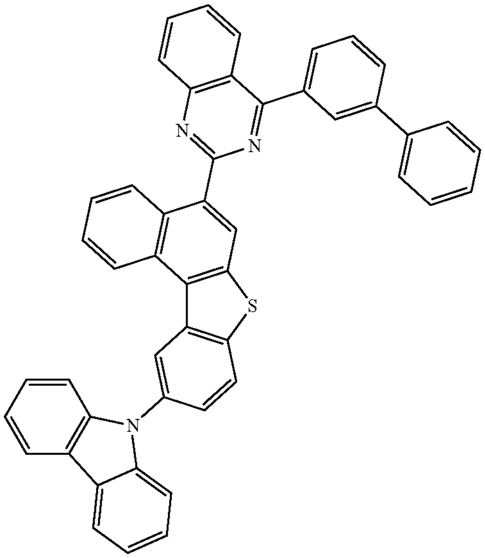
F376
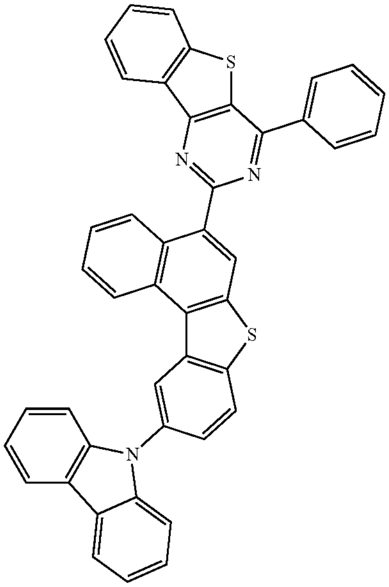
F377
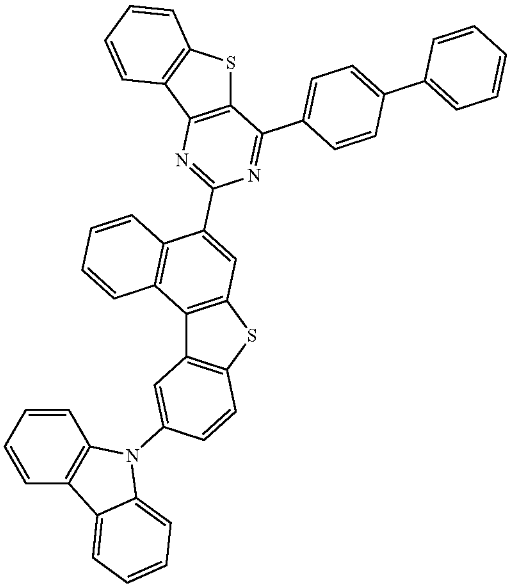
F378
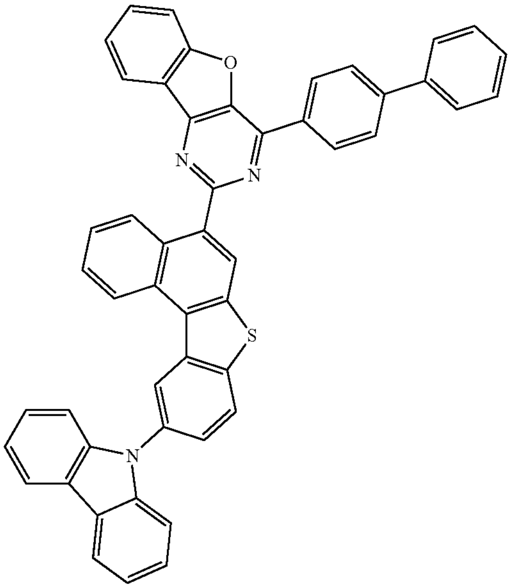

-continued
F379
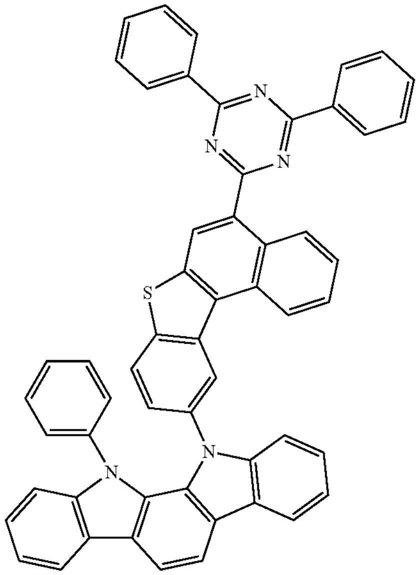
F380
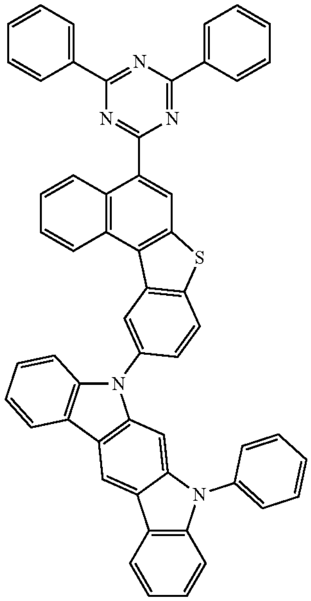
F381
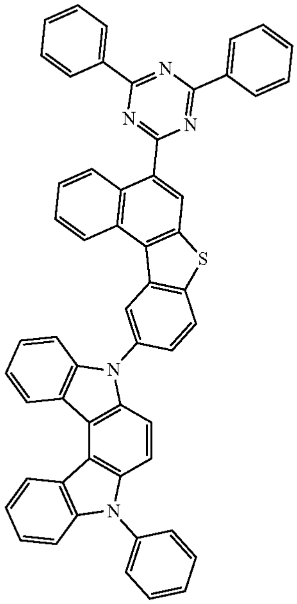
F382
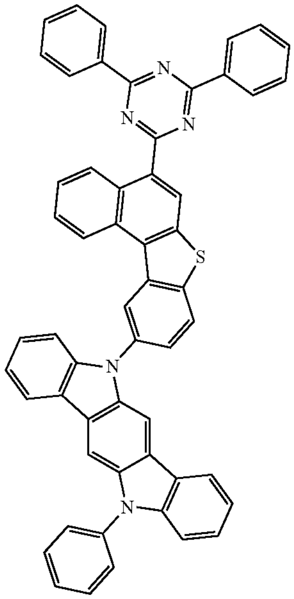

-continued
F383
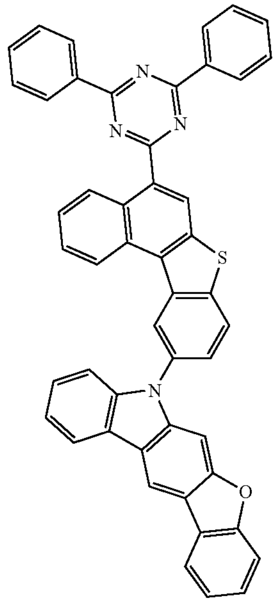
F384
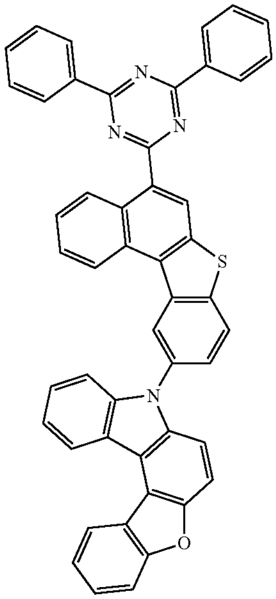
F385
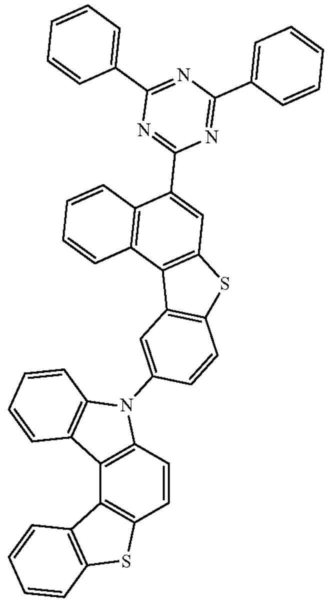
F386
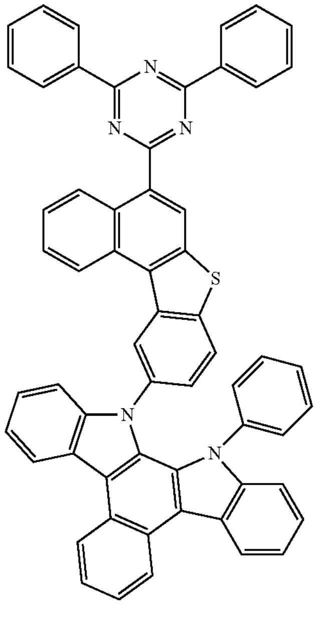

-continued
F387
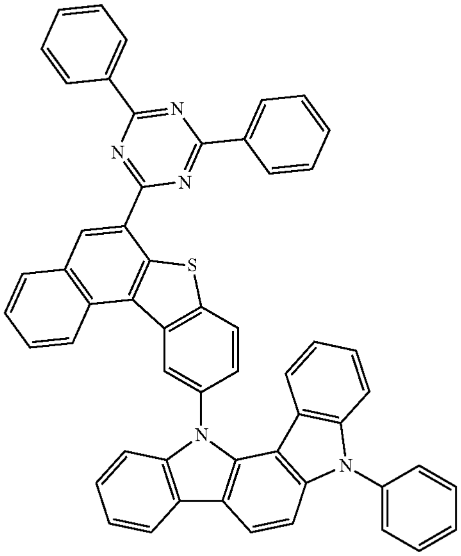
F388
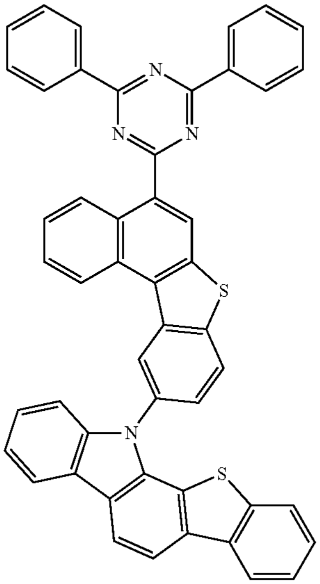
F389
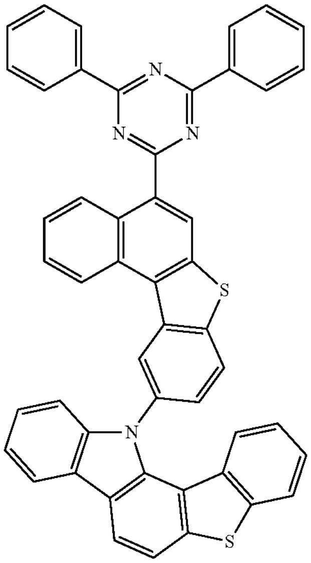
F390
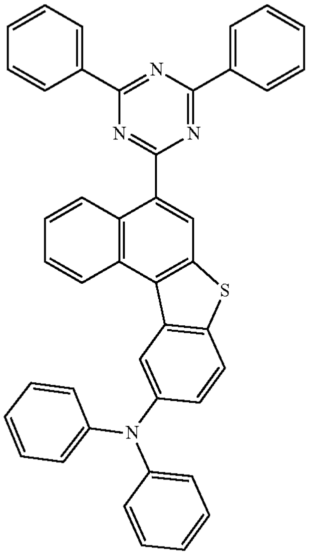

-continued
F391
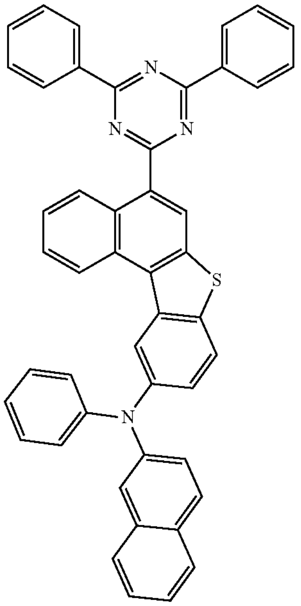
F392
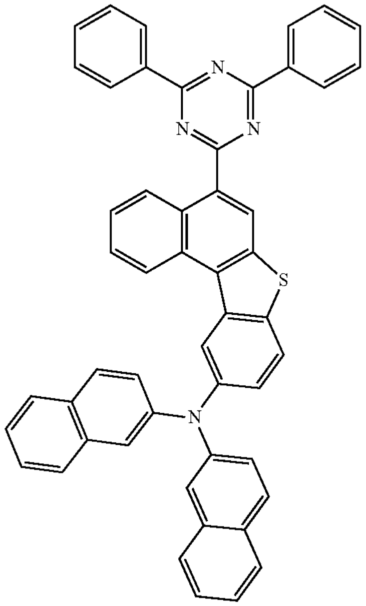
F393
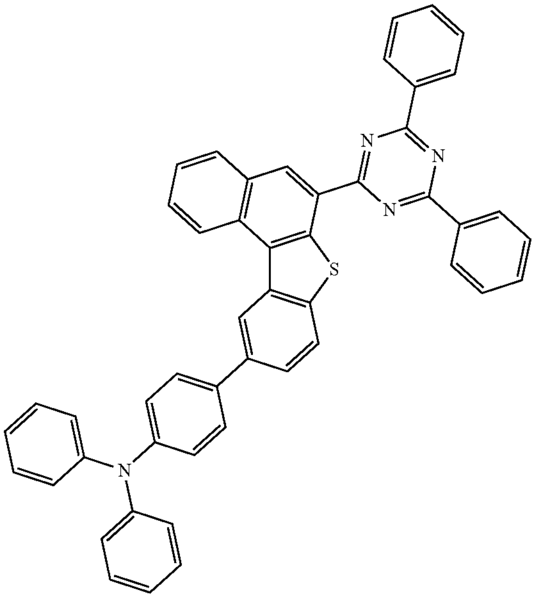
F394
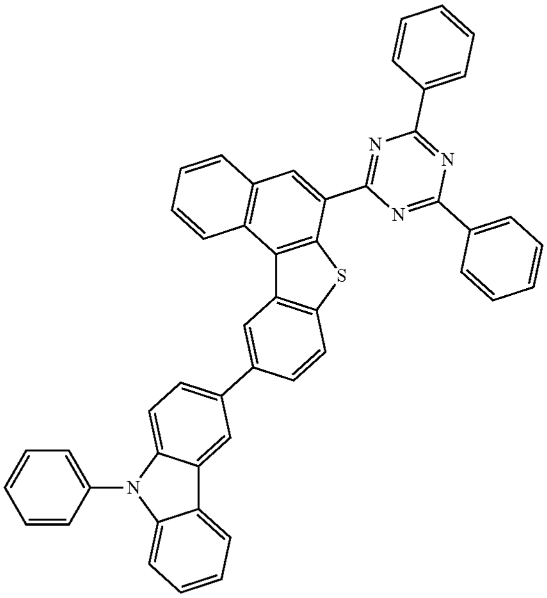

-continued
F395
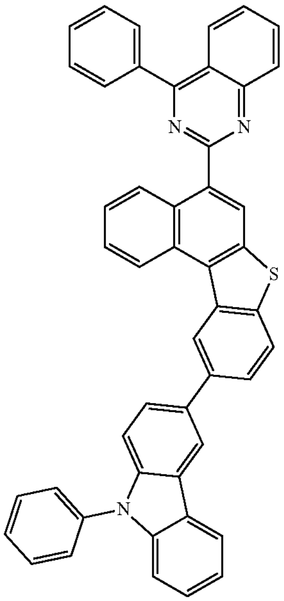
F396
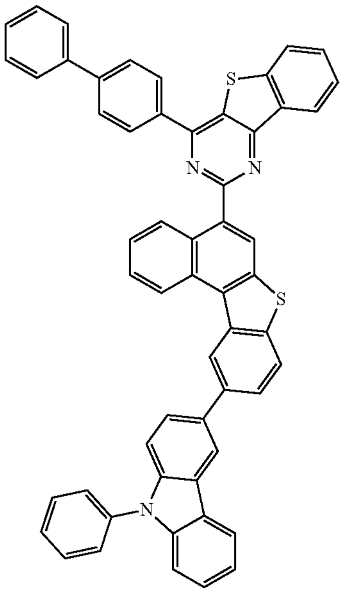
F397
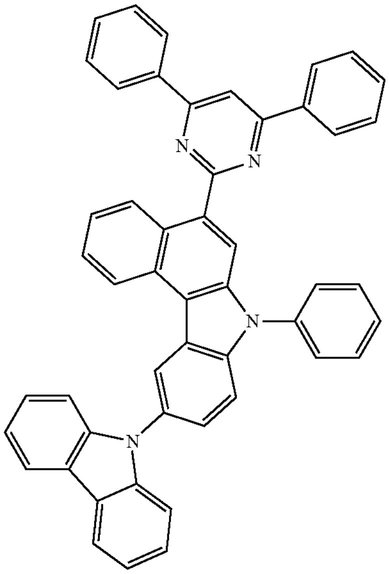
F398
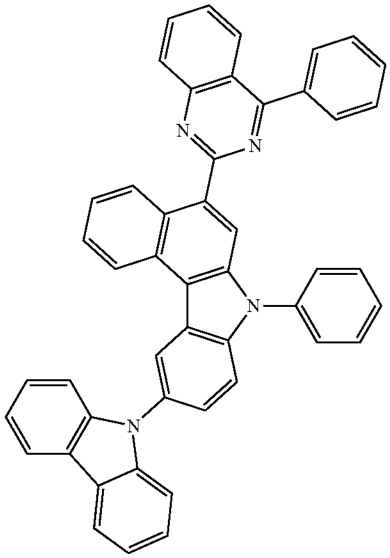

-continued
F399
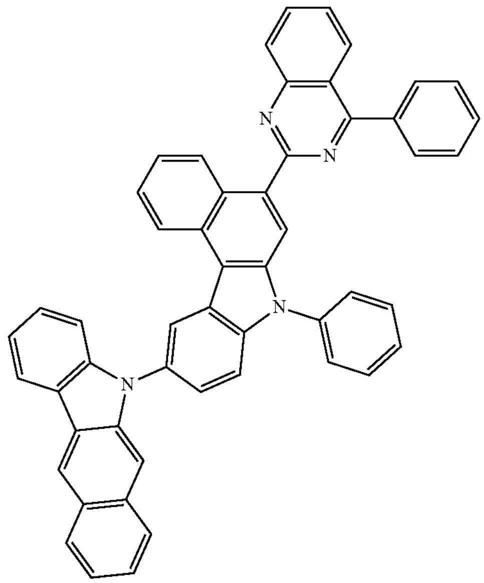
F400
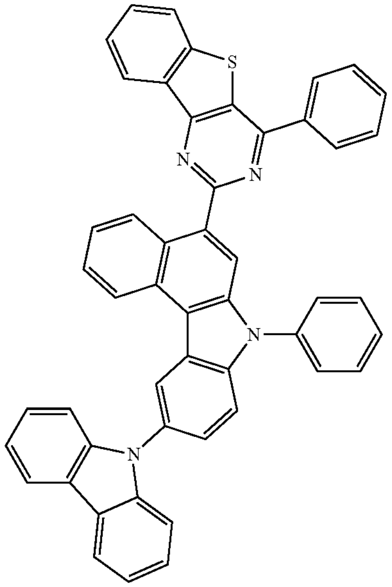
F401
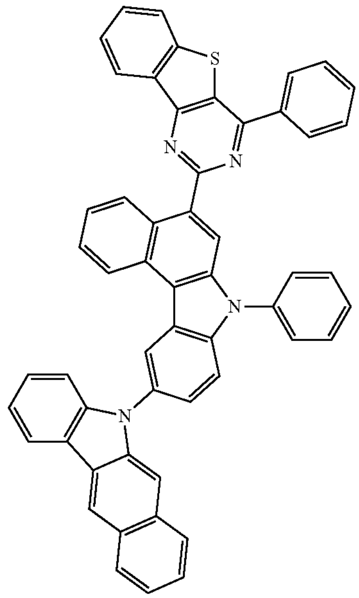
F402
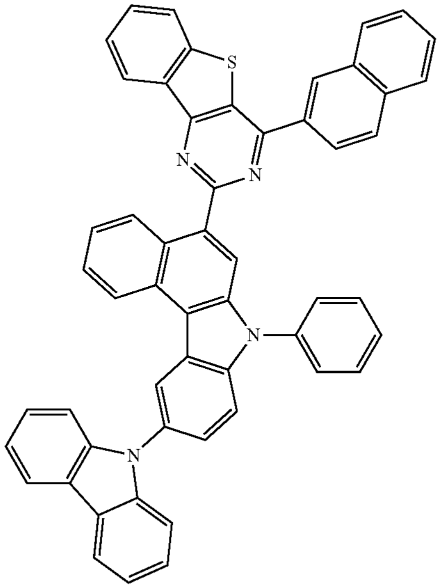

-continued
F403
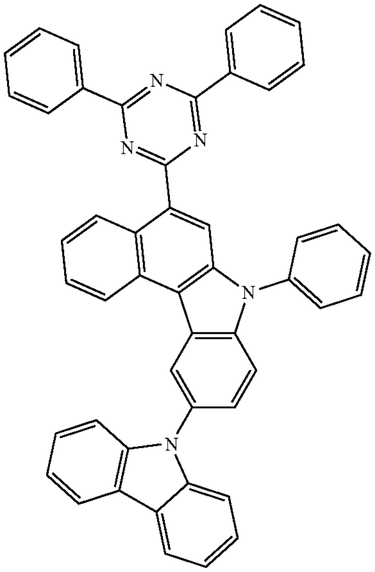
F404
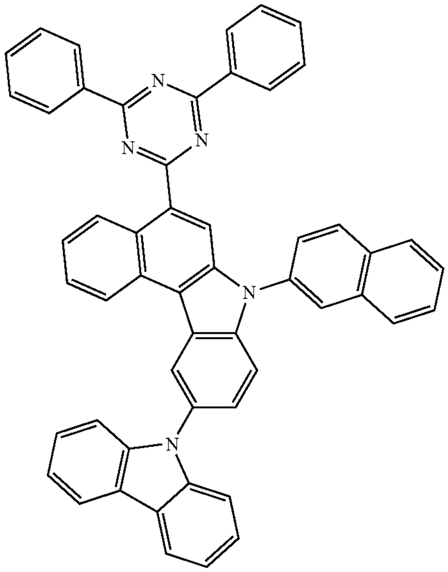
F405
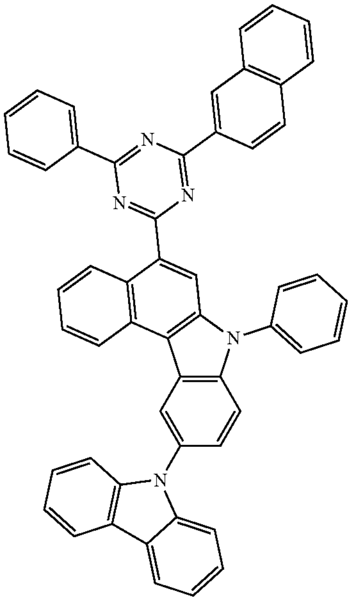
F406
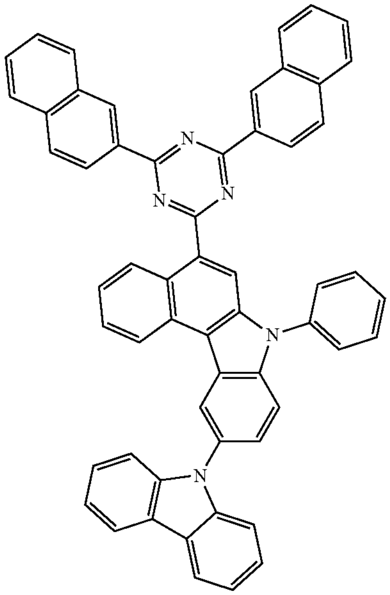

-continued
F407
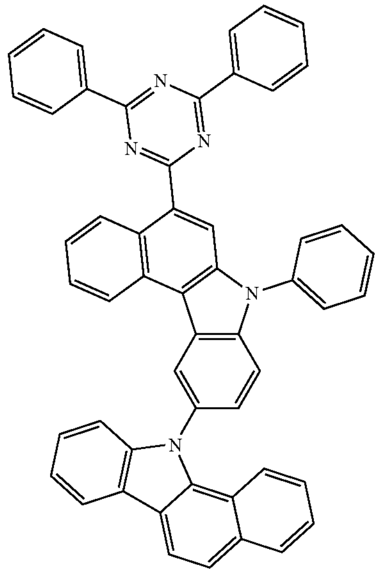
F408
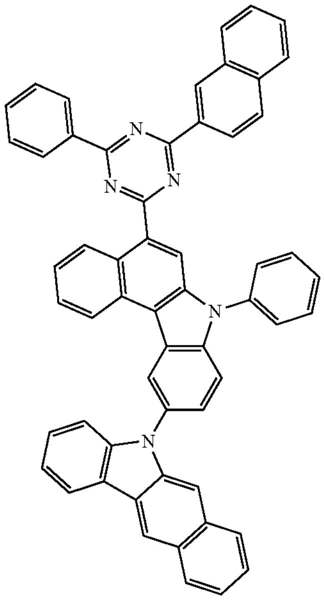
F409
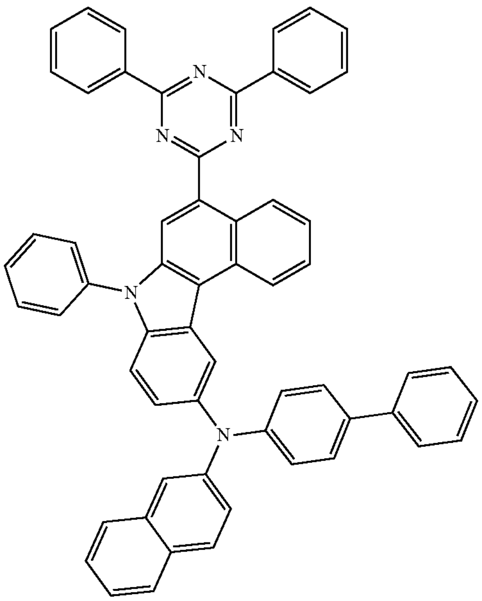
F410
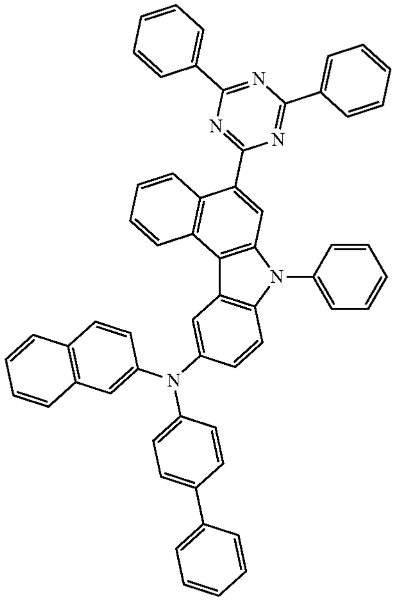

-continued
F411
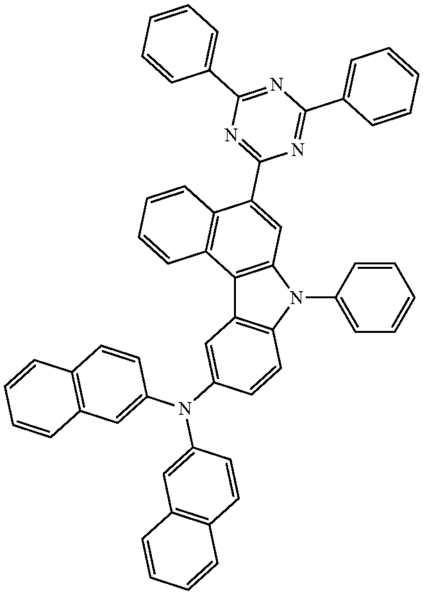
F412
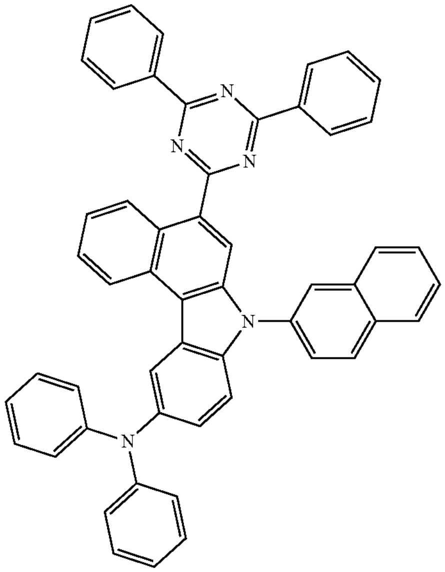
F413
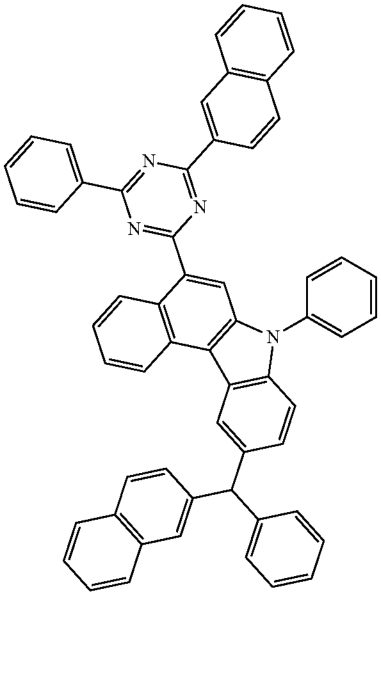
F414
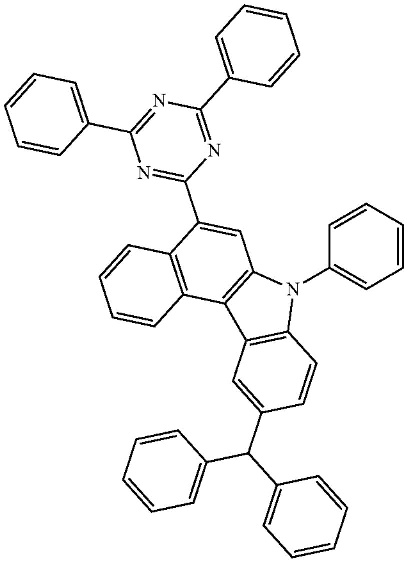

-continued
F415
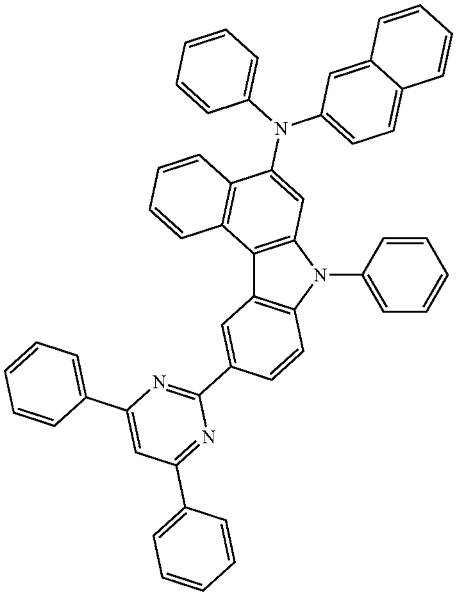
F416
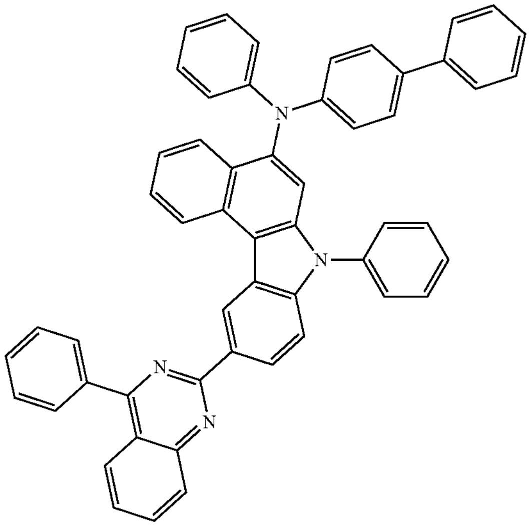
F417
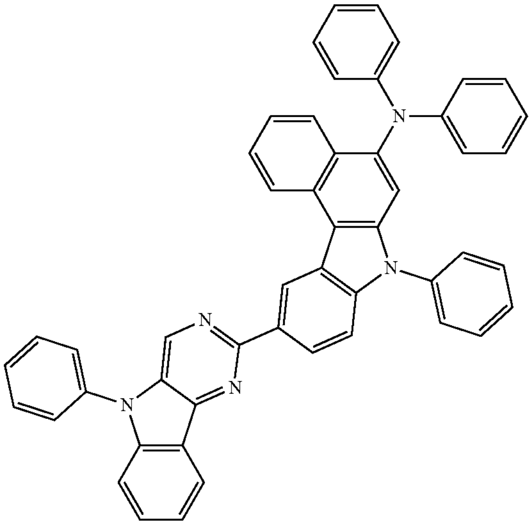
F418
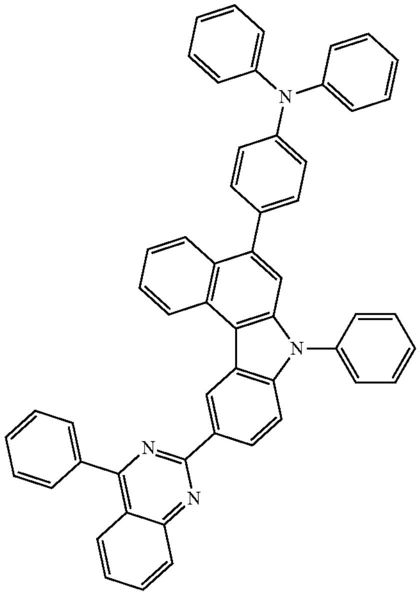

-continued
F419
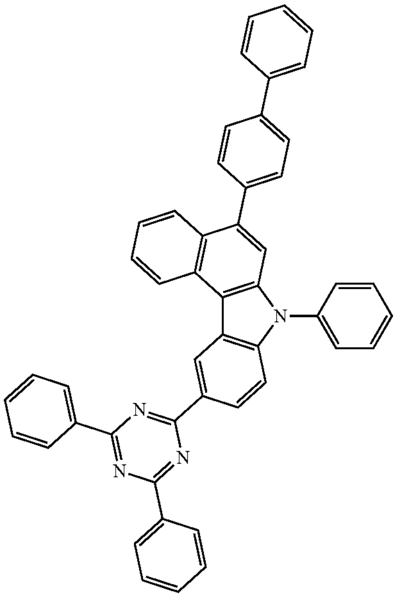
F420
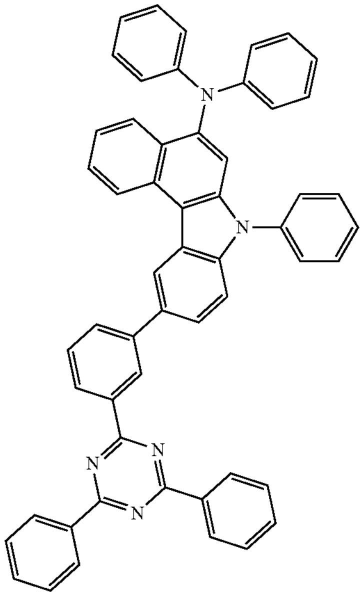
F421
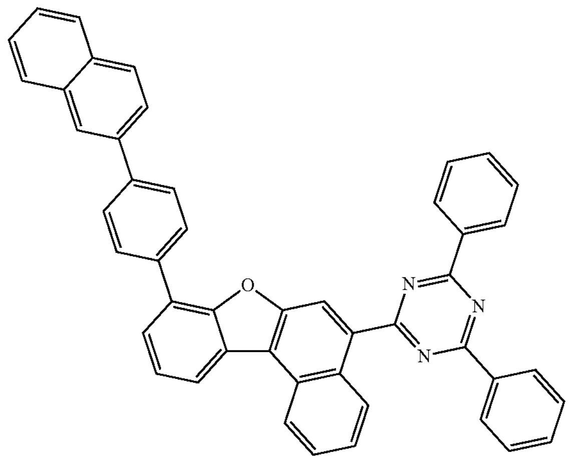
F222
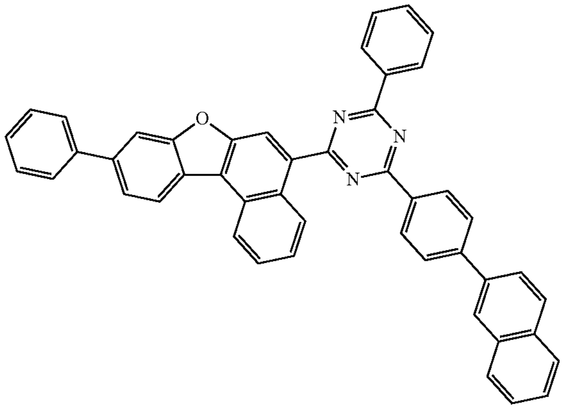
F423
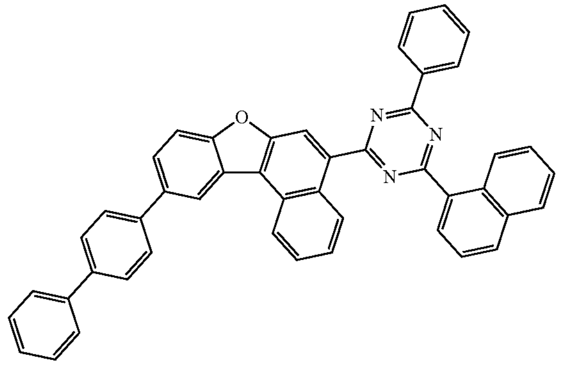
F424
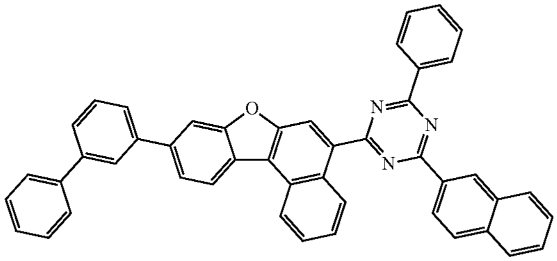

-continued
F425
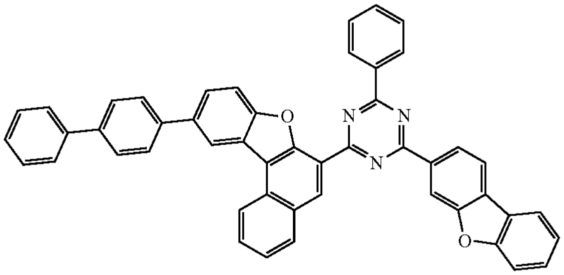
F426
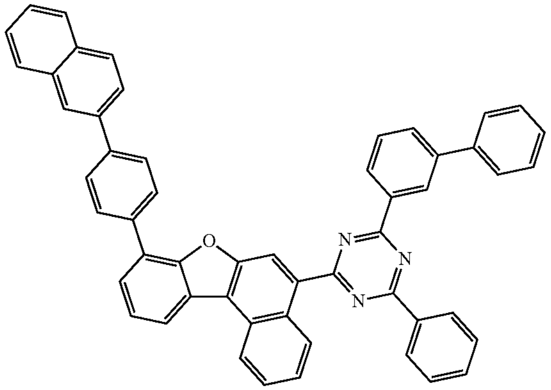
F427
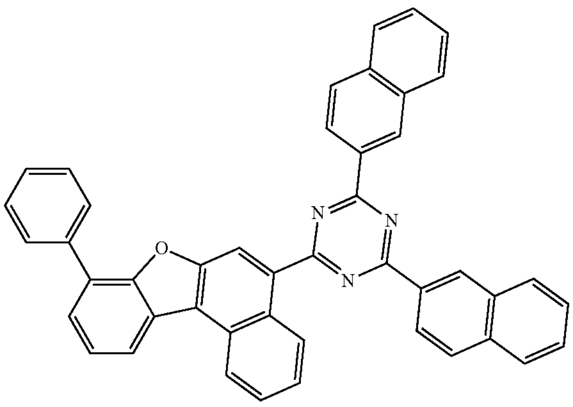
F428
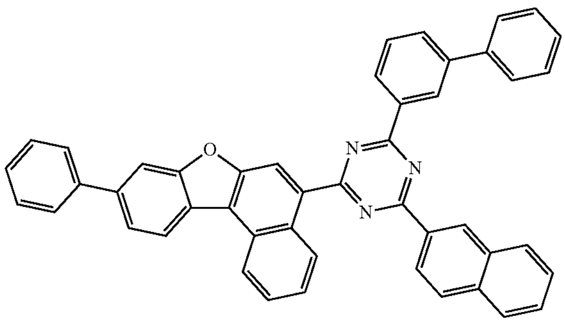
F429
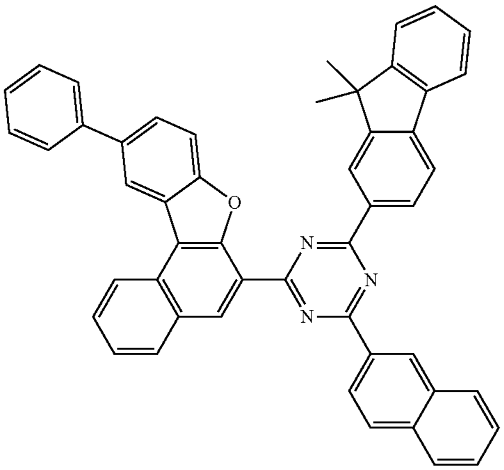
F430
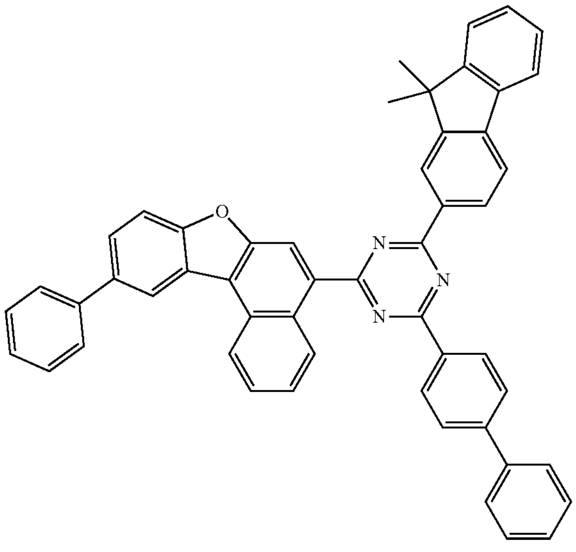

-continued
F431
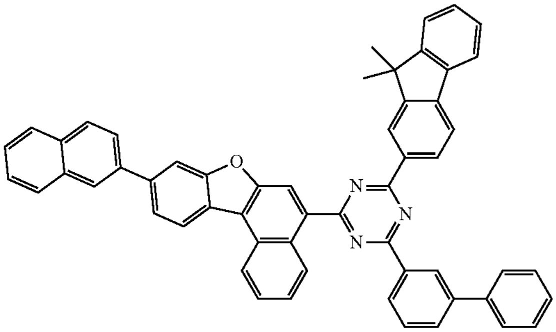
F432
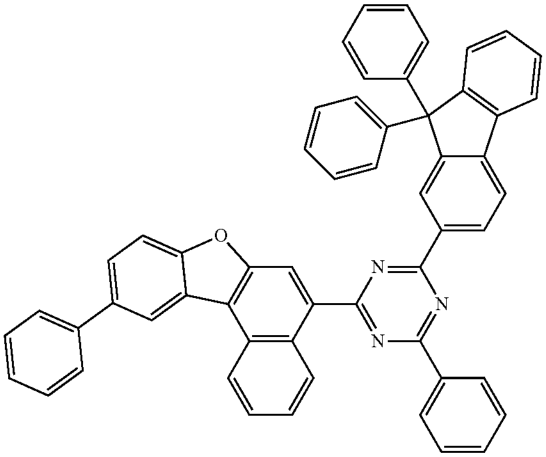
F433
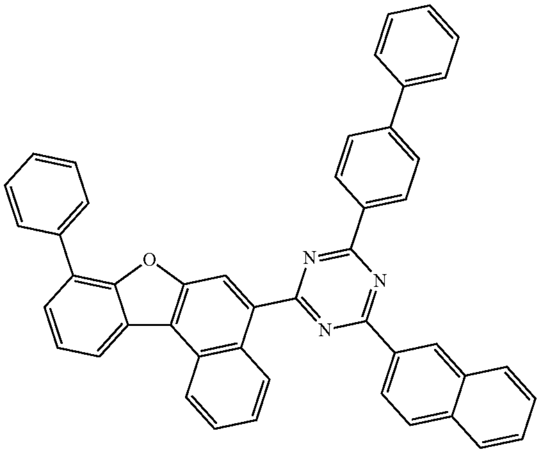
F434
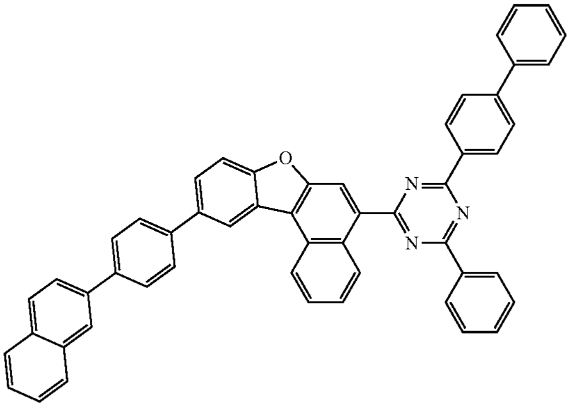
F435
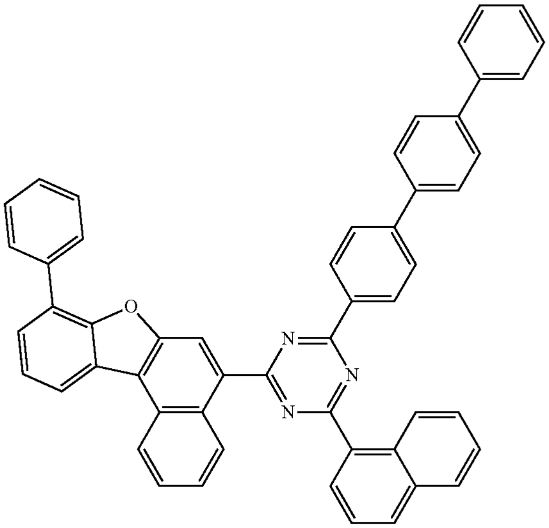
F436
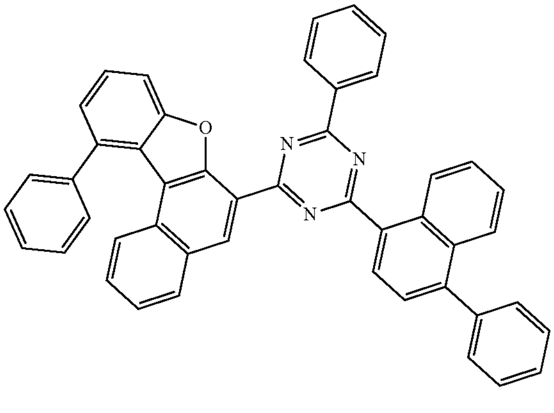

-continued
F437
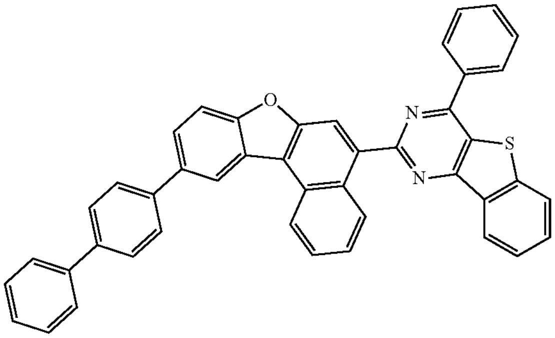
F438
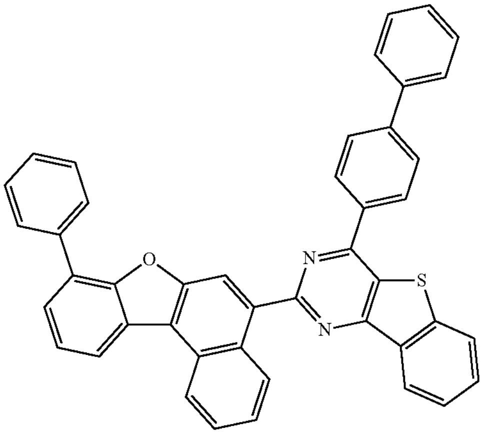
F439
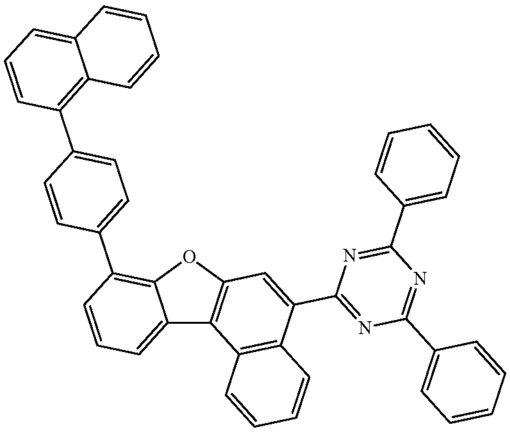
F440
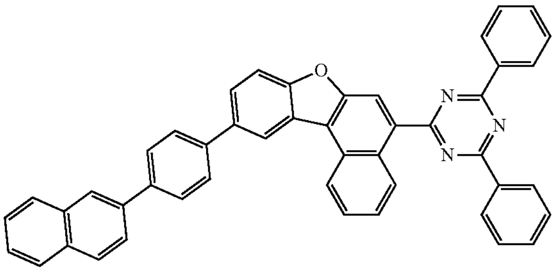
F441
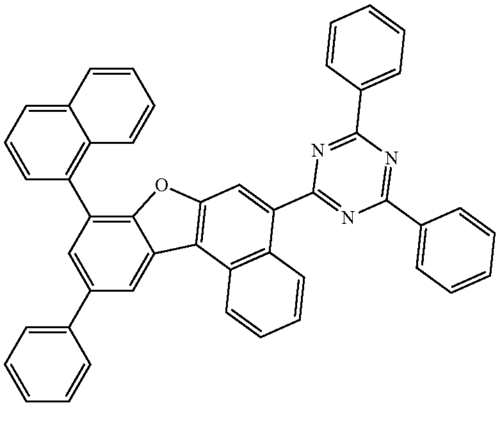
F442
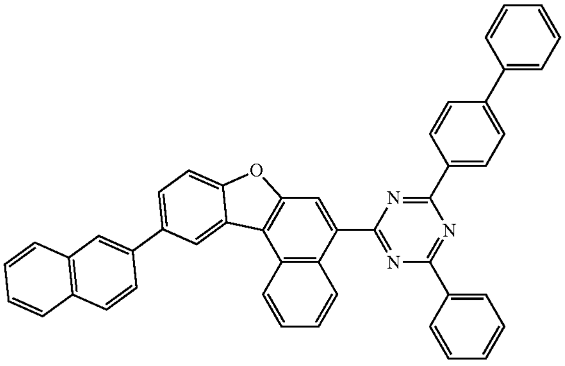

-continued
F443
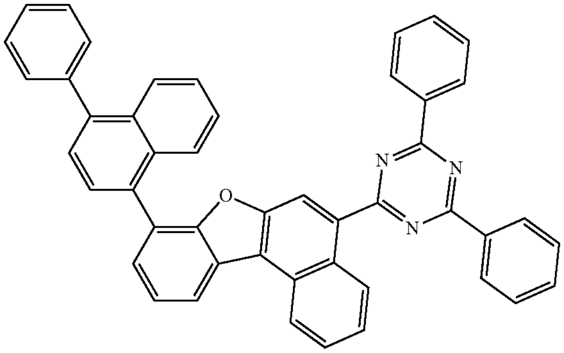
F444
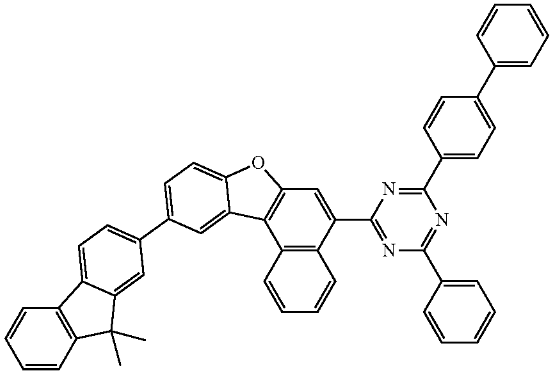
F445
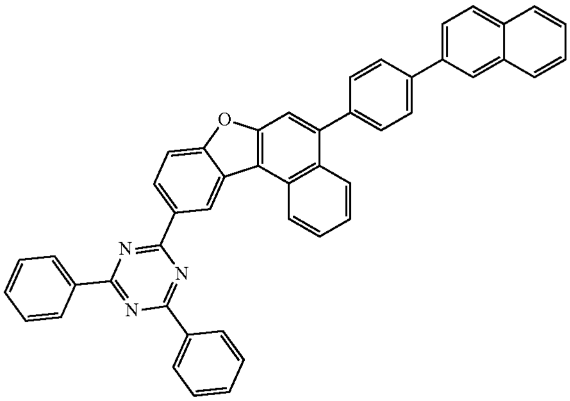
F446
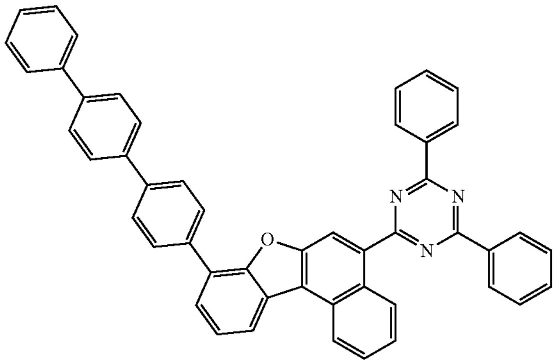
F447
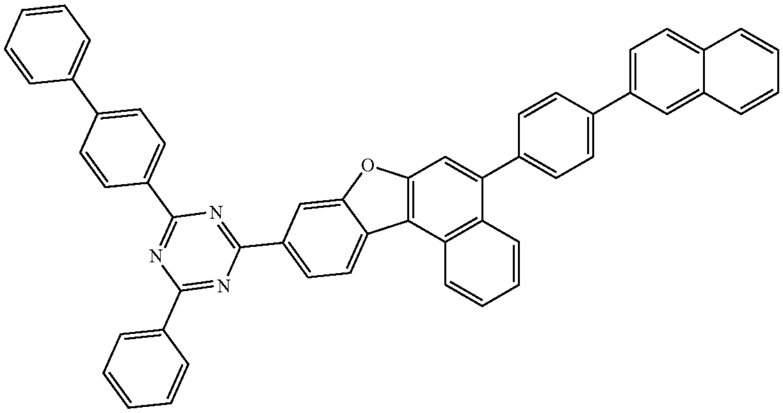

-continued
F448
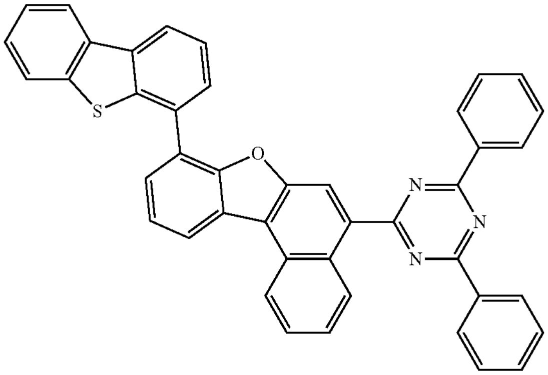
F449
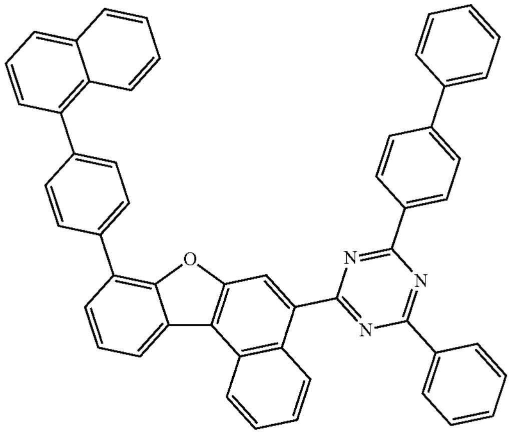
F450
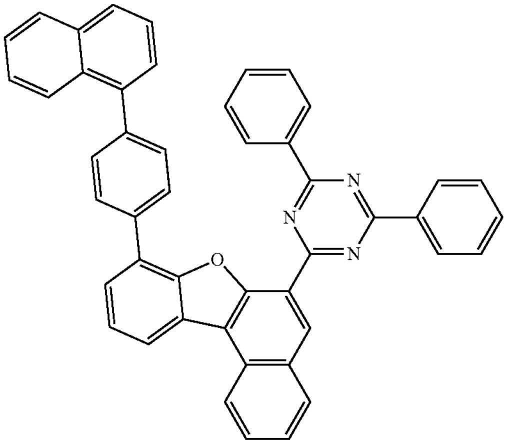
F451
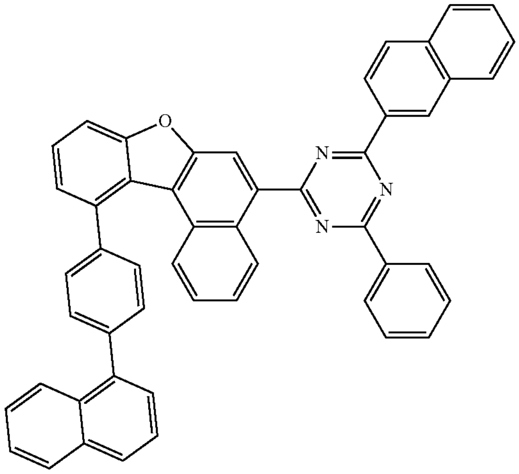
F452
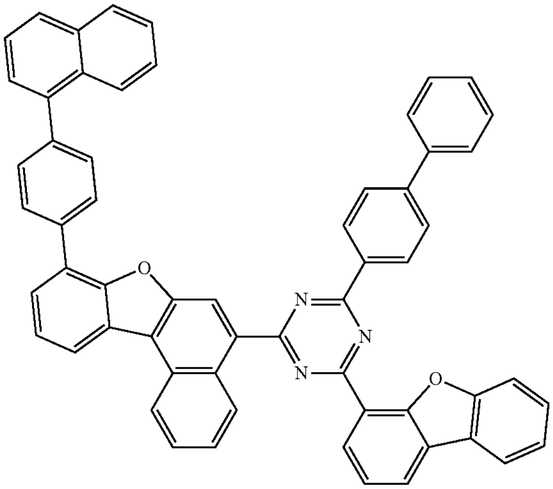
F453
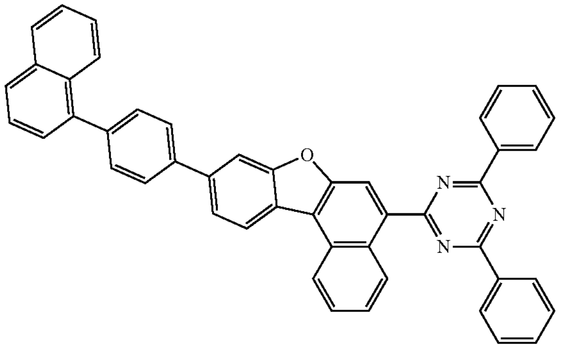

-continued
F454
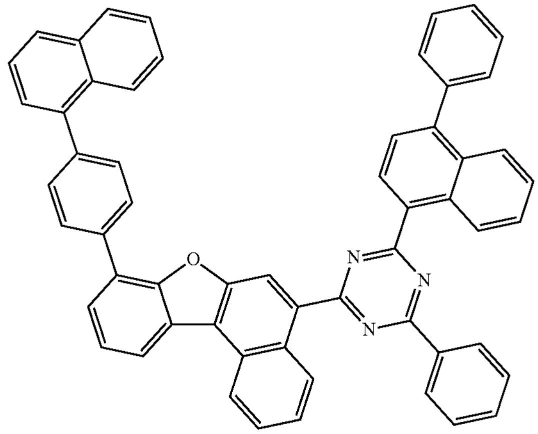
F455
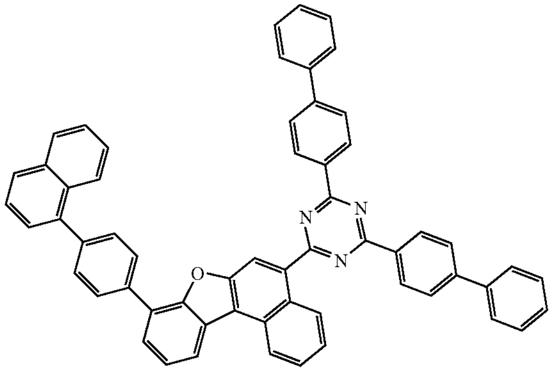
F456
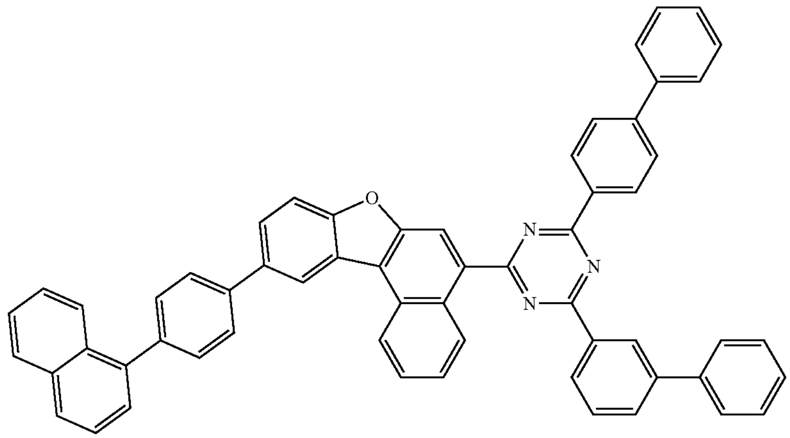
F457
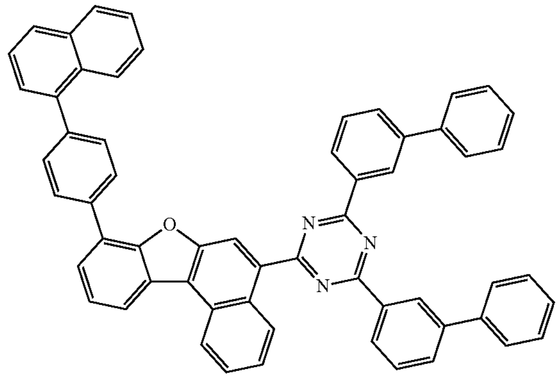
F458
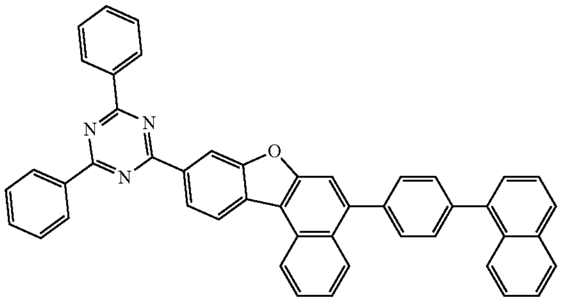

-continued
F459
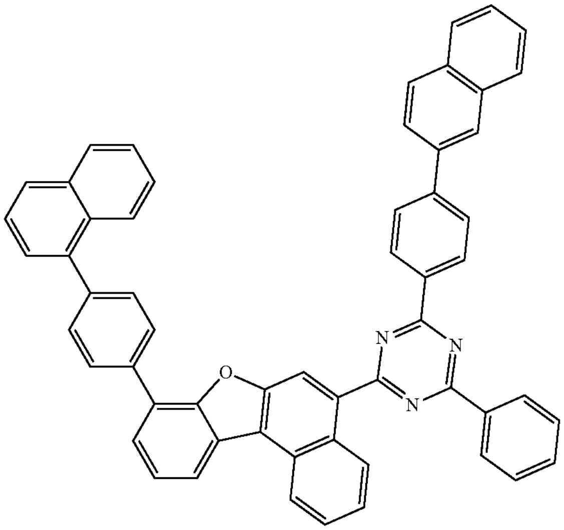
F460
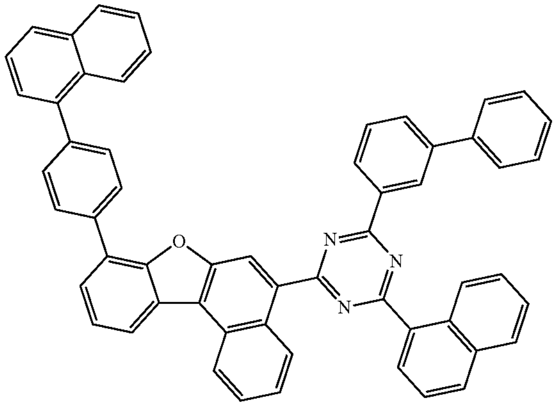
F461
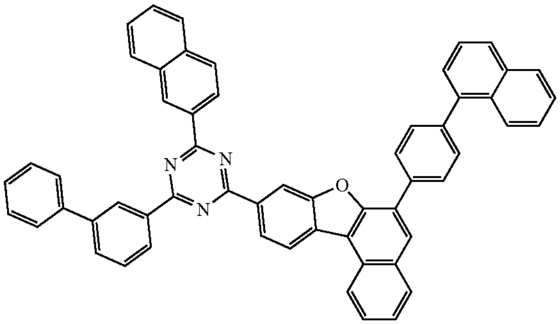
F462
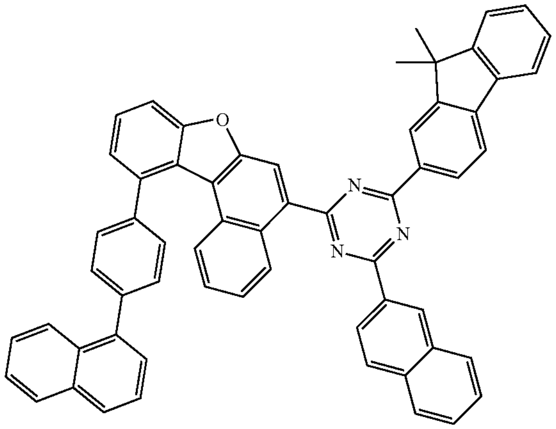
F463
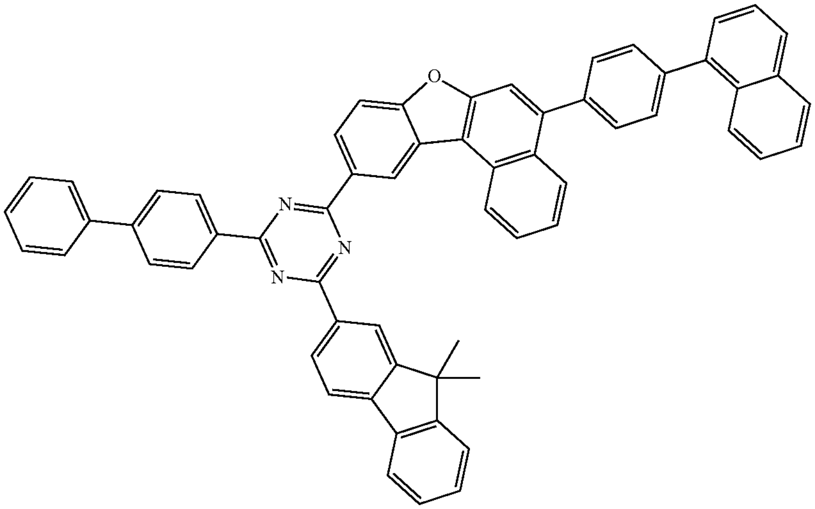

-continued
F464
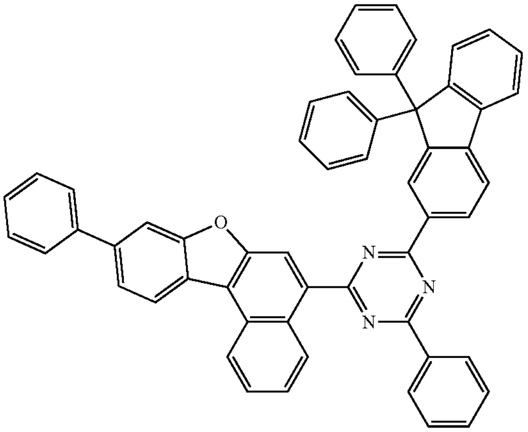
F465
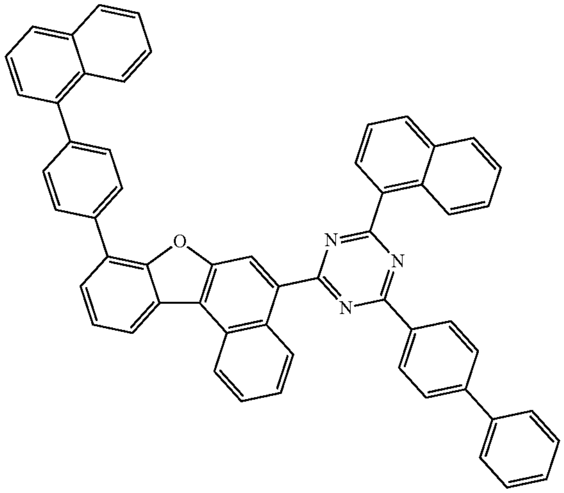
F466
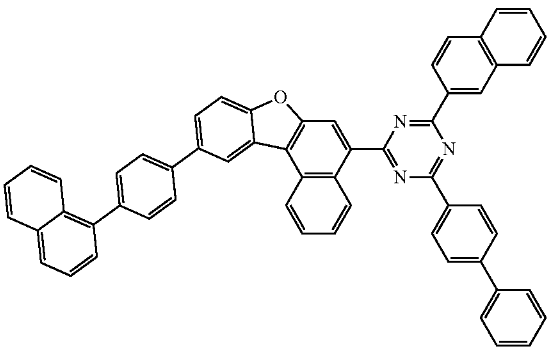
F467
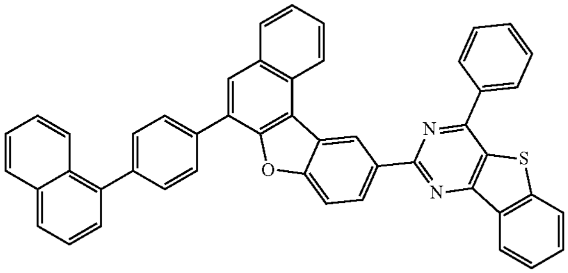
F468
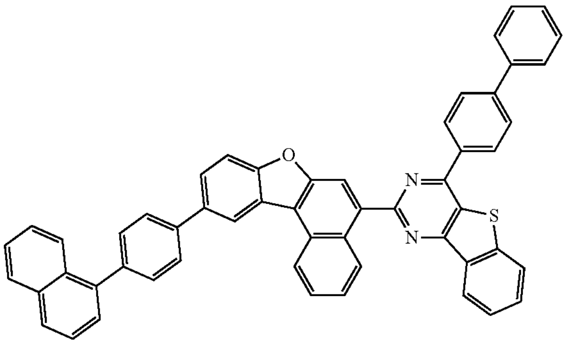
F469
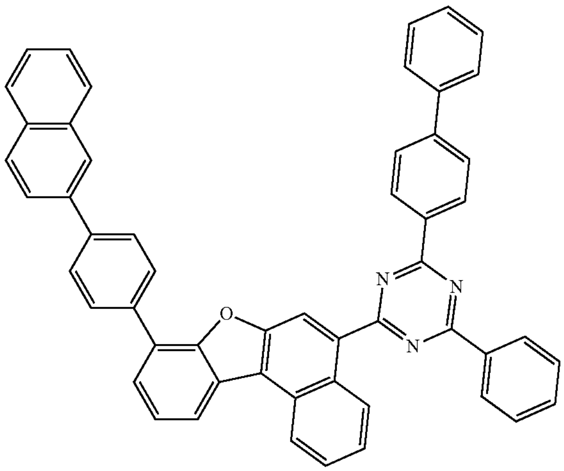

-continued
F470
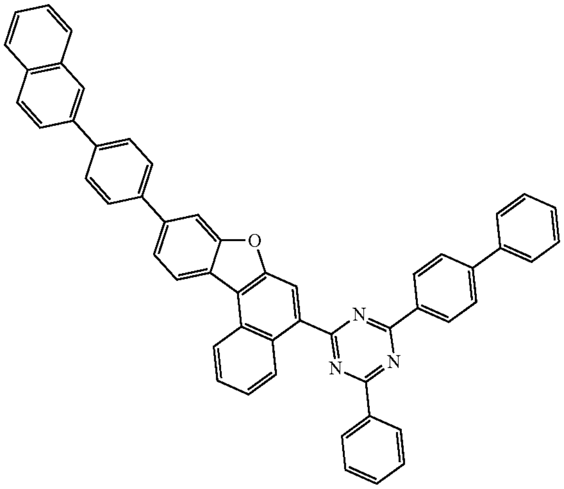
F471
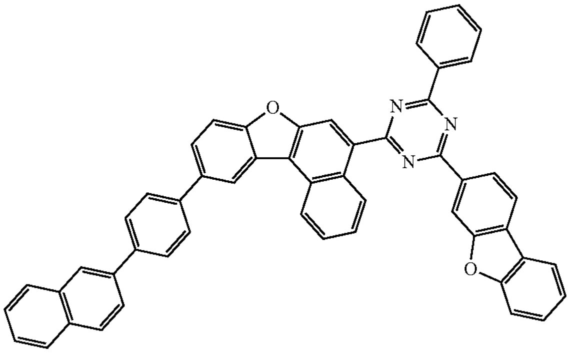
F472
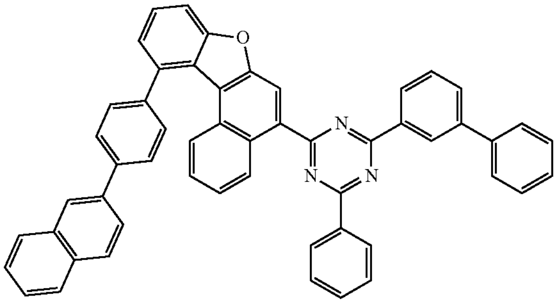
F473
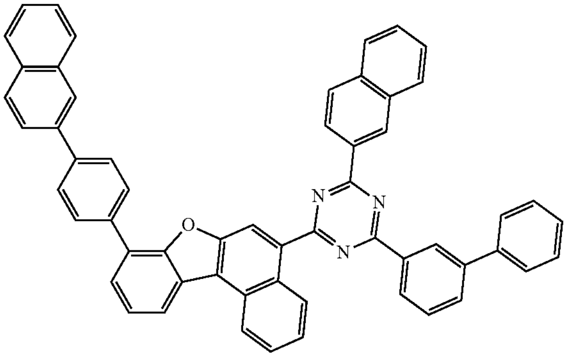
F474
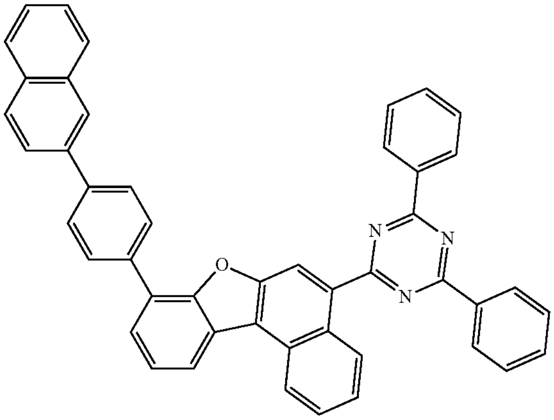
F475
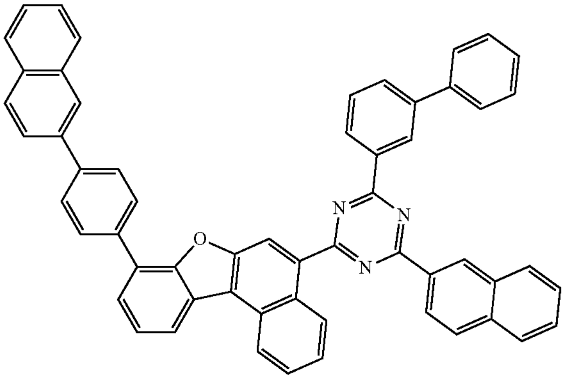

-continued
F476
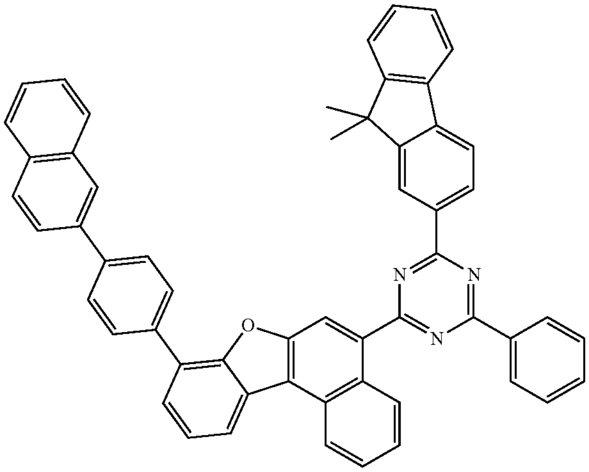
F477
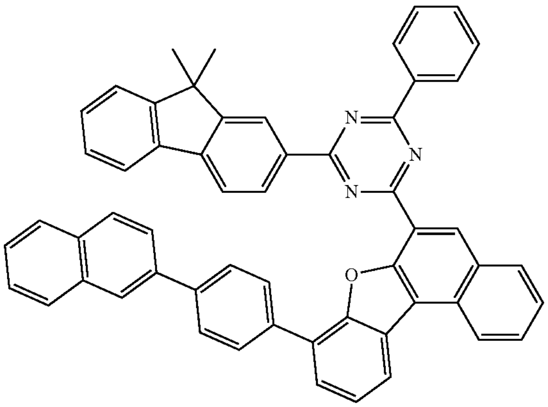
F478
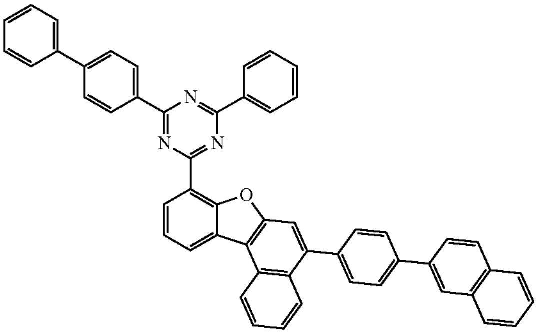
F479
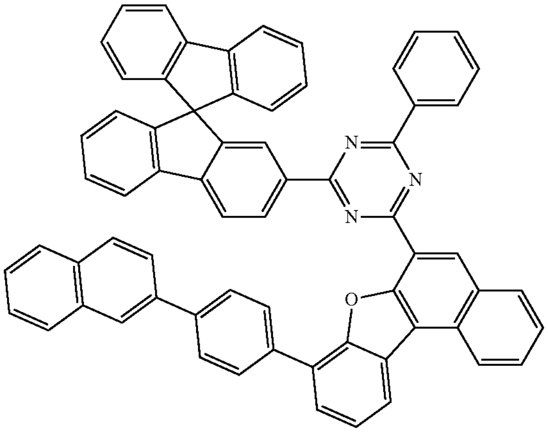
F480
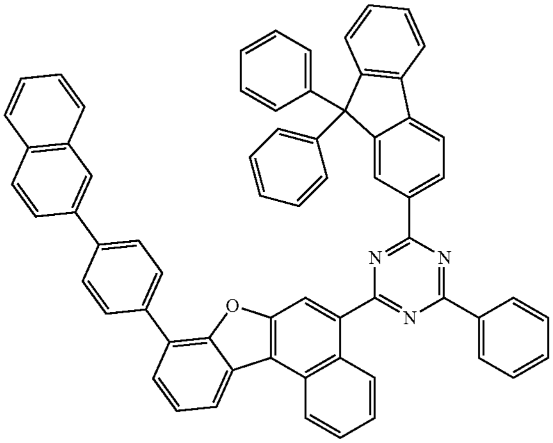

-continued
F481
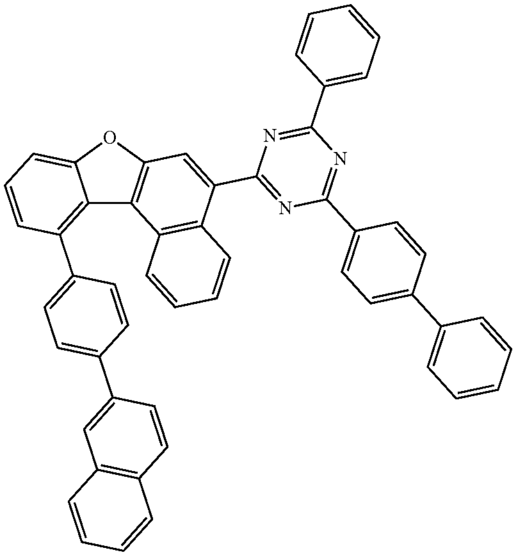
F482
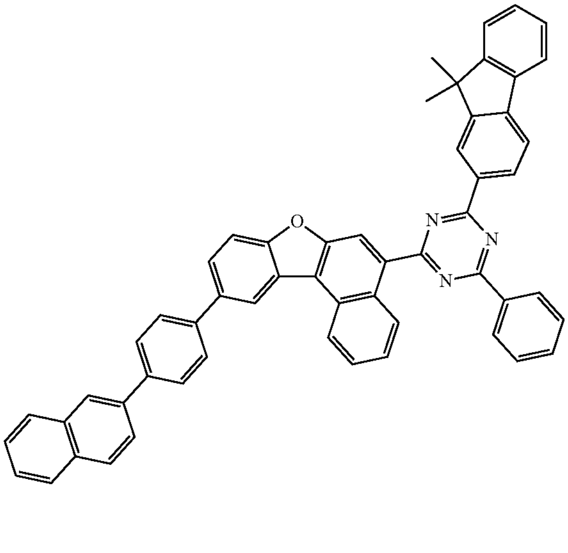
F483
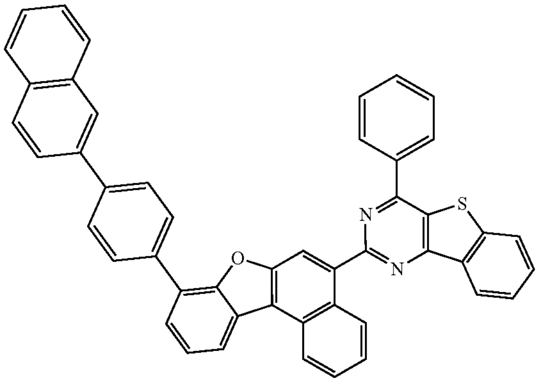
F484
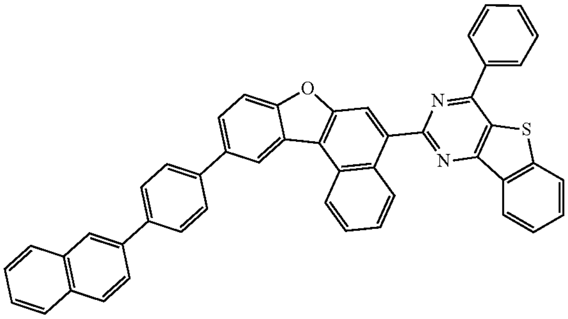
F485
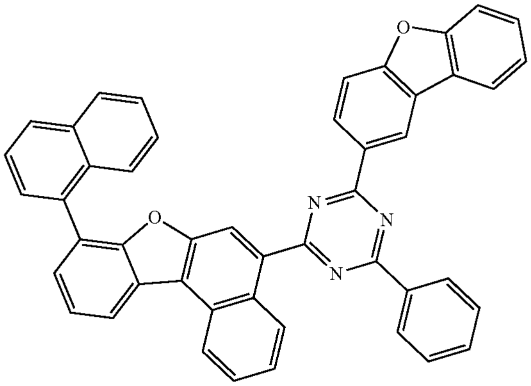
F486
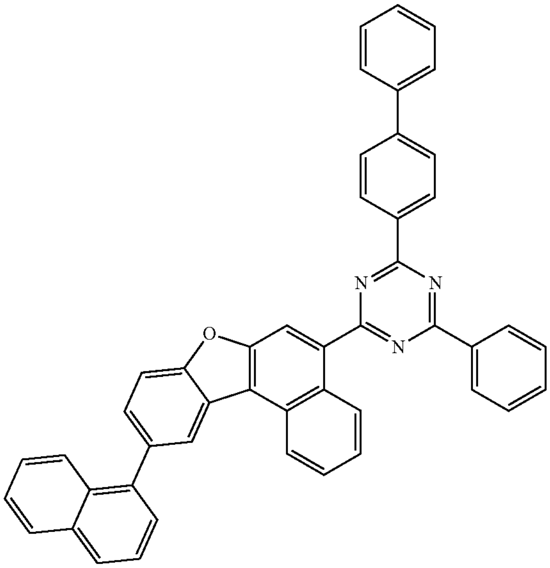

-continued
F487
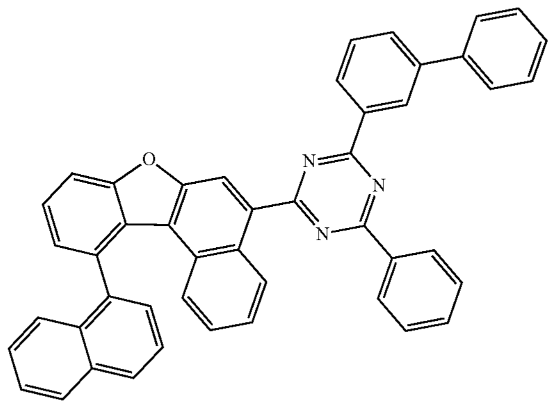
F488
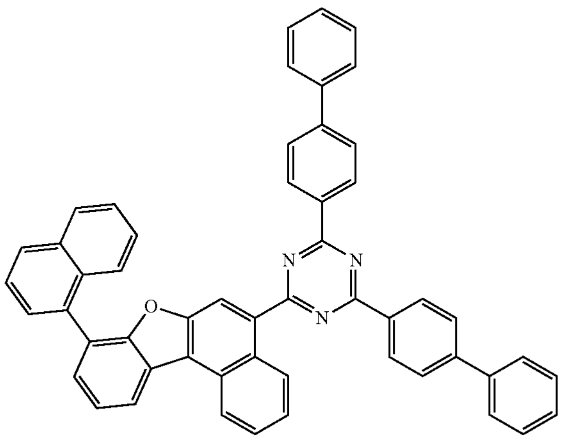
F489
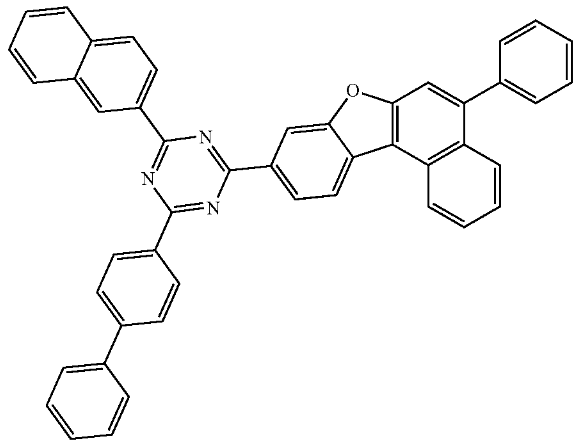
F490
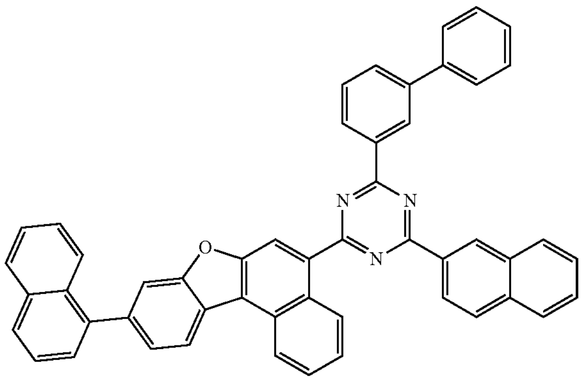
F491
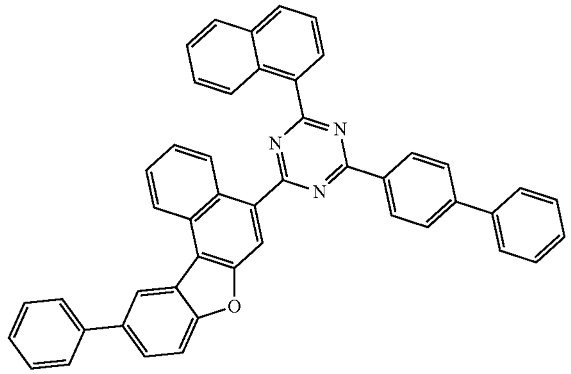
F492
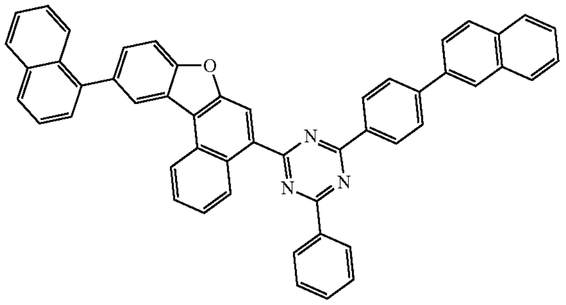

-continued
F493
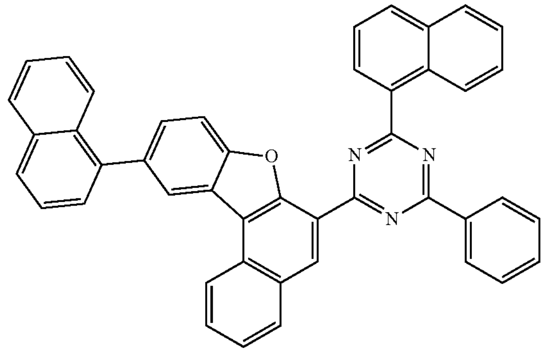
F494
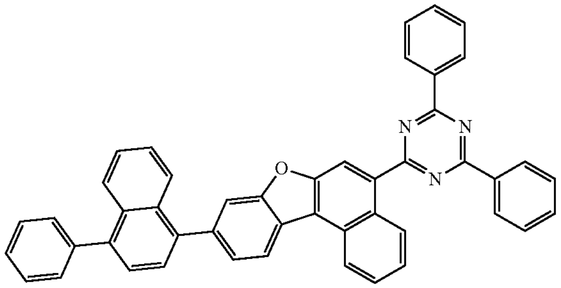
F495
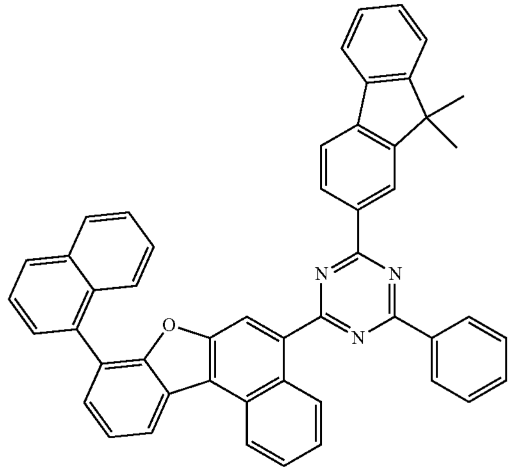
F496
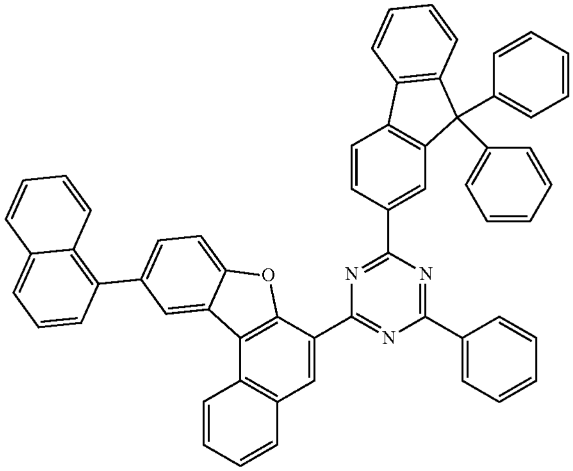
F497
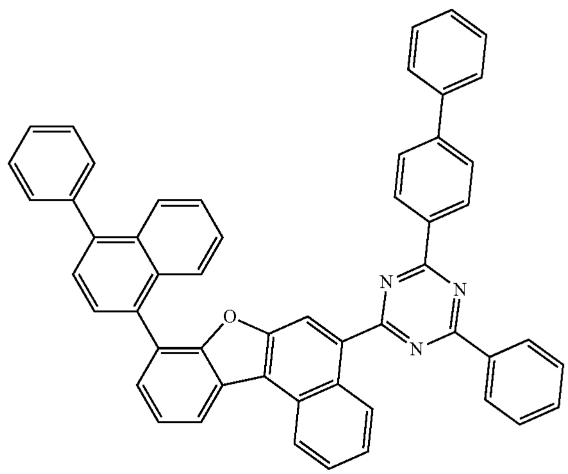
F498
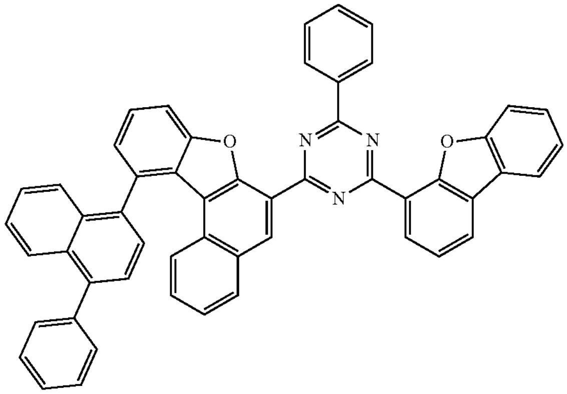

-continued
F499
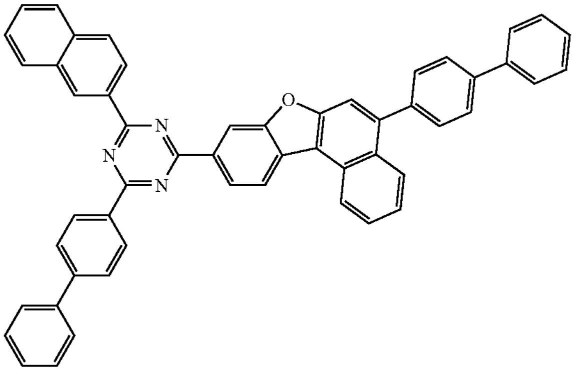
F500
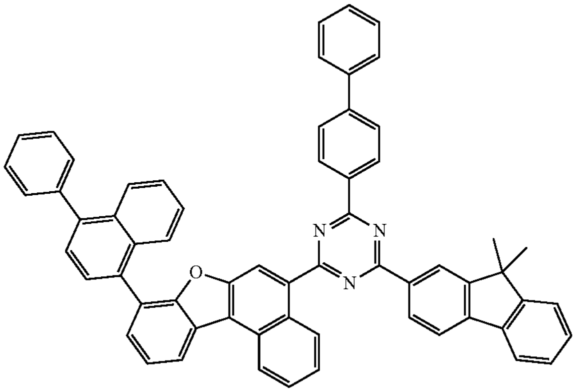
F501
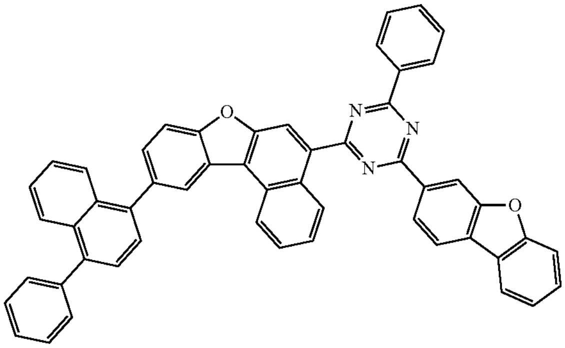
F502
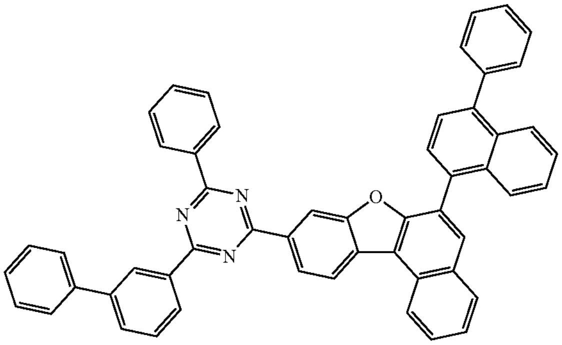
F503
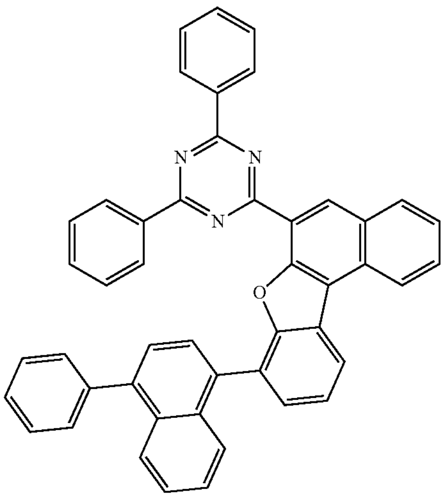
F504
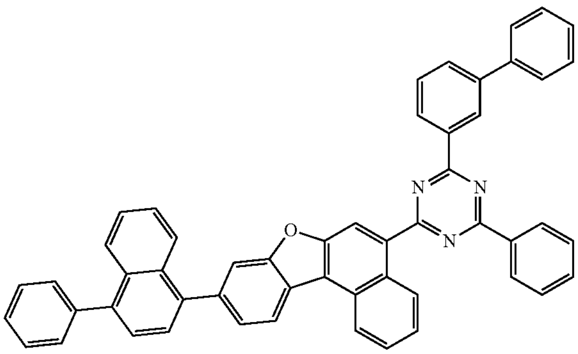

-continued
F505
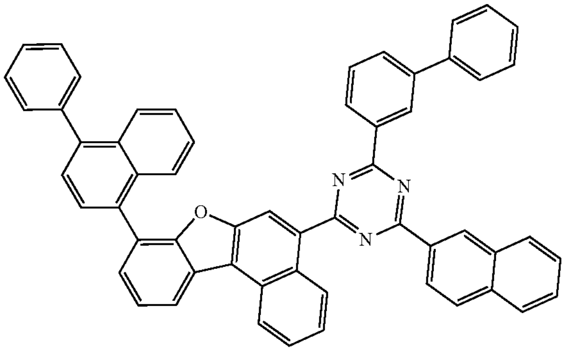
F506
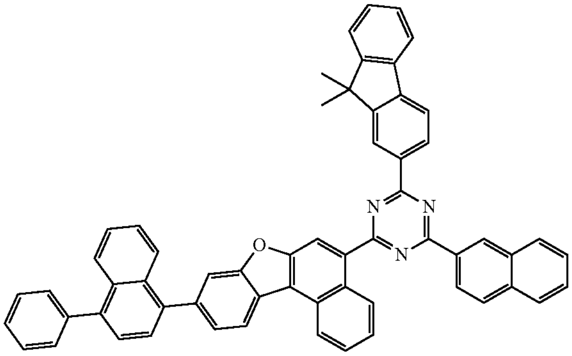
F507
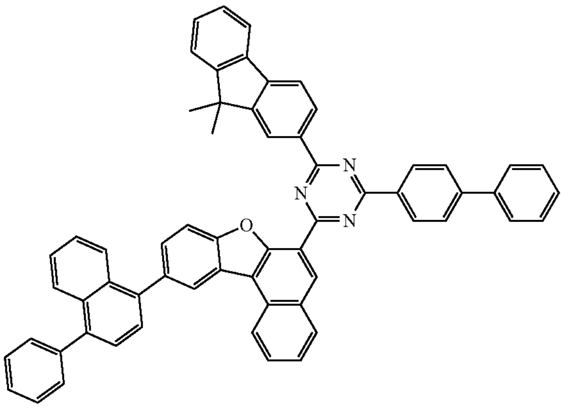
F508
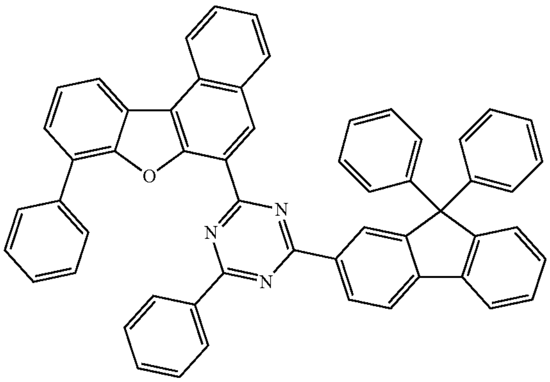
F509
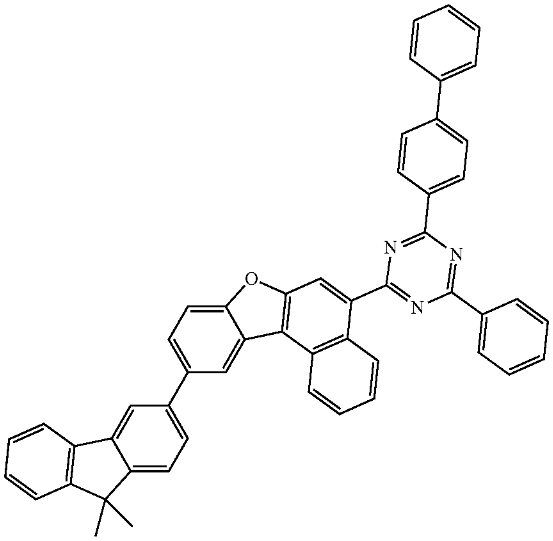
F510
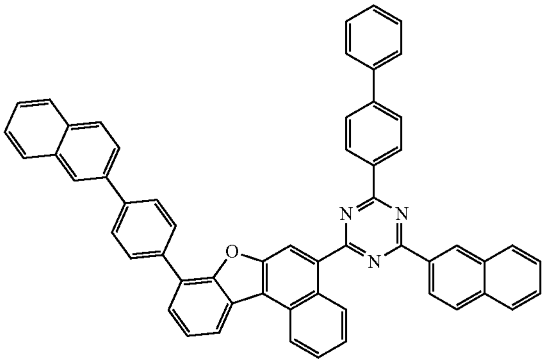

-continued
F511
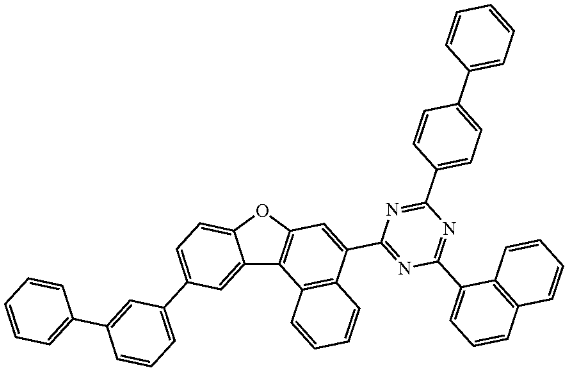
F512
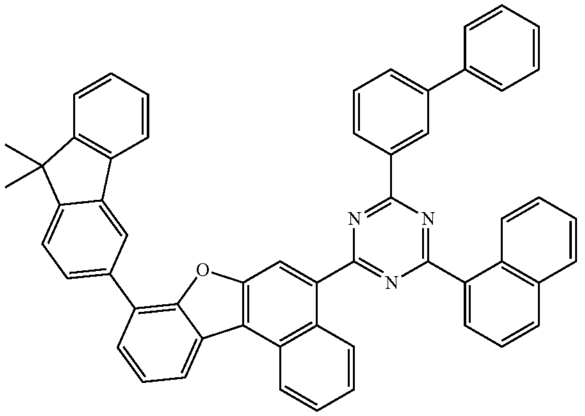
F513
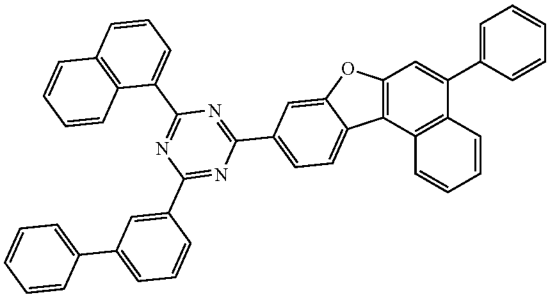
F514
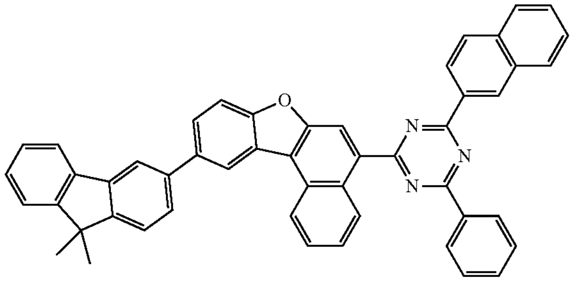
F515
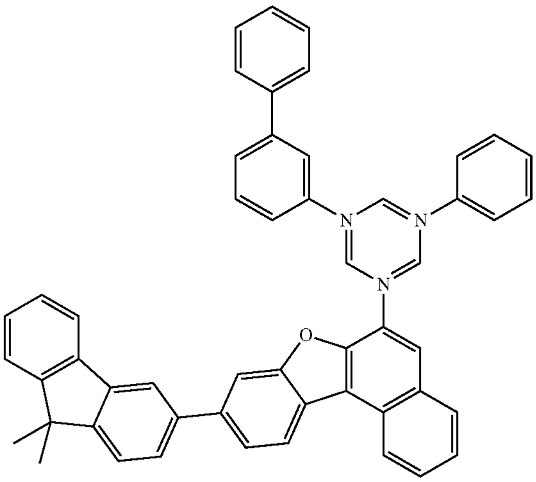
F516
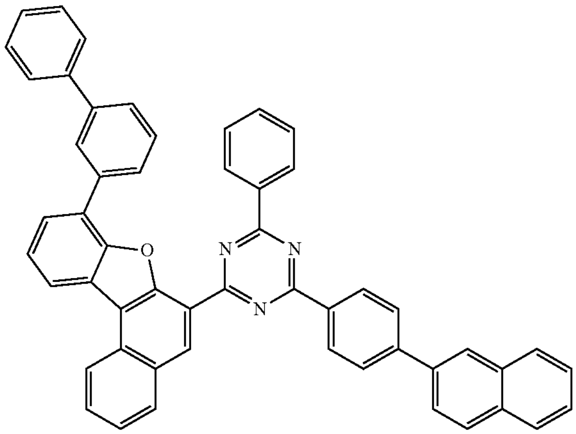

-continued
F517
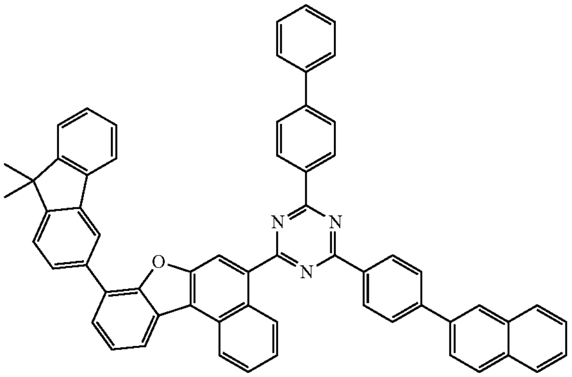
F518
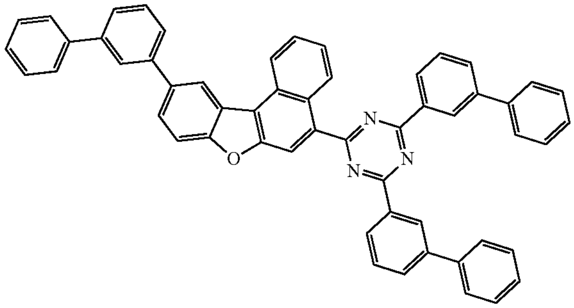
F519
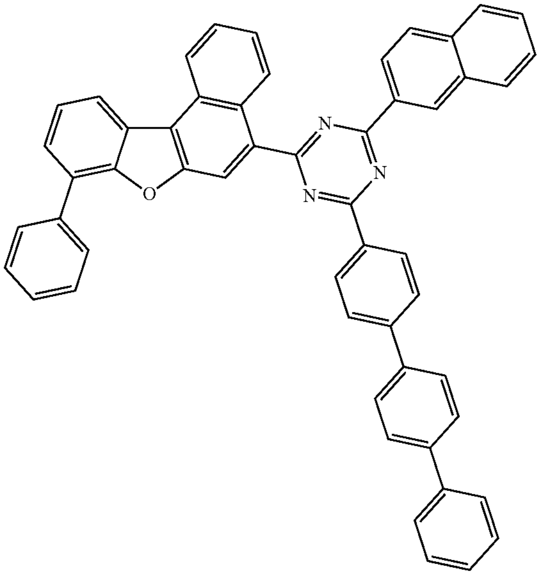
F520
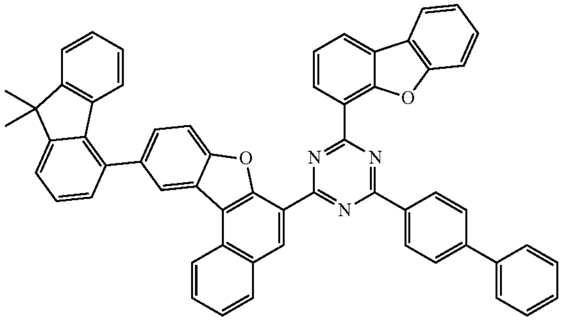
F521
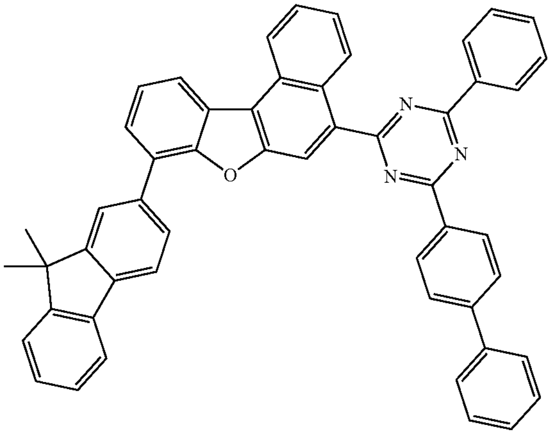
F522
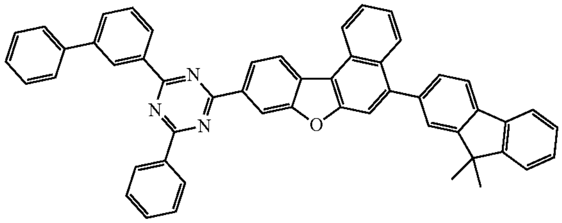

-continued
F523
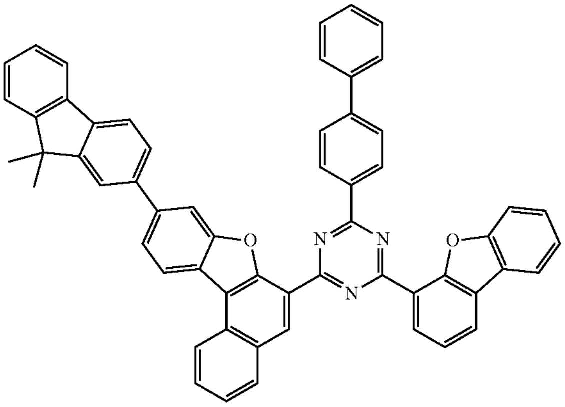
F524
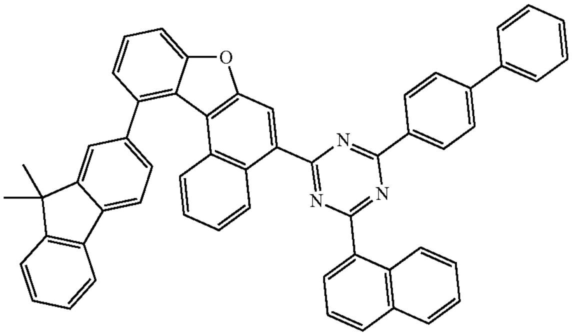
F525
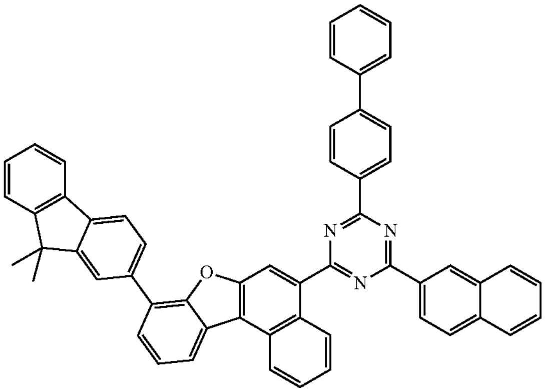
F526
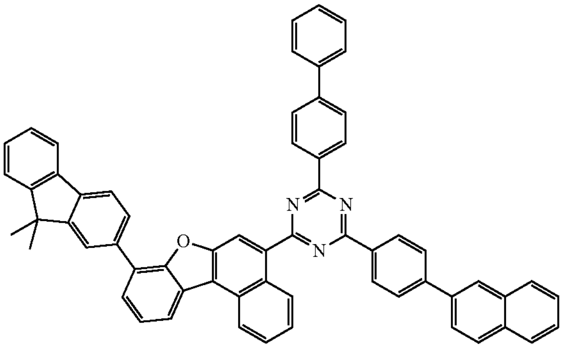
F527
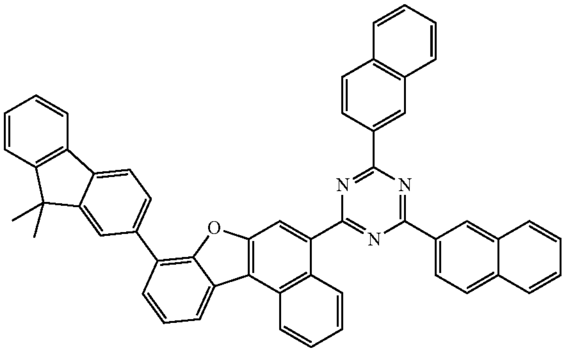
F528
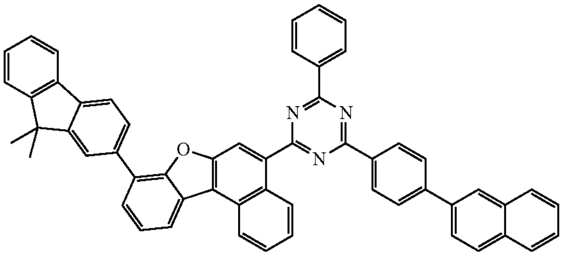
F529
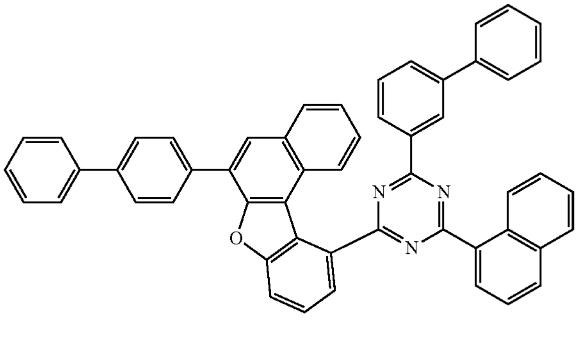
F530
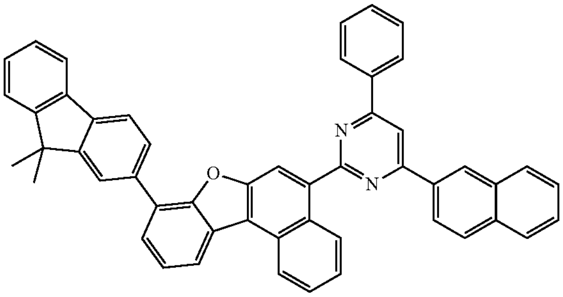

-continued
F531
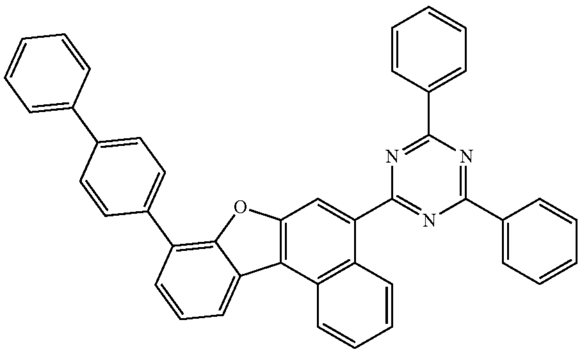
F532
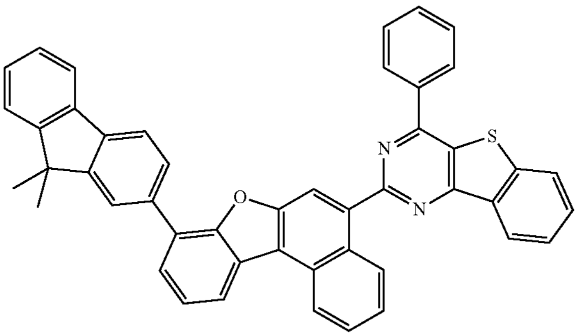
F533
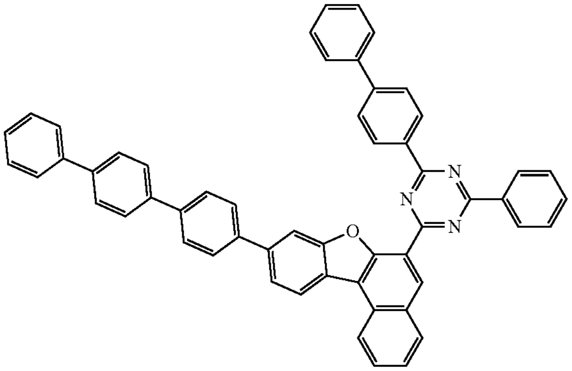
F534
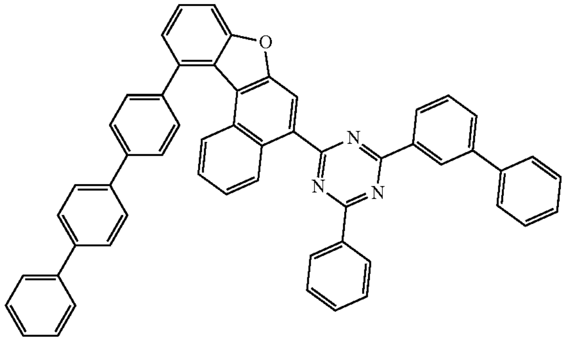
F535
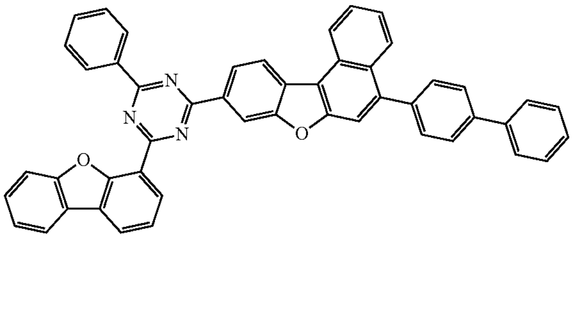
F536
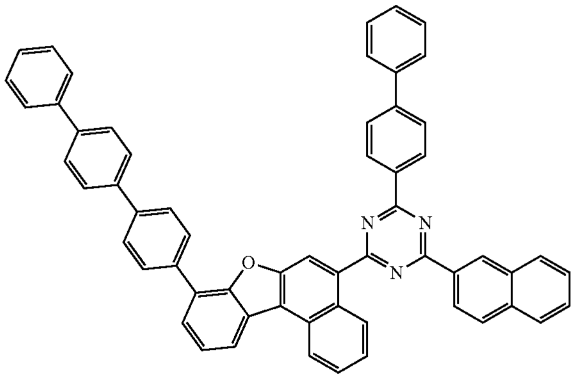

-continued
F537
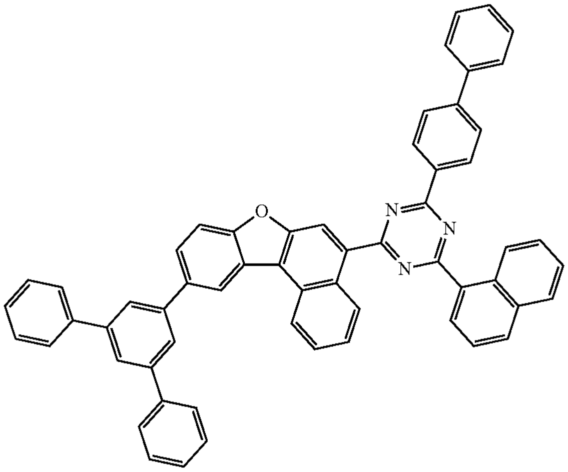
F538
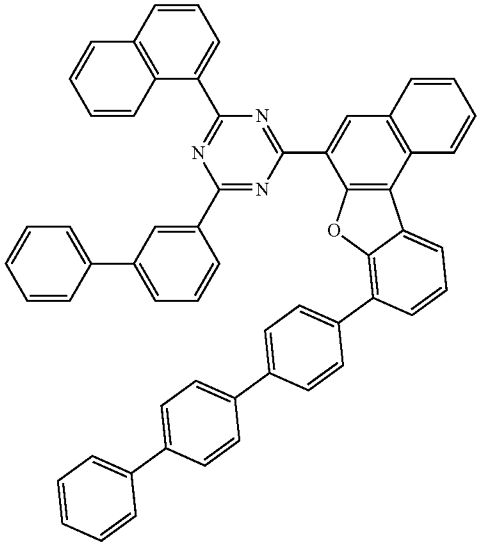
F539
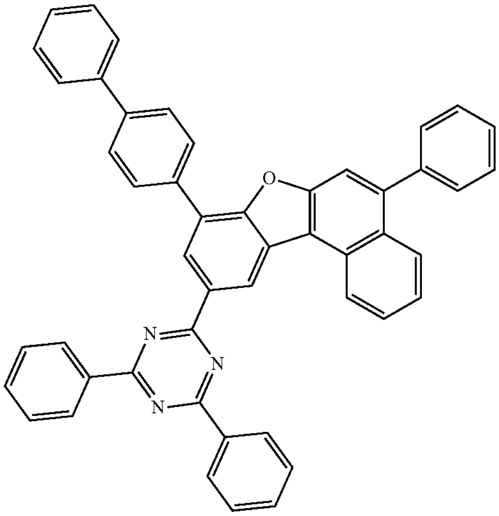
F540
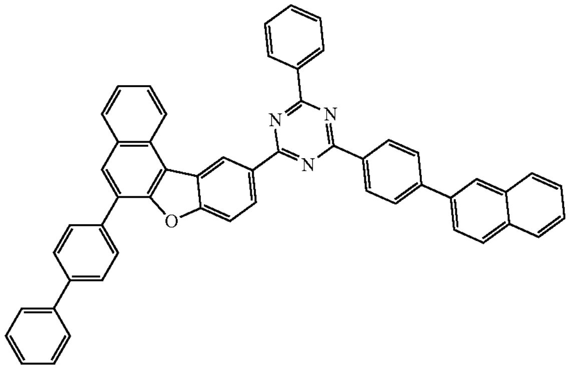
F541
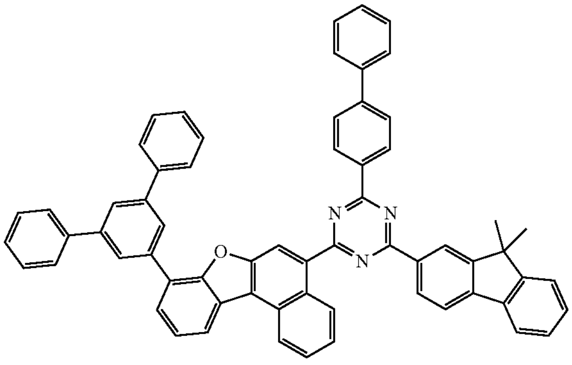
F542
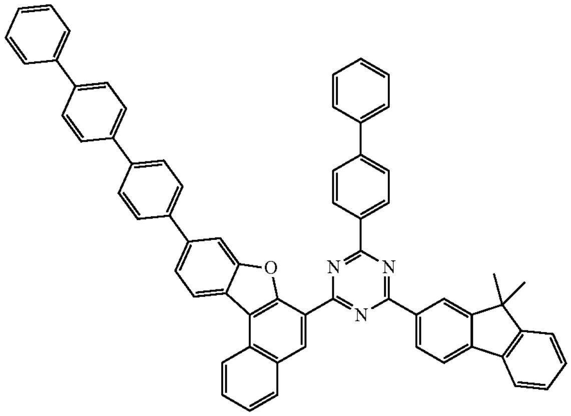

-continued
F543
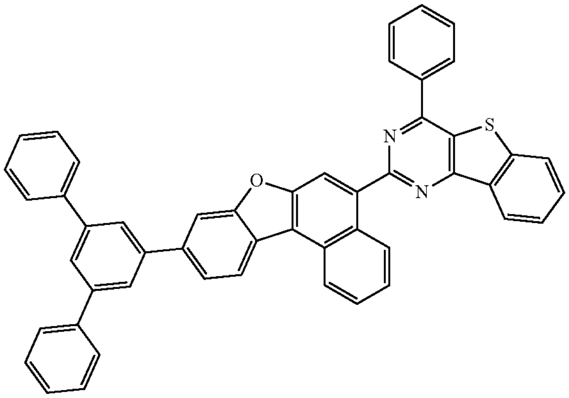
F544
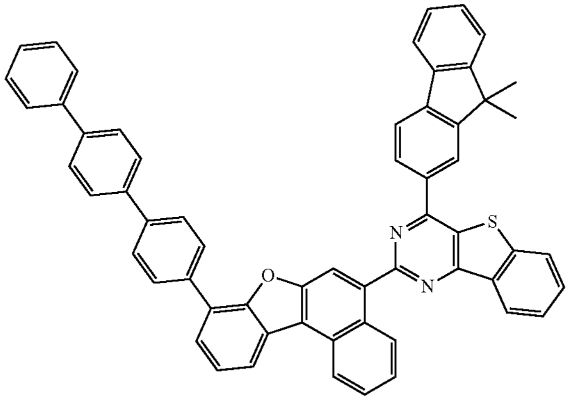
F545
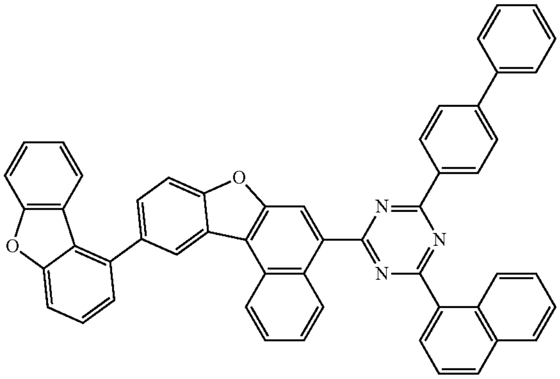
F546
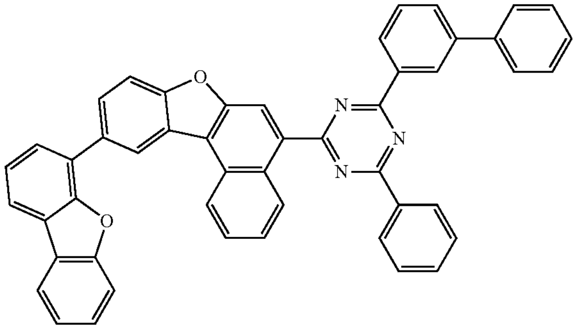
F547
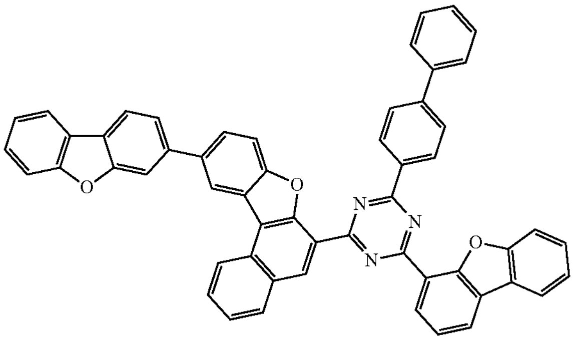
F548
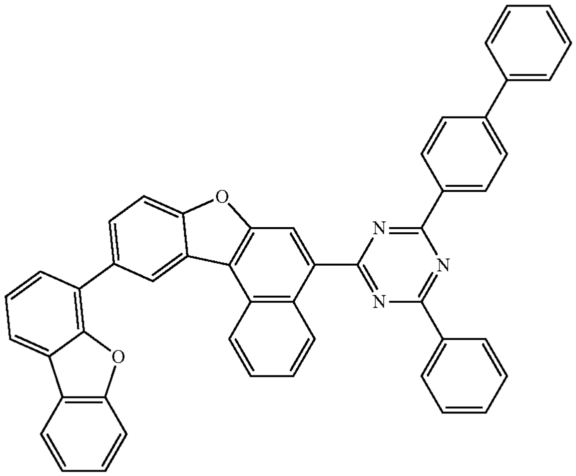

-continued
F549
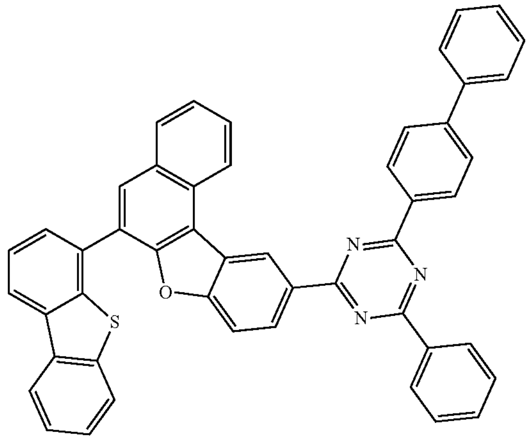
F550
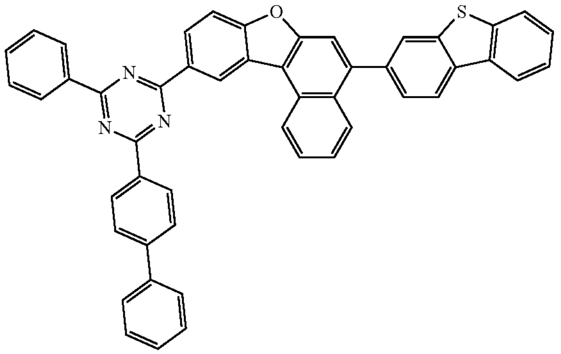
F551
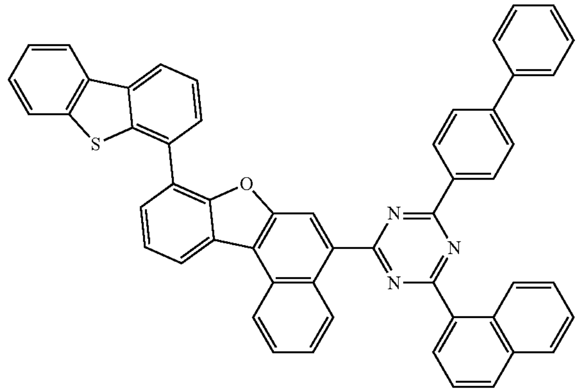
F552
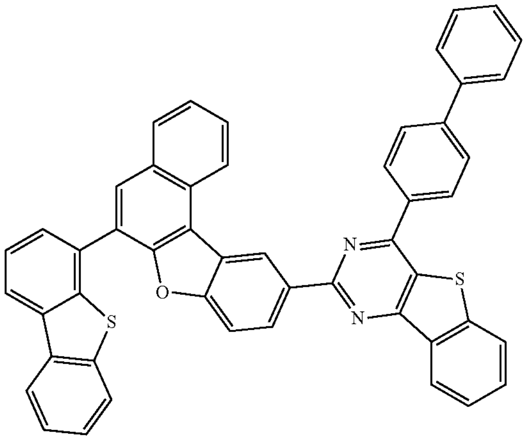
F553
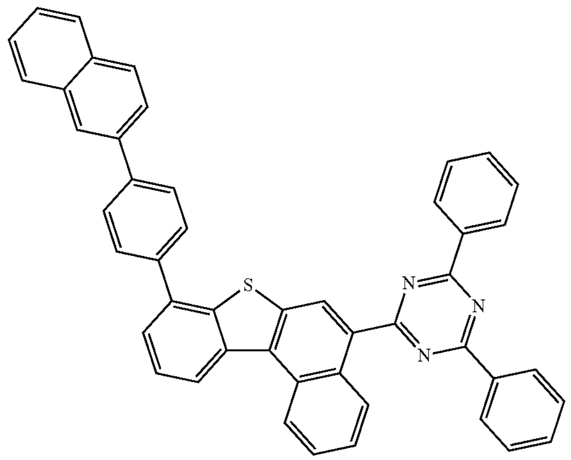
F554
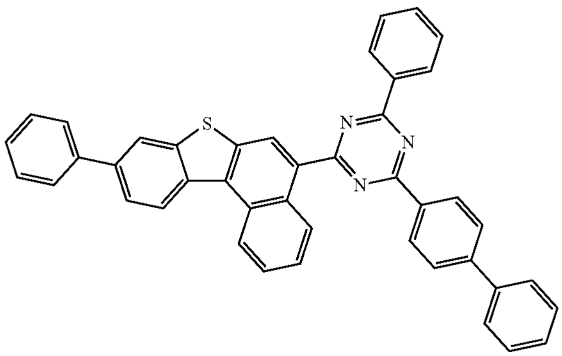

-continued
F555
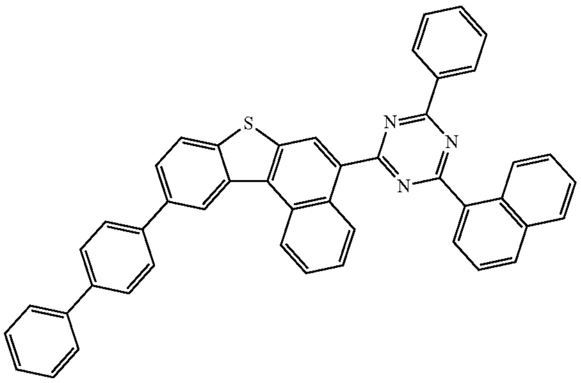
F556
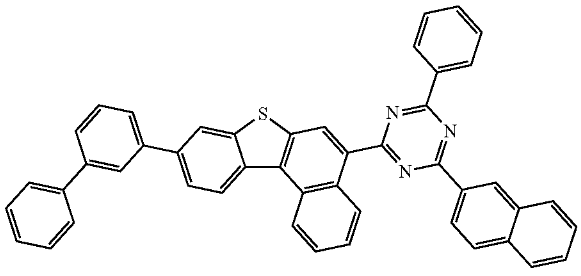
F557
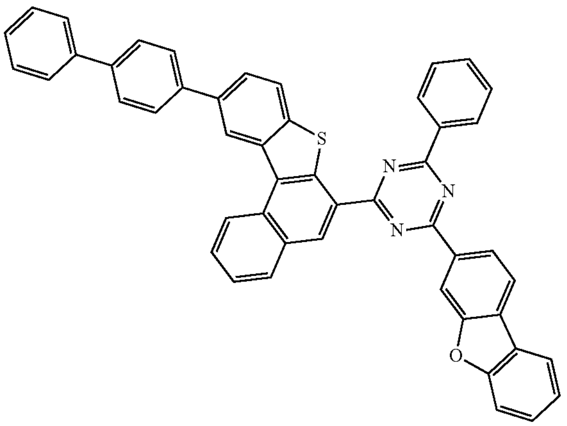
F558
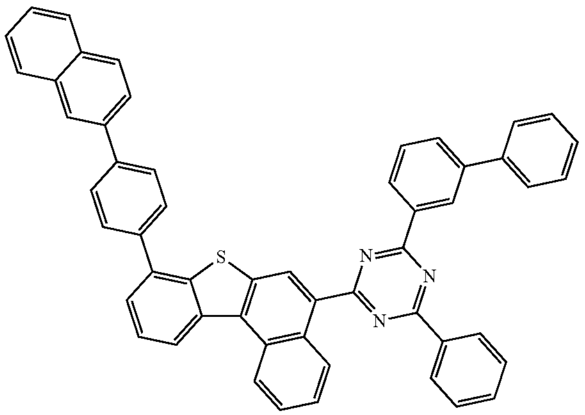
F559
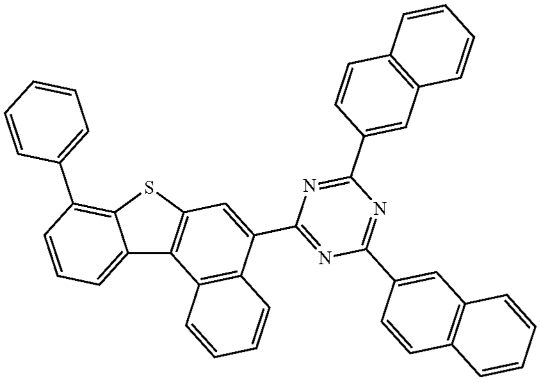
F560
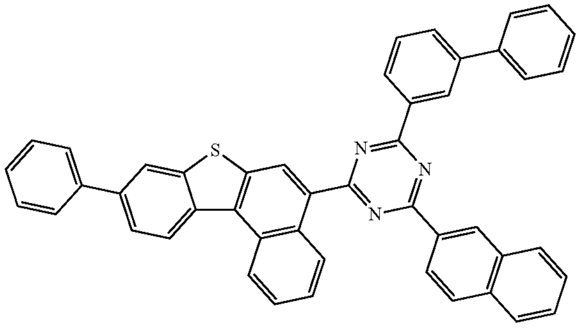

-continued
F561
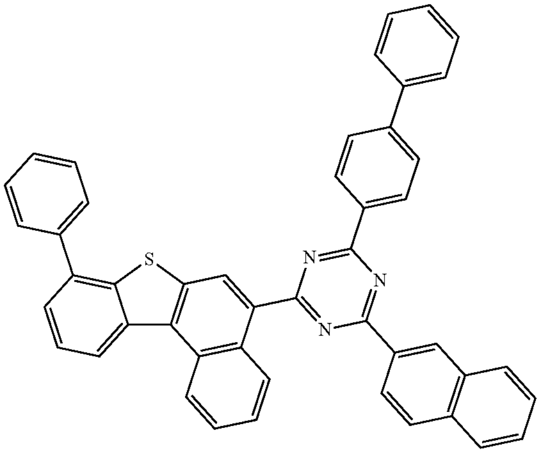
F562
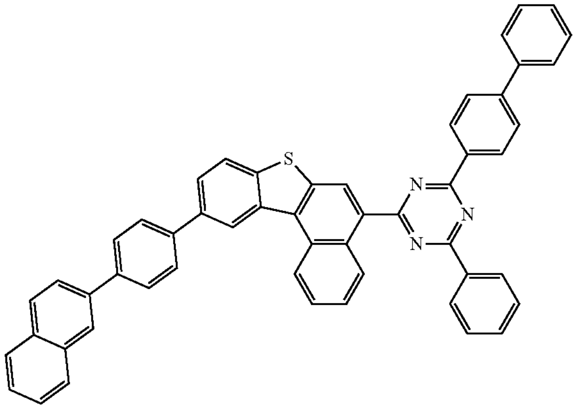
F563
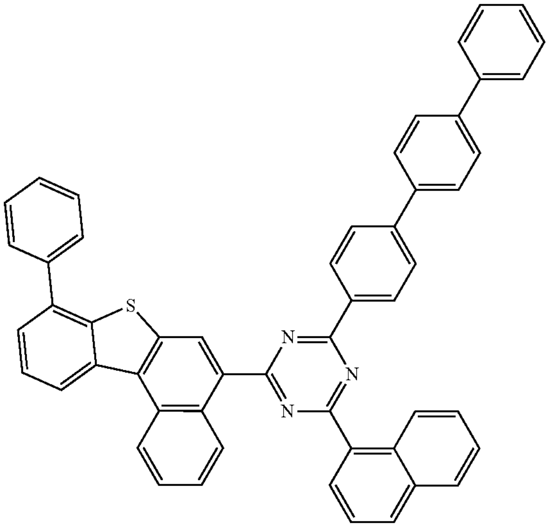
F564
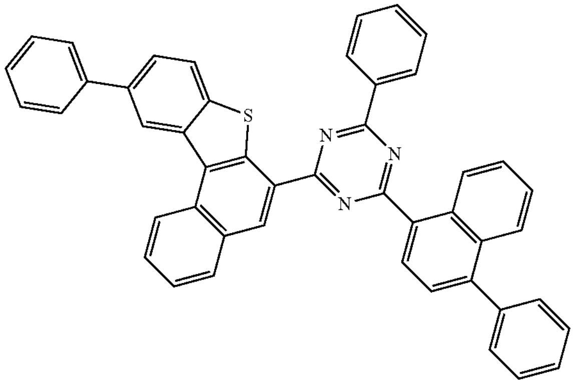
F565
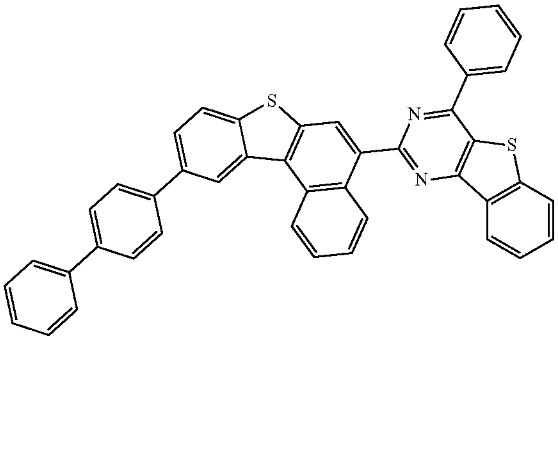
F566
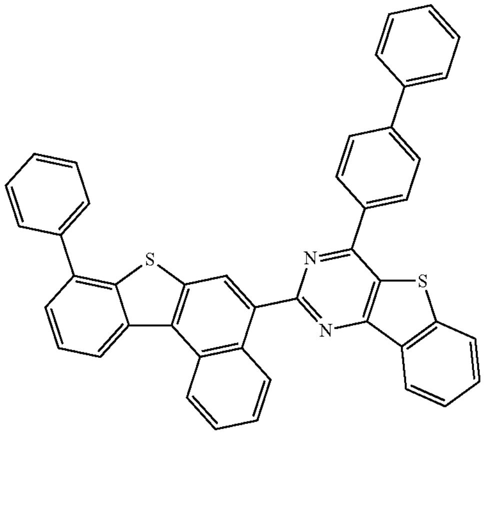

-continued
F567
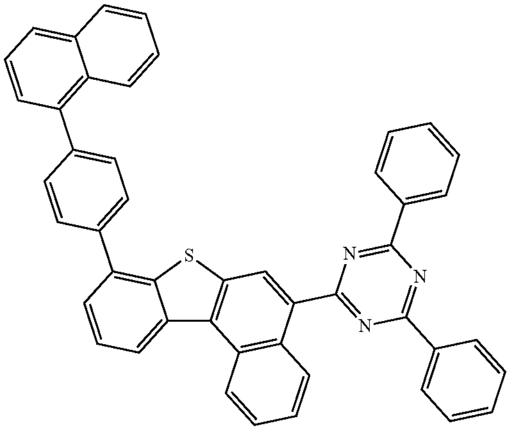
F568
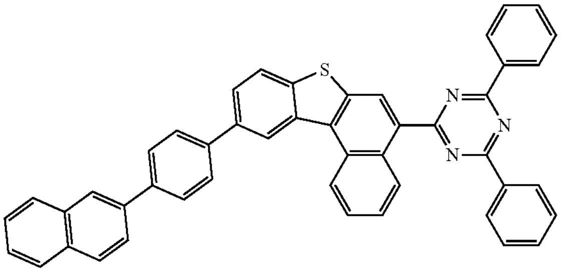
F569
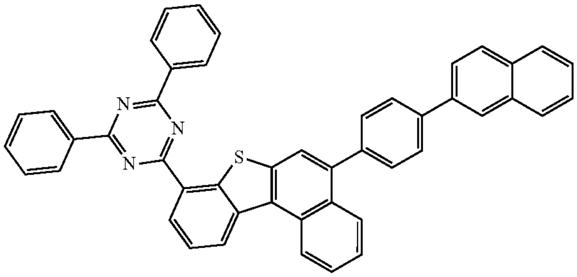
F570
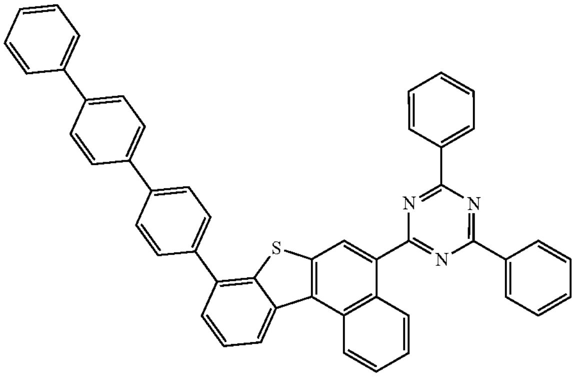
F571
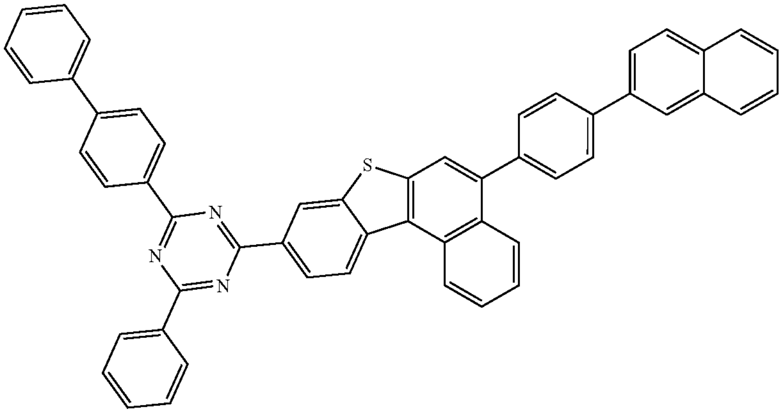

-continued
F572
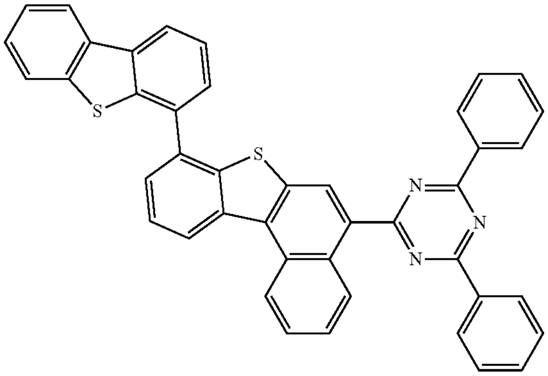
F573
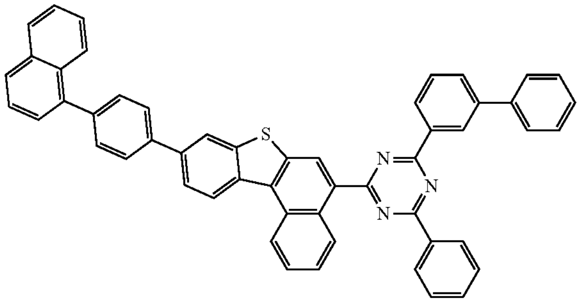
F574
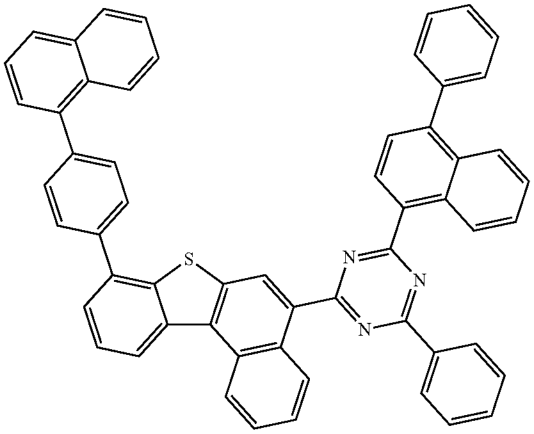
F575
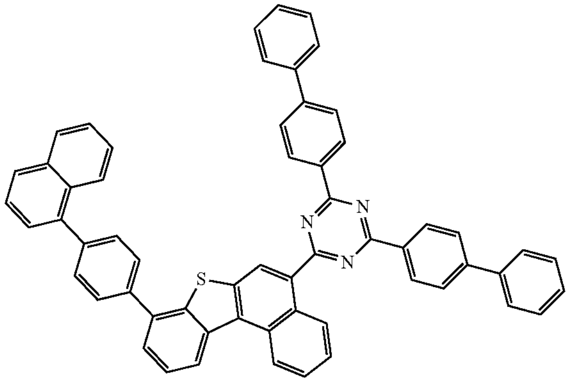
F576
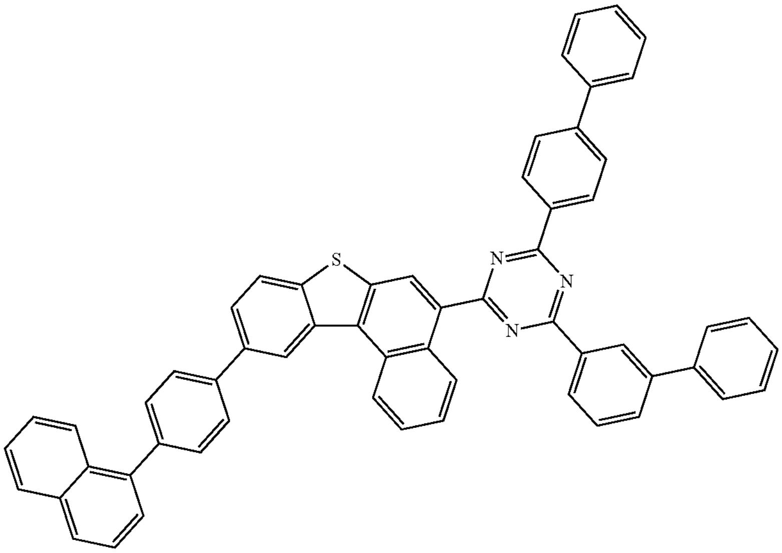

-continued
F577
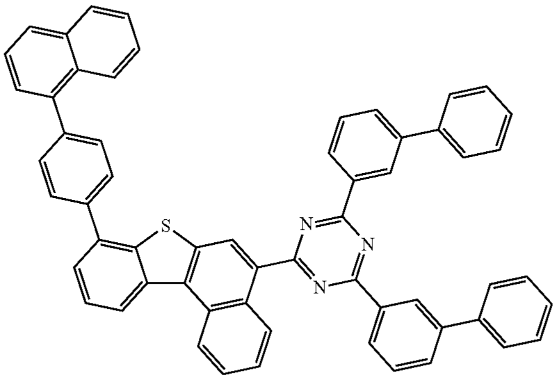
F578
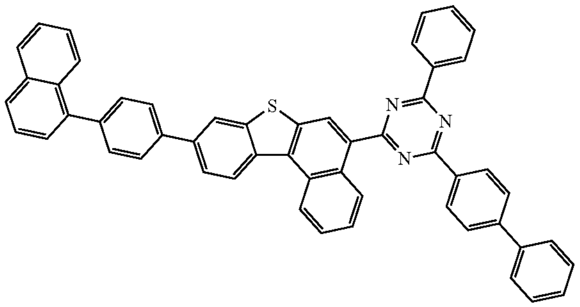
F579
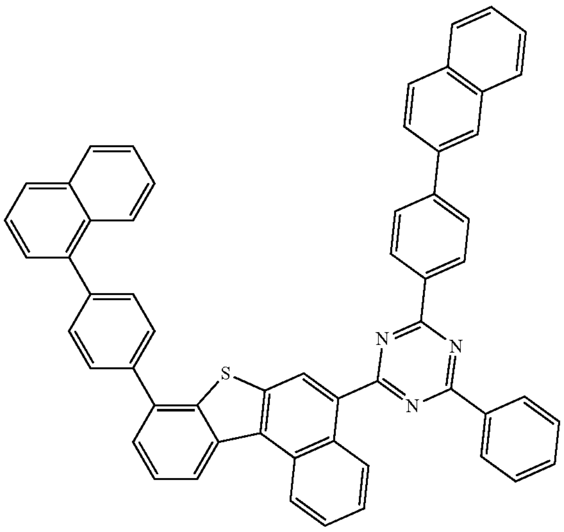
F580
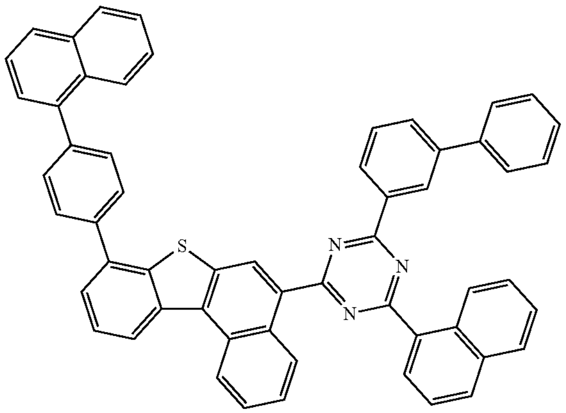
F581
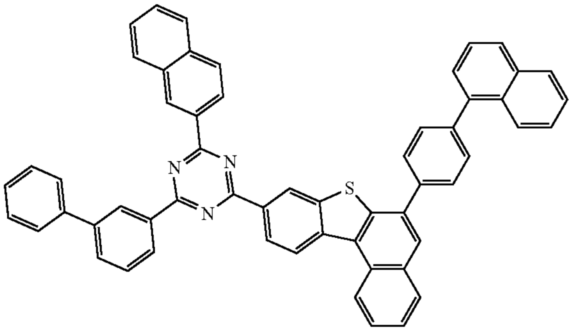
F582
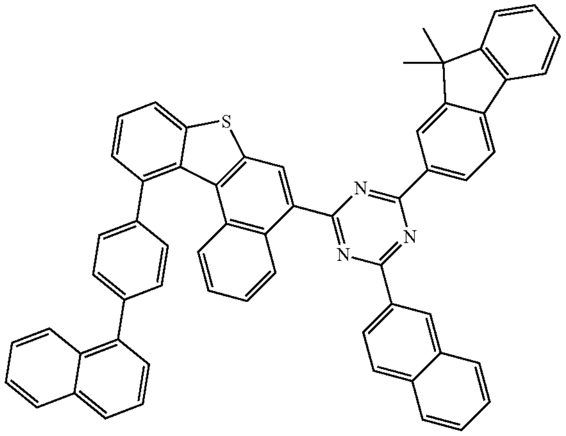

-continued
F583
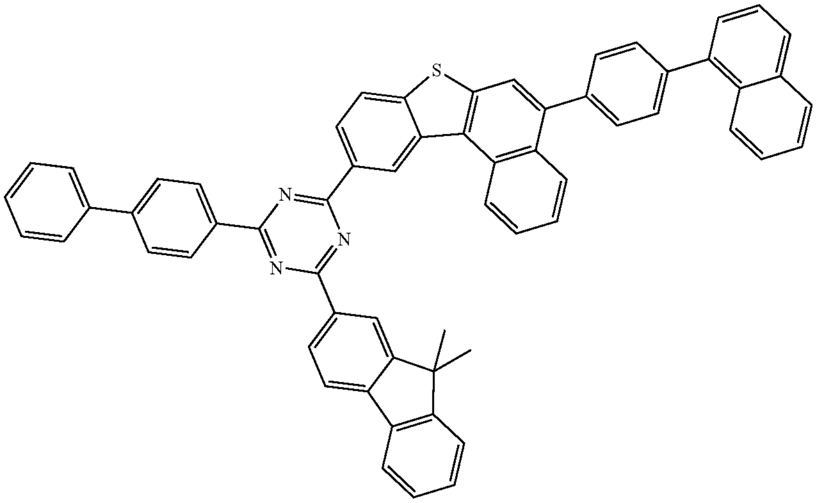
F584
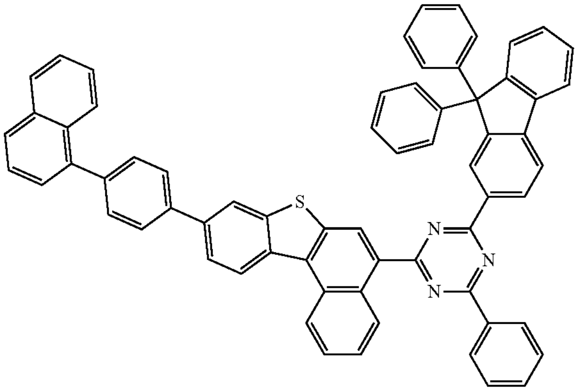
F585
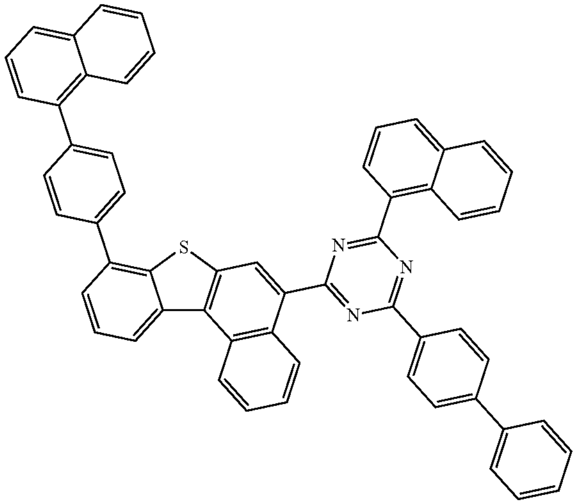
F586
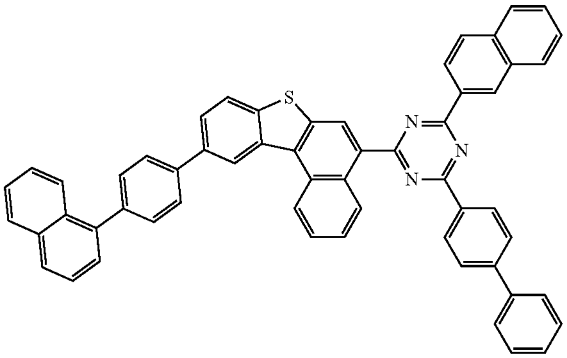
F587
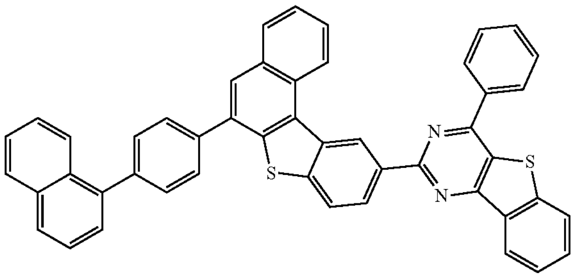

-continued
F588
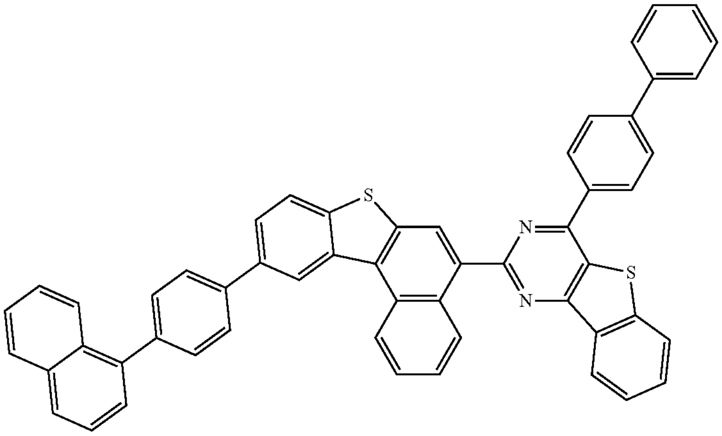
F589
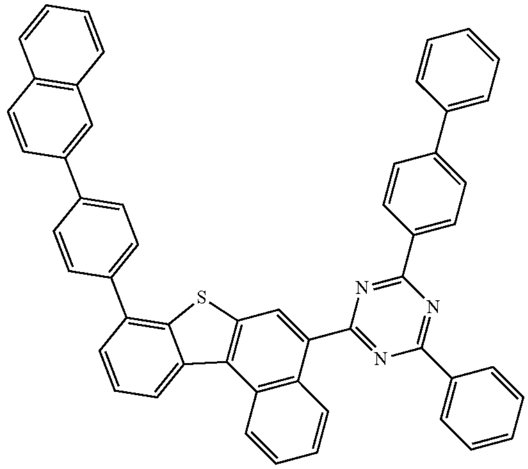
F590
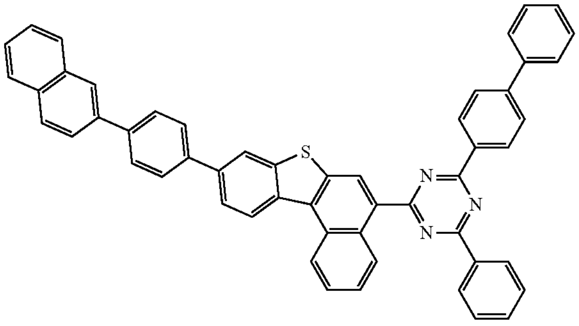
-continued
F591
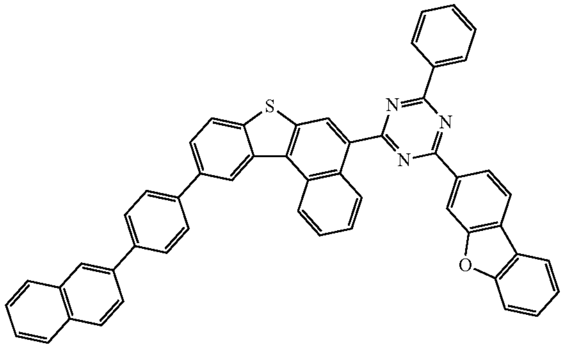
F592
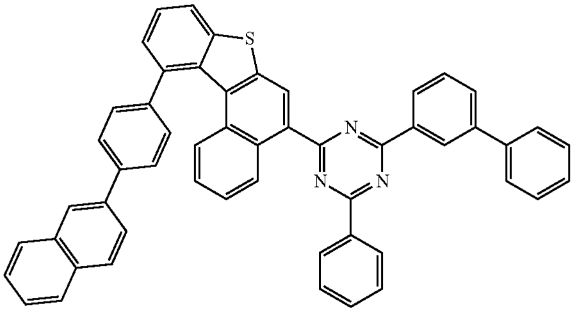

-continued
F593
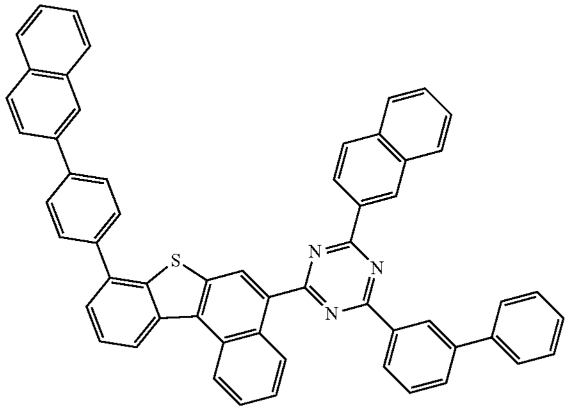
F594
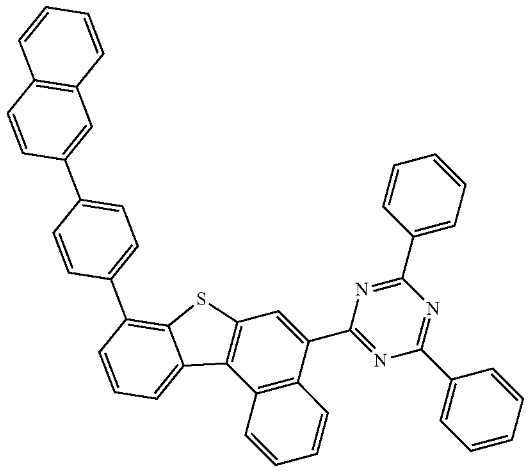
F595
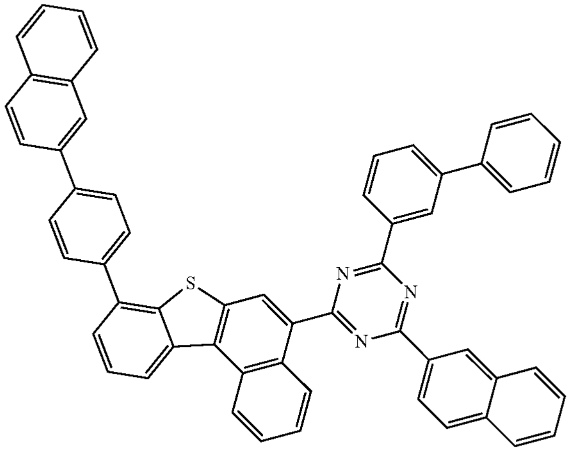
-continued
F596
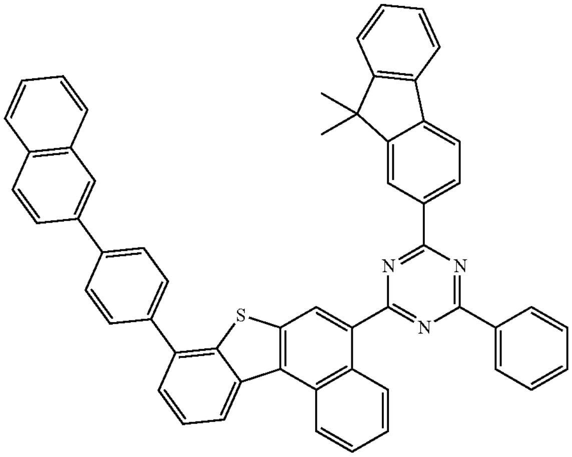
F597
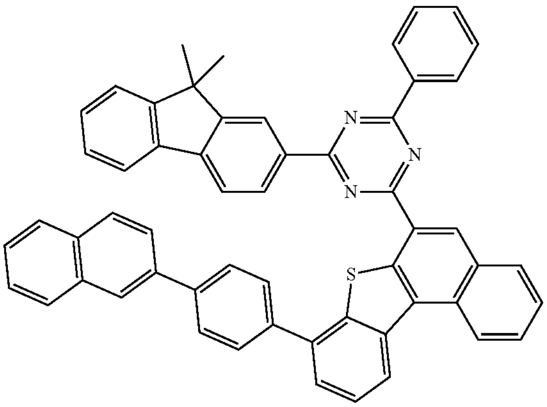
F598
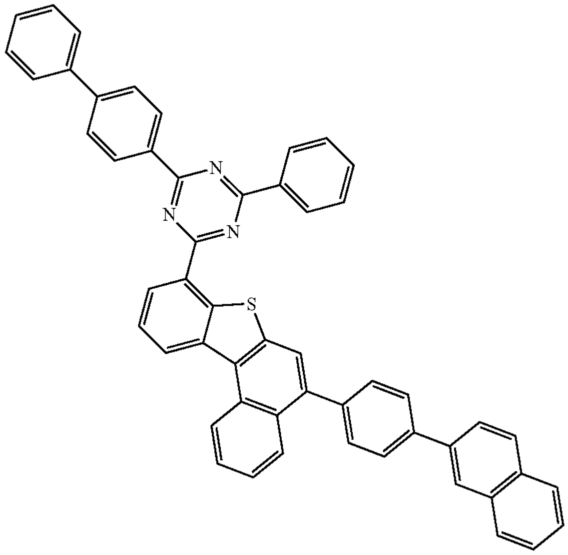

-continued
F599
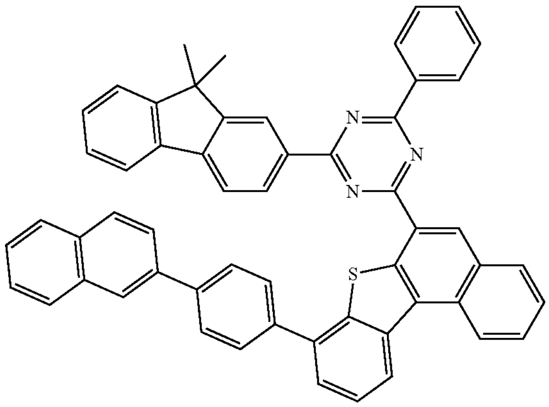
F600
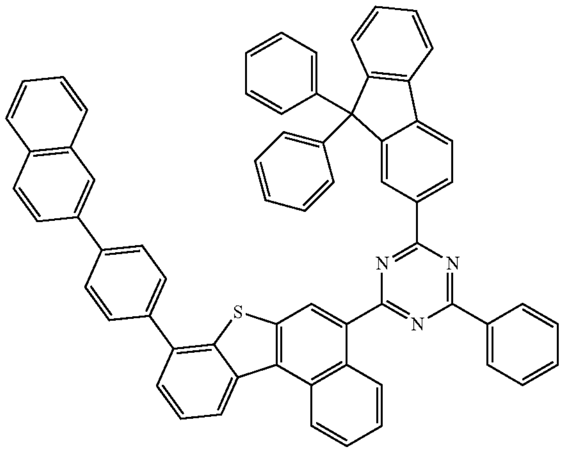
F601
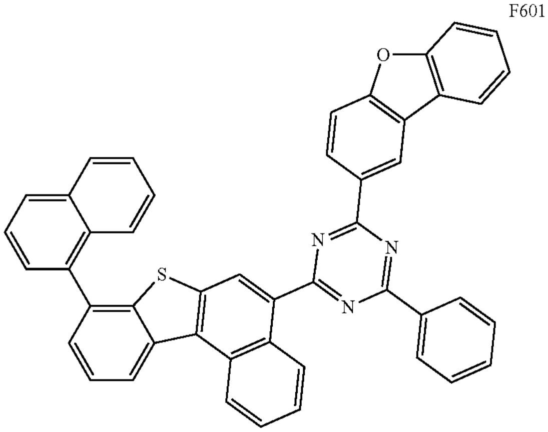
-continued
F602
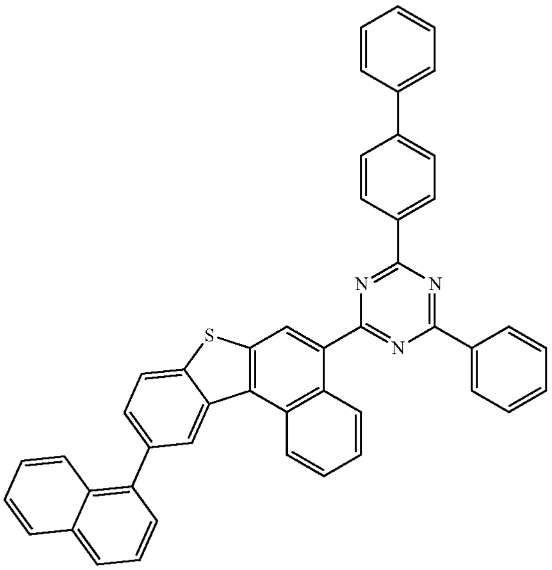
F603
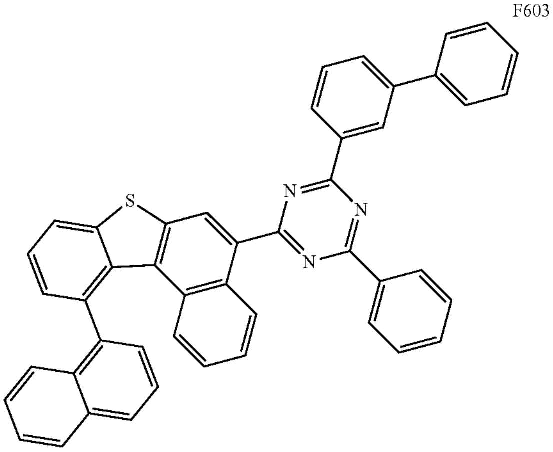
F604
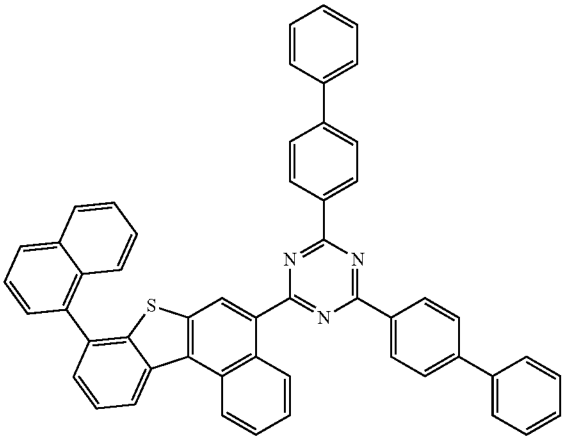

-continued
F605
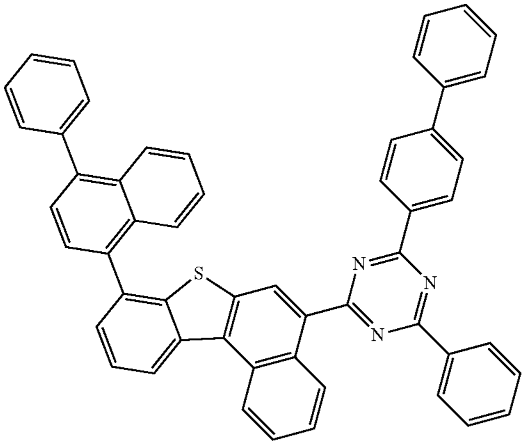
F606
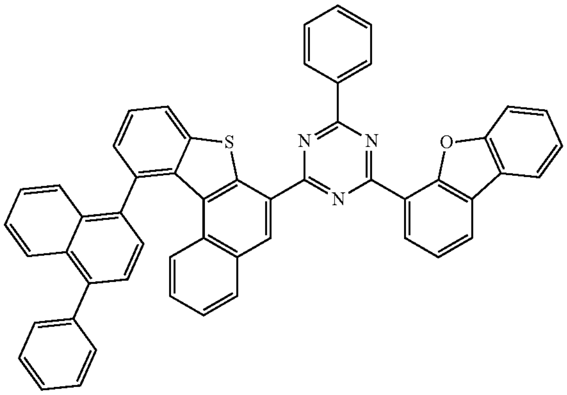
F607
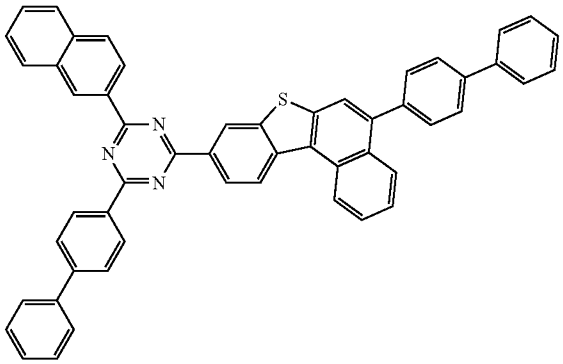
-continued
F608
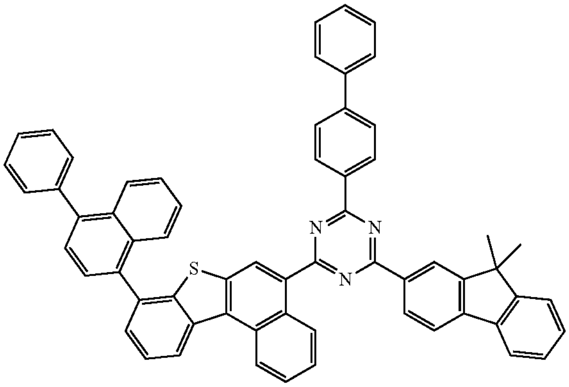
F609
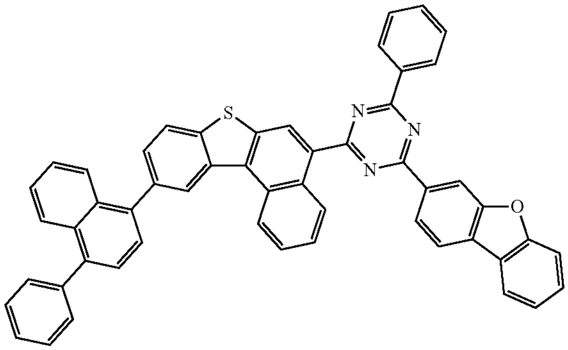
F610
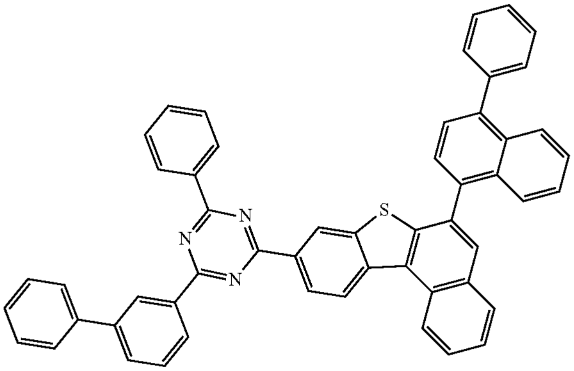

F611
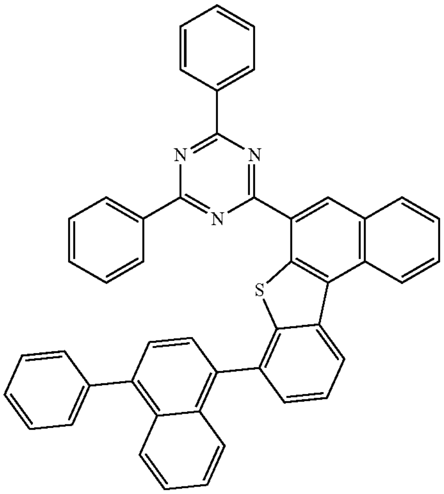
F612
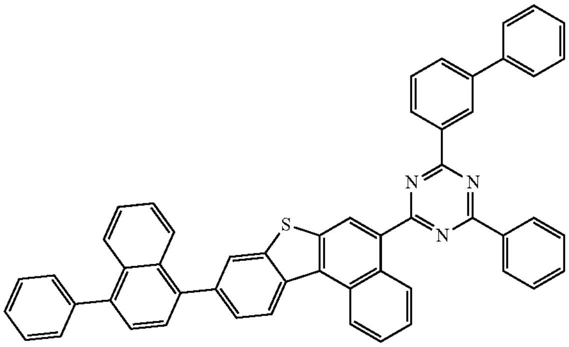
F613
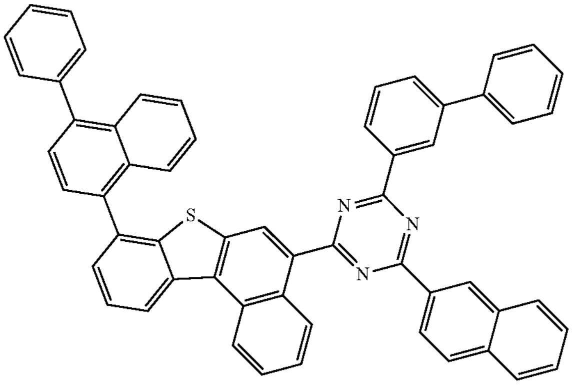
F614
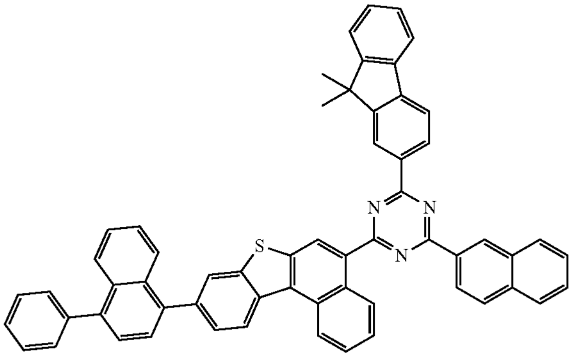
F615
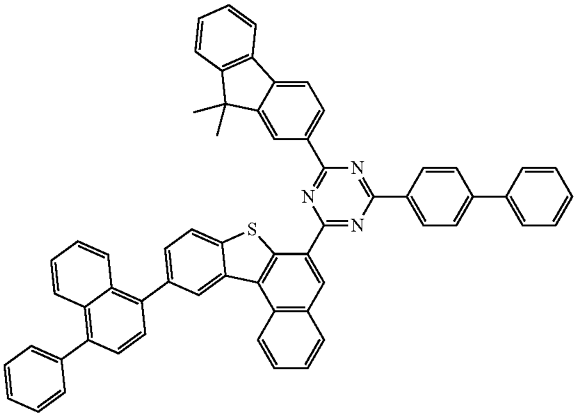
F616
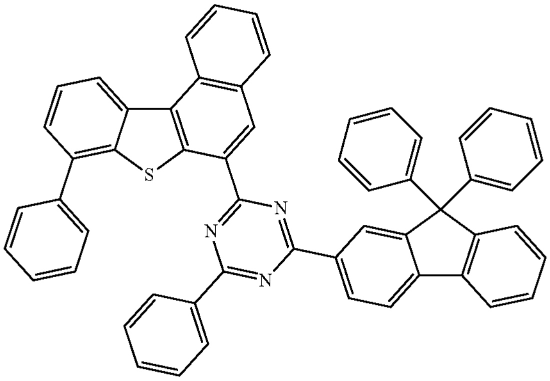
F617
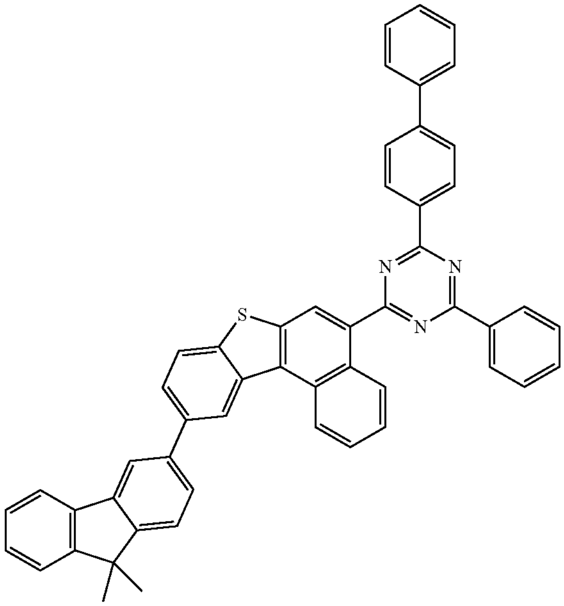

-continued
F618
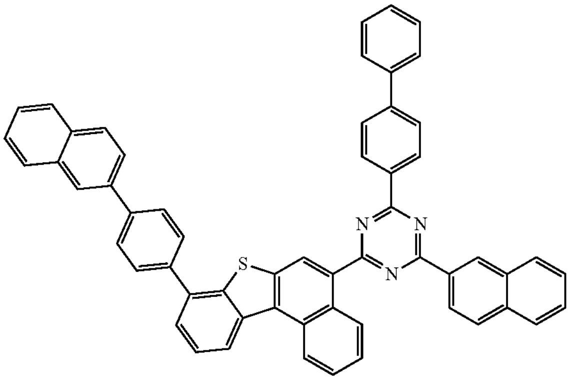
F619
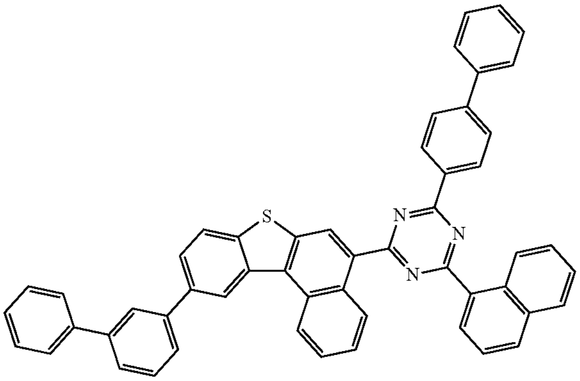
F620
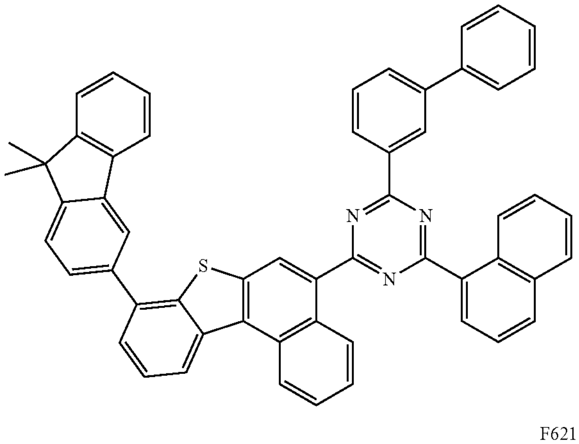
F621
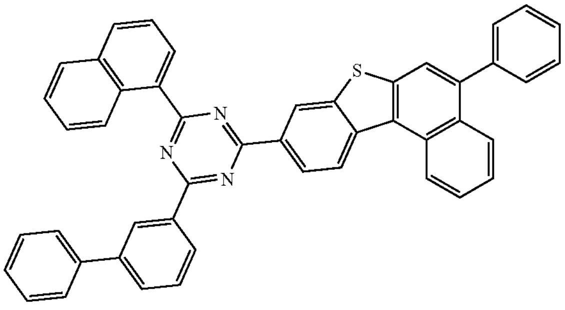
-continued
F622
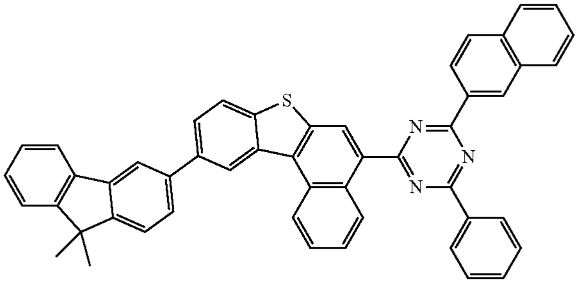
F623
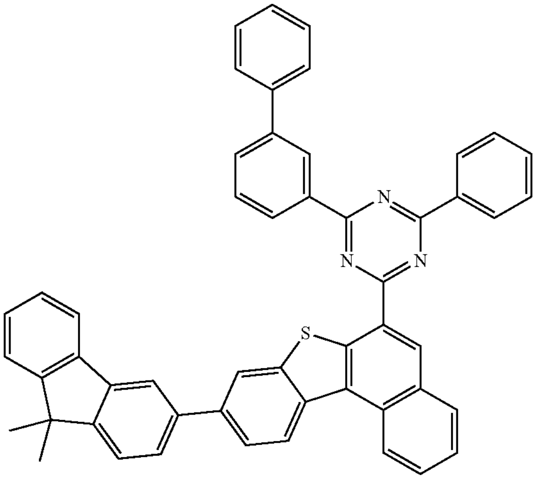
F624
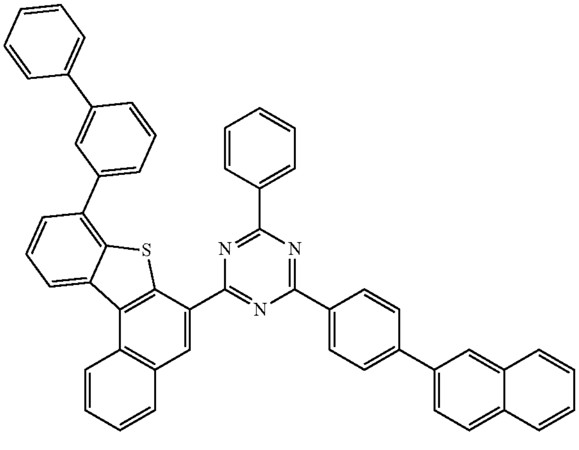

-continued
F625
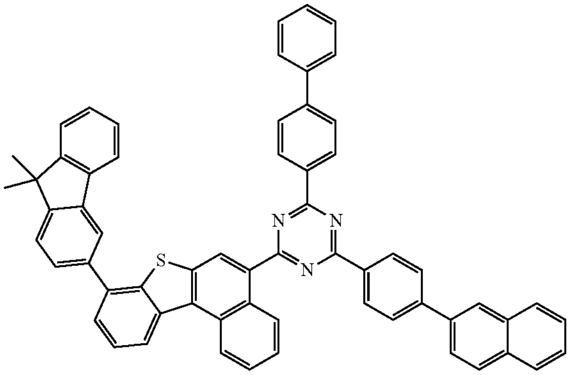
F626
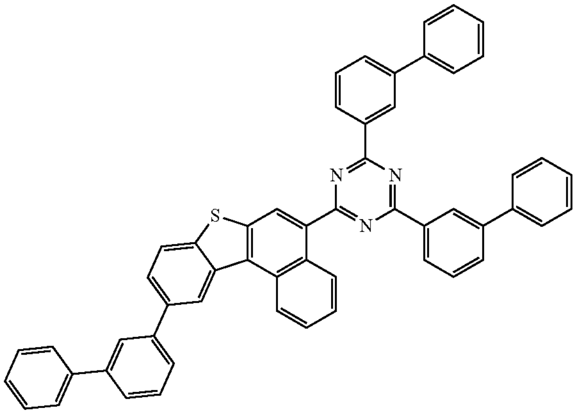
F627
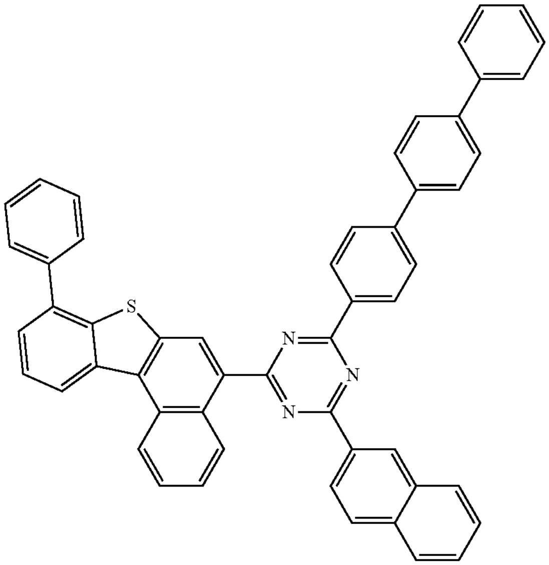
-continued
F628
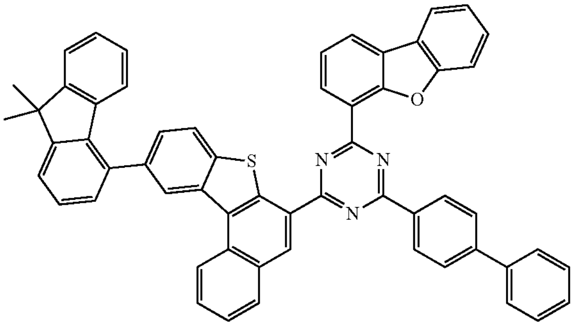
F629
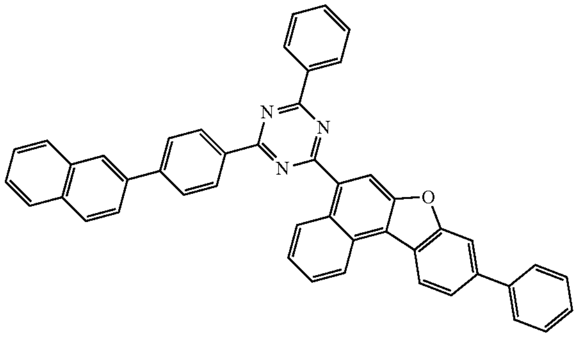
F630
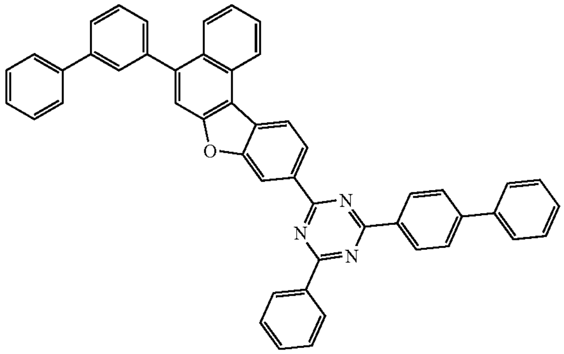
F631
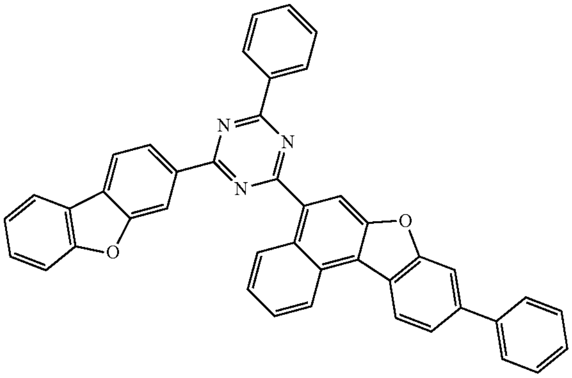

-continued
F632
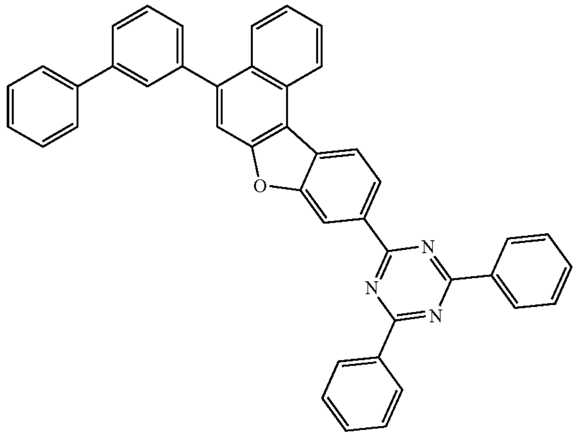
F633
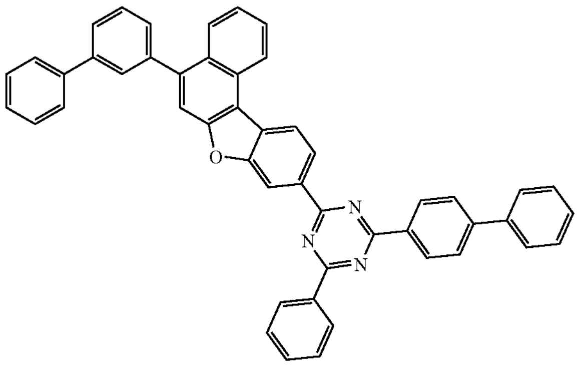
F634
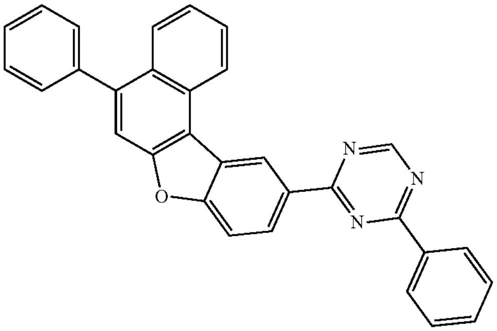
F635
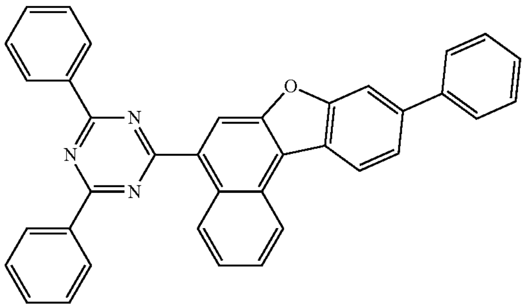
-continued
F636
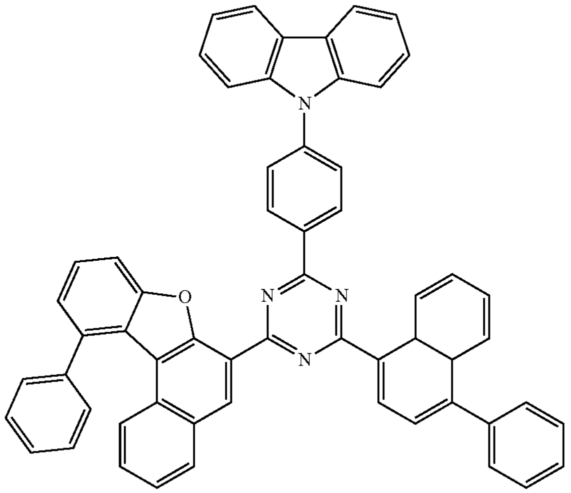
F637
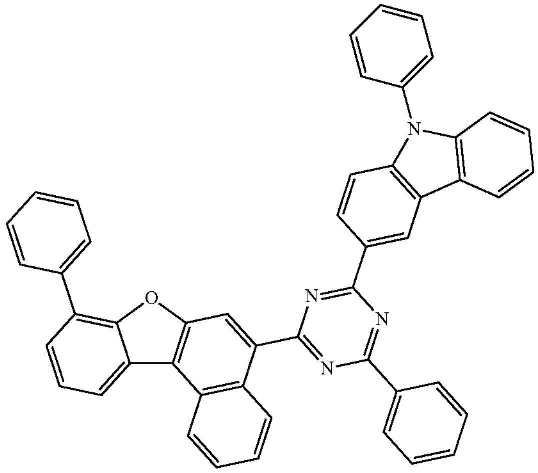
F638
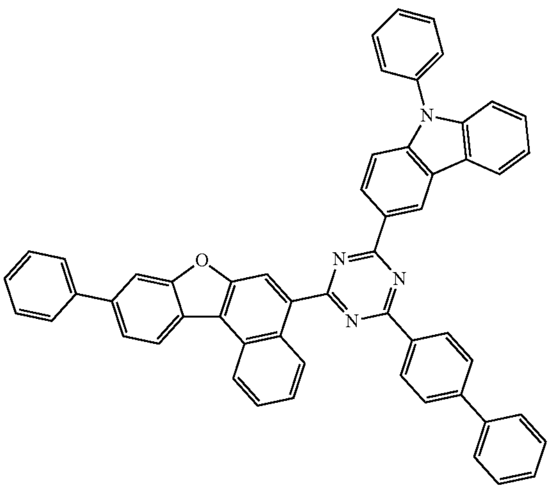

-continued
F639
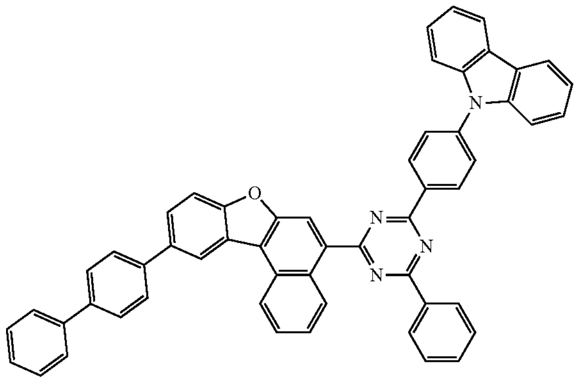
F640
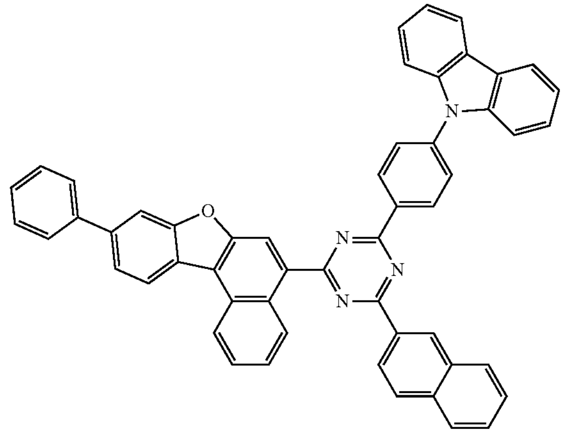
F641
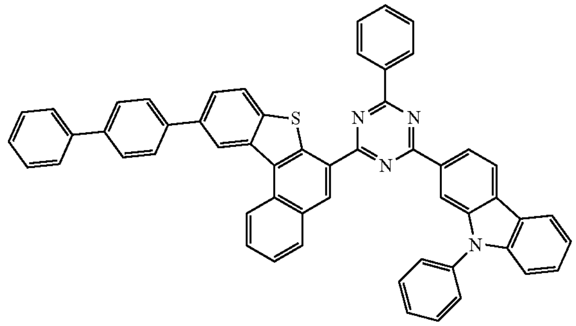
-continued
F642
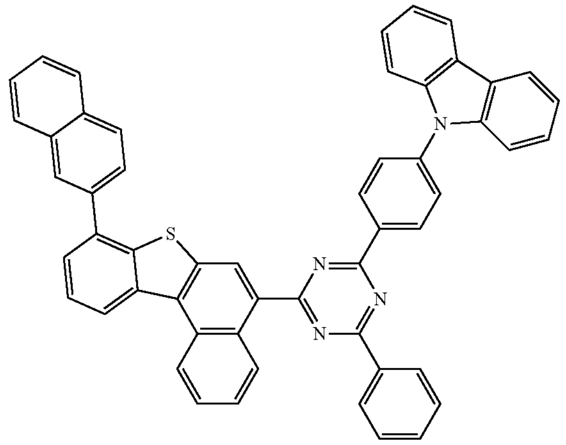
F643
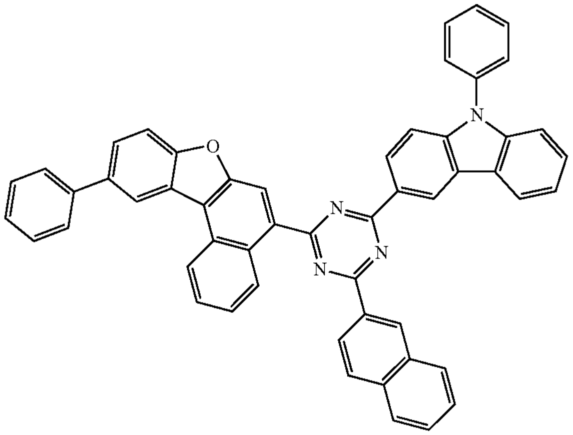
F644
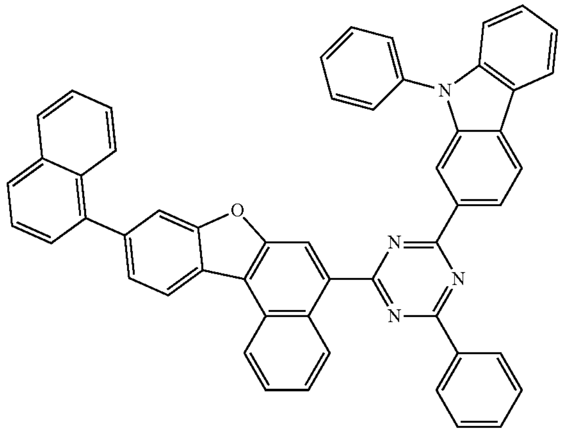

-continued

F645

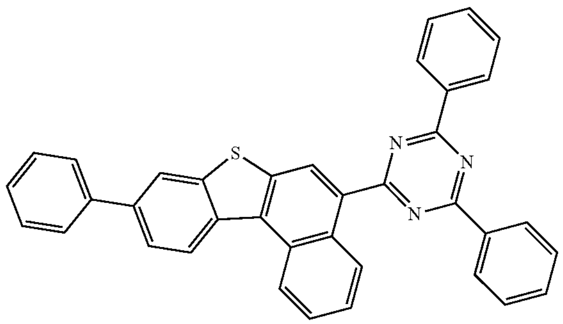

F646

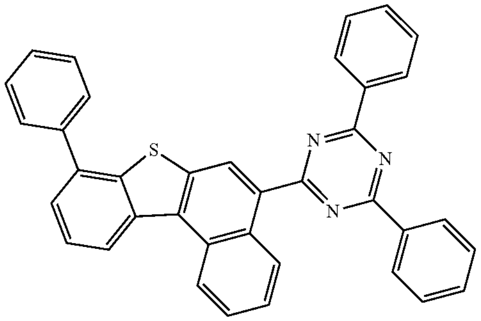

F647

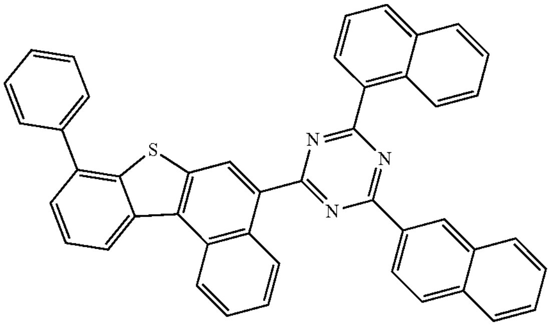

F648

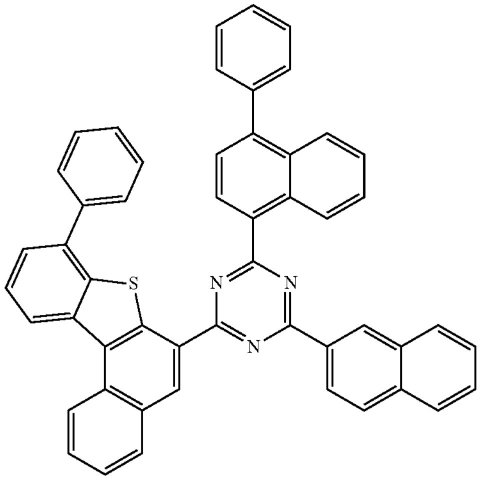

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

One embodiment of the present specification provides an organic light emitting device including a first electrode; a second electrode; and one or more organic material layers provided between the first electrode and the second electrode, wherein one or more layers of the organic material layers include one or more types of the multicyclic compound represented by Chemical Formula 1.

In one embodiment of the present specification, the organic material layer may include two types of the multicyclic compound represented by Chemical Formula 1.

In the organic light emitting device provided in one embodiment of the present specification, the organic material layer further includes a compound represented by the following Chemical Formula 4.

[Chemical Formula 4]

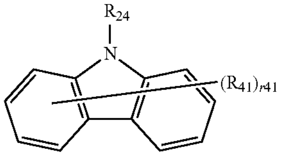

In Chemical Formula 4, $R_{24}$ is a substituted or unsubstituted aryl group, $R_{41}$ is hydrogen; deuterium; a substituted or unsubstituted alkyl group; a substituted or unsubstituted amine group; a substituted or unsubstituted aryl group; or a substituted or unsubstituted heteroaryl group, or groups adjacent to each other may bond to form a substituted or unsubstituted ring, r41 is an integer of 1 to 8, and when r41 is an integer of 2 or greater, substituents in the parentheses are the same as or different from each other.

In one embodiment of the present specification, $R_{24}$ is a substituted or unsubstituted C6 to C30 aryl group.

In one embodiment of the present specification, $R_{24}$ is a substituted or unsubstituted phenyl group; a substituted or unsubstituted biphenyl group; or a substituted or unsubstituted naphthyl group.

In one embodiment of the present specification, $R_{24}$ is a phenyl group unsubstituted or substituted with an aryl group; a biphenyl group; or a naphthyl group unsubstituted or substituted with an aryl group.

In one embodiment of the present specification, $R_{24}$ is a substituted or unsubstituted phenyl group.

In one embodiment of the present specification, the substituted or unsubstituted ring formed by $R_{41}$ bonding to groups adjacent to each other may be a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring.

In one embodiment of the present specification, the compound represented by Chemical Formula 4 is represented by the following Chemical Formula 4-1 or Chemical Formula 4-2.

[Chemical Formula 4-1]

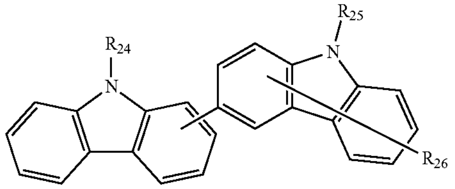

[Chemical Formula 4-2]

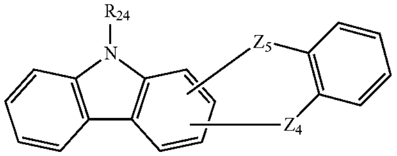

In Chemical Formulae 4-1 and 4-2, $R_{24}$ has the same definition as in Chemical Formula 4, $Z_4$ and $Z_5$ are each independently a direct bond; $NR_{27}$; or $CR_{28}R_{29}$, $R_{25}$ is a substituted or unsubstituted aryl group, and $R_{26}$ to $R_{29}$ are each independently hydrogen; deuterium; a substituted or unsubstituted alkyl group; a substituted or unsubstituted aryl group; or a substituted or unsubstituted heteroaryl group.

In one embodiment of the present specification, $R_{25}$ is a substituted or unsubstituted phenyl group; or a substituted or unsubstituted biphenyl group.

In one embodiment of the present specification, $R_{27}$ is a substituted or unsubstituted phenyl group; a substituted or unsubstituted biphenyl group; or a substituted or unsubstituted naphthyl group.

In one embodiment of the present specification, $R_{27}$ is a phenyl group unsubstituted or substituted with an aryl group; a biphenyl group; or a naphthyl group unsubstituted or substituted with an aryl group.

In one embodiment of the present specification, Chemical Formula 4 is represented by any one of the following compounds.

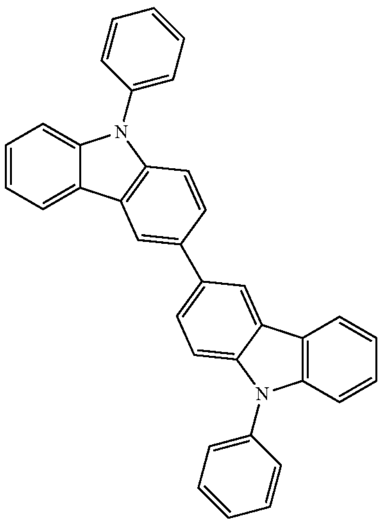

-continued

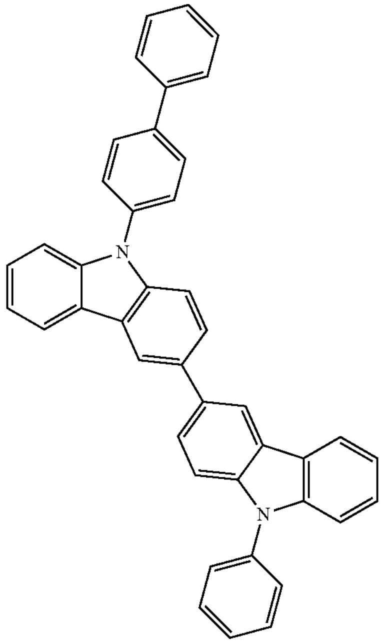

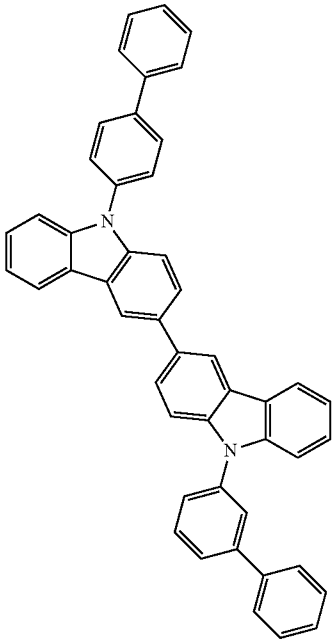

-continued
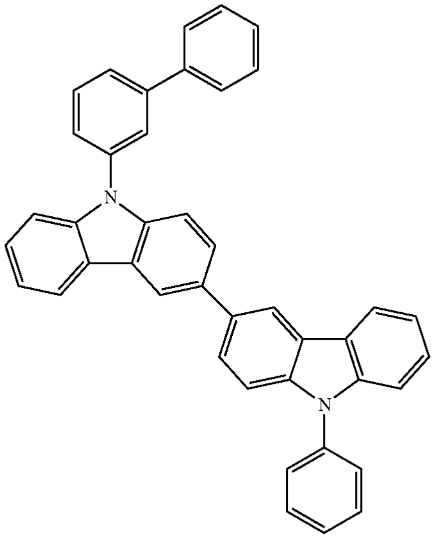
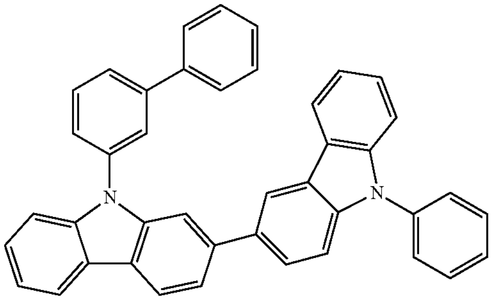
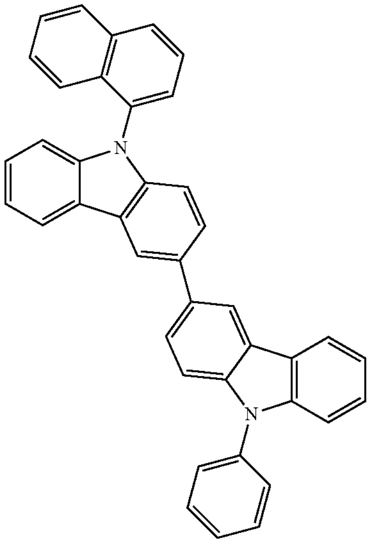
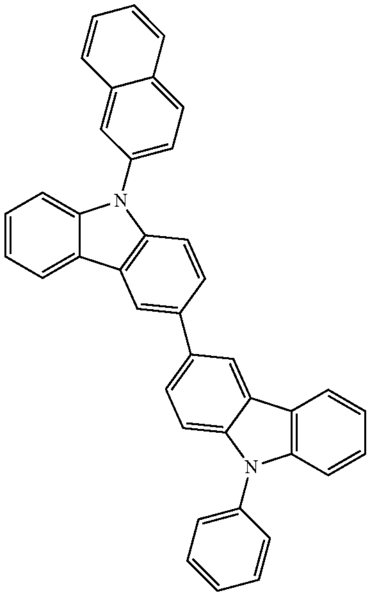
-continued
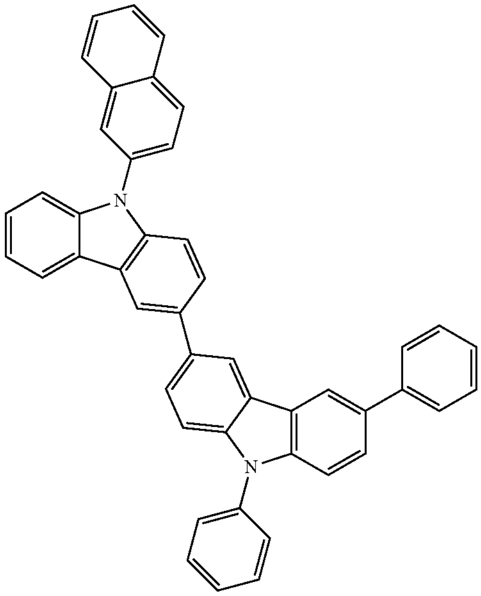

-continued
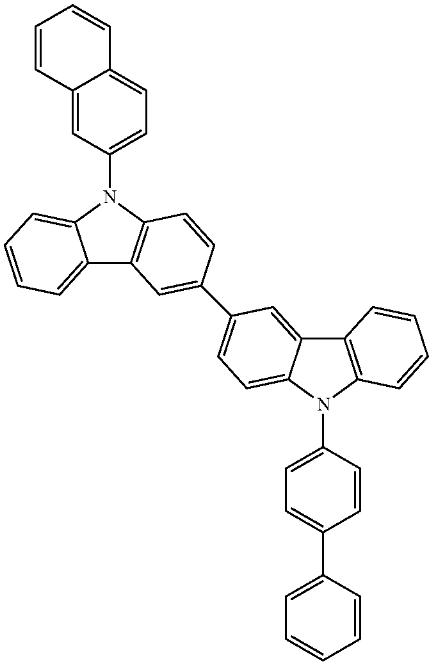
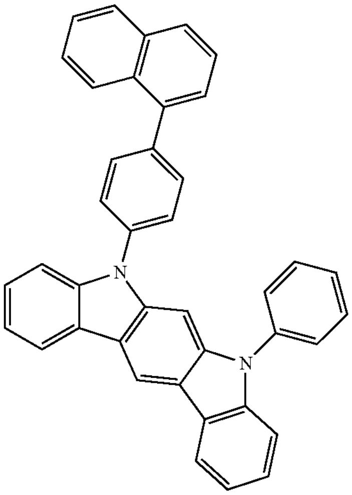
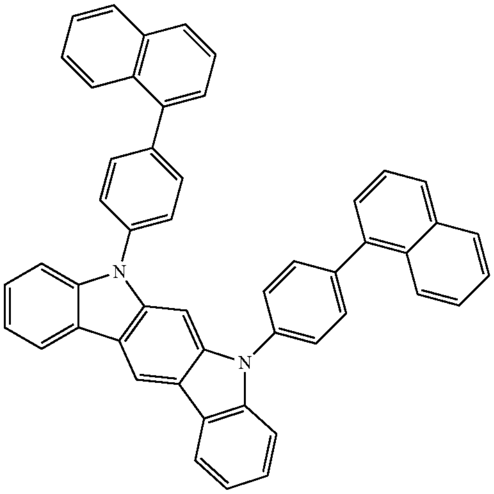
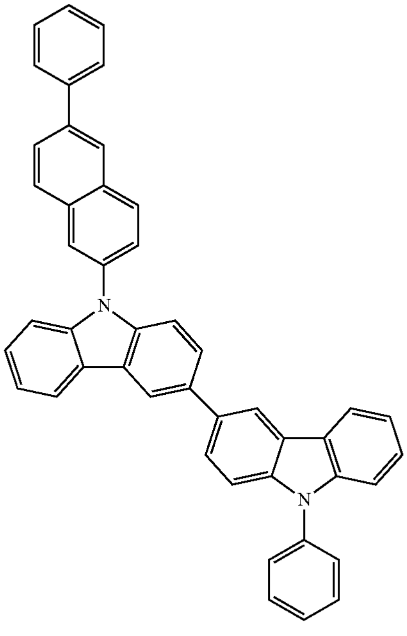
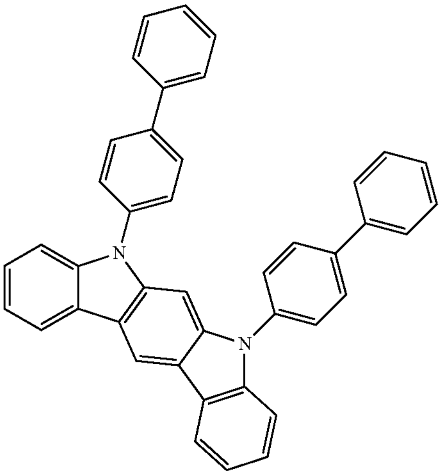

-continued
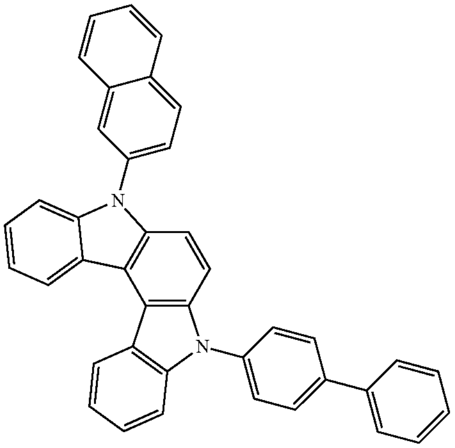
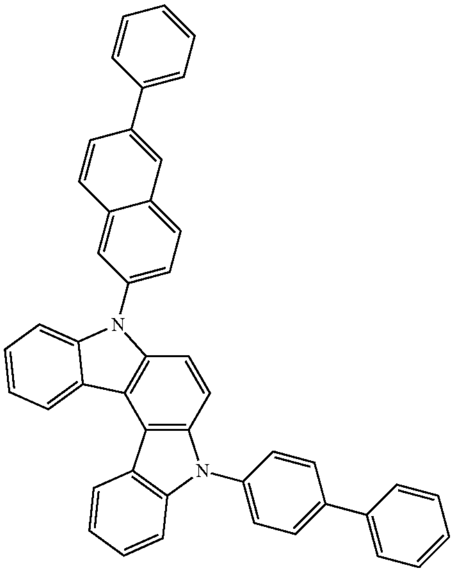
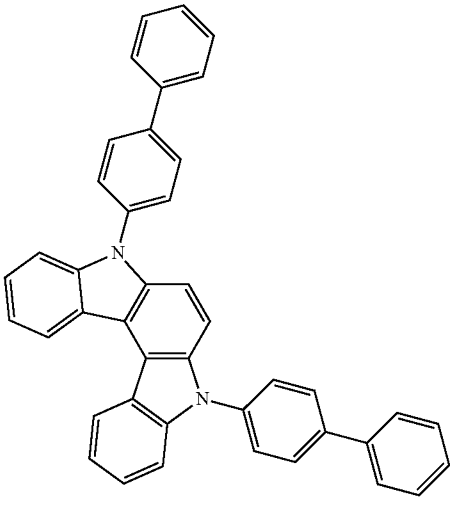
-continued
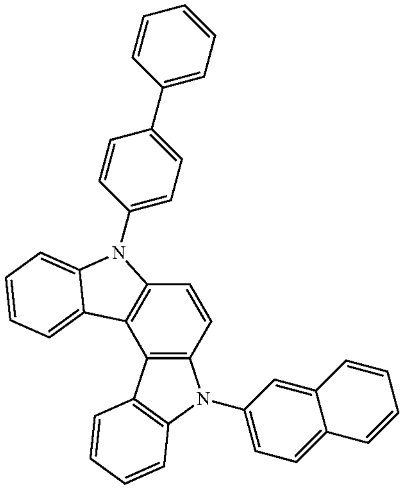
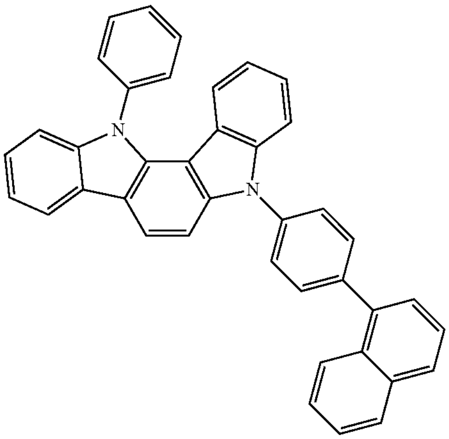
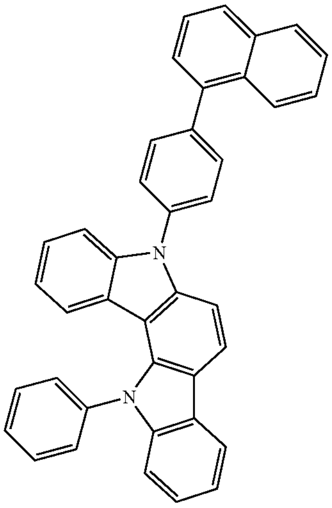

-continued

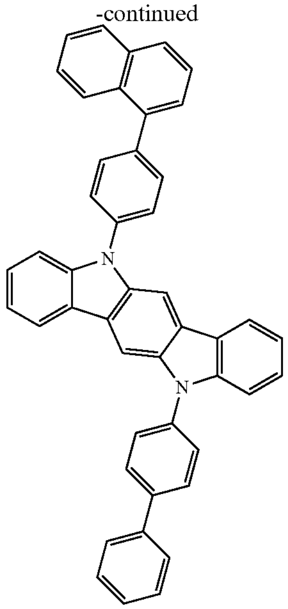

In the organic light emitting device provided in one embodiment of the present specification, the organic material layer further includes a compound represented by the following Chemical Formula 5.

[Chemical Formula 5]

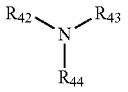

In Chemical Formula 5, $R_{42}$ to $R_{44}$ are each independently a substituted or unsubstituted aryl group; or a substituted or unsubstituted heteroaryl group.

In one embodiment of the present specification, $R_{42}$ to $R_{44}$ are each independently a substituted or unsubstituted C6 to C30 aryl group; or a substituted or unsubstituted C2 to C30 heteroaryl group.

In one embodiment of the present specification, Chemical Formula 5 is represented by any one of the following compounds.

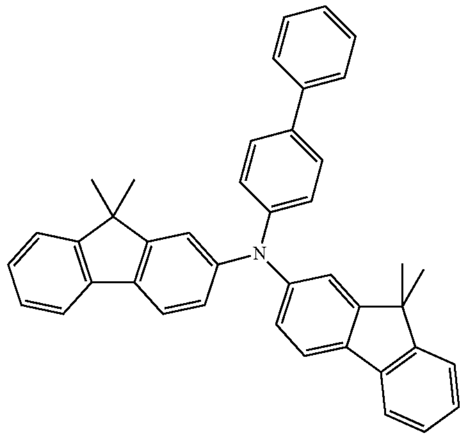

-continued

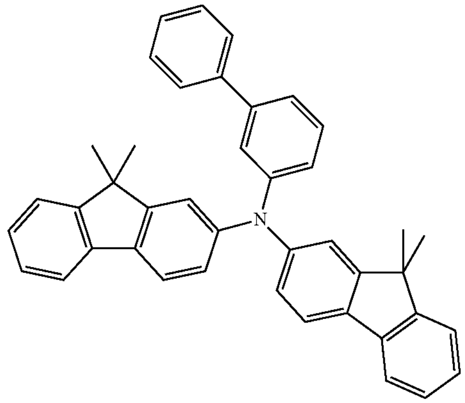

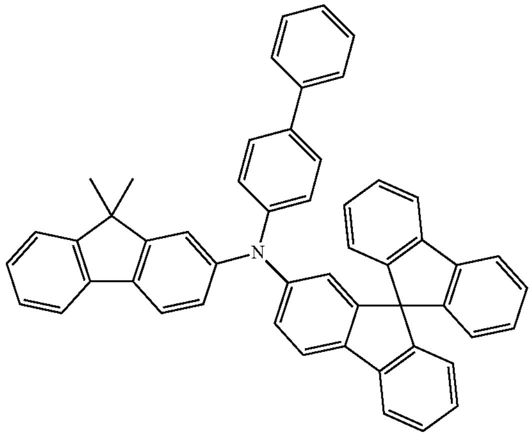

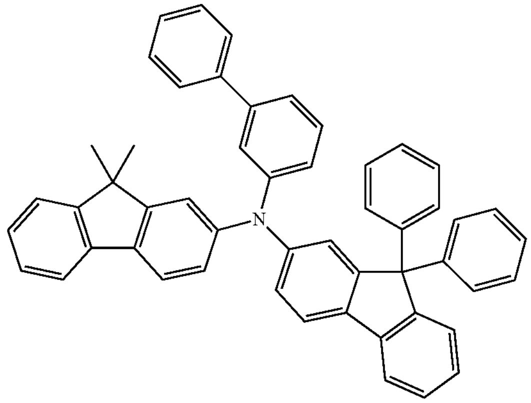

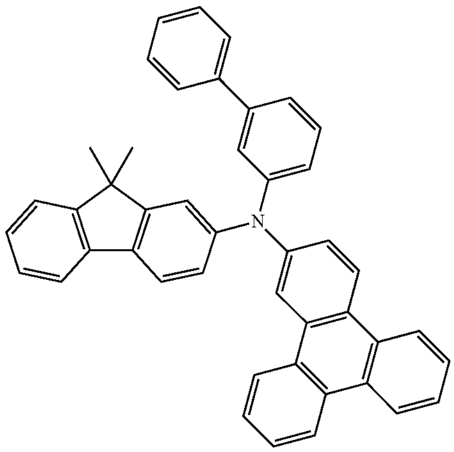

-continued

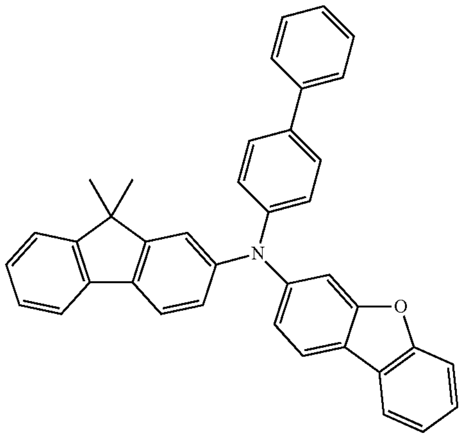

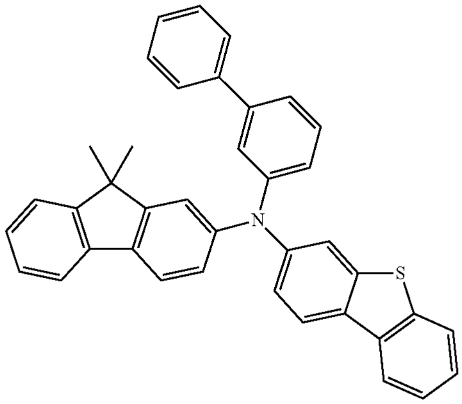

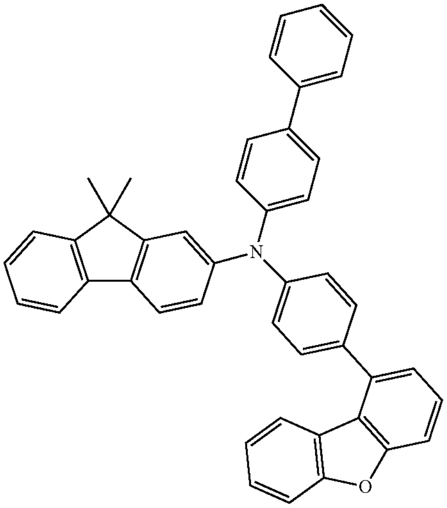

-continued

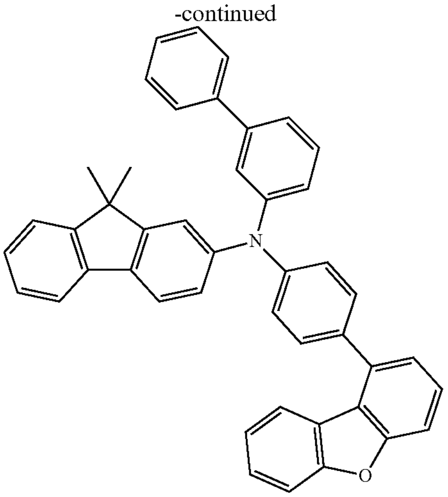

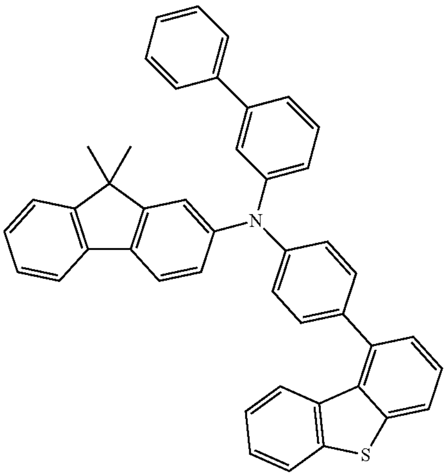

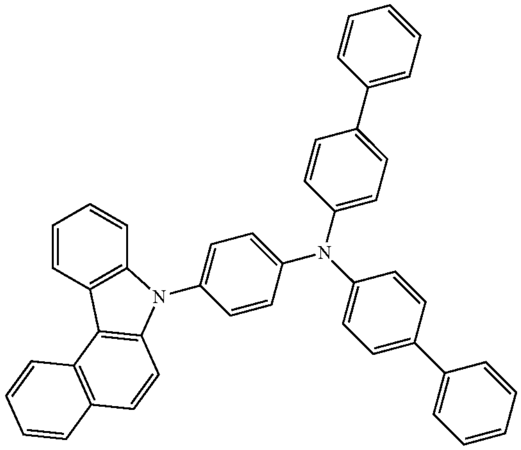

In one embodiment of the present specification, the first electrode may be an anode, and the second electrode may be a cathode.

In another embodiment of the present specification, the first electrode may be a cathode, and the second electrode may be an anode.

In one embodiment of the present specification, the organic light emitting device may be a blue organic light emitting device, and the multicyclic compound according to Chemical Formula 1 may be used as a material of the blue organic light emitting device. For example, the multicyclic compound according to Chemical Formula 1 may be included in a host material of a red light emitting layer of the blue organic light emitting device.

In another embodiment of the present specification, the organic light emitting device may be a green organic light emitting device, and the multicyclic compound according to Chemical Formula 1 may be used as a material of the green organic light emitting device. For example, the multicyclic compound according to Chemical Formula 1 may be included in a host material of a red light emitting layer of the green organic light emitting device.

In another embodiment of the present specification, the organic light emitting device may be a red organic light emitting device, and the multicyclic compound according to Chemical Formula 1 may be used as a material of the red organic light emitting device. For example, the multicyclic compound according to Chemical Formula 1 may be included in a host material of a red light emitting layer of the red organic light emitting device.

Specific details on the multicyclic compound represented by Chemical Formula 1 are the same as the descriptions provided above.

The organic light emitting device of the present specification may be manufactured using common organic light emitting device manufacturing methods and materials except that one or more organic material layers are formed using the multicyclic compound described above.

The multicyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present specification may be formed in a single layer structure, or may also be formed in a multilayer structure in which two or more organic material layers are laminated. For example, the organic light emitting device according to one embodiment of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include a smaller number of organic material layers.

In the organic light emitting device of the present specification, the organic material layer includes a light emitting layer, and the light emitting layer may include the multicyclic compound.

In another organic light emitting device, the organic material layer includes a light emitting layer, the light emitting layer includes a host, and the host may include one or more types of the multicyclic compound. For example, the host may include two types of the multicyclic compound.

When forming a host by combining two types of the multicyclic compound, more favorable efficiency and lifetime are obtained compared to when using one host. Each host has physical properties of relatively faster electron migration or faster hole migration in one device. Such properties become a problem in controlling a charge balance in a light emitting layer using one type of host. However, by mixing two hosts, such relative properties of a single host may be compensated, and driving, lifetime and efficiency of a device may be improved. Accordingly, values of lifetime, efficiency and driving results change depending on the changes in the ratio when using two types of hosts, and how to combine different hosts is the most important challenge.

In another organic light emitting device, the organic material layer includes a light emitting layer, the light emitting layer includes a host, and the host includes two types of the multicyclic compound and may include two types of the compound in a weight ratio of 1:5 to 5:1 or 1:3 to 3:1.

In another organic light emitting device, the organic material layer includes a light emitting layer, the light emitting layer includes a host, and the host may include one type of the multicyclic compound and one type of the compound of Chemical Formula 4 or 5.

In another organic light emitting device, the organic material layer includes a light emitting layer, the light emitting layer includes a host, and the host may include one type of the multicyclic compound and one type of the compound of Chemical Formula 4 or 5 in a weight ratio of 1:5 to 5:1 or 1:3 to 3:1.

The organic light emitting device of the present disclosure may further include one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present specification. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 includes a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer including the multicyclic compound represented by Chemical Formula 1 may further include other materials as necessary.

In the organic light emitting device according to one embodiment of the present specification, materials other than the multicyclic compound represented by Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly

[3,4-(ethylene-1,2-dioxy)thiophene](PEDOT), polypyrrole and polyaniline, and the like, but are not limited thereto.

As the cathode material, materials having relatively small work function may be used, and metals, metal oxides, conductive polymers or the like may be used. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present specification may be a top-emission type, a bottom-emission type or a dual-emission type depending on the materials used.

The multicyclic compound according to one embodiment of the present specification may also be used in an organic electronic device including an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

Structures of Compounds A1 to A7 used in the following preparation examples are as follows.

A1

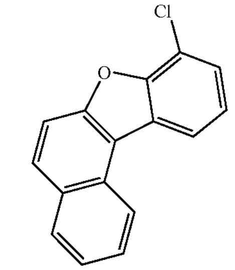

A2

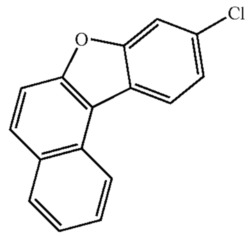

A3

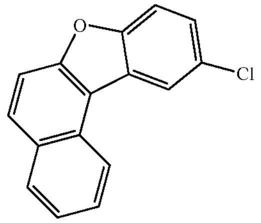

A4

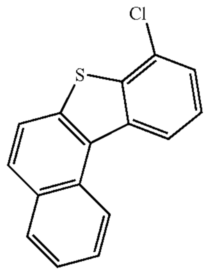

A5

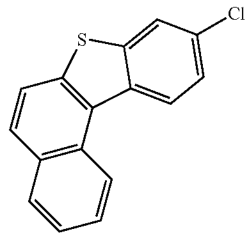

A6
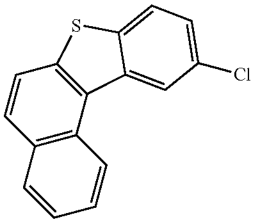
A7
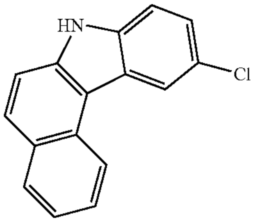
Structures of Compounds B1 to B42 used in the following preparation examples are as follows.
B1
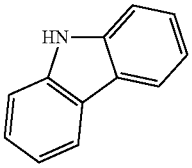
B2
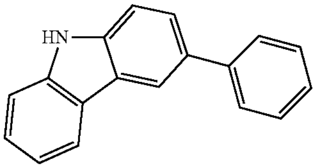
B3
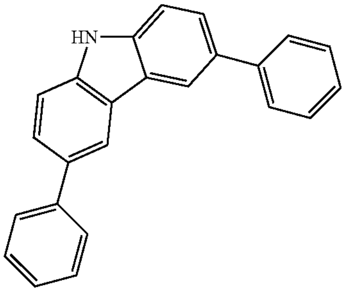
B4
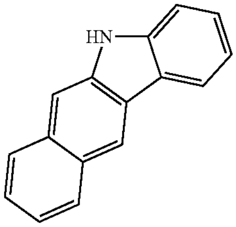
B5
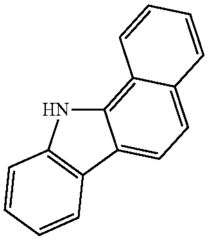
B6
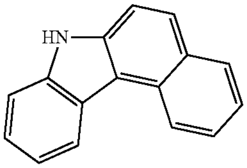
B7
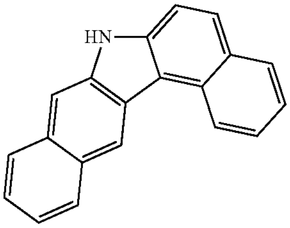
B8
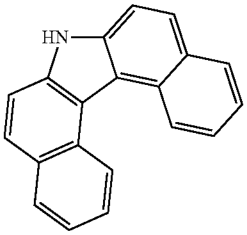
B9
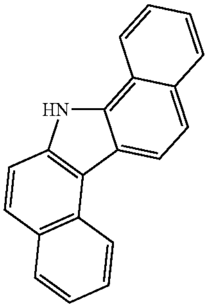
B10
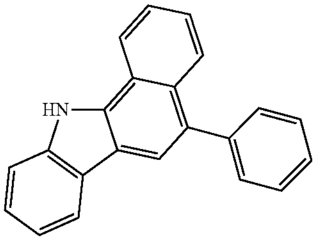

-continued
B11
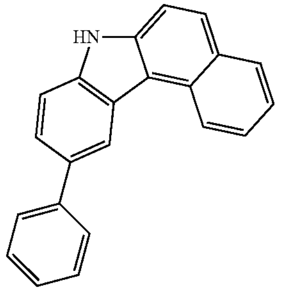
B12
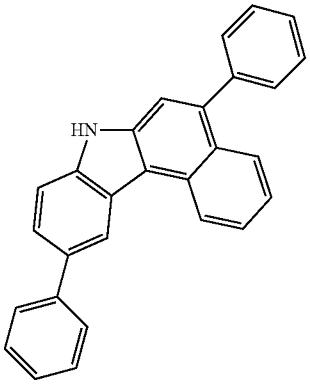
B13
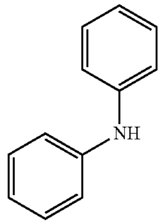
B14
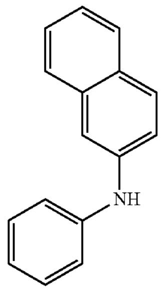
B15
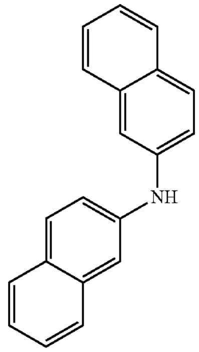
-continued
B16
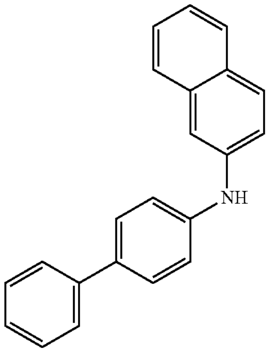
B17
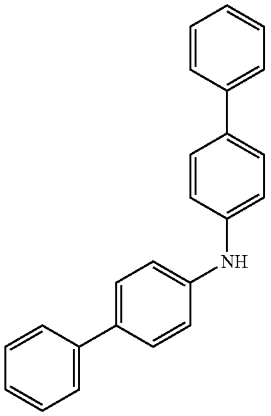
B18
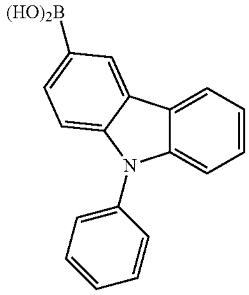
B19
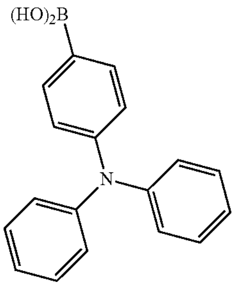

-continued
B20
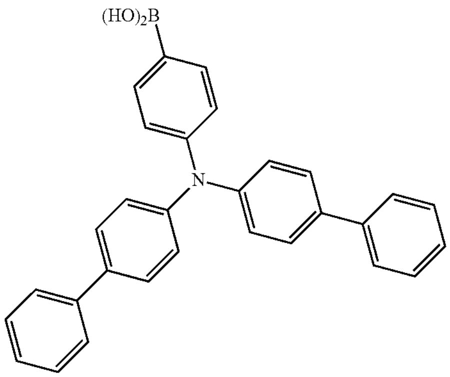
B21
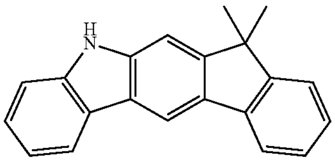
B22
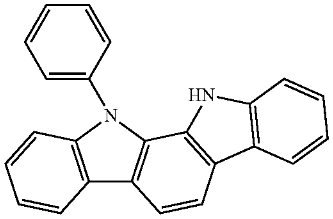
B23
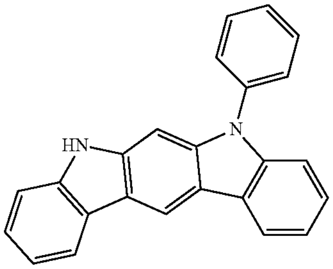
B24
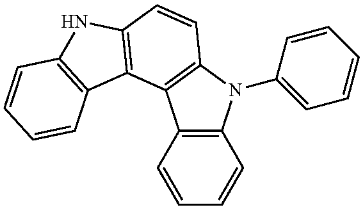
B25
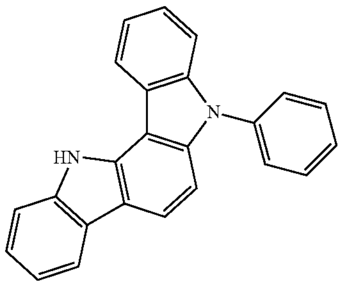
-continued
B26
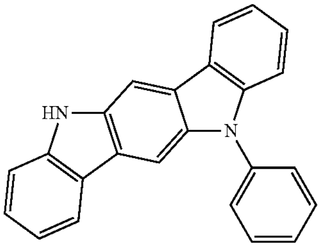
B27
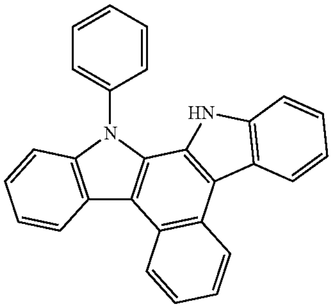
B28
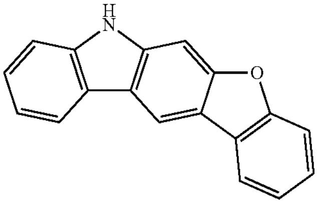
B29
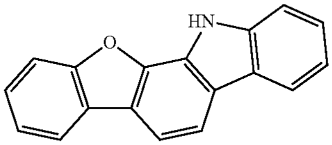
B30
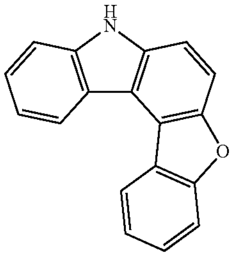
B31
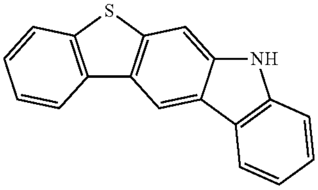

-continued
B32
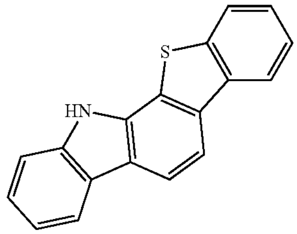
B33
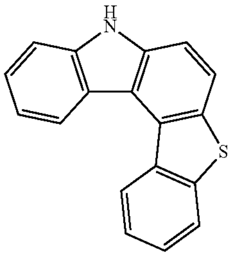
B34
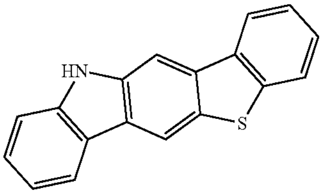
B35
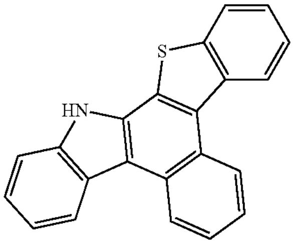
B36
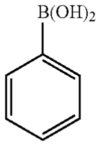
B37
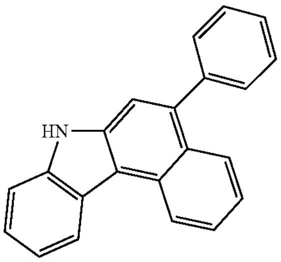
-continued
B38
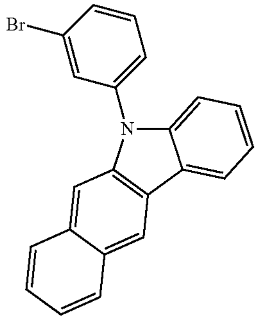
B39
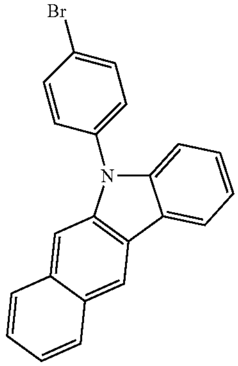
B40
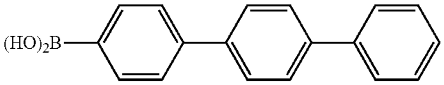
B41
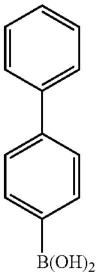
B42
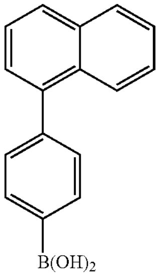
Structures of Compounds E1 to E19 used in the following preparation examples are as follows.

E1
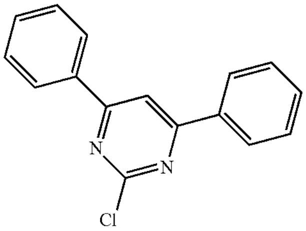
E2
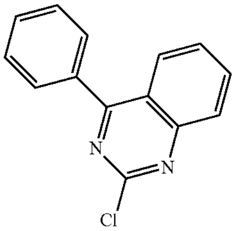
E3
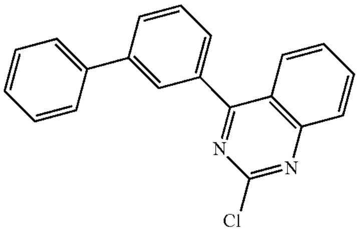
E4
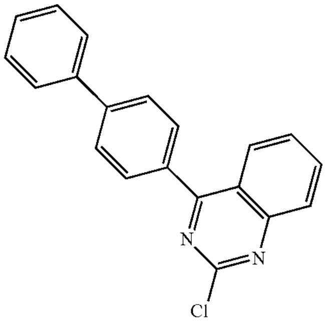
E5
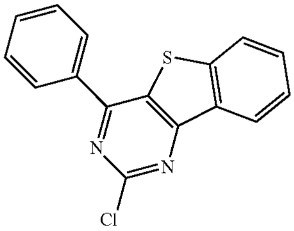
E6
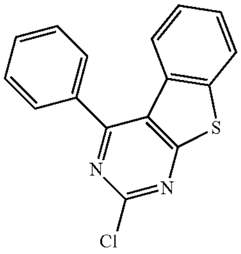
-continued
E7
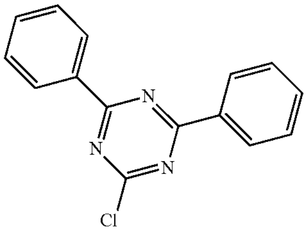
E8
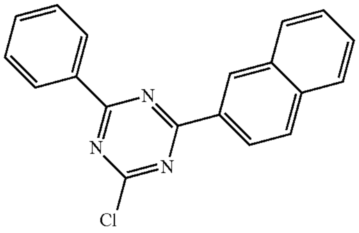
E9
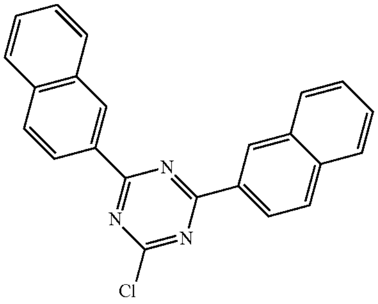
E10
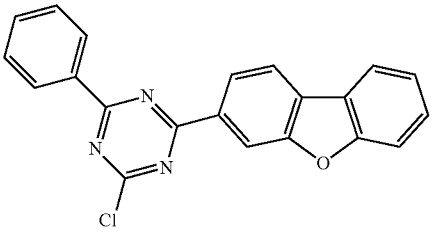
E11
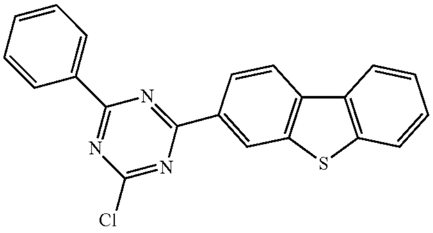
E12
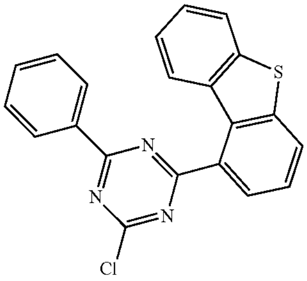

-continued

E13

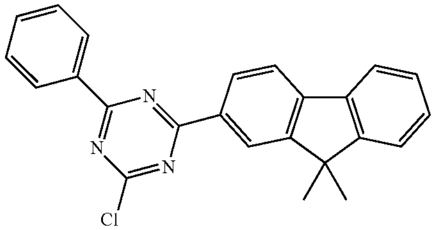

E14

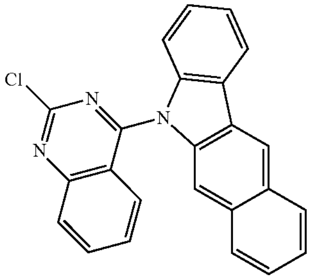

E15

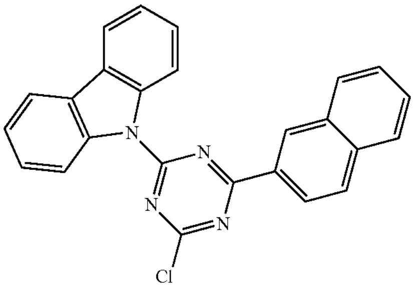

E16

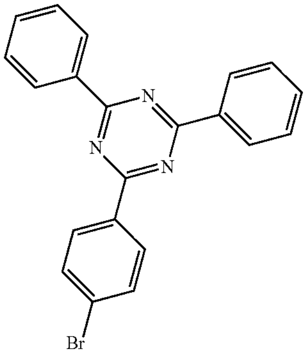

E17

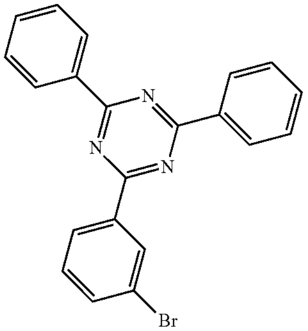

-continued

E18

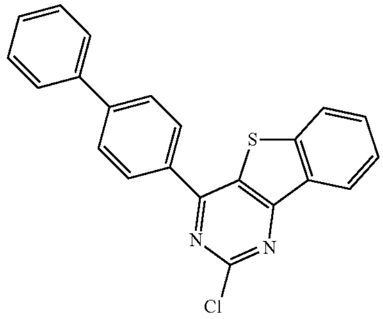

E19

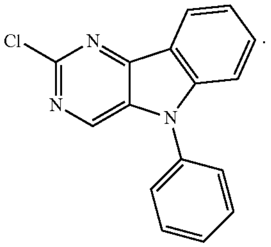

As the compounds, commercially available reagents were used for the compounds other than E10 to E15, and Compounds E10 to E15 were synthesized as follows.

Synthesis of Compound E

<Compounds E10 to E13>

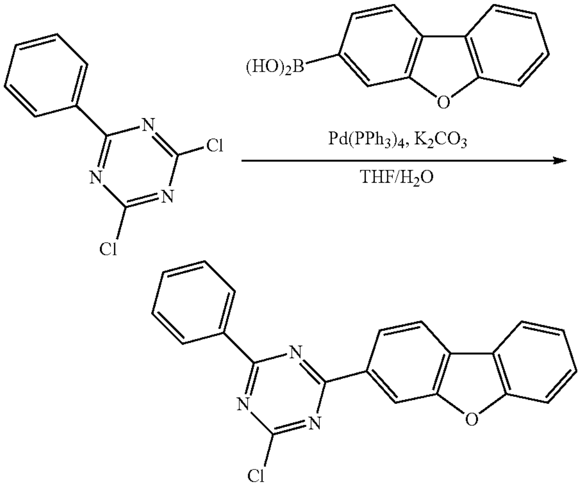

E10

2,4-Dichloro-6-phenyl-1,3,5-triazine (15 g, 66.4 mmol), dibenzo[b,d]furan-3-ylboronic acid (16.9 g, 79.6 mmol), $Pd(PPh_3)_4$ (3.8 g, 3.32 mmol) and $K_2CO_3$ (18.3 g, 132.8 mmol) were introduced to a 500 mL round bottom flask, and after setting up the flask to be under the nitrogen atmosphere, THF (200 mL) and $H_2O$ (40 mL) were introduced thereto, and the result was stirred for 5 hours at 80° C. After the reaction was terminated, the reaction temperature was lowered to room temperature, and the result was washed with water and extracted with methylene chloride. The extracted organic layer was dried with $Mg_2SO_4$, and then concentrated. The result was silica gel columned and recrystallized to obtain white solid Compound E10 (6.3 g, 9.8 mmol, yield 69%).

Compounds E11 to E13 were synthesized in a similar manner as in the above-described synthesis method using starting materials of the following Table 1.
TABLE 1
| Starting Material | Compound E (Yield %) |
| --- | --- |
| 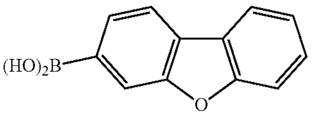 [SMILES: OB(O)c1ccc2c(c1)oc1ccccc12] | 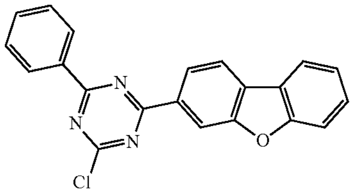 E10 (69) |
| 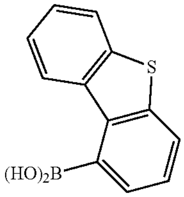 [SMILES: OB(O)c1cccc2sc3ccccc3c12] | 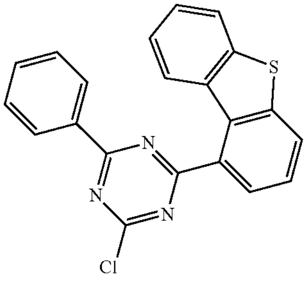 E12 (78) |
| 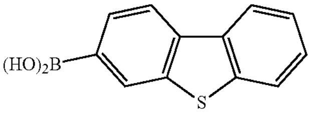 [SMILES: OB(O)c1ccc2c(c1)sc1ccccc12] | 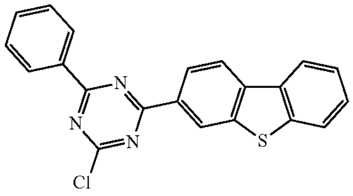 E11 (67) |
| 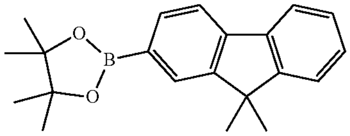 [SMILES: CC1(C)c2ccccc2-c2ccc(B3OC(C)(C)C(C)(C)O3)cc21] | 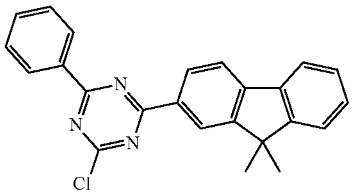 E13 (78) |

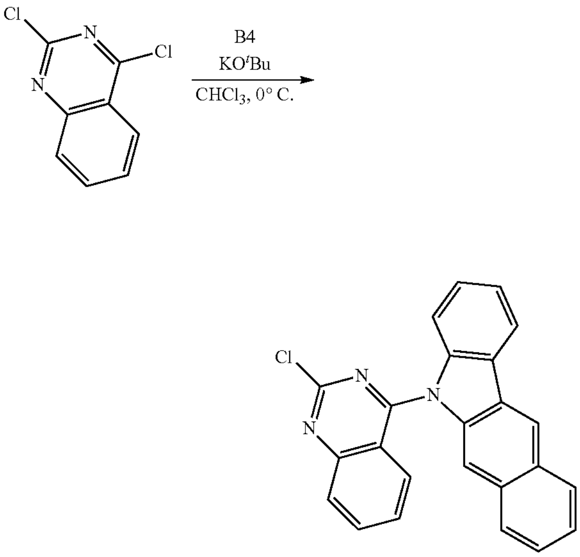

E14

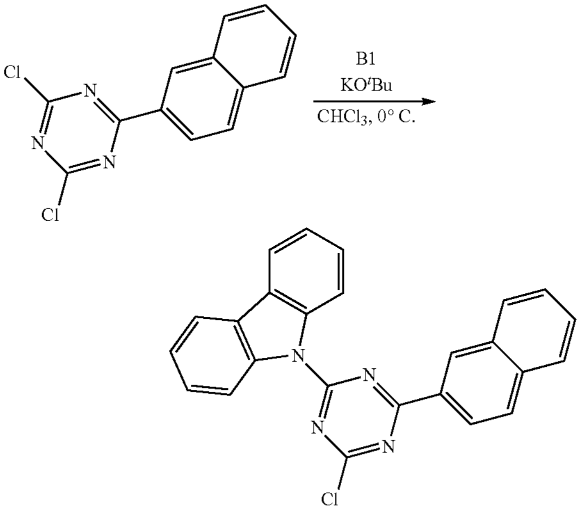

E15

2,4-Dichloroquinazoline (15 g, 50.2 mmol) and KO$^t$Bu (5.6 g, 50.2 mmol) were introduced to a 250 mL round bottom flask, and after setting up the flask to be under the nitrogen atmosphere, $CHCl_3$ (150 mL) was introduced thereto, the result was stirred for 30 minutes at 0° C., and Compound B4 (10.9 g, 50.2 mmol) was slowly added dropwise thereto. After the reaction was terminated in 1 hour, the reaction was terminated by introducing methanol (50 mL) thereto, and the result was washed with water and then extracted with methylene chloride. The extracted organic layer was dried with $Mg_2SO_4$ and then concentrated. The result was silica gel columned and recrystallized to obtain white solid Compound E14 (17 g, 45 mmol, yield 69%).

White solid Compound E15 (7 g, yield 80%) was obtained in a similar manner as above using 2,4-dichloro-6-(naphthalen-2-yl)-1,3,5-triazine and B1 as starting materials.

[Preparation Example 1] Preparation of Compound F

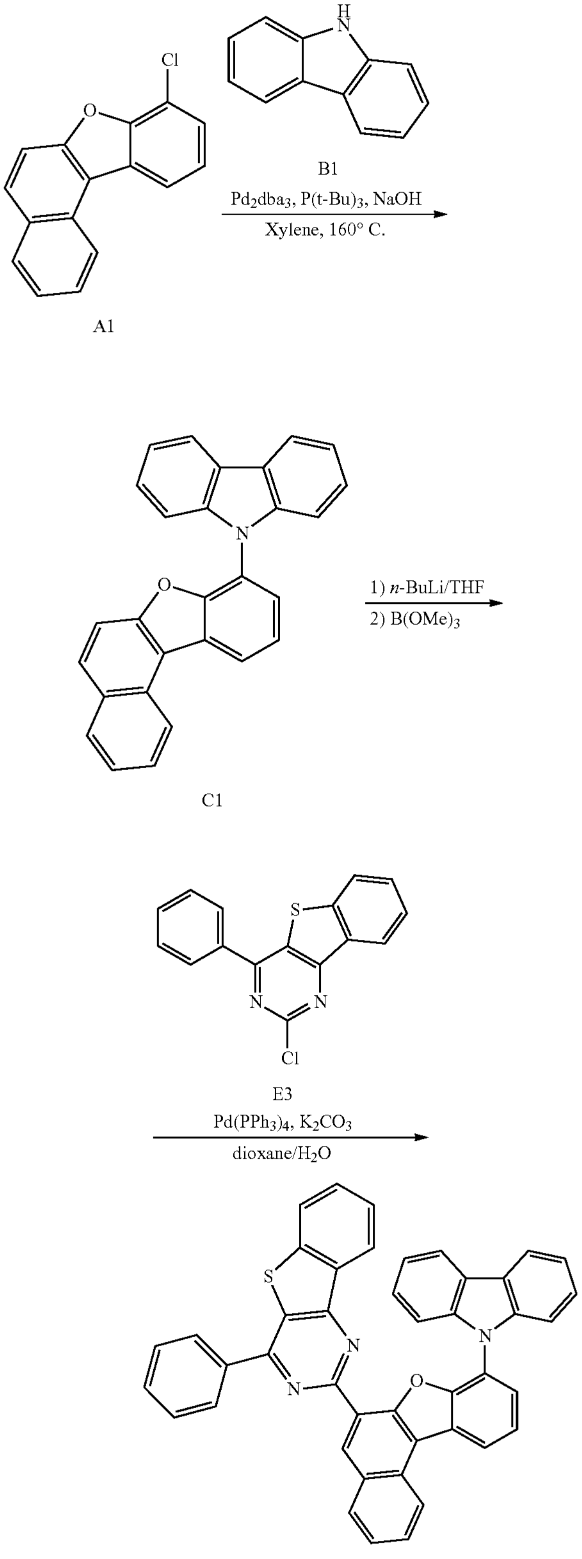

A1

C1

F4

Synthesis of Compound C

Synthesis Example 1-1

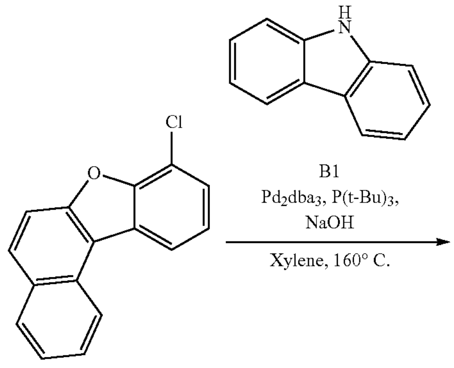

A1

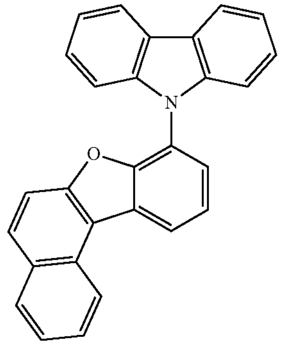

C1

Compound A1 (20 g, 79.1 mmol), Compound B1 (15.8 g, 94.92 mmol), $Pd_2dba_3$ (3.6 g, 3.95 mmol), $P(t\text{-}Bu)_3$ (3.2 g, 15.8 mmol) and NaOH (6.3 g, 158 mmol) were introduced to a 500 mL round bottom flask, and after setting up the flask to be under the nitrogen atmosphere, xylene (300 mL) was introduced thereto, and the result was stirred for 12 hours at 160° C. After the reaction was terminated, the reaction temperature was lowered to room temperature, and the result was washed with water and extracted with methylene chloride. The extracted organic layer was dried with $Mg_2SO_4$ and then concentrated. The result was silica gel columned and recrystallized to obtain Compound C1 (26.7 g, 70 mmol, yield 89%).

Compounds C2 to C27 were synthesized in the same manner as in the above-described synthesis method of Synthesis Example 1-1 using Compounds A and B of the following Table 2 instead of Compounds A1 and B1.

TABLE 2

| Compound A | Compound B | Compound C (Yield %) |
|---|---|---|
| A1 | B1 | 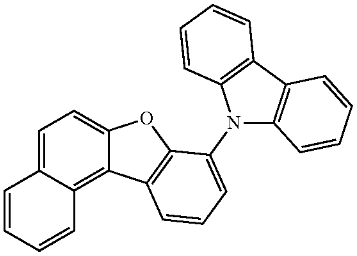 C1 (89) |
| A1 | B23 | 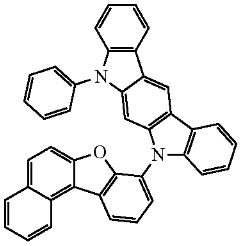 C3 (87) |
| A4 | B1 | 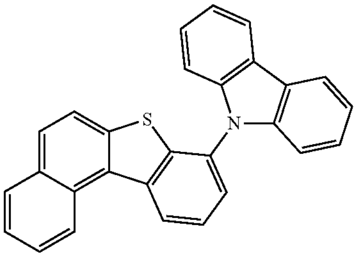 C5 (92) |
| A1 | E14 | 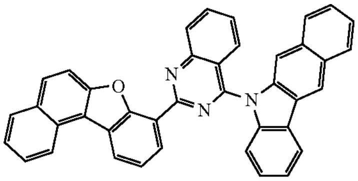 C7 (84) |
| A2 | B4 | 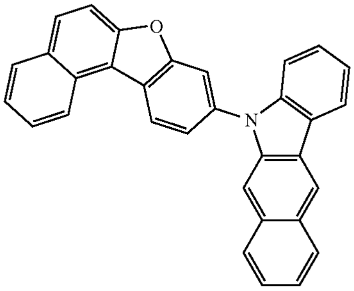 C9 (76) |

TABLE 2-continued
| Compound A | Compound B | Compound C (Yield %) |
|---|---|---|
| A2 | B35 | 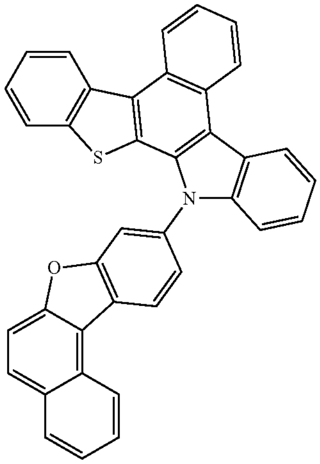 C11 (88) |
| A2 | B16 | 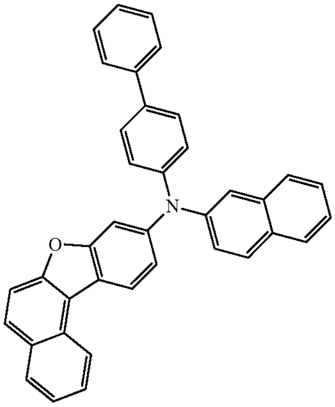 C13 (90) |
| A5 | B5 | 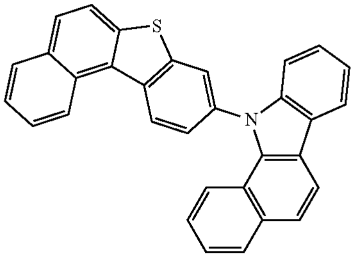 C15 (89) |
| A5 | B28 | 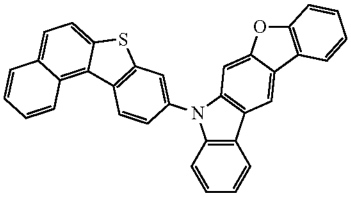 C17 (83) |
| A3 | B12 | 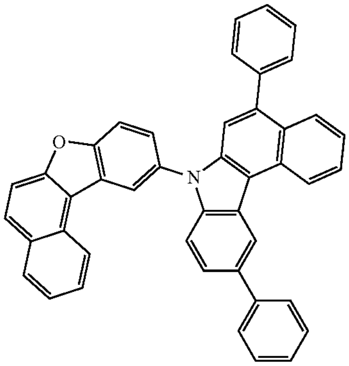 C19 (85) |
| A3 | B4 | 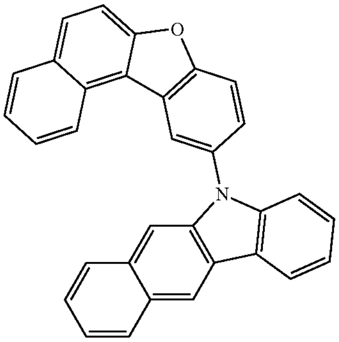 C21 (84) |
| A3 | B2 | 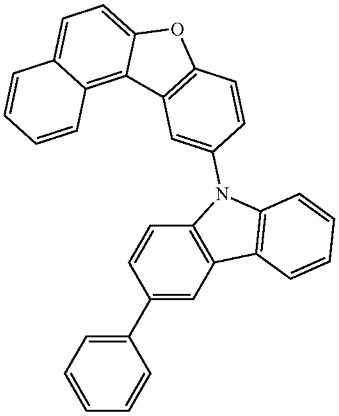 C23 (79) |

TABLE 2-continued
| Compound A | Compound B | Compound C (Yield %) |
|---|---|---|
| A3 | B26 | 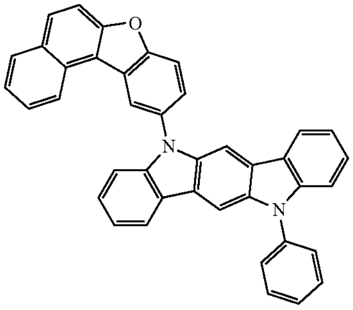 C25 (92) |
| A3 | B17 | 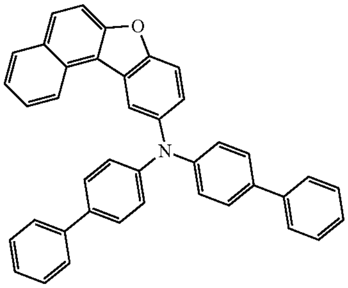 C27 (76) |
| A1 | B4 | 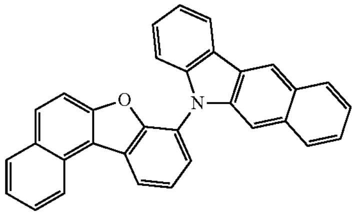 C2 (89) |
| A1 | B17 | 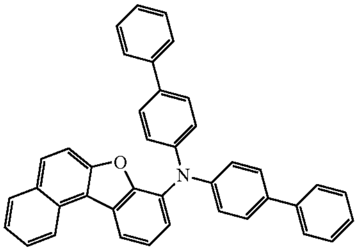 C4 (90) |
| A4 | B4 | 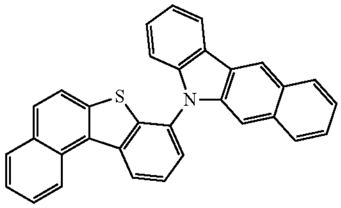 C6 (91) |
TABLE 2-continued
| Compound A | Compound B | Compound C (Yield %) |
|---|---|---|
| A2 | B1 | 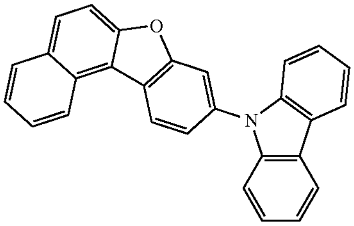 C8 (78) |
| A2 | B23 | 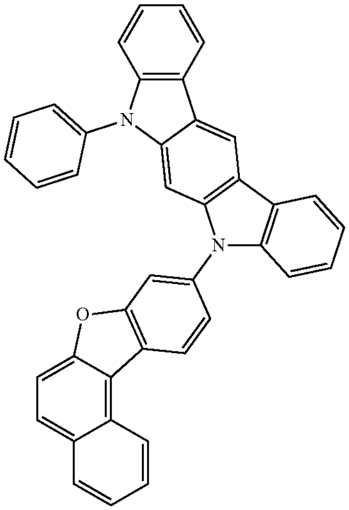 C10 (94) |
| A2 | B17 | 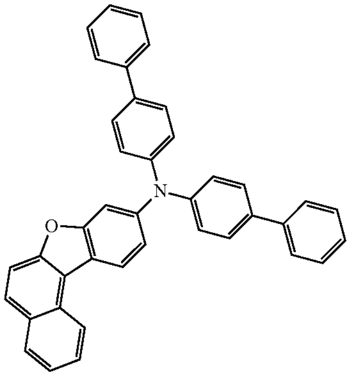 C12 (78) |
| A5 | B4 | 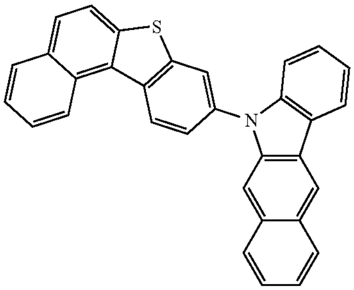 C14 (90) |

TABLE 2-continued
| Compound A | Compound B | Compound C (Yield %) |
|---|---|---|
| A5 | B26 | 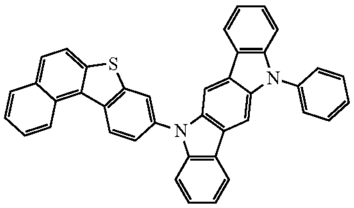 C16 (88) |
| A5 | B17 | 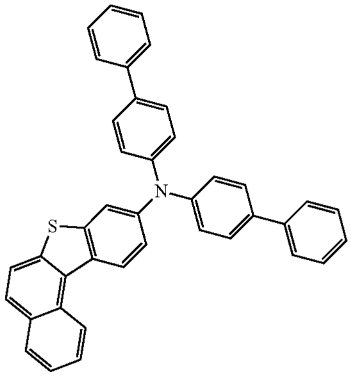 C18 (74) |
| A3 | B3 | 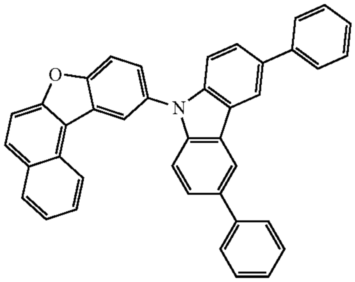 C20 (86) |
| A3 | B1 | 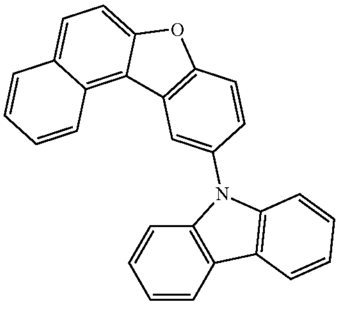 C22 (74) |
TABLE 2-continued
| Compound A | Compound B | Compound C (Yield %) |
|---|---|---|
| A3 | B23 | 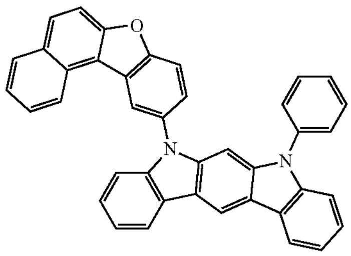 C24 (79) |
| A3 | B34 | 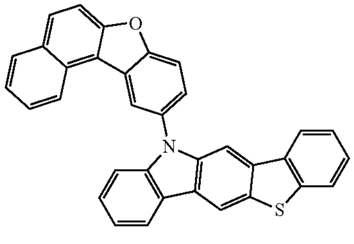 C26 (89) |
Synthesis Example 1-2
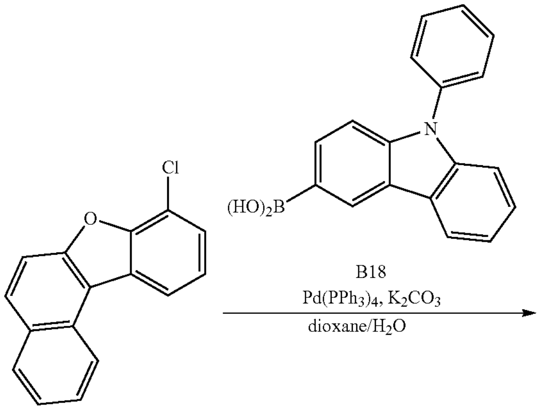
A1

-continued

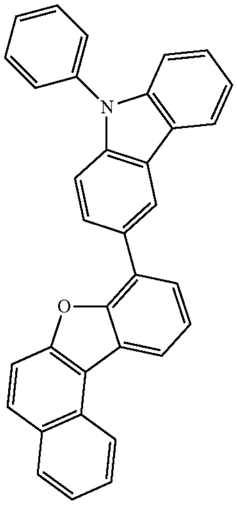

C28

Compound A1 (20 g, 79.1 mmol), Compound B18 (15.8 g, 94.92 mmol), $Pd(PPh_3)_4$ (4.5 g, 3.95 mmol) and $K_2CO_3$ (21.8 g, 158 mmol) were introduced to a 500 mL round bottom flask, and after setting up the flask to be under the nitrogen atmosphere, dioxane (250 mL) and $H_2O$ (50 mL) were introduced thereto, and the result was stirred for 4 hours at 120° C. After the reaction was terminated, the reaction temperature was lowered to room temperature, and the result was washed with water and extracted with methylene chloride. The extracted organic layer was dried with $Mg_2SO_4$ and then concentrated. The result was silica gel columned and recrystallized to obtain Compound C28 (33 g, 72 mmol, yield 91%).

Compounds C29 to C31 were synthesized in the same manner as in the above-described synthesis method of Synthesis Example 1-2 using Compound A of the following Table 3 instead of Compound A1.

TABLE 3

| Compound A | Compound B | Compound C (Yield %) |
|---|---|---|
| A1 | B18 | 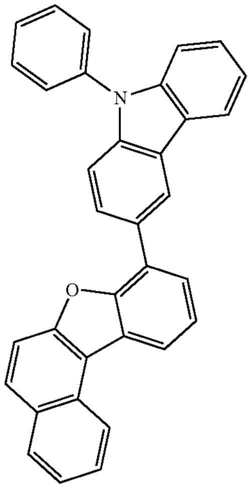 C28 (91) |
| A2 | B18 | 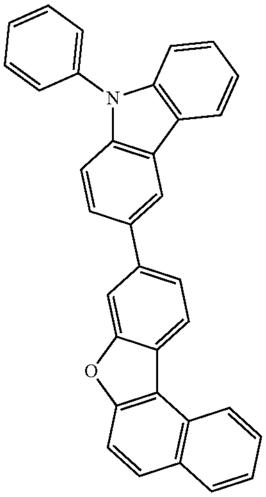 C29 (88) |
| A3 | B18 | 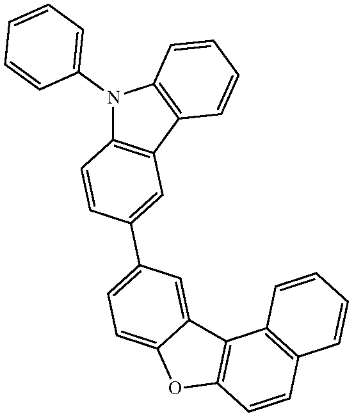 C30 (71) |
| A6 | B18 | 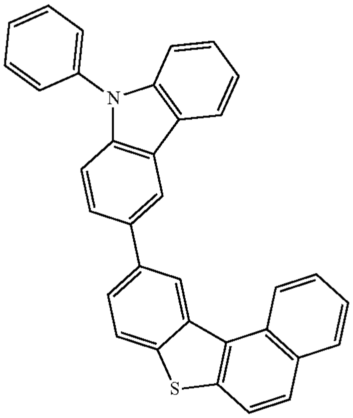 C31 (76) |

Synthesis of Compound D

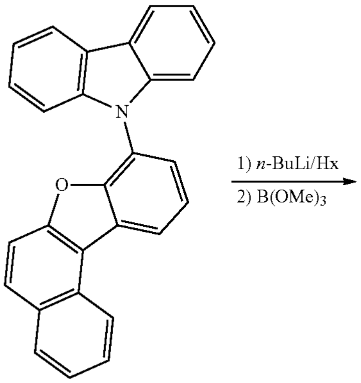

C1

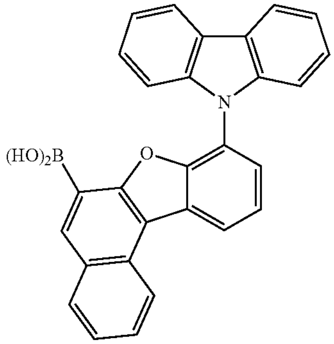

D1

Compound C1 (26 g, 67.8 mmol) was introduced to a 250 mL round bottom flask, and after setting up the flask to be under the nitrogen atmosphere, THE (250 mL) was introduced thereto, and the inner temperature of the reaction vessel was calibrated to −78° C. 2.5 M (in hexane) n-BuLi (29.8 mL) was slowly added dropwise thereto, and after stirring the result for 2 hours, $B(OMe)_3$ (9.8 mL, 101.7 mmol) was slowly added dropwise thereto at room temperature. After the reaction was terminated in 2 hours, the reaction was completely terminated using ethanol (20 mL), and the result was washed with water and extracted with methylene chloride. The extracted organic layer was dried with $Mg_2SO_4$ and then concentrated. The result was silica gel columned to obtain white solid Compound D1 (23.8 g, 55.6 mmol, yield 82%).

Compounds D2 to D31 were synthesized in the same manner as in the above-described synthesis method using Compound C of the following Table 4 instead of C1.

TABLE 4

| Compound C | Compound D (Yield %) |
|---|---|
| C1 | 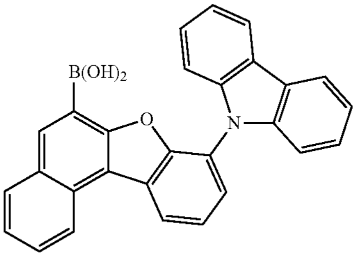 D1 (82) |
| C2 | 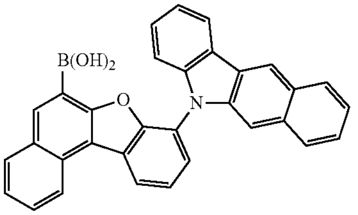 D2 (78) |
| C3 | 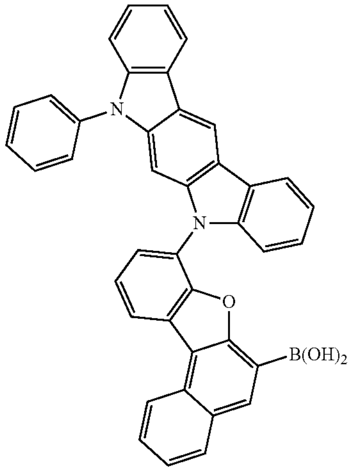 D3 (77) |
| C4 | 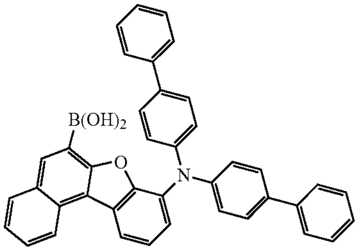 D4 (75) |

TABLE 4-continued
| Compound C | Compound D (Yield %) |
|---|---|
| C5 | 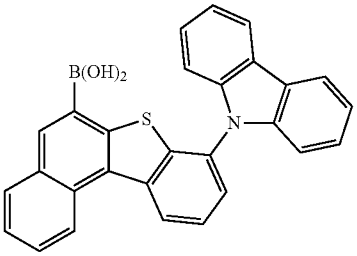 D5 (84) |
| C6 | 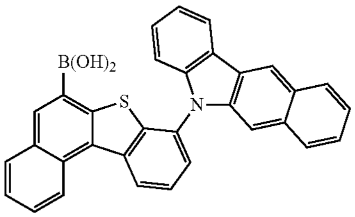 D6 (88) |
| C7 | 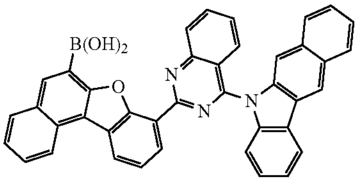 D7 (48) |
| C8 | 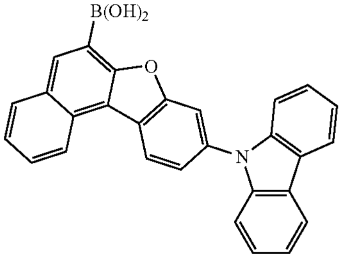 D8 (90) |
| C9 | 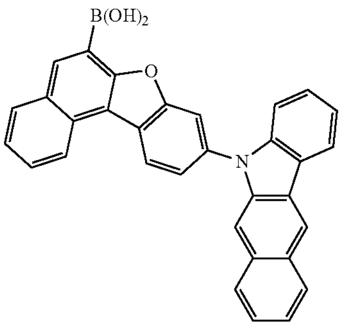 D9 (69) |
TABLE 4-continued
| Compound C | Compound D (Yield %) |
|---|---|
| C10 | 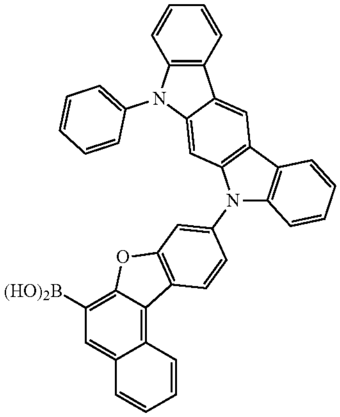 D10 (79) |
| C11 | 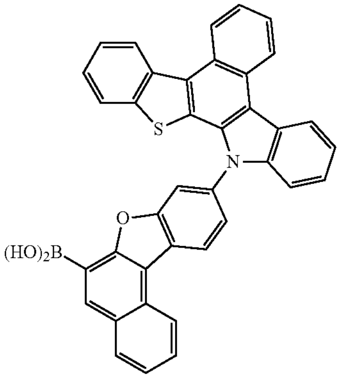 D11 (55) |
| C12 | 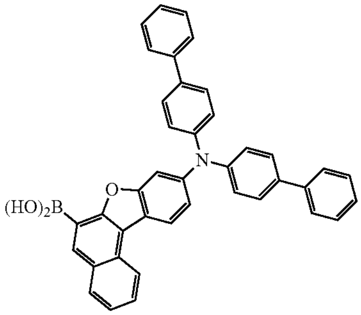 D12 (80) |

TABLE 4-continued
| Compound C | Compound D (Yield %) |
|---|---|
| C13 | 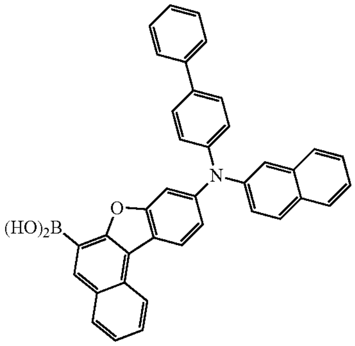 D13 (81) |
| C14 | 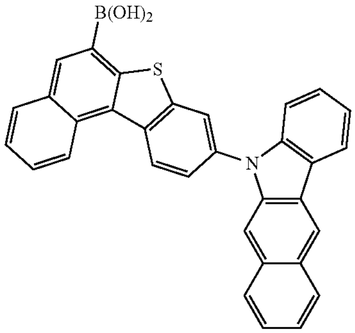 D14 (78) |
| C15 | 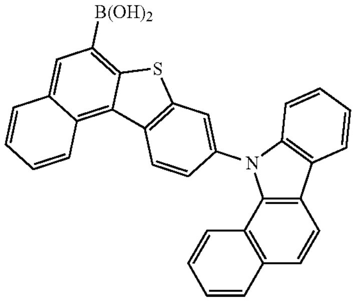 D15 (63) |
| C16 | 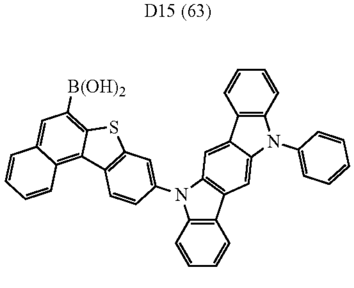 D16 (78) |
TABLE 4-continued
| Compound C | Compound D (Yield %) |
|---|---|
| C17 | 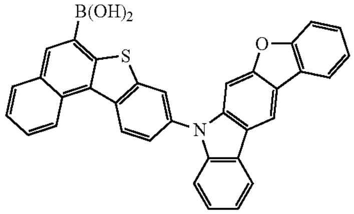 D17 (69) |
| C18 | 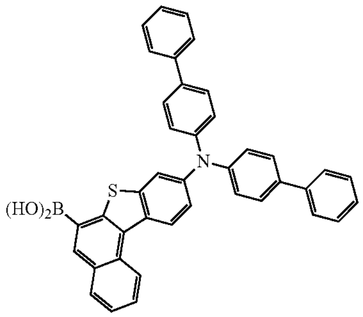 D18 (70) |
| C19 | 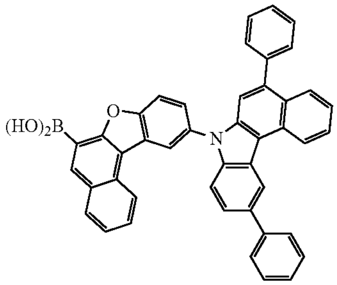 D19 (88) |
| C20 | 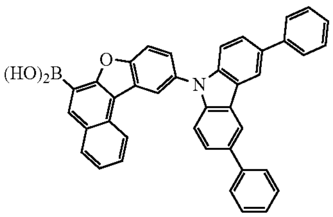 D20 (83) |

TABLE 4-continued
| Compound C | Compound D (Yield %) |
| --- | --- |
| C21 | 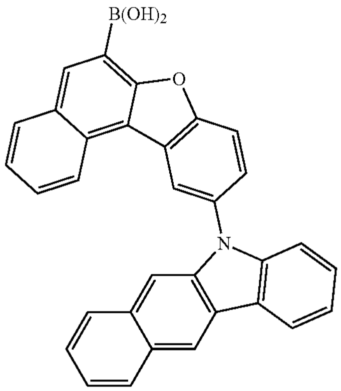 D31 (89) |
| C22 | 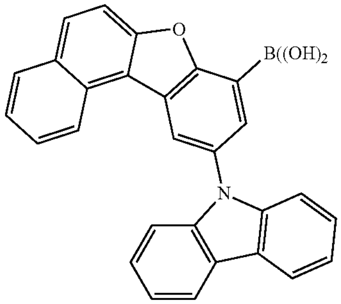 D22 (58) |
| C23 | 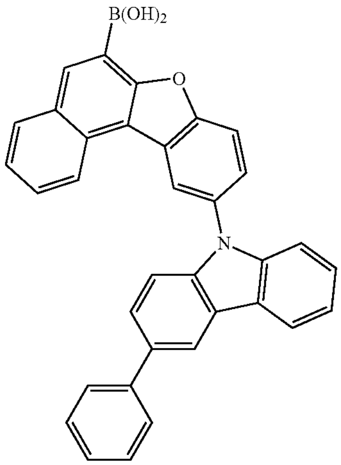 D23 (76) |
| C24 | 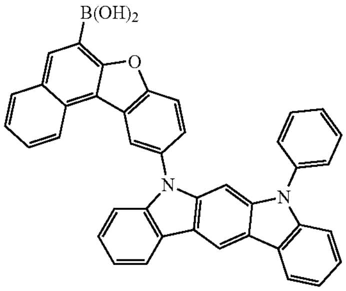 D24 (92) |
| C25 | 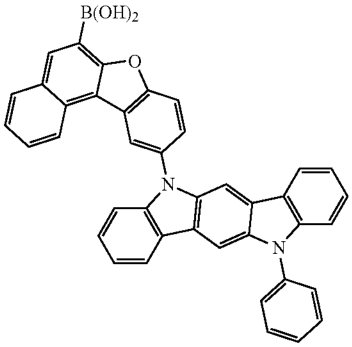 D25 (77) |
| C26 | 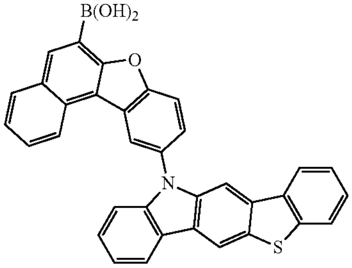 D26 (82) |
| C27 | 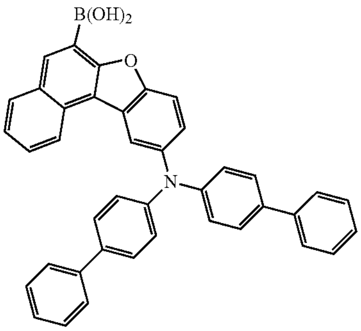 D27 (68) |

TABLE 4-continued
| Compound C | Compound D (Yield %) |
|---|---|
| C28 | 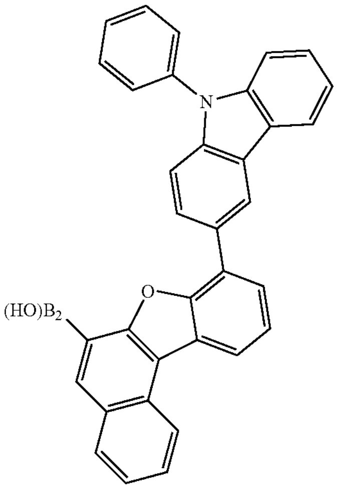<br>D28 (52) |
| C29 | 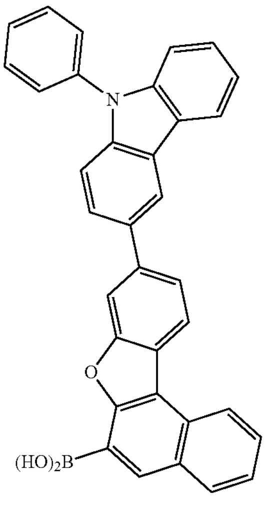<br>D29 (55) |
| C30 | 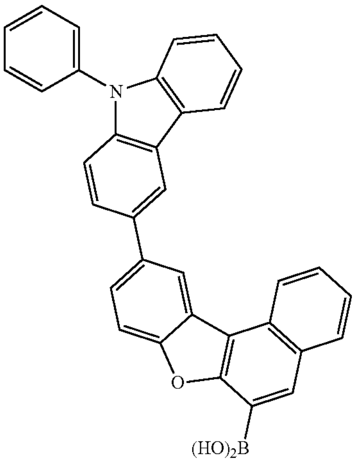<br>D30 (49) |
| C31 | 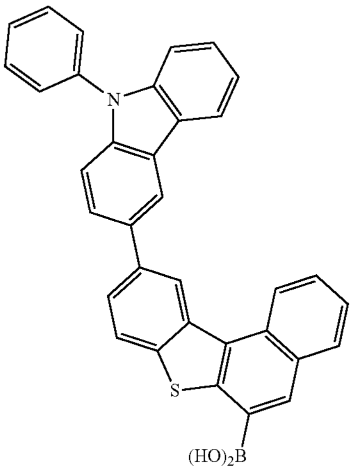<br>D31 (57) |
Synthesis of Compound F
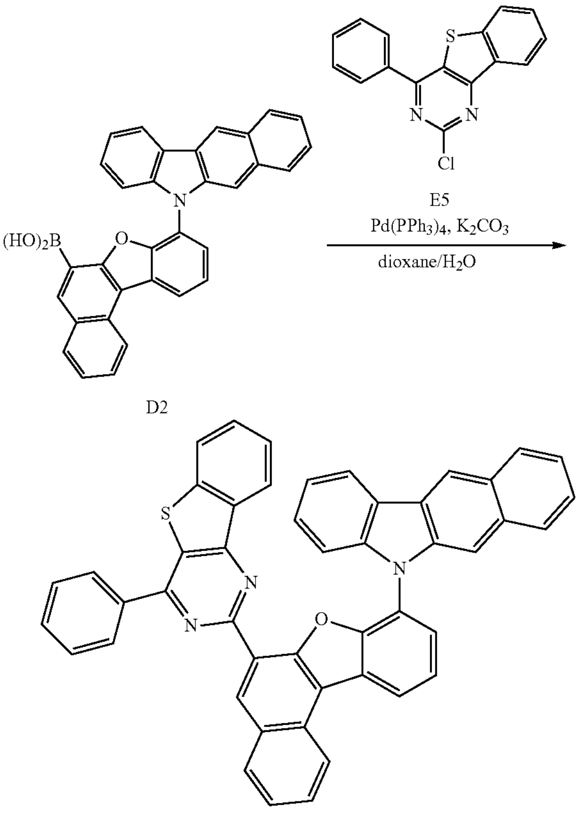
D2
F5
Compound D2 (5 g, 10.5 mmol), Compound E5 (3.7 g, 12.6 mmol), $Pd(PPh_3)_4$ (0.6 g, 0.53 mmol) and $K_2CO_3$ (2.9 g, 21 mmol) were introduced to a 250 mL round bottom flask, and after setting up the flask to be under the nitrogen atmosphere, dioxane (80 mL) and $H_2O$ (20 mL) were introduced thereto, and the result was stirred for 3 hours at 120° C. After the reaction was terminated, the reaction temperature was lowered to room temperature, and the result was washed with water and extracted with methylene chloride. The extracted organic layer was dried with $Mg_2SO_4$ and then concentrated. The result was silica gel columned and recrystallized to obtain yellow solid Compound F5 (6.1 g, 8.8 mmol, yield 84%).

Compound F of the following Table 5 was synthesized in the same manner as in the above-described synthesis method using Compounds D and E of the following Table 5 instead of Compounds D2 and E5.

TABLE 5

| Compound D | Compound E | Compound F (Yield %) | Compound D | Compound E | Compound F (Yield %) |
|---|---|---|---|---|---|
| D2 | E5 | F5(84) | D1 | E11 | F11(86) |
| D2 | E13 | F14(80) | D3 | E7 | F20(94) |
| D4 | E7 | F30(79) | D28 | E7 | F34(88) |
| D5 | E2 | F98(86) | D5 | E4 | F99(90) |

TABLE 5-continued

| Compound D | Compound E | Compound F (Yield %) | Compound D | Compound E | Compound F (Yield %) |
|---|---|---|---|---|---|
| D6 | E7 | F104(74) | D8 | E1 | F145(77) |
| D9 | E2 | F146(92) | D8 | E5 | F148(73) |
| D9 | E5 | F149(90) | D9 | E12 | F157(71) |
| D8 | E13 | F158(85) | D10 | E7 | F164(89) |
| D11 | E7 | F172(73) | D12 | E7 | F174(69) |
| D13 | E7 | F175(88) | D29 | E2 | F179(78) |
| D29 | E5 | F180(86) | D14 | E1 | F217(82) |
| D14 | E5 | F220(86) | D15 | E7 | F224(70) |
| D14 | E9 | F226(88) | D16 | E7 | F231(84) |
| D17 | E7 | F233(81) | D18 | E7 | F236(91) |
| D19 | E5 | F294(91) | D20 | E7 | F296(88) |
| D21 | E10 | F298(89) | D22 | E15 | F299(66) |
| D22 | E13 | F302(84) | D22 | E16 | F304(89) |
| D24 | E7 | F308(92) | D25 | E7 | F310(73) |
| D26 | E7 | F317(90) | D27 | E7 | F318(64) |
| D30 | E7 | F322(69) | D31 | E7 | F394(90) |

[Preparation Example 2] Preparation of Compound F

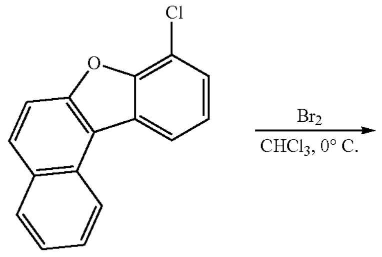

A1

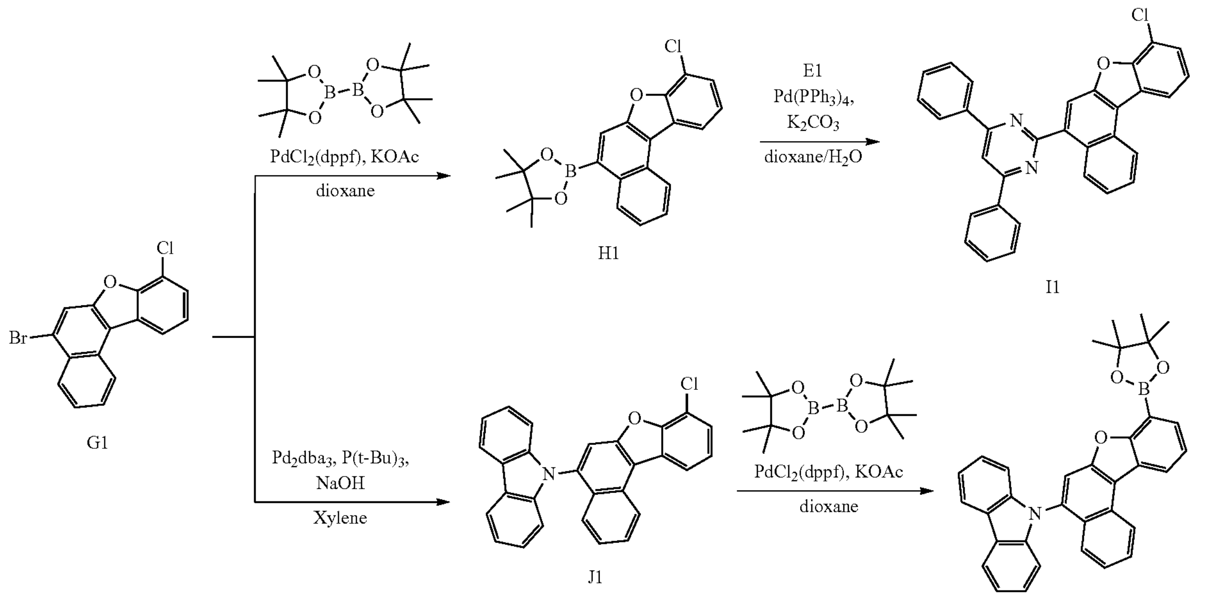

G1

H1

I1

J1

K1

Synthesis of Compound G

Compound A1 (25 g, 98.9 mmol) was introduced to a 1 L round bottom flask, and after setting up the flask to be under the nitrogen atmosphere, $CHCl_3$ (300 mL) was introduced thereto, and the result was stirred for 30 minutes at 0° C. The inner temperature was calibrated to 0° C., and then $Br_2$ (5.35 mL, 104 mmol) was slowly added dropwise thereto. After the reaction was terminated, precipitated solids were washed with methanol (150 mL) and then filtered. The filtered white solids were recrystallized to obtain white solid Compound G1 (30.2 g, 90.9 mmol, yield 92%).

Synthesis of Compound H

Compound G1 (30.2 g, 90.9 mmol), 4,4,4',4',5,5,5',5'-octamethyl-2,2'-bi(1,3,2-dioxaborolane) (27.7 g, 109 mmol), $PdCl_2$(dppf) (3.3 g, 4.5 mmol) and KOAc (17.8 g, 182 mmol) were introduced to a 500 mL round bottom flask, and after setting up the flask to be under the nitrogen atmosphere, dioxane (250 mL) was introduced thereto, and the result was stirred for 6 hours at 120° C. After the reaction was terminated, the reaction temperature was lowered to room temperature, and the result was washed with water and extracted with methylene chloride. The extracted organic layer was dried with $Mg_2SO_4$ and then concentrated. The result was silica gel columned and recrystallized to obtain white solid Compound H1 (30.2 g, 80 mmol, yield 88%).

Synthesis of Compound I

Compound H1 (5 g, 13.2 mmol), Compound E1 (3.5 g, 13.2 mmol), $Pd(PPh_3)_4$ (0.7 g, 0.66 mmol) and $K_2CO_3$ (3.7 g, 26.4 mmol) were introduced to a 250 mL round bottom flask, and after setting up the flask to be under the nitrogen atmosphere, dioxane (80 mL) and $H_2O$ (20 mL) were introduced thereto, and the result was stirred for 3 hours at 120° C. After the reaction was terminated, the reaction temperature was lowered to room temperature, and the result was washed with water and extracted with methylene chloride. The extracted organic layer was dried with $Mg_2SO_4$ and then concentrated. The result was silica gel columned and recrystallized to obtain yellow solid Compound I1 (5.8 g, 12.1 mmol, 92%).

Synthesis of Compound F (1)

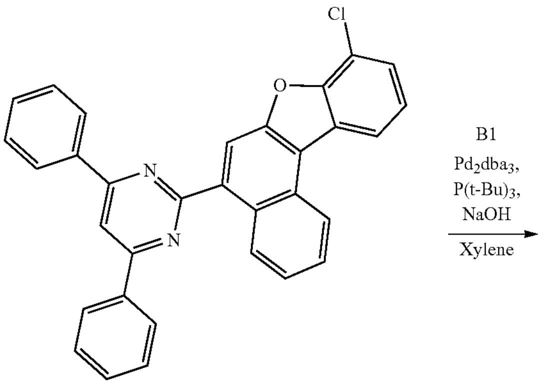

I1

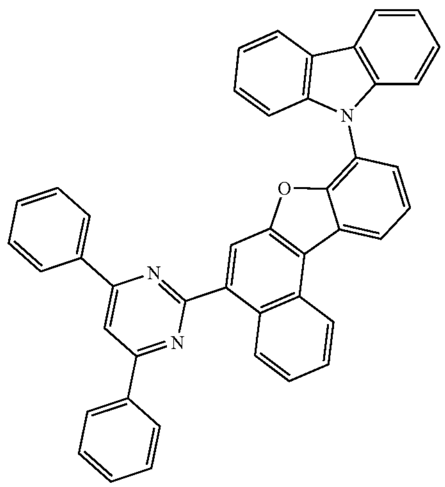

F37

Compound I1 (5 g, 10.4 mmol), Compound B1 (2.3 g, 13.5 mmol), $Pd_2dba_3$ (0.47 g, 0.52 mmol), P $(t\text{-}Bu)_3$ (0.8 g, 4.16 mmol) and NaOH (0.8 g, 20.8 mmol) were introduced to a 100 mL round bottom flask, and after setting up the flask to be under the nitrogen atmosphere, xylene (50 mL) was introduced thereto, and the result was stirred for 8 hours at 160° C. After the reaction was terminated, the reaction temperature was lowered to room temperature, and the result was washed with water and extracted with methylene chloride. The extracted organic layer was dried with $Mg_2SO_4$ and then concentrated. The result was silica gel columned and recrystallized to obtain Compound F37 (5 g, 8.2 mmol, yield 79%).

Compound F of the following Table 6 was synthesized in the same manner as in Syntheses of Compounds G, H, I and F using Compounds A, G, H, E, I and B of the following Table 6 instead of Compounds A1, G1, H1, E1, I1 and B1.

TABLE 6
| Compound A | Compound G (Yield %) | Compound H (Yield %) | Compound E | Compound I (Yield %) | Compound B | Compound F (Yield %) |
|---|---|---|---|---|---|---|
| A1 | 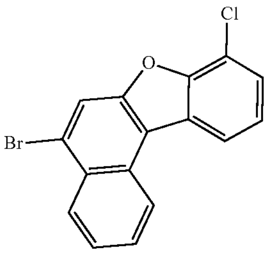 G1 (92) | 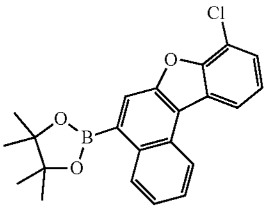 H1 (88) | E1 | 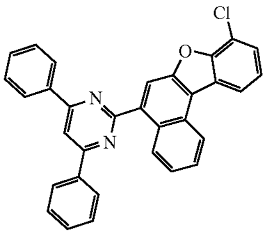 I1 (92) | B1 | F37 (79) |
| A1 | G1 | H1 | E18 | 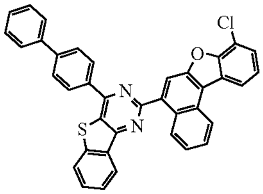 I2 (86) | B1 | F41 (82) |
| A1 | G1 | H1 | E7 | 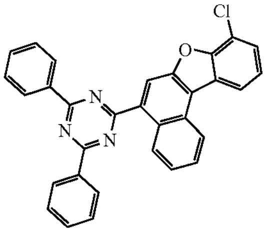 I3 (90) | B4 | F44 (59) |
| A1 | G1 | H1 | E7 | I3 | B34 | F59 (61) |
| A1 | G1 | H1 | E7 | I3 | B13 | F66 (79) |
| A1 | G1 | H1 | E7 | I3 | B17 | F69 (81) |
| A1 | G1 | H1 | E8 | 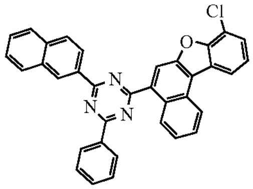 I4 (76) | B1 | F45 (83) |
| A1 | G1 | H1 | E9 | 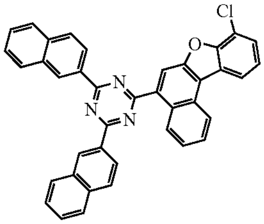 I5 (78) | B1 | F46 (87) |

TABLE 6-continued
| Compound A | Compound G (Yield %) | Compound H (Yield %) | Compound E | Compound I (Yield %) | Compound B | Compound F (Yield %) |
|---|---|---|---|---|---|---|
| A1 | G1 | H1 | E17 | 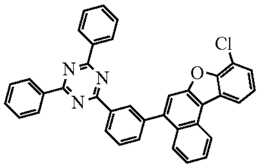 I6 (85) | B1 | F53 (69) |
| A2 | 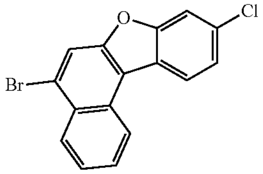 G2 (95) | 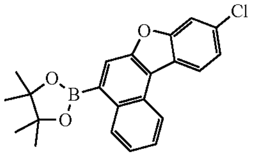 H2 (89) | E7 | 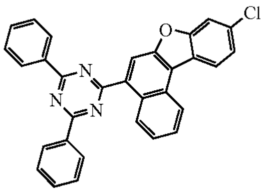 I7 (76) | B4 | F187 (67) |
| A2 | G2 | H2 | E7 | I7 | B5 | F188 (79) |
| A2 | G2 | H2 | E7 | I7 | B37 | F202 (80) |
| A2 | G2 | H2 | E7 | I7 | B4 | F204 (82) |
| A2 | G2 | H2 | E7 | I7 | B34 | F205 (67) |
| A2 | G2 | H2 | E7 | I7 | B16 | F212 (69) |
| A2 | G2 | H2 | E7 | I7 | B20 | F213 (80) |
| A2 | G2 | H2 | E9 | 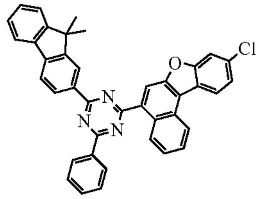 I8 (87) | B1 | F194 (69) |
| A2 | G2 | H2 | E8 | 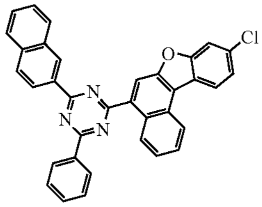 I9 (90) | B11 | F203 (88) |
| A3 | 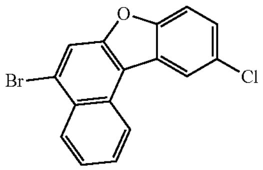 G3 (90) | 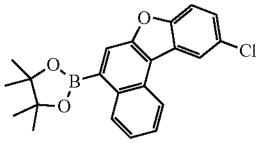 H3 (89) | E3 | 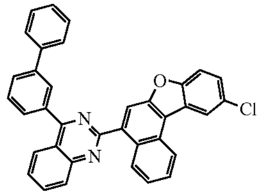 I10 (89) | B1 | F327 (76) |
| A3 | G3 | H3 | E5 | 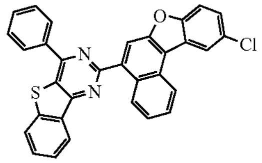 I11 (80) | B4 | F328 (76) |

TABLE 6-continued
| Compound A | Compound G (Yield %) | Compound H (Yield %) | Compound E | Compound I (Yield %) | Compound B | Compound F (Yield %) |
|---|---|---|---|---|---|---|
| A3 | G3 | H3 | E15 | 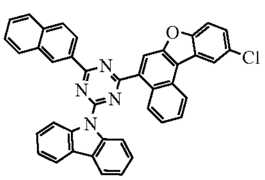 I12 (79) | B36 | F334 (94) |
| A3 | G3 | H3 | E12 | 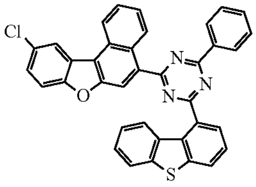 I13 (86) | B6 | F337 (73) |
| A3 | G3 | H3 | E7 | 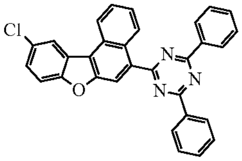 I14 (90) | B24 | F344 (67) |
| A3 | G3 | H3 | E7 | I14 | B26 | F345 (64) |
| A4 | 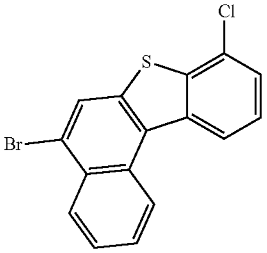 G4 (88) | 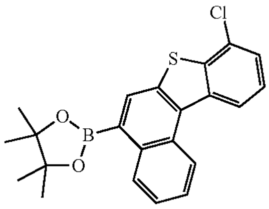 H4 (95) | E5 | 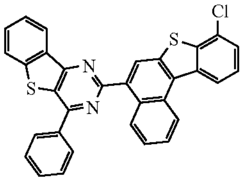 I15 (80) | B4 | F113 (54) |
| A4 | G4 | H4 | E6 | 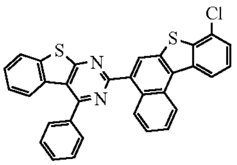 I16 (82) | B4 | F114 (89) |

TABLE 6-continued

| Compound A | Compound G (Yield %) | Compound H (Yield %) | Compound E | Compound I (Yield %) | Compound B | Compound F (Yield %) |
|---|---|---|---|---|---|---|
| A5 | 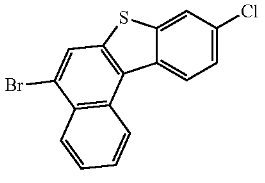 G5 (94) | 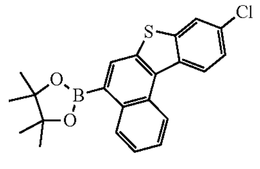 H5 (88) | E7 | 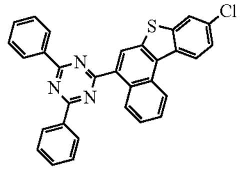 I17 (85) | B34 | F251 (82) |
| A6 | 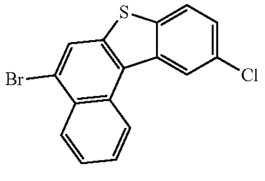 G6 (91) | 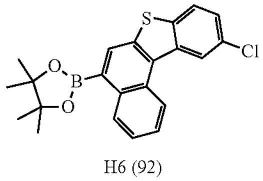 [SMILES: CC1(C)OB(c2cc3sc4ccc(Cl)cc4c3c3ccccc23)OC1(C)C] H6 (92) | E5 | 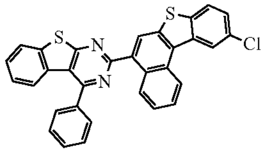 I18 (87) | B1 | F386 (86) |
| A6 | G6 | H6 | E7 | 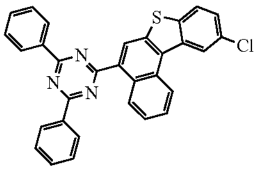 I19 (89) | B23 | F380 (90) |
| A6 | G6 | H6 | E7 | I19 | B24 | F381 (87) |
| A6 | G6 | H6 | E7 | I19 | B27 | F386 (84) |
| A6 | G6 | H6 | E7 | I19 | B14 | F391 (79) |
| A7 | G7 (78) | — | — | — | — | — |

Synthesis of Compound J

Compound G1 (20 g, 60 mmol), Compound B1 (13 g, 78 mmol), $Pd_2dba_3$ (2.7 g, 3.0 mmol), P $(t\text{-}Bu)_3$ (2.4 g, 12 mmol) and NaOH (4.8 g, 120 mmol) were introduced to a 500 mL round bottom flask, and after setting up the flask to be under the nitrogen atmosphere, xylene (150 mL) was introduced thereto, and the result was stirred for 8 hours at 160° C. After the reaction was terminated, the reaction temperature was lowered to room temperature, and the result was washed with water and extracted with methylene chloride. The extracted organic layer was dried with $Mg_2SO_4$ and then concentrated. The result was silica gel columned and recrystallized to obtain Compound J1 (14.2 g, 34.2 mmol, yield 57%).

Synthesis of Compound K

Compound J1 (14.2 g, 34.2 mmol), 4,4,4',4',5,5,5',5'-octamethyl-2,2'-bi(1,3,2-dioxaborolane) (11.3 g, 44.5 mmol), $PdCl_2(dppf)$ (1.3 g, 1.7 mmol) and KOAc (6.7 g, 68.4 mmol) were introduced to a 250 mL round bottom flask, and after setting up the flask to be under the nitrogen atmosphere, dioxane (150 mL) was introduced thereto, and the result was stirred for 6 hours at 120° C. After the reaction was terminated, the reaction temperature was lowered to room temperature, and the result was washed with water and extracted with methylene chloride. The extracted organic layer was dried with $Mg_2SO_4$ and then concentrated. The result was silica gel columned and recrystallized to obtain white solid Compound K1 (15.5 g, 30.4 mmol, yield 89%).

Synthesis of Compound F (2)

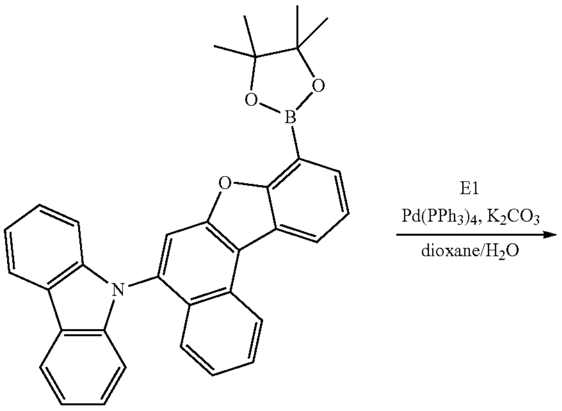

K1

-continued

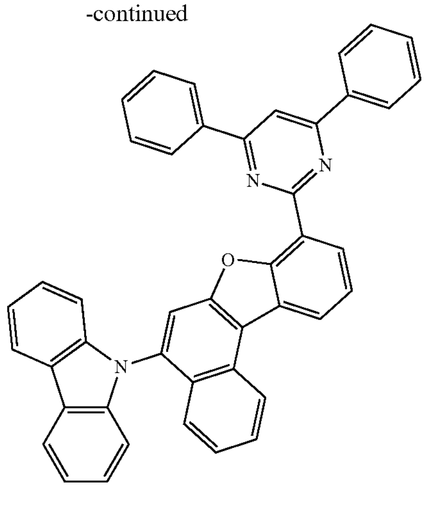

F85

Compounds J and K were synthesized in the same manner as in Synthesis of Compound J and K using Compounds G and B of the following Table 7 instead of Compounds G1 and B1, and Compound F of the following Table 7 was synthesized in the same manner as in Synthesis of Compound F of Preparation Example 1 using Compounds K and E of the following Table 7 instead of Compounds D1 and E5.

TABLE 7

| Compound G | Compound B | Compound J (yield %) | Compound K (yield %) | Compound E | Compound F (yield %) |
|---|---|---|---|---|---|
| G1 | B1 | 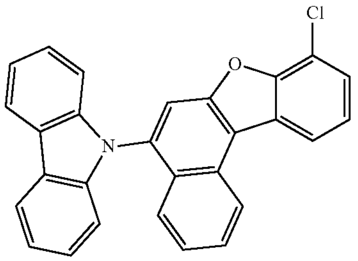 J1 (57) | 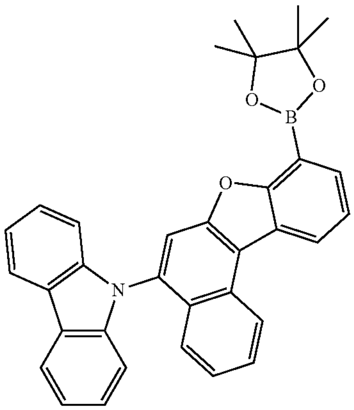 K1 (89) | E1 | F85 (89) |

TABLE 7-continued
| Compound G | Compound B | Compound J (yield %) | Compound K (yield %) | Compound E | Compound F (yield %) |
|---|---|---|---|---|---|
| G1 | B36 | 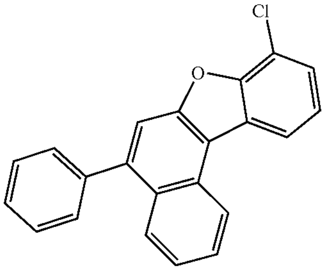 J2 (92) | 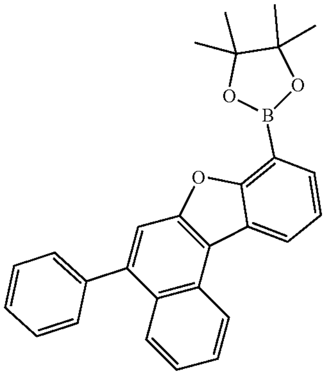 K2 (90) | E14 | F95 (64) |
| G4 | B38 | 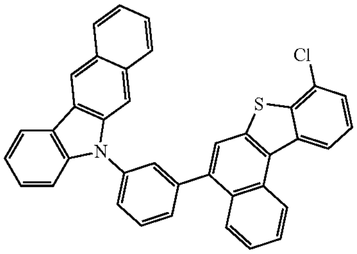 J3 (92) | 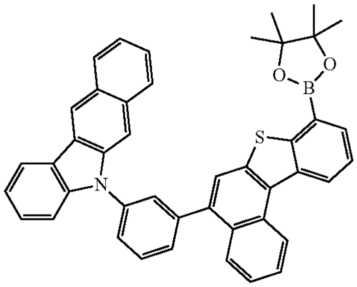 K3 (78) | E7 | F135 (90) |
| G4 | B39 | 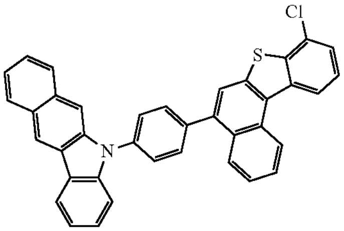 J4 (80) | 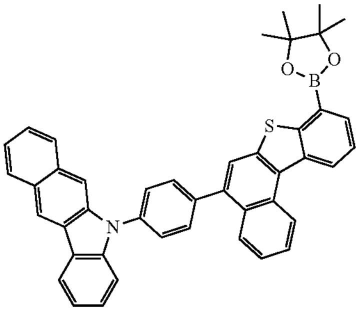 K4 (88) | E7 | F136 (88) |
| G4 | B40 | 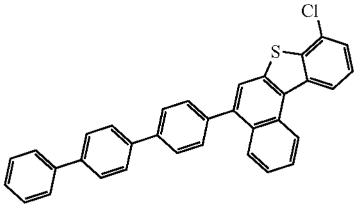 J5 (90) | 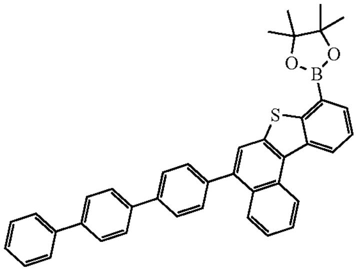 K5 (89) | E7 | F139 (79) |

TABLE 7-continued
| Compound G | Compound B | Compound J (yield %) | Compound K (yield %) | Compound E | Compound F (yield %) |
|---|---|---|---|---|---|
| G2 | B17 | 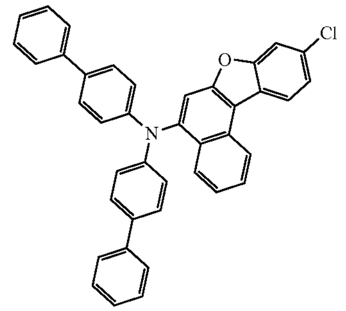 J6 (69) | 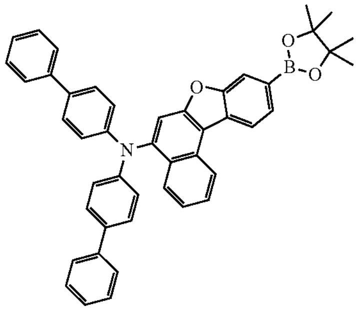 K6 (79) | E7 | F260 (91) |
| G2 | B18 | 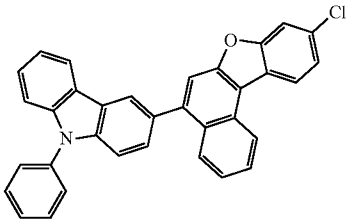 J7 (68) | 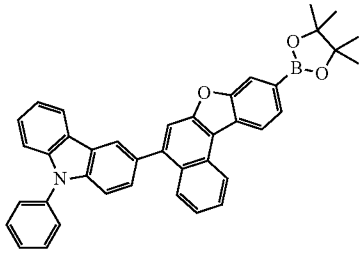 K7 (78) | E8 | F266 (87) |
| G5 | B17 | 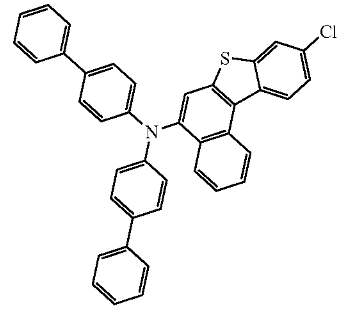 J8 (82) | 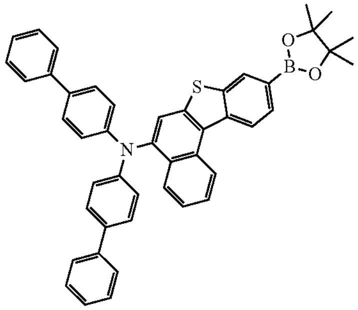 K8 (88) | E7 | F278 (79) |
| G5 | B38 | 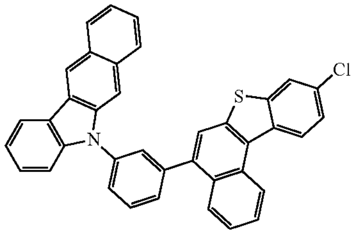 J9 (89) | 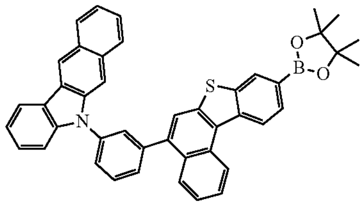 K9 (81) | E7 | F288 (76) |

TABLE 7-continued

| Compound G | Compound B | Compound J (yield %) | Compound K (yield %) | Compound E | Compound F (yield %) |
|---|---|---|---|---|---|
| G3 | B17 | 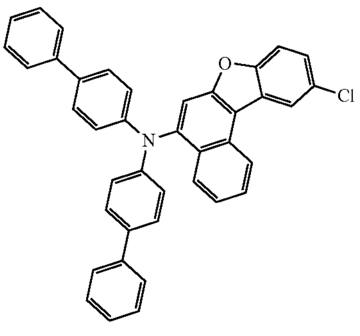 J10 (84) | 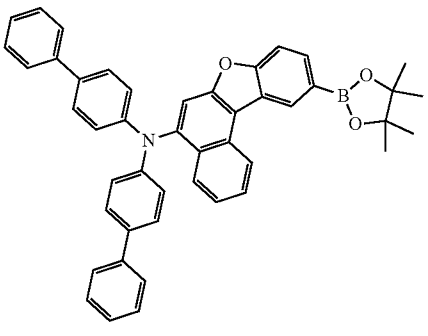 K10 (90) | E7 | F371 (86) |

[Preparation Example 3] Preparation of Compound F

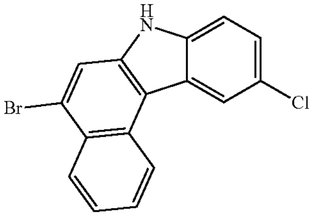

G7

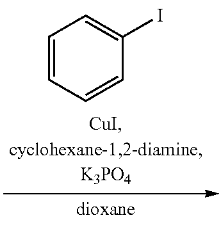

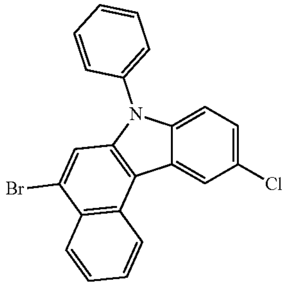

L1

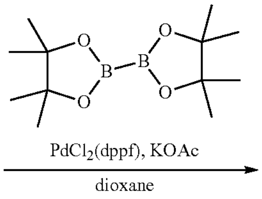

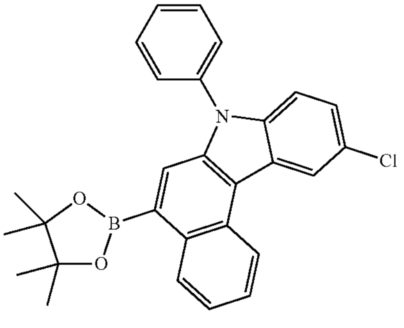

M1

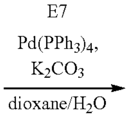

-continued

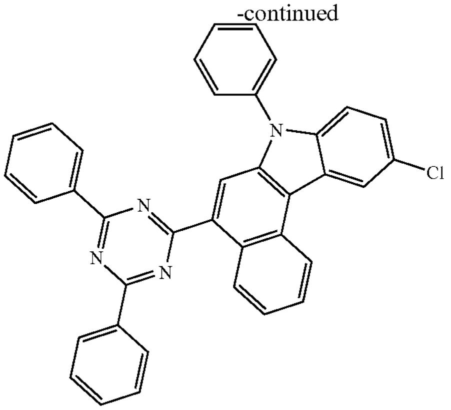

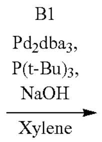

N1

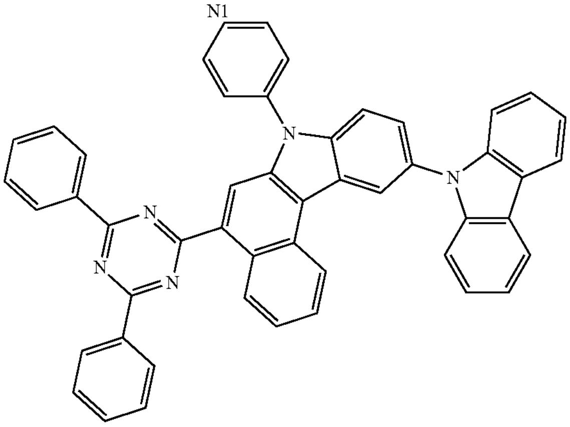

F403

Synthesis of Compound L

Compound G7 (26 g, 79.1 mmol), CuI (15 g, 79.1 mmol), iodo-benzene (24 g, 118.6 mmol), (1R,2S)-cyclohexane-1, 2-diamine (9 g, 79.1 mmol) and $K_3PO_4$ (33.5 g, 158 mmol) were introduced to a 500 mL round bottom flask, and after setting up the flask to be under the nitrogen atmosphere, toluene (300 mL) was introduced thereto, and the result was stirred for 8 hours at 120° C. After the reaction was terminated, the reaction temperature was lowered to room temperature, and the result was washed with water and extracted with methylene chloride. The extracted organic layer was dried with $Mg_2SO_4$ and then concentrated. The result was silica gel columned and recrystallized to obtain Compound L1 (29.7 g, 73.5 mmol, yield 93%).

Synthesis of Compound M

Compound L1 (29.7 g, 73.5 mmol), 4,4,4',4',5,5,5',5'-octamethyl-2,2'-bi(1,3,2-dioxaborolane) (24 g, 95.5 mmol), $PdCl_2$(dppf) (3.7 g, 7.3 mmol) and KOAc (14.4 g, 147 mmol) were introduced to a 500 mL round bottom flask, and after setting up the flask to be under the nitrogen atmosphere, dioxane (250 mL) was introduced thereto, and the result was stirred for 6 hours at 120° C. After the reaction was terminated, the reaction temperature was lowered to room temperature, and the result was washed with water and extracted with methylene chloride. The extracted organic layer was dried with $Mg_2SO_4$ and then concentrated. The result was silica gel columned and recrystallized to obtain white solid Compound M1 (27 g, 60 mmol, yield 82%).

Synthesis of Compound N

Compound M1 (5.3 g, 11.7 mmol), Compound E7 (4.2 g, 14.04 mmol), $Pd(PPh_3)_4$ (0.7 g, 0.59 mmol) and $K_2CO_3$ (3.2 g, 23.4 mmol) were introduced to a 250 mL round bottom flask, and after setting up the flask to be under the nitrogen atmosphere, dioxane (80 mL) and $H_2O$ (20 mL) were introduced thereto, and the result was stirred for 3 hours at 120° C. After the reaction was terminated, the reaction temperature was lowered to room temperature, and the result was washed with water and extracted with methylene chloride. The extracted organic layer was dried with $Mg_2SO_4$ and then concentrated. The result was silica gel columned and recrystallized to obtain yellow solid Compound N1 (6.3 g, 9.8 mmol, yield 84%).

Synthesis of Compound F

Compound N of the following Table 8 was synthesized in the same manner as in Synthesis of Compound N using Compound E or Compound B of the following Table 8 instead of Compound E7, and Compound F of the following Table 8 was synthesized in the same manner as in Synthesis of Compound F (1) of Preparation Example 2 using Compound B or Compound E of the following Table 8 instead of Compound B1.

TABLE 8

| Compound G (yield %) | Compound L (yield %) | Compound M (yield %) | Compound E or B | Compound N (yield %) | Compound B or E | Compound F (yield %) |
|---|---|---|---|---|---|---|
| G7(78) | L1(89) | M1(82) | E7 | N1(84) | B1 | F403(76) |
| G7 | L1 | M1 | E9 | N2(89) | B1 | F406(88) |
| G7 | L1 | M1 | E7 | N1(84) | B16 | F409(79) |
| G7 | L1 | M1 | B19 | N3(79) | E2 | F418(92) |

[Preparation Example 4] Preparation of Compound F

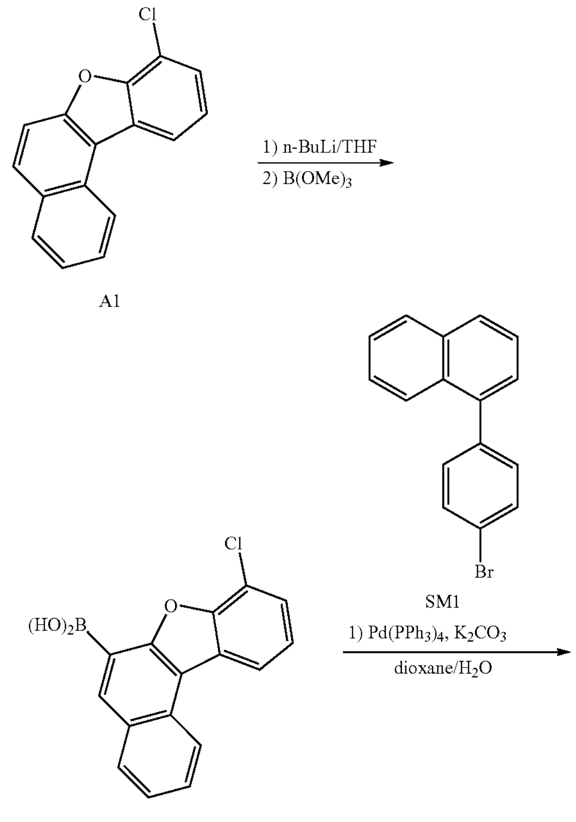

A1

SM1

O1

-continued

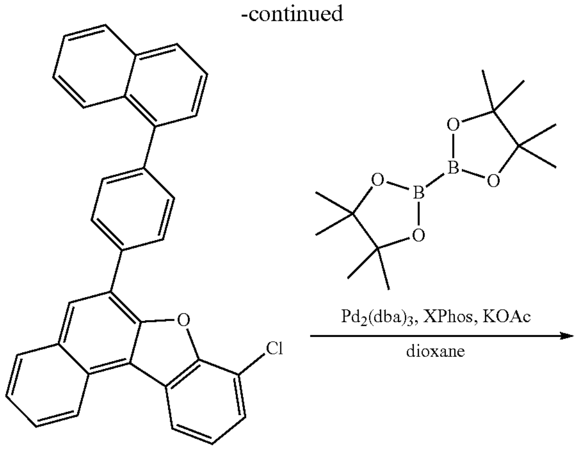

P1

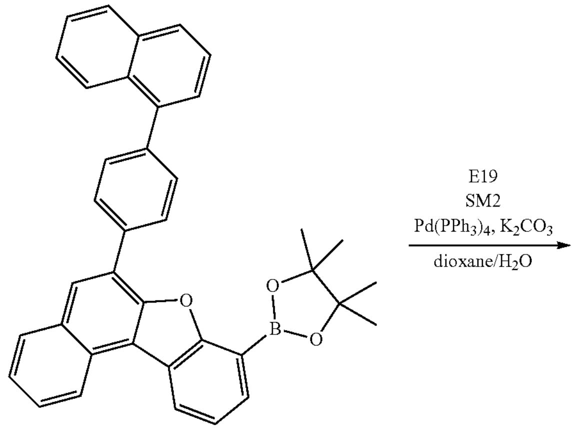

P1-1

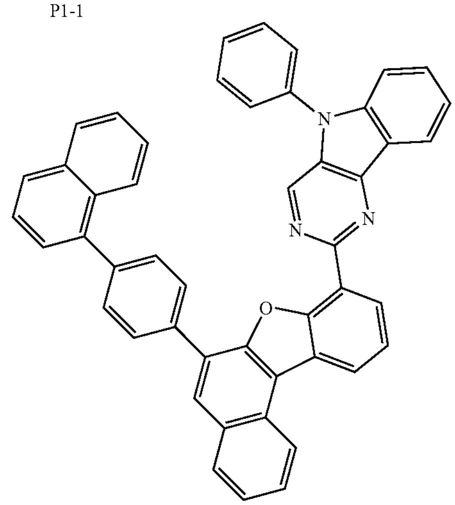

F79

Synthesis of Compound O

Compound A1 (52 g, 135.6 mmol) was introduced to a 1 L round bottom flask, and after setting up the flask to be under the nitrogen atmosphere, THF (400 mL) was introduced thereto, and the inner temperature of the reaction vessel was calibrated to −78° C. 2.5 M (in hexane) n-BuLi (59.6 ml) was slowly added dropwise thereto, and after stirring the result for 2 hours at 60° C., $B(OMe)_3$ (19.7 mL, 203.4 mmol) was slowly added dropwise thereto at room temperature. After the reaction was terminated in 2 hours, the reaction was completely terminated using ethanol (60 mL), and the result was washed with water and extracted with methylene chloride. The extracted organic layer was dried with $Mg_2SO_4$ and then concentrated. The result was silica gel columned to obtain white solid Compound O1 (18.4 g, 62.4 mmol, yield 46%).

Synthesis of Compound P

Compound O1 (5 g, 13.5 mmol), 1-(4-bromophenyl) naphthalene (4.6 g, 16.2 mmol), $Pd(PPh_3)_4$ (0.8 g, 0.67 mmol) and $K_2CO_3$ (3.7 g, 27 mmol) were introduced to a 250 mL round bottom flask, and after setting up the flask to be under the nitrogen atmosphere, dioxane (80 mL) and $H_2O$ (20 mL) were introduced thereto, and the result was stirred for 12 hours at 120° C. After the reaction was terminated, the reaction temperature was lowered to room temperature, and the result was washed with water and extracted with methylene chloride. The extracted organic layer was dried with $Mg_2SO_4$ and then concentrated. The result was silica gel columned and recrystallized to obtain white solid Compound P1 (2.9 g, 6.5 mmol, yield 48%).

Synthesis of Compound P-1

Compound P1 (2.9 g, 6.4 mmol), 4,4,4',4',5,5,5',5'-octamethyl-2,2'-bi(1,3,2-dioxaborolane) (2.5 g, 9.8 mmol), $Pd_2(dba)_3$ (0.3 g, 0.3 mmol), XPhos (2,4',6'-diisopropyl-1,1'-biphenyl-2-yl dicyclohexylphosphine) (1.2 g, 2.6 mmol) and KOAc (1.3 g, 13 mmol) were introduced to a 100 mL round bottom flask, and after setting up the flask to be under the nitrogen atmosphere, dioxane (50 mL) was introduced thereto, and the result was stirred for 3 hours at 110° C. After the reaction was terminated, the reaction temperature was lowered to room temperature, and the result was washed with water and extracted with methylene chloride. The extracted organic layer was dried with $Mg_2SO_4$ and then concentrated. The result was silica gel columned and recrystallized to obtain white solid Compound P1-1 (3.0 g, 5.54 mmol, yield 85%).

Synthesis of Compound F

Compound P1-1 (3.0 g, 5.54 mmol), Compound E19 (1.8 g, 6.6 mmol), $Pd(PPh_3)_4$ (0.3 g, 0.27 mmol) and $K_2CO_3$ (1.5 g, 11 mmol) were introduced to a 100 mL round bottom flask, and after setting up the flask to be under the nitrogen atmosphere, dioxane (40 mL) and $H_2O$ (10 mL) were introduced thereto, and the result was stirred for 4 hours at 120° C. After the reaction was terminated, the reaction temperature was lowered to room temperature, and the result was washed with water and extracted with methylene chloride. The extracted organic layer was dried with $Mg_2SO_4$ and then concentrated. The result was silica gel columned and recrystallized to obtain yellow solid Compound F79 (3.1 g, 4.7 mmol, yield 85%).

Compound F of the following Table 9 was synthesized in the same manner as in Syntheses of Compounds O, P and F using Compounds A, O, SM1, P and E of the following Table 9 instead of Compounds A1, O1, 1-(4-bromophenyl) naphthalene, P1, P1-1 and E19.

TABLE 9

| Compound A | Compound O (yield %) | Compound SM1 | Compound P (yield %) | Compound P-1 (yield %) | Compound E | Compound F (yield %) |
|---|---|---|---|---|---|---|
| A1 | O1 (46) | 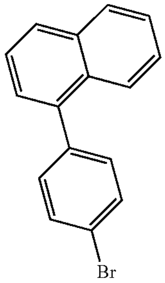 [SMILES: Brc1ccc(-c2cccc3ccccc23)cc1] | P1 (48) | P1-1 (78) | E19 | F79 (85) |
| A1 | O1 | 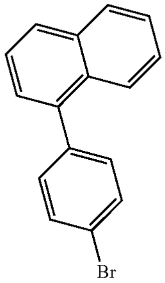 [SMILES: Brc1ccc(-c2cccc3ccccc23)cc1] | P1 | P1-1 (78) | E7 | F80 (88) |
| A4 | O2 (44) | 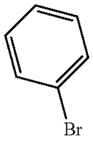 | P2 (88) | P2-1 (74) | E14 | F132 (89) |
| A1 | O1 | 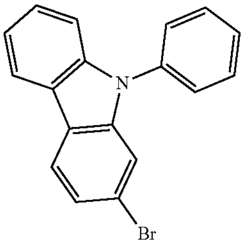 [SMILES: Brc1ccc2c3ccccc3n(-c3ccccc3)c2c1] | P3 (76) | P3-1 (68) | E7 | F358 (79) |

Compounds other than the compounds described in Preparation Examples 1 to 4 were also prepared in the same manner as the compounds described in Preparation Examples 1 to 4, and the synthesis identification results are shown in the following Tables 10 and 11.

TABLE 10

| Example | $^1$H NMR ($CDCl_3$, 200 Mz) |
|---|---|
| F5 | δ = 9.29(s, 1H), 9.18(d, 1H), 9.16(d, 1H), 8.92(d, 2H), 8.71(s, 1H), 8.24~8.21(m, 4H), 8.08(d, 2H), 7.58~7.50(m, 6H), 7.49~7.44(m, 7H), 7.39(d, 1H), 7.33(t, 1H). |
| F11 | δ = 9.31(d, 1H), 9.24~9.18(d, 2H), 9.03~8.99(m, 3H), 8.83(d, 4H), 8.30(d, 1H), 7.94~7.87(d, 2H), 7.77 (t, 1H), 7.67~7.60(m, 7H), 7.57-7.36(m, 7H). |
| F14 | δ = 9.21(s, 1H), 9.06(d, 1H), 8.98(d, 2H), 8.94(s, 1H), 8.64(s, 1H), 8.55(d, 1H), 8.29(d, 1H), 8.08(d, 1H), 7.97(s, 1H), 7.89-7.85(m, 5H), 7.73 (t, 1H), 7.64-7.41(m, 13H), 7.33(t, 1H), 3.19(s, 6H). |
| F20 | δ = 9.31(d, 1H), 9.24~9.18(d, 2H), 9.03~8.99(m, 3H), 8.83(d, 4H), 8.30(d, 1H), 7.94~7.87(d, 2H), 7.77(t, 1H), 7.67~7.60(m, 13H), 7.57~7.26(m, 8H). |
| F30 | δ = 9.24(s, 1H), 8.86(d, 1H), 8.85~8.83(m, 5H), 8.72(d, 1H), 8.79(d, 4H), 8.40(d, 1H), 8.0 (d, 1H), 7.87(t, 1H), 7.78~7.69 (m, 6H), 7.68~7.59(m, 7H), 7.52~7.47(m, 6H), 7.29 (t, 2H). |

TABLE 10-continued

| Example | $^{1}H$ NMR ($CDCl_3$, 200 Mz) |
|---|---|
| F34 | δ = 9.29(s, 1H), 8.86(d, 1H), 8.85~8.83(m, 5H), 8.72(d, 1H), 8.83(d, 4H), 8.40(d, 1H), 8.02(d, 1H), 7.90 (t, 1H), 7.81~7.77(m, 2H), 7.68~7.62(m, 8H), 7.52~7.47(m, 4H), 7.35(t, 1H). |
| F37 | δ = 9.27(s, 1H), 9.24(d, 1H), 9.19(s, 1H), 8.78(d, 2H), 8.71(d, 2H), 8.69(d, 1H), 8.66(d, 1H), 8.08(d, 2H), 7.68~7.64(m, 7H), 7.64(d, 2H), 7.36~7.32(m, 5H). 7.27(t, 2H). |
| F41 | δ = 9.22(d, 1H), 9.18(s, 1H), 8.76(d, 4H), 8.69(d, 1H), 8.66(d, 1H), 8.14~8.13(m, 2H), 7.82(d, 2H), 7.69~7.66(m, 6H), 7.65~7.63(m, 6H), 7.33~7.30(m, 2H). 7.29(d, 2H), 7.16(t, 1H). |
| F44 | δ = 9.24(d, 1H), 9.21(s, 1H) , 8.78(d, 4H), 8.69(d, 1H), 8.66(d, 1H), 8.08(d, 2H), 7.72(s, 1H), 7.68~7.65(m, 5H), 7.62(s, 1H), 7.35~7.30(m, 6H), 7.29~7.28(m, 3H), 7.27(t, 2H). |
| F45 | δ = 9.24(d, 1H), 9.22(s, 1H), 9.19(s, 1H), 8.78(d, 2H), 8.70(d, 1H), 8.67~8.65(m, 4H), 8.49(s, 1H), 8.36(d, 1H), 8.33(d, 1H), 8.29(d, 2H), 7.68~7.65(m, 6H), 7.64(d, 2H), 7.37~7.35(m, 4H). 7.33(t, 1H). |
| F46 | δ = 9.22d, 1H), 9.20(s, 1H), 9.19(s, 1H), 8.78(d, 2H), 8.70(d, 1H), 8.67~8.66(m, 2H), 8.52(s, 2H), 8.36(d, 1H), 8.35~8.34(m, 2H), 8.33(d, 1H), 8.29(d, 2H), 7.65~7.63(m, 6H), 7.57(d, 2H), 7.37~7.35(m, 4H). 7.37(t, 2H). |
| F53 | δ = 9.42(s, 1H), 9.33(d, 1H), 9.08(d, 1H), 8.80(d, 4H), 8.70(d, 1H), 8.67~8.65(m, 4H), 8.52(s, 1H), 8.36(d, 1H), 8.33(d, 1H), 8.24(d, 2H), 7.67(d, 2H), 7.66~7.65(m, 4H), 7.64(d, 2H), 7.37~7.35(m, 4H). 7.30(t, 1H). |
| F59 | δ = 9.23(d, 1H), 9.21 (s, 1H), 8.77(d, 4H), 8.68(d, 1H), 8.66(d, 1H), 8.04(d, 2H), 7.78(s, 1H), 7.66(s, 1H), 7.68~7.65(m, 5H), 7.62(s, 1H), 7.35~7.30(m, 6H), 7.29~7.28(m, 3H), 7.23(t, 1H). |
| F66 | δ = 9.21(d, 1H), 9.19 (s, 1H), 8.78(d, 4H), 8.60(d, 1H), 8.48(d, 1H), 8.08(d, 2H), 7.66~7.63(m, 5H), 7.58(d, 1H), 7.35~7.30(m, 6H), 7.25~7.22(m, 4H), 7.18(t, 2H). |
| F69 | δ = 9.19(d, 1H), 9.16 (s, 1H), 8.76(d, 4H), 8.59(d, 1H), 8.44(d, 1H), 8.12(d, 2H), 7.79(d, 2H) 7.66~7.63(m, 5H), 7.58(d, 1H), 7.39(d, 2H), 7.35~7.30(m, 8H), 7.25~7.22(m, 6H), 7.18(t, 2H). |
| F79 | δ = 9.06(d, 1H), 8.86(d, 1H), 8.84(d, 1H), 8.76(s, 1H), 8.49(d, 1H), 8.46(d, 1H), 8.39(d, 2H), 8.36~8.33(m, 4H), 8.21(d, 1H), 7.86~7.84(m, 4H), 7.58(d, 1H), 7.49~7.45(m, 6H), 7.32~7.29(m, 4H), 7.14(t, 1H). |
| F80 | δ = 9.17d, 1H), 8.87(d, 4H), 8.89(d, 1H), 8.59(d, 1H), 8.56(d, 1H), 8.39(d, 2H), 8.38~8.35(m, 4H), 8.22(d, 1H), 7.90~7.86(m, 5H), 7.47~7.45(m, 5H), 7.32~7.29(m, 4H). |
| F85 | δ = 9.22(s, 1H), 9.19(d, 1H), 9.18(s, 1H), 8.78(d, 4H), 8.68(d, 1H), 8.59(d, 1H), 8.08(d, 2H), 7.68~7.65(m, 7H), 7.64(d, 2H), 7.36~7.32(m, 5H). 7.27(t, 2H). |
| F95 | δ = 9.22(s, 1H), 9.19(d, 1H), 9.18(s, 1H), 8.78(d, 4H), 8.68(d, 1H), 8.59(d, 1H), 8.08(d, 2H), 7.68~7.65(m, 7H), 7.64(d, 2H), 7.36~7.32(m, 5H). 7.27(t, 2H). |
| F96 | δ = 9.36(s, 1H), 9.24(d, 1H), 8.98(d, 1H), 8.96(d, 1H), 8.79(s, 1H), 8.66(d, 1H), 8.48~8.45(m, 4H), 8.29(t, 1H), 8.16~8.14(m, 3H), 7.88~7.86(m, 2H), 7.59~7.55(m, 4H), 7.38~7.34(m, 6H), 7.29(t, 1H). |
| F98 | δ = 8.97(s, 1H), 8.78(d, 1H), 8.52(d, 1H), 8.38~8.34(m, 5H), 8.27(d, 2H), 7.83~7.81(m, 4H), 7.78~7.76(m, 4H), 7.59(d, 1H), 7.46(d, 2H), 7.38~7.36(m, 3H), 7.30(t, 1H). |
| F99 | δ = 8.98(s, 1H), 8.78(d, 1H), 8.49(d, 1H), 8.37~8.34(m, 5H), 8.29(d, 2H), 7.84~7.81(m, 4H), 7.75~7.73(m, 4H), 7.62(d, 1H), 7.42(d, 2H), 7.40(d, 2H), 7.36~7.34(m, 5H), 7.29(t, 1H). |
| F104 | δ = 8.91(d, 1H), 8.84(d, 4H), 8.63(d, 1H), 8.53(d, 1H), 8.28(d, 1H), 8.08(d, 1H), 7.97(s, 1H), 7.90~7.85(m, 3H), 7.87(t, 3H), 7.71~7.39(m, 11H), 7.29(t, 1H). |
| F113 | δ = 9.16(s, 1H), 9.07(d, 1H), 8.72~8.70(m, 3H), 8.68(d, 1H), 8.63(s, 1H), 8.36~8.33(m, 3H), 7.88~7.76(m, 3H), 7.70(t, 2H), 7.44~7.27(m, 11H), 7.26(t, 1H). |
| F114 | δ = 9.16(s, 1H), 9.08(d, 1H), 8.75~8.73(m, 3H), 8.69(d, 1H), 8.66(s, 1H), 8.36~8.33(m, 3H), 7.88~7.74(m, 4H), 7.68(t, 1H), 7.44~7.40(m, 7H), 7.33~7.29(m, 4H), 7.26(t, 1H). |
| F132 | δ = 9.46(d, 1H), 8.82(d, 1H), 8.16(d, 1H), 8.78(d, 2H), 8.69(s, 1H), 8.48(s, 1H), 8.39~8.36(m, 3H), 8.30(d, 1H), 7.72(s, 1H), 7.70~7.68(m,4H), 7.58(d, 1H), 7.57~7.55(m, 3H), 7.43~7.40(m, 6H), 7.33 (t, 1H). |
| F135 | δ = 9.26(d, 1H), 9.18(d, 1H) , 8.97(d, 4H), 8.93(d, 1H), 877(s, 1H), 8.88(s, 1H), 8.67(d, 1H), 8.63~8.61(m, 2H), 8.38~8.37(m, 3H), 8.19(s, 1H), 7.70(s, 1H), 7.69~7.67(m, 4H), 7.56~7.53(m, 4H), 7.40~7.36(m, 4H), 7.35(d, 2H), 7.29(t, 1H). |
| F136 | δ = 9.26(d, 1H), 9.18(d, 1H), 8.97(d, 4H), 8.93(d, 1H), 8.79 (s, 1H), 8.67(d, 1H), 8.63~8.61(m, 2H), 8.38(d, 2H), |

TABLE 10-continued

| Example | $^1$H NMR ($CDCl_3$, 200 Mz) |
|---|---|
| | 8.37(m, 1H), 8.19(s, 1H), 7.69(s, 1H), 7.68~7.67(m, 4H), 7.54(d, 2H), 7.40~7.37(m, 7H), 7.36(d, 2H), 7.32(t, 1H). |
| F139 | δ = 9.22(d, 1H), 9.10(d, 1H), 8.87(d, 4H), 8.71(d, 1H), 8.56~8.54(m, 3H), 8.28(d, 1H), 7.64~7.59(m, 6H), 7.54~7.50(m, 4H), 7.48(d, 2H), 7.46(d, 2H), 7.40~7.38(m, 5H), 7.31(t, 1H). |
| F145 | δ = 9.12(s, 1H), 8.92(s, 1H), 8.82(d, 4H), 8.76(d, 1H), 8.39(d, 1H), 8.26(d, 1H), 8.24(d, 1H), 7.98(d, 1H), 7.69~7.64(m, 4H), 7.60~7.58(m, 3H), 7.54(d, 1H), 7.52~7.48(m, 5H), 7.46(d, 1H), 7.40 (t, 2H). |
| F146 | δ = 9.18(s, 1H), 9.10(d, 1H), 8.84(d, 1H), 8.69(s, 1H), 8.46(s, 1H), 8.29~8.28(m, 3H), 8.24(d, 2H), 8.21(d, 1H), 7.89(d, 1H), 7.64~7.60(m, 3H), 7.56(d, 1H), 7.51~7.48(m, 6H), 7.44~7.42(m, 3H), 7.38~7.36(m, 2H). |
| F148 | δ = 9.20(s, 1H), 8.84(d, 1H), 8.66(d, 1H), 8.26~8.24(m, 2H), 8.16(d, 1H), 8.14(d, 1H), 7.95(s, 1H), 7.89(d, 1H), 7.64~7.59(m, 6H), 7.52(d, 1H), 7.50~7.48(m, 6H), 7.46(d, 1H), 7.38 (t, 2H). |
| F149 | δ = 9.24(s, 1H), 9.18(d, 1H), 8.68(d, 1H), 8.60(s, 1H), 8.28(d, 1H), 8.26(d, 1H), 8.24~8.23(m, 3H), 7.77(d, 1H), 7.72(d, 1H), 7.75~7.71(m, 7H), 7.62(s, 1H), 7.46(d, 1H), 7.45(d, 1H), 7.41~7.38(m, 5H), 7.30(t, 1H). |
| F157 | δ = 9.16(d, 1H), 8.89(d, 2H), 8.63(d, 1H), 8.53~8.49(m, 3H), 8.36 (d, 1H), 8.15(d, 1H), 7.97(s, 1H), 7.90~7.87(m, 3H), 7.87(t, 3H), 7.71~7.39(m, 13H), 7.26(t, 1H). |
| F158 | δ = 9.16(d, 1H), 9.02(d, 1H), 8.63(d, 1H), 8.36(d, 1H), 8.17(d, 1H), 8.16(d, 1H), 8.15(d, 1H), 7.90~7.87(m, 4H), 7.87(t, 1H), 7.70(t, 1H), 7.71~7.39(m, 13H), 7.26(t, 1H), 7.07(s, 1H), 3.16(s, 6H). |
| F164 | δ = 9.27(d, 1H), 9.08(d, 1H), 8.65(s, 1H), 8.17(d, 1H), 8.14(d, 1H), 8.12~8.08(m, 5H), 8.04~7.97(m, 3H), 7.80(t, 1H), 7.64(t, 1H), 7.49~7.37(m, 4H), 7.35~7.19(m, 14H). |
| F172 | δ = 9.25(d, 1H), 9.06(d, 1H), 8.63(s, 1H), 8.23(d, 1H), 8.16(d, 1H), 8.11~8.08(m, 5H), 8.04~7.97(m, 3H), 7.77(t, 1H), 7.64(t, 1H), 7.48~7.37(m, 4H), 7.35~7.19(m, 11H). |
| F174 | δ = 9.22(d, 1H), 9.04(d, 1H), 8.60(s, 1H), 8.17(d, 1H), 8.15(d, 1H), 8.12~8.09(m, 5H), 8.02~7.98(m, 3H), 7.80(t, 1H), 7.64(t, 1H), 7.52(d, 2H), 7.51(d, 2H), 7.45~7.36(m, 7H), 7.35~7.18(m, 8H), 7.14(t, 2H). |
| F175 | δ = 9.24(d, 1H), 9.04(d, 1H), 8.62(s, 1H), 8.16(d, 1H), 8.14(d, 1H), 8.13~8.09(m, 5H), 8.02~7.98(m, 3H), 7.78(t, 1H), 7.66(t, 1H), 7.59(d, 1H), 7.57(d, 1H), 7.49(d, 2H), 7.48~7.46(m, 4H), 7.45~7.36(m, 4H), 7.35~7.24(m, 6H), 7.17(t, 1H). |
| F179 | δ = 9.18(d, 1H), 8.98(d, 1H), 8.60(s, 1H), 8.27(d, 2H), 8.24~8.22(m, 3H), 8.00~7.97(m, 3H), 7.69(t, 1H), 7.62(s, 1H), 7.61(t, 1H), 7.44~7.35(m, 8H), 7.31~7.27(m, 5H), 7.21(t, 1H), 7.18(t, 1H). |
| F180 | δ = 9.21(d, 1H), 8.99(d, 1H), 8.63(s, 1H), 8.49(d, 1H), 8.46(d, 1H), 8.36~8.32(m, 4H), 8.00~7.97(m, 3H), 7.69(t, 1H), 7.62(s, 1H), 7.61(t, 1H), 7.42~7.33(m, 7H), 7.33~7.29(m, 6H), 7.18(t, 1H). |
| F187 | δ = 9.41(d, 1H), 8.92(d, 1H), 8.87~8.81(m, 5H), 8.74(d, 1H), 8.66(s, 1H), 8.31(d, 1H), 8.11~8.08(m, 2H), 7.90~7.87(m, 4H), 7.76(t, 1H), 7.66~7.60(m, 6H), 7.56~7.44(m, 4H), 7.37(t, 1H). |
| F188 | δ = 9.39(d, 1H), 8.92(d, 1H), 8.87~8.81(m, 5H), 8.74(d, 1H), 8.58(d, 1H), 8.51(d, 1H), 8.24(d, 1H), 8.08 (d, 1H), 7.92~7.87(m, 4H), 7.73(t, 1H), 7.66~7.59(m, 6H), 7.54~7.44(m, 4H), 7.36(t, 1H). |
| F194 | δ = 9.40(d, 1H), 8.90(d, 1H), 8.86~8.82(m, 3H), 8.77(s, 1H), 8.71(d, 1H), 8.55(d, 1H), 8.51(d, 1H), 8.27(d, 1H), 8.17(d, 2H), 8.05 (d, 1H), 7.92~7.87(m, 4H), 7.78~7.75(m, 2H), 7.64~7.57(m, 5H), 7.54~7.44(m, 6H). |
| F200 | δ = 9.40(d, 1H), 8.88(s, 2H), 8.84~8.78(m, 5H), 8.63(d, 1H), 8.3(t, 1H), 7.98(s, 1H), 7.83(t, 1H), 7.75~7.73(m, 2H), 7.67~7.50(m, 11H), 7.43(d, 1H), 7.41~7.32(m, 7H). |
| F202 | δ = 9.38(d, 1H), 8.93(d, 2H), 8.82(d, 4H), 8.74~8.68(m, 2H), 8.63(d, 1H), 8.05~8.01(m, 2H), 7.87(s, 1H), 7.79~7.26(m, 18H), 7.21(t, 1H). |
| F203 | δ = 9.39(d, 1H), 8.94(d, 1H), 8.83~8.76(m, 3H), 8.74(d, 1H), 8.66(s, 1H), 8.31(d, 1H), 8.27(s, 1H), 8.22(d, 1H), 8.19(d, 1H), 7.94(d, 1H), 7.89(d, 1H), 7.84(d, 1H), 7.72~7.64(m, 5H), 7.59(s, 1H), 7.56(d, 1H). 7.53(d, 1H), 7.52~7.49(m, 3H), 7.48~7.36(m, 8H), 7.34(t, 1H). |
| F204 | δ = 9.36(d, 1H), 8.92(d, 2H), 8.84(d, 4H), 8.74~8.68(m, 2H), 8.62(d, 1H), 8.06~8.01(m, 2H), 7.90(s, 1H), 7.79~7.26(m, 15H). |
| F205 | δ = 9.41(d, 1H), 8.93(d, 1H), 8.83~8.76(m, 5H), 8.74(d, 1H), 8.65(s, 1H), 8.32(d, 1H), 8.29(s, 1H), 8.09(d, 1H), 8.01(d, |

TABLE 10-continued

| Example | $^1$H NMR ($CDCl_3$, 200 Mz) |
|---|---|
| | 1H), 7.81(s, 1H), 7.65~7.49(m, 6H), 7.43(t, 2H), 7.41~7.32(m, 5H), 7.29(t, 1H). |
| F212 | δ = 9.36(d, 1H), 8.92(d, 1H), 8.80~8.74(m, 5H), 8.71(d, 1H), 8.64(s, 1H), 8.28(d, 1H), 8.24(d, 1H), 7.79(d, 1H), 7.70~7.63(m, 5H), 7.59(s, 1H), 7.55(d, 1H). 7.53(d, 1H), 7.52~7.36(m, 12H), 7.21(t, 2H). |
| F213 | δ = 9.35(d, 1H), 8.92(d, 1H), 8.80~8.75(m, 5H), 8.70(d, 1H), 8.63(s, 1H), 8.29(d, 1H), 8.11(d, 1H), 7.85(d, 1H), 7.69~7.60(m, 5H), 7.59(s, 1H), 7.57~7.56(m, 3H), 7.54(s, 1H), 7.49(d, 2H), 7.47~7.36(m, 14H), 7.21(t, 2H). |
| F217 | δ = 9.36(d, 1H), 9.13(s, 1H), 8.98(d, 1H), 8.91(s, 1H), 8.85(d, 1H), 8.83(d, 2H), 8.59(d, 1H), 8.54~8.49(m, 5H), 8.51(s, 1H), 8.34(d, 1H), 7.73(t, 2H), 7.62~7.57(m, 5H), 7.59~7.48(m, 6H), 7.34(t, 1H). |
| F220 | δ = 9.29(d, 1H), 8.87(d, 1H), 8.91(s, 1H), 8.72(d, 1H), 8.69~8.68(m, 2H), 8.57(d, 1H), 8.54(d, 1H), 8.51(s, 1H), 8.34(d, 1H), 7.76(t, 2H), 7.62~7.57(m, 6H), 7.59~7.48(m, 8H), 7.34(t, 1H). |
| F224 | δ = 9.17(s, 1H), 9.10(d, 1H), 8.84(d, 4H), 8.76(d, 1H), 8.15(d, 1H), 7.89~7.87(m, 3H), 7.69(d, 1H), 7.60(d, 1H), 7.56(d, 1H), 7.55(d, 1H), 7.54~7.52(m, 6H), 7.46~7.41(m, 5H), 7.40(d, 1H), 7.39(d, 1H). |
| F226 | δ = 9.17(s, 1H), 8.92(d, 1H), 8.82(d, 2H), 8.74(s, 2H), 8.69~8.63(m, 4H), 8.39~8.37(m, 4H), 8.26(d, 2H), 8.22~8.19(m, 3H), 7.76~7.72(m, 5H), 7.44~7.32(m, 6H). |
| F231 | δ = 9.22(s, 1H), 9.09(d, 1H), 8.89(d, 4H), 8.69(d, 1H), 8.22(d, 1H), 8.08(d, 1H), 7.89~7.87(m, 3H), 7.69(d, 1H), 7.67(s, 1H), 7.62(d, 2H), 7.56~7.53(m, 7H), 7.43~7.39(m, 7H), 7.40(d, 1H), 7.29(s, 1H), 7.19(t, 1H). |
| F233 | δ = 9.17(s, 1H), 9.10(d, 1H), 8.84(d, 4H), 8.76(d, 1H), 8.15(d, 1H), 7.89~7.87(m, 3H), 7.69(d, 1H), 7.67(s, 1H), 7.56~7.53(m, 7H), 7.46~7.41(m, 6H), 7.40(d, 1H), 7.37(s, 1H). |
| F236 | δ = 9.26(s, 1H), 9.14(d, 1H), 9.07(d, 1H), 8.94(d, 4H), 8.76(d, 1H), 8.66~8.63(m, 4H), 8.51(d, 2H), 7.67(s, 1H), 7.59~7.56(m, 4H), 7.49(d, 4H), 7.35~7.30(m, 7H), 7.31(t, 2H), 7.27~7.25(m, 4H). |
| F251 | δ = 9.24(s, 1H), 9.08(d, 1H), 8.89(d, 4H), 8.83(d, 1H), 8.16(d, 1H), 7.89~7.87(m, 3H), 7.65(d, 1H), 7.59(s, 1H), 7.54~7.50(m, 7H), 7.46~7.42(m, 6H), 7.40(s, 1H), 7.39(d, 1H). |
| F256 | δ = 9.16(s, 1H), 9.09(d, 1H), 9.05(d, 1H), 8.92(d, 4H), 8.72(d, 1H), 8.65~8.63(m, 4H), 8.48(d, 2H), 7.66(s, 1H), 7.57~7.55(m, 4H), 7.48(d, 4H), 7.35~7.32(m, 7H), 7.29(t, 2H), 7.27~7.25(m, 4H). |
| F260 | δ = 9.12(s, 1H), 8.99(d, 1H), 8.88(d, 4H), 8.51(d, 1H), 8.33(s, 1H), 8.07(d, 2H), 7.72(d, 2H) 7.67~7.62(m, 5H), 7.53(d, 1H), 7.41(d, 2H), 7.35~7.28(m, 8H), 7.22~7.18(m, 6H), 7.13(t, 2H). |
| F266 | δ = 9.32(s, 1H), 9.11(d, 1H), 9.00(s, 1H), 8.88(d, 2H), 8.76(s, 1H), 8.48(d, 1H), 8.33(t, 1H), 7.99~7.89(m, 5H), 7.74~7.67(m, 5H), 7.64~7.56(m, 6H), 7.53~7.37(m, 4H), 7.18~7.10(m, 4H). |
| F274 | δ = 9.09(d, 1H), 8.91(s, 1H), 8.75(d, 4H), 8.54(d, 1H), 8.41(d, 1H), 8.08(d, 2H), 7.70(d, 2H) 7.65~7.62(m, 5H), 7.56(d, 1H), 7.38(d, 2H), 7.34~7.28(m, 8H), 7.22~7.19(m, 6H), 7.14(t, 2H). |
| F275 | δ = 8.83(s, 1H), 8.51(d, 4H), 8.33(s, 1H), 8.09(d, 2H), 7.84~7.67(m, 7H), 7.55(d, 2H), 7.41~7.29(m, 8H), 7.15~7.03(m, 8H). |
| F278 | δ = 9.01(s, 1H), 8.81(d, 1H), 8.63(d, 4H), 8.42(d, 1H), 8.30(s, 1H), 8.10(d, 2H), 7.69(d, 2H) 7.62~7.56(m, 6H), 7.33(d, 2H), 7.30~7.19(m, 14H), 7.04(t, 2H). |
| F288 | δ = 9.22(s, 1H), 9.06(d, 1H), 8.99(s, 1H), 8.70(d, 4H), 8.49(d, 1H), 8.38(d, 1H), 8.26(t, 1H), 7.99~7.89(m, 6H), 7.73~7.70(m, 5H), 7.60~7.57(m, 4H), 7.44~7.31(m, 4H), 7.12~7.05(m, 3H). |
| F294 | δ = 9.11(s, 1H), 9.01(d, 1H), 8.78~8.68(m, 6H), 8.55(d, 2H), 8.31~8.16(m, 6H), 7.91~7.75(m, 8H), 7.61(t, 1H), 7.39~7.30(m, 9H), 7.14(t, 1H). |
| F296 | δ = 9.11(d, 1H), 8.99(s, 1H), 8.81(d, 4H), 8.59(d, 1H), 8.45(d, 1H), 8.12(d, 2H), 7.79(d, 2H) 7.72~7.62(m, 3H), 7.51(d, 1H), 7.36(d, 2H), 7.33~7.28(m, 6H), 7.19~7.11(m, 6H), 7.04(t, 4H). |
| F298 | δ = 9.05 (s, 1H), 8.83(d, 2H), 8.51(d, 1H), 8.33(s, 1H), 8.09(d, 2H), 7.78~7.67(m, 7H), 7.55(d, 4H), 7.41~7.33(m, 6H), 7.15~7.09(m, 6H). |
| F299 | δ = 8.99 (s, 1H), 8.75(d, 2H), 8.49(d, 1H), 8.21(s, 1H), 8.05(d, 2H), 7.72~7.62(m, 6H), 7.42(d, 2H), 7.35~7.28(m, 6H), 7.20~7.15(m, 6H), 7.02(t, 4H). |

TABLE 10-continued

| Example | $^1$H NMR ($CDCl_3$, 200 Mz) |
|---|---|
| F302 | δ = 9.15(d, 1H), 9.01(d, 1H), 8.92(d, 2H), 8.76(d, 1H), 8.55(s, 1H), 8.21(d, 2H), 7.89~7.78(m, 5H), 7.66(d, 1H), 7.45~7.30(m, 6H), 7.23~7.17(m, 6H), 7.05(t, 2H), 1.63~1.59(m, 6H). |
| F304 | δ = 9.12(d, 1H), 9.01(dd, 2H), 8.89(d, 1H), 8.54(d, 4H), 8.39(s, 1H), 8.28(s, 1H), 8.15(d, 1H), 7.90~7.85(m, 2H), 7.78~7.74(m, 2H), 7.65~7.60(m, 4H), 7.53~7.34(m, 7H), 7.22~7.20(m, 4H). |
| F308 | δ = 9.21(s, 1H), 9.10(d, 1H), 9.01(d, 1H), 8.78(d, 4H), 8.65(d, 1H), 8.41(s, 1H), 8.32(s, 1H), 8.00~7.93(m, 3H), 7.81~7.76(m, 3H), 7.59~7.50(m, 5H), 7.45~7.36(m, 6H), 7.17~7.13(m, 6H). |
| F310 | δ = 9.09(s, 1H), 9.02(d, 1H), 8.93(d, 1H), 8.69(d, 4H), 8.51(d, 1H), 8.35(s, 1H), 8.20(t, 1H), 7.98~7.91(m, 3H), 7.70~7.65(m, 2H), 7.55~7.50(m, 6H), 7.43~7.32(m, 6H), 7.11~7.02(m, 6H). |
| F317 | δ = 9.20(s, 1H), 9.11(d, 1H), 8.98(s, 1H), 8.74(d, 4H), 8.61(d, 1H), 8.41(t, 1H), 8.29(t, 1H), 8.01~7.95(m, 3H), 7.79~7.69(m, 2H), 7.58(s, 1H), 7.53~7, 39(m, 6H), 7.18~7.12(m, 6H). |
| F318 | δ = 9.16(d, 1H), 9.01(d, 1H), 8.83(d, 4H), 8.65(s, 1H), 8.35(d, 1H), 8.11(d, 2H), 7.76(d, 2H) 7.67~7.59(m, 5H), 7.48(d, 1H), 7.37(d, 2H), 7.34~7.28(m, 8H), 7.20~7.15(m, 6H), 7.10(t, 2H). |
| F322 | δ = 9.19(d, 1H), 9.05(d, 1H), 8.91(d, 4H), 8.69(s, 1H), 8.42(d, 1H), 8.23(d, 2H), 7.70~7.61(m, 5H), 7.46(d, 1H), 7.36~7.29(m, 6H), 7.20~7.12(m, 6H), 7.05(t, 2H). |
| F327 | δ = 9.10(s, 1H), 9.02(d, 1H), 8.83~8.73(m, 2H), 8.66(d, 1H), 8.43(d, 1H), 8.21~8.13(m, 6H), 7.99~7.81(m, 6H), 7.70(s, 1H), 7.51(t, 1H), 7.43~7.31(m, 8H), 7.12(t, 1H). |
| F328 | δ = 9.12(s, 1H), 9.04(d, 1H), 8.78~8.69(m, 2H), 8.61(d, 1H), 8.54(s, 1H), 8.43(d, 1H), 8.20~8.11(m, 5H), 7.91~7.79(m, 6H), 7.69(s, 1H), 7.59(t, 1H), 7.45~7.39(m, 6H), 7.18(t, 1H). |
| F334 | δ = 9.38(s, 1H), 8.88(d, 1H), 8.65(d, 2H), 8.52(d, 1H), 8.28(s, 1H), 8.08(d, 2H), 7.70~7.62(m, 5H), 7.45(d, 2H), 7.37~7.29(m, 5H), 7.21~7.17(m, 6H), 7.06(t, 2H). |
| F337 | δ = 9.36(d, 1H), 8.92(d, 2H), 8.84(d, 4H), 8.74~8.68(m, 2H), 8.62(d, 1H), 8.06~8.01(m, 4H), 7.90(s, 1H), 7.79~7.26(m, 15H). |
| F344 | δ = 9.34(d, 1H), 9.21~9.17(d, 2H), 9.04~8.98(m, 3H), 8.81(d, 4H), 8.37(d, 1H), 7.94~7.87(d, 2H), 7.73(t, 1H), 7.61~7.50(m, 11H), 7.43~7.32(m, 8H). |
| F345 | δ = 9.32(s, 1H), 9.25~9.19(d, 2H), 9.01(s, 1H), 8.85(d, 4H), 8.53(s, 1H), 8.35(d, 1H), 7.99~7.88(d, 2H), 7.76(t, 1H), 7.65~7.50(m, 12H), 7.45~7.31(m, 8H). |
| F356 | δ = 9.11(d, 1H), 8.82(d, 4H), 8.71(d, 1H), 8.53(d, 1H), 8.49(d, 1H), 8.31(d, 2H), 8.28~8.18(m, 4H), 8.05(d, 1H), 7.88~7.81(m, 4H), 7.50~7.46(m, 4H), 7.34~7.30(m, 4H). |
| F358 | δ = 9.18(d, 1H), 9.02(s, 1H), 8.83(d, 4H), 8.65(d, 1H), 8.41(d, 1H), 8.12(d, 2H), 7.65~7.61(m, 5H), 7.50(d, 1H), 7.36~7.29(m, 6H), 7.23~7.17(m, 6H), 7.12(t, 2H). |
| F371 | δ = 9.09(d, 1H), 8.91(s, 1H), 8.75(d, 4H), 8.54(d, 1H), 8.41(d, 1H), 8.08(d, 2H), 7.70(d, 2H) 7.65~7.62(m, 5H), 7.56(d, 1H), 7.38(d, 2H), 7.34~7.28(m, 8H), 7.22~7.19(m, 6H), 7.14(t, 2H). |
| F376 | δ = 9.13(s, 1H), 9.05(d, 1H), 8.70~8.68(m, 2H), 8.58(d, 1H), 8.54(d, 1H), 8.35~8.31(m, 2H), 7.87~7.75(m, 11H), 7.68(t, 1H), 7.43~7.30(m, 4H), 7.19(t, 1H). |
| F380 | δ = 9.19(s, 1H), 9.08(d, 1H), 8.99(d, 1H), 8.75(d, 4H), 8.63(d, 1H), 8.39(t, 1H), 8.27(t, 1H), 7.99~7.93(m, 3H), 7.71~7.64(m, 2H), 7.58~7.52(m, 6H), 7.48~7, 39(m, 6H), 7.18~7.12(m, 6H). |
| F381 | δ = 9.31(d, 1H), 9.11(d, 1H), 9.02(d, 1H), 8.91(s, 1H), 8.85(s, 1H), 8.8~8.78(m, 4H), 8.28(d, 1H), 8.22(s, 1H), 7.85~7.82(m, 2H), 7.77(t, 1H), 7.67~7.62(m, 11H), 7.57~7.26(m, 8H). |
| F386 | δ = 9.23(s, 1H), 9.12(d, 1H), 9.01(d, 1H), 8.89(d, 4H), 8.67(d, 1H), 8.45(t, 1H), 8.30(t, 1H), 8.05~7.96(m, 3H), 7.69~7.62(m, 2H), 7.59~7.53(m, 6H), 7.49~7.38(m, 8H), 7.17~7.09(m, 6H). |
| F391 | δ = 9.16(s, 1H), 9.05(d, 1H), 8.97(d, 1H), 8.72(d, 4H), 8.51(d, 1H), 8.39(d, 1H), 8.27(t, 1H), 7.95~7.89(m, 2H), 7.74~7.70(m, 2H), 7.64~7.57(m, 4H), 7.53~7.37(m, 6H), 7.19~7.10(m, 6H). |
| F393 | δ = 9.34(d, 1H), 9.19(dd, 2H), 8.99(s, 1H), 8.84(d, 4H), 8.41(s, 1H), 8.30(s, 1H), 8.25(d, 1H), 7.92~7.88(m, 2H), 7.78~7.76(m, 2H), 7.67~7.62(m, 4H), 7.58~7.34(m, 8H), 7.22~7.20(m, 5H). |

TABLE 10-continued

| Example | $^{1}H$ NMR ($CDCl_3$, 200 Mz) |
|---|---|
| F394 | δ = 9.37(d, 1H), 9.17(s, 1H), 8.84~8.80(m, 5H), 8.66(s, 1H), 8.46(d, 1H), 8.25(d, 1H), 7.92~7.88(m, 2H), 7.78(t, 1H), 7.58(t, 1H), 7.49~7.44(m, 6H), 7.42~7.34(m, 7H), 7.28(t, 1H), 7.22(d, 2H). |
| F403 | δ = 9.20(d, 1H), 8.88(s, 1H), 8.82(d, 1H), 8.77(d, 4H), 8.59(s, 1H), 8.24(d, 2H), 7.80~7.72(m, 6H), 7.66~7.55(m, 9H), 7.52~7.45(m, 3H), 7.41(d, 1H), 7.34(t, 2H). |
| F406 | δ = 9.21(d, 1H), 8.89(s, 1H), 8.83(d, 1H), 8.76(d, 4H), 8.63(s, 1H), 8.24(d, 2H), 7.80~7.72(m, 6H), 7.67~7.57(m, 11H), 7.52~7.45(m, 6H), 7.34(t, 2H). |
| F409 | δ = 9.16(d, 1H), 8.90(d, 1H), 8.74(d, 4H), 8.79(s, 1H), 8.52(s, 1H), 8.29(d, 1H), 7.85(t, 1H), 7.71~7.54(m, 12H), 7.48(s, 1H), 7.46(d, 1H), 7.42(d, 1H), 7.40(s, 1H), 7.38~7.36(m, 4H), 7.29~7.26(m, 5H), 7.18(d, 2H). |
| F418 | δ = 9.13(d, 1H), 8.89(d, 1H), 8.77(d, 4H), 8.81(s, 1H), 8.49(s, 1H), 8.21(d, 1H), 7.81(t, 1H), 7.71~7.54(m, 12H), 7.44(d, 1H), 7.36(t, 1H), 7.28(d, 2H), 7.27~7.23(m, 6H), 6.87~6.84(m, 4H). |
| F422 | δ = 8.55(m, 2H), 8.28(d, 2H), 8.00(d, 2H), 7.95(d, 1H), 7.92(d, 1H), 7.85(d, 2H), 7.75-7.73(m, 2H), 7.64(s, 2H), 7.59-7.51(m, 11H), 7.41~7.40(m, 2H), 7.25(d, 2H). |
| F440 | δ = 8.55(m, 2H), 8.28(d, 4H), 8.00(m, 2H), 7.92(d, 1H), 7.73-7.71(m, 3H), 7.64(s, 1H), 7.59-7.51(m, 9H), 7.41~7.40(m, 2H), 7.25(s, 4H). |
| F445 | δ = 8.55(m, 2H), 8.00(m, 2H), 7.92(d, 1H), 7.81(d, 1H), 7.73-7.71(m, 3H), 7.64(s, 1H), 7.59-7.51(m, 9H), 7.41~7.40(m, 2H), 7.25(s, 4H). |
| F453 | δ = 8.55(m, 3H), 8.42(d, 1H), 8.28(d, 4H), 8.08(m, 1H), 8.04(d, 1H), 7.95(d, 1H), 7.75(d, 1H), 7.64(s, 2H), 7.61-7.51(m, 9H), 7.41~7.40(m, 2H), 7.25(s, 4H). |
| F458 | δ = 8.55(m, 3H), 8.42(d, 1H), 8.28(d, 4H), 8.08(m, 1H), 8.04(d, 1H), 7.95(d, 1H), 7.75(d, 1H), 7.64(s, 2H), 7.61-7.51(m, 9H), 7.41~7.40(m, 2H), 7.25(s, 4H). |
| F629 | δ = 8.55(m, 2H), 8.28(d, 2H), 8.00(m, 2H), 7.92(d, 1H), 7.85(d, 2H), 7.73(m, 1H), 7.64(m, 2H), 7.59-7.51(m, 11H), 7.41~7.40(m, 2H), 7.25(d, 2H). |
| F631 | δ = 8.55(m, 2H), 8.28(d, 2H), 7.95(m, 2H), 7.89(d, 1H), 7.75(d, 2H), 7.66(d, 1H), 7.64(s, 3H), 7.55-7.51(m, 8H), 7.41~7.32(m, 4H). |
| F634 | δ = 8.55(m, 2H), 8.28(d, 4H), 7.79(d, 2H), 7.81(d, 1H), 7.72-7.71(m, 2H), 7.64(s, 1H), 7.55-7.51(m, 8H), 7.41~7.40(m, 3H). |
| F645 | δ = 8.55(m, 2H), 8.11(d, 1H), 8.08(s, 2H), 8.05(d, 1H), 7.55-7.51(m, 10H), 7.41~7.40(m, 3H). |

TABLE 11

| Compound | FD-Mass | Compound | FD-Mass |
|---|---|---|---|
| F1 | m/z = 613.7200 (C44H27N3O, 613.2154) | F2 | m/z = 587.6820 (C42H25N3O, 587.1998) |
| F3 | m/z = 637.7420 (C46H27N3O, 637.2154) | F4 | m/z = 643.7640 (C44H25N3OS, 643.1718) |
| F5 | m/z = 693.8240 (C48H27N3OS, 693.1875) | F6 | m/z = 808.9590 (C56H32N4OS, 808.2297) |
| F7 | m/z = 614.7080 (C43H26N4O, 614.2107) | F8 | m/z = 704.7890 (C49H28N4O2, 704.2212) |
| F9 | m/z = 704.7890 (C49H28N4O2, 704.2212) | F10 | m/z = 754.8490 (C53H30N4O2, 754.2369) |
| F11 | m/z = 720.8500 (C49H28N4OS, 720.1984) | F12 | m/z = 720.8500 (C49H28N4OS, 720.1984) |
| F13 | m/z = 770.9100 (C53H30N4OS, 770.2140) | F14 | m/z = 780.9310 (C56H36N4O, 780.2889) |
| F15 | m/z = 740.8660 (C53H32N4O, 740.2576) | F16 | m/z = 740.8660 (C53H32N4O, 740.2576) |
| F17 | m/z = 690.8060 (C49H30N4O, 690.2420) | F18 | m/z = 740.8660 (C53H32N4O, 740.2576) |
| F19 | m/z = 720.8500 (C49H28N4OS, 720.1984) | F20 | m/z = 779.9030 (C55H33N5O, 779.2685) |
| F21 | m/z = 779.9030 (C55H33N5O, 779.2685) | F22 | m/z = 720.8500 (C49H28N4OS, 720.1984) |
| F23 | m/z = 720.8500 (C49H28N4OS, 720.1984) | F24 | m/z = 704.7890 (C49H28N4O2, 704.2212) |
| F25 | m/z = 664.7680 (C47H28N4O, 664.2263) | F26 | m/z = 740.8660 (C53H32N4O, 740.2576) |

TABLE 11-continued

| Compound | FD-Mass | Compound | FD-Mass |
|---|---|---|---|
| F27 | m/z = 779.9030 (C55H33N5O, 779.2685) | F28 | m/z = 720.8500 (C49H28N4OS, 720.1984) |
| F29 | m/z = 692.8220 (C49H32N4O, 692.2576) | F30 | m/z = 768.9200 (C55H36N4O, 768.2889) |
| F31 | m/z = 666.7840 (C47H30N4O, 666.2420) | F32 | m/z = 722.8660 (C49H30N4OS, 772.2140) |
| F33 | m/z = 692.8220 (C49H32N4O, 692.2576) | F34 | m/z = 690.8060 (C49H30N4O, 690.2420) |
| F35 | m/z = 663.7800 (C48H29N3O, 663.2311) | F36 | m/z = 795.9600 (C56H33N3OS, 795.2344) |
| F37 | m/z = 613.7200 (C44H27N3O, 613.2154) | F38 | m/z = 587.6820 (C42H25N3O, 587.1998) |
| F39 | m/z = 663.7800 (C48H29N3O, 663.2311) | F40 | m/z = 643.7640 (C44H25N3OS, 643.1718) |
| F41 | m/z = 719.8620 (C50H29N3OS, 719.2031) | F42 | m/z = 693.8240 (C48H27N3OS, 693.1875) |
| F43 | m/z = 627.7030 (C44H25N3O2, 627.1947) | F44 | m/z = 664.7680 (C47H28N4O, 664.2263) |
| F45 | m/z = 664.7680 (C47H28N4O, 664.2263) | F46 | m/z = 714.8280 (C51H30N4O, 714.2420) |
| F47 | m/z = 704.7890 (C49H28N4O2, 704.2212) | F48 | m/z = 720.8500 (C49H28N4OS, 720.1984) |
| F49 | m/z = 770.9100 (C53H30N4OS, 770.2140) | F50 | m/z = 730.8710 (C52H34N4O, 730.2733) |
| F51 | m/z = 690.8060 (C49H30N4O, 690.2420) | F52 | m/z = 740.8660 (C53H32N4O, 740.2576) |
| F53 | m/z = 690.8060 (C49H30N4O, 690.2420) | F54 | m/z = 740.8660 (C53H32N4O, 740.2576) |
| F55 | m/z = 779.9030 (C55H33N5O, 779.2685) | F56 | m/z = 779.9030 (C55H33N5O, 779.2685) |
| F57 | m/z = 779.9030 (C55H33N5O, 779.2685) | F58 | m/z = 779.9030 (C55H33N5O, 779.2685) |
| F59 | m/z = 720.8500 (C49H28N4OS, 720.1984) | F60 | m/z = 704.7890 (C49H28N4O2, 704.2212) |
| F61 | m/z = 720.8500 (C49H28N4OS, 720.1984) | F62 | m/z = 704.7890 (C49H28N4O2, 704.2212) |
| F63 | m/z = 779.9030 (C55H33N5O, 779.2685) | F64 | m/z = 720.8500 (C49H28N4OS, 720.1984) |
| F65 | m/z = 720.8500 (C49H28N4OS, 720.1984) | F66 | m/z = 616.7240 (C43H28N4O, 616.2263) |
| F67 | m/z = 666.7840 (C47H30N4O, 666.2420) | F68 | m/z = 716.8440 (C51H32N4O, 716.2576) |
| F69 | m/z = 768.9200 (C55H36N4O, 768.2889) | F70 | m/z = 690.8060 (C49H30N4O, 690.2420) |
| F71 | m/z = 663.7800 (C48H29N3O, 663.2311) | F72 | m/z = 782.9610 (C56H34N2OS, 782.2392) |
| F73 | m/z = 663.7800 (C48H29N3O, 663.2311) | F74 | m/z = 741.8940 (C54H35N3O, 741.2780) |
| F75 | m/z = 740.8660 (C53H32N4O, 740.2576) | F76 | m/z = 650.7810 (C48H30N2O, 650.2358) |
| F77 | m/z = 706.8630 (C50H30N2OS, 706.2079) | F78 | m/z = 677.8070 (C49H31N3O, 677.2467) |
| F79 | m/z = 663.7800 (C48H29N3O, 663.2311) | F80 | m/z = 651.7690 (C47H29N3O, 651.2311) |
| F81 | m/z = 677.8070 (C49H31N3O, 677.2467) | F82 | m/z = 727.8670 (C53H33N3O, 727.2624) |
| F83 | m/z = 742.8820 (C53H34N4O, 742.2733) | F84 | m/z = 637.7420 (C46H27N3O, 637.2154) |
| F85 | m/z = 613.7200 (C44H27N3O, 613.2154) | F86 | m/z = 768.9200 (C55H36N4O, 768.2889) |
| F87 | m/z = 740.8660 (C53H32N4O, 740.2576) | F88 | m/z = 740.8660 (C53H32N4O, 740.2576) |
| F89 | m/z = 650.7810 (C48H30N2O, 650.2358) | F90 | m/z = 677.8070 (C49H31N3O, 677.2467) |
| F91 | m/z = 677.8070 (C49H31N3O, 677.2467) | F92 | m/z = 727.8670 (C53H33N3O, 727.2624) |
| F93 | m/z = 742.8820 (C53H34N4O, 742.2733) | F94 | m/z = 766.9040 (C55H34N4O, 766.2733) |
| F95 | m/z = 637.7420 (C46H27N3O, 637.2154) | F96 | m/z = 693.8240 (C48H27N3OS, 693.1875) |
| F97 | m/z = 629.7810 (C44H27N3S, 629.1926) | F98 | m/z = 603.7430 (C42H25N3S, 603.1769) |
| F99 | m/z = 679.8410 (C48H29N3S, 679.2082) | F100 | m/z = 659.8250 (C44H25N3S2, 659.1490) |
| F101 | m/z = 709.8850 (C48H27N3S, 709.1646) | F102 | m/z = 709.8850 (C48H27N3S, 709.1646) |
| F103 | m/z = 795.9640 (C55H33N5S, 795.2457) | F104 | m/z = 680.8290 (C47H28N4S, 680.2035) |

TABLE 11-continued

| Compound | FD-Mass | Compound | FD-Mass |
|---|---|---|---|
| F105 | m/z = 736.9110 (C49H28N4S2, 736.1755) | F106 | m/z = 708.8830 (C49H32N4S, 708.2348) |
| F107 | m/z = 758.9430 (C53H34N4S, 758.9430) | F108 | m/z = 708.8830 (C49H32N4S, 708.2348) |
| F109 | m/z = 755.2395 (C54H33N3S, 755.2395) | F110 | m/z = 603.7430 (C42H25N3S, 603.1769) |
| F111 | m/z = 679.8410 (C48H29N3S, 679.2082) | F112 | m/z = 659.8250 (C44H25N3S2, 659.1490) |
| F113 | m/z = 709.8850 (C48H27N3S, 709.1646) | F114 | m/z = 709.8850 (C48H27N3S, 709.1646) |
| F115 | m/z = 795.9600 (C56H33N3OS, 795.2344) | F116 | m/z = 679.8410 (C48H29N3S, 679.2082) |
| F117 | m/z = 736.9110 (C49H28N4S2, 736.1755) | F118 | m/z = 708.8830 (C49H32N4S, 708.2348) |
| F119 | m/z = 758.9430 (C53H34N4S, 758.9430) | F120 | m/z = 708.8830 (C49H32N4S, 708.2348) |
| F121 | m/z = 679.8410 (C48H29N3S, 679.2082) | F122 | m/z = 757.9550 (C54H35N3S, 757.2552) |
| F123 | m/z = 756.9270 (C53H32N4S, 756.2348) | F124 | m/z = 666.8420 (C48H30N2S, 666.2130) |
| F125 | m/z = 722.9240 (C50H30N2S2, 722.1850) | F126 | m/z = 693.8680 (C49H31N3S, 693.2239) |
| F127 | m/z = 679.8410 (C48H29N3S, 679.2082) | F128 | m/z = 667.8300 (C47H29N3S, 667.20082) |
| F129 | m/z = 693.8680 (C49H31N3S, 693.2239) | F130 | m/z = 743.9280 (C53H33N3S, 743.2395) |
| F131 | m/z = 758.9430 (C53H34N4S, 758.9430) | F132 | m/z = 653.8030 (C46H27N3S, 653.1926) |
| F133 | m/z = 629.7810 (C44H27N3S, 629.1926) | F134 | m/z = 784.9810 (C55H36N4S, 784.2661) |
| F135 | m/z = 756.9270 (C53H32N4S, 756.2348) | F136 | m/z = 756.9270 (C53H32N4S, 756.2348) |
| F137 | m/z = 666.8420 (C48H30N2S, 666.2130) | F138 | m/z = 693.8680 (C49H31N3S, 693.2239) |
| F139 | m/z = 693.8680 (C49H31N3S, 693.2239) | F140 | m/z = 743.9280 (C53H33N3S, 743.2395) |
| F141 | m/z = 758.9430 (C53H34N4S, 758.9430) | F142 | m/z = 782.9650 (C55H34N4S, 782.2504) |
| F143 | m/z = 653.8030 (C46H27N3S, 653.1926) | F144 | m/z = 709.8850 (C48H27N3S, 709.1646) |
| F145 | m/z = 613.7200 (C44H27N3O, 613.2154) | F146 | m/z = 637.7420 (C46H27N3O, 637.2154) |
| F147 | m/z = 663.7800 (C48H29N3O, 663.2311) | F148 | m/z = 643.7640 (C44H25N3OS, 643.1718) |
| F149 | m/z = 693.8240 (C48H27N3OS, 693.1875) | F150 | m/z = 771.9380 (C54H33N3OS, 771.2344) |
| F151 | m/z = 664.7680 (C47H28N4O, 664.2263) | F152 | m/z = 766.9040 (C55H34N4O, 766.2733) |
| F153 | m/z = 704.7890 (C49H28N4O2, 704.2212) | F154 | m/z = 754.8490 (C53H30N4O2, 754.2369) |
| F155 | m/z = 720.8500 (C49H28N4OS, 720.1984) | F156 | m/z = 720.8500 (C49H28N4OS, 720.1984) |
| F157 | m/z = 770.9100 (C53H30N4OS, 770.2140) | F158 | m/z = 730.8710 (C52H34N4O, 730.2733) |
| F159 | m/z = 690.8060 (C49H30N4O, 690.2420) | F160 | m/z = 690.8060 (C49H30N4O, 690.2420) |
| F161 | m/z = 740.8660 (C53H32N4O, 740.2576) | F162 | m/z = 740.8660 (C53H32N4O, 740.2576) |
| F163 | m/z = 779.9030 (C55H33N5O, 779.2685) | F164 | m/z = 779.9030 (C55H33N5O, 779.2685) |
| F165 | m/z = 779.9030 (C55H33N5O, 779.2685) | F166 | m/z = 779.9030 (C55H33N5O, 779.2685) |
| F167 | m/z = 704.7890 (C49H28N4O2, 704.2212) | F168 | m/z = 704.7890 (C49H28N4O2, 704.2212) |
| F169 | m/z = 720.8500 (C49H28N4OS, 720.1984) | F170 | m/z = 720.8500 (C49H28N4OS, 720.1984) |
| F171 | m/z = 779.9030 (C55H33N5O, 779.2685) | F172 | m/z = 770.9100 (C53H30N4OS, 770.2140) |
| F173 | m/z = 692.8220 (C49H32N4O, 692.2576) | F174 | m/z = 768.9200 (C55H36N4O, 768.2889) |
| F175 | m/z = 742.8820 (C53H34N4O, 742.2733) | F176 | m/z = 716.8440 (C51H32N4O, 716.2576) |
| F177 | m/z = 692.8220 (C49H32N4O, 692.2576) | F178 | m/z = 690.8060 (C49H30N4O, 690.2420) |
| F179 | m/z = 663.7800 (C48H29N3O, 663.2311) | F180 | m/z = 719.8620 (C50H29N3OS, 719.2031) |
| F181 | m/z = 613.7200 (C44H27N3O, 613.2154) | F182 | m/z = 587.6820 (C42H25N3O, 587.1998) |

TABLE 11-continued

| Compound | FD-Mass | Compound | FD-Mass |
|---|---|---|---|
| F183 | m/z = 663.7800 (C48H29N3O, 663.2311) | F184 | m/z = 643.7640 (C44H25N3OS, 643.1718) |
| F185 | m/z = 719.8620 (C50H29N3OS, 719.2031) | F186 | m/z = 703.8010 (C50H29N3O2, 703.2260) |
| F187 | m/z = 614.7080 (C43H26N4O, 614.2107) | F188 | m/z = 704.7890 (C49H28N4O2, 704.2212) |
| F189 | m/z = 704.7890 (C49H28N4O2, 704.2212) | F190 | m/z = 754.8490 (C53H30N4O2, 754.2369) |
| F191 | m/z = 720.8500 (C49H28N4OS, 720.1984) | F192 | m/z = 720.8500 (C49H28N4OS, 720.1984) |
| F193 | m/z = 770.9100 (C53H30N4OS, 770.2140) | F194 | m/z = 714.8280 (C51H30N4O, 714.2420) |
| F195 | m/z = 690.8060 (C49H30N4O, 690.2420) | F196 | m/z = 690.8060 (C49H30N4O, 690.2420) |
| F197 | m/z = 690.8060 (C49H30N4O, 690.2420) | F198 | m/z = 740.8660 (C53H32N4O, 740.2576) |
| F199 | m/z = 779.9030 (C55H33N5O, 779.2685) | F200 | m/z = 779.9030 (C55H33N5O, 779.2685) |
| F201 | m/z = 779.9030 (C55H33N5O, 779.2685) | F202 | m/z = 740.8660 (C53H32N4O, 740.2576) |
| F203 | m/z = 740.8660 (C53H32N4O, 740.2576) | F204 | m/z = 664.7680 (C47H28N4O, 664.2263) |
| F205 | m/z = 720.8500 (C49H28N4OS, 720.1984) | F206 | m/z = 779.9030 (C55H33N5O, 779.2685) |
| F207 | m/z = 779.9030 (C55H33N5O, 779.2685) | F208 | m/z = 720.8500 (C49H28N4OS, 720.1984) |
| F209 | m/z = 720.8500 (C49H28N4OS, 720.1984) | F210 | m/z = 768.9200 (C55H36N4O, 768.2889) |
| F211 | m/z = 666.7840 (C47H30N4O, 666.2420) | F212 | m/z = 742.8820 (C53H34N4O, 742.2733) |
| F213 | m/z = 845.0180 (C61H40N4O, 844.3202) | F214 | m/z = 690.8060 (C49H30N4O, 690.2420) |
| F215 | m/z = 663.7800 (C48H29N3O, 663.2311) | F216 | m/z = 795.9600 (C56H33N3OS, 795.2344) |
| F217 | m/z = 679.8410 (C48H29N3S, 679.2082) | F218 | m/z = 755.9390 (C54H33N3S, 755.2395) |
| F219 | m/z = 679.8410 (C48H29N3S, 679.2082) | F220 | m/z = 709.8850 (C48H27N3S, 709.1646) |
| F221 | m/z = 711.9010 (C48H29N3S2, 711.1803) | F222 | m/z = 759.9450 (C52H29N3S2, 759.1803) |
| F223 | m/z = 735.9230 (C50H29N3S2, 735.1803) | F224 | m/z = 680.8290 (C47H28N4S, 680.2035) |
| F225 | m/z = 680.8290 (C47H28N4S, 680.2035) | F226 | m/z = 730.8890 (C51H30N4S, 730.2191) |
| F227 | m/z = 833.0250 (C59H36N4S, 832.2661) | F228 | m/z = 730.8890 (C51H30N4S, 730.2191) |
| F229 | m/z = 736.9110 (C49H28N4S2, 736.1755) | F230 | m/z = 795.9640 (C55H33N5S, 795.2457) |
| F231 | m/z = 795.9640 (C55H33N5S, 795.2457) | F232 | m/z = 795.9640 (C55H33N5S, 795.2457) |
| F233 | m/z = 720.8500 (C49H28N4OS, 720.1984) | F234 | m/z = 736.9110 (C49H28N4S2, 736.1755) |
| F235 | m/z = 682.8450 (C47H30N4S, 682.2191) | F236 | m/z = 784.9810 (C55H36N4S, 784.2661) |
| F237 | m/z = 708.8830 (C49H32N4S, 708.2348) | F238 | m/z = 706.8670 (C49H30N4S, 706.2191) |
| F239 | m/z = 679.8410 (C48H29N3S, 679.2082) | F240 | m/z = 735.9230 (C50H29N3S2, 735.1803) |
| F241 | m/z = 705.8790 (C50H31N3S, 705.2239) | F242 | m/z = 756.9270 (C53H32N4S, 756.2348) |
| F243 | m/z = 680.8290 (C47H28N4S, 680.2035) | F244 | m/z = 782.9650 (C55H34N4S, 782.2504) |
| F245 | m/z = 736.9110 (C49H28N4S2, 736.1755) | F246 | m/z = 631.7570 (C42H25N5S, 631.1831) |
| F247 | m/z = 735.9230 (C50H29N3S2, 735.1803) | F248 | m/z = 736.9110 (C49H28N4S2, 736.1755) |
| F249 | m/z = 795.9640 (C55H33N5S, 795.2457) | F250 | m/z = 680.8290 (C47H28N4S, 680.2035) |
| F251 | m/z = 736.9110 (C49H28N4S2, 736.1755) | F252 | m/z = 756.9270 (C53H32N4S, 756.2348) |
| F253 | m/z = 690.8060 (C49H30N4O, 690.2420) | F254 | m/z = 664.7680 (C47H28N4O, 664.2263) |
| F255 | m/z = 740.8660 (C53H32N4O, 740.2576) | F256 | m/z = 768.9200 (C55H36N4O, 768.2889) |
| F257 | m/z = 677.8070 (C49H31N3O, 677.2467) | F258 | m/z = 753.9050 (C55H35N3O, 753.27780) |
| F259 | m/z = 742.8820 (C53H34N4O, 742.2733) | F260 | m/z = 768.9200 (C55H36N4O, 768.2889) |

TABLE 11-continued

| Compound | FD-Mass | Compound | FD-Mass |
|---|---|---|---|
| F261 | m/z = 792.9420 (C57H36N4O, 792.9420) | F262 | m/z = 715.8560 (C52H33N3O, 715.2624) |
| F263 | m/z = 741.8940 (C54H35N3O, 741.2780) | F264 | m/z = 753.9050 (C55H35N3O, 753.2780) |
| F265 | m/z = 843.0020 (C61H38N4O, 842.3046) | F266 | m/z = 740.8660 (C53H32N4O, 740.2576) |
| F267 | m/z = 714.8280 (C51H30N4O, 714.2420) | F268 | m/z = 690.8060 (C49H30N4O, 690.2420) |
| F269 | m/z = 664.7680 (C47H28N4O, 664.2263) | F270 | m/z = 740.8660 (C53H32N4O, 740.2576) |
| F271 | m/z = 706.8670 (C49H30N4S, 706.2191) | F272 | m/z = 680.8290 (C47H28N4S, 680.2035) |
| F273 | m/z = 756.9270 (C53H32N4S, 756.2348) | F274 | m/z = 784.9810 (C55H36N4S, 784.2661) |
| F275 | m/z = 693.8680 (C49H31N3S, 693.2239) | F276 | m/z = 769.9660 (C55H35N3S, 769.2552) |
| F277 | m/z = 758.9430 (C53H34N4S, 758.2504) | F278 | m/z = 784.9810 (C55H36N4S, 784.2661) |
| F279 | m/z = 809.0030 (C57H36N4S, 808.2661) | F280 | m/z = 731.9170 (C52H33N3S, 731.2395) |
| F281 | m/z = 757.9550 (C54H35N3S, 757.2552) | F282 | m/z = 769.9660 (C55H35N3S, 769.2552) |
| F283 | m/z = 825.0460 (C58H40N4S, 825.0460) | F284 | m/z = 756.9270 (C53H32N4S, 756.2348) |
| F285 | m/z = 730.8890 (C51H30N4S, 730.2191) | F286 | m/z = 706.8670 (C49H30N4S, 706.2191) |
| F287 | m/z = 680.8290 (C47H28N4S, 680.2035) | F288 | m/z = 756.9270 (C53H32N4S, 756.2348) |
| F289 | m/z = 663.7800 (C48H29N3O, 663.2311) | F290 | m/z = 739.8780 (C54H33N3O, 739.2624) |
| F291 | m/z = 713.8400 (C52H31N3O, 713.2467) | F292 | m/z = 643.7640 (C44H25N3OS, 643.1718) |
| F293 | m/z = 693.8240 (C48H27N3OS, 693.1875) | F294 | m/z = 846.0240 (C59H35N5S, 845.2613) |
| F295 | m/z = 816.9640, C59H36N4O, 816.2889) | F296 | m/z = 766.9040 (C55H34N4O, 766.2733) |
| F297 | m/z = 720.8500 (C49H28N4OS, 720.1984) | F298 | m/z = 754.8490 (C53H30N4O2, 754.2369) |
| F299 | m/z = 753.8650 (C53H31N5O, 7532529) | F300 | m/z = 720.8500 (C49H28N4OS, 720.1984) |
| F301 | m/z = 770.9100 (C53H30N4OS, 770.2140) | F302 | m/z = 730.8710 (C52H34N4O, 730.2733) |
| F303 | m/z = 690.8060 (C49H30N4O, 690.2420) | F304 | m/z = 690.8060 (C49H30N4O, 690.2420) |
| F305 | m/z = 766.9040 (C55H34N4O, 766.2733) | F306 | m/z = 740.8660 (C53H32N4O, 740.2576) |
| F307 | m/z = 779.9030 (C55H33N5O, 779.2685) | F308 | m/z = 779.9030 (C55H33N5O, 779.2685) |
| F309 | m/z = 704.7890 (C49H28N4O2, 704.2212) | F310 | m/z = 704.7890 (C49H28N4O2, 704.2212) |
| F311 | m/z = 720.8500 (C49H28N4OS, 720.1984) | F312 | m/z = 770.9100 (C53H30N4OS, 770.2140) |
| F313 | m/z = 779.9030 (C55H33N5O, 779.2685) | F314 | m/z = 720.8500 (C49H28N4OS, 720.1984) |
| F315 | m/z = 720.8500 (C49H28N4OS, 720.1984) | F316 | m/z = 768.9200 (C55H36N4O, 768.2889) |
| F317 | m/z = 742.8820 (C53H34N4O, 742.2733) | F318 | m/z = 716.8440 (C51H32N4O, 716.2576) |
| F319 | m/z = 692.8220 (C49H32N4O, 692.2576) | F320 | m/z = 690.8060 (C49H30N4O, 690.2420) |
| F321 | m/z = 663.7800 (C48H29N3O, 663.2311) | F322 | m/z = 795.9600 (C56H33N3OS, 795.2344) |
| F323 | m/z = 613.7200 (C44H27N3O, 613.2154) | F324 | m/z = 587.6820 (C42H25N3O, 587.1998) |
| F325 | m/z = 663.7800 (C48H29N3O, 663.2311) | F326 | m/z = 693.8240 (C48H27N3OS, 693.1875) |
| F327 | m/z = 719.8620 (C50H29N3OS, 719.2031) | F328 | m/z = 703.8010 (C50H29N3O2, 703.2260) |
| F329 | m/z = 714.8280 (C51H30N4O, 714.2420) | F330 | m/z = 703.8050 (C49H29N5O, 703.2372) |
| F331 | m/z = 753.8650 (C53H31N5O, 7532529) | F332 | m/z = 714.8280 (C51H30N4O, 714.2420) |
| F333 | m/z = 720.8500 (C49H28N4OS, 720.1984) | F334 | m/z = 664.7680 (C47H28N4O, 664.2263) |
| F335 | m/z = 770.9100 (C53H30N4OS, 770.2140) | F336 | m/z = 730.8710 (C52H34N4O, 730.2733) |
| F337 | m/z = 690.8060 (C49H30N4O, 690.2420) | F338 | m/z = 740.8660 (C53H32N4O, 740.2576) |

TABLE 11-continued

| Compound | FD-Mass | Compound | FD-Mass |
|---|---|---|---|
| F339 | m/z = 690.8060 (C49H30N4O, 690.2420) | F340 | m/z = 740.8660 (C53H32N4O, 740.2576) |
| F341 | m/z = 779.9030 (C55H33N5O, 779.2685) | F342 | m/z = 779.9030 (C55H33N5O, 779.2685) |
| F343 | m/z = 779.9030 (C55H33N5O, 779.2685) | F344 | m/z = 704.7890 (C49H28N4O2, 704.2212) |
| F345 | m/z = 720.8500 (C49H28N4OS, 720.1984) | F346 | m/z = 720.8500 (C49H28N4OS, 720.1984) |
| F347 | m/z = 666.7840 (C47H30N4O, 666.2420) | F348 | m/z = 768.9200 (C55H36N4O, 768.2889) |
| F349 | m/z = 716.8440 (C51H32N4O, 716.2576) | F350 | m/z = 692.8220 (C49H32N4O, 692.2576) |
| F351 | m/z = 690.8060 (C49H30N4O, 690.2420) | F352 | m/z = 663.7800 (C48H29N3O, 663.2311) |
| F353 | m/z = 795.9600 (C56H33N3OS, 795.2344) | F354 | m/z = 601.7090 (C43H27N3O, 601.2154) |
| F355 | m/z = 651.7690 (C47H29N3O, 651.2311) | F356 | m/z = 690.8060 (C49H30N4O, 690.2420) |
| F357 | m/z = 690.8060 (C49H30N4O, 690.2420) | F358 | m/z = 740.8660 (C53H32N4O, 740.2576) |
| F359 | m/z = 676.8190 (C50H32N2O, 676.2515) | F360 | m/z = 741.8940 (C54H35N3O, 741.2780) |
| F361 | m/z = 715.8560 (C52H33N3O, 715.2624) | F362 | m/z = 666.7840 (C47H30N4O, 666.2420) |
| F363 | m/z = 768.9200 (55H36N4O, 768.2889) | F364 | m/z = 766.9040 (C55H34N4O, 766.2733) |
| F365 | m/z = 676.8190 (C50H32N2O, 67 6.2515) | F366 | m/z = 741.8940 (C54H35N3O, 741.2780) |
| F367 | m/z = 715.8560 (C52H33N3O, 715.2624) | F368 | m/z = 666.7840 (C47H30N4O, 666.2420) |
| F369 | m/z = 768.9200 (C55H36N4O, 768.2889) | F370 | m/z = 664.7680 (C47H28N4O, 664.2263) |
| F371 | m/z = 629.7810 (C44H27N3S, 629.1926) | F372 | m/z = 603.7430 (C42H25N3S, 603.1769) |
| F373 | m/z = 679.8410 (C48H29N3S, 679.2082) | F374 | m/z = 659.8250 (C44H25N3S2, 659.1490) |
| F375 | m/z = 735.9230 (C50H29N3S2, 735.1803) | F376 | m/z = 719.8620 (C50H29N3OS, 719.2031) |
| F377 | m/z = 795.9640 (C55H33N5S, 795.2457) | F378 | m/z = 7 95.9640 (C55H33N5S, 795.2457) |
| F379 | m/z = 795.9640 (C55H33N5S, 795.2457) | F380 | m/z = 7 95.9640 (C55H33N5S, 795.2457) |
| F381 | m/z = 720.8500 (C49H28N4OS, 720.1984) | F382 | m/z = 720.8500 (C49H28N4OS, 720.1984) |
| F383 | m/z = 736.9110 (C49H28N4S2, 736.1755) | F384 | m/z = 846.0240 (C59H35N5S, 845.2613) |
| F385 | m/z = 795.9640 (C55H33N5S, 795.2457) | F386 | m/z = 736.9110 (C49H28N4S2, 736.1755) |
| F387 | m/z = 736.9110 (C49H28N4S2, 736.1755) | F388 | m/z = 632.7850 (C43H28N4S, 632.2035) |
| F389 | m/z = 682.8450 (C47H30N4S, 682.2191) | F390 | m/z = 732.9050 (C51H32N4S, 732.2348) |
| F391 | m/z = 708.8830 (C49H32N4S, 708.2348) | F392 | m/z = 706.8670 (C49H30N4S, 706.2191) |
| F393 | m/z = 679.8410 (C48H29N3S, 679.2082) | F394 | m/z = 812.0210 (C56H33N3S2, 811.2116) |
| F395 | m/z = 688.8340 (C50H32N4, 688.2627) | F396 | m/z = 662.7960 (C48H30N4, 662.2470) |
| F397 | m/z = 712.8560 (C52H32N4, 712.2627) | F398 | m/z = 718.8780 (C50H30N4S, 718.2191) |
| F399 | m/z = 768.9380 (C54H32N4S, 768.2348) | F400 | m/z = 768.9380 (C54H32N4S, 768.2348) |
| F401 | m/z = 689.8220 (C49H31N5, 689.2579) | F402 | m/z = 739.8820 (C53H33N5, 739.2736) |
| F403 | m/z = 739.8820 (C53H33N5, 739.2736) | F404 | m/z = 789.9420 (C57H35N5, 789.2892) |
| F405 | m/z = 689.8220 (C49H31N5, 689.2579) | F406 | m/z = 789.9420 (C57H35N5, 789.2892) |
| F407 | m/z = 767.9360 (C55H37N5, 767.3049) | F408 | m/z = 817.9960 (C59H39N5, 817.3205) |
| F409 | m/z = 817.9960 (C59H39N5, 817.3205) | F410 | m/z = 741.8980 (C53H35N5, 741.2892) |
| F411 | m/z = 791.9580 (C57H37N5, 791.3049) | F412 | m/z = 691.8380 (C49H33N5, 691.2736) |
| F413 | m/z = 740.9100 (C54H36N4, 740.2940) | F414 | m/z = 740.9100 (C54H36N4, 740.2940) |
| F415 | m/z = 703.8490 (C50H33N5, 703.2736) | F416 | m/z = 740.9100 (C54H36N4, 740.2940) |

TABLE 11-continued

| Compound | FD-Mass | Compound | FD-Mass |
|---|---|---|---|
| F417 | m/z = 676.8230 (C49H32N4, 676.2627) | F418 | m/z = 767.9360 (C55H37N5, 767.3049) |
| F419 | m/z = 676.8230 (C49H32N4, 676.2627) | F420 | m/z = 767.9360 (C55H37N5, 767.3049) |
| F421 | m/z = 651.23 (C47H29N3O, 651.75) | F422 | m/z = 651.23 (C47H29N3O, 651.75) |
| F423 | m/z = 651.23 (C47H29N3O, 651.75) | F424 | m/z = 651.23 (C47H29N3O, 651.75) |
| F425 | m/z = 691.23 (C49H29N3O2, 691.77) | F426 | m/z = 727.26 (C53H33N3O, 727.85) |
| F427 | m/z = 625.22 (C45H27N3O, 625.72) | F428 | m/z = 651.23 (C47H29N3O, 651.75) |
| F429 | m/z = 691.26 (C50H33N3O, 691.82) | F430 | m/z = 717.28 (C52H35N3O, 717.85) |
| F431 | m/z = 767.29 (C56H37N3O, 767.91) | F432 | m/z = 765.28 (C56H35N3O, 765.90) |
| F433 | m/z = 651.23 (C47H29N3O, 651.75) | F434 | m/z = 727.26 (C53H33N3O, 727.85) |
| F435 | m/z = 767.29 (C56H37N3O, 767.91) | F436 | m/z = 765.28 (C56H35N3O, 765.90) |
| F437 | m/z = 630.18 (C44H26N2OS, 630.76) | F438 | m/z = 630.18 (C44H26N2OS, 630.76) |
| F439 | m/z = 651.23 (C47H29N3O, 651.75) | F440 | m/z = 651.23 (C47H29N3O, 651.75) |
| F441 | m/z = 651.23 (C47H29N3O, 651.75) | F442 | m/z = 651.23 (C47H29N3O, 651.75) |
| F443 | m/z = 651.23 (C47H29N3O, 651.75) | F444 | m/z = 717.28 (C52H35N3O, 717.85) |
| F445 | m/z = 651.23 (C47H29N3O, 651.75) | F446 | m/z = 677.25 (C49H31N3O, 677.79) |
| F447 | m/z = 727.26 (C53H33N3O, 727.85) | F448 | m/z = 631.17 (C43H25N3OS, 631.74) |
| F449 | m/z = 727.26 (C53H33N3O, 727.85) | F450 | m/z = 651.23 (C47H29N3O, 651.75) |
| F451 | m/z = 701.25 (C51H31N3O, 701.81) | F452 | m/z = 817.27 (C59H35N3O2, 817.93) |
| F453 | m/z = 651.23 (C47H29N3O, 651.75) | F454 | m/z = 777.28 (C57H35N3O, 777.91) |
| F455 | m/z = 803.29 (C59H37N3O, 803.94) | F456 | m/z = 803.29 (C59H37N3O, 803.94) |
| F457 | m/z = 803.29 (C59H37N3O, 803.94) | F458 | m/z = 651.23 (C47H29N3O, 651.75) |
| F459 | m/z = 777.28 (C57H35N3O, 777.91) | F460 | m/z = 777.28 (C57H35N3O, 777.91) |
| F461 | m/z = 777.28 (C57H35N3O, 777.91) | F462 | m/z = 817.31 (C60H39N3O, 817.97) |
| F463 | m/z = 843.32 (C62H41N3O, 844.01) | F464 | m/z = 765.28 (C56H35N3O, 765.90) |
| F465 | m/z = 777.28 (C57H35N3O, 777.91) | F466 | m/z = 777.28 (C57H35N3O, 777.91) |
| F467 | m/z = 680.19 (C48H28N2OS, 680.81) | F468 | m/z = 756.22 (C54H32N2OS, 756.91) |
| F469 | m/z = 727.26 (C53H33N3O, 727.85) | F470 | m/z = 727.26 (C53H33N3O, 727.85) |
| F471 | m/z = 741.24 (C53H31N3O2, 741.83) | F472 | m/z = 727.26 (C53H33N3O, 727.85) |
| F473 | m/z = 777.28 (C57H35N3O, 777.91) | F474 | m/z = 651.23 (C47H29N3O, 651.75) |
| F475 | m/z = 777.28 (C57H35N3O, 777.91) | F476 | m/z = 767.29 (C56H37N3O, 767.91) |
| F477 | m/z = 767.29 (C56H37N3O, 767.91) | F478 | m/z = 727.26 (C53H33N3O, 727.85) |
| F479 | m/z = 889.31 (C66H39N3O, 890.04) | F480 | m/z = 891.32 (C66H41N3O, 892.05) |
| F481 | m/z = 727.26 (C53H33N3O, 727.85) | F482 | m/z = 767.29 (C56H37N3O, 767.91) |
| F483 | m/z = 680.19 (C48H28N2OS, 680.81) | F484 | m/z = 680.19 (C48H28N2OS, 680.81) |
| F485 | m/z = 665.21 (C47H27N3O2, 665.74) | F486 | m/z = 651.23 (C47H29N3O, 651.75) |
| F487 | m/z = 651.23 (C47H29N3O, 651.75) | F488 | m/z = 727.26 (C53H33N3O, 727.85) |
| F489 | m/z = 651.23 (C47H29N3O, 651.75) | F490 | m/z = 701.25 (C51H31N3O, 701.81) |
| F491 | m/z = 651.23 (C47H29N3O, 651.75) | F492 | m/z = 701.25 (C51H31N3O, 701.81) |
| F493 | m/z = 625.22 (C45H27N3O, 625.72) | F494 | m/z = 651.23 (C47H29N3O, 651.75) |

TABLE 11-continued

| Compound | FD-Mass | Compound | FD-Mass |
|---|---|---|---|
| F495 | m/z = 691.26 (C50H33N3O, 691.82) | F496 | m/z = 815.29 (C60H37N3O, 815.96) |
| F497 | m/z = 727.26 (C53H33N3O, 727.85) | F498 | m/z = 741.24 (C53H31N3O2, 741.83) |
| F499 | m/z = 727.26 (C53H33N3O, 727.85) | F500 | m/z = 843.32 (C62H41N3O, 844.01) |
| F501 | m/z = 741.24 (C53H31N3O2, 741.83) | F502 | m/z = 727.26 (C53H33N3O, 727.85) |
| F503 | m/z = 651.23 (C47H29N3O, 651.75) | F504 | m/z = 727.26 (C53H33N3O, 727.85) |
| F505 | m/z = 777.28 (C57H35N3O, 777.91) | F506 | m/z = 817.31 (C60H39N3O, 817.97) |
| F507 | m/z = 843.32 (C62H41N3O, 844.01) | F508 | m/z = 765.28 (C56H35N3O, 765.90) |
| F509 | m/z = 717.28 (C52H35N3O, 717.85) | F510 | m/z = 777.28 (C57H35N3O, 777.91) |
| F511 | m/z = 727.26 (C53H33N3O, 727.85) | F512 | m/z = 767.29 (C56H37N3O, 767.91) |
| F513 | m/z = 651.23 (C47H29N3O, 651.75) | F514 | m/z = 691.26 (C50H33N3O, 691.82) |
| F515 | m/z = 717.28 (C52H35N3O, 717.85) | F516 | m/z = 727.26 (C53H33N3O, 727.85) |
| F517 | m/z = 843.32 (C62H41N3O, 844.01) | F518 | m/z = 753.28 (C55H35N3O, 753.89) |
| F519 | m/z = 727.26 (C53H33N3O, 727.85) | F520 | m/z = 807.29 (C58H37N3O2, 807.93) |
| F521 | m/z = 717.28 (C52H35N3O, 717.85) | F522 | m/z = 717.28 (C52H35N3O, 717.85) |
| F523 | m/z = 807.29 (C58H37N3O2, 807.93) | F524 | m/z = 767.29 (C56H37N3O, 767.91) |
| F525 | m/z = 767.29 (C56H37N3O, 767.91) | F526 | m/z = 843.32 (C62H41N3O, 844.01) |
| F527 | m/z = 741.28 (C54H35N3O, 741.88) | F528 | m/z = 767.29 (C56H37N3O, 767.91) |
| F529 | m/z = 727.26 (C53H33N3O, 727.85) | F530 | m/z = 691.26 (C50H33N3O, 691.82) |
| F531 | m/z = 601.22 (C43H27N3O, 601.69) | F532 | m/z = 670.21 (C47H30N2OS, 670.82) |
| F533 | m/z = 753.28 (C55H35N3O, 753.89) | F534 | m/z = 753.28 (C55H35N3O, 753.89) |
| F535 | m/z = 691.23 (C49H29N3O2, 691.77) | F536 | m/z = 803.29 (C59H37N3O, 803.94) |
| F537 | m/z = 803.29 (C59H37N3O, 803.94) | F538 | m/z = 803.29 (C59H37N3O, 803.94) |
| F539 | m/z = 677.25 (C49H31N3O, 677.79) | F540 | m/z = 727.26 (C53H33N3O, 727.85) |
| F541 | m/z = 869.34 (C64H43N3O, 870.05) | F542 | m/z = 869.34 (C64H43N3O, 870.05) |
| F543 | m/z = 706.21 (C50H30N2OS, 706.85) | F544 | m/z = 822.27 (C59H38N2OS, 823.01) |
| F545 | m/z = 741.24 (C53H31N3O2, 741.83) | F546 | m/z = 691.23 (C49H29N3O2, 691.77) |
| F547 | m/z = 781.24 (C55H31N3O3, 781.85) | F548 | m/z = 691.23 (C49H29N3O2, 691.77) |
| F549 | m/z = 707.20 (C49H29N3OS, 707.84) | F550 | m/z = 707.20 (C49H29N3OS, 707.84) |
| F551 | m/z = 757.22 (C53H31N3OS, 757.90) | F552 | m/z = 736.16 (C50H28N2OS2, 736.90) |
| F553 | m/z = 667.21 (C47H29N3S, 667.82) | F554 | m/z = 617.19 (C43H27N3S, 617.76) |
| F555 | m/z = 667.21 (C47H29N3S, 667.82) | F556 | m/z = 667.21 (C47H29N3S, 667.82) |
| F557 | m/z = 707.20 (C49H29N3OS, 707.84) | F558 | m/z = 743.24 (C53H33N3S, 743.91) |
| F559 | m/z = 641.19 (C45H27N3S, 641.78) | F560 | m/z = 667.21 (C47H29N3S, 667.82) |
| F561 | m/z = 667.21 (C47H29N3S, 667.82) | F562 | m/z = 743.24 (C53H33N3S, 743.91) |
| F563 | m/z = 743.24 (C53H33N3S, 743.91) | F564 | m/z = 667.21 (C47H29N3S, 667.82) |
| F565 | m/z = 646.15 (C44H26N2S2, 646.82) | F566 | m/z = 646.15 (C44H26N2S2, 646.82) |
| F567 | m/z = 667.21 (C47H29N3S, 667.82) | F568 | m/z = 667.21 (C47H29N3S, 667.82) |
| F569 | m/z = 667.21 (C47H29N3S, 667.82) | F570 | m/z = 693.22 (C49H31N3S, 693.86) |
| F571 | m/z = 743.24 (C53H33N3S, 743.91) | F572 | m/z = 647.15 (C43H25N3S2, 647.81) |

TABLE 11-continued

| Compound | FD-Mass | Compound | FD-Mass |
|---|---|---|---|
| F573 | m/z = 743.24 (C53H33N3S, 743.91) | F574 | m/z = 793.26 (C57H35N3S, 793.97) |
| F575 | m/z = 819.27 (C59H37N3S, 820.01) | F576 | m/z = 819.27 (C59H37N3S, 820.01) |
| F577 | m/z = 819.27 (C59H37N3S, 820.01) | F578 | m/z = 743.24 (C53H33N3S, 743.91) |
| F579 | m/z = 793.26 (C57H35N3S, 793.97) | F580 | m/z = 793.26 (C57H35N3S, 793.97) |
| F581 | m/z = 793.26 (C57H35N3S, 793.97) | F582 | m/z = 833.29 (C60H39N3S, 834.04) |
| F583 | m/z = 859.30 (C62H41N3S, 860.07) | F584 | m/z = 907.30 (C66H41N3S, 908.12) |
| F585 | m/z = 793.26 (C57H35N3S, 793.97) | F586 | m/z = 793.26 (C57H35N3S, 793.97) |
| F587 | m/z = 696.17 (C48H28N2S2, 696.88) | F588 | m/z = 772.20 (C54H32N2S2, 772.98) |
| F589 | m/z = 743.24 (C53H33N3S, 743.91) | F590 | m/z = 743.24 (C53H33N3S, 743.91) |
| F591 | m/z = 757.22 (C53H31N3OS, 757.90) | F592 | m/z = 743.24 (C53H33N3S, 743.91) |
| F593 | m/z = 793.26 (C57H35N3S, 793.97) | F594 | m/z = 667.21 (C47H29N3S, 667.82) |
| F595 | m/z = 793.26 (C57H35N3S, 793.97) | F596 | m/z = 783.27 (C56H37N3S, 783.98) |
| F597 | m/z = 783.27 (C56H37N3S, 783.98) | F598 | m/z = 743.24 (C53H33N3S, 743.91) |
| F599 | m/z = 783.27 (C56H37N3S, 783.98) | F600 | m/z = 907.30 (C66H41N3S, 908.12) |
| F601 | m/z = 681.19 (C47H27N3OS, 681.80) | F602 | m/z = 667.21 (C47H29N3S, 667.82) |
| F603 | m/z = 667.21 (C47H29N3S, 667.82) | F604 | m/z = 743.24 (C53H33N3S, 743.91) |
| F605 | m/z = 743.24 (C53H33N3S, 743.91) | F606 | m/z = 757.22 (C53H31N3OS, 757.90) |
| F607 | m/z = 743.24 (C53H33N3S, 743.91) | F608 | m/z = 859.30 (C62H41N3S, 860.07) |
| F609 | m/z = 757.22 (C53H31N3OS, 757.90) | F610 | m/z = 743.24 (C53H33N3S, 743.91) |
| F611 | m/z = 667.21 (C47H29N3S, 667.82) | F612 | m/z = 743.24 (C53H33N3S, 743.91) |
| F613 | m/z = 793.26 (C57H35N3S, 793.97) | F614 | m/z = 833.29 (C60H39N3S, 834.04) |
| F615 | m/z = 859.30 (C62H41N3S, 860.07) | F616 | m/z = 781.26 (C56H35N3S, 781.96) |
| F617 | m/z = 733.26 (C52H35N3S, 733.92) | F618 | m/z = 793.26 (C57H35N3S, 793.97) |
| F619 | m/z = 743.24 (C53H33N3S, 743.91) | F620 | m/z = 783.27 (C56H37N3S, 783.98) |
| F621 | m/z = 667.21 (C47H29N3S, 667.82) | F622 | m/z = 707.24 (C50H33N3S, 707.88) |
| F623 | m/z = 733.26 (C52H35N3S, 733.92) | F624 | m/z = 743.24 (C53H33N3S, 743.91) |
| F625 | m/z = 859.30 (C62H41N3S, 860.07) | F626 | m/z = 769.26 (C55H35N3S, 769.95) |
| F627 | m/z = 743.24 (C53H33N3S, 743.91) | F628 | m/z = 823.27 (C58H37N3OS, 824.00) |
| F629 | m/z = 651.23 (C47H29N3O, 651.75) | F630 | m/z = 677.25 (C49H31N3O, 677.79) |
| F631 | m/z = 615.19 (C43H25N3O2, 615.68) | F632 | m/z = 601.22 (C43H27N3O, 601.69) |
| F633 | m/z = 677.25 (C49H31N3O, 677.79) | F634 | m/z = 525.18 (C37H23N3O, 525.60) |
| F635 | m/z = 525.18 (C37H23N3O, 525.60) | F636 | m/z = 816.29 (C59H36N4O, 816.94) |
| F637 | m/z = 690.24 (C49H30N4O, 690.79) | F638 | m/z = 766.27 (C55H34N4O, 766.88) |
| F639 | m/z = 766.27 (C55H34N4O, 766.88) | F640 | m/z = 740.26 (C53H32N4O, 740.85) |
| F641 | m/z = 782.25 (C55H34N4S, 782.95) | F642 | m/z = 756.23 (C53H32N4S, 756.91) |
| F643 | m/z = 740.26 (C53H32N4O, 740.85) | F644 | m/z = 740.26 (C53H32N4O, 740.85) |
| F645 | m/z = 541.16 (C37H23N3S, 541.66) | F646 | m/z = 541.16 (C37H23N3S, 541.66) |
| F647 | m/z = 637.22 (C46H27N3O, 637.73) | F648 | m/z = 673.13 (C44H23N3OS2, 673.80) |

[Experimental Example]<Experimental Example 1>

1) Manufacture of Organic Light Emitting Device

A glass substrate on which indium tin oxide (ITO) was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treated for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), the following 2-TNATA (4,4',4"-tris[2-naphthyl(phenyl)amino]triphenylamine) as a hole injection layer and the following NPB (N,N'-di(1-naphthyl)-N,N'-diphenyl-(1,1'-biphenyl)-4,4'-diamine) as a hole transfer layer, which are common layers, were formed.

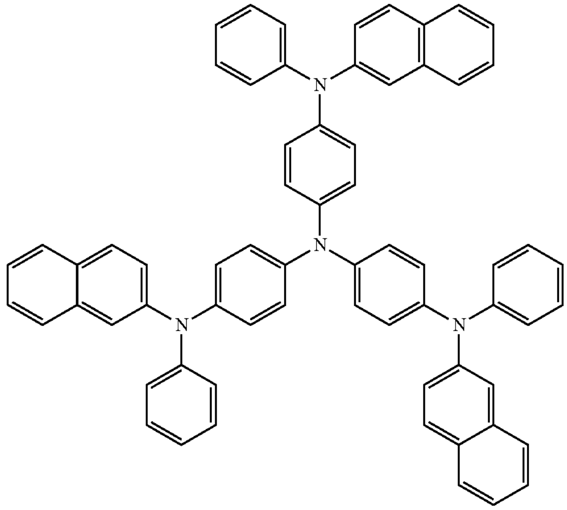

2-TNATA

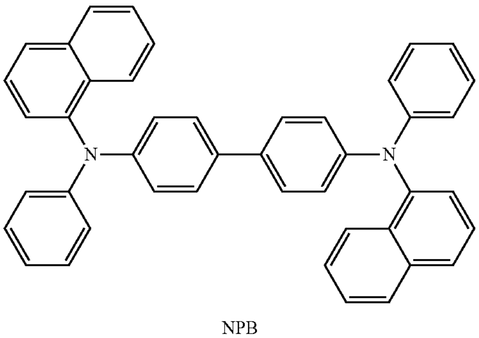

NPB

A light emitting layer was thermal vacuum deposited thereon as follows. As the light emitting layer, one or two types of the compound described in the following Table 12 were deposited in one source of supply as a red host, and using the following $(piq)_2(Ir)_{(acac)}$ as a red phosphorescent dopant, the $(piq)_2(Ir)_{(acac)}$ was 3% doped to the host to be deposited to 500 Å. After that, the following BCP was deposited to 60 Å as a hole blocking layer, $Alq_3$ was deposited to 200 Å thereon as an electron transfer layer. After that, BCP was deposited to 60 Å as a hole blocking layer, and $Alq_3$ was deposited to 200 Å thereon as an electron transfer layer. Lastly, lithium fluoride (LiF) was deposited to a thickness of 10 Å on the electron transfer layer to form an electron injection layer, and on the electron injection layer, an aluminum (A1) cathode was deposited to a thickness of 1,200 Å to form a cathode, and as a result, an organic electroluminescent device was manufactured.

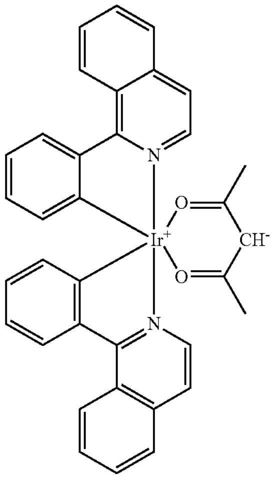

$(piq)_2(Ir)_{(acac)}$

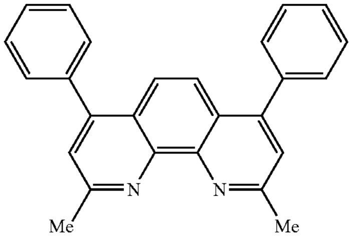

BCP

Meanwhile, all the organic compounds required to manufacture the OLED were vacuum sublimation purified under $10^{-6}$ torr to $10^{-8}$ torr for each material to be used in the organic light emitting device (OLED) manufacture.

2) Driving Voltage and Light Emission Efficiency of Organic Electroluminescent Device For the organic electroluminescent devices manufactured as above, electroluminescent (EL) properties were measured using M7000 manufactured by McScience Inc., and with the measurement results, $T_{90}$ was measured when standard luminance was 6,000 cd/m$^2$ using a lifetime measurement system (M6000) manufactured by McScience Inc. Properties of the organic electroluminescent device of the present disclosure are as shown in the following Table 12.

TABLE 12

| | Compound | Driving Voltage (V) | Efficiency (cd/A) | Color Coordinate (x, y) | Lifetime ($T_{90}$) |
|---|---|---|---|---|---|
| Comparative Example 1 | A | 5.36 | 16.8 | (0.681, 0.319) | 44 |
| Comparative Example 2 | B | 5.43 | 15.9 | (0.682, 0.316) | 29 |
| Comparative Example 3 | C | 5.29 | 20.1 | (0.683, 0.315) | 49 |
| Comparative Example 4 | D | 5.31 | 16.2 | (0.681, 0.318) | 52 |
| Comparative Example 5 | E | 5.21 | 18.7 | (0.680, 0.319) | 65 |
| Comparative Example 6 | F | 4.98 | 7.9 | (0.679, 0.321) | 8 |
| Comparative Example 7 | G | 5.44 | 4.8 | (0.679, 0.321) | 5 |
| Comparative Example 8 | H | 5.59 | 7.8 | (0.679, 0.321) | 5 |
| Comparative Example 9 | I | 5.59 | 8.2 | (0.679, 0.321) | 5 |
| Comparative Example 10 | J | 5.48 | 9.2 | (0.679, 0.321) | 22 |
| Comparative Example 11 | K | 5.22 | 19.7 | (0.679, 0.321) | 55 |
| Comparative Example 12 | L | 5.24 | 15.9 | (0.679, 0.321) | 87 |
| Comparative Example 13 | M | 5.59 | 7.8 | (0.679, 0.321) | 5 |
| Comparative Example 14 | N | 5.43 | 15.9 | (0.682, 0.316) | 29 |
| Comparative Example 15 | O | 5.36 | 16.8 | (0.681, 0.319) | 43 |
| Example 1 | F4 | 3.84 | 25.2 | (0.681, 0.318) | 109 |
| Example 2 | F11 | 3.87 | 22.2 | (0.680, 0.319) | 165 |
| Example 3 | F11:G (3:1) | 3.79 | 25.9 | (0.680, 0.319) | 159 |
| Example 4 | F11:H (3:1) | 4.14 | 37.8 | (0.680, 0.319) | 89 |
| Example 5 | F14 | 3.87 | 23.2 | (0.681, 0.318) | 137 |
| Example 6 | F20 | 3.79 | 22.8 | (0.682, 0.316) | 119 |
| Example 7 | F30 | 3.59 | 26.8 | (0.683, 0.315) | 79 |
| Example 8 | F34 | 4.06 | 22.0 | (0.681, 0.318) | 144 |
| Example 8 | F37 | 3.99 | 25.9 | (0.680, 0.319) | 138 |
| Example 9 | F41 | 3.88 | 27.8 | (0.680, 0.319) | 148 |
| Example 10 | F41:G (2:1) | 3.90 | 28.8 | (0.680, 0.319) | 146 |
| Example 11 | F41:G (3:1) | 3.89 | 26.5 | (0.680, 0.319) | 186 |
| Example 12 | F44 | 3.78 | 28.2 | (0.681, 0.318) | 202 |
| Example 13 | F44:G (1:1) | 4.11 | 36.2 | (0.681, 0.318) | 151 |
| Example 14 | F44:G (1:2) | 4.21 | 37.6 | (0.681, 0.318) | 121 |
| Example 15 | F44:G (2:1) | 3.92 | 33.8 | (0.681, 0.318) | 228 |
| Example 14 | F44:G (2.5:1) | 3.80 | 33.7 | (0.681, 0.318) | 244 |
| Example 15 | F44:H (2.5:1) | 4.02 | 36.9 | (0.681, 0.318) | 189 |
| Example 16 | F44:I (2.5:1) | 4.22 | 39.5 | (0.681, 0.318) | 170 |
| Example 17 | F45 | 3.80 | 27.9 | (0.682, 0.316) | 178 |
| Example 18 | F46 | 3.91 | 26.5 | (0.683, 0.315) | 221 |
| Example 19 | F53 | 4.21 | 23.8 | (0.681, 0.318) | 103 |
| Example 20 | F59 | 3.98 | 26.2 | (0.680, 0.319) | 121 |
| Example 21 | F66 | 4.49 | 24.2 | (0.680, 0.319) | 87 |
| Example 22 | F69 | 3.82 | 27.9 | (0.681, 0.318) | 140 |
| Example 23 | F69:F187 (1:3) | 3.86 | 31.8 | (0.679, 0.320) | 162 |
| Example 24 | F79 | 3.99 | 27.2 | (0.682, 0.316) | 99 |
| Example 25 | F80 | 4.04 | 26.4 | (0.681, 0.318) | 88 |
| Example 26 | F85 | 3.87 | 27.2 | (0.681, 0.318) | 69 |
| Example 27 | F95 | 3.65 | 24.9 | (0.682, 0.316) | 123 |
| Example 28 | F96 | 3.78 | 23.9 | (0.681, 0.318) | 148 |
| Example 29 | F98 | 4.41 | 20.9 | (0.682, 0.316) | 90 |
| Example 30 | F99 | 4.38 | 21.2 | (0.681, 0.318) | 109 |
| Example 31 | F104 | 3.89 | 26.8 | (0.681, 0.318) | 122 |
| Example 32 | F104:G (2:1) | 4.11 | 33.4 | (0.681, 0.318) | 105 |
| Example 33 | F113 | 3.78 | 22.9 | (0.682, 0.316) | 121 |
| Example 34 | F114 | 3.78 | 23.1 | (0.681, 0.318) | 78 |
| Example 35 | F132 | 3.79 | 24.9 | (0.681, 0.318) | 139 |
| Example 36 | F135 | 4.01 | 30.1 | (0.682, 0.316) | 92 |
| Example 37 | F136 | 3.98 | 29.6 | (0.681, 0.318) | 98 |
| Example 38 | F139 | 3.99 | 25.8 | (0.681, 0.318) | 121 |
| Example 39 | F145 | 4.43 | 19.9 | (0.681, 0.318) | 138 |
| Example 40 | F146 | 4.17 | 20.9 | (0.682, 0.316) | 136 |
| Example 41 | F148 | 3.98 | 23.6 | (0.681, 0.318) | 129 |
| Example 42 | F149 | 3.78 | 24.5 | (0.682, 0.316) | 134 |
| Example 43 | F157 | 3.77 | 23.8 | (0.681, 0.318) | 109 |

TABLE 12-continued

| | Compound | Driving Voltage (V) | Efficiency (cd/A) | Color Coordinate (x, y) | Lifetime ($T_{90}$) |
|---|---|---|---|---|---|
| Example 44 | F158 | 3.76 | 26.7 | (0.681, 0.318) | 92 |
| Example 45 | F164 | 3.58 | 26.4 | (0.681, 0.318) | 79 |
| Example 46 | F172 | 3.58 | 27.2 | (0.680, 0.319) | 99 |
| Example 47 | F174 | 3.58 | 26.2 | (0.681, 0.318) | 76 |
| Example 48 | F175 | 3.49 | 25.9 | (0.680, 0.319) | 78 |
| Example 49 | F179 | 3.92 | 23.9 | (0.681, 0.318) | 127 |
| Example 50 | F180 | 4.01 | 20.6 | (0.681, 0.318) | 129 |
| Example 51 | F187 | 3.78 | 26.9 | (0.681, 0.318) | 144 |
| Example 52 | F187:F212 (2:1) | 3.64 | 28.0 | (0.681, 0.318) | 152 |
| Example 52 | F188 | 3.59 | 23.3 | (0.680, 0.319) | 109 |
| Example 53 | F194 | 3.88 | 26.2 | (0.681, 0.318) | 114 |
| Example 54 | F200 | 3.78 | 24.9 | (0.681, 0.318) | 98 |
| Example 55 | F202 | 3.82 | 25.2 | (0.680, 0.319) | 129 |
| Example 56 | F202:F226 (1:1) | 3.79 | 28.2 | (0.680, 0.319) | 148 |
| Example 57 | F203 | 3.78 | 24.9 | (0.681, 0.318) | 136 |
| Example 58 | F204 | 3.75 | 25.9 | (0.682, 0.316) | 126 |
| Example 59 | F212 | 3.63 | 24.9 | (0.682, 0.316) | 99 |
| Example 60 | F213 | 3.88 | 25.1 | (0.681, 0.318) | 132 |
| Example 61 | F217 | 3.78 | 26.8 | (0.681, 0.318) | 144 |
| Example 62 | F220 | 3.83 | 23.2 | (0.682, 0.316) | 91 |
| Example 63 | F224 | 3.92 | 22.9 | (0.681, 0.318) | 104 |
| Example 64 | F226 | 3.69 | 25.9 | (0.681, 0.318) | 132 |
| Example 65 | F231 | 3.77 | 25.9 | (0.681, 0.317) | 138 |
| Example 66 | F233 | 3.87 | 24.2 | (0.682, 0.316) | 78 |
| Example 67 | F236 | 3.83 | 24.6 | (0.681, 0.318) | 128 |
| Example 68 | F251 | 3.90 | 23.2 | (0.681, 0.318) | 89 |
| Example 69 | F256 | 3.91 | 26.9 | (0.682, 0.316) | 127 |
| Example 70 | F260 | 3.88 | 26.4 | (0.681, 0.318) | 139 |
| Example 71 | F266 | 4.17 | 29.8 | (0.682, 0.316) | 79 |
| Example 72 | F274 | 3.78 | 23.0 | (0.681, 0.318) | 102 |
| Example 73 | F274:F275 (2:1) | 3.98 | 25.9 | (0.681, 0.318) | 57 |
| Example 74 | F275 | 4.25 | 29.4 | (0.681, 0.318) | 42 |
| Example 75 | F278 | 3.59 | 27.9 | (0.682, 0.316) | 105 |
| Example 76 | F288 | 4.21 | 28.6 | (0.681, 0.317) | 87 |
| Example 77 | F294 | 3.90 | 27.8 | (0.682, 0.316) | 92 |
| Example 78 | F296 | 3.98 | 29.4 | (0.681, 0.318) | 118 |
| Example 79 | F296:G (3:1) | 4.04 | 32.9 | (0.681, 0.318) | 99 |
| Example 80 | F296:H (3:1) | 4.08 | 29.6 | (0.681, 0.318) | 134 |
| Example 81 | F298 | 3.90 | 27.2 | (0.681, 0.317) | 121 |
| Example 82 | F299 | 4.12 | 28.6 | (0.682, 0.316) | 96 |
| Example 83 | F302 | 4.06 | 24.1 | (0.681, 0.318) | 109 |
| Example 84 | F304 | 4.09 | 29.2 | (0.683, 0.316) | 74 |
| Example 85 | F308 | 3.87 | 27.4 | (0.681, 0.318) | 102 |
| Example 86 | F310 | 3.87 | 26.9 | (0.681, 0.318) | 122 |
| Example 87 | F317 | 3.93 | 25.9 | (0.683, 0.316) | 119 |
| Example 88 | F318 | 3.68 | 27.9 | (0.681, 0.318) | 111 |
| Example 89 | F322 | 4.09 | 29.2 | (0.681, 0.318) | 82 |
| Example 90 | F327 | 4.01 | 25.9 | (0.683, 0.316) | 58 |
| Example 91 | F328 | 3.66 | 24.1 | (0.681, 0.318) | 79 |
| Example 92 | F334 | 3.89 | 23.3 | (0.681, 0.318) | 107 |
| Example 93 | F337 | 4.12 | 20.9 | (0.681, 0.318) | 132 |
| Example 94 | F344 | 3.98 | 23.1 | (0.683, 0.316) | 158 |
| Example 95 | F345 | 4.04 | 22.9 | (0.681, 0.318) | 146 |
| Example 96 | F356 | 3.66 | 28.9 | (0.681, 0.318) | 82 |
| Example 97 | F358 | 4.02 | 27.0 | (0.683, 0.316) | 99 |
| Example 98 | F371 | 3.78 | 28.0 | (0.683, 0.316) | 109 |
| Example 99 | F376 | 3.89 | 26.9 | (0.681, 0.318) | 88 |
| Example 100 | F380 | 3.79 | 25.9 | (0.683, 0.316) | 108 |
| Example 101 | F381 | 3.82 | 24.7 | (0.682, 0.316) | 139 |
| Example 102 | F386 | 3.79 | 25.2 | (0.682, 0.316) | 78 |
| Example 103 | F391 | 3.69 | 24.8 | (0.681, 0.317) | 117 |
| Example 104 | F393 | 3.77 | 23.2 | (0.682, 0.316) | 111 |
| Example 105 | F394 | 4.21 | 24.6 | (0.681, 0.318) | 72 |
| Example 106 | F403 | 3.92 | 27.8 | (0.681, 0.317) | 78 |
| Example 107 | F406 | 3.81 | 26.9 | (0.682, 0.316) | 89 |
| Example 108 | F409 | 3.59 | 29.0 | (0.681, 0.317) | 69 |
| Example 109 | F418 | 3.72 | 25.9 | (0.681, 0.318) | 93 |
| Example 110 | F421 | 3.95 | 21.9 | (0.683, 0.316) | 118 |
| Example 111 | F421:H (1:2) | 4.11 | 22.6 | (0.681, 0.318) | 121 |
| Example 112 | F421:F216 (1:2) | 3.99 | 24.1 | (0.681, 0.318) | 128 |
| Example 113 | F422 | 4.07 | 20.7 | (0.681, 0.318) | 110 |
| Example 114 | F422:I (1:2) | 3.98 | 17.2 | (0.681, 0.318) | 98 |
| Example 115 | F422:F213 (1:3) | 3.64 | 27.8 | (0.681, 0.317) | 159 |
| Example 116 | F422:F213 (1:2) | 3.64 | 28.0 | (0.681, 0.317) | 157 |
| Example 117 | F422:F213 (1:1) | 3.81 | 28.1 | (0.681, 0.317) | 138 |
| Example 118 | F422:F213 (2:1) | 3.79 | 28.3 | (0.681, 0.317) | 110 |

TABLE 12-continued
| | Compound | Driving Voltage (V) | Efficiency (cd/A) | Color Coordinate (x, y) | Lifetime ($T_{90}$) |
|---|---|---|---|---|---|
| Example 119 | F422:F213 (3:1) | 3.79 | 28.3 | (0.681, 0.318) | 105 |
| Example 120 | F440 | 4.19 | 22.3 | (0.681, 0.318) | 93 |
| Example 121 | F445 | 4.21 | 21.8 | (0.683, 0.316) | 57 |
| Example 122 | F453 | 4.16 | 22.3 | (0.681, 0.318) | 88 |
| Example 123 | F458 | 3.79 | 21.6 | (0.681, 0.318) | 111 |
| Example 124 | F556 | 4.13 | 20.8 | (0.681, 0.318) | 137 |
| Example 125 | F556:F213 (1:1.5) | 3.88 | 27.5 | (0.681, 0.317) | 149 |
| Example 126 | F556:F352 (1:2) | 3.68 | 28.2 | (0.681, 0.317) | 151 |
| Example 127 | F558 | 3.97 | 21.1 | (0.683, 0.316) | 88 |
| Example 128 | F598 | 4.14 | 20.9 | (0.681, 0.318) | 121 |
| Example 129 | F598:F352 (1:2) | 3.68 | 28.2 | (0.681, 0.317) | 151 |
| Example 130 | F607 | 3.98 | 21.7 | (0.681, 0.318) | 82 |
| Example 131 | F618 | 4.03 | 22.1 | (0.683, 0.316) | 99 |
| Example 132 | F629 | 4.03 | 21.2 | (0.683, 0.316) | 102 |
| Example 133 | F631 | 3.99 | 21.8 | (0.681, 0.318) | 95 |
| Example 134 | F634 | 4.02 | 22.3 | (0.681, 0.317) | 117 |
| Example 135 | F641 | 4.13 | 20.1 | (0.682, 0.316) | 113 |
| Example 136 | F645 | 4.08 | 21.3 | (0.681, 0.318) | 73 |
A
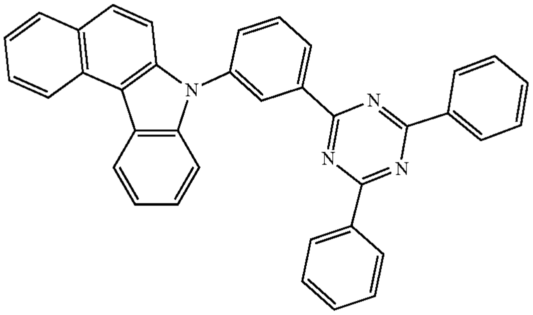
B
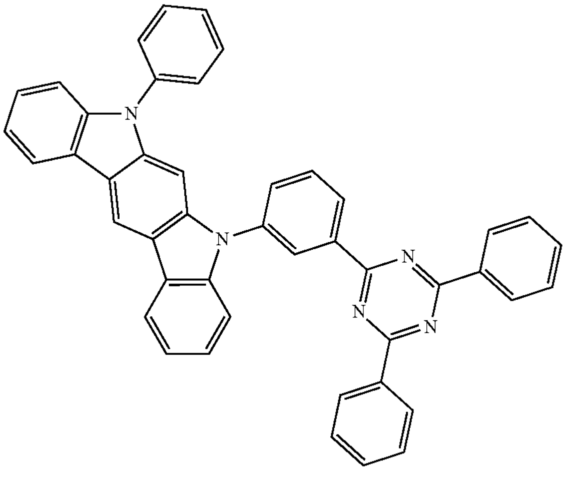
-continued
C
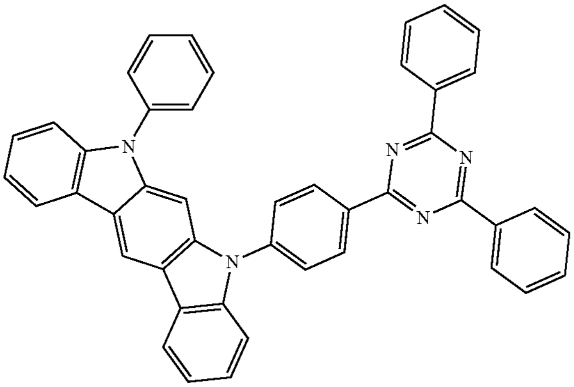
D
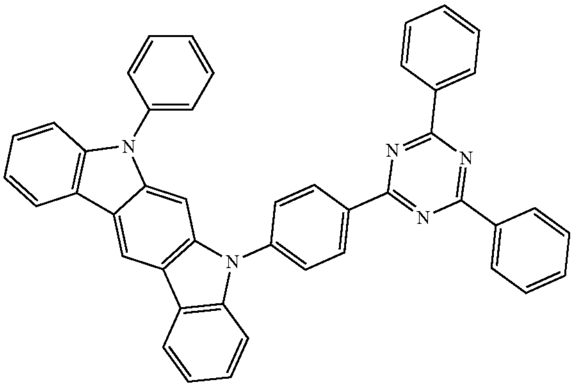

-continued
E
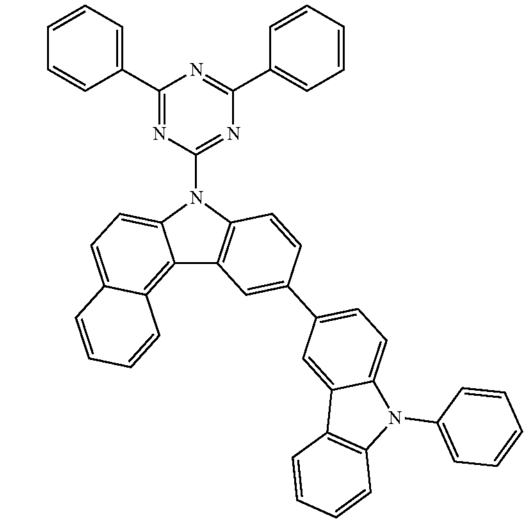
F
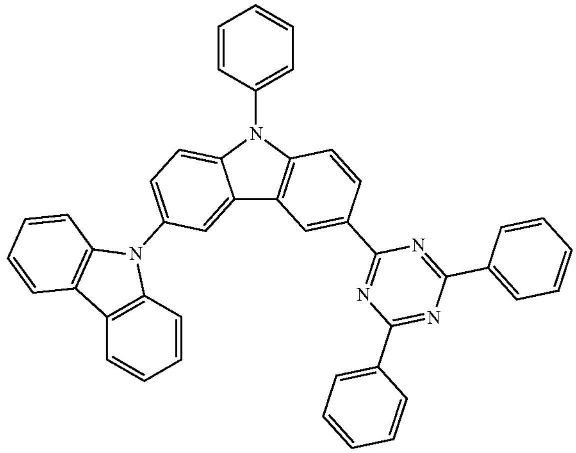
G
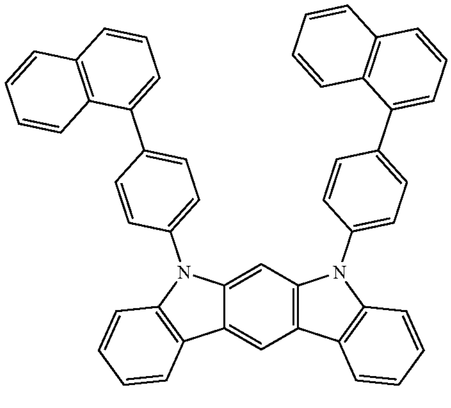
-continued
H
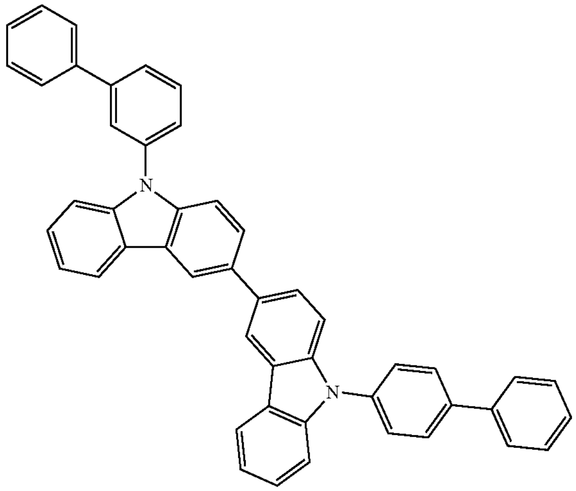
I
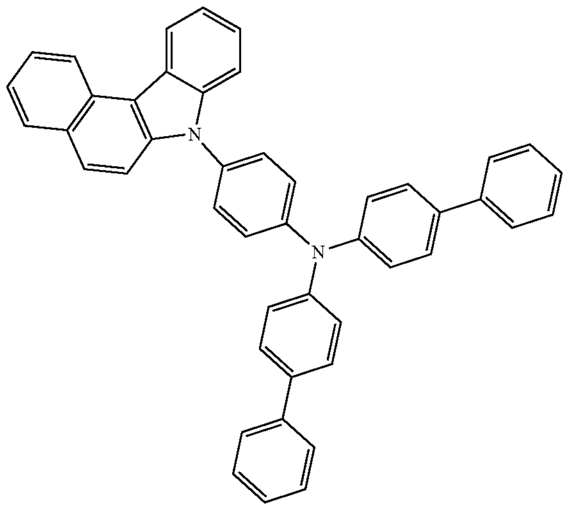
J
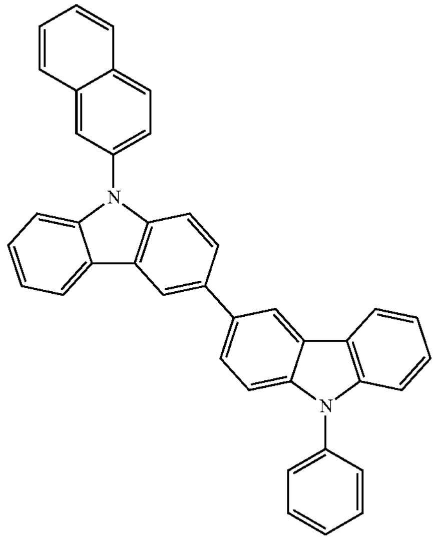

-continued

K

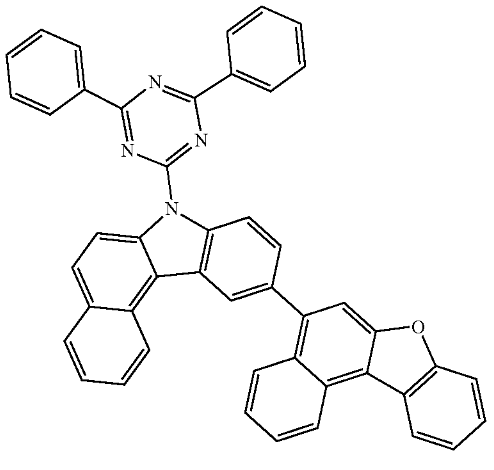

L

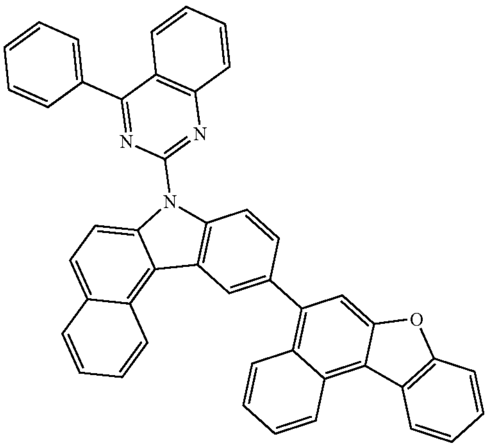

M

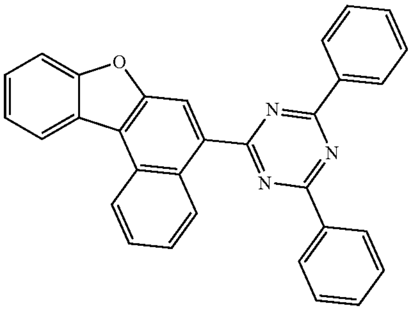

N

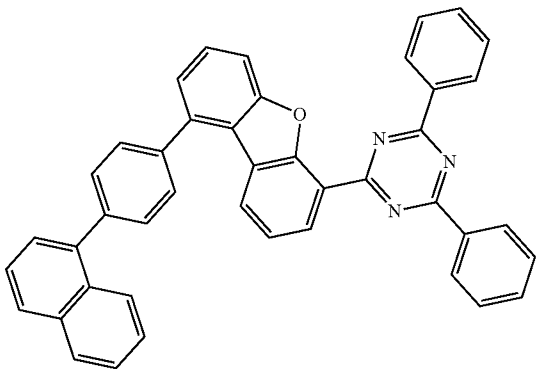

-continued

O

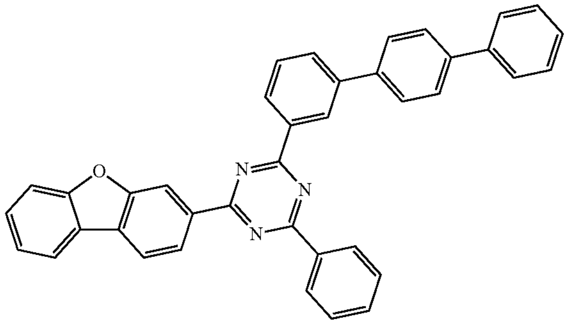

As shown in Table 12, it was identified that, when using the compound represented by Chemical Formula 1 as a light emitting layer of an organic light emitting device, superior effects were obtained in properties of lifetime, efficiency and driving voltage compared to other cases.

The invention claimed is:

1. A multicyclic compound represented by the following Chemical Formula 2 or 3:

[Chemical Formula 2]

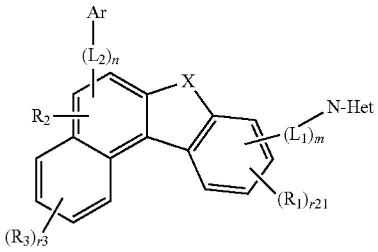

[Chemical Formula 3]

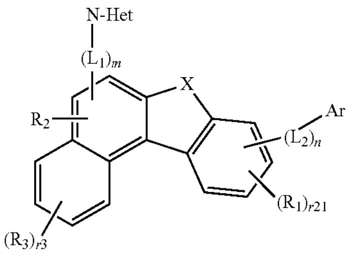

wherein, in Chemical Formulae 2 and 3,

X is O; S; or $NR_{21}$;

$L_1$ and $L_2$ are the same as or different from each other, and each independently a direct bond; or a substituted or unsubstituted arylene group;

Ar is selected from among the following structural formulae:

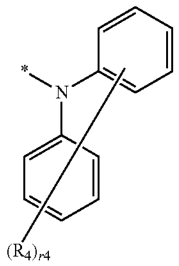

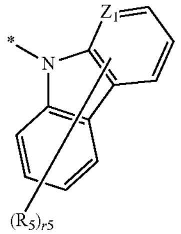

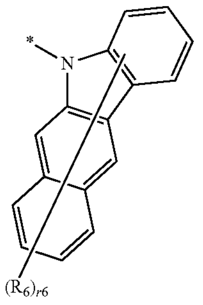

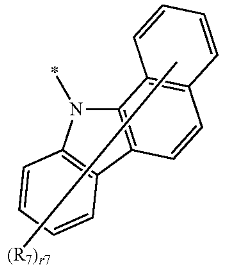

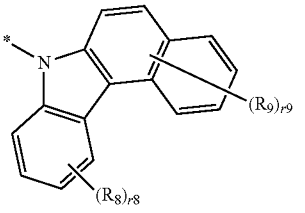

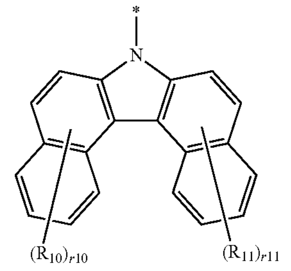

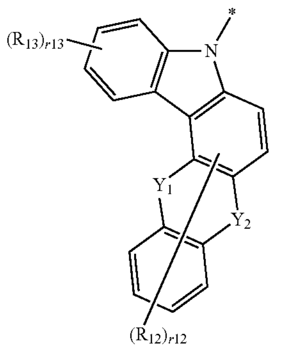

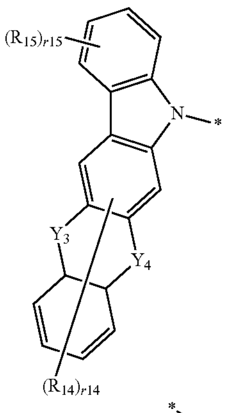

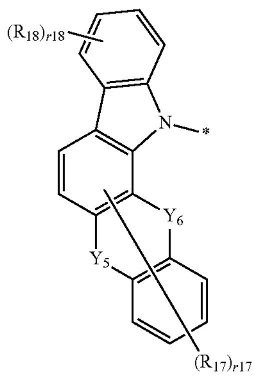

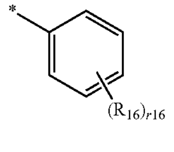

in the structural formulae, $Y_1$ to $Y_6$ are the same as or different from each other, and each independently a direct bond; O; S; or $NR_{22}$, $Z_1$ is N or $CR_{31}$, $R_5$ to $R_{15}$, $R_{18}$ and $R_{31}$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, $R_4$, $R_{16}$ and $R_{17}$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or bond to adjacent groups to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring, $R_{22}$ is a substituted or unsubstituted aryl group, r4, r6 and r7 are each an integer of 1 to 10, r5 is an integer of 1 to 7, r8, r13, r15 and r18 are each an integer of 1 to 4, r9 to r12, r14 and r17 are each an integer of 1 to 6, r16 is an integer of 1 to 5, and when r4 to r18 are an integer of 2 or greater, substituents in the parentheses are the same as or different from each other, N-Het is selected from among the following structural formulae:

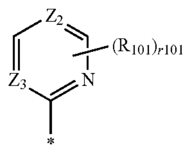

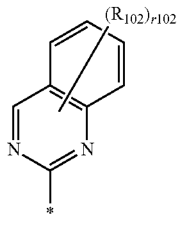

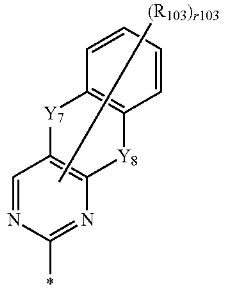

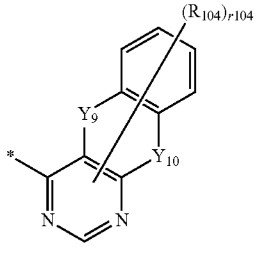

in the structural formulae, $Y_7$ to $Y_{10}$ are the same as or different from each other, and each a direct bond; O; S; or $NR_{23}$;

$Z_2$ and $Z_3$ are each N or $CR_{32}$;

$R_{101}$ to $R_{104}$ and $R_{32}$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic hydrocarbon ring, a substituted or unsubstituted aromatic hydrocarbon ring, a substituted or unsubstituted aliphatic heteroring, or a substituted or unsubstituted aromatic heteroring;

$R_{23}$ is a substituted or unsubstituted aryl group;

r101 is 1 or 2;

r102 to r104 are each an integer of 1 to 5; and when r101 is 2 and r102 to r104 are an integer of 2 or greater, substituents in the parentheses are the same as or different from each other, $R_1$ to $R_3$ are the same as or different from each other, and each independently hydrogen; deuterium; a substituted or unsubstituted phenyl group; a substituted or unsubstituted biphenyl group; or a substituted or unsubstituted naphthyl group;

$R_{21}$ is a phenyl group; or a naphthyl group;

m and n are each an integer of 1 to 5;

r21 is an integer of 1 to 3;

r3 is an integer of 1 to 4; and when m, n, r21 and r3 are an integer of 2 or greater, substituents in the parentheses are the same as or different from each other.

2. The multicyclic compound of claim 1, wherein $R_1$ to $R_3$ are each independently hydrogen; a phenyl group; a biphenyl group; or a naphthyl group.

3. The multicyclic compound of claim 1, wherein Chemical Formula 1 is represented by any one of the following compounds:

F1

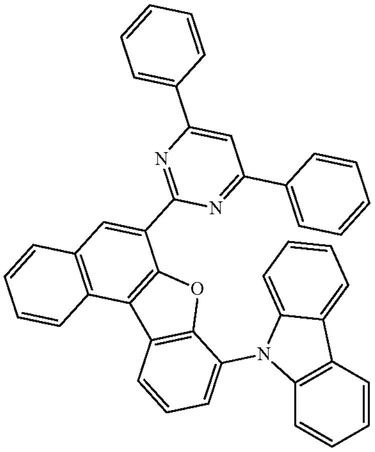

-continued

F2

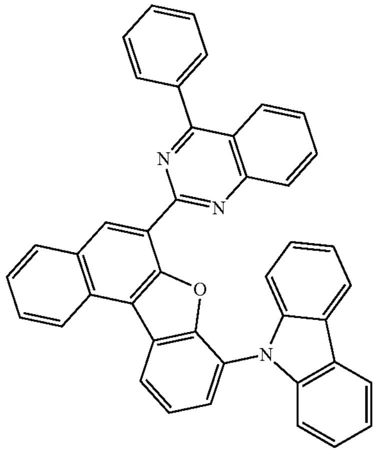

F3

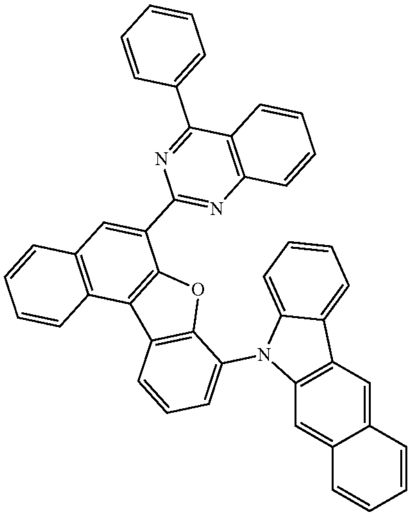

F4

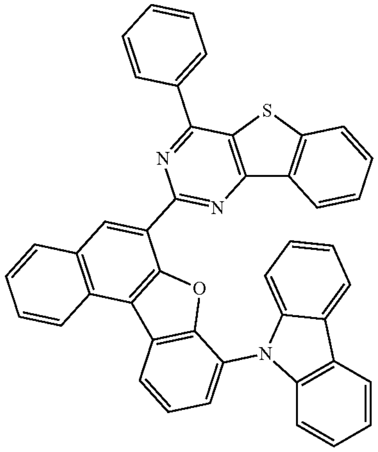

-continued
F5
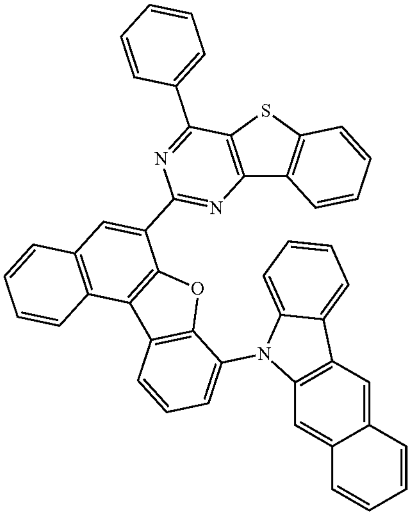
F6
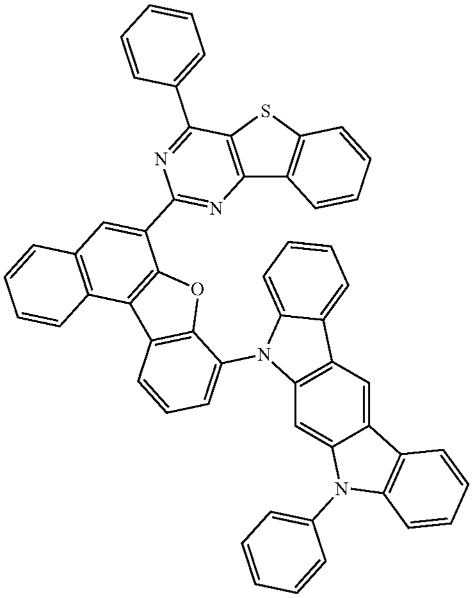
F7
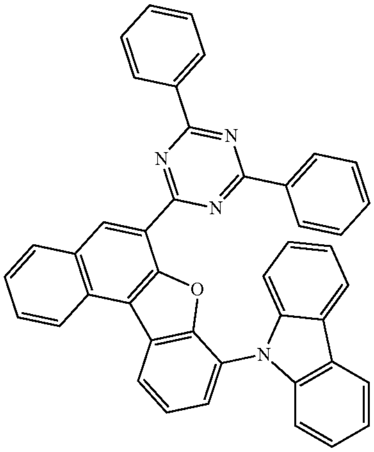
-continued
F8
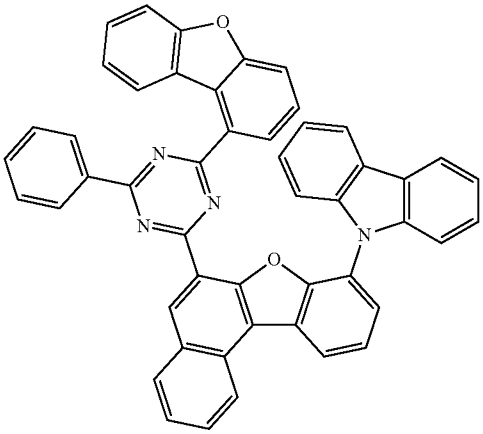
F9
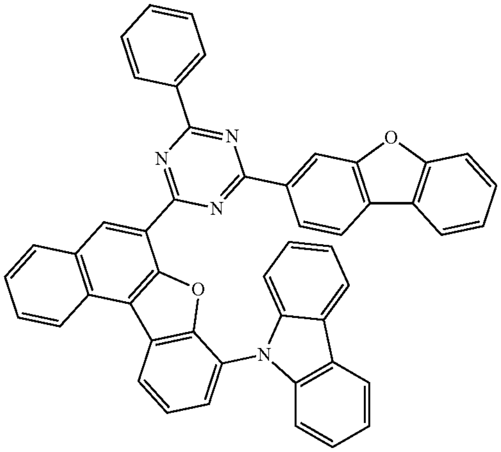
F10
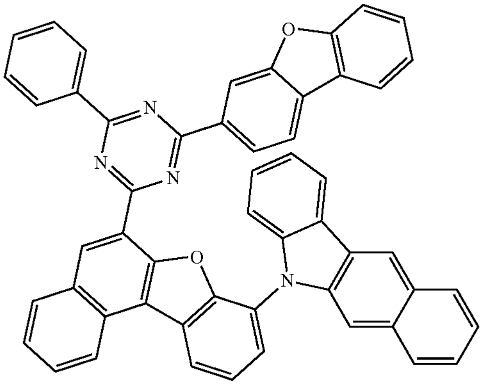

-continued
F11
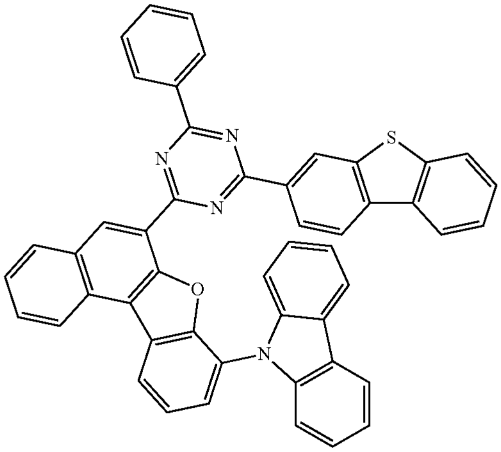
F12
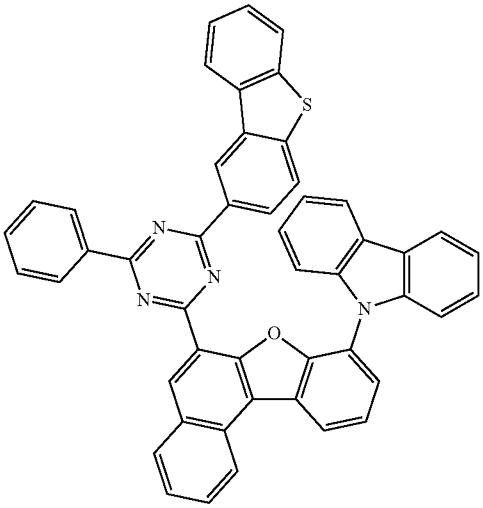
F13
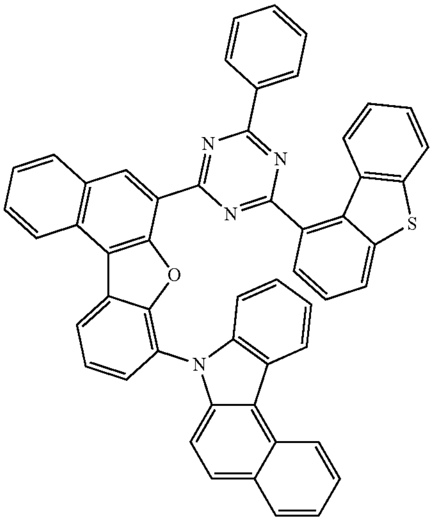
-continued
F14
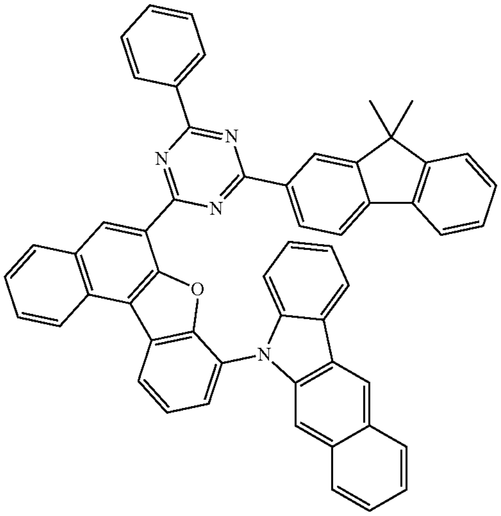
F15
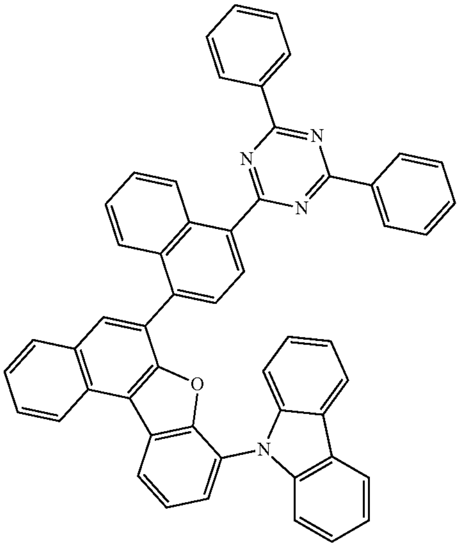

-continued
F16
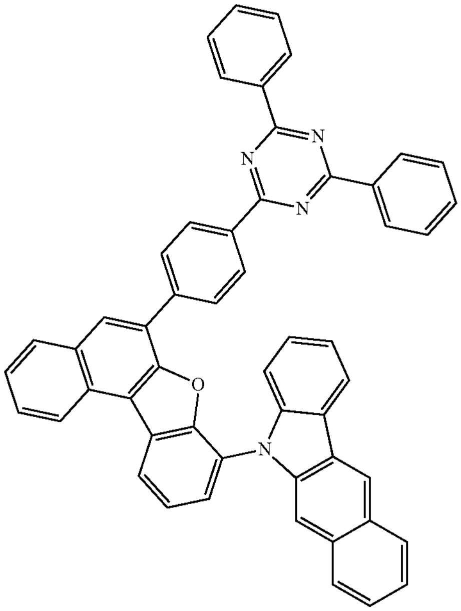
F17
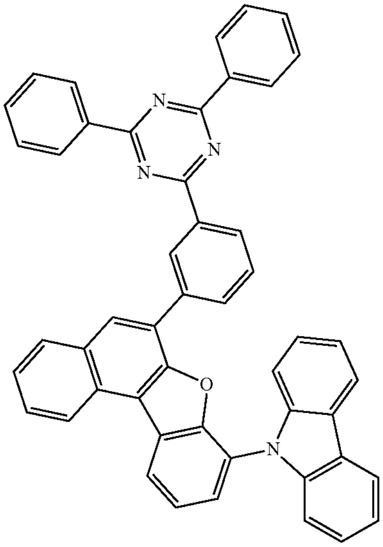
-continued
F18
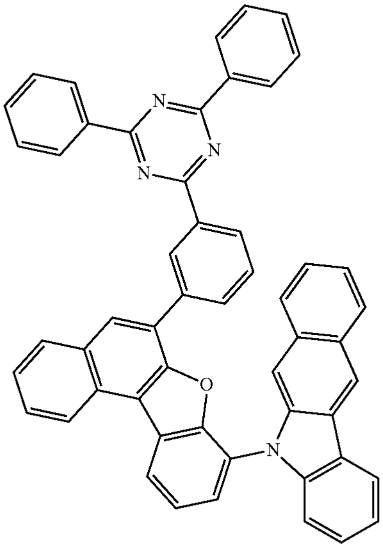
F19
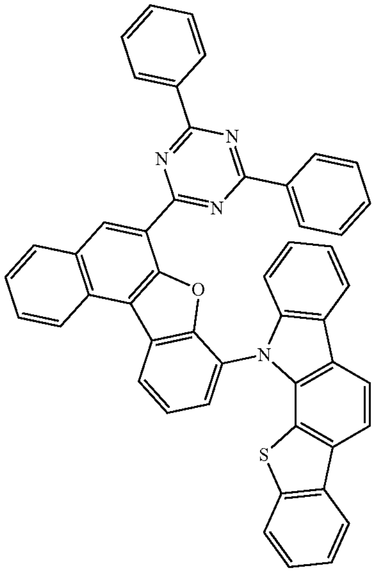

F20
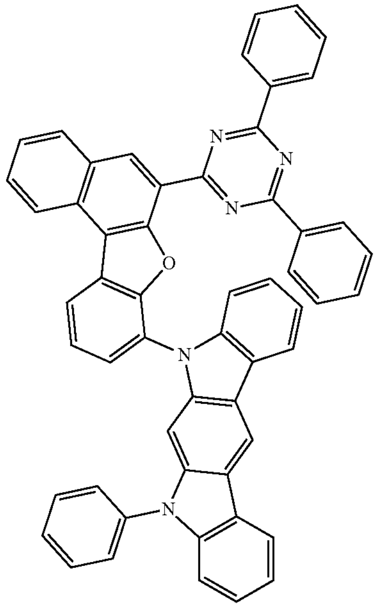
F21
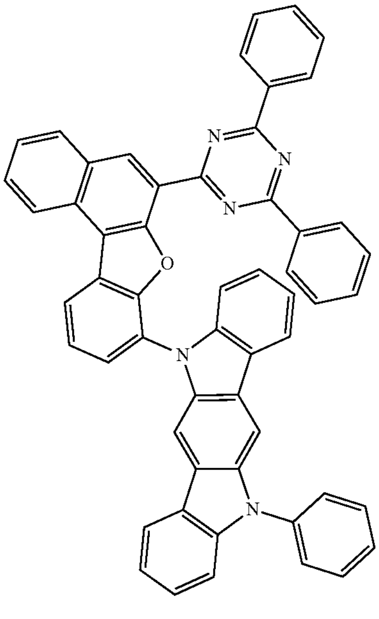
F22
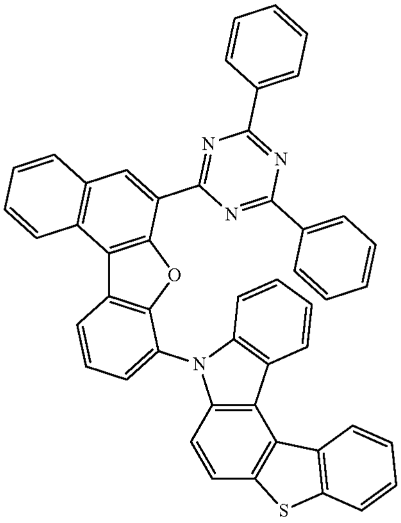
F23
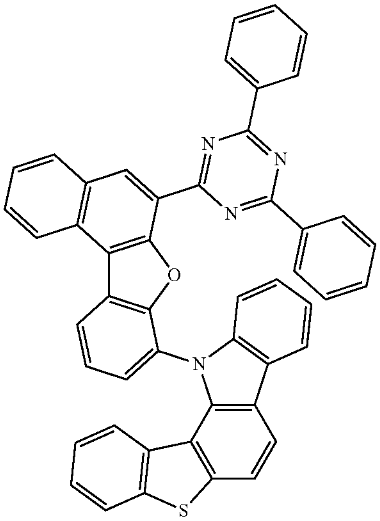
F24
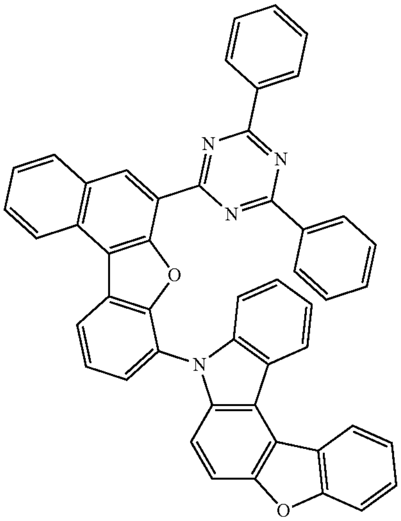

-continued
F25
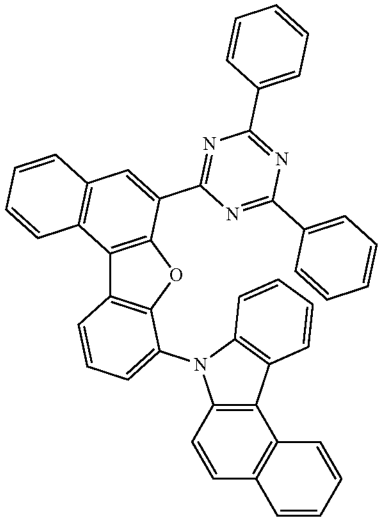
F26
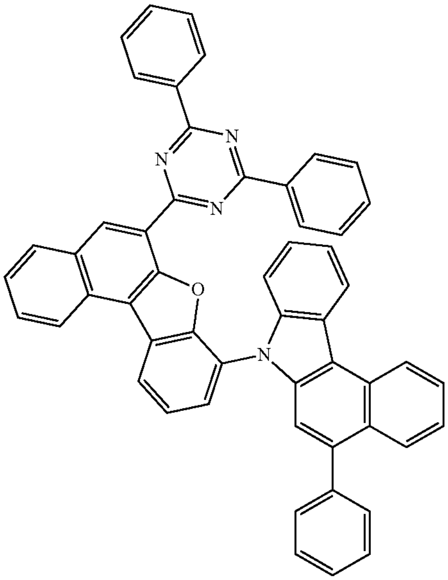
-continued
F27
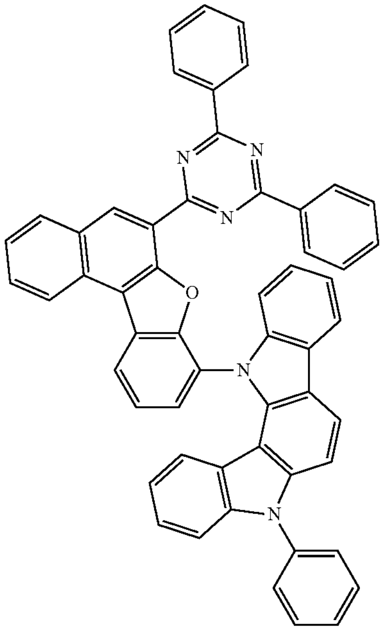
F28
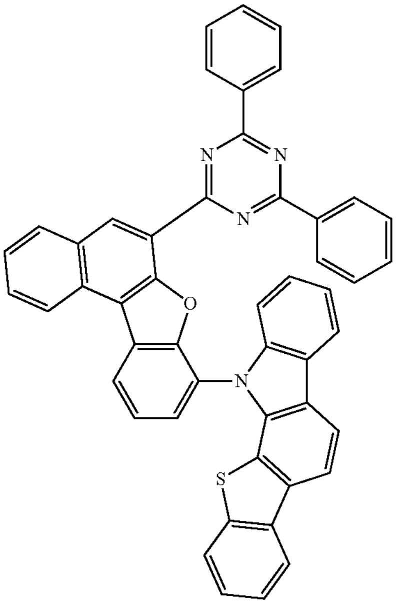

-continued
F29
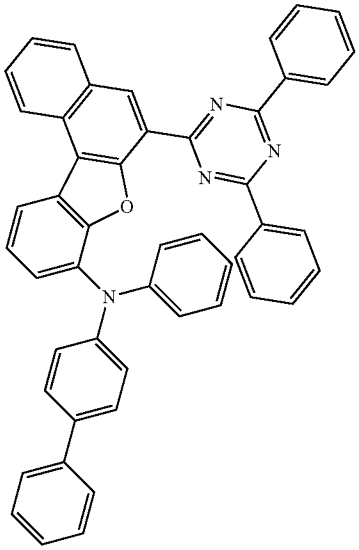
F30
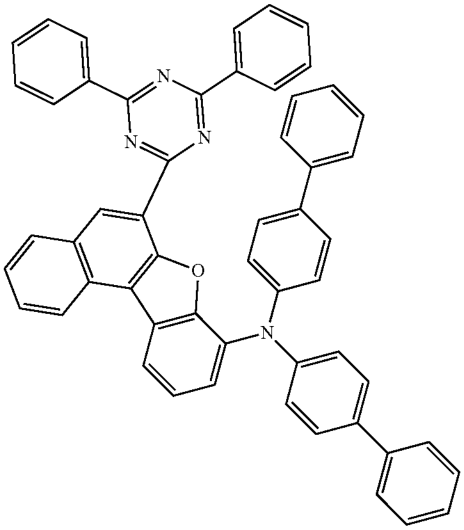
F31
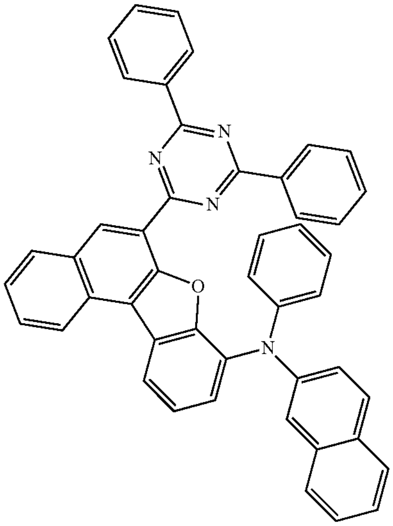
-continued
F32
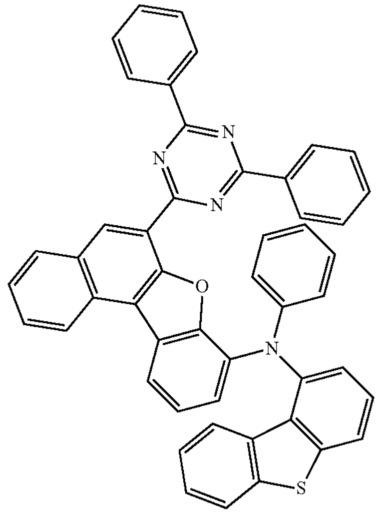
F33
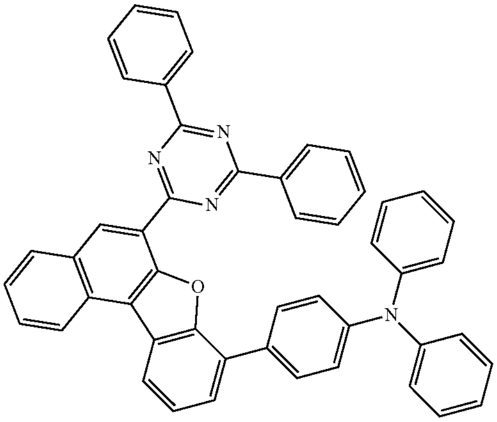
F34
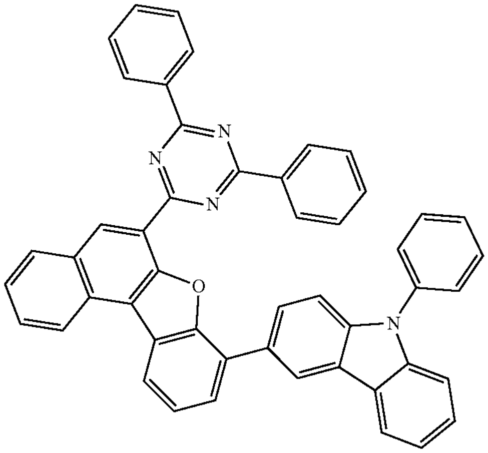

-continued
F35
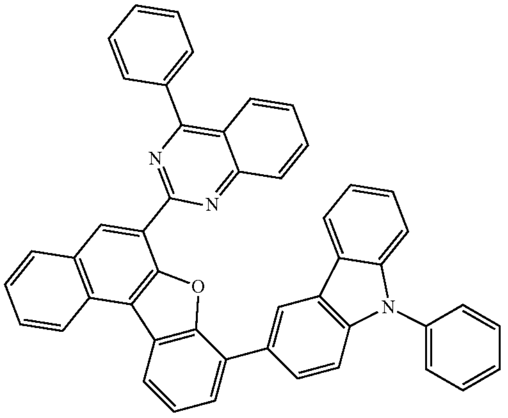
F36
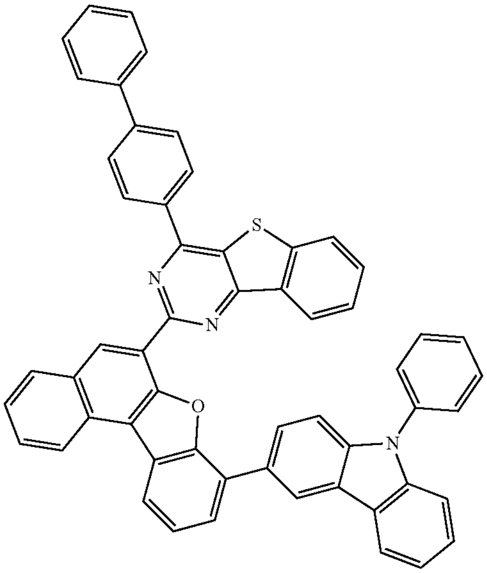
F37
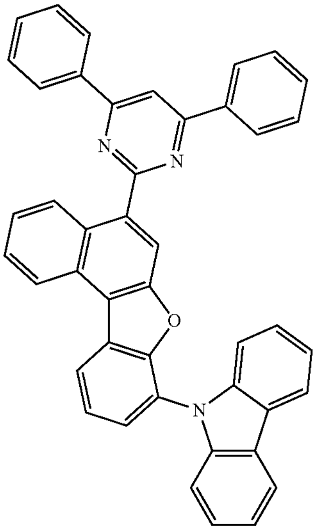
-continued
F38
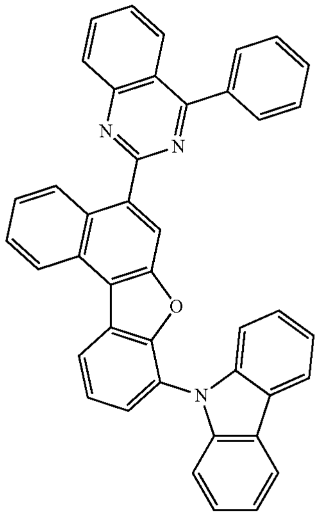
F39
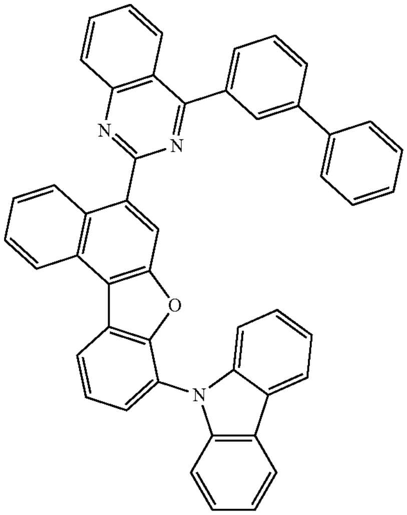
F40
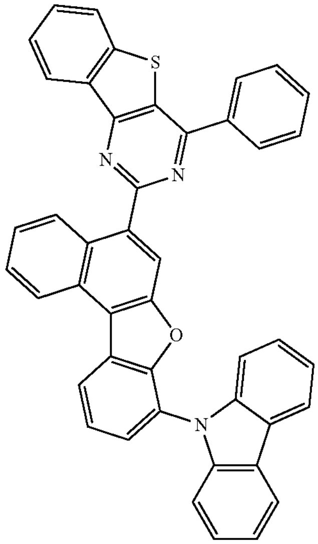

-continued
F41
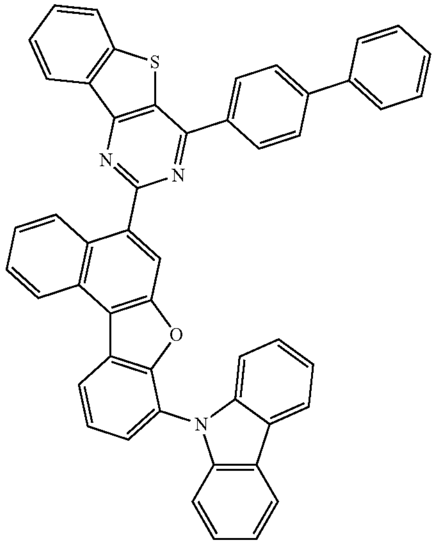
F42
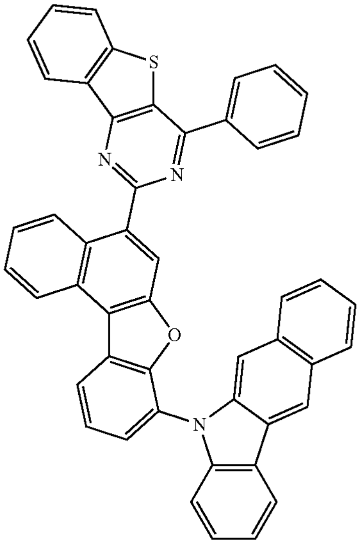
F43
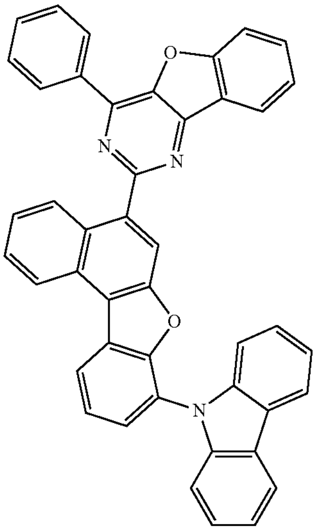
-continued
F44
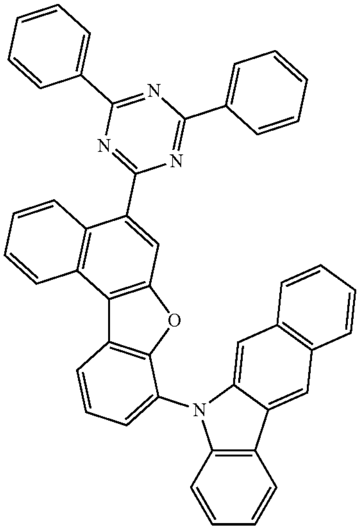
F45
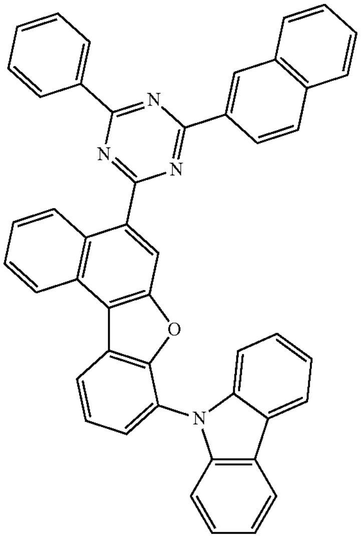
F46
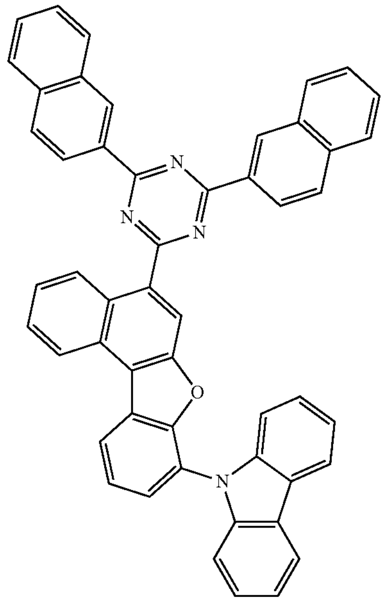

-continued
F47
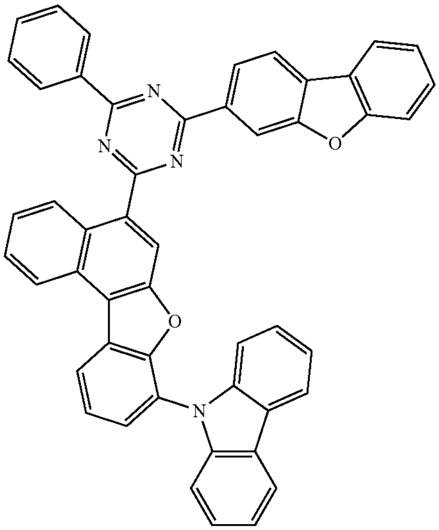
F49
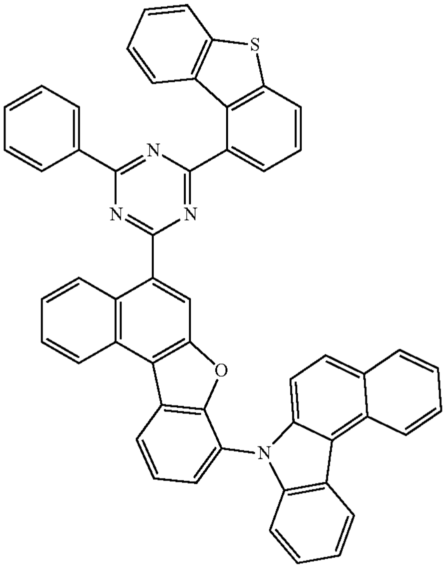
F48
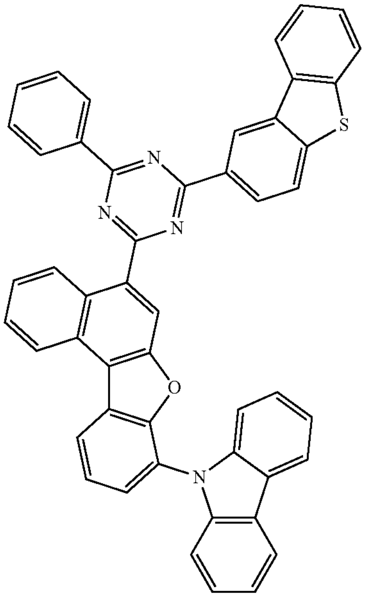
F50
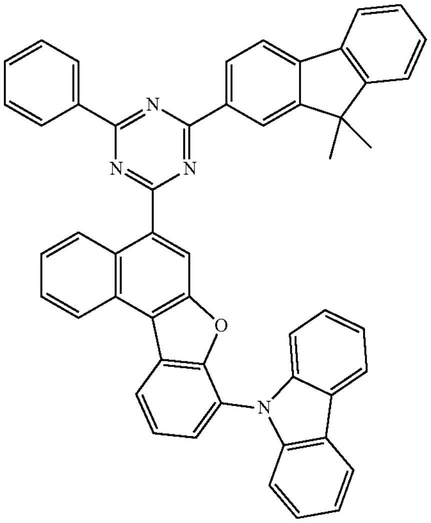

-continued
F51
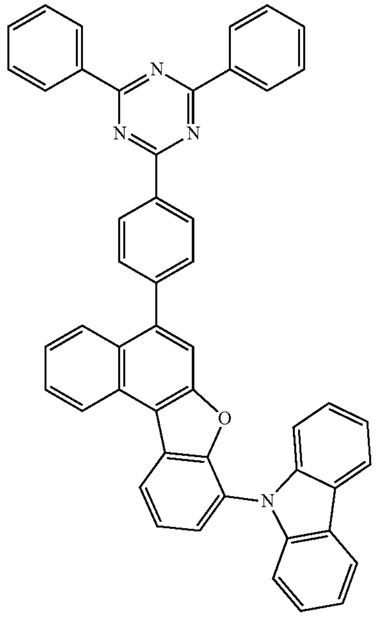
F52
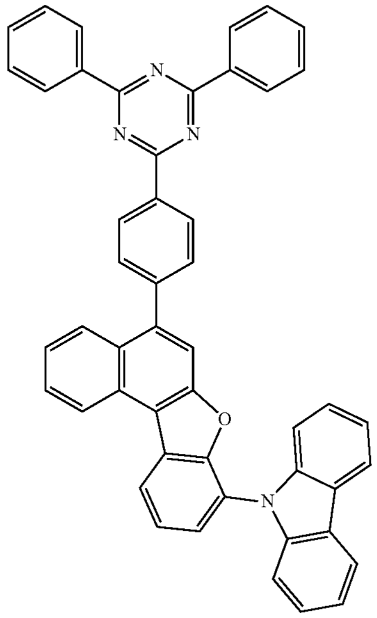
-continued
F53
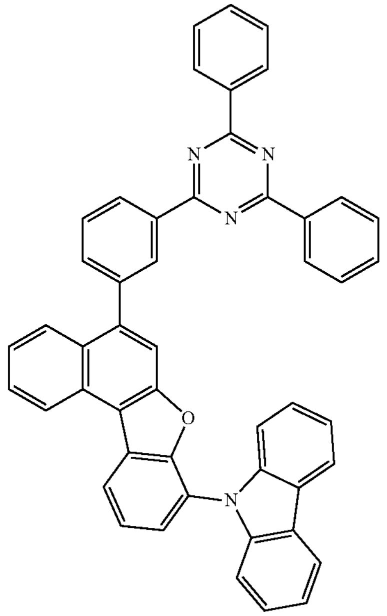
F54
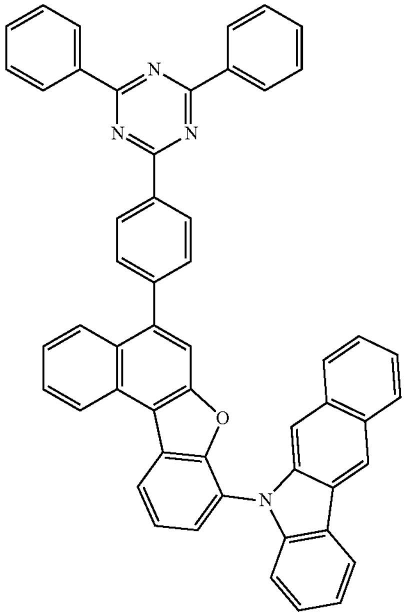

F55
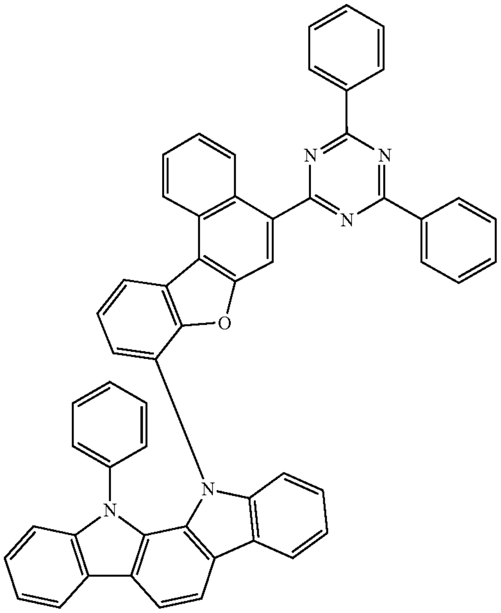
F56
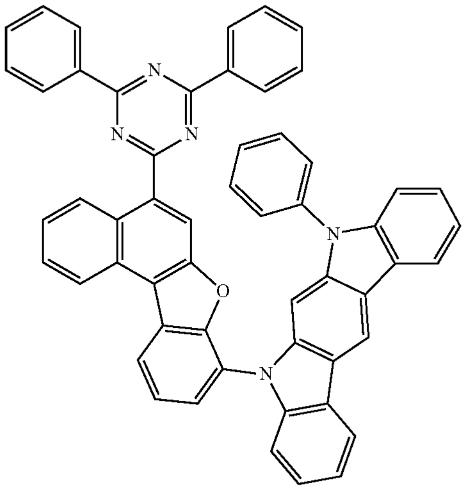
F57
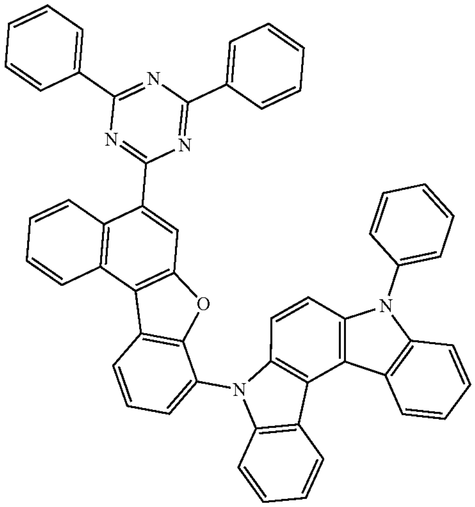
F58
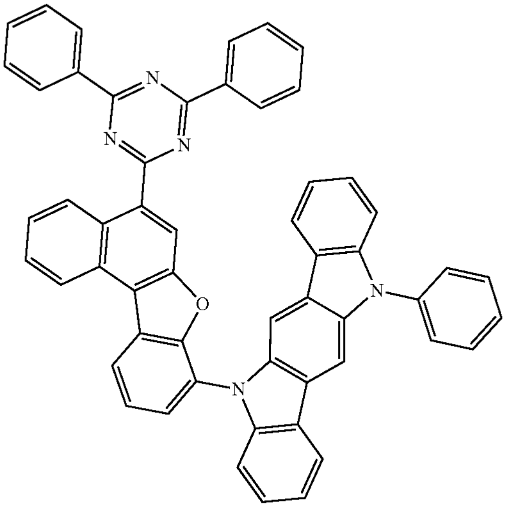
F59
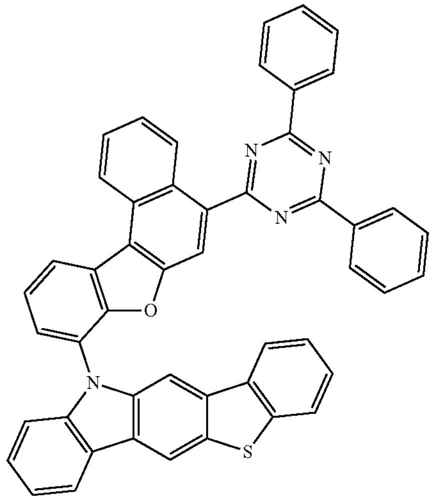
F60
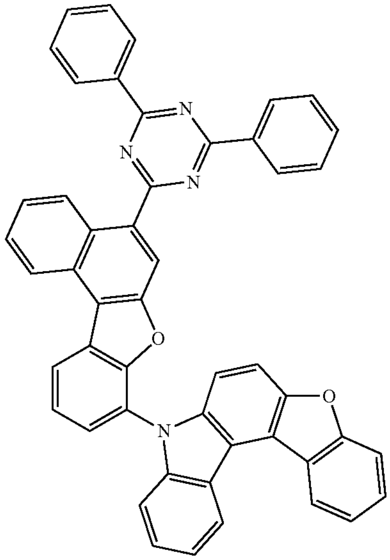

-continued
F61
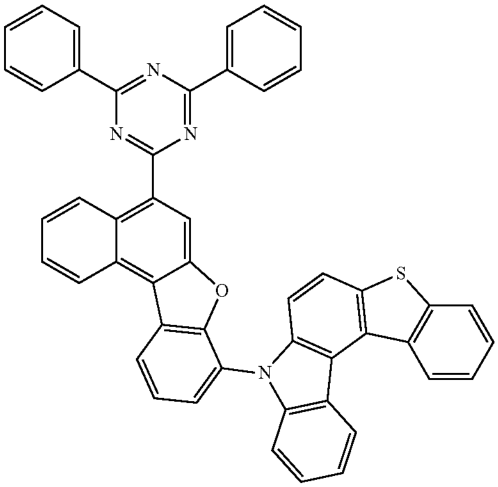
F62
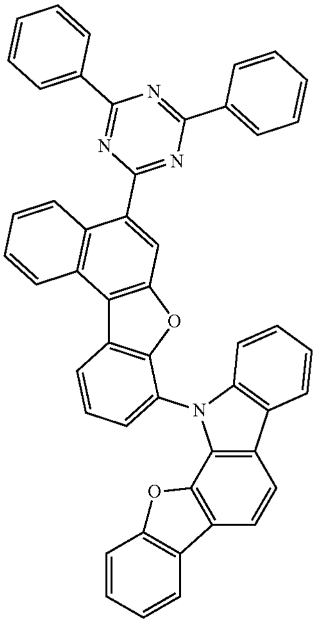
-continued
F63
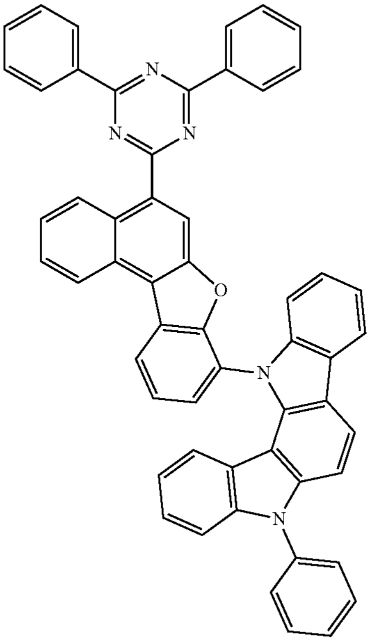
F64
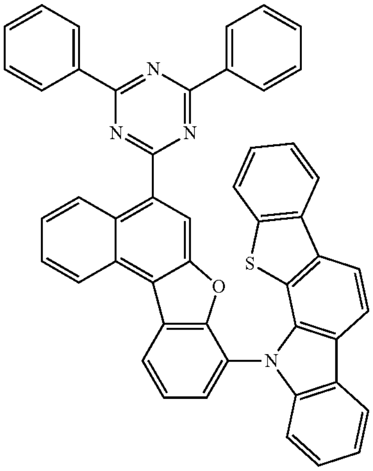
F65
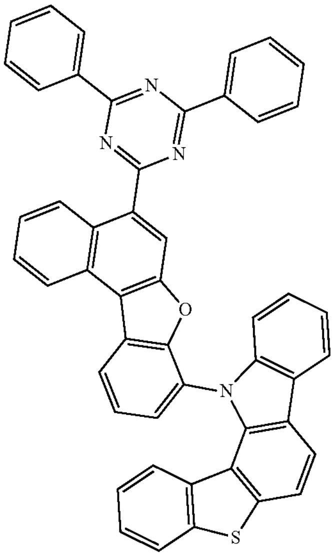

-continued
F66
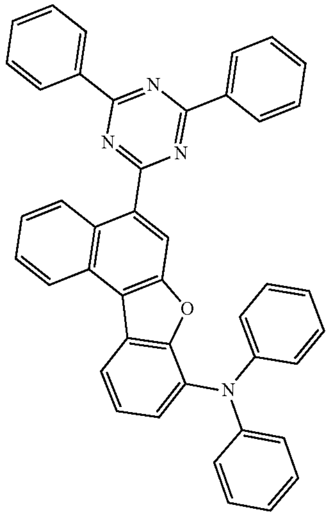
F67
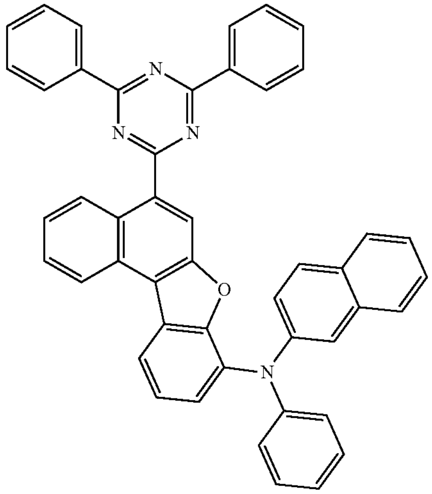
F68
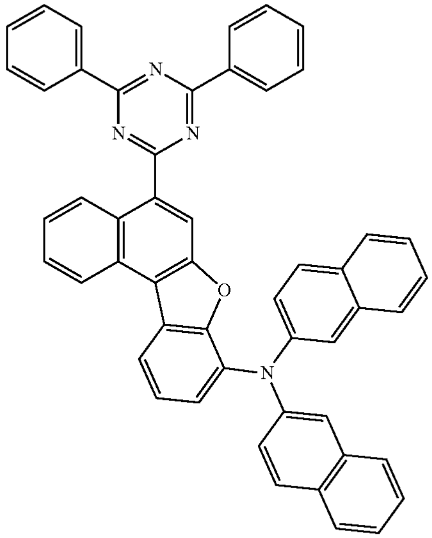
-continued
F69
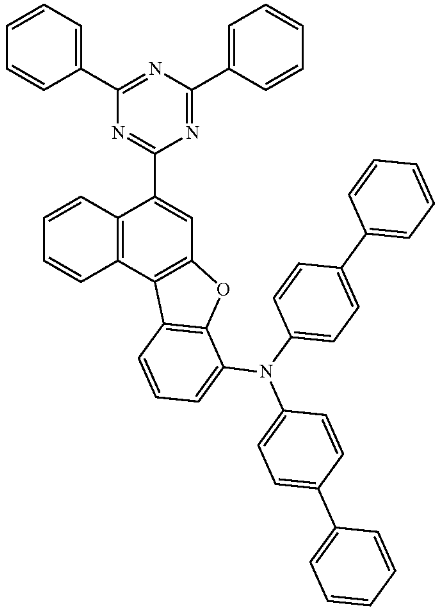
F70
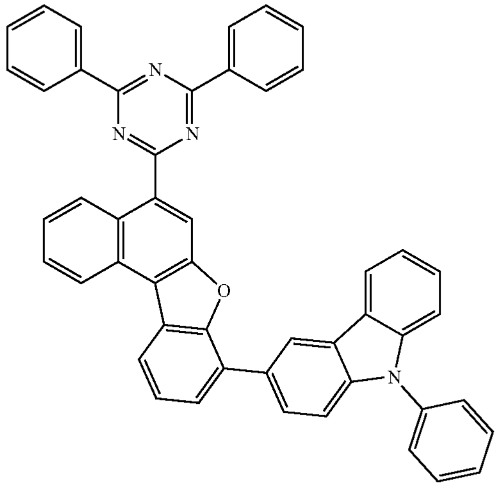

-continued
F71
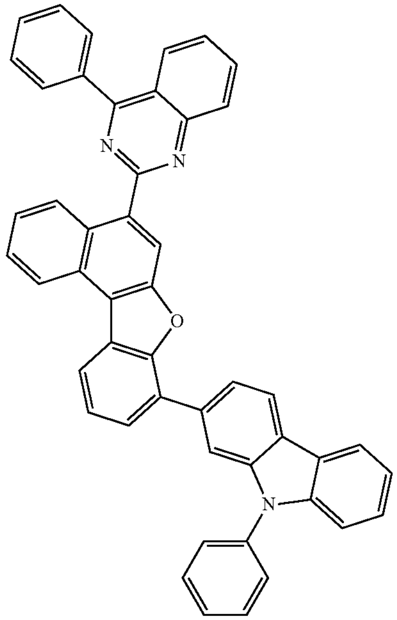
F72
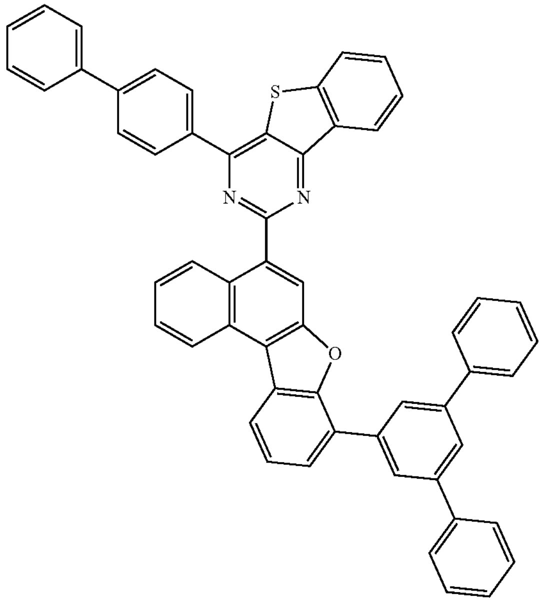
-continued
F73
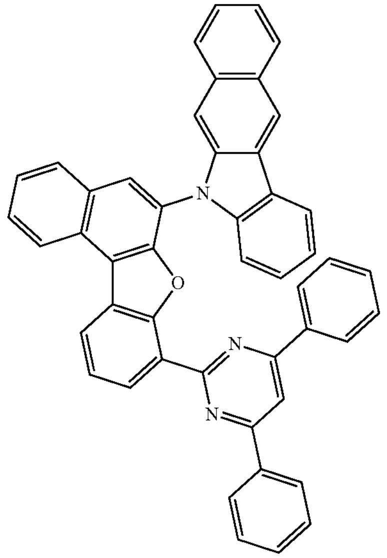
F74
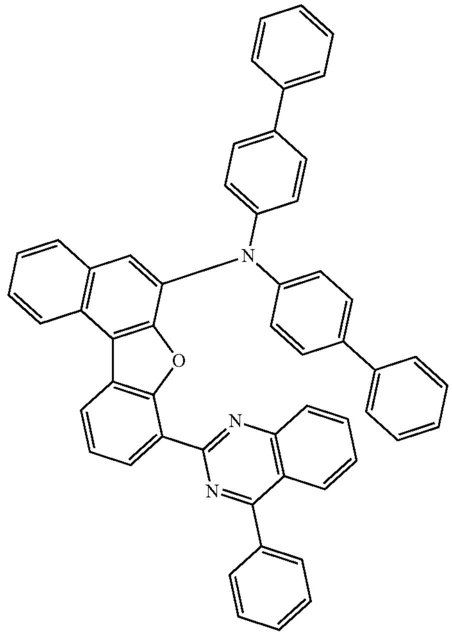
F75
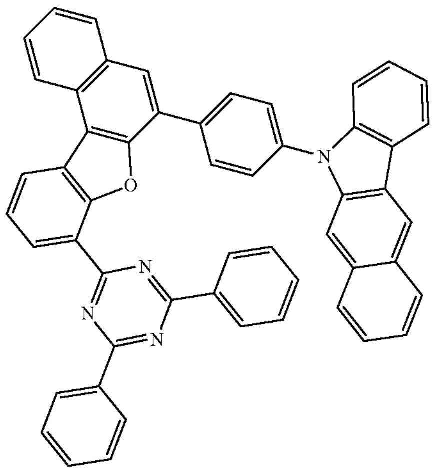

-continued
F76
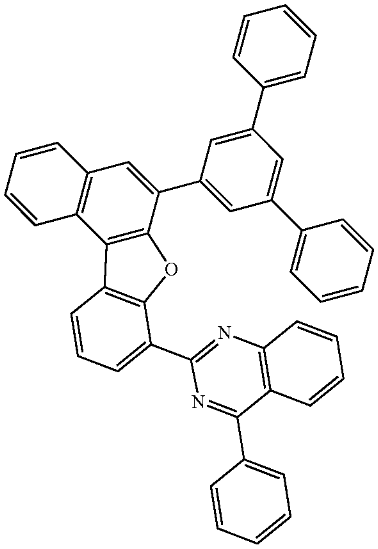
F77
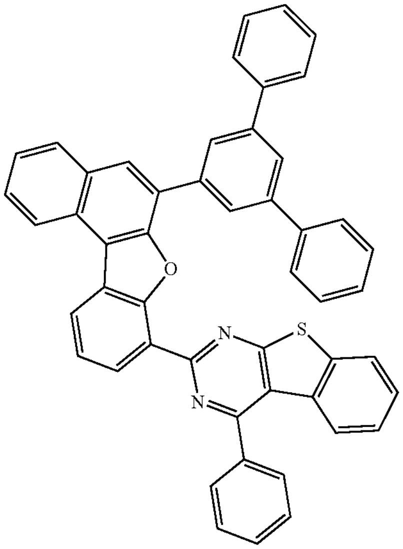
-continued
F78
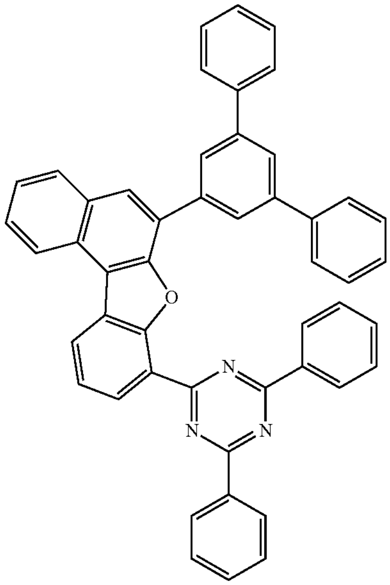
F79
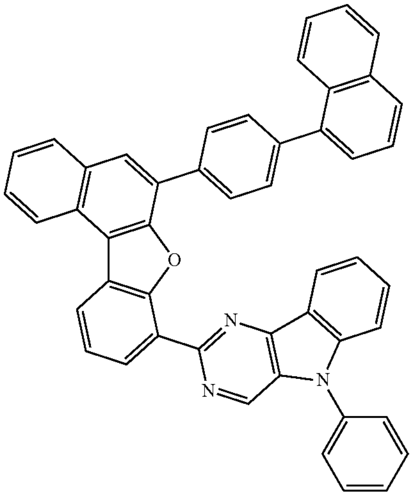
F80
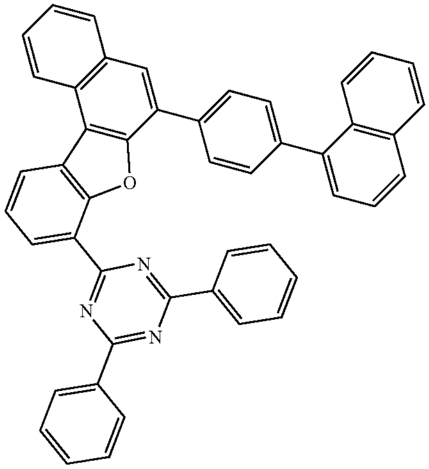

-continued
F81
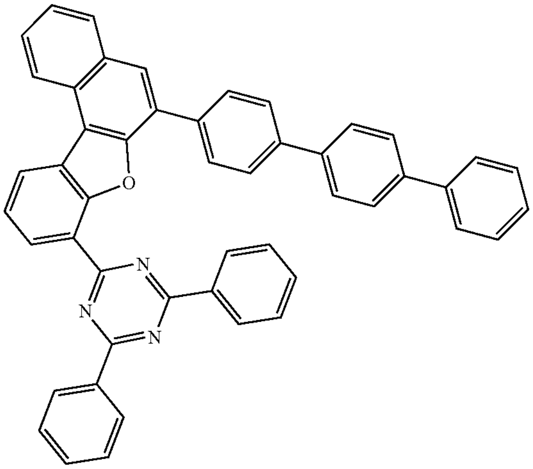
F82
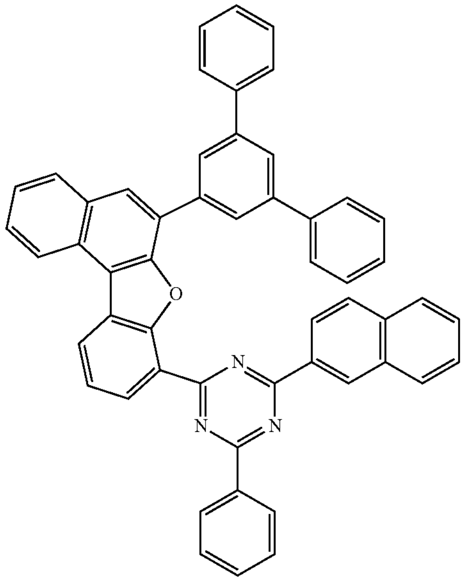
F83
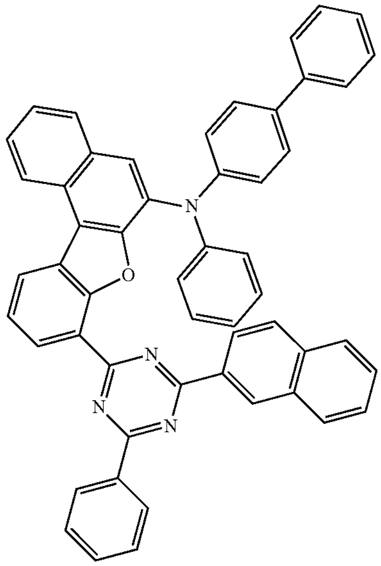
-continued
F84
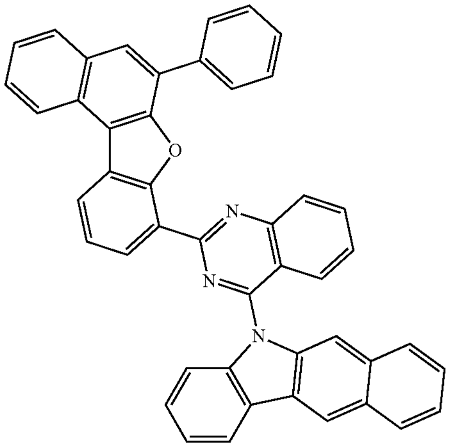
F85
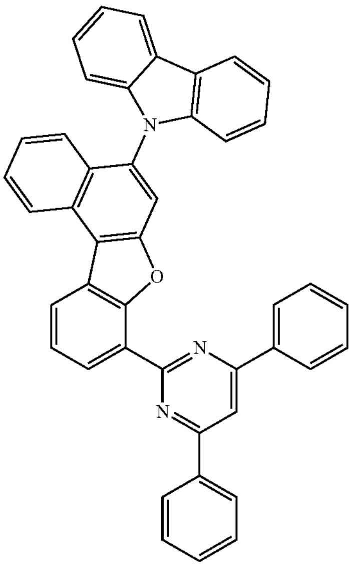
F86
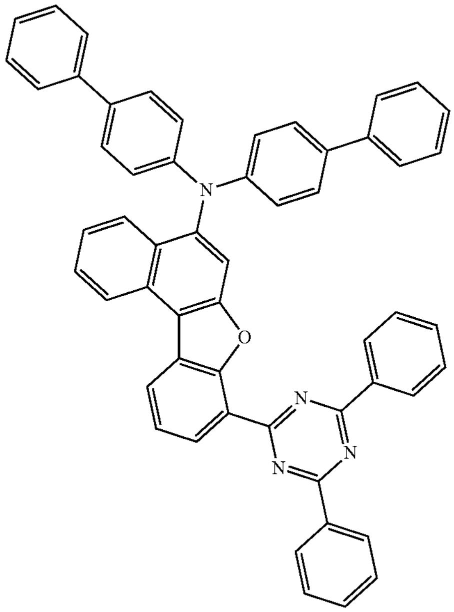

-continued
F87
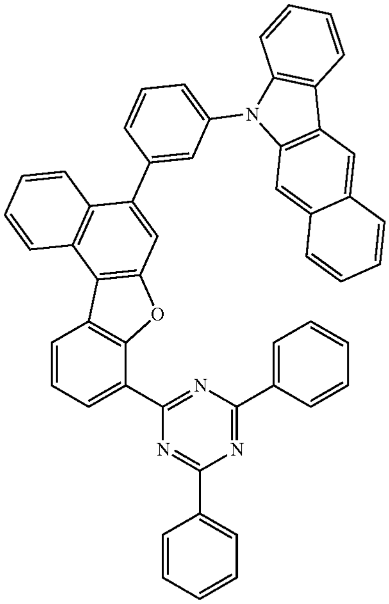
F88
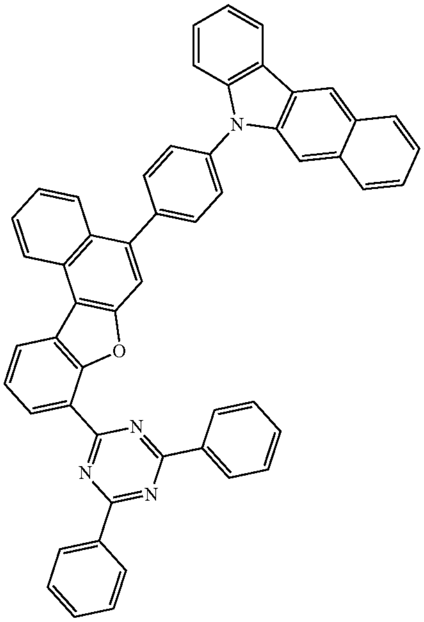
-continued
F89
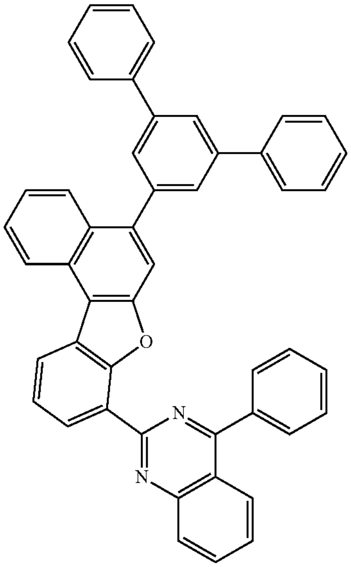
F90
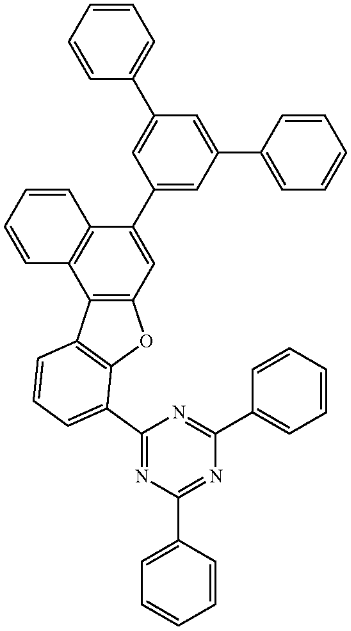

-continued
F91
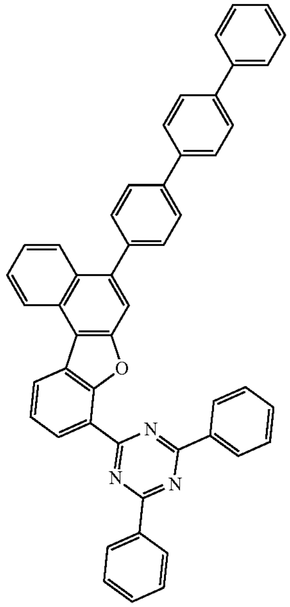
F92
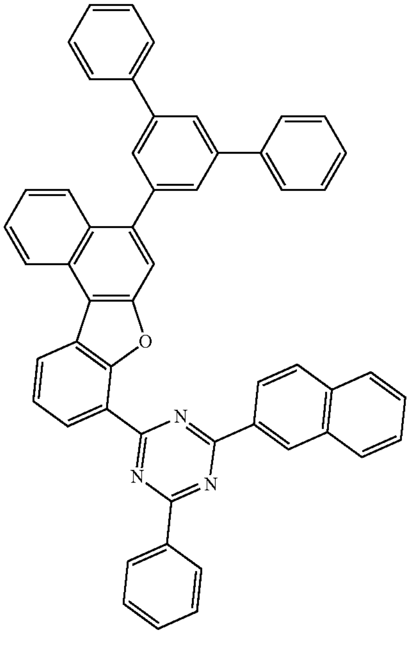
-continued
F93
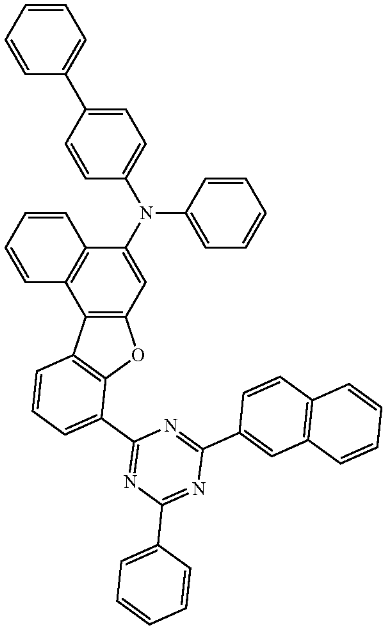
F94
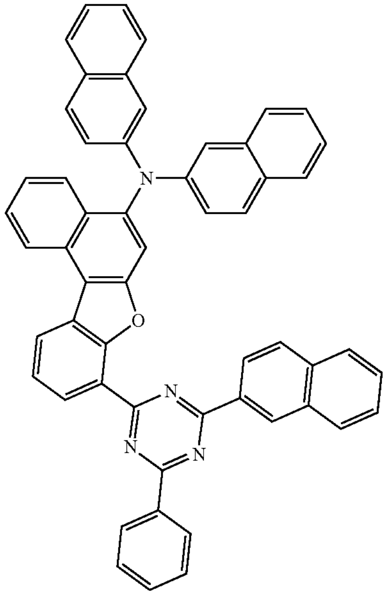

-continued
F95
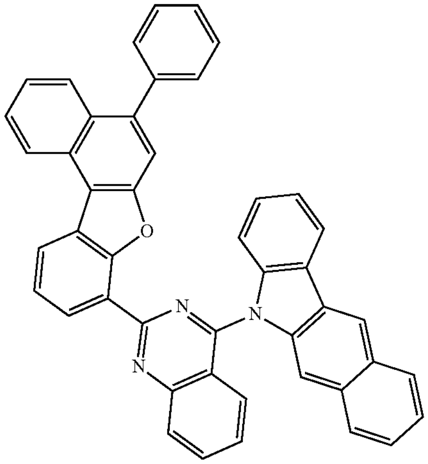
F96
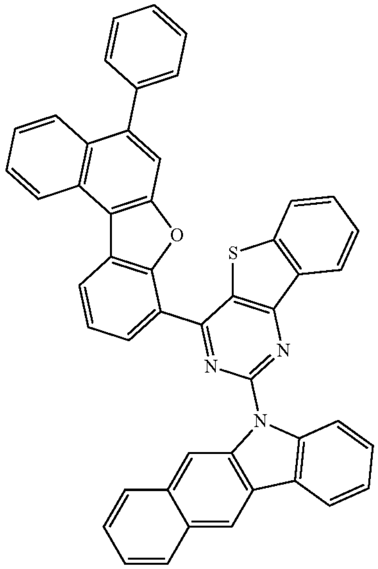
F97
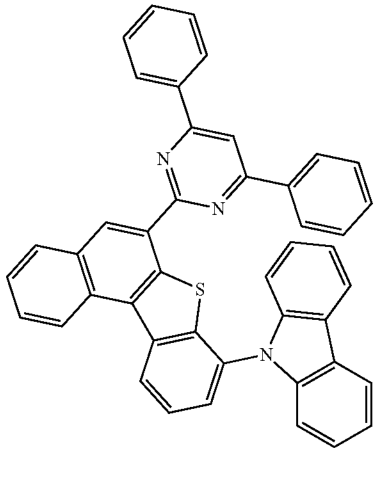
-continued
F98
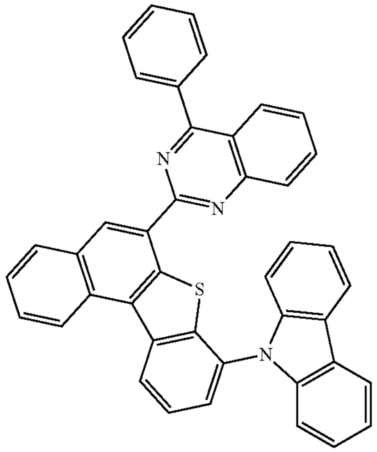
F99
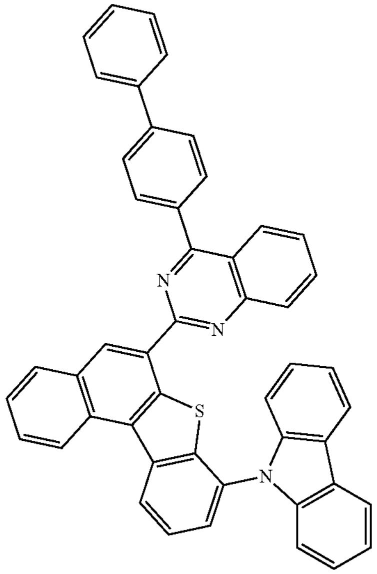
F100
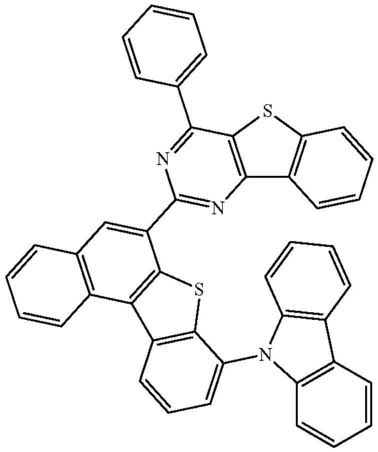

-continued
F101
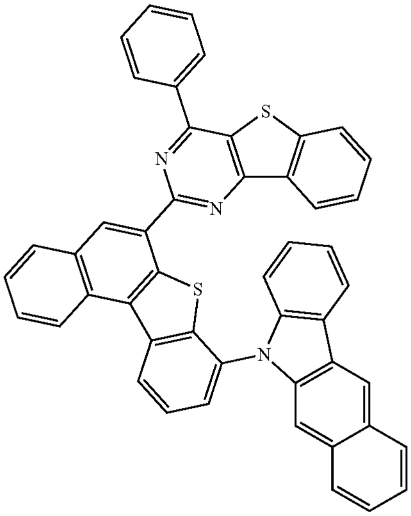
F102
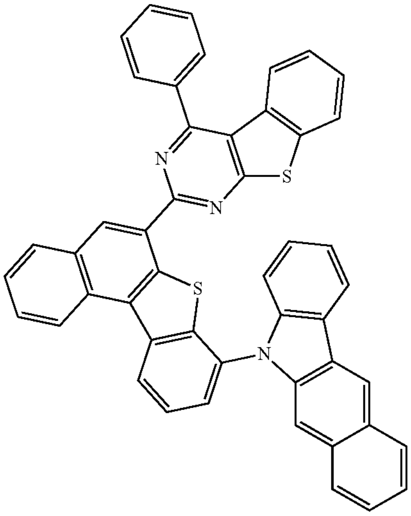
F103
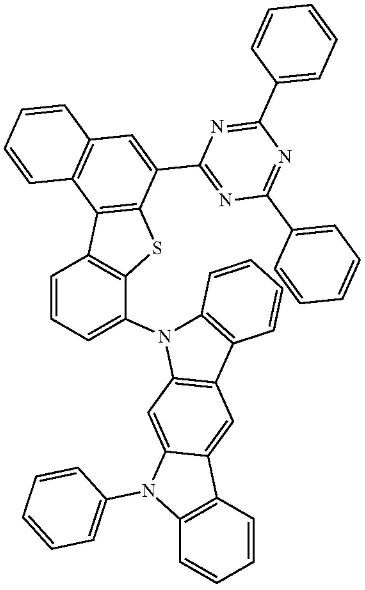
-continued
F104
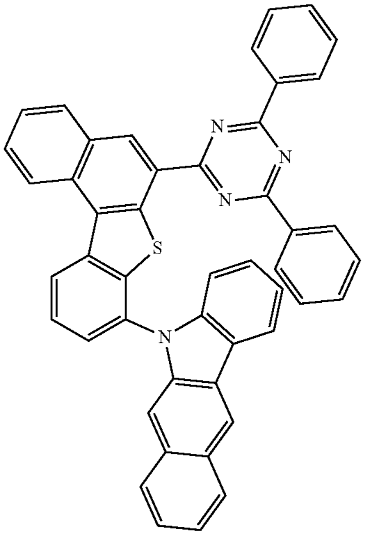
F105
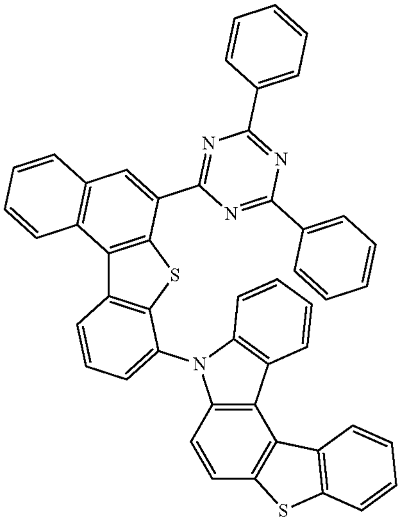
F106
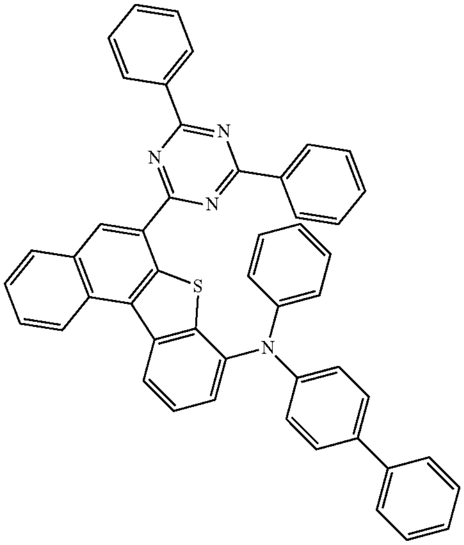

-continued
F107
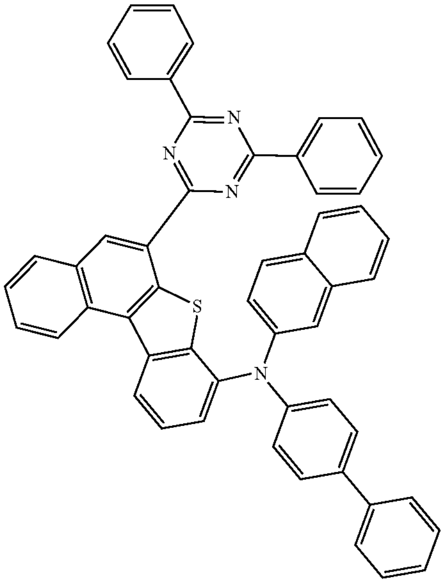
F108
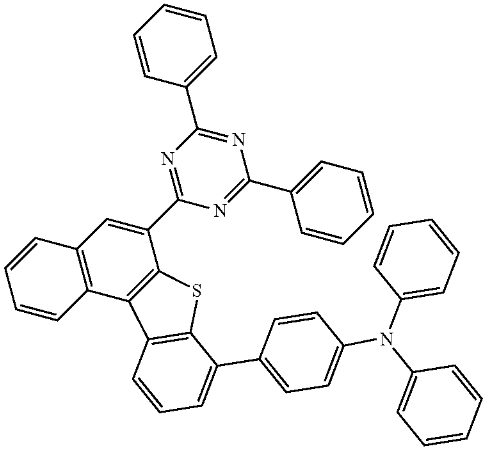
F109
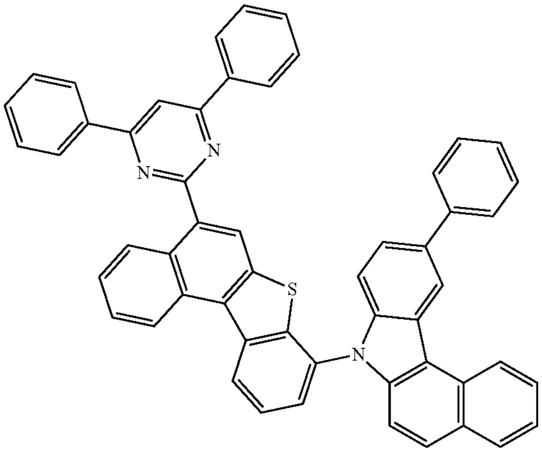
-continued
F110
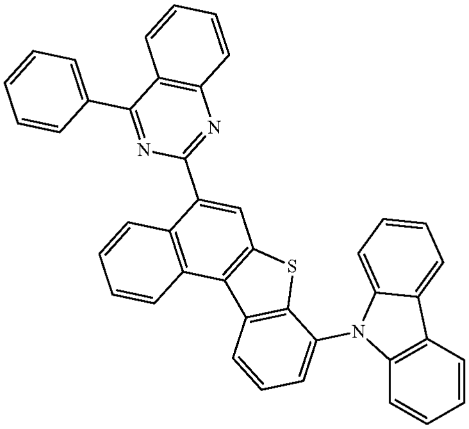
F111
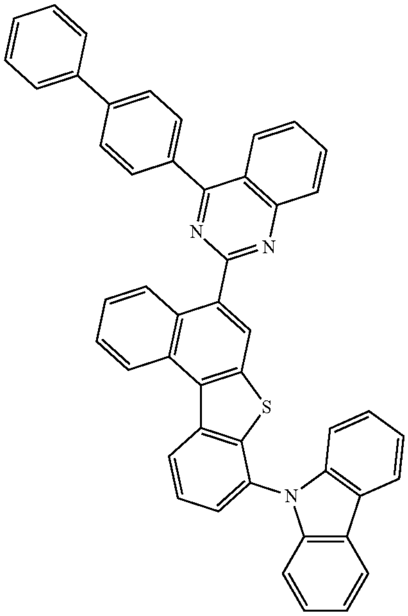
F112
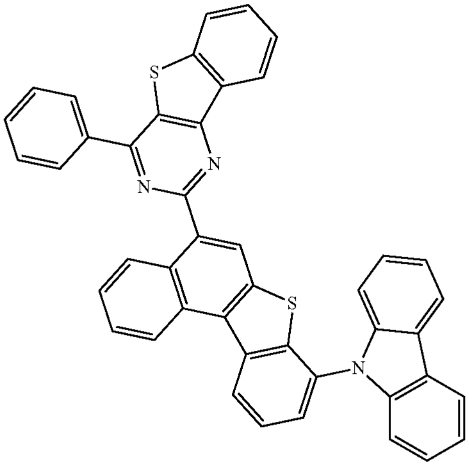

-continued
F113
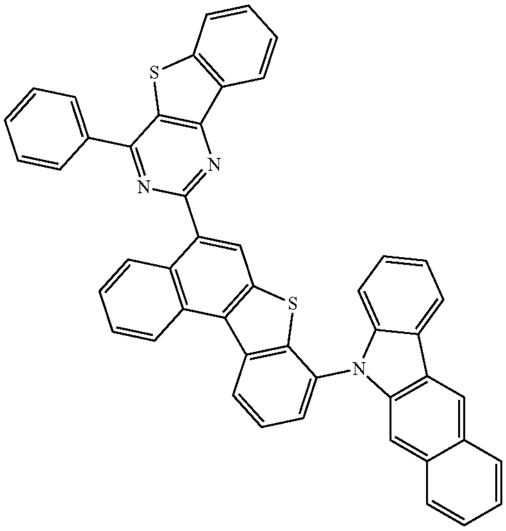
F114
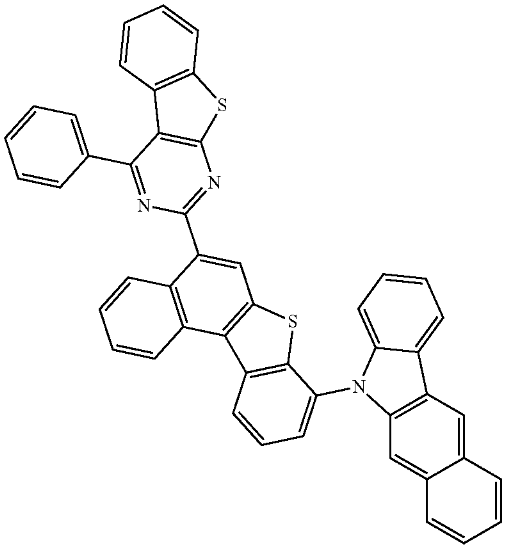
-continued
F115
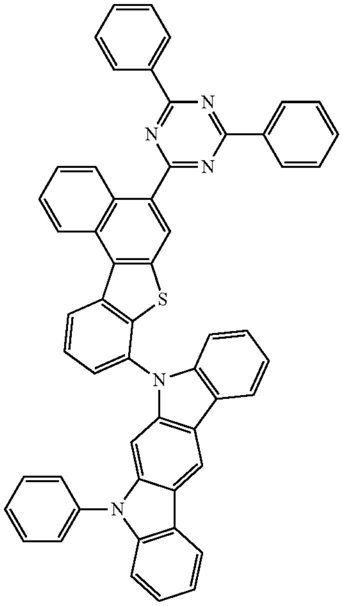
F116
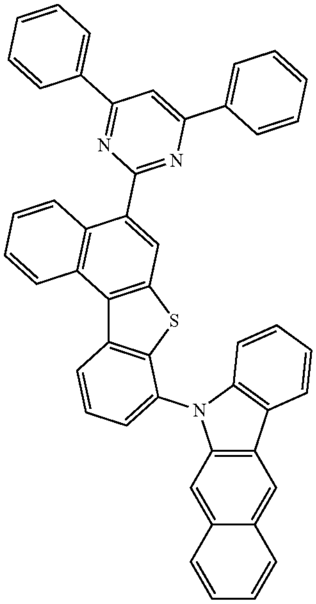

-continued
F117
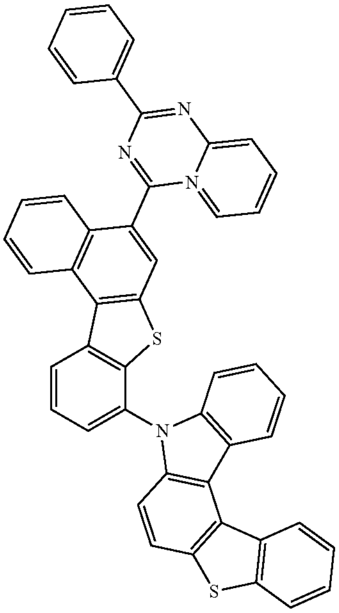
F118
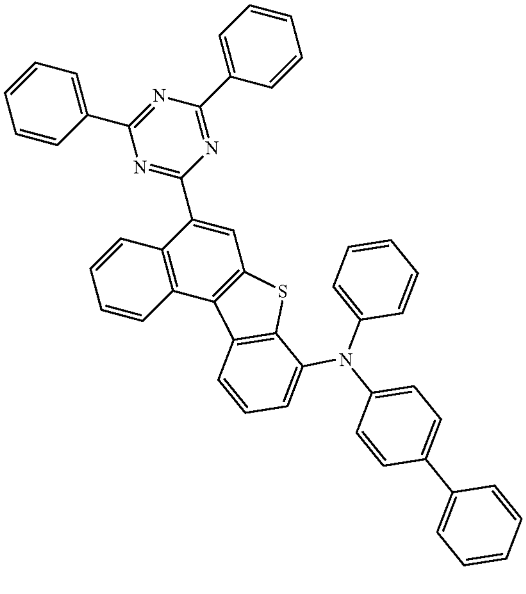
-continued
F119
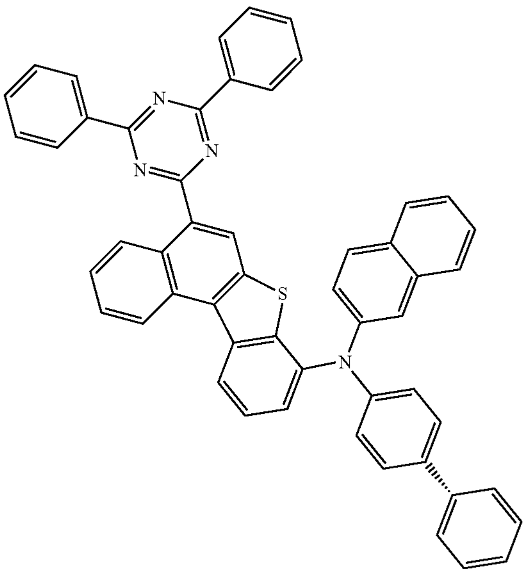
F120
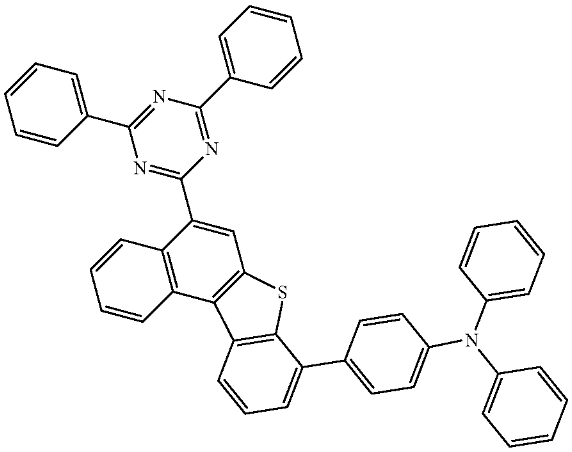
F121
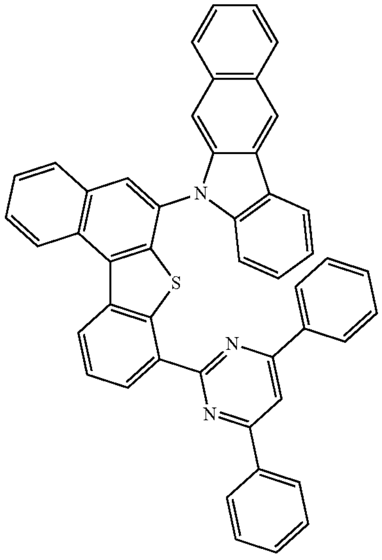

-continued
F122
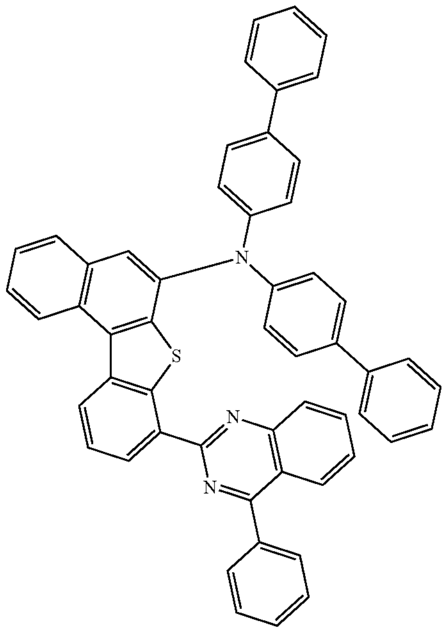
F123
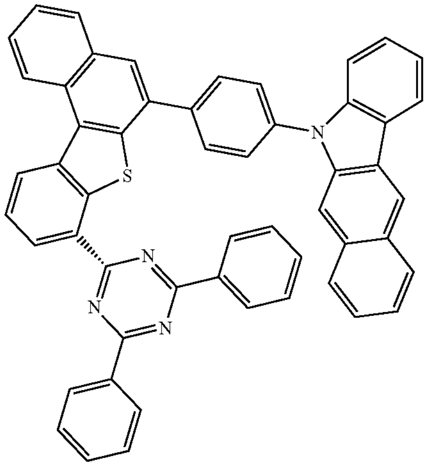
F124
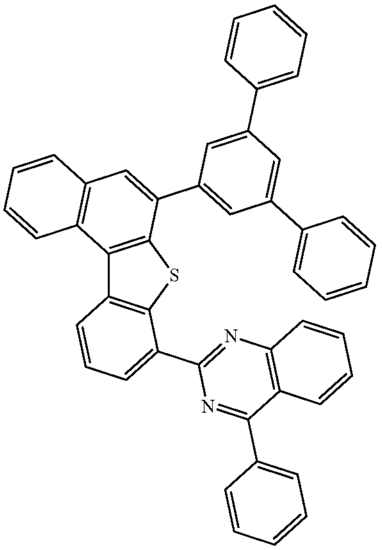
-continued
F125
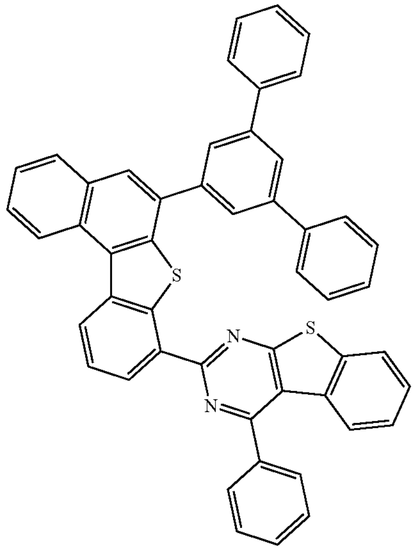
F126
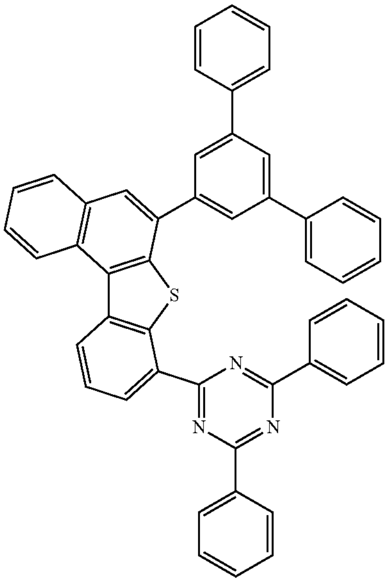
F127
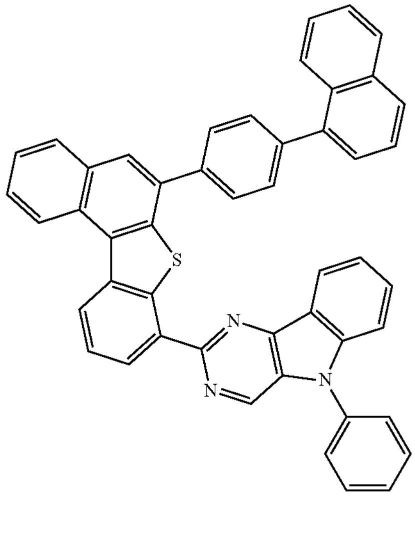

-continued
F128
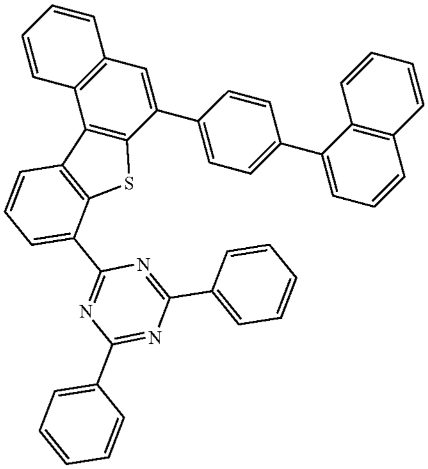
F129
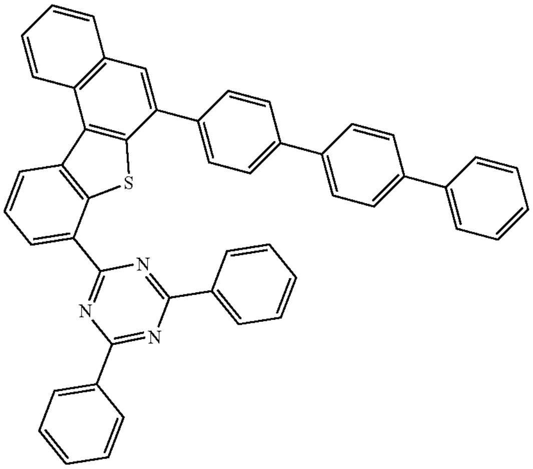
F130
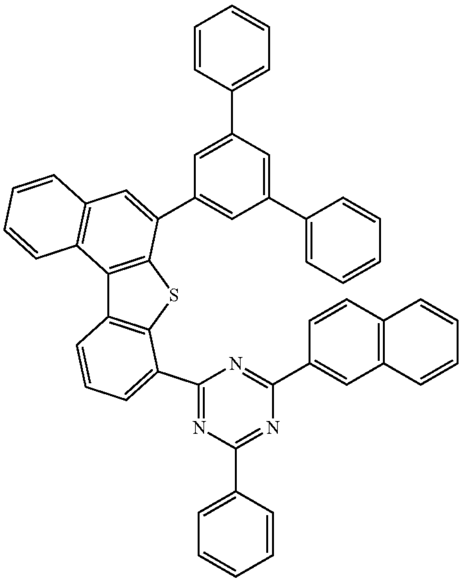
-continued
F131
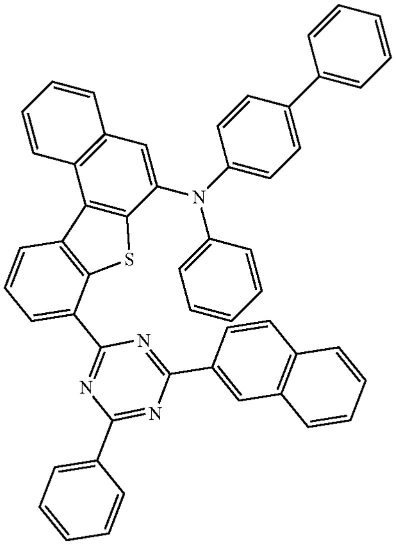
F132
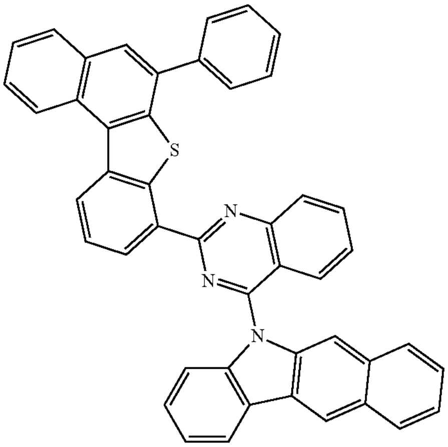
F133
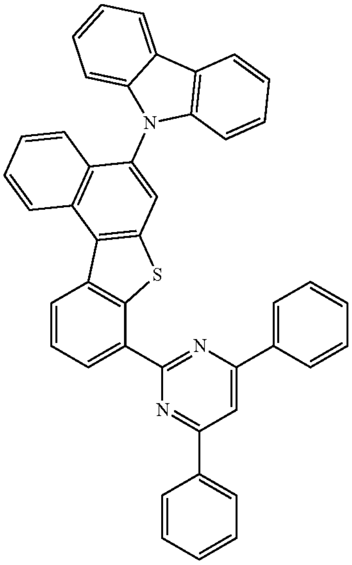

-continued
F134
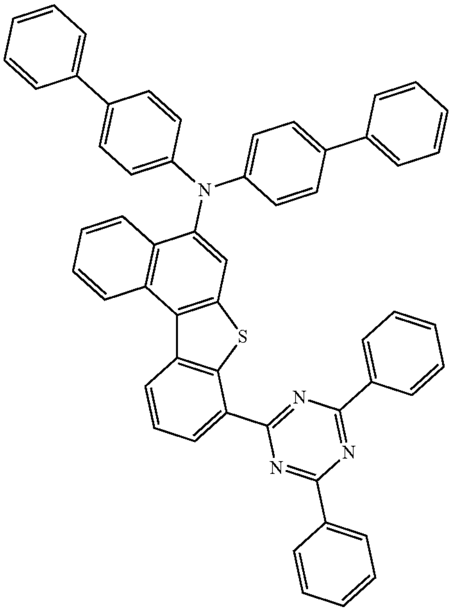
F135
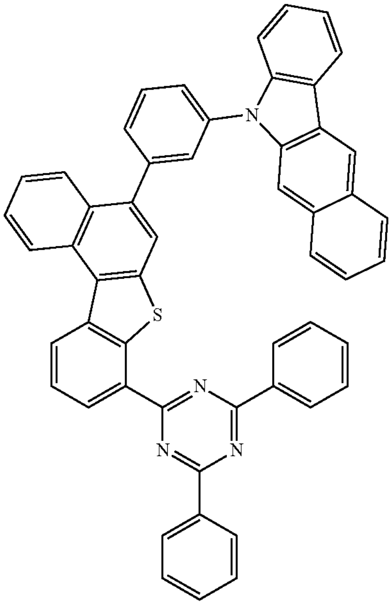
-continued
F136
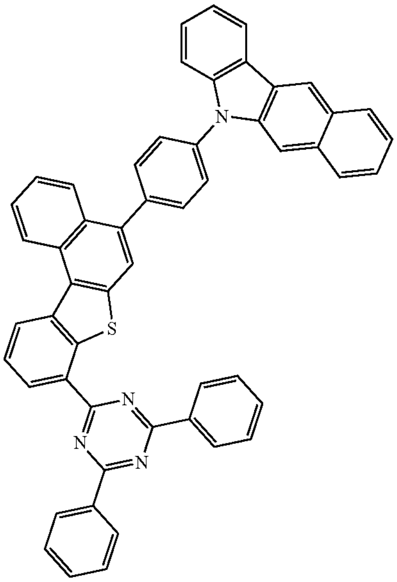
F137
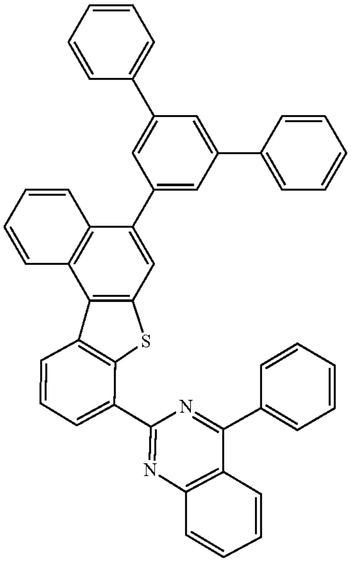

-continued
F138
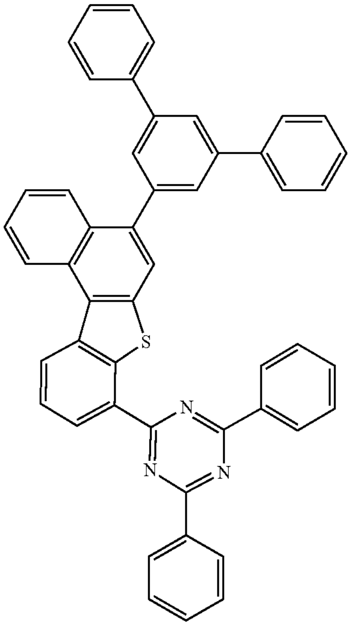
F139
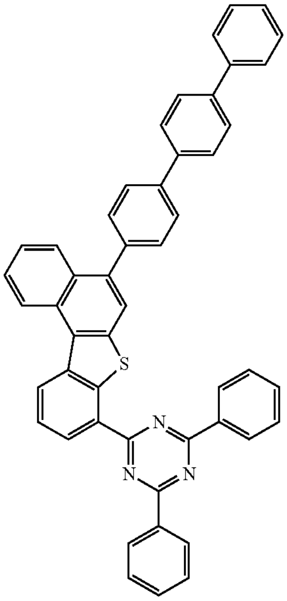
-continued
F140
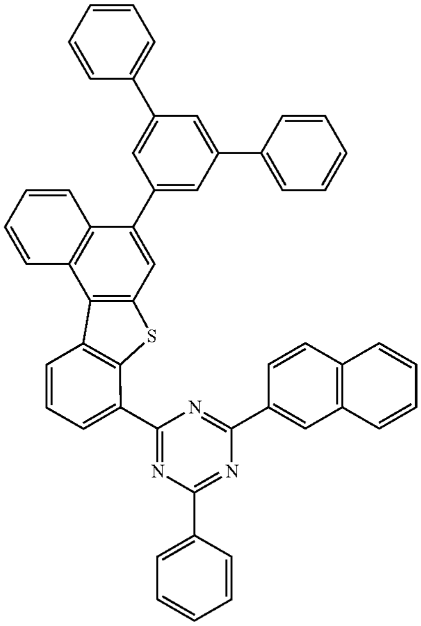
F141
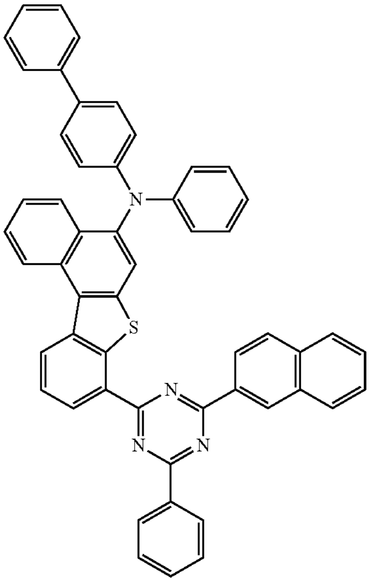

-continued
F142
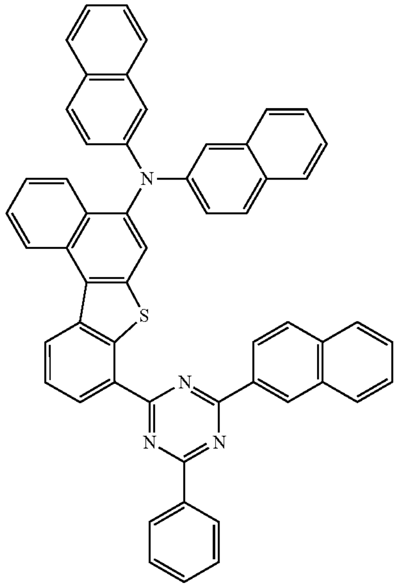
F143
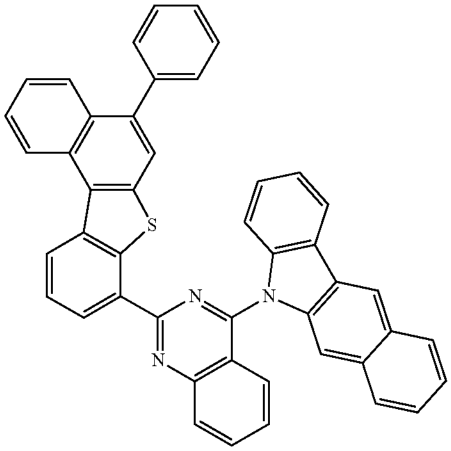
F144
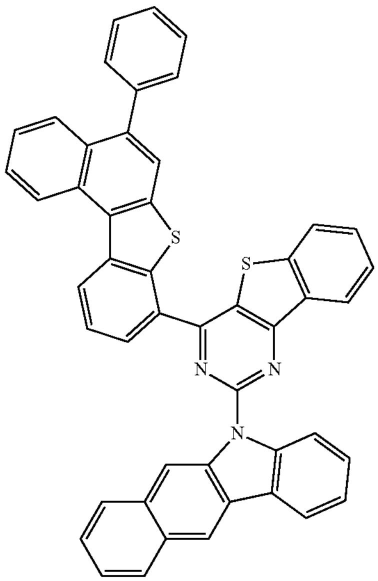
F145
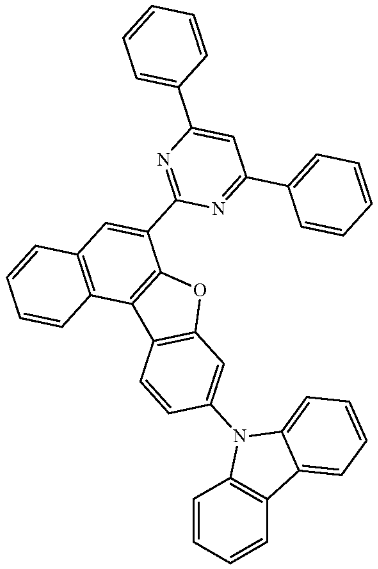
F146
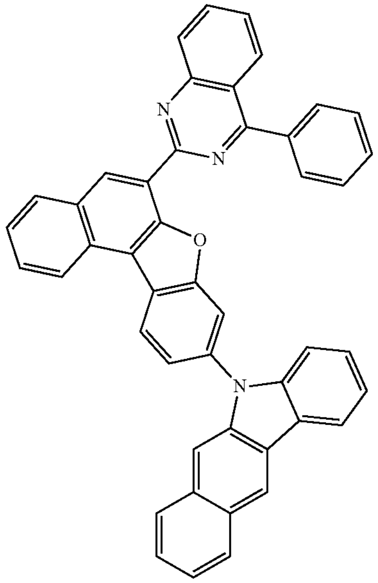

-continued
F147
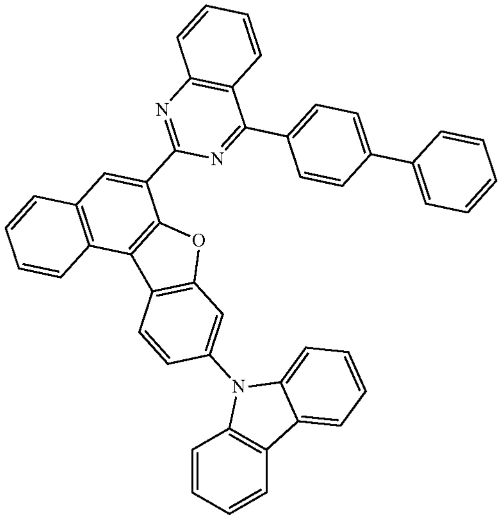
F148
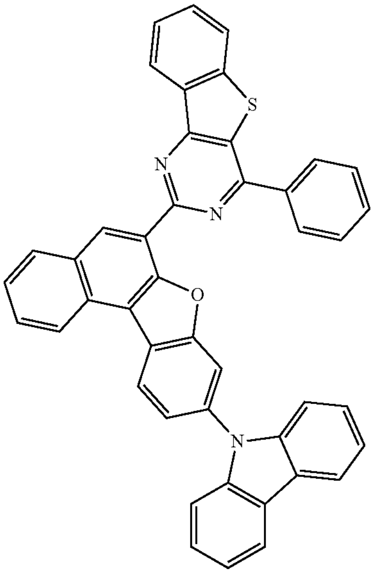
-continued
F149
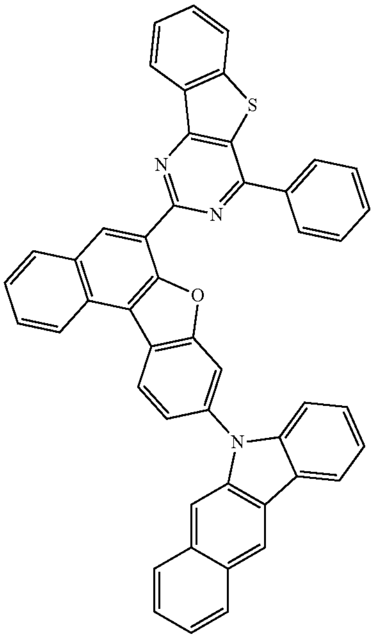
F150
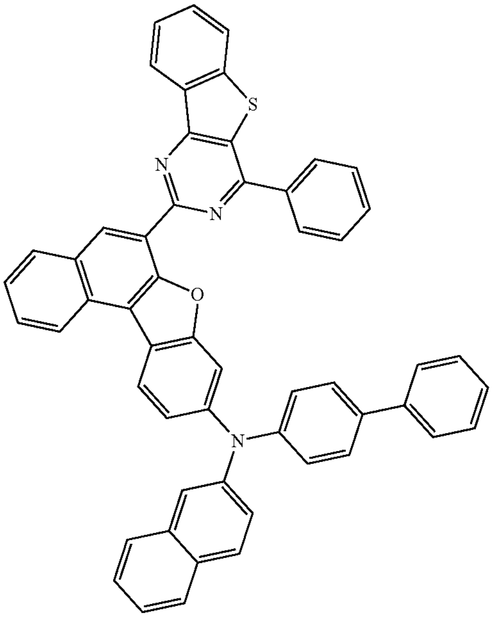

-continued
F151
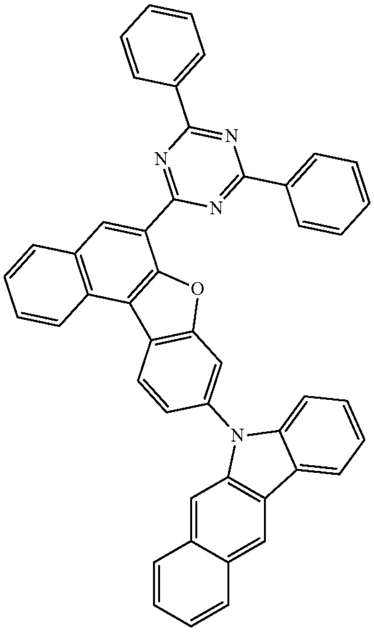
F152
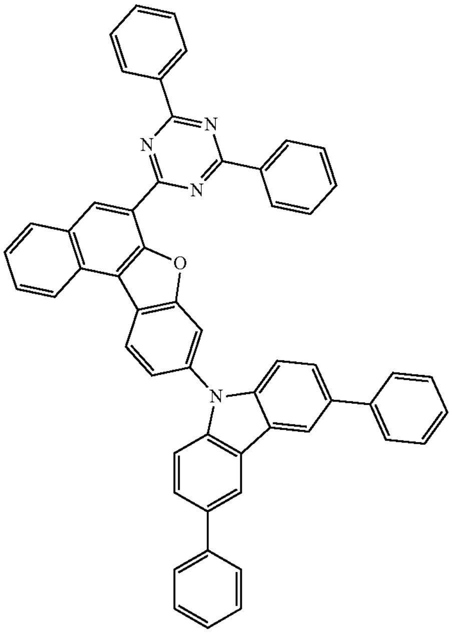
-continued
F153
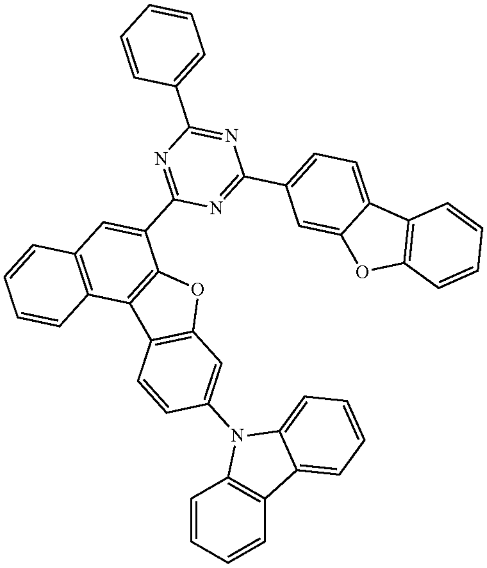
F154
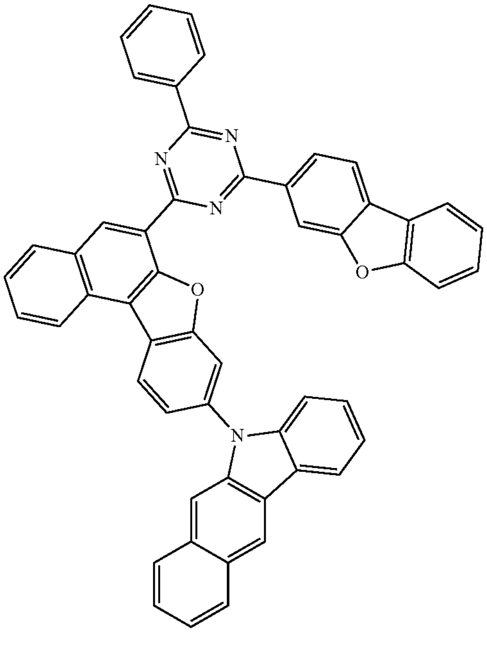

-continued
F155
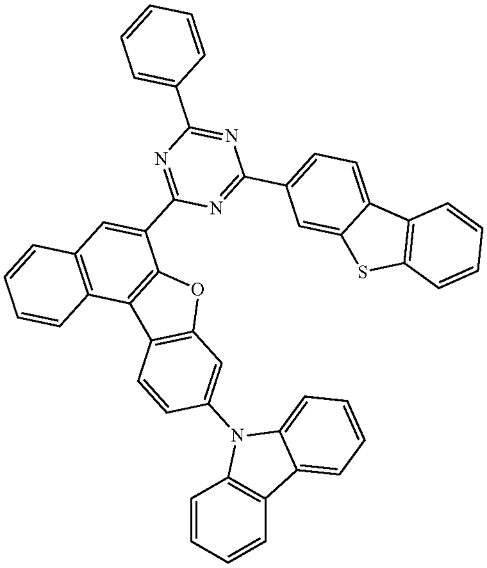
F156
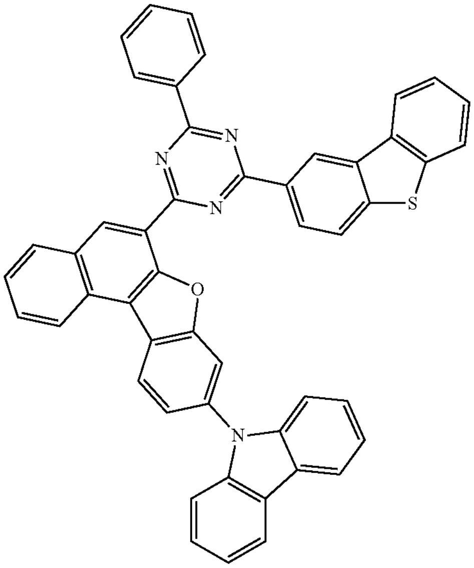
-continued
F157
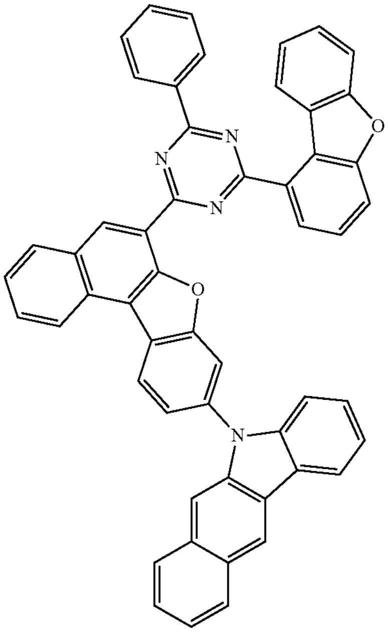
F158
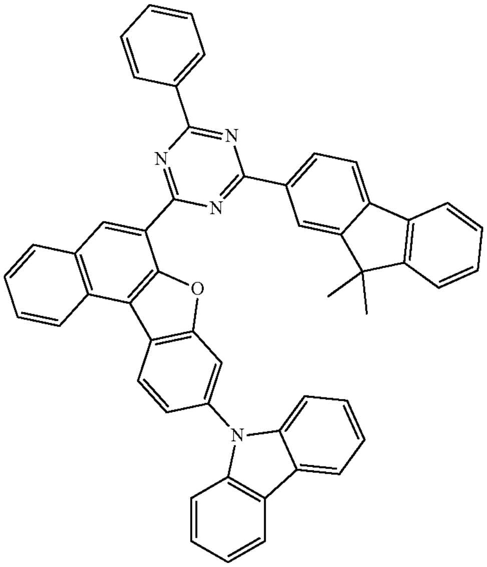

-continued
F159
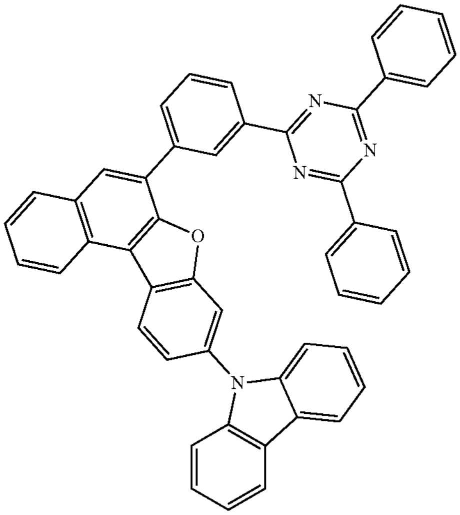
F160
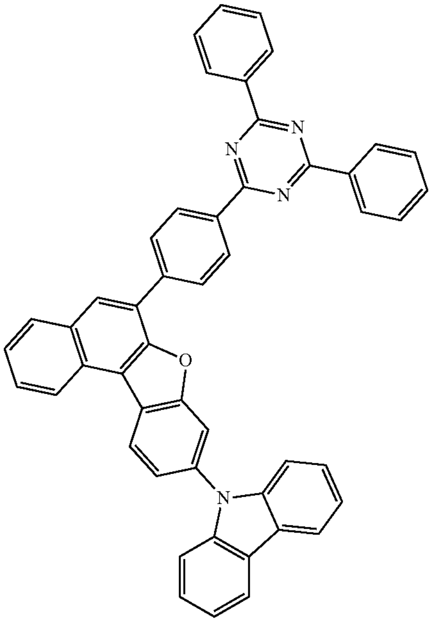
-continued
F161
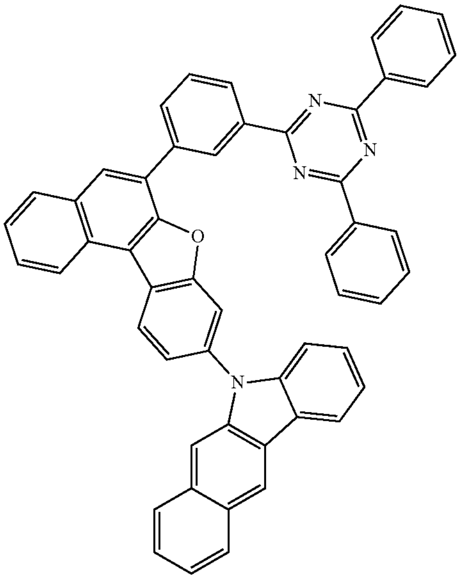
F162
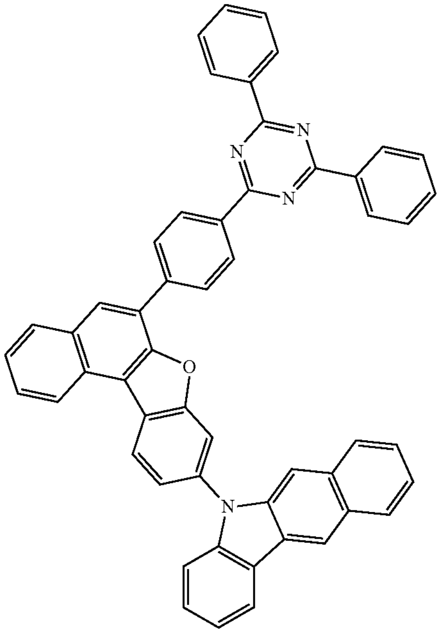

-continued
F163
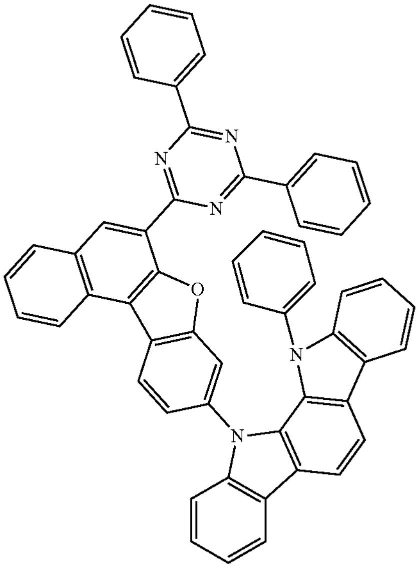
F164
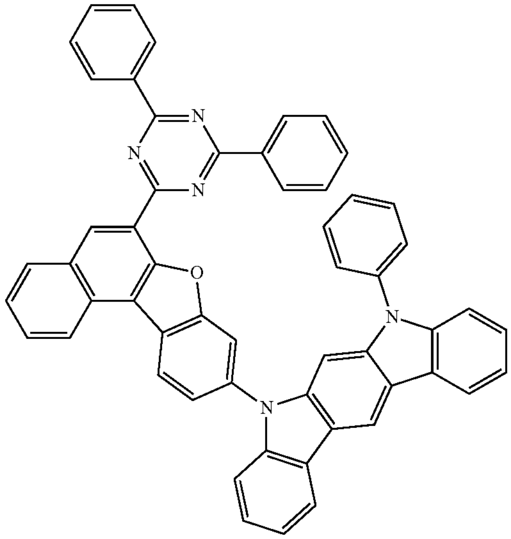
-continued
F165
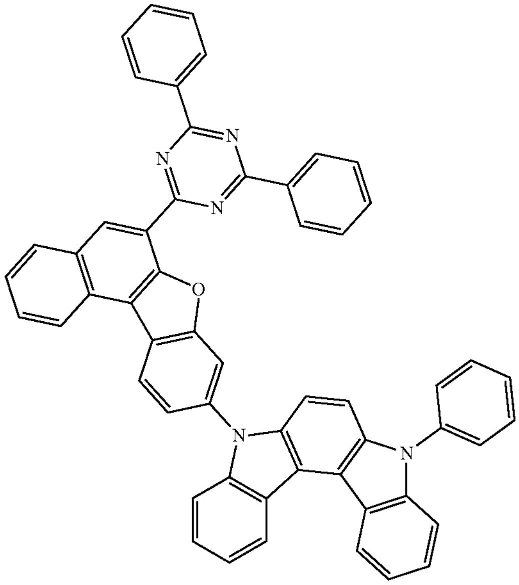
F166
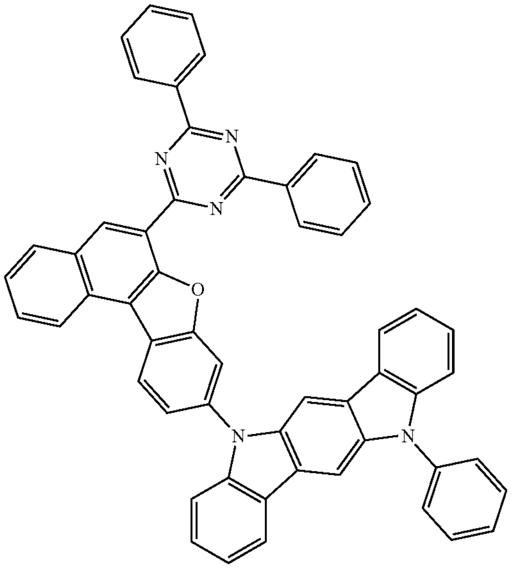

-continued
F167
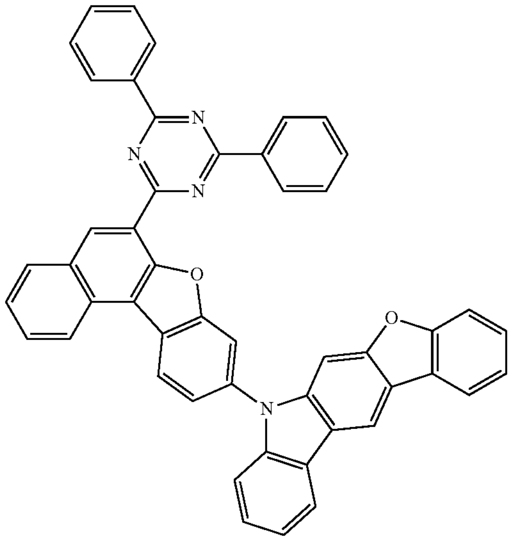
F168
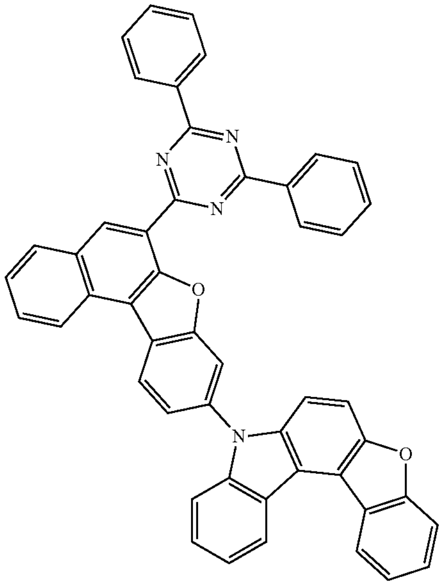
-continued
F169
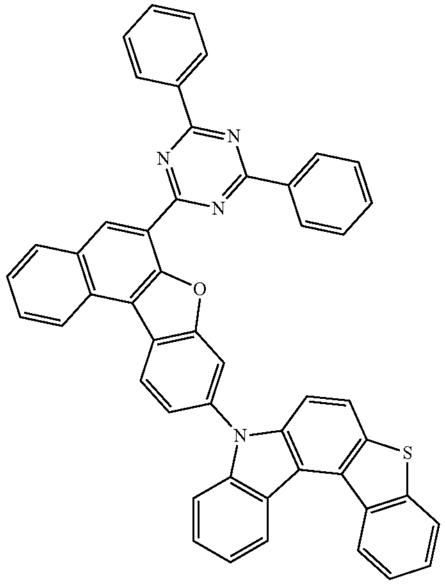
F170
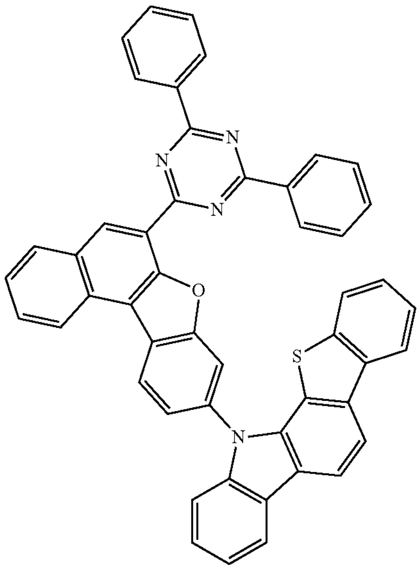

F171
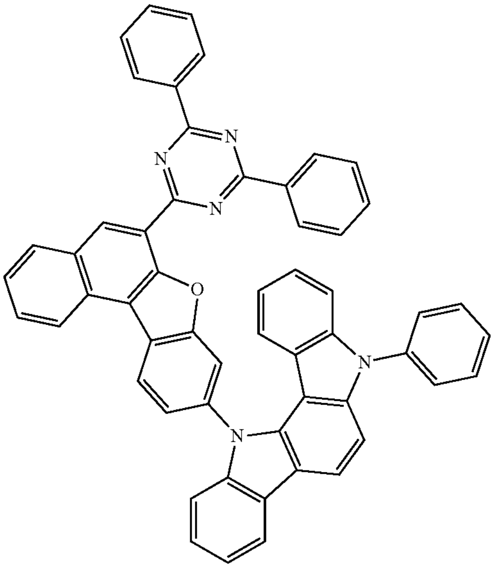
F172
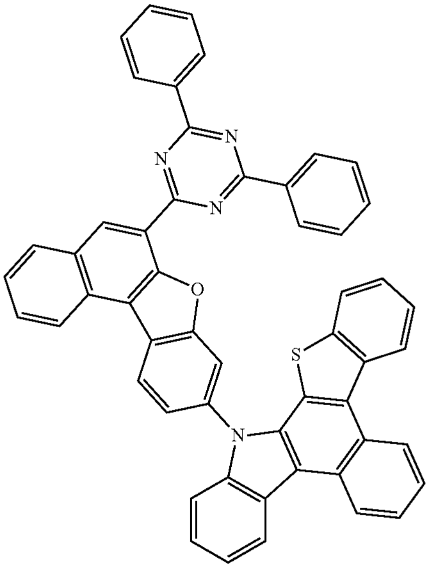
F173
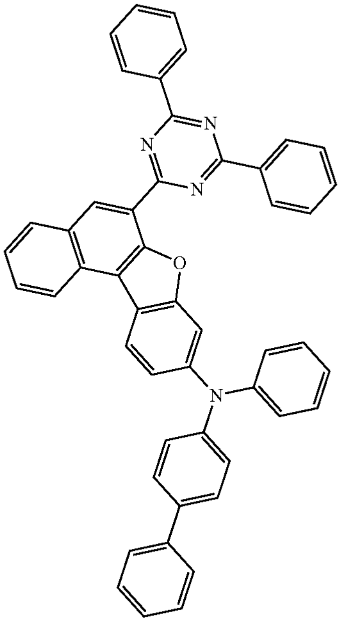
F174
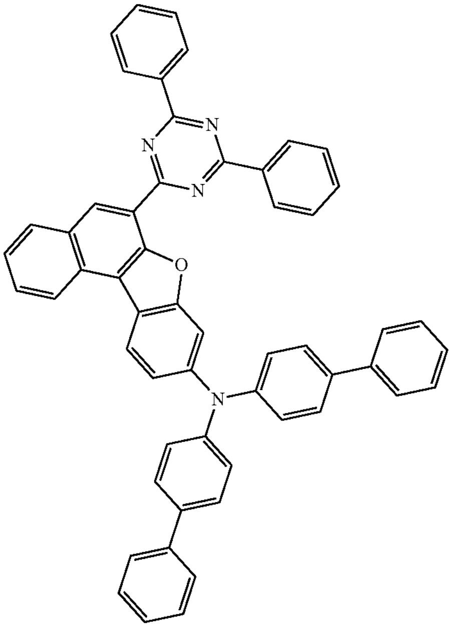

-continued
F175
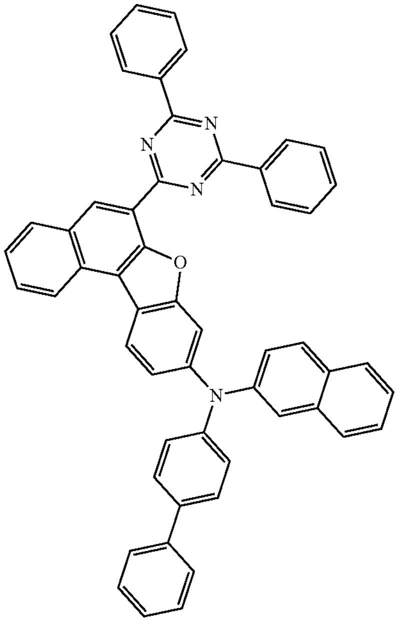
F176
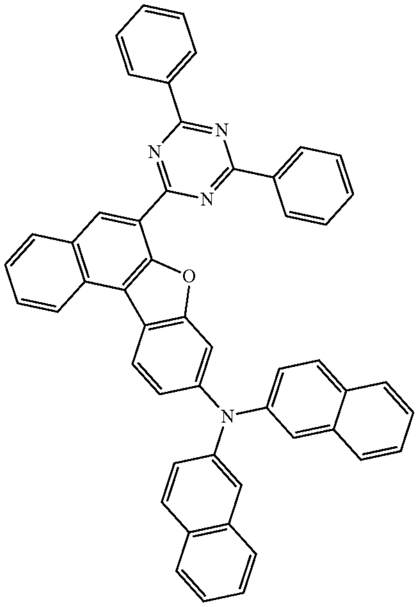
-continued
F177
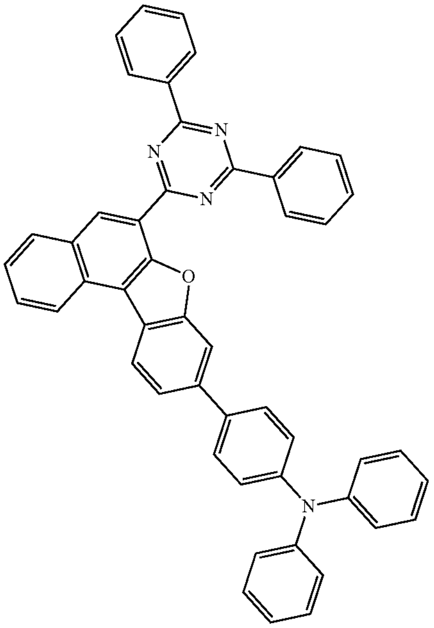
F178
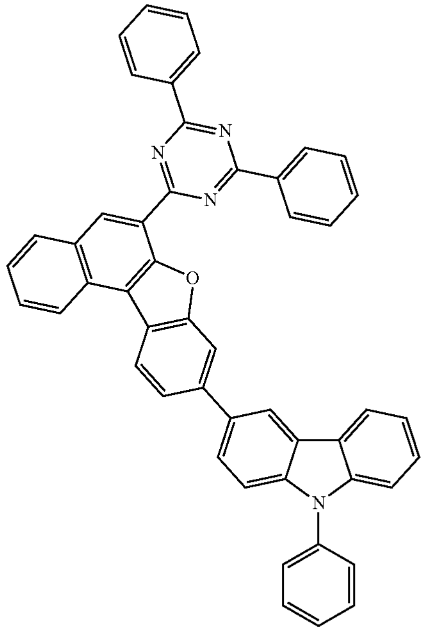

-continued
F179
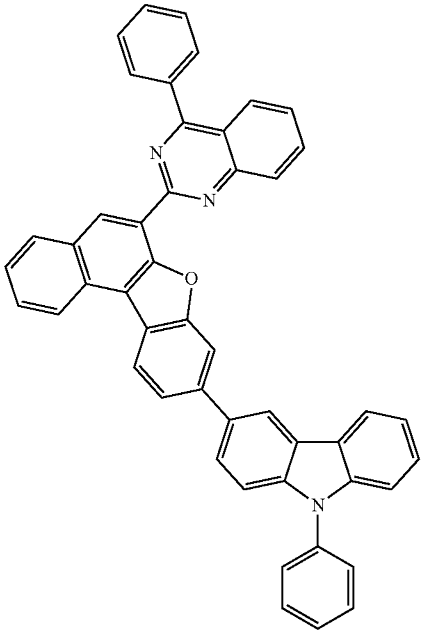
F180
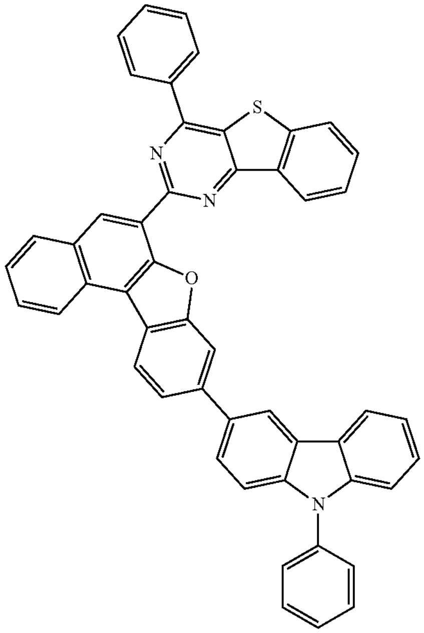
-continued
F181
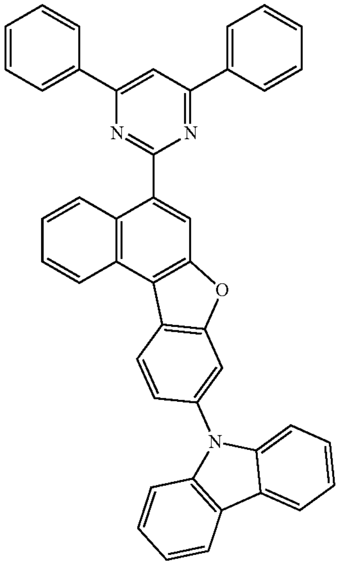
F182
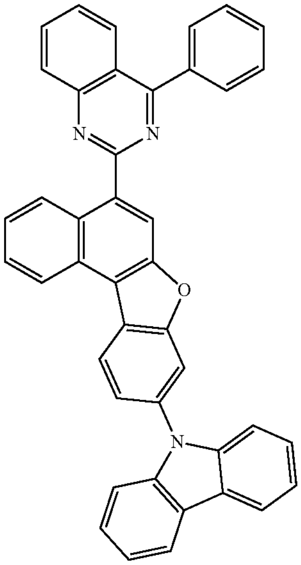

-continued
F183
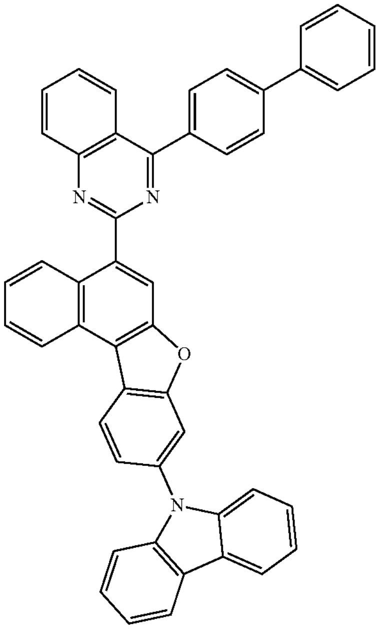
F184
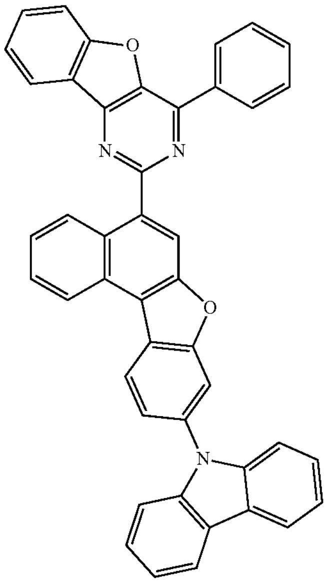
-continued
F185
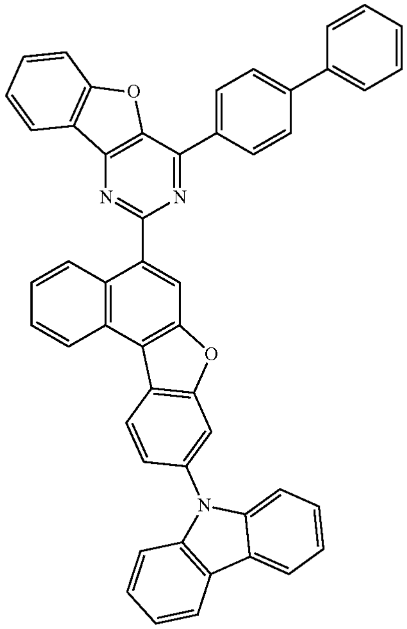
F186
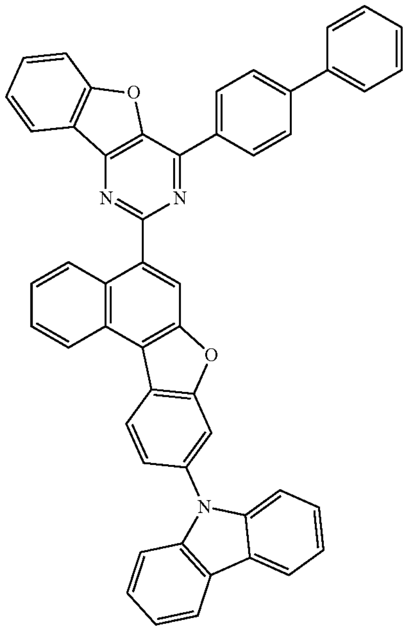

-continued
F187
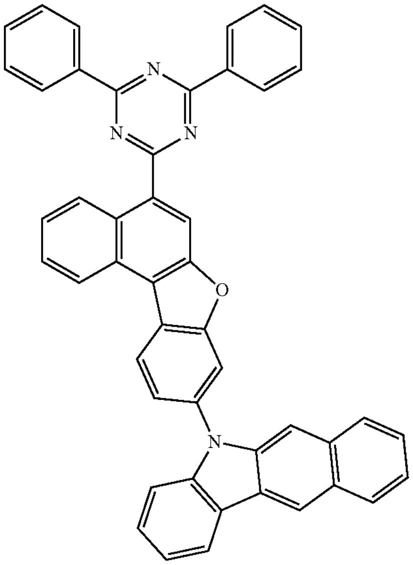
F188
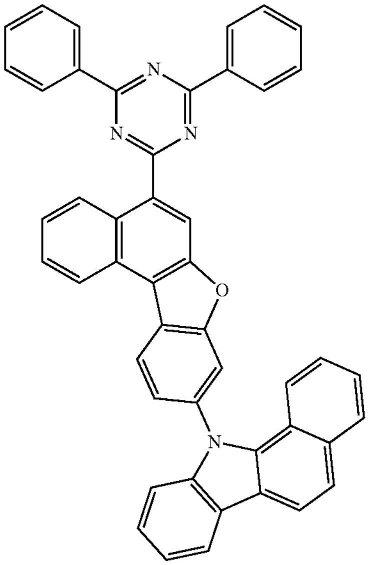
-continued
F189
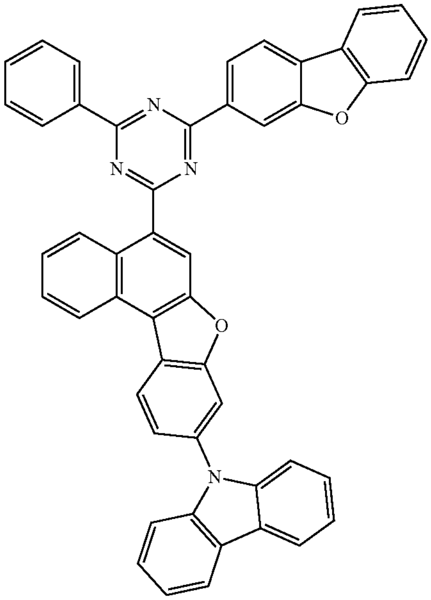
F190
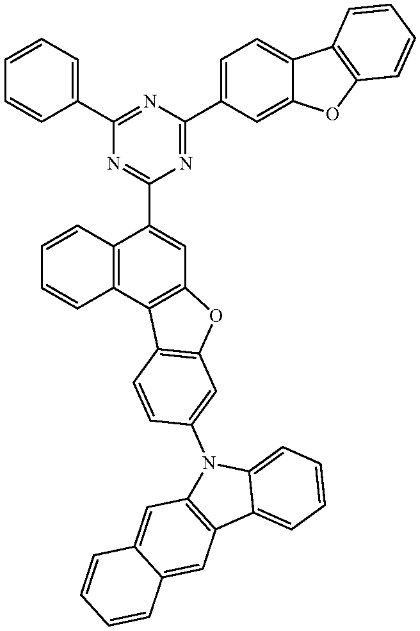

-continued
F191
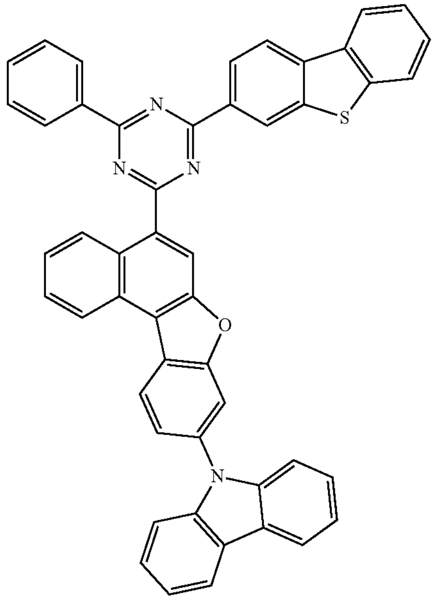
F192
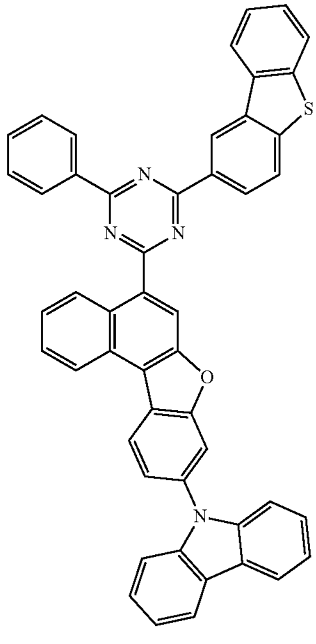
-continued
F193
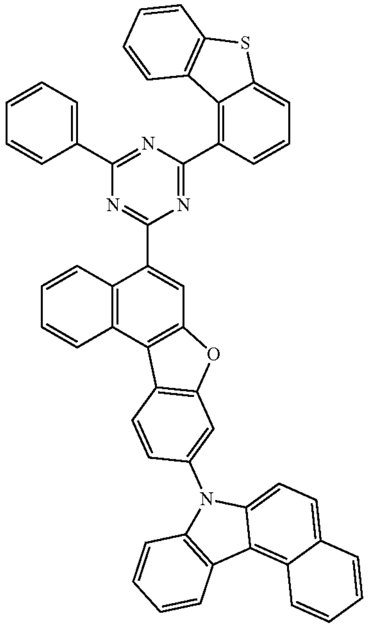
F194
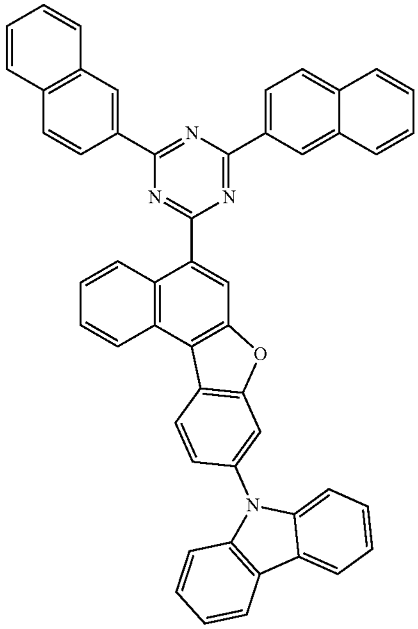

-continued
F195
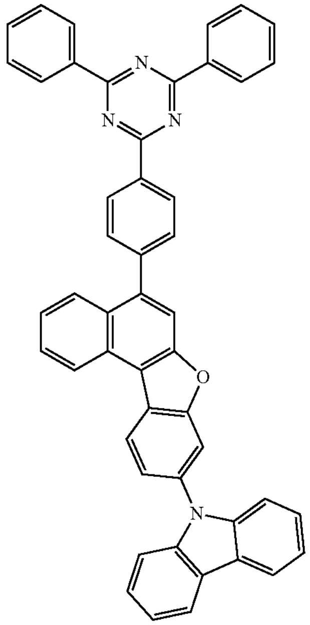
F196
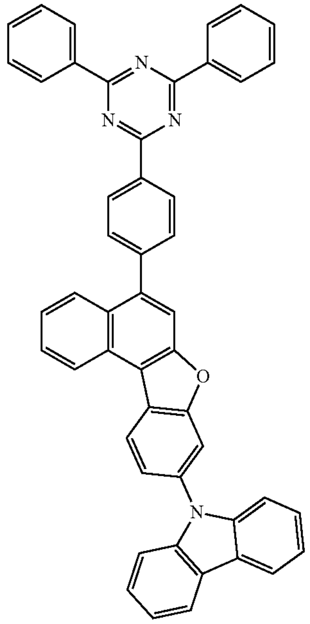
-continued
F197
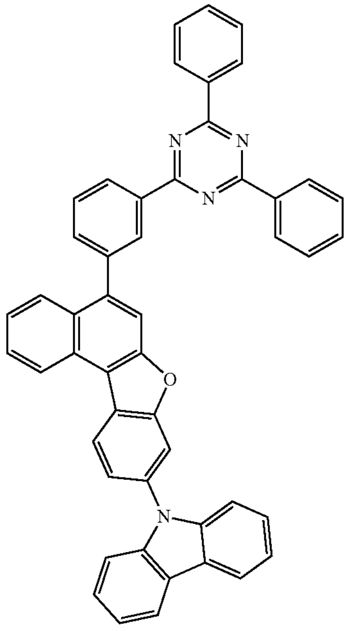
F198
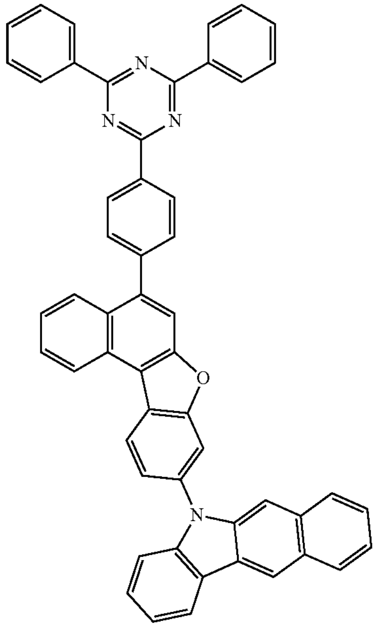

-continued
F199
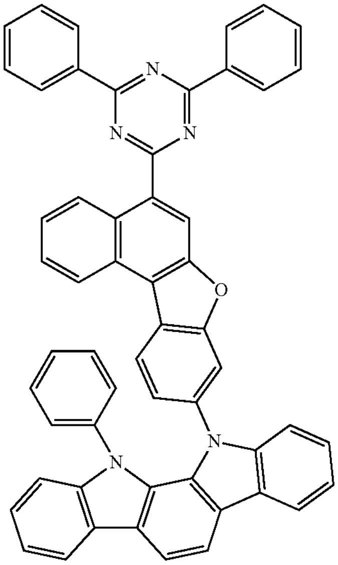
-continued
F201
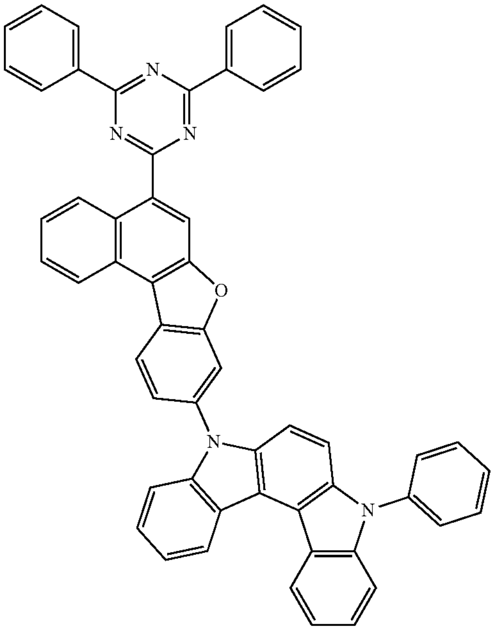
F200
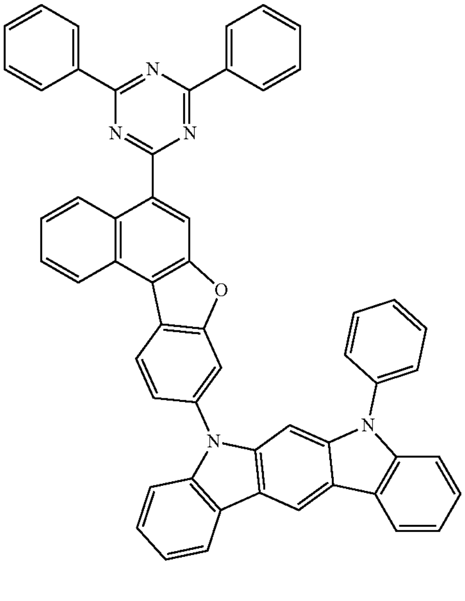
F202
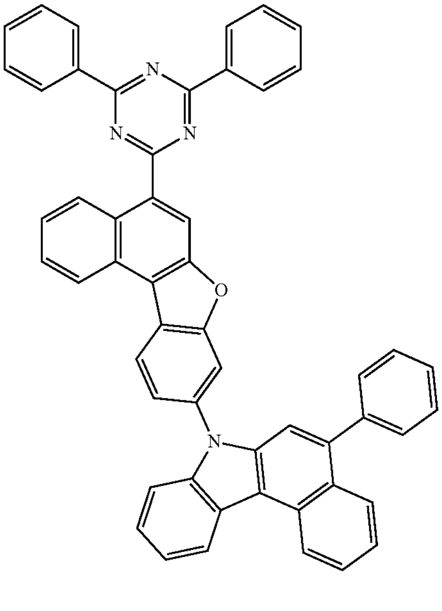

-continued
F203
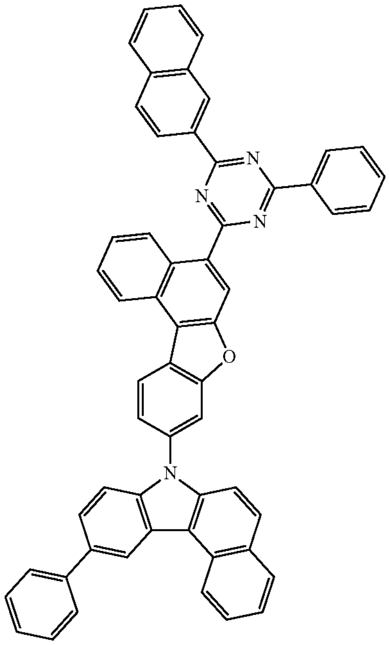
F204
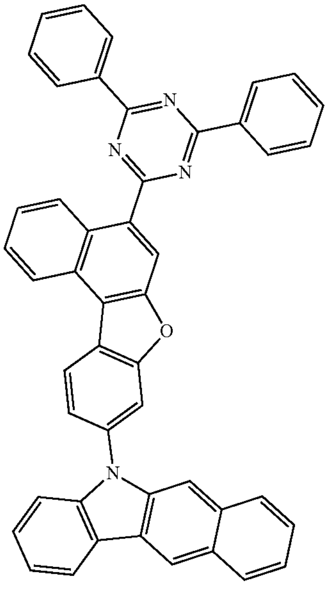
-continued
F205
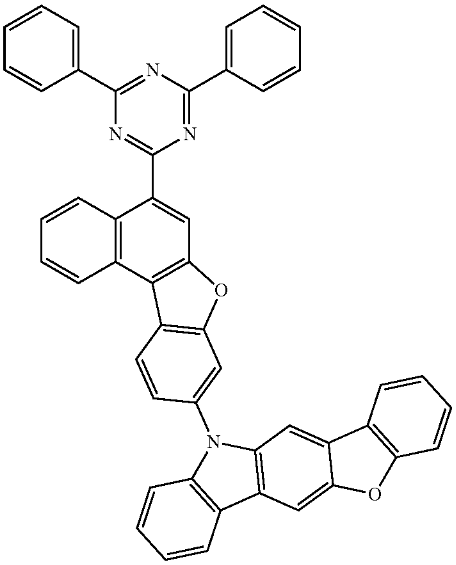
F206
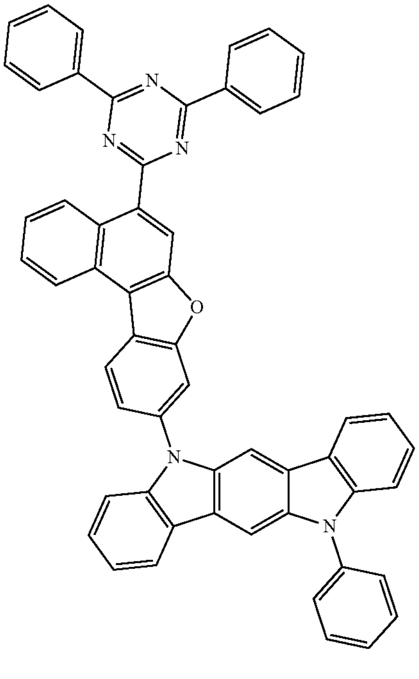

-continued
F207
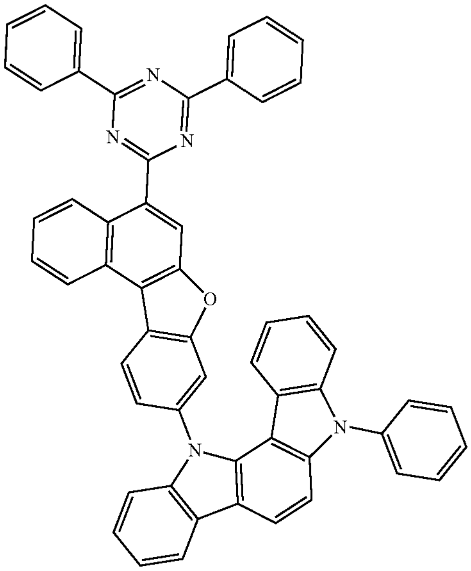
F208
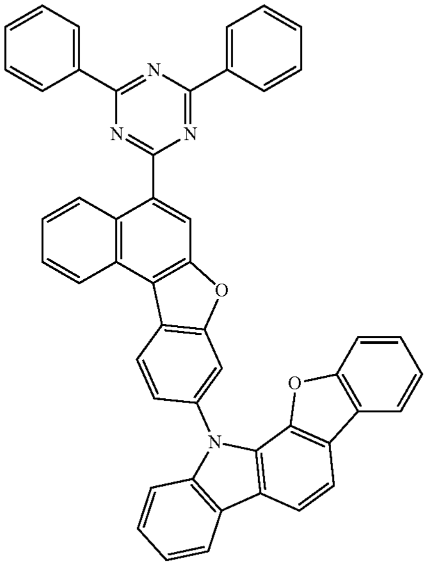
-continued
F209
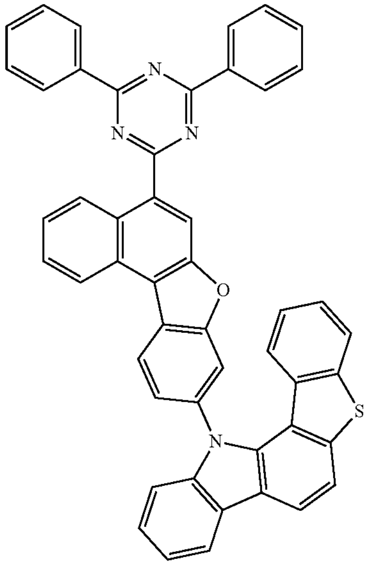
F210
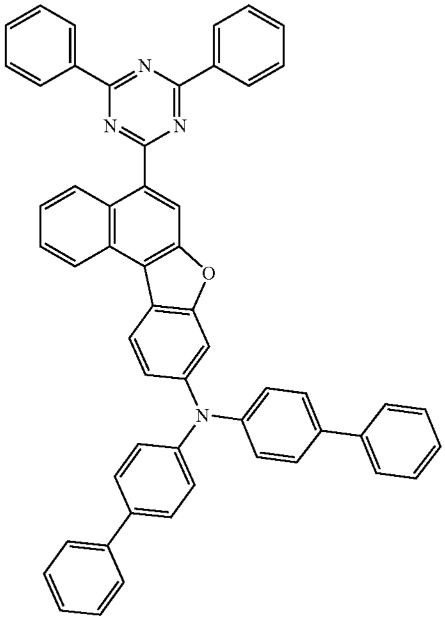

-continued
F211
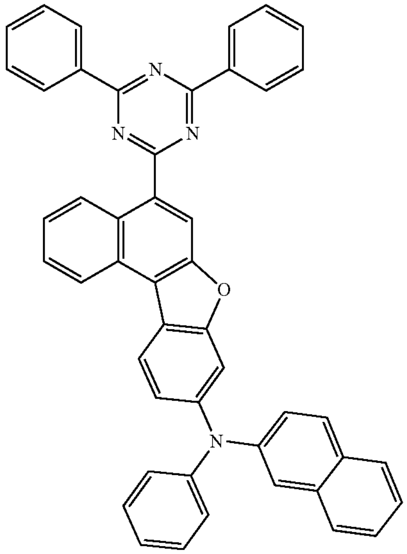
F212
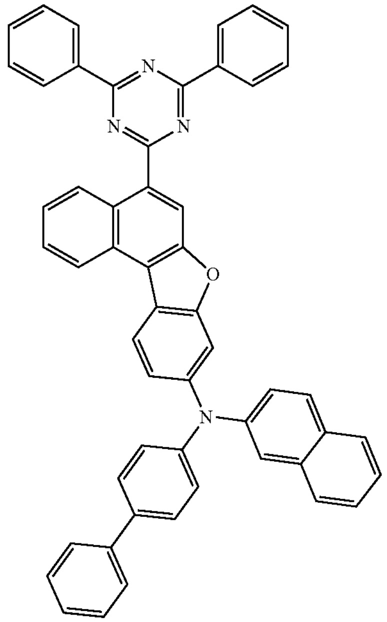
-continued
F213
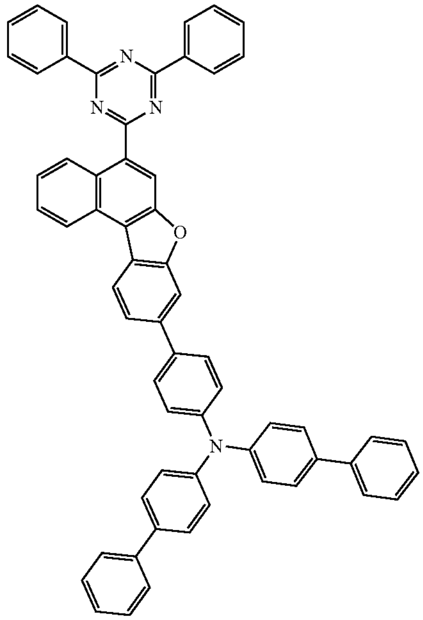
F214
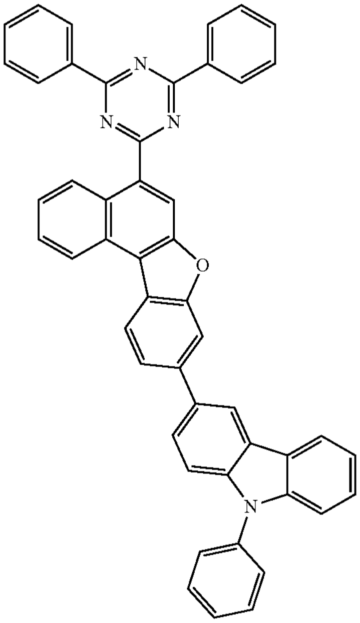

-continued
F215
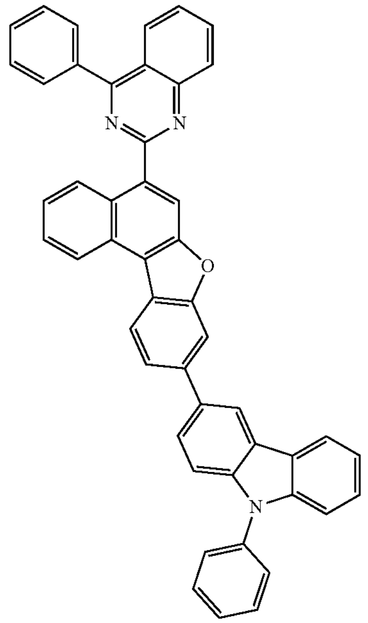
F216
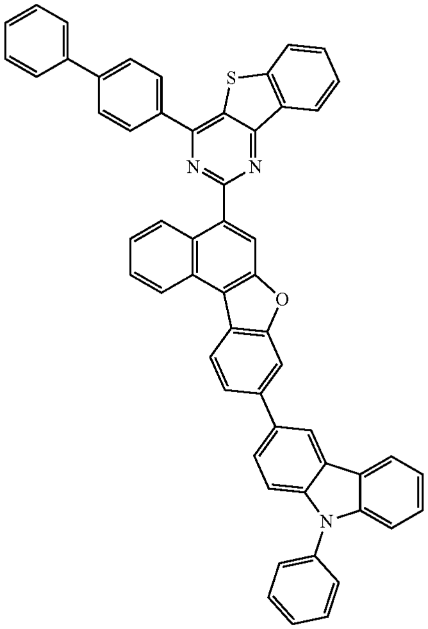
-continued
F217
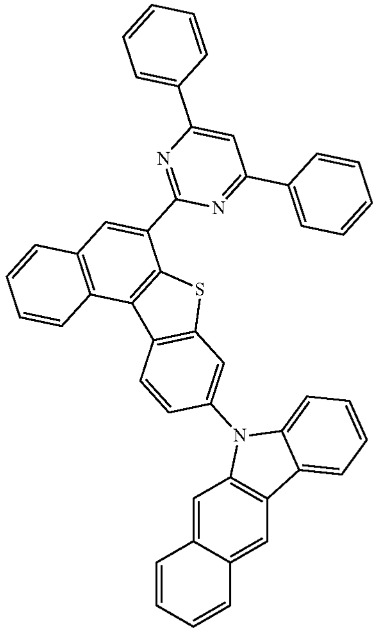
F218
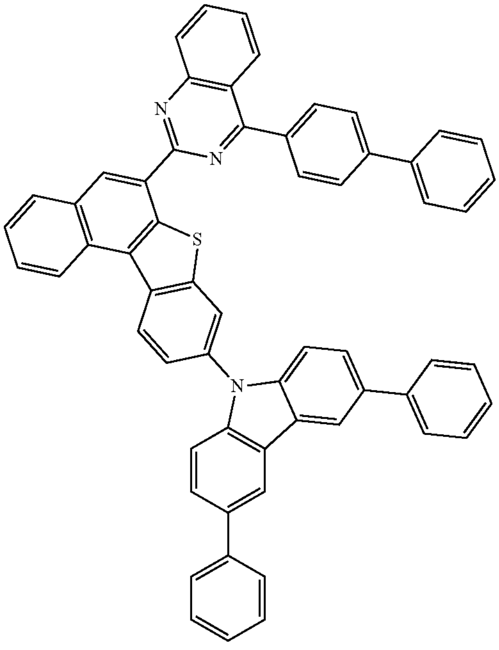

-continued
F219
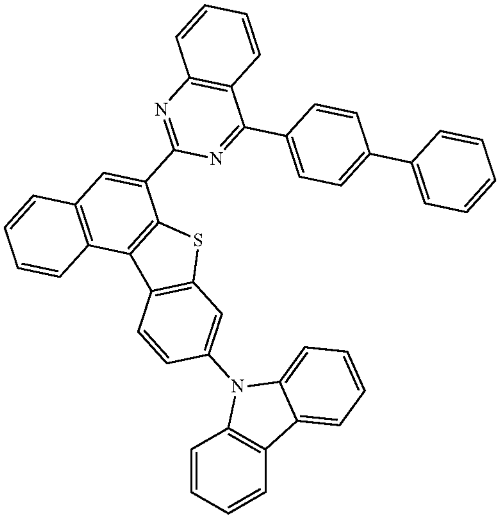
F220
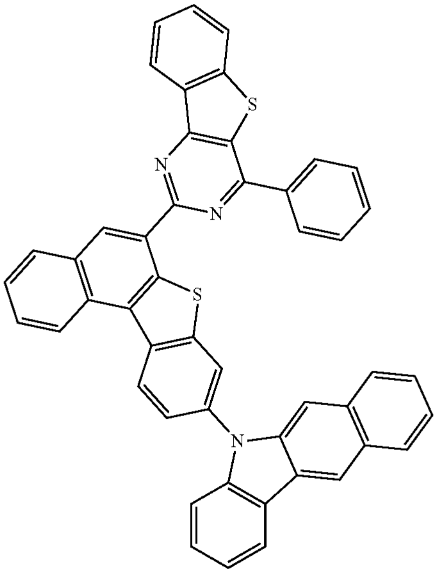
F221
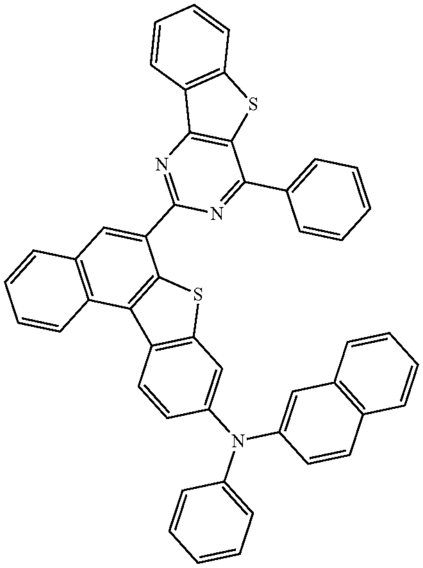
-continued
F222
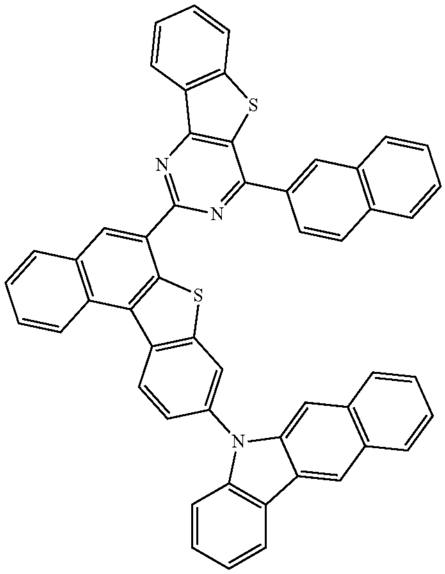
F223
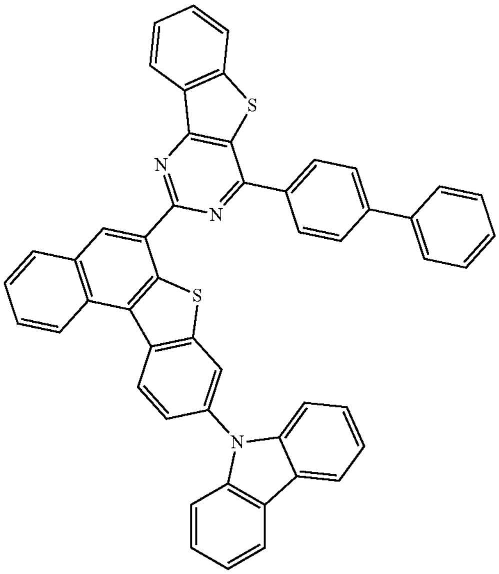

-continued
F224
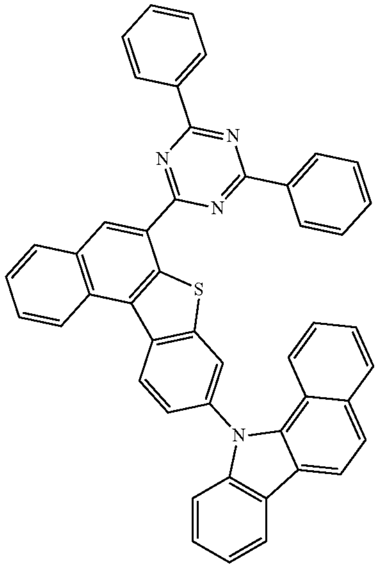
F225
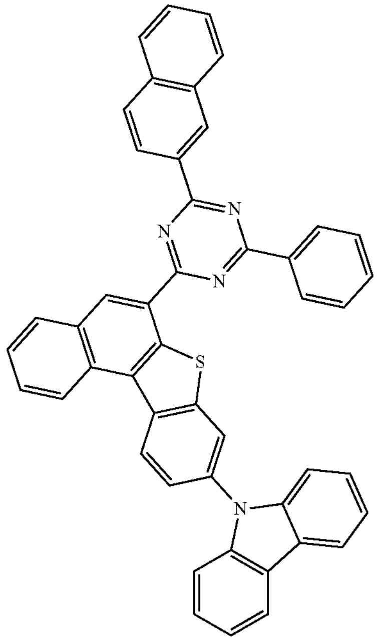
-continued
F226
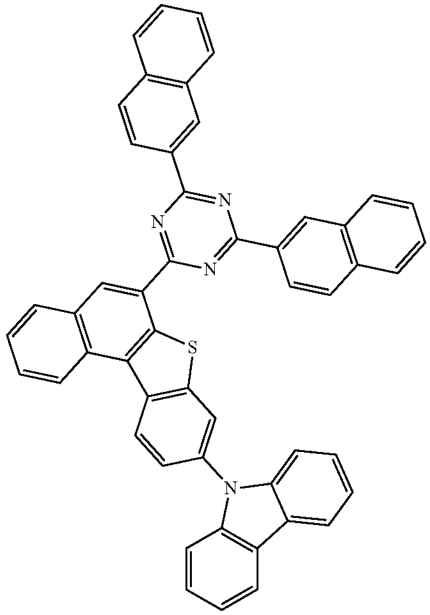
F227
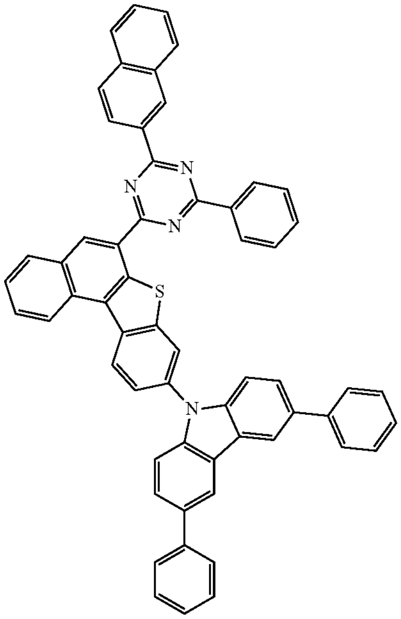

-continued
F228
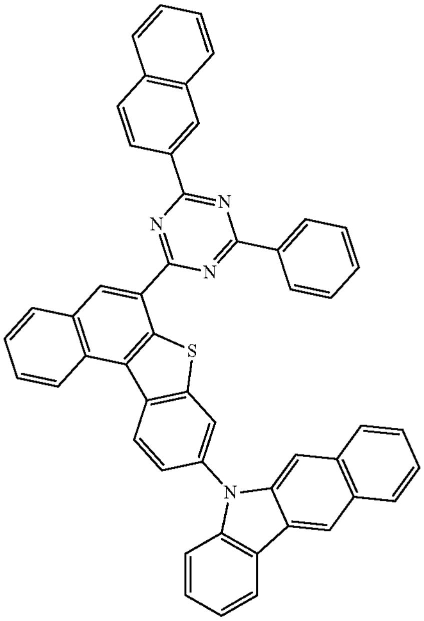
F229
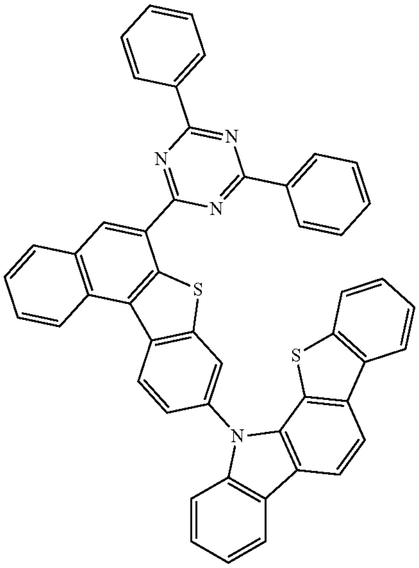
-continued
F230
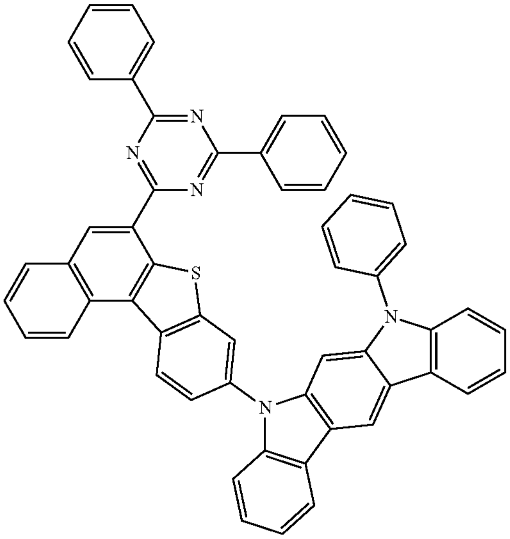
F231
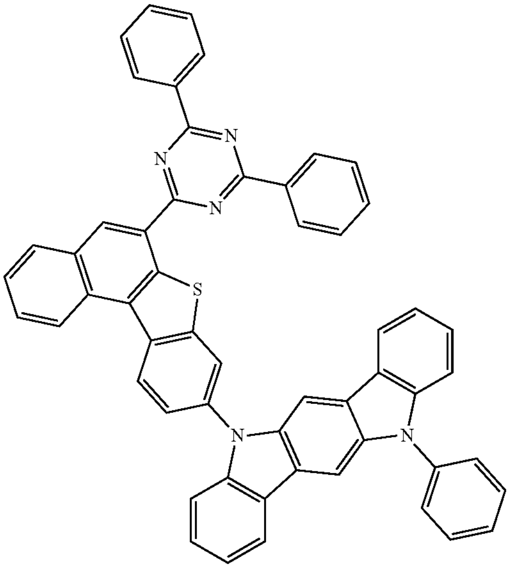

-continued
F232
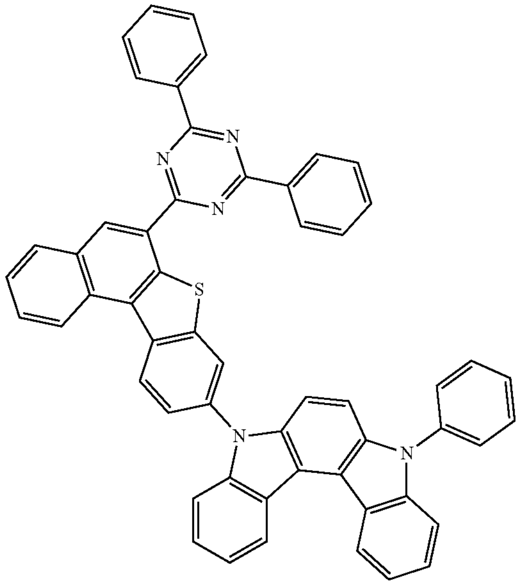
F233
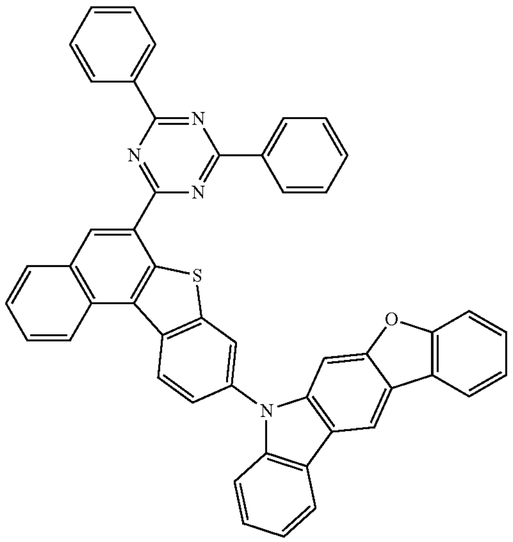
-continued
F234
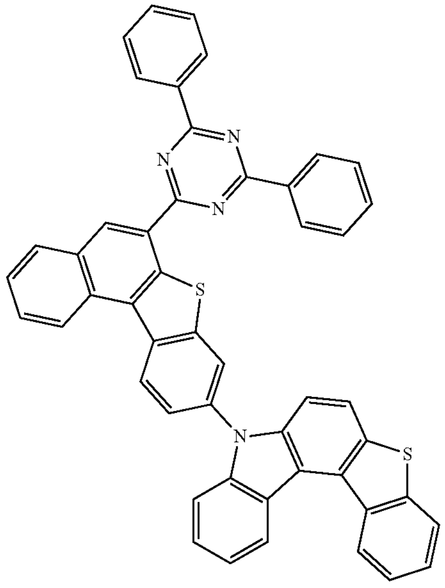
F235
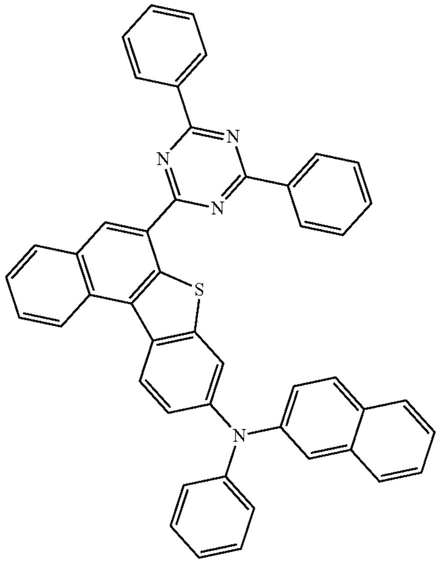

-continued
F236
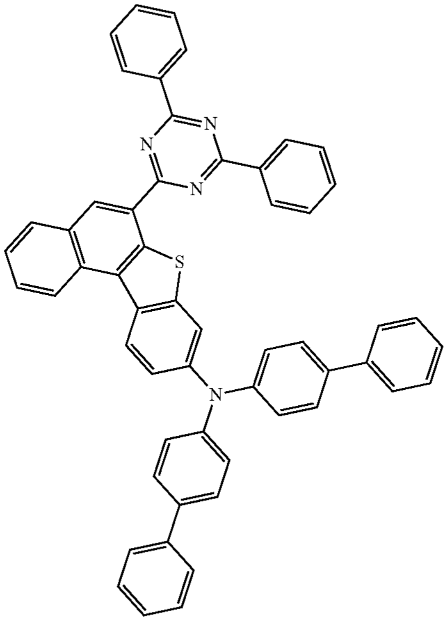
F237
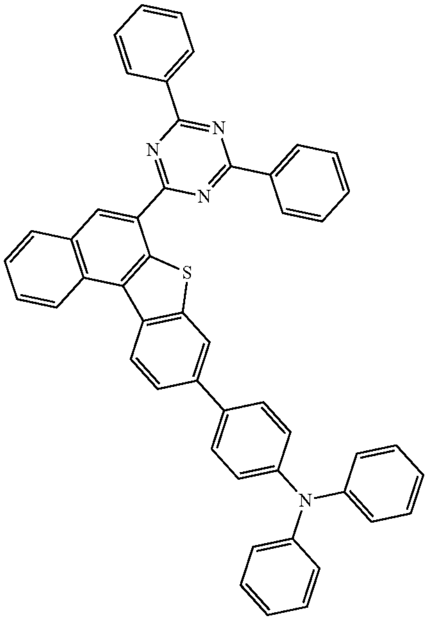
-continued
F238
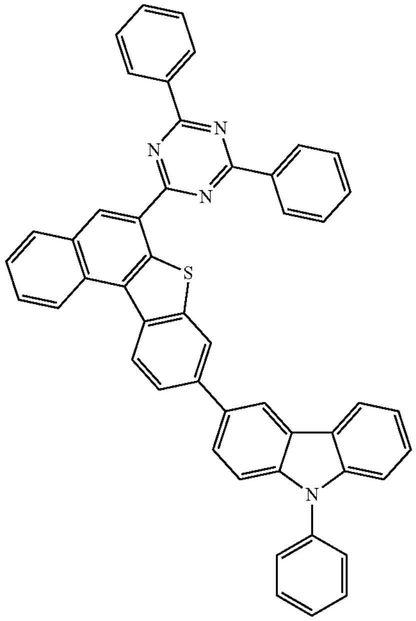
F239
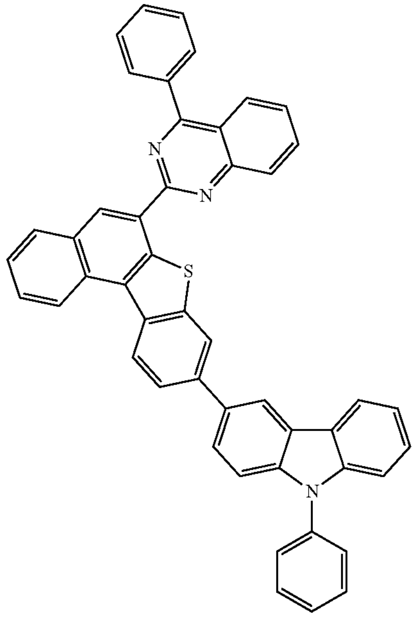

-continued
F240
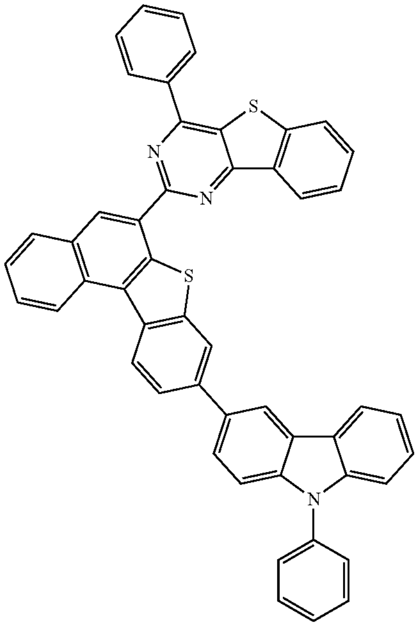
F241
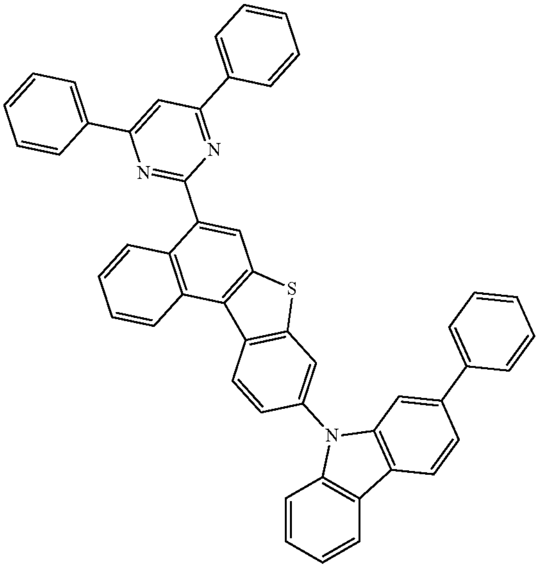
-continued
F242
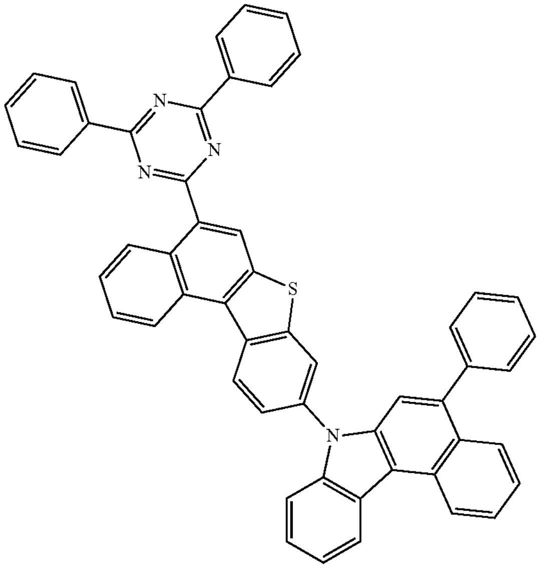
F243
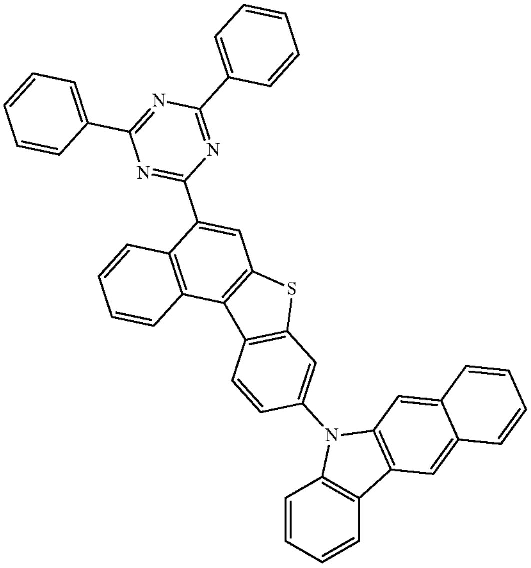

F244
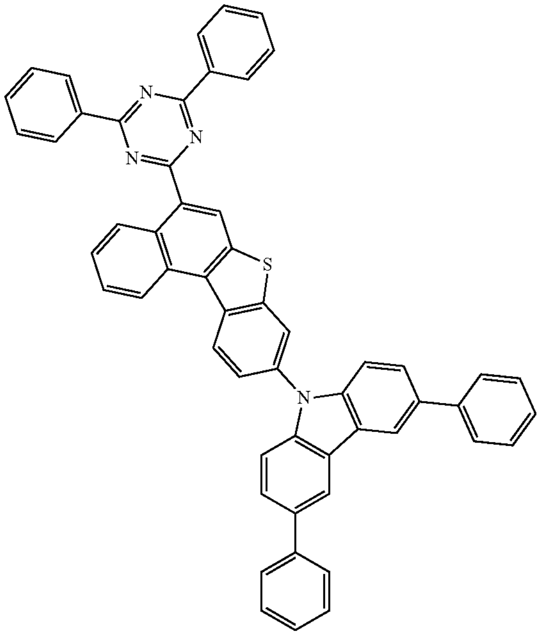
F245
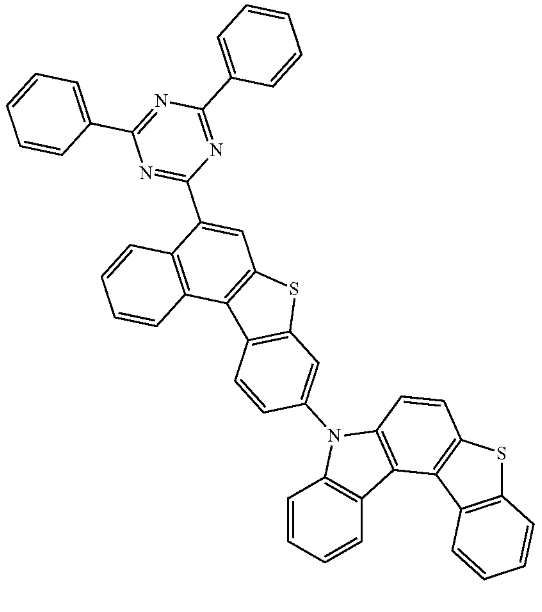
F246
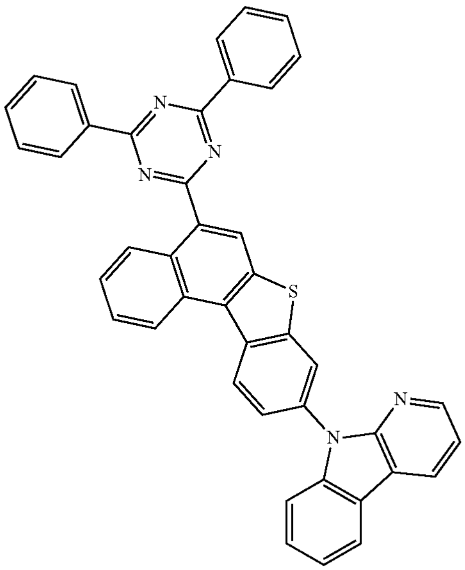
F247
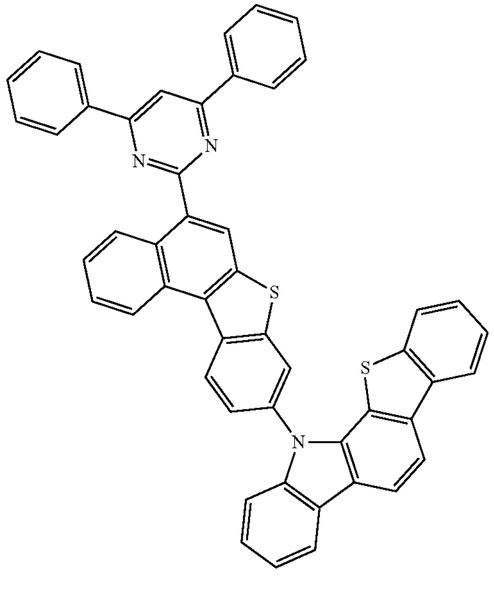

-continued
F248
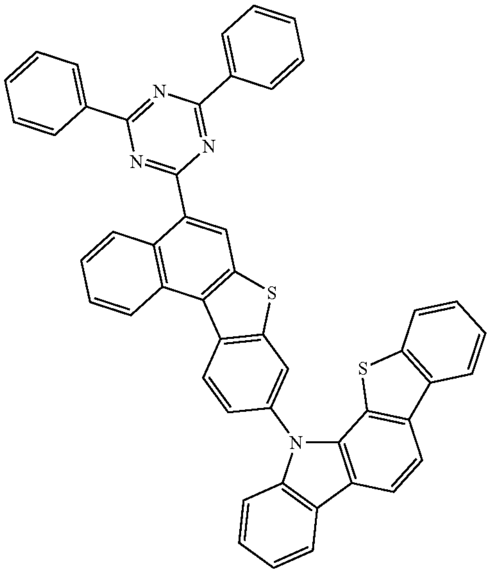
F249
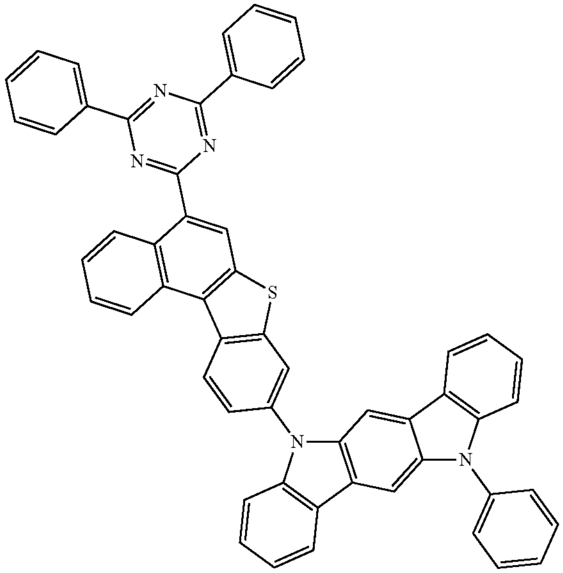
-continued
F250
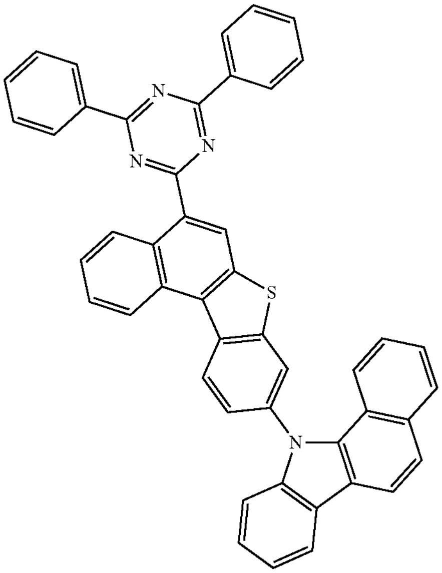
F251
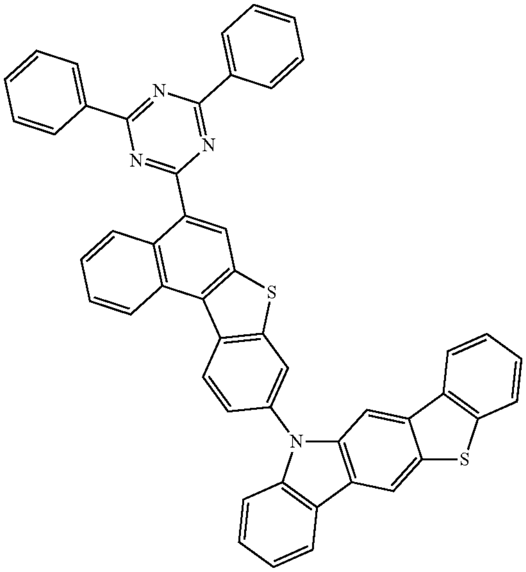

-continued
F252
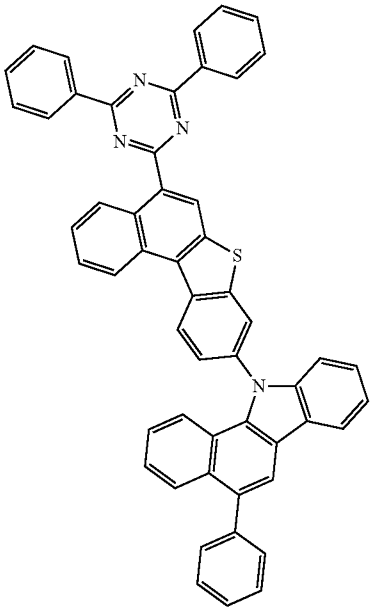
F253
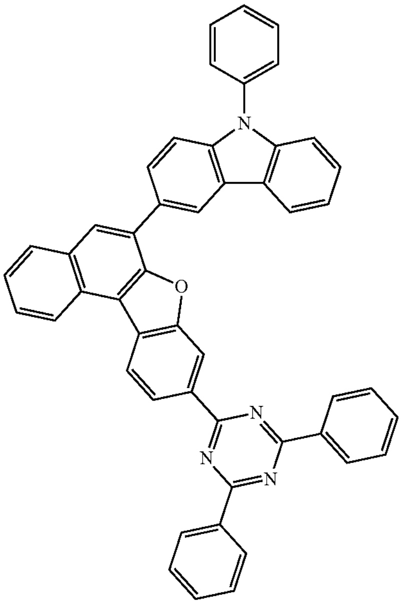
-continued
F254
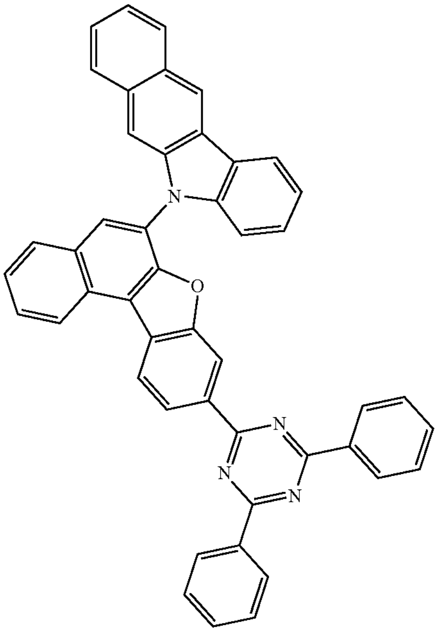
F255
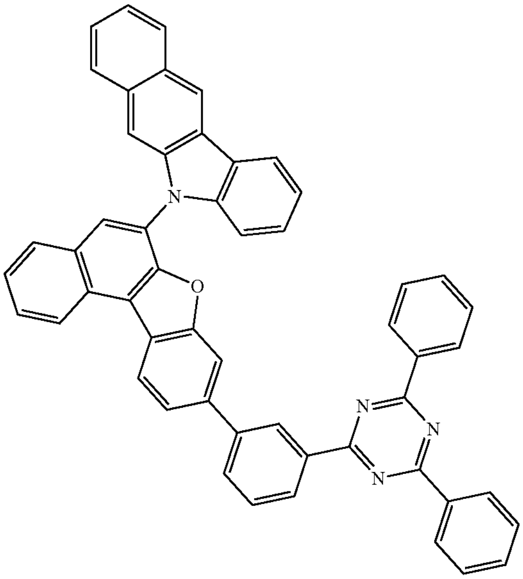

-continued
F256
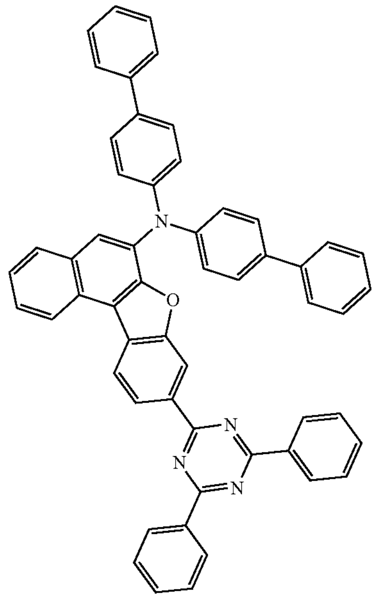
F257
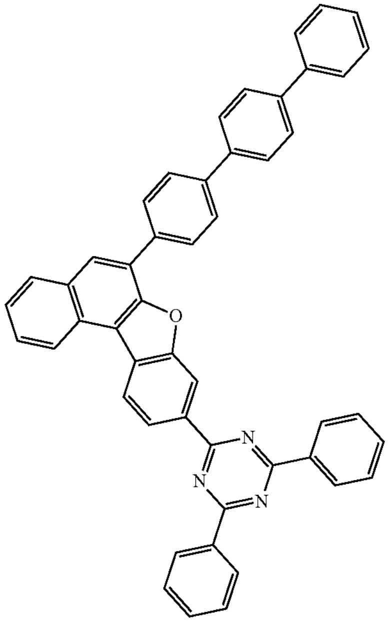
-continued
F258
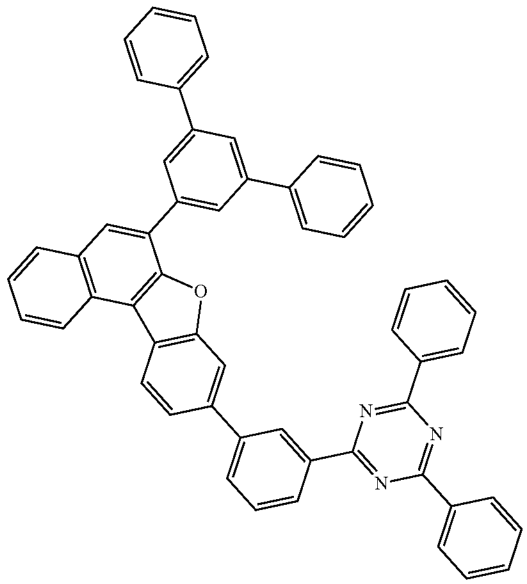
F259
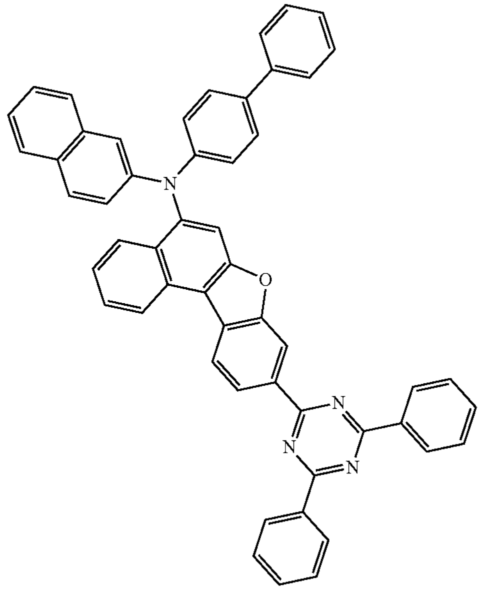

-continued
F260
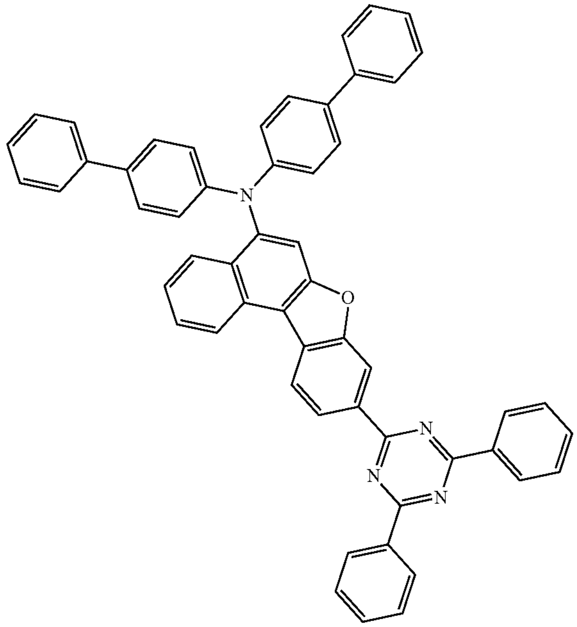
F261
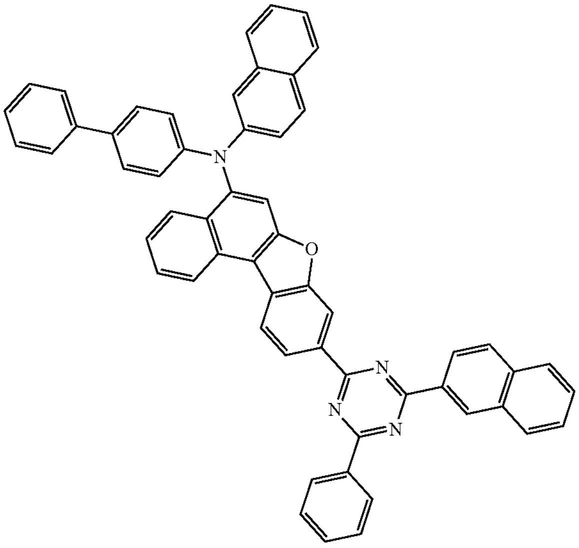
-continued
F262
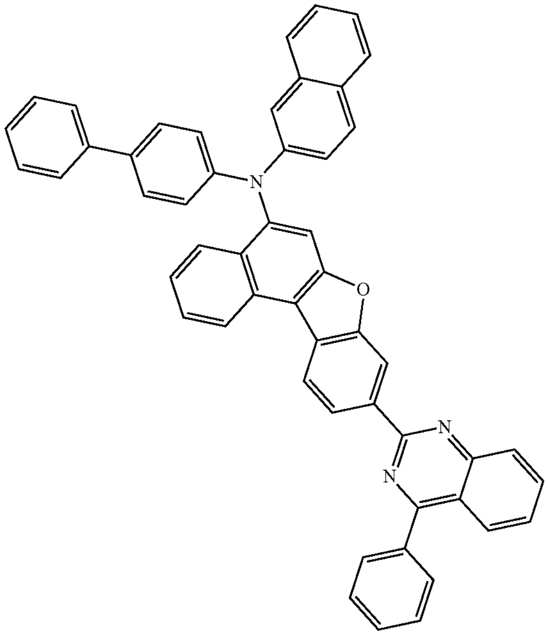
F263
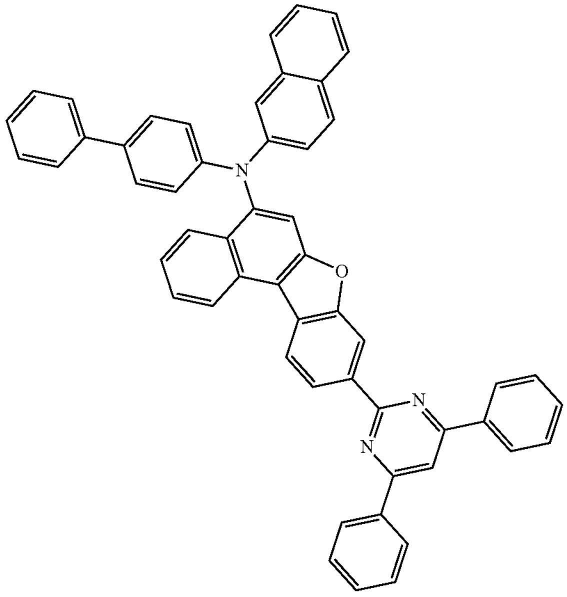

-continued
F264
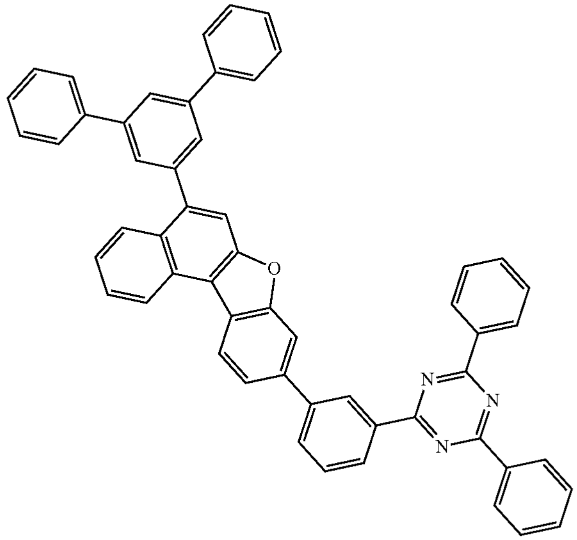
F265
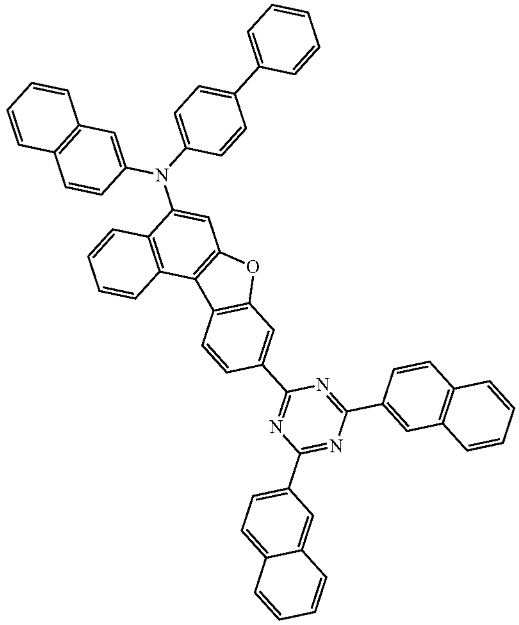
-continued
F266
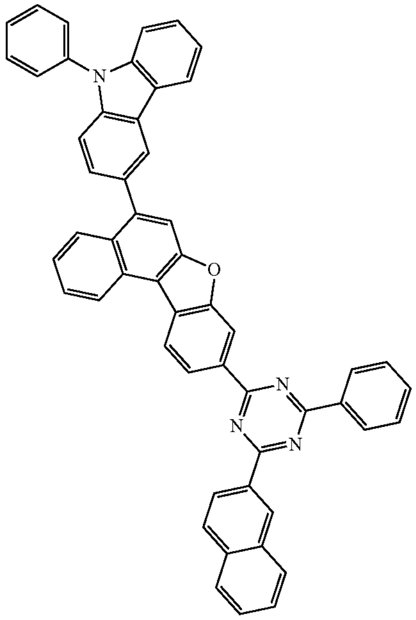
F267
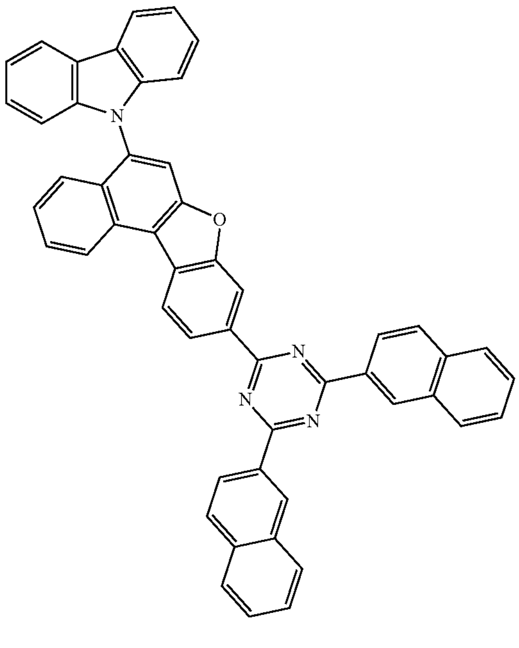

-continued
F268
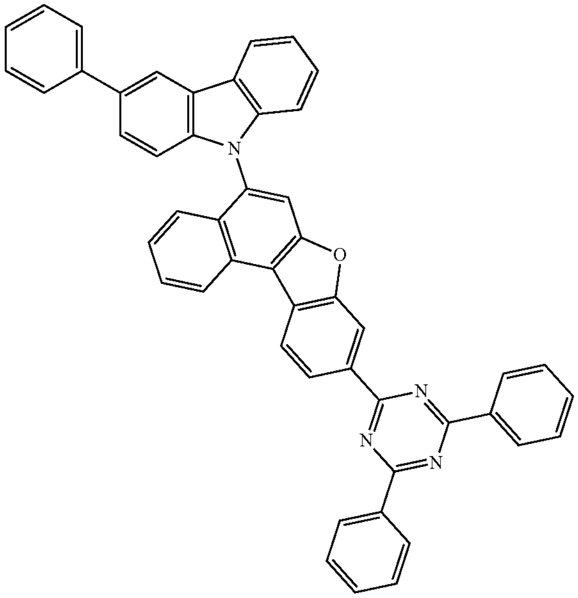
F269
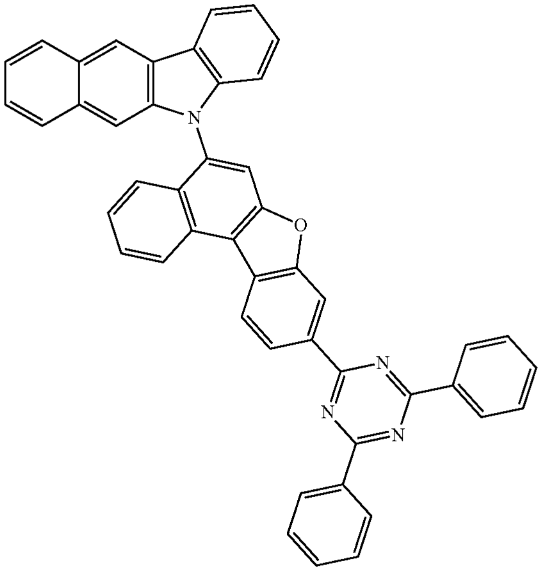
-continued
F270
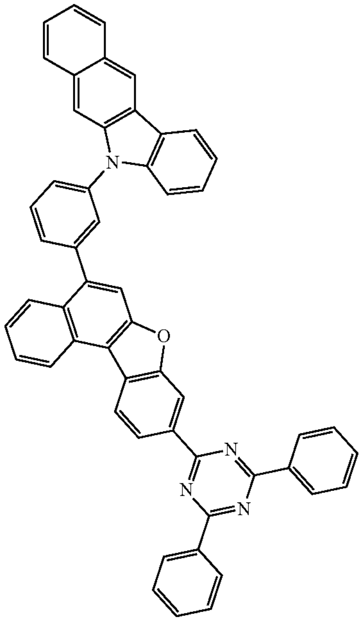
F271
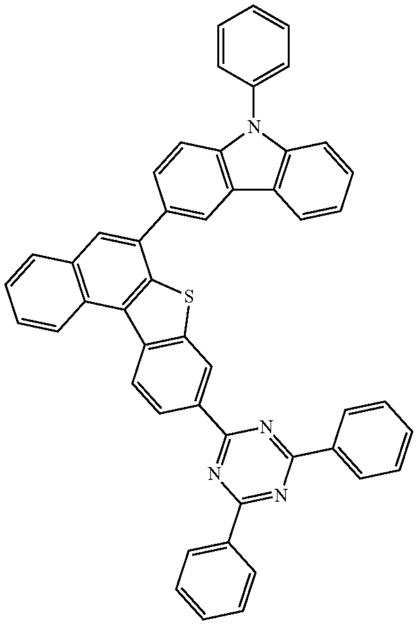

-continued
F272
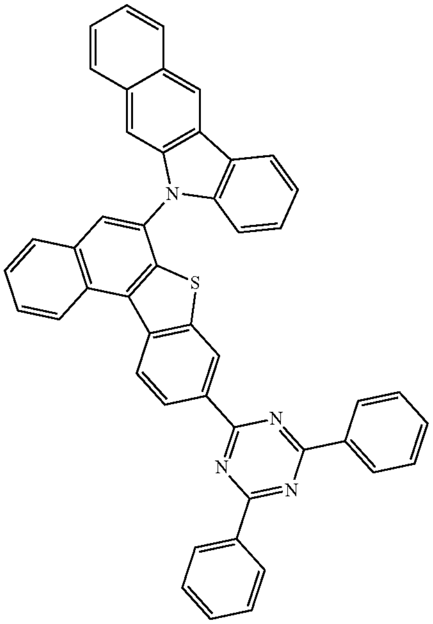
F273
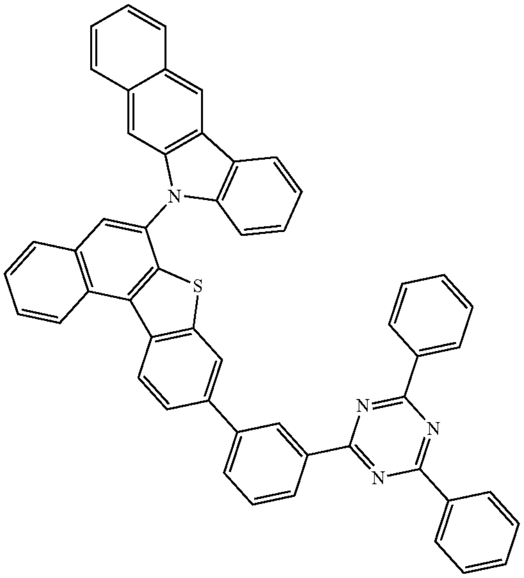
-continued
F274
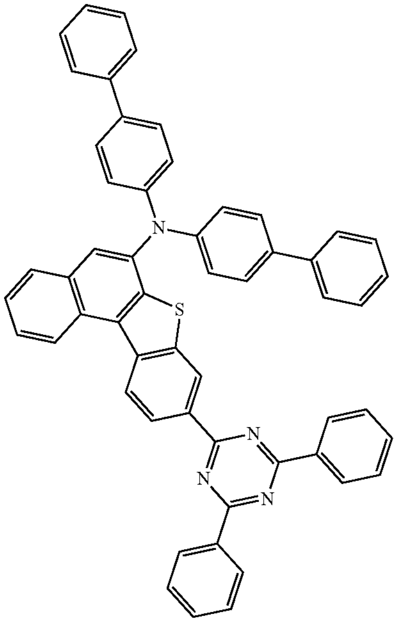
F275
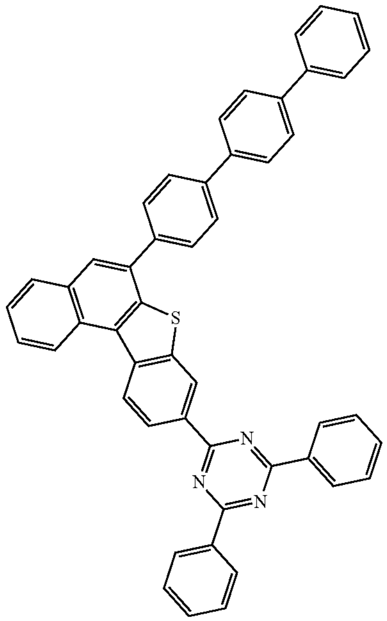

-continued
F276
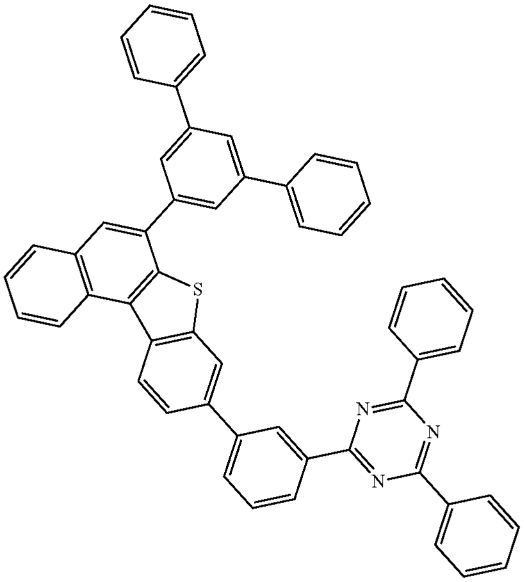
F277
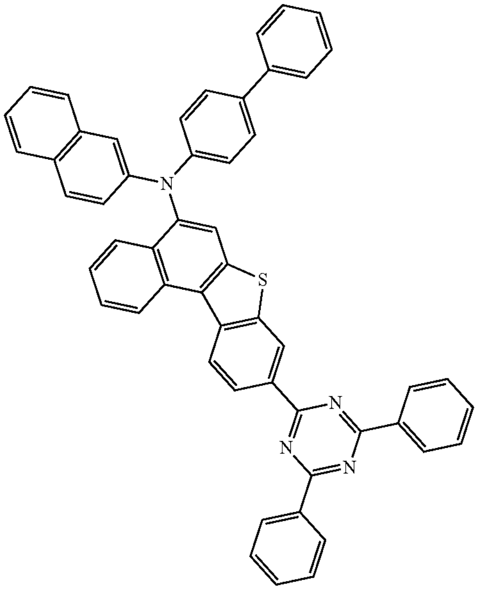
-continued
F278
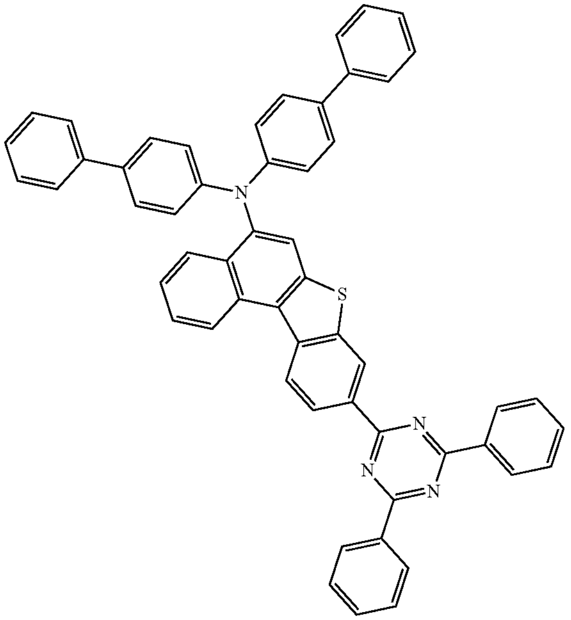
F279
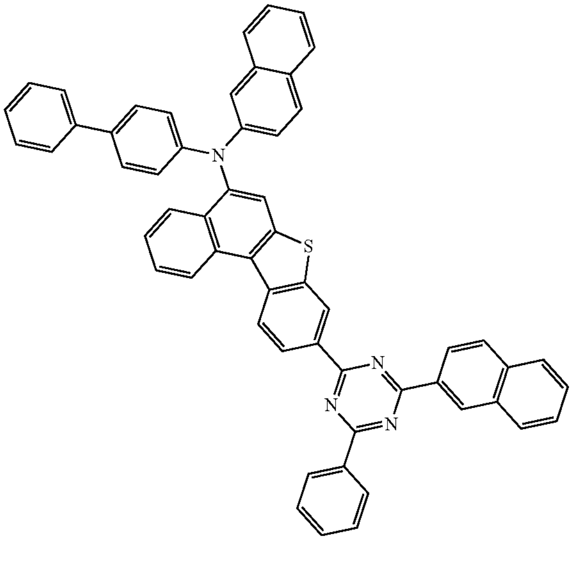

-continued
F280
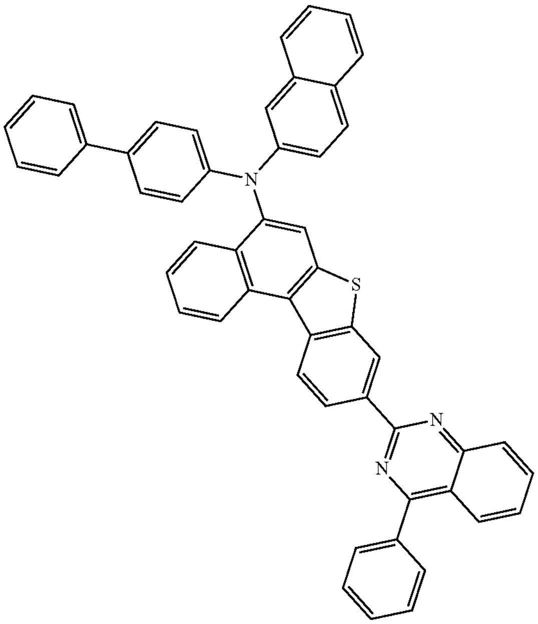
F281
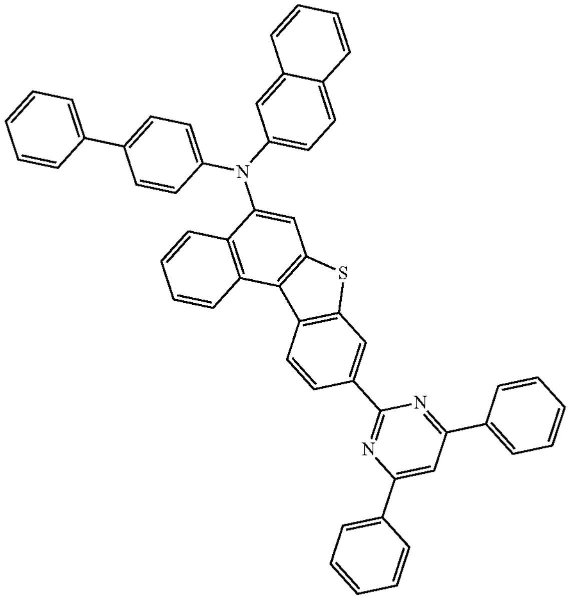
-continued
F282
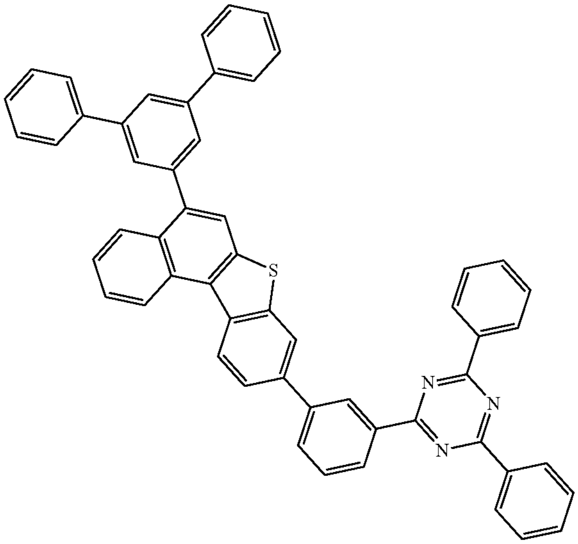
F283
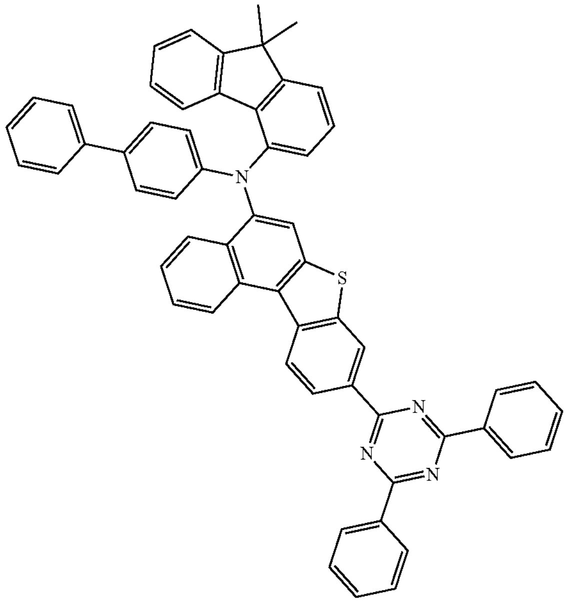

-continued
F284
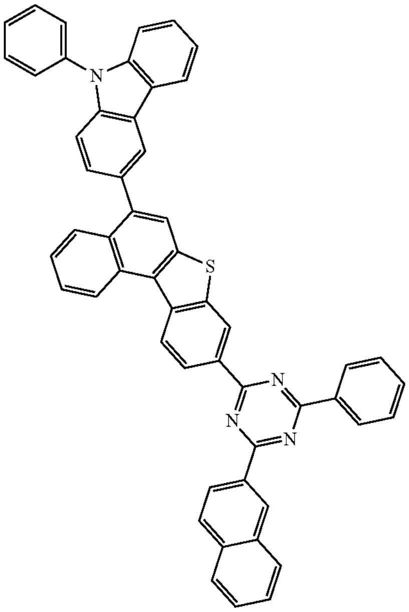
F285
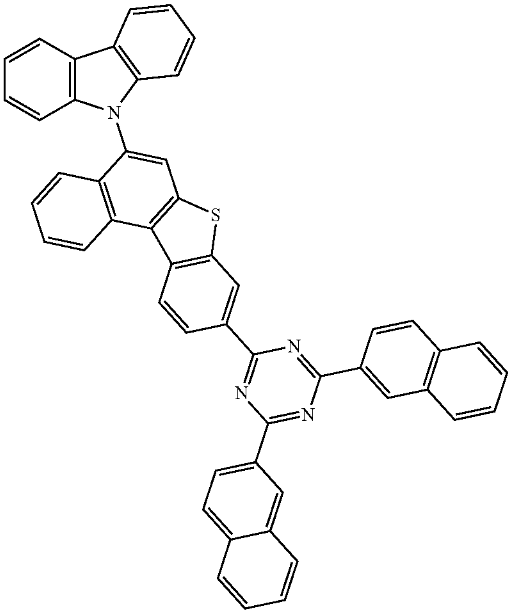
-continued
F286
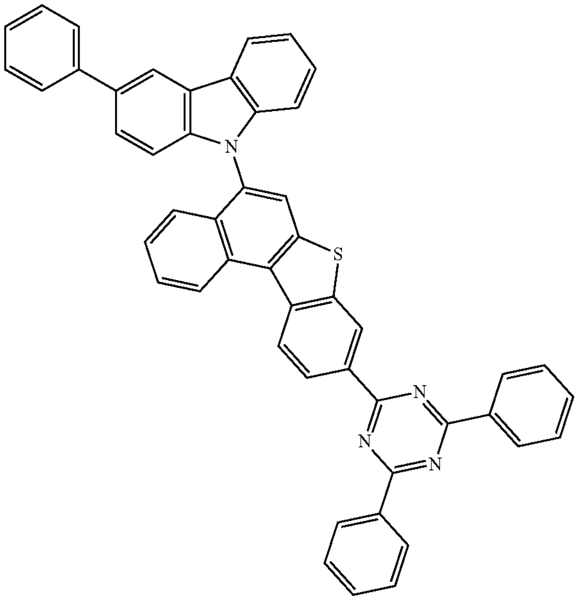
F287
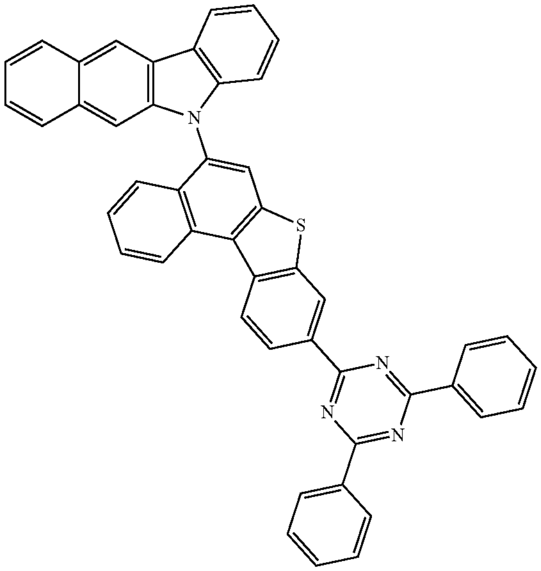

-continued
F288
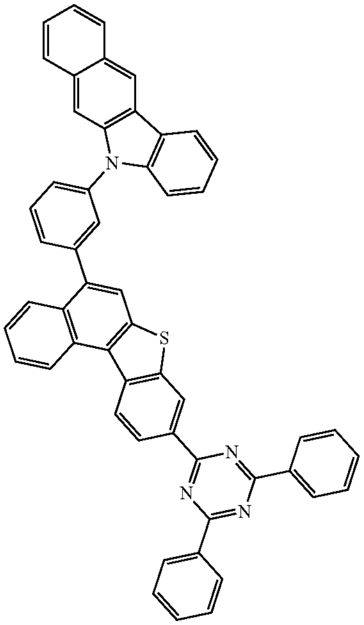
F289
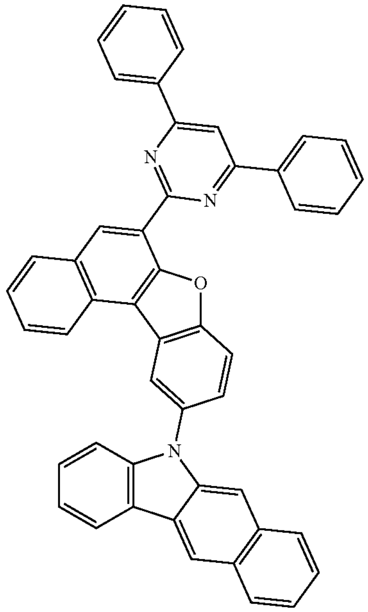
-continued
F290
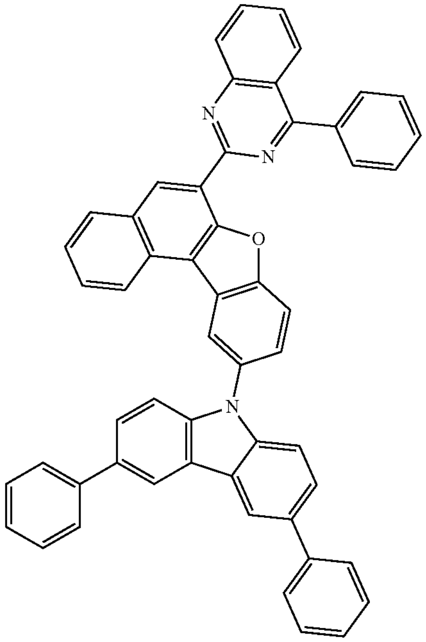
F291
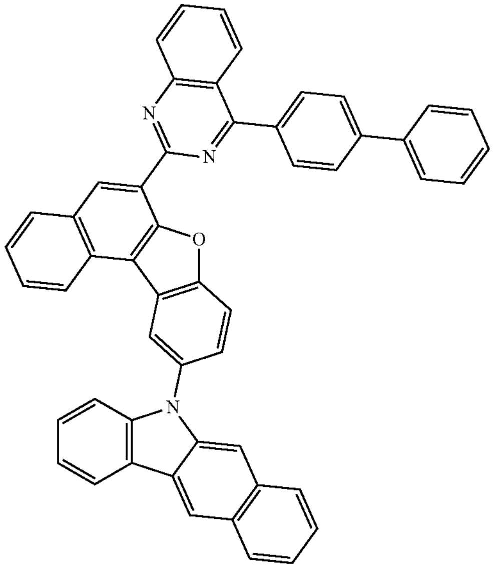

-continued
F292
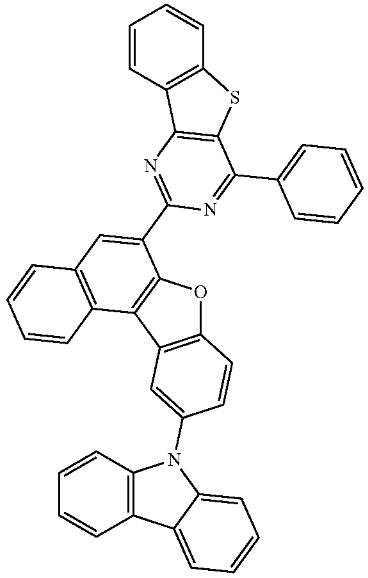
F293
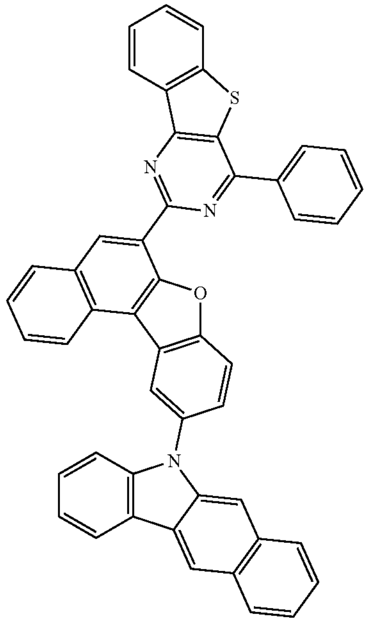
-continued
F294
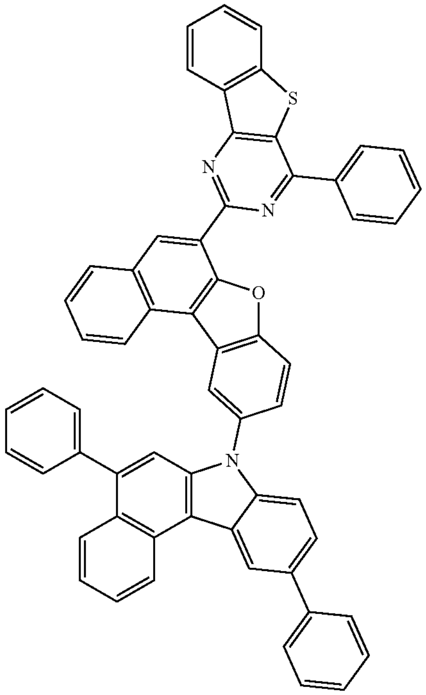
F295
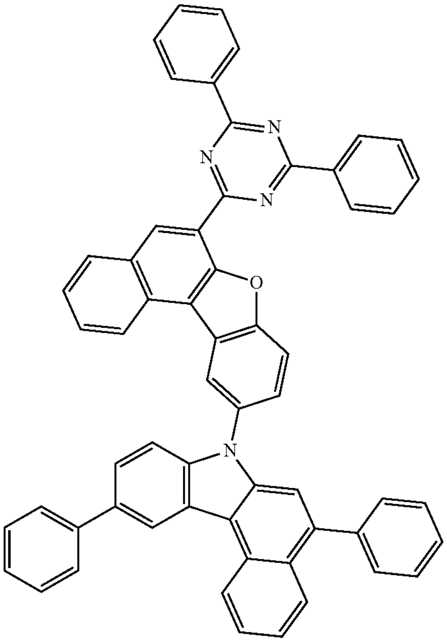

-continued
F296
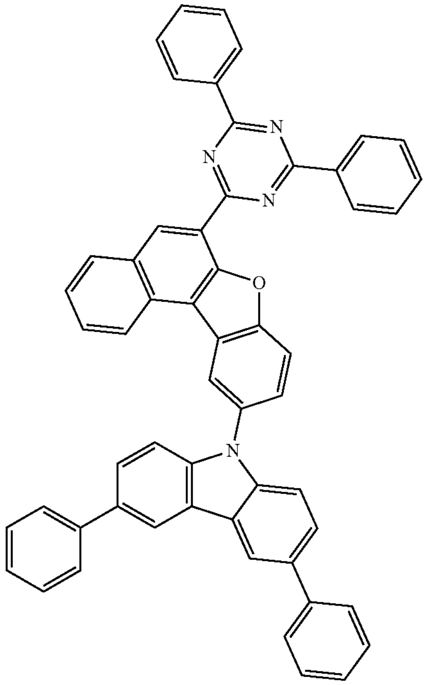
F297
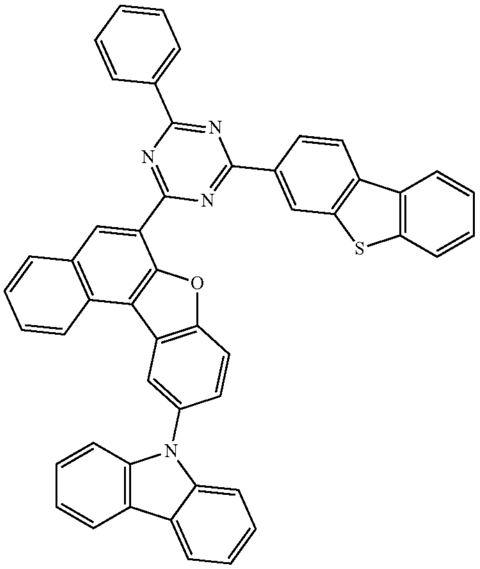
-continued
F298
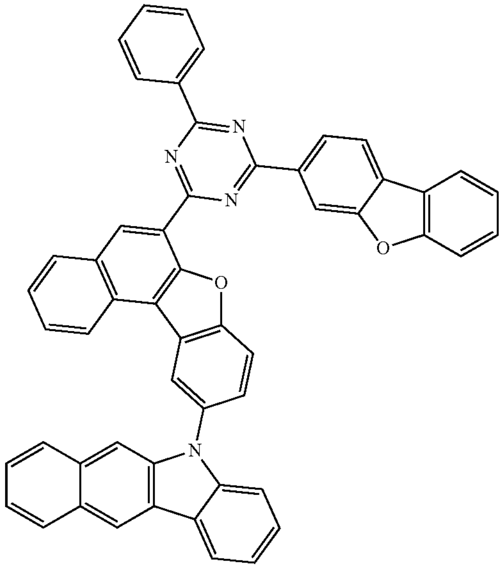
F299
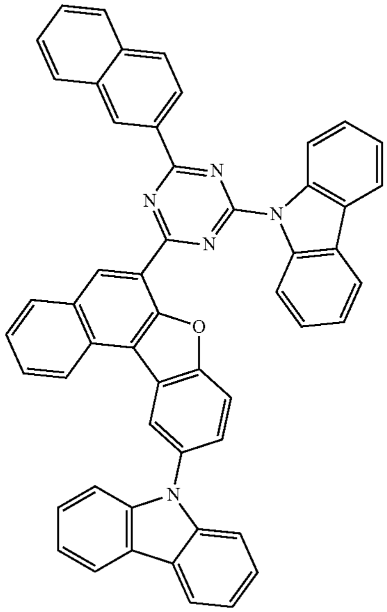

-continued
F300
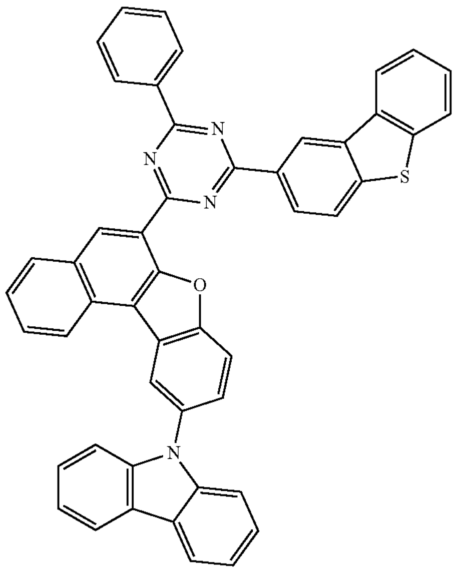
F301
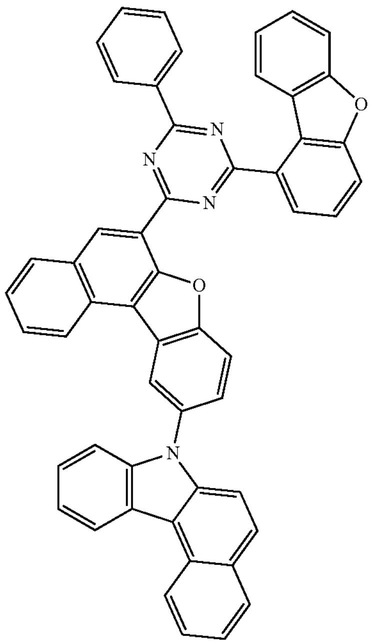
-continued
F302
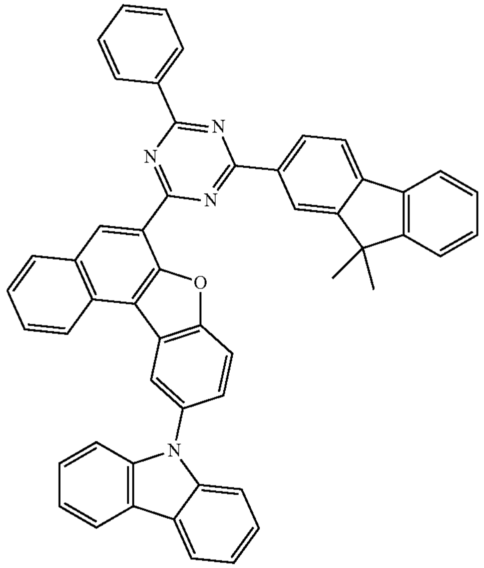
F303
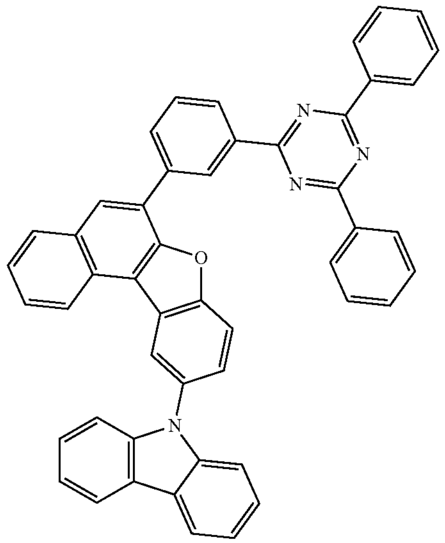

-continued
F304
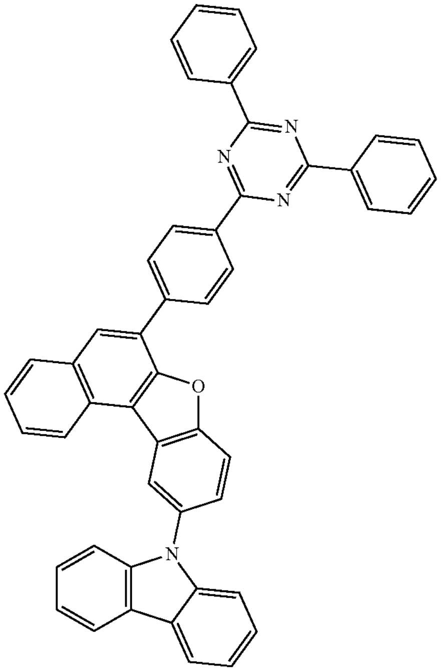
F305
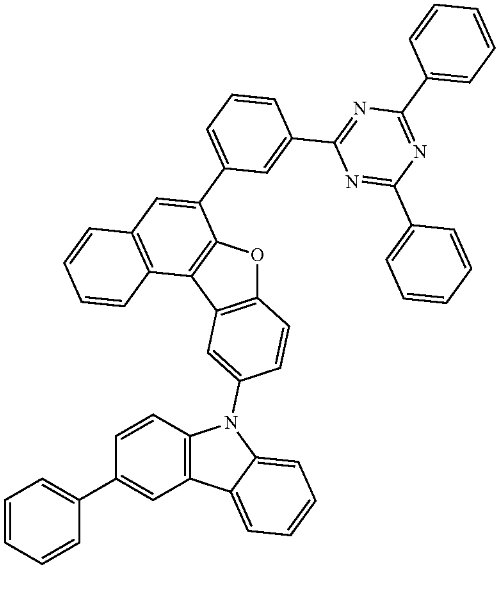
-continued
F306
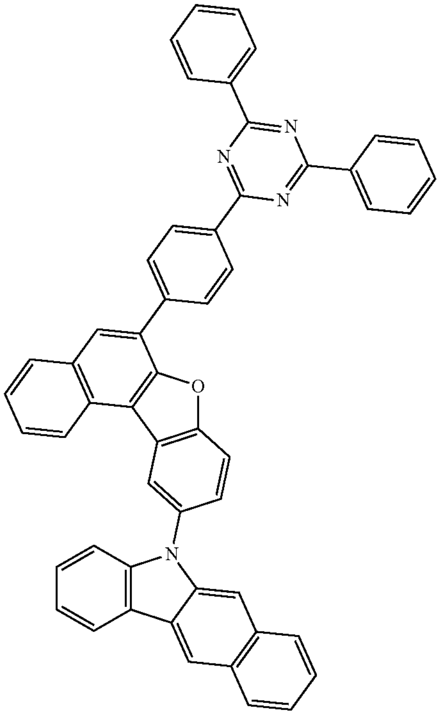
F307
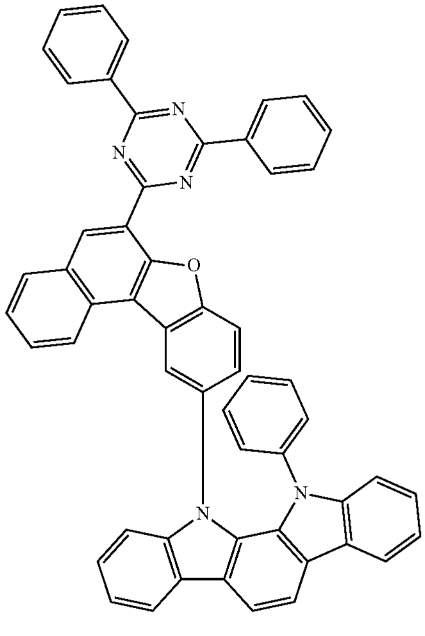

-continued
F308
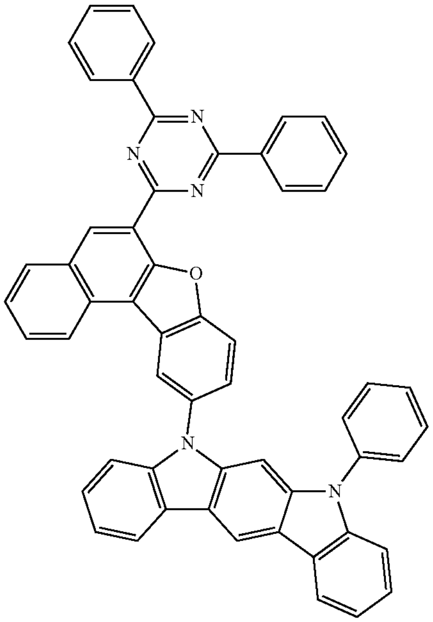
F309
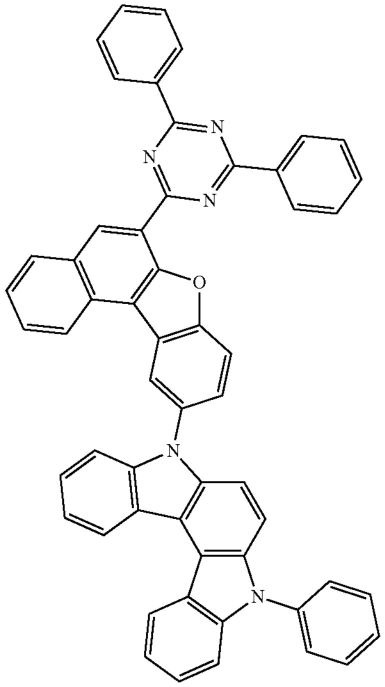
-continued
F310
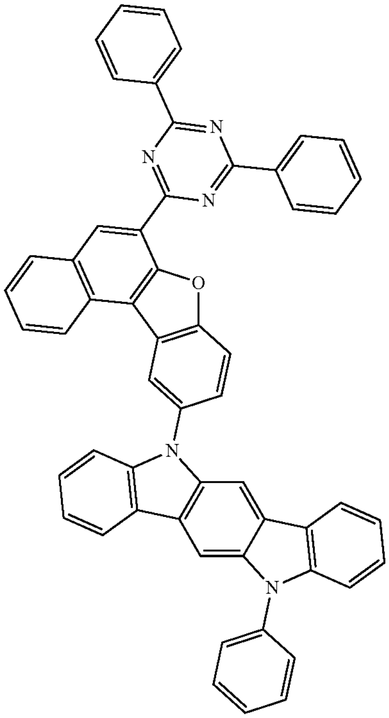
F311
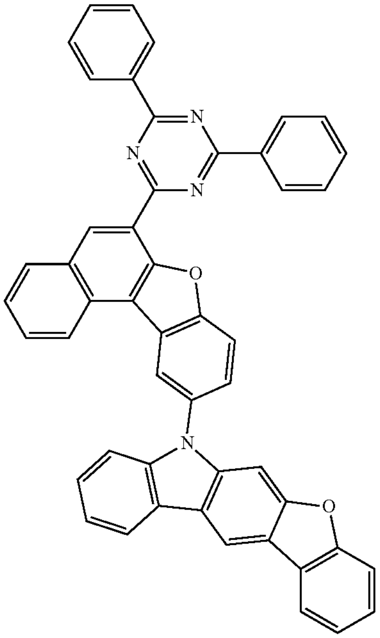

-continued
F312
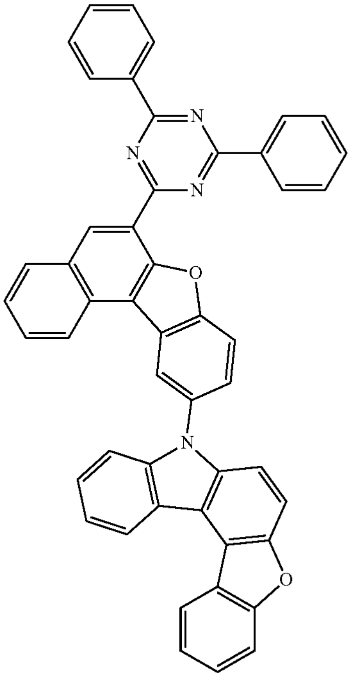
F313
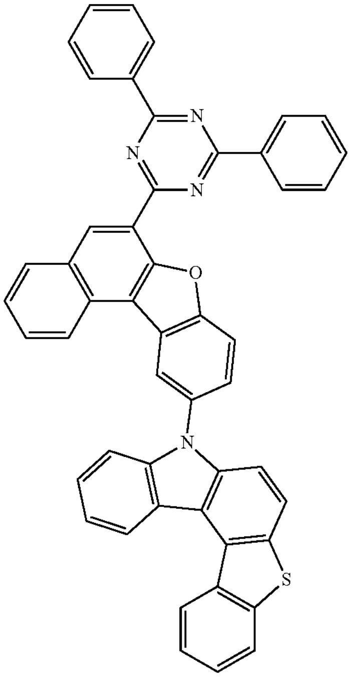
-continued
F314
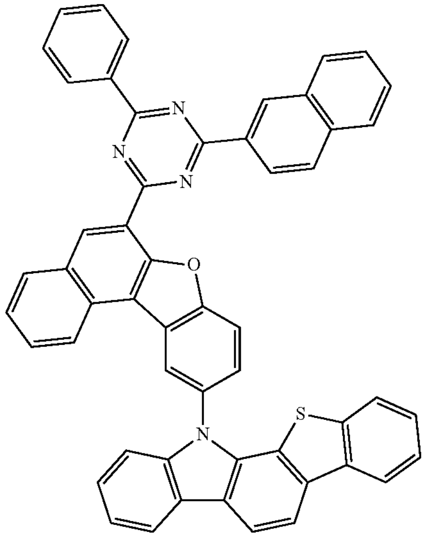
F315
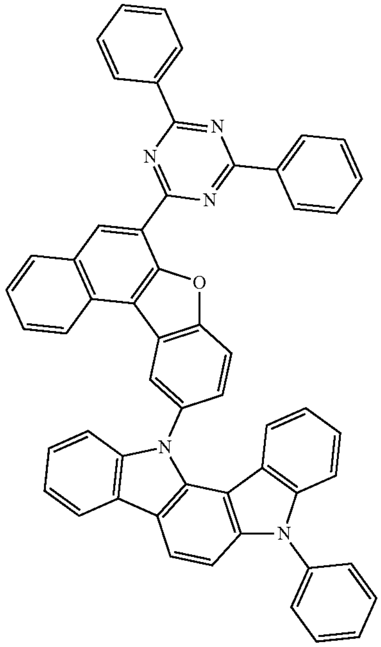

-continued
F316
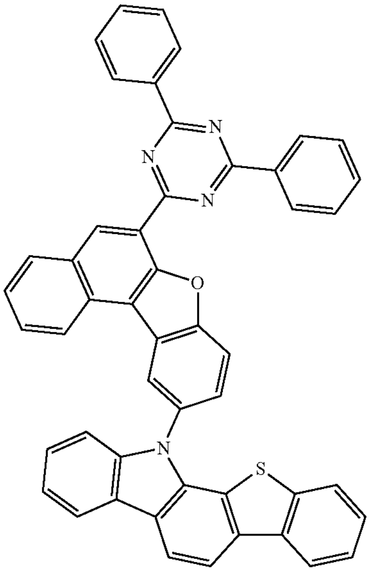
F317
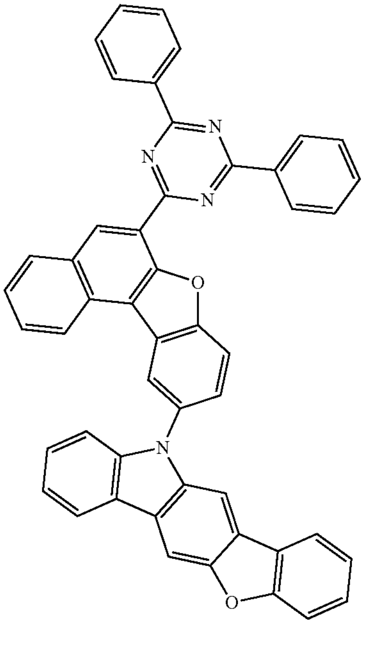
-continued
F318
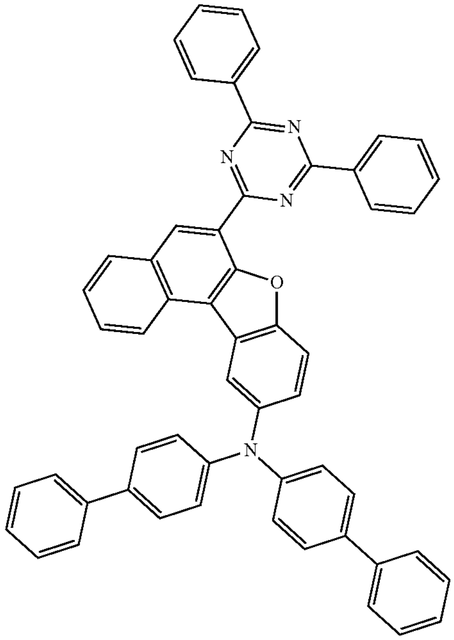
F319
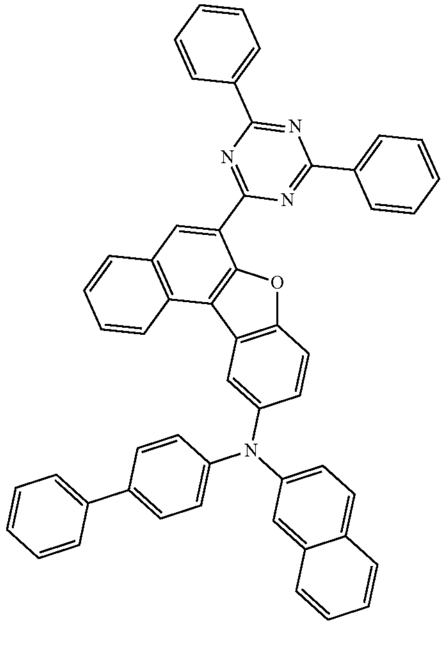

-continued
F320
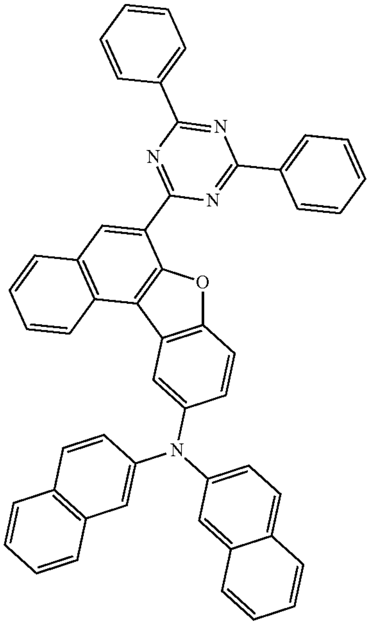
F321
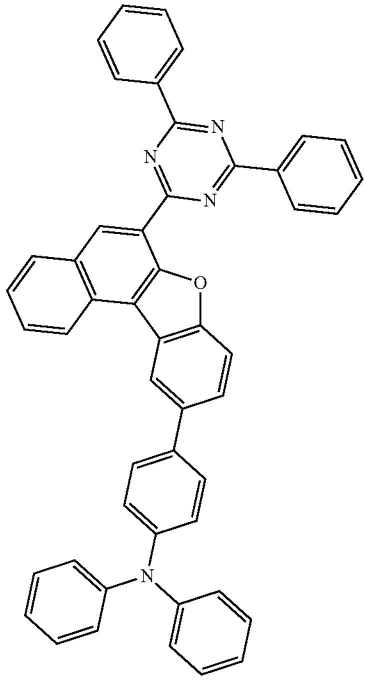
-continued
F322
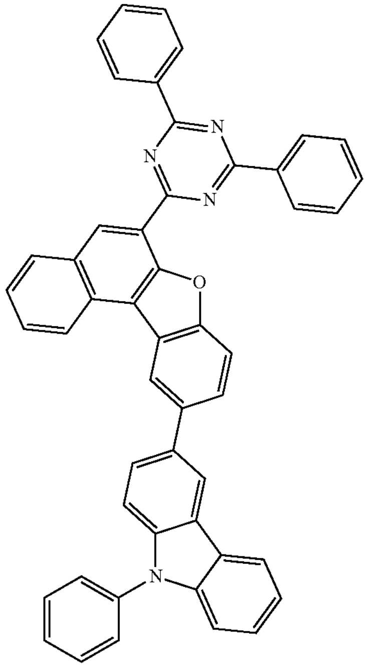
F323
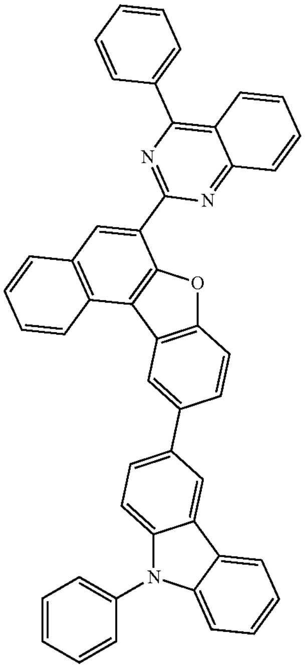

-continued
F324
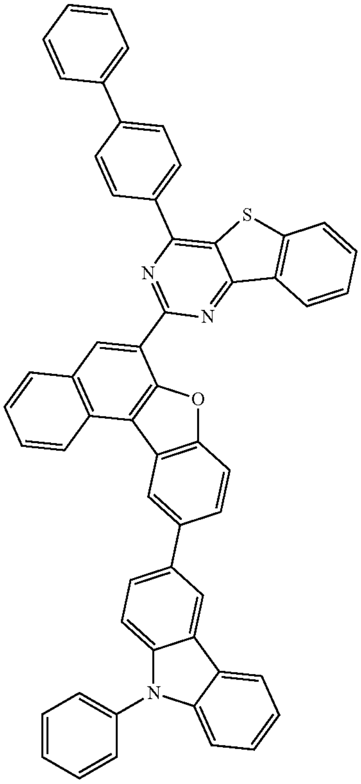
F325
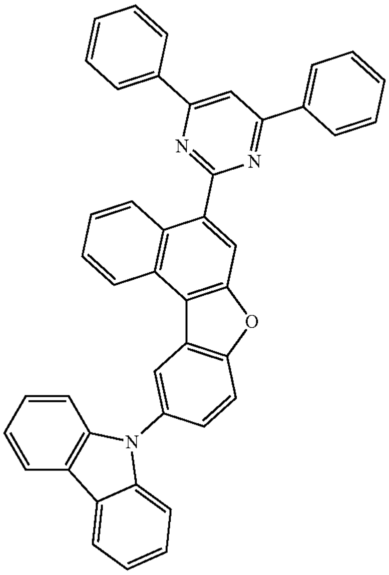
-continued
F326
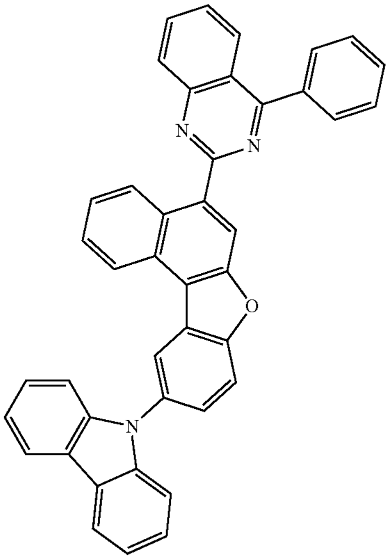
F327
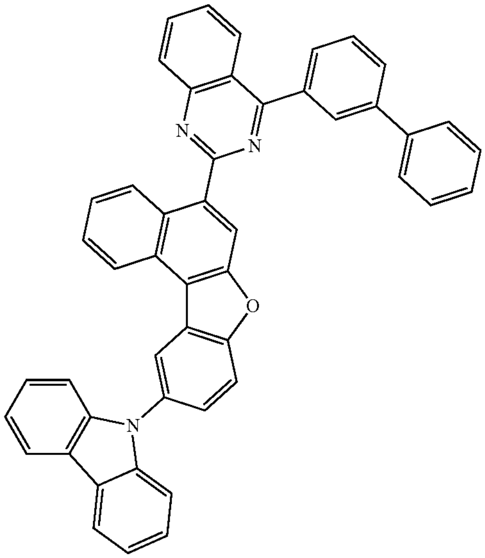

-continued
F328
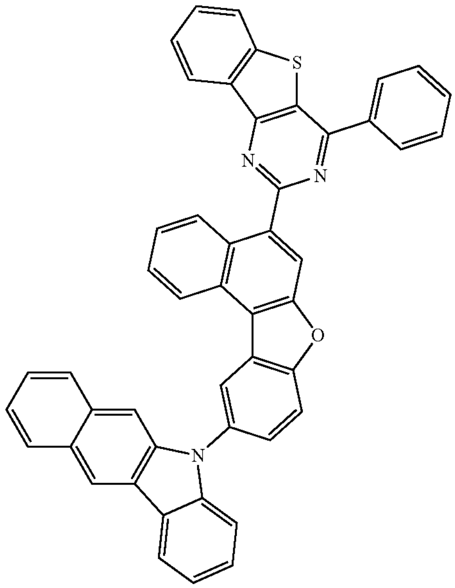
F329
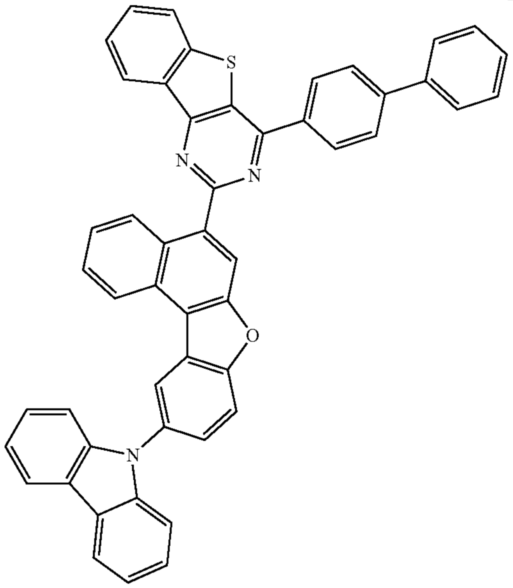
-continued
F330
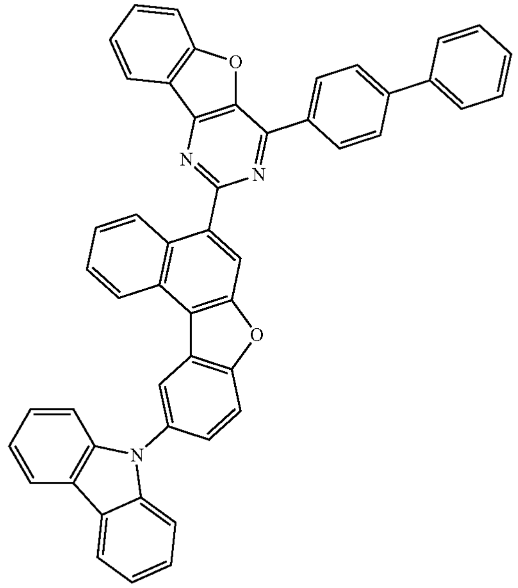
F331
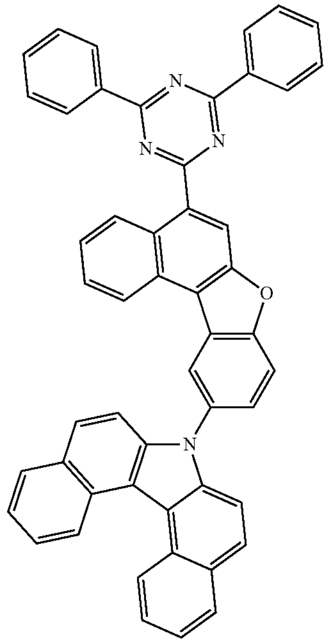

-continued
F332
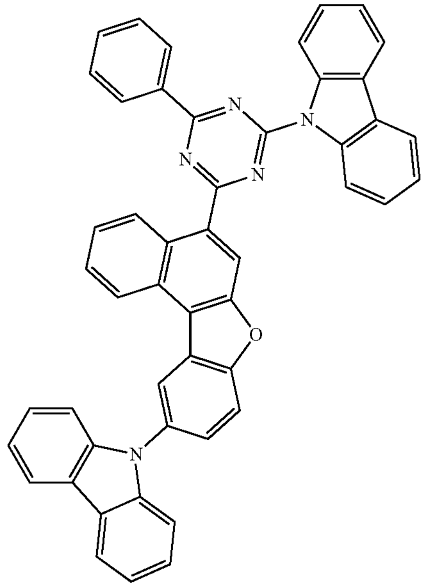
F333
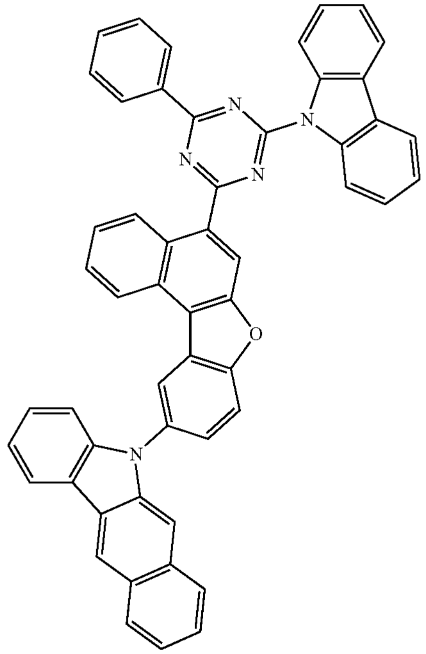
-continued
F334
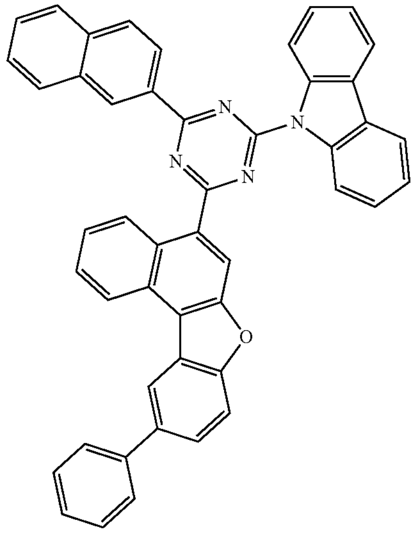
F335
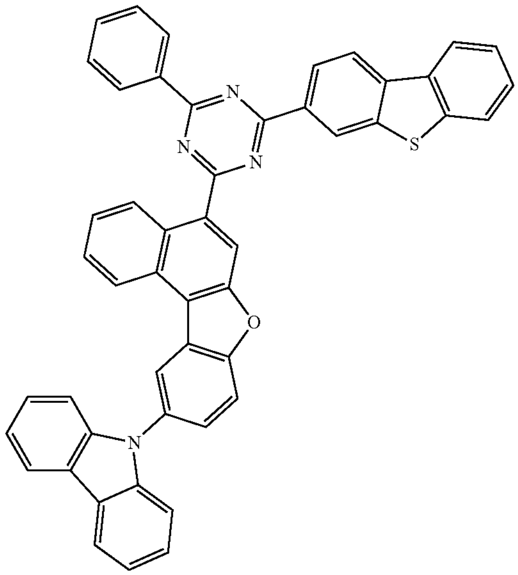

-continued
F336
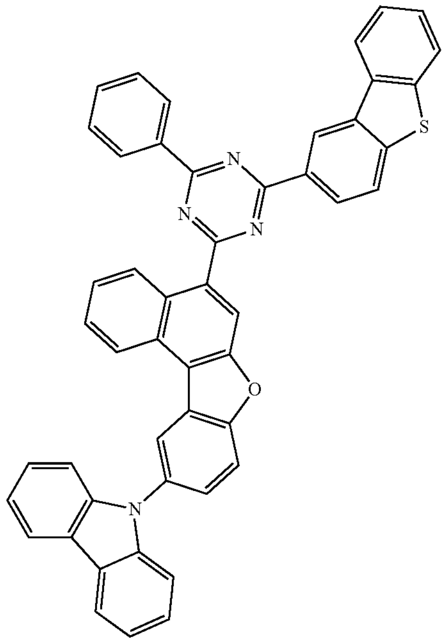
F337
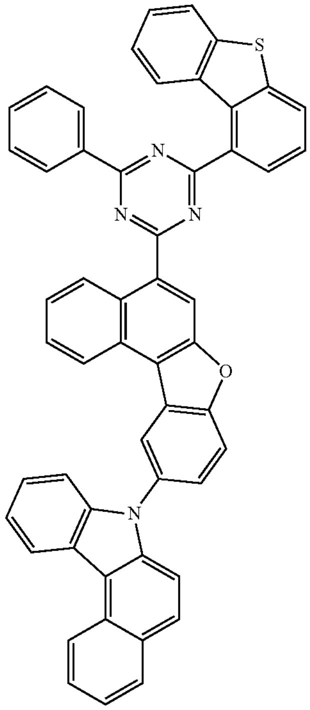
-continued
F338
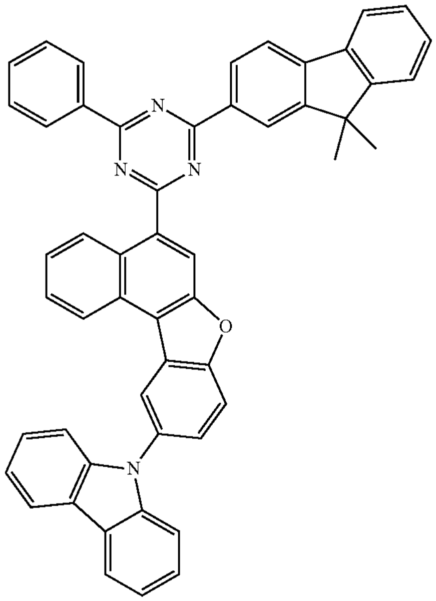
F339
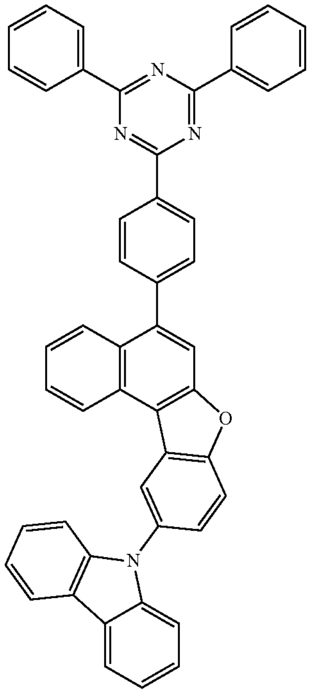

-continued
F340
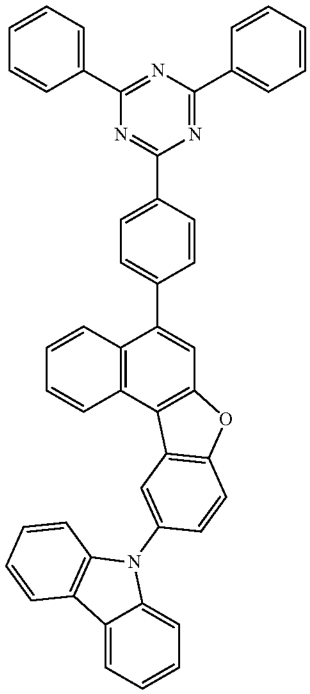
F341
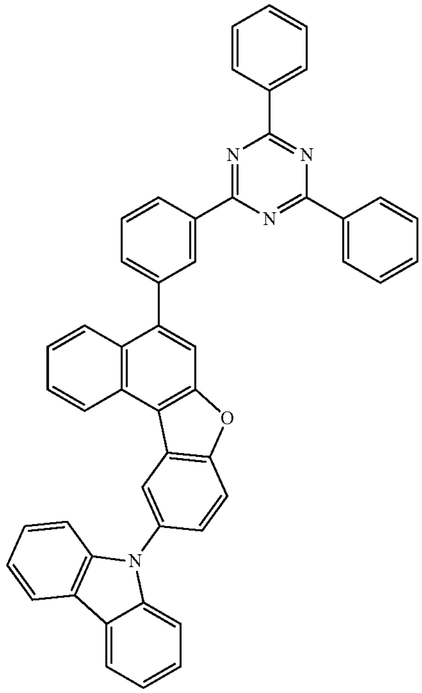
-continued
F342
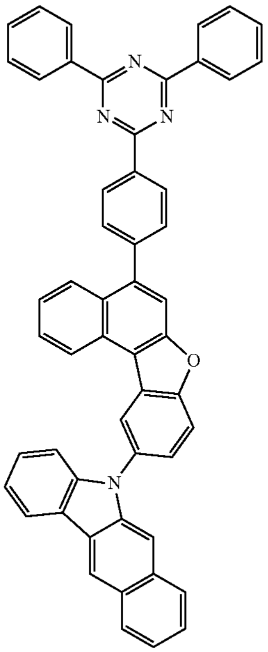
F343
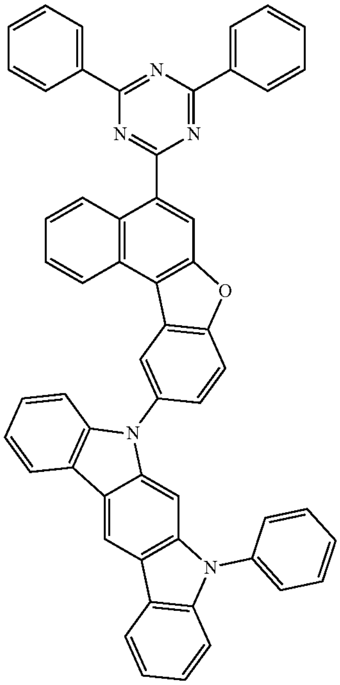

-continued
F344
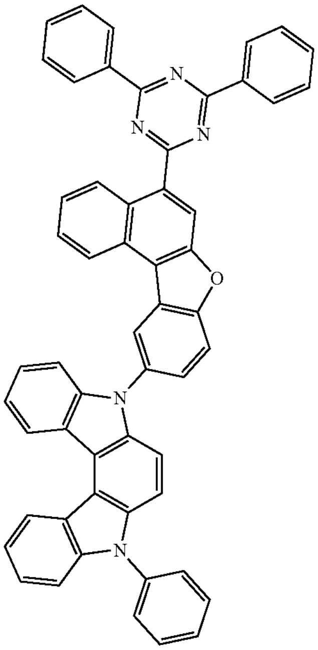
F345
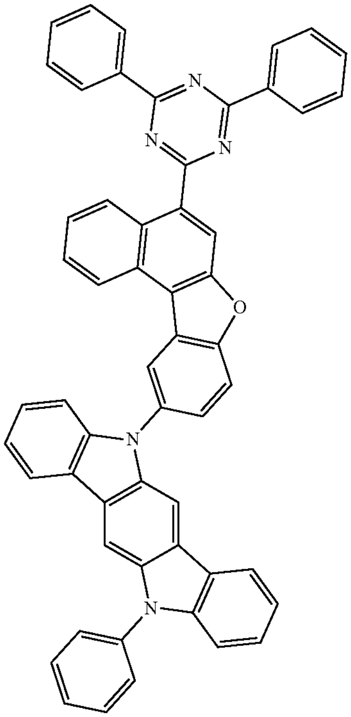
-continued
F346
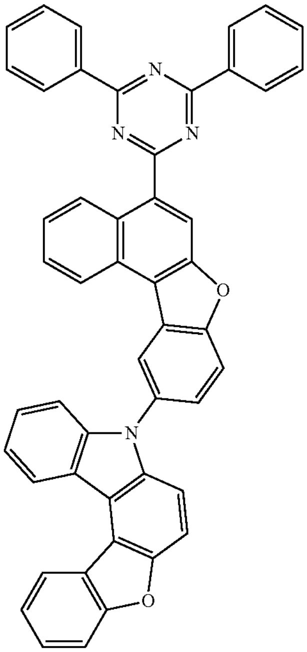
F347
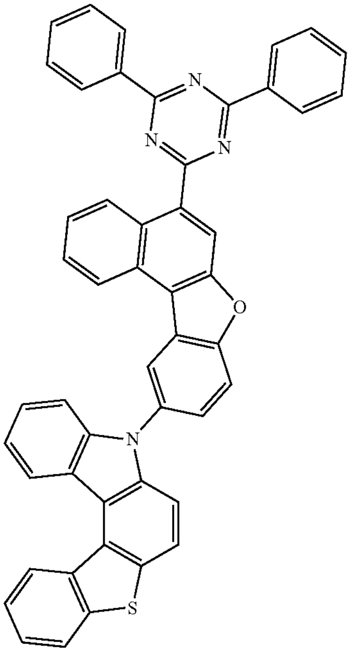

-continued
F348
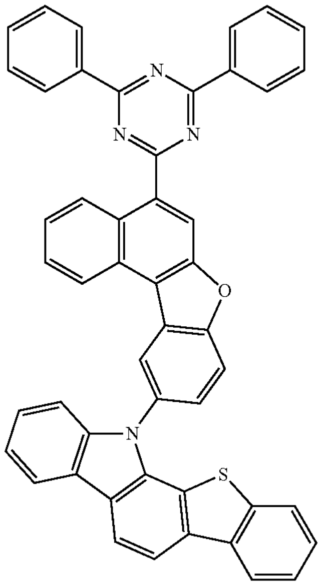
F349
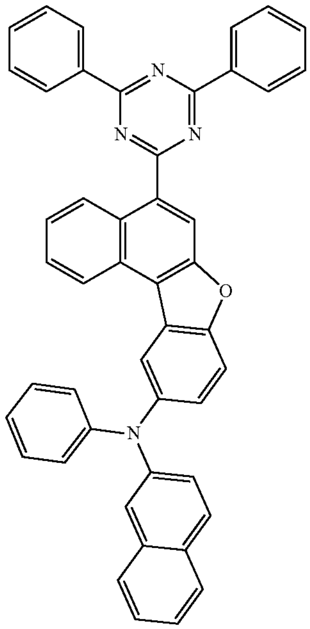
-continued
F350
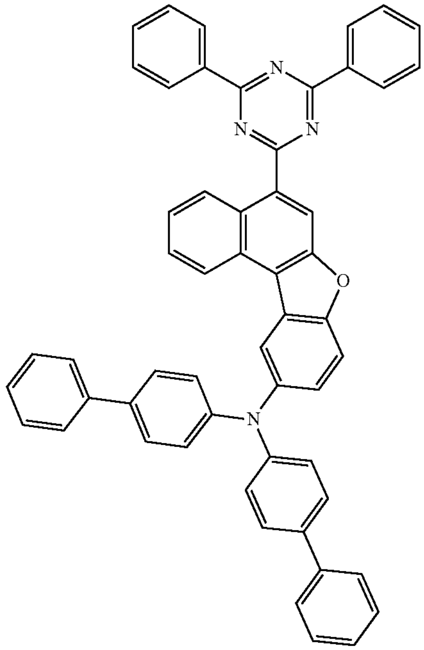
F351
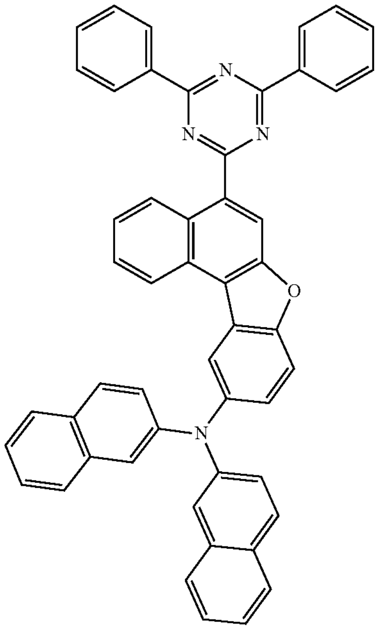

-continued
F352
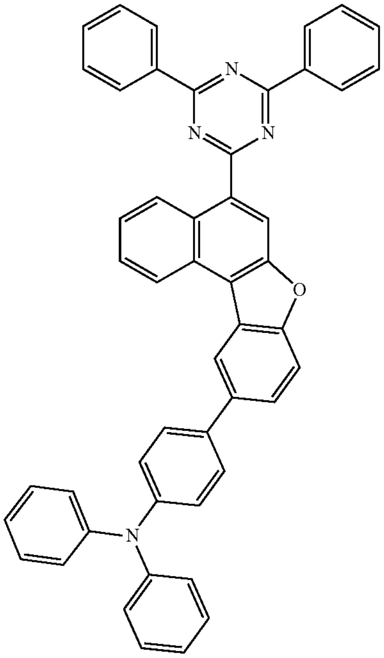
F353
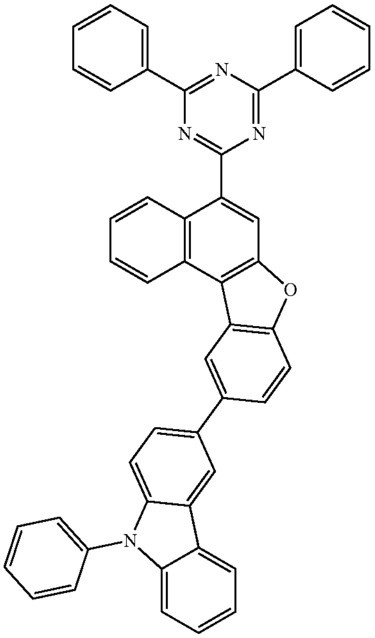
-continued
F354
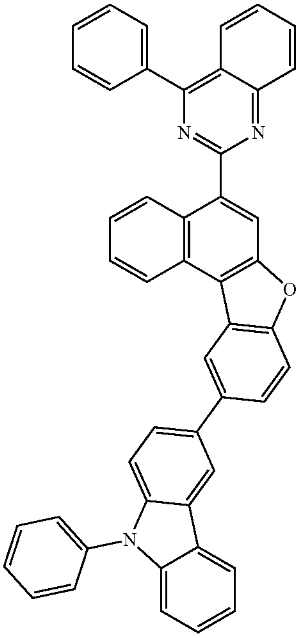
F355
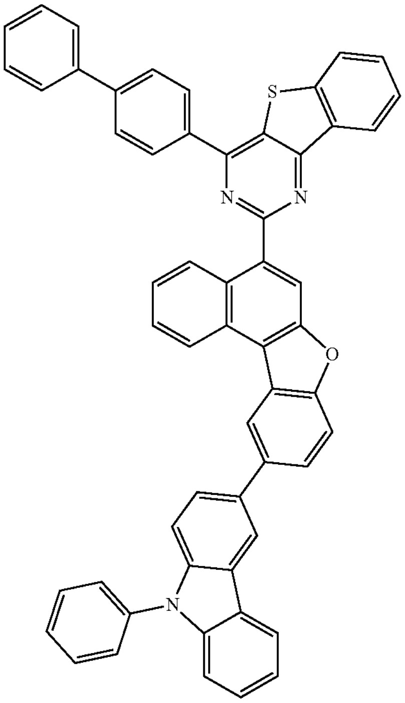

-continued
F356
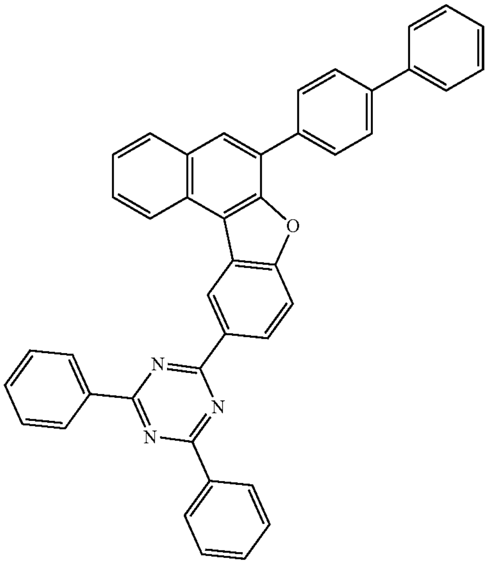
F357
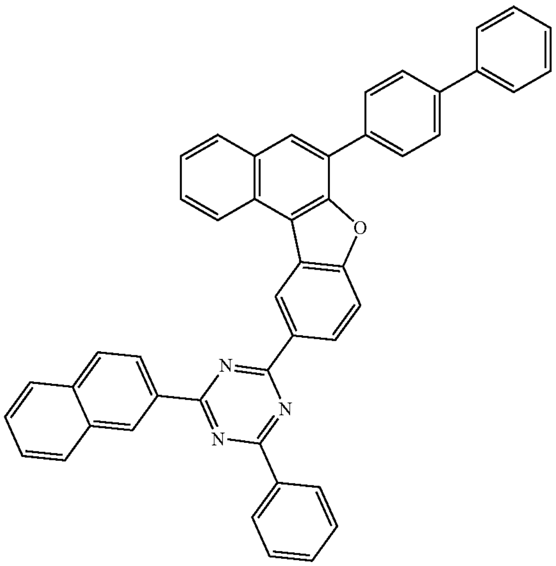
-continued
F358
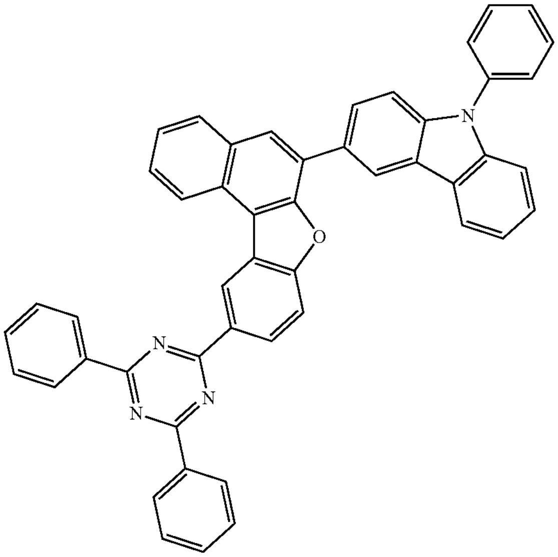
F359
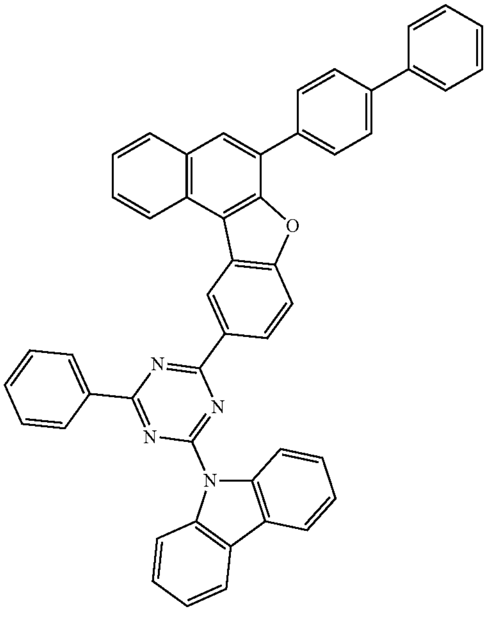

-continued
F360
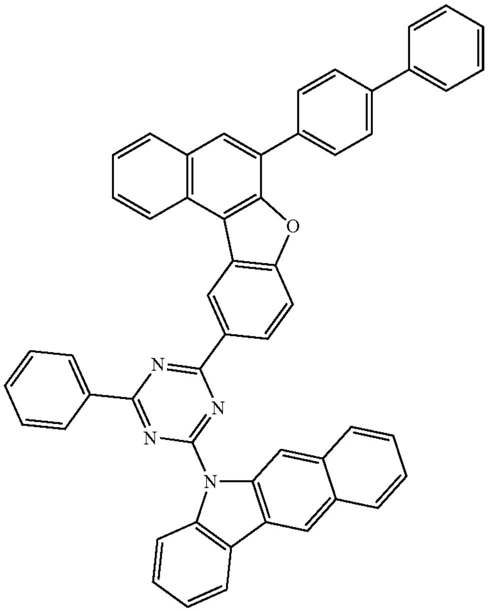
F361
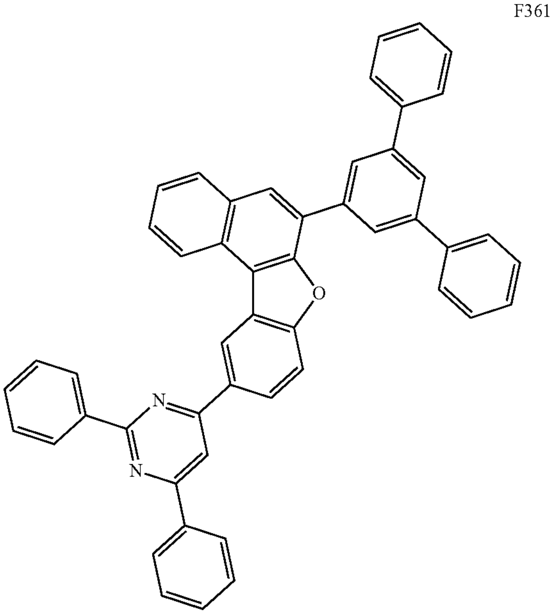
-continued
F362
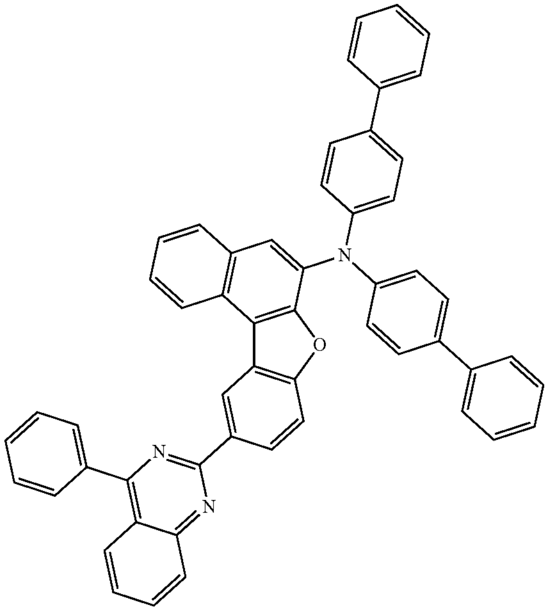
F363
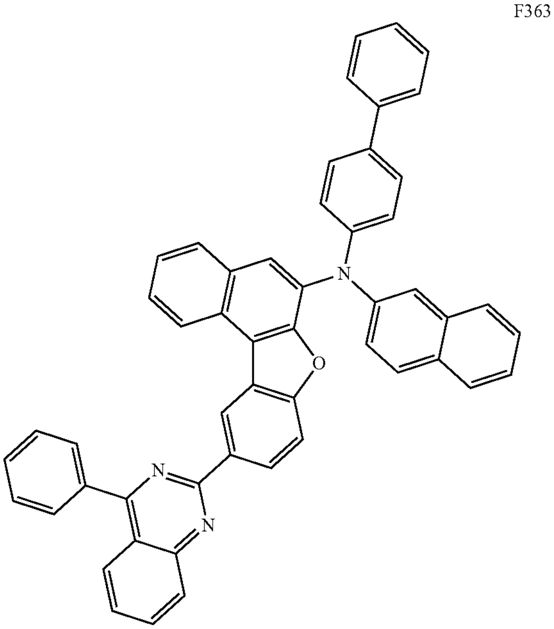

-continued
F364
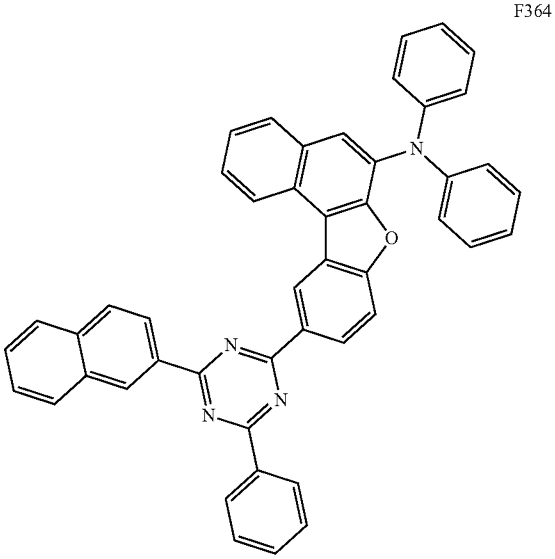
F365
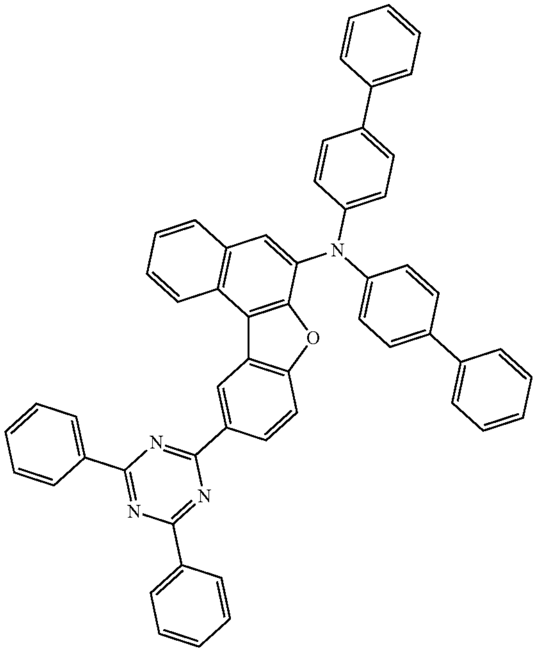
-continued
F366
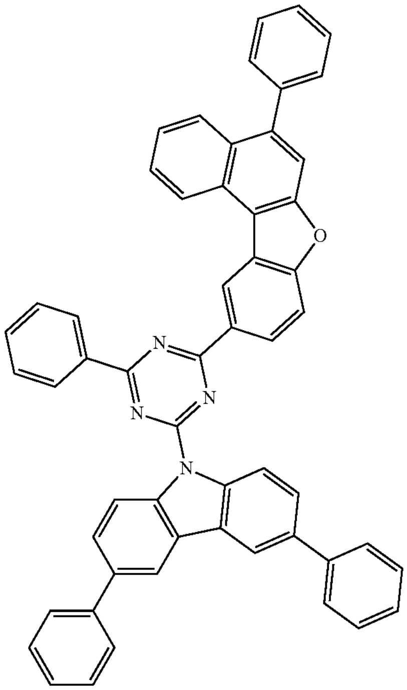
F367
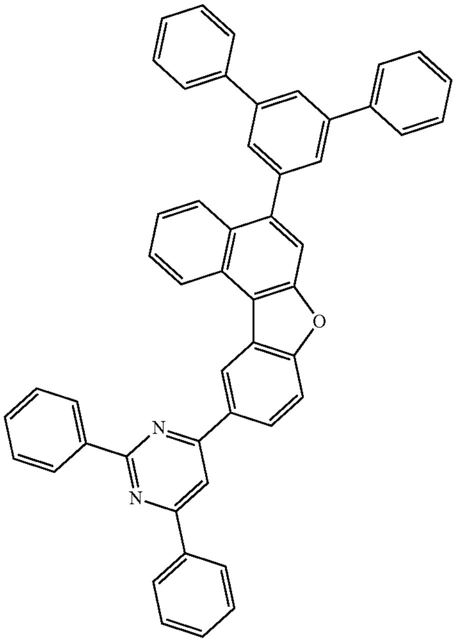

F368
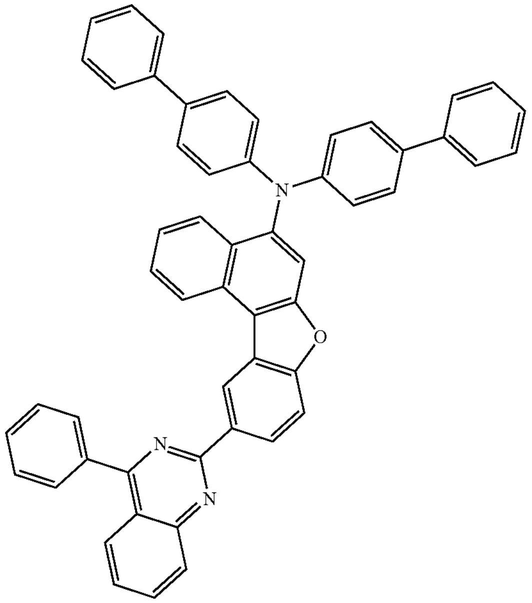
F369
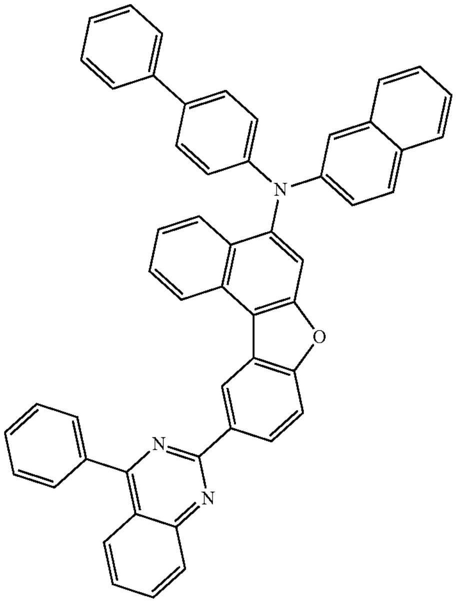
F370
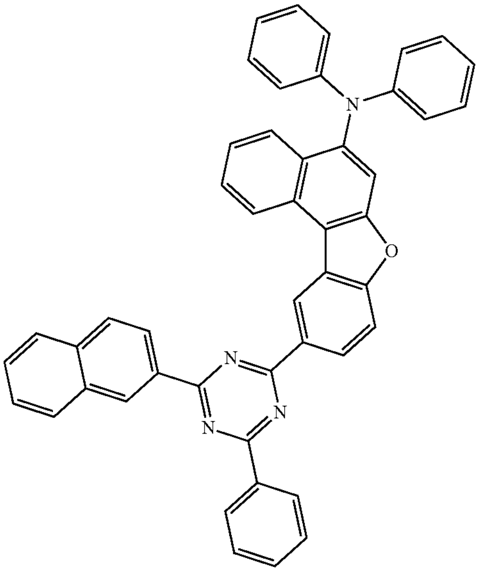
F371
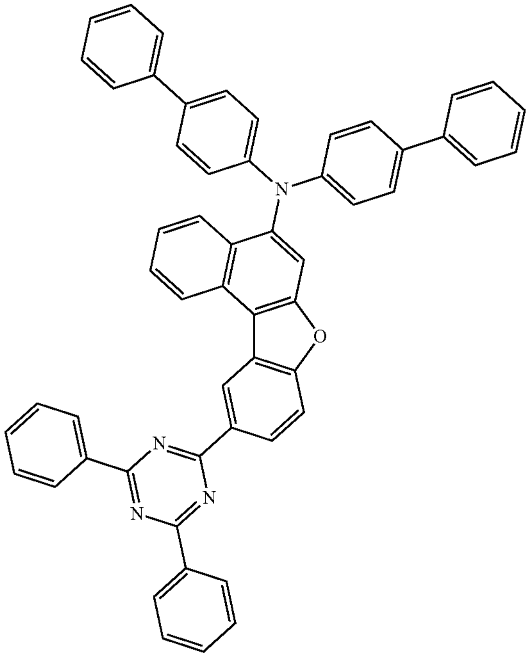

-continued
F372
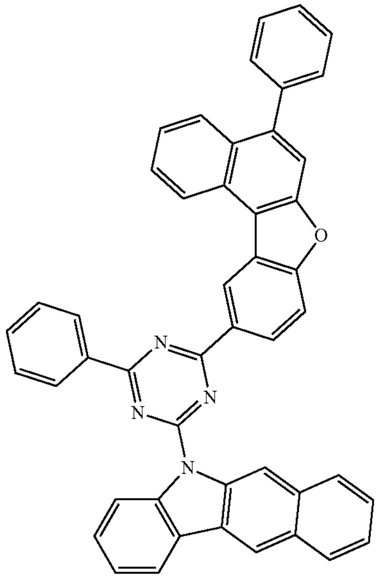
F373
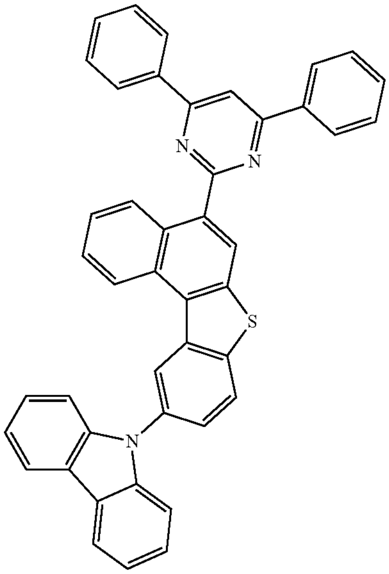
-continued
F374
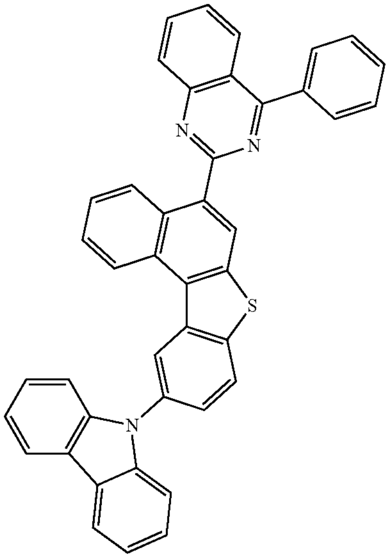
F375
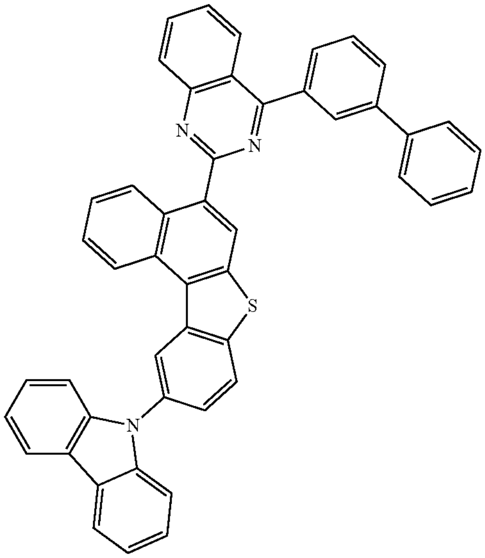

-continued
F376
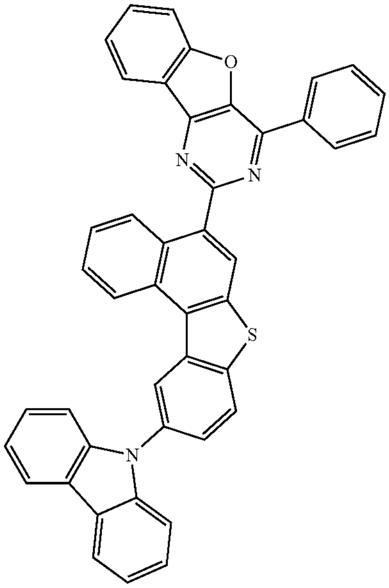
F377
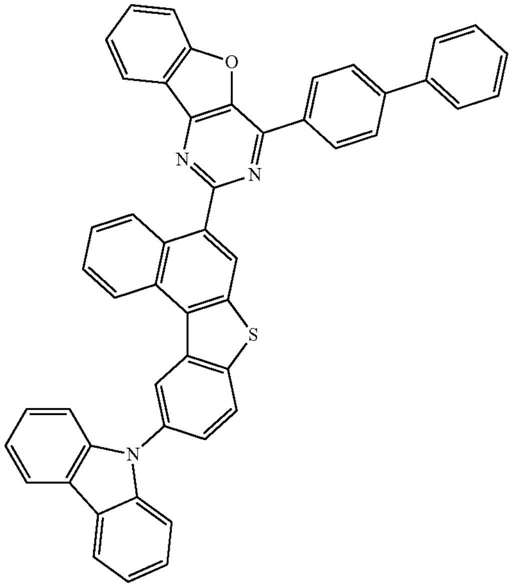
-continued
F378
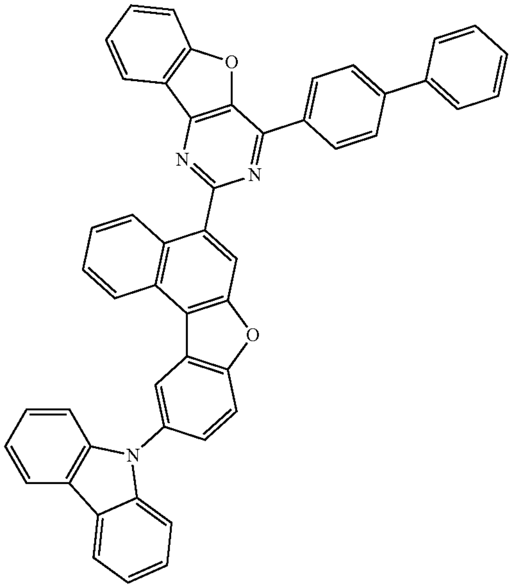
F379
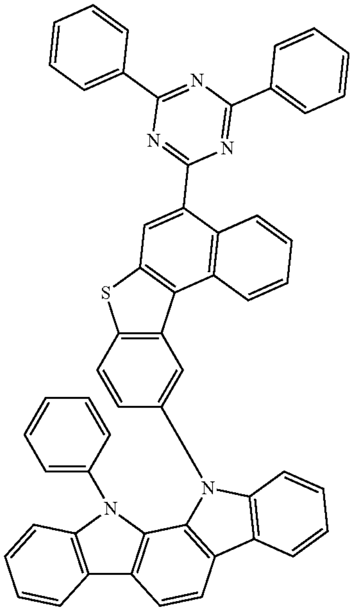

-continued
F380
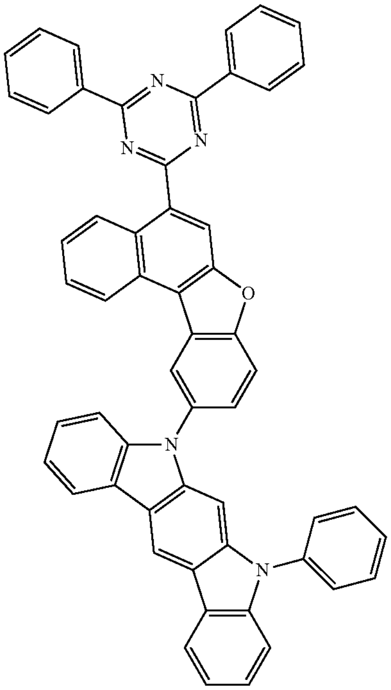
F381
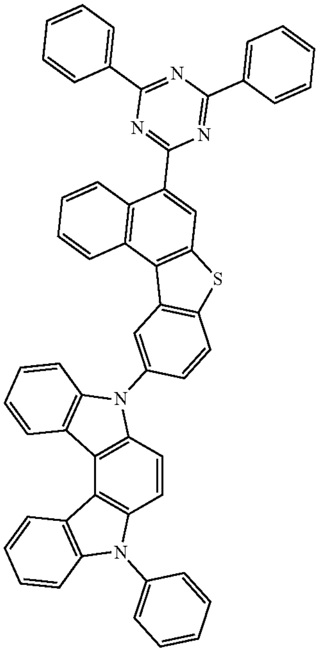
-continued
F382
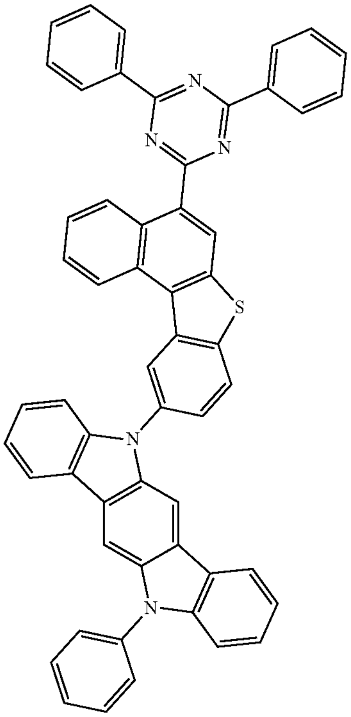
F383
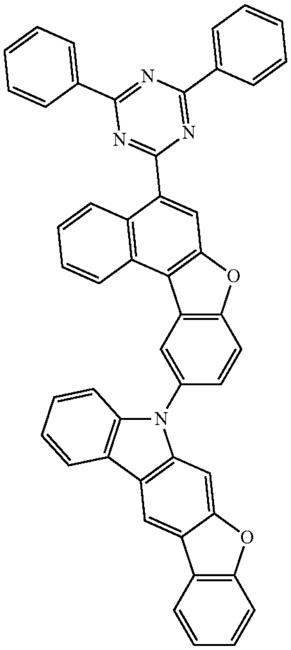

-continued
F384
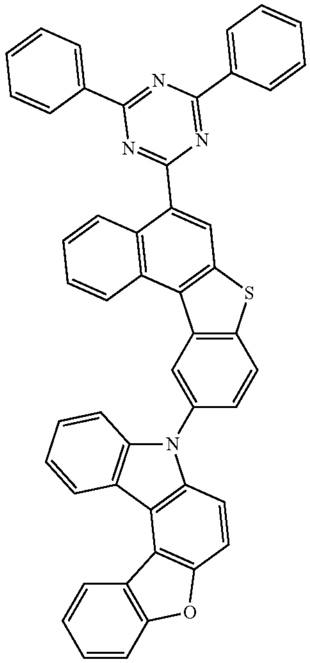
F385
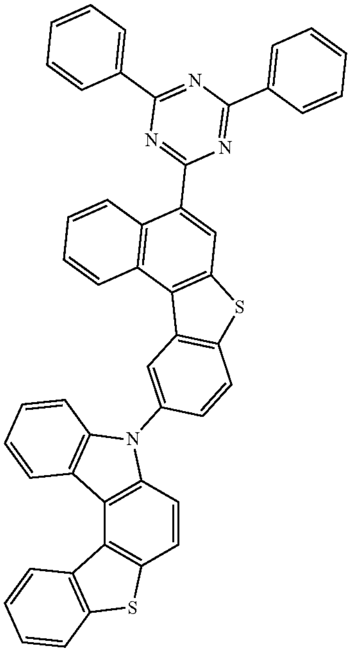
-continued
F386
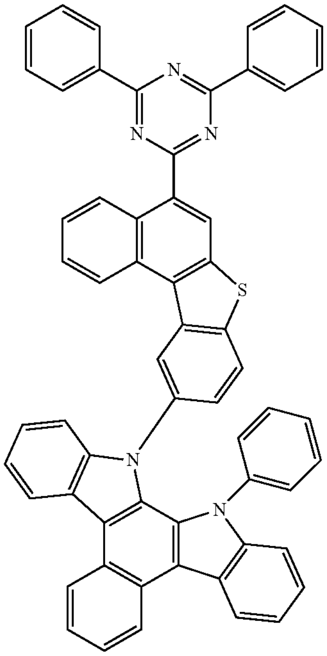
F387
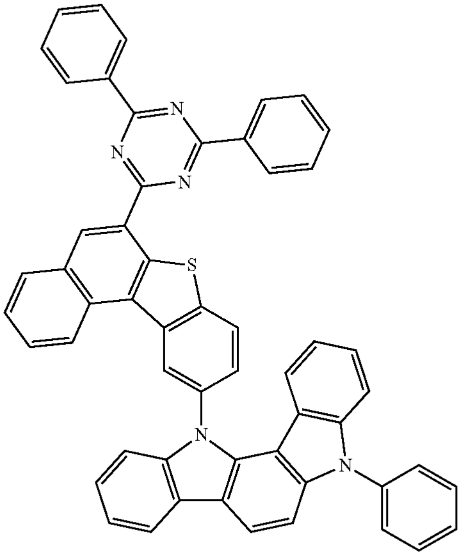

-continued
F388
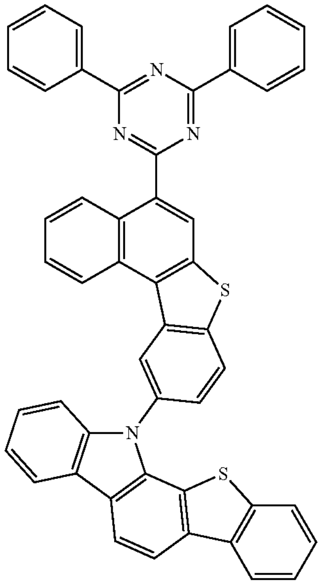
F389
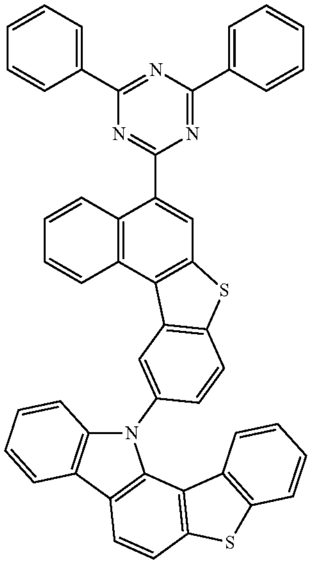
-continued
F390
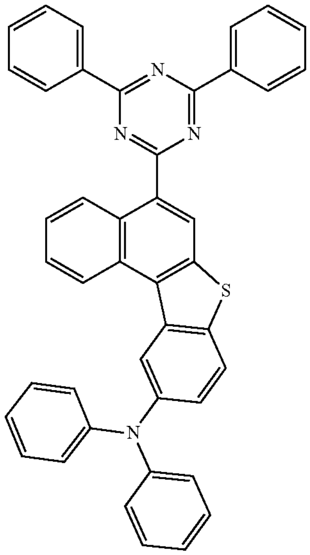
F391
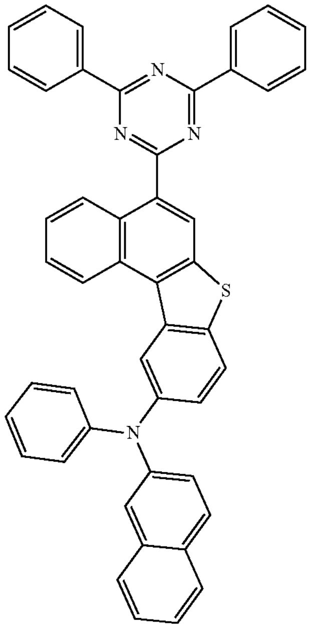

-continued
F392
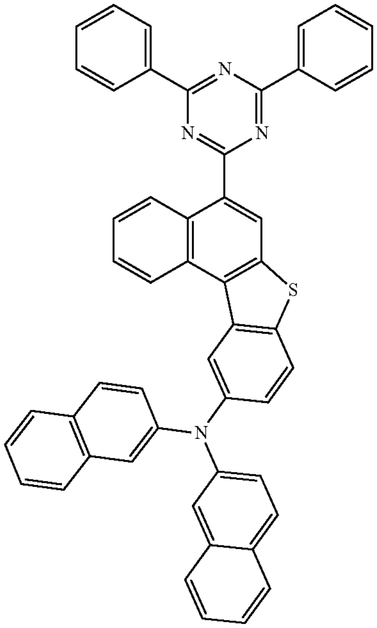
F393
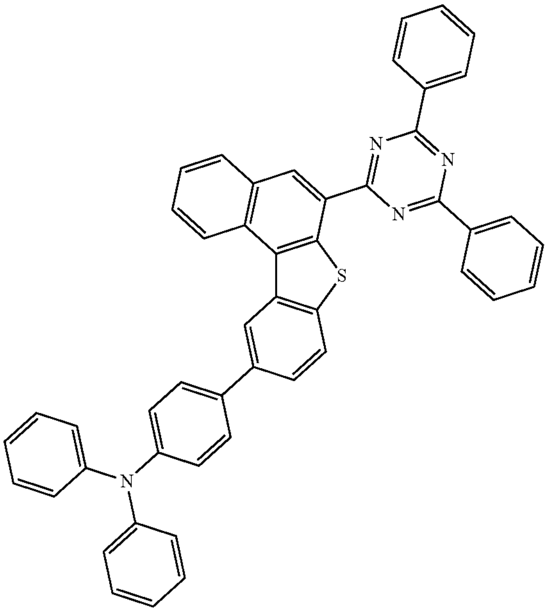
-continued
F394
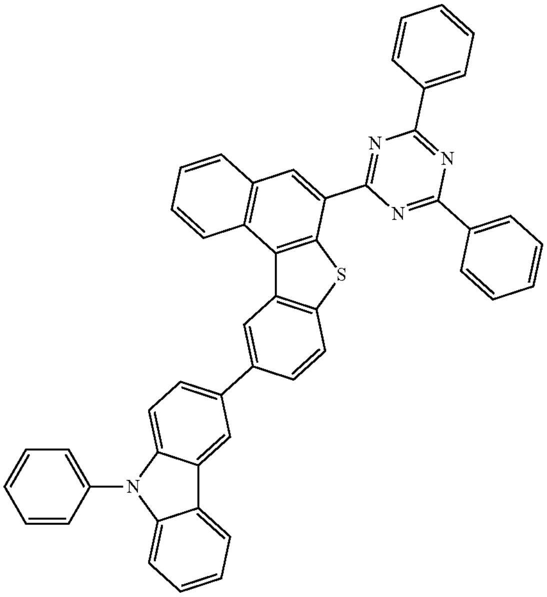
F395
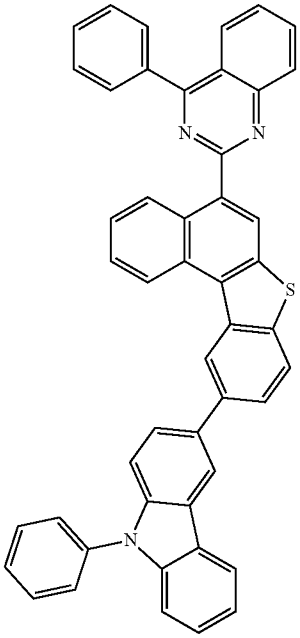

-continued
F396
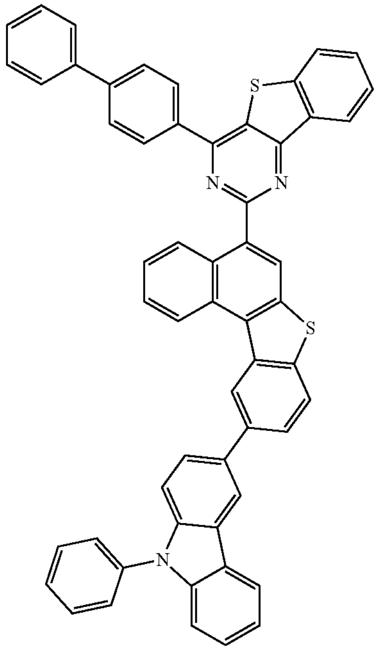
-continued
F398
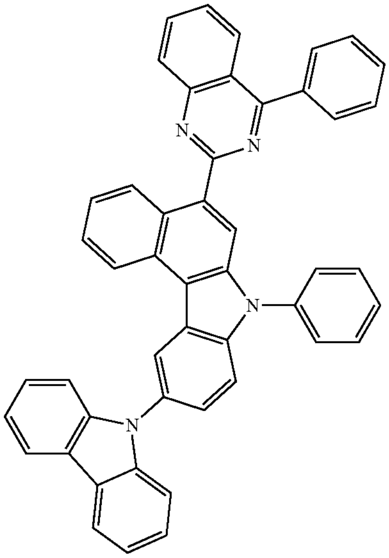
F397
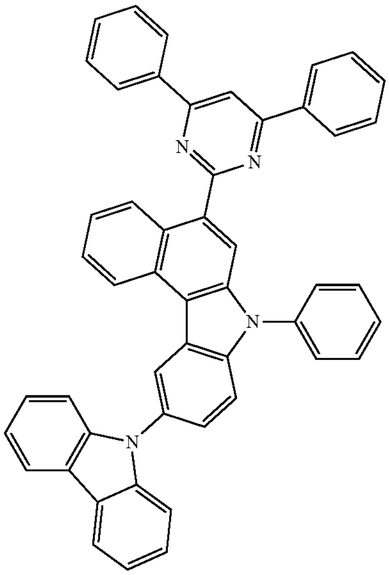
F399
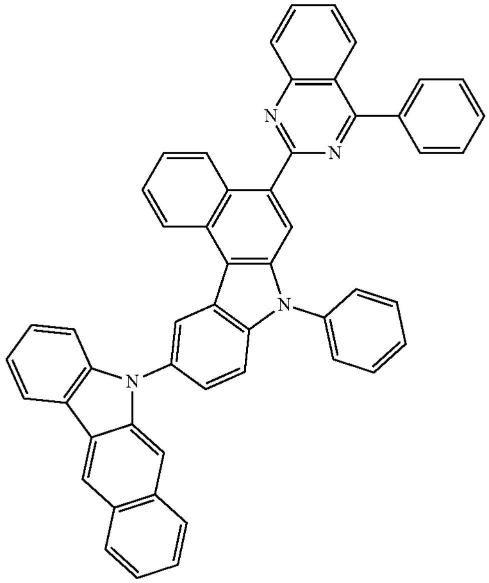

-continued
F400
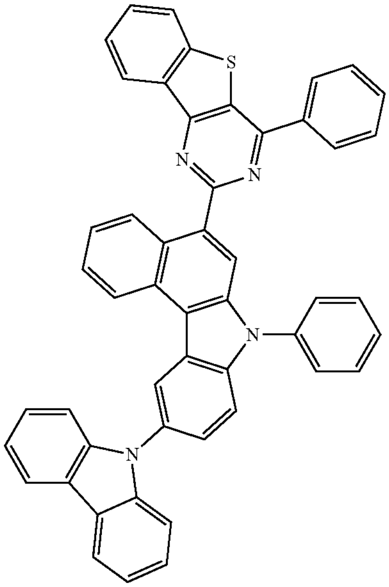
F402
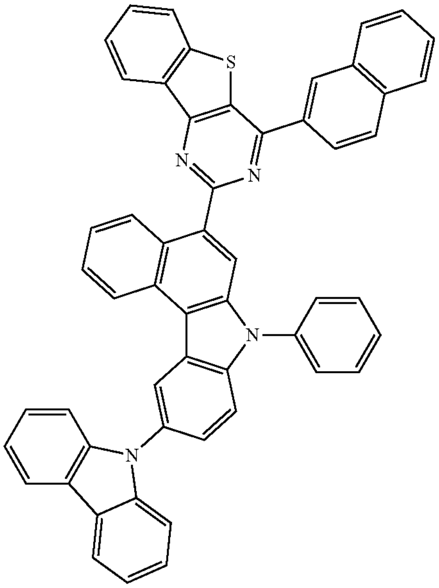
F401
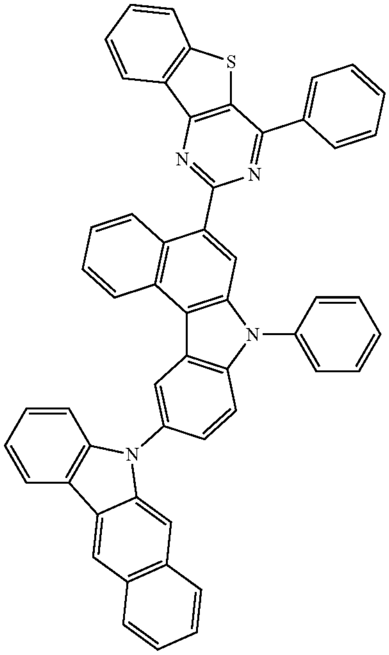
F403
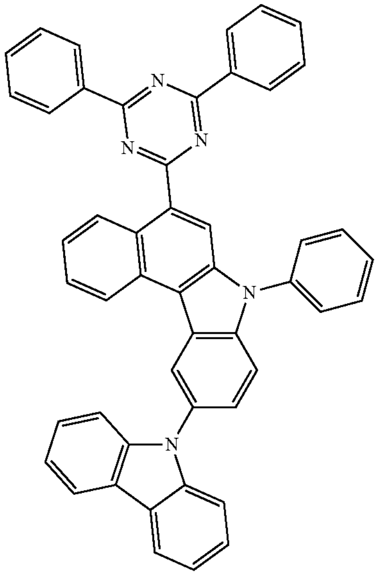

-continued
F404
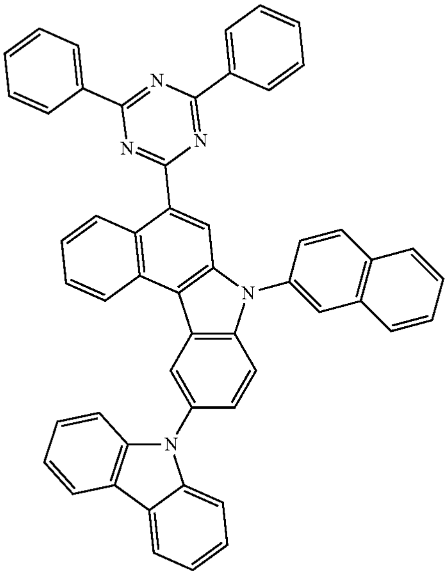
F405
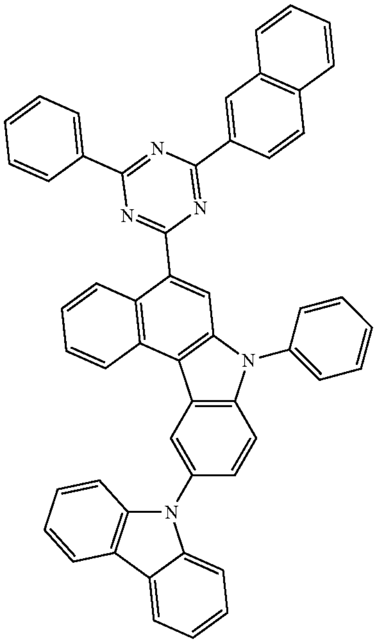
-continued
F406
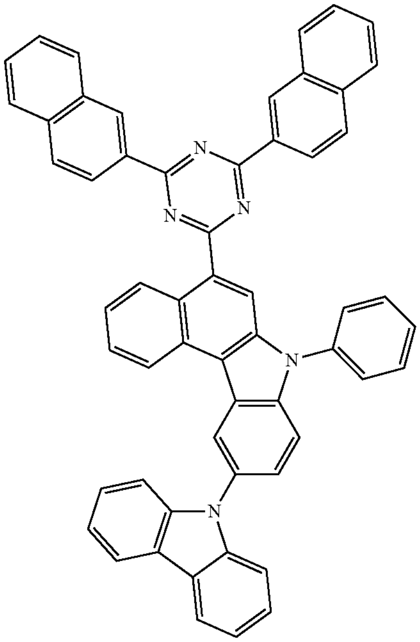
F407
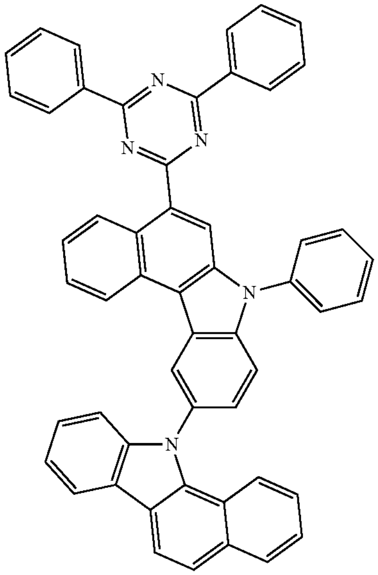

-continued
F408
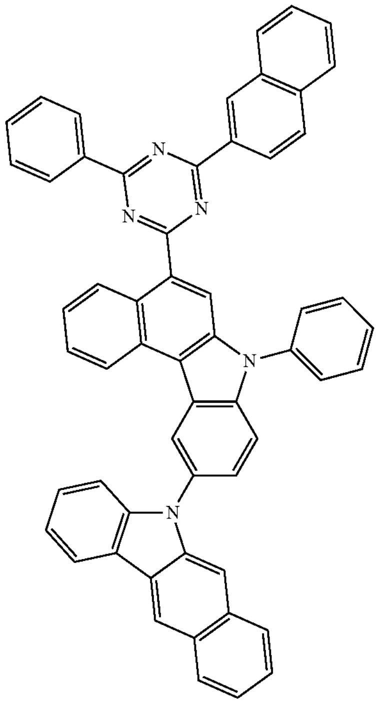
F409
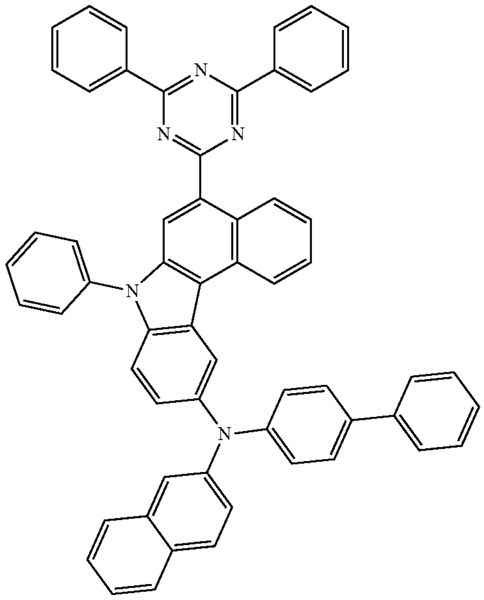
-continued
F410
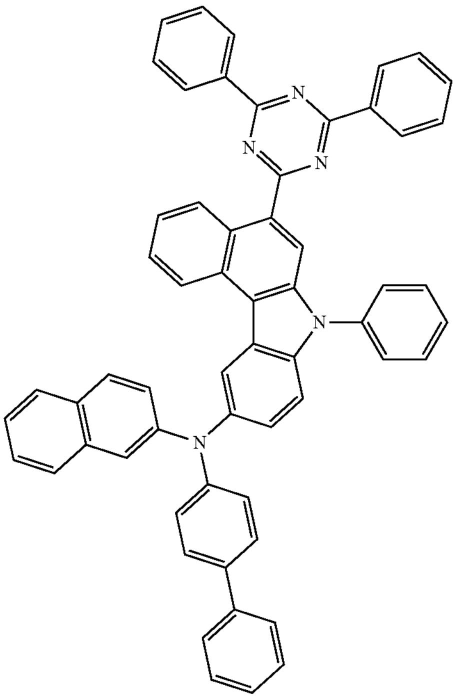
F411
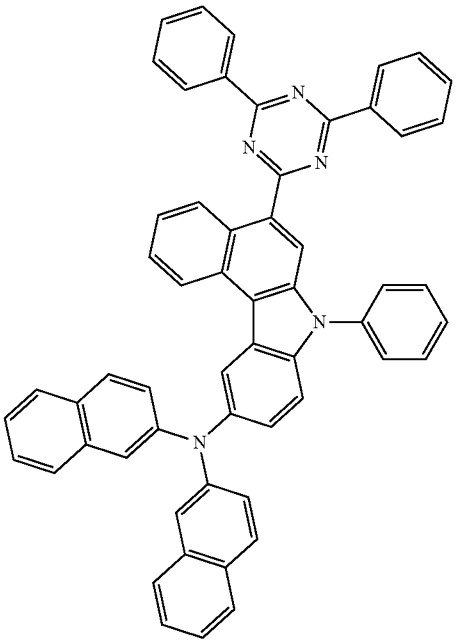

-continued
F412
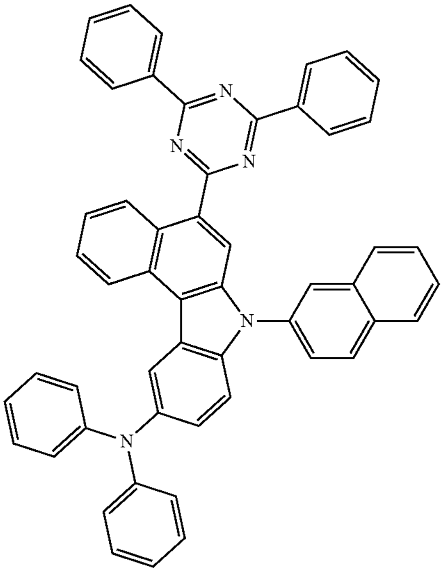
F413
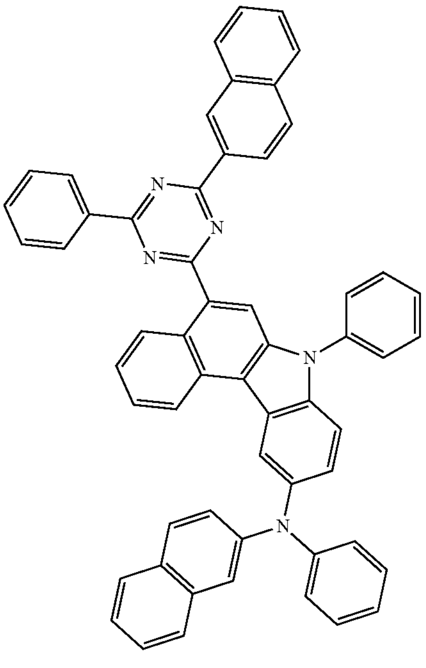
-continued
F414
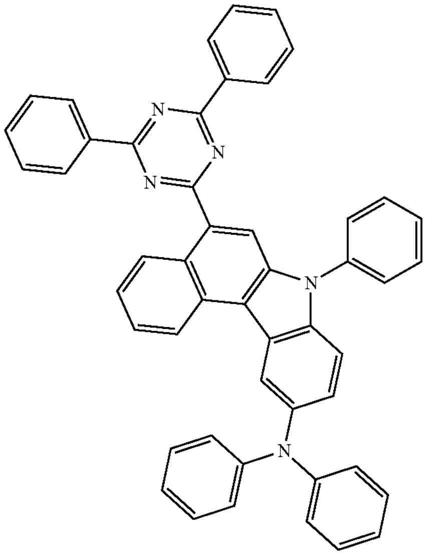
F415
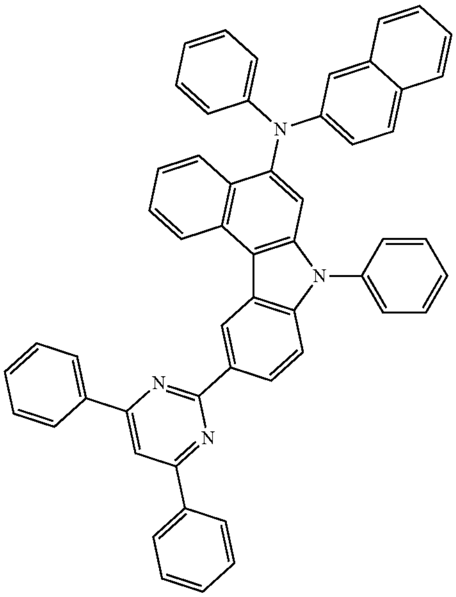

-continued
F416
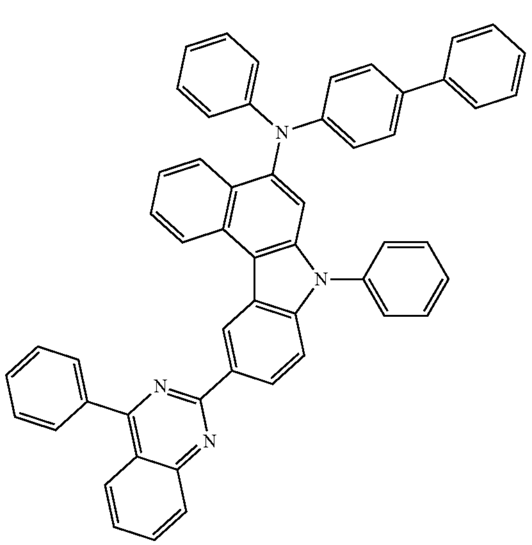
F417
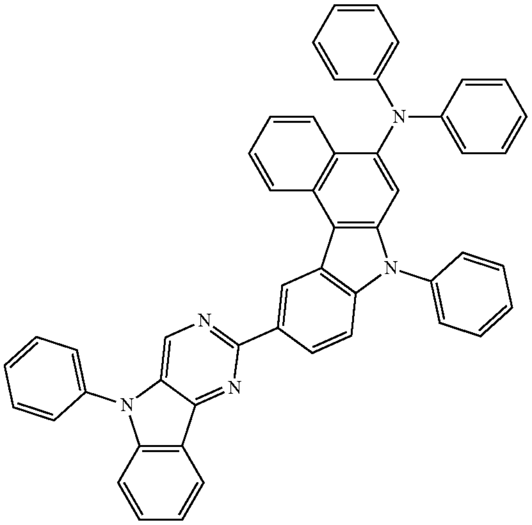
-continued
F418
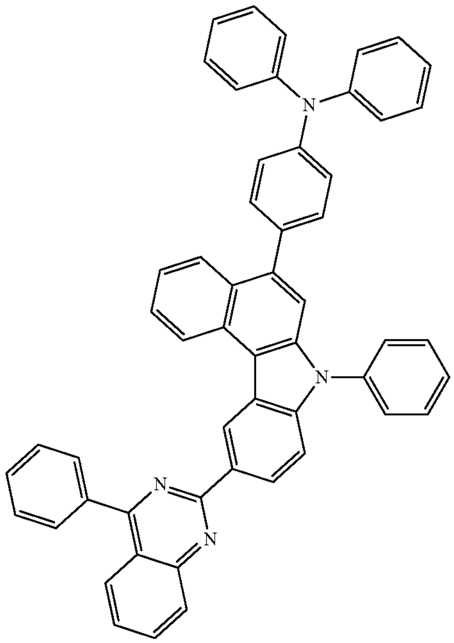
F419
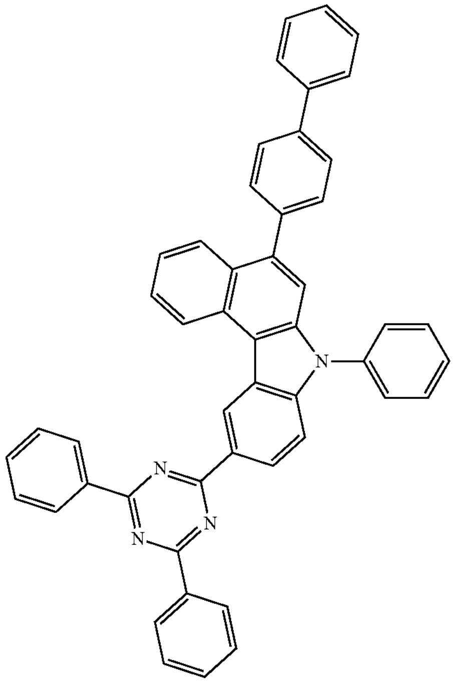

-continued
F420
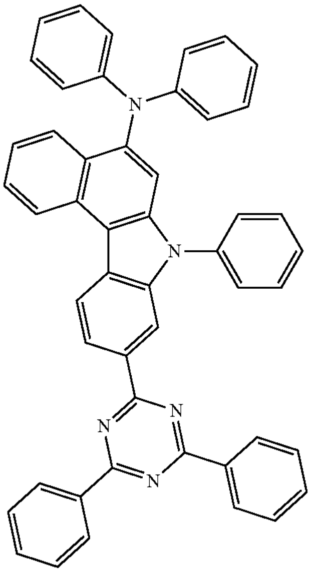
F421
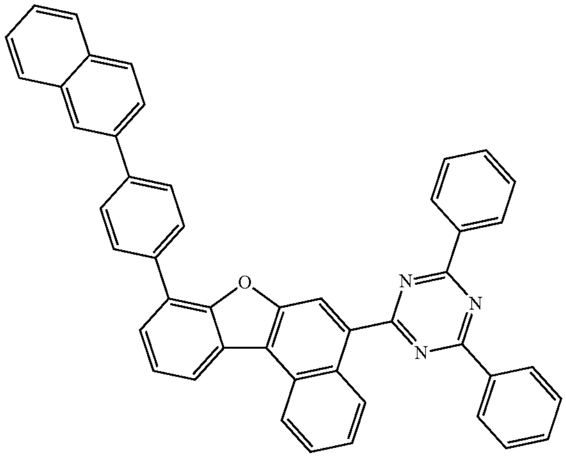
F422
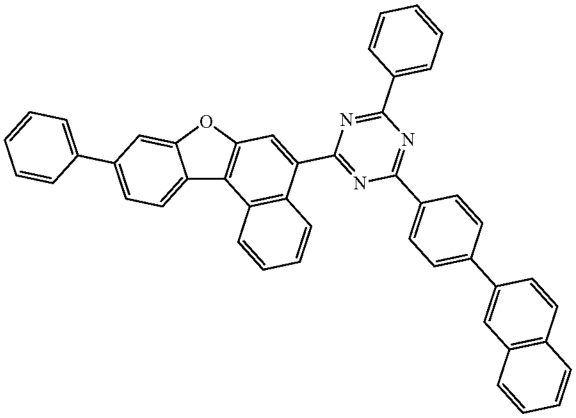
F423
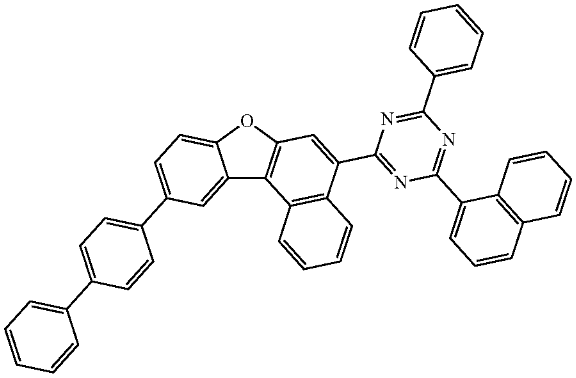
F424
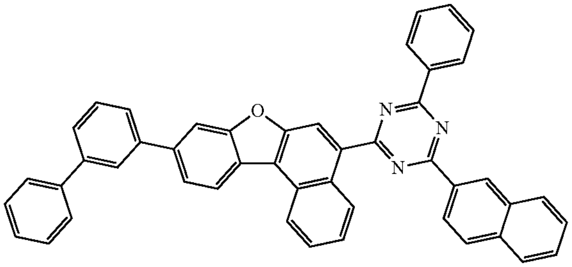

-continued
F425
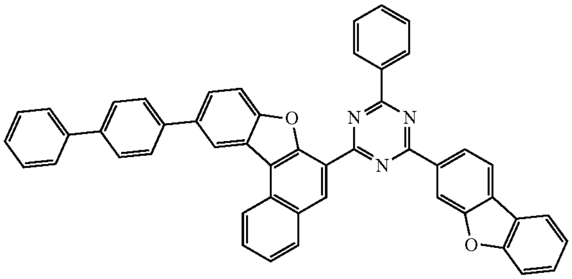
F426
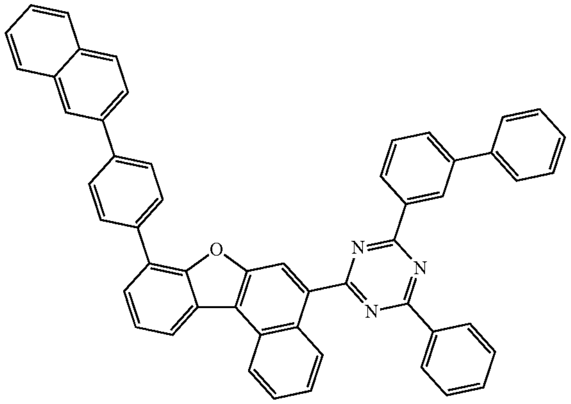
F427
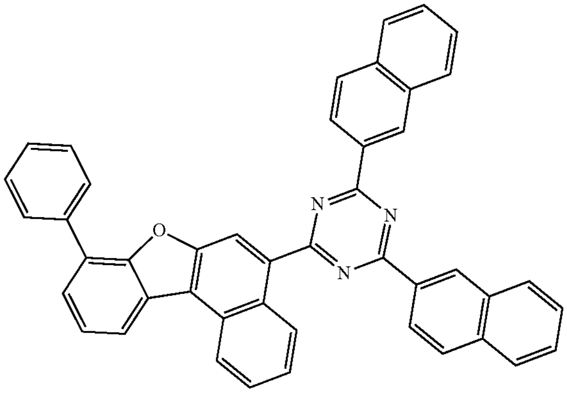
F428
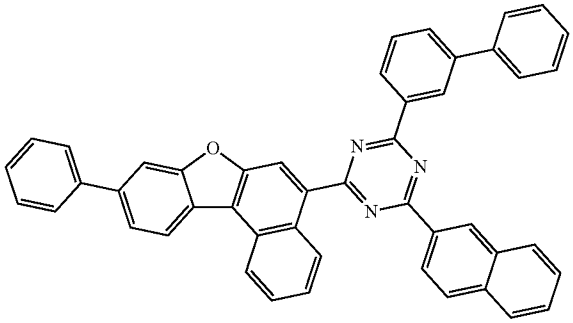
F429
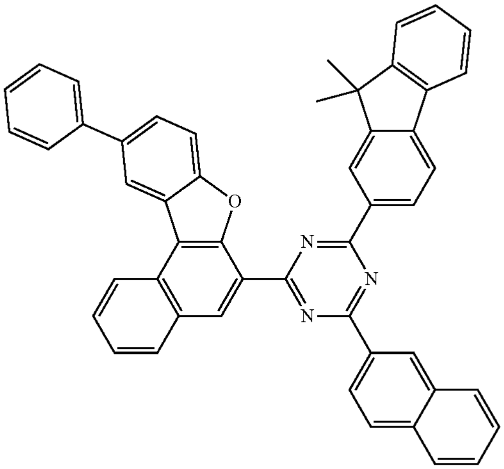
F430
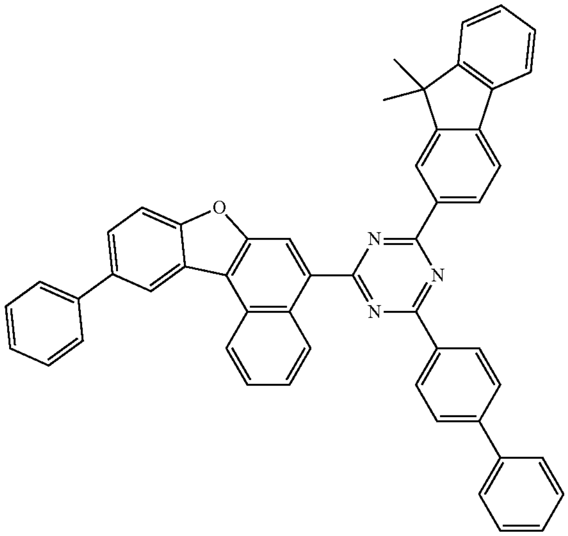

-continued
F431
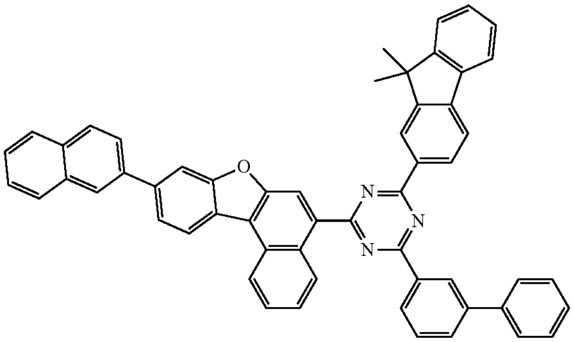
F432
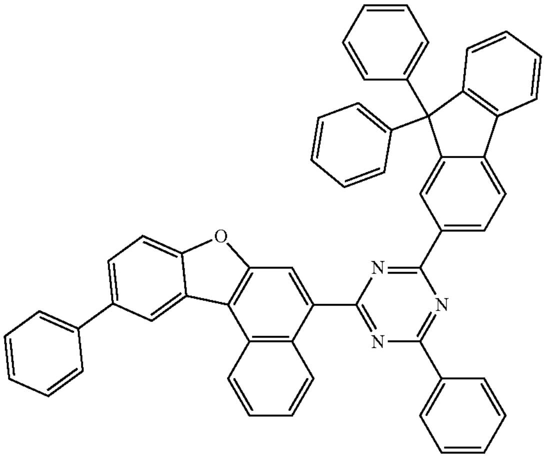
F433
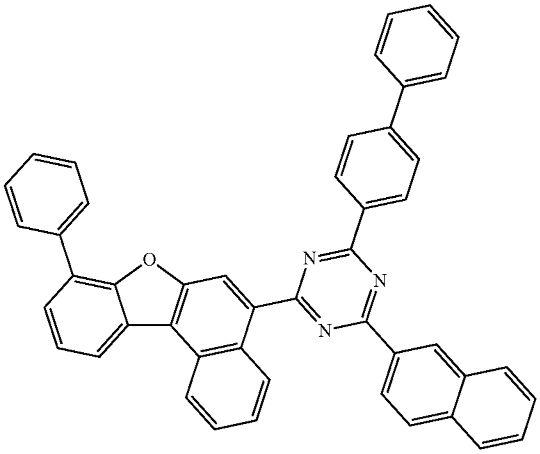
F434
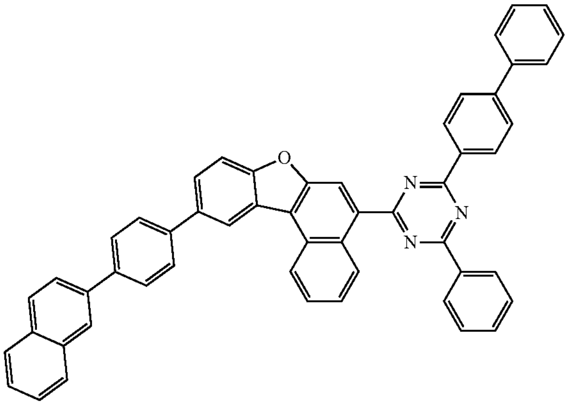
F435
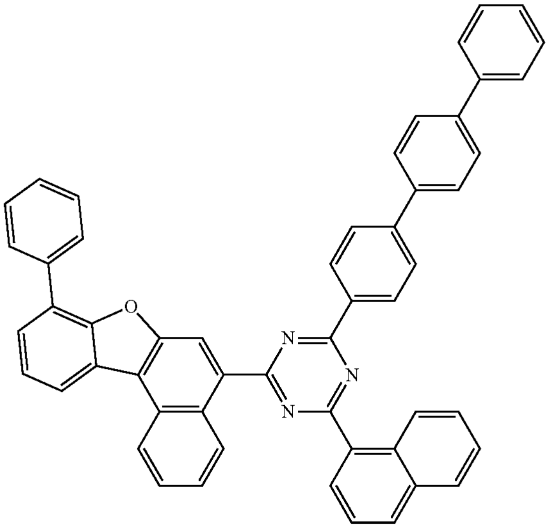
F436
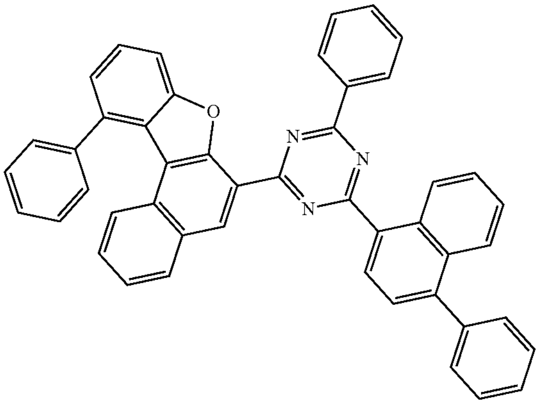

-continued
F437
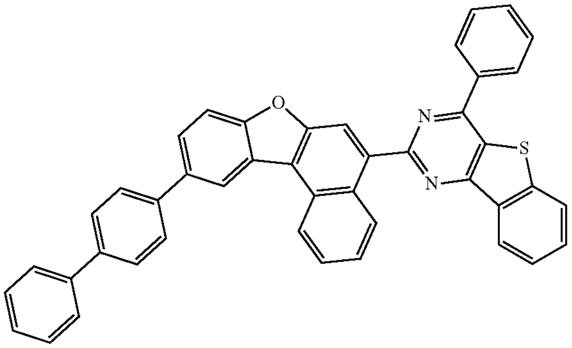
F438
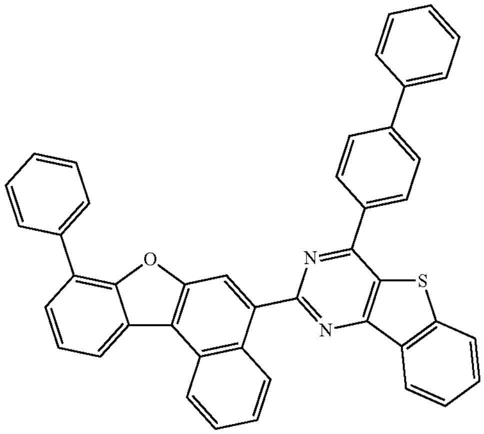
F439
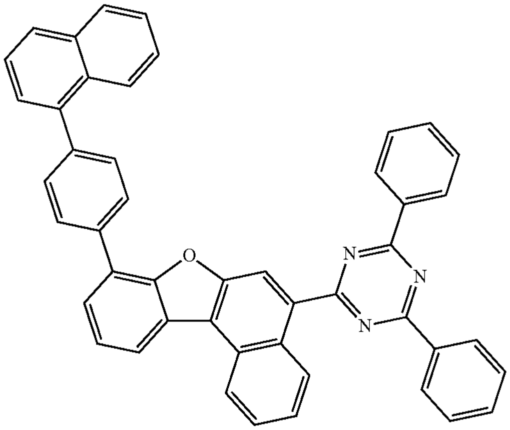
F440
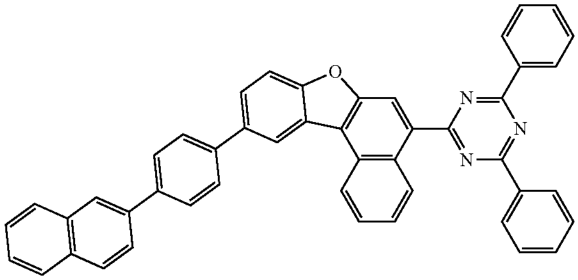
F441
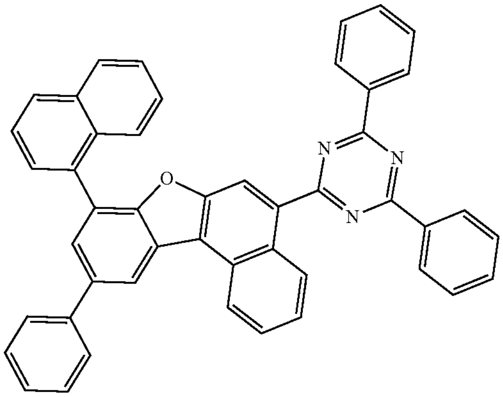
F442
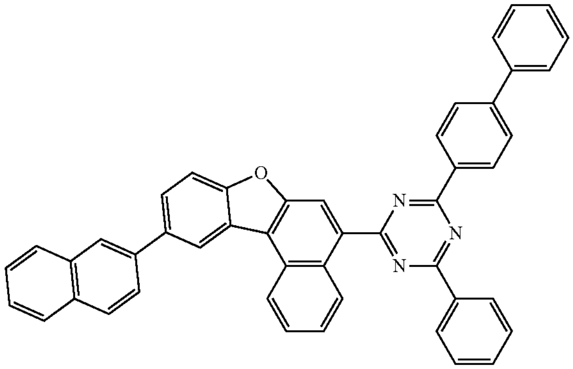

-continued
F443
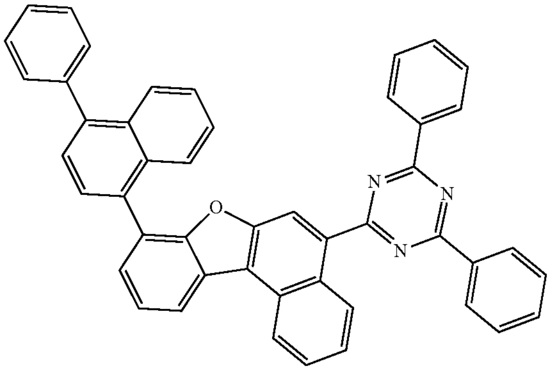
F444
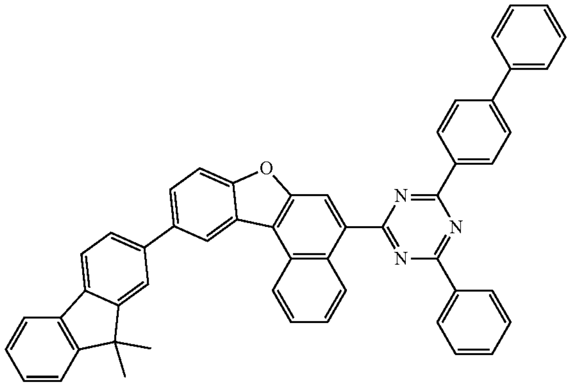
F445
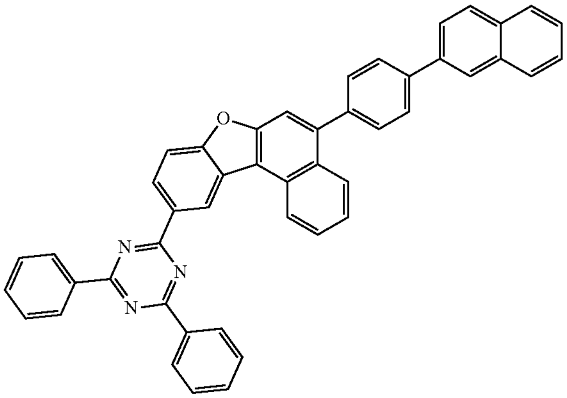
F446
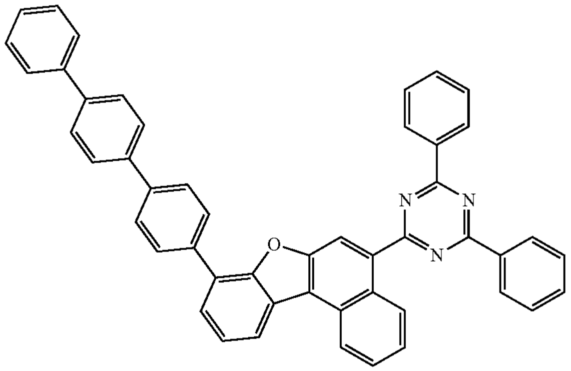
F447
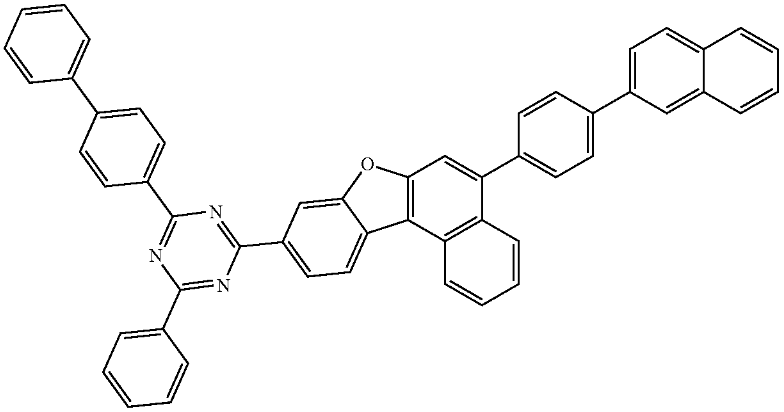

-continued
F448
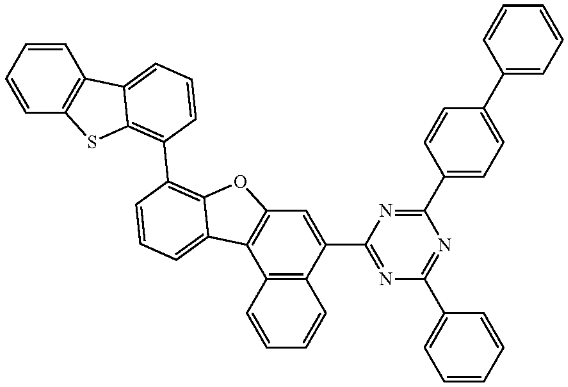
F449
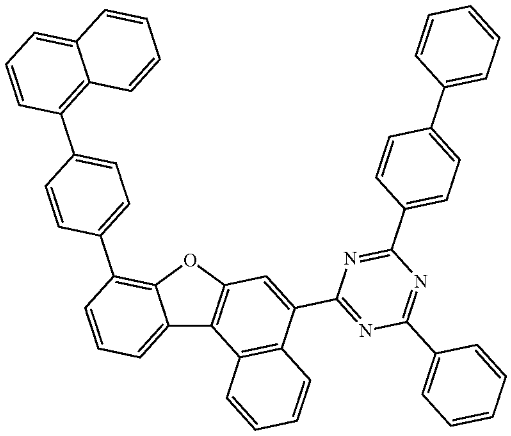
F450
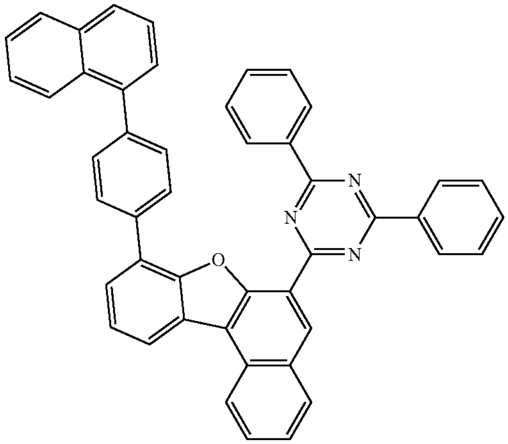
F451
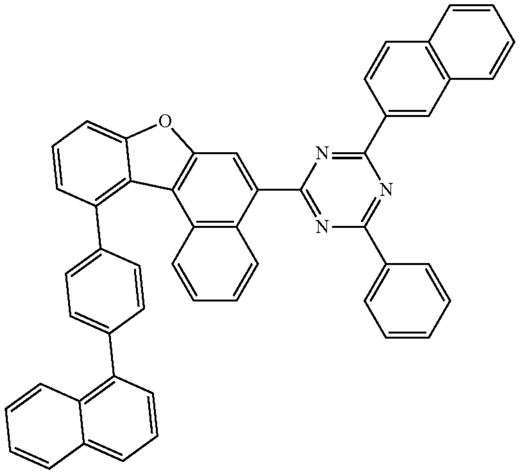
F452
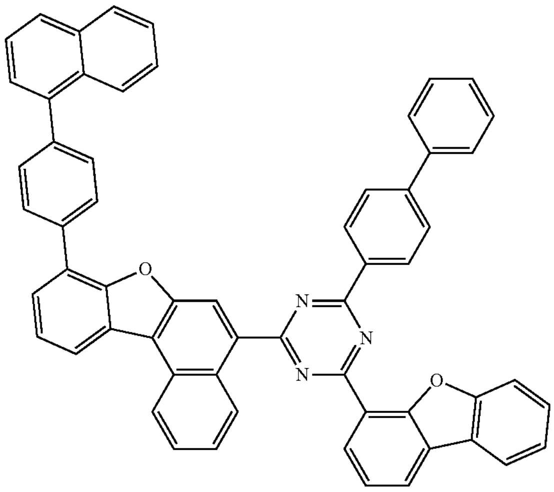
F453
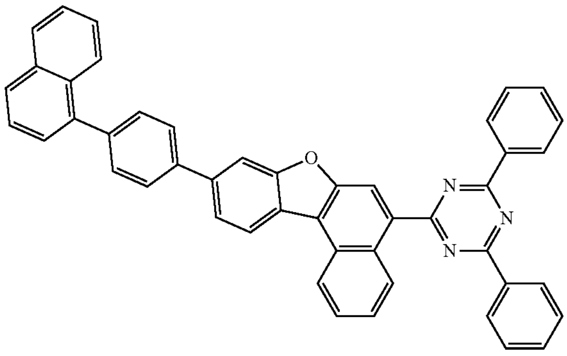

-continued
F454
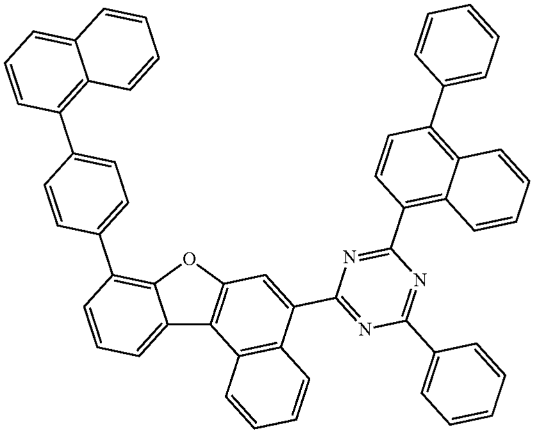
F455
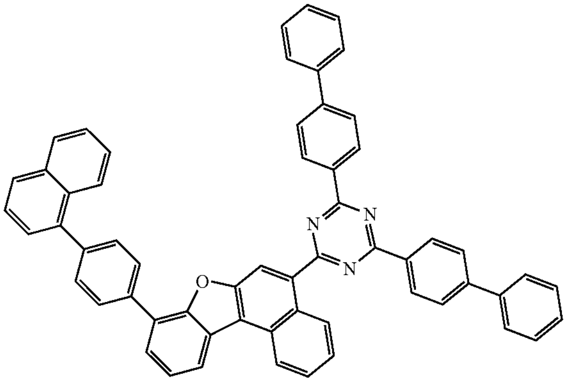
F456
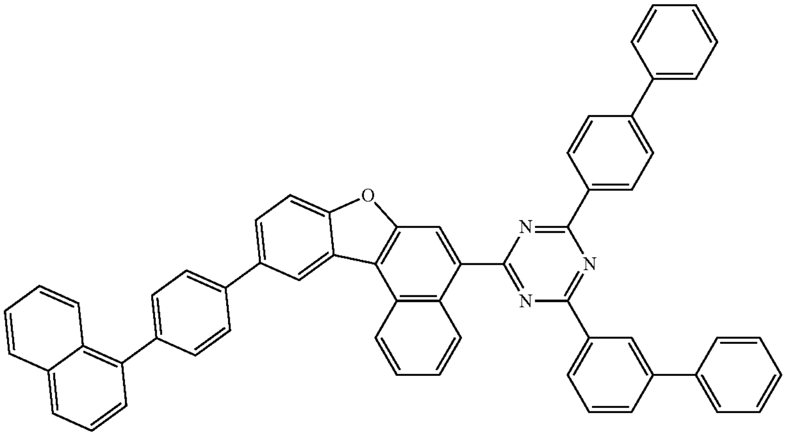
F457
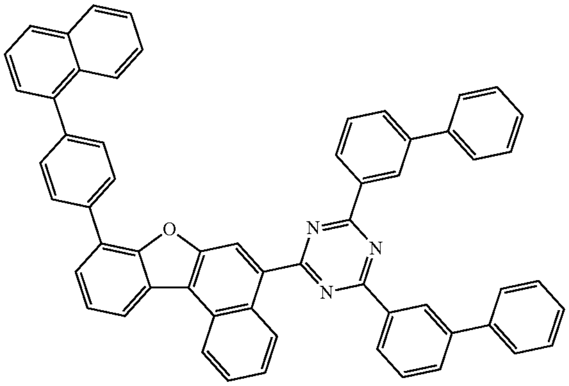
F458
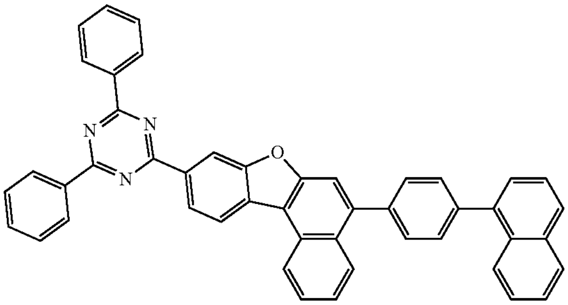

-continued
F459
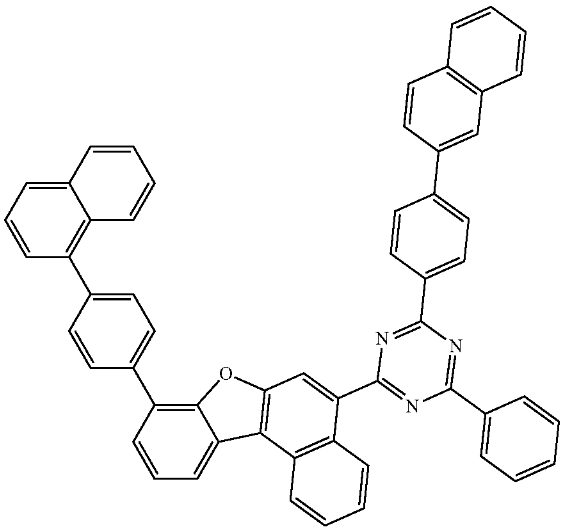
F460
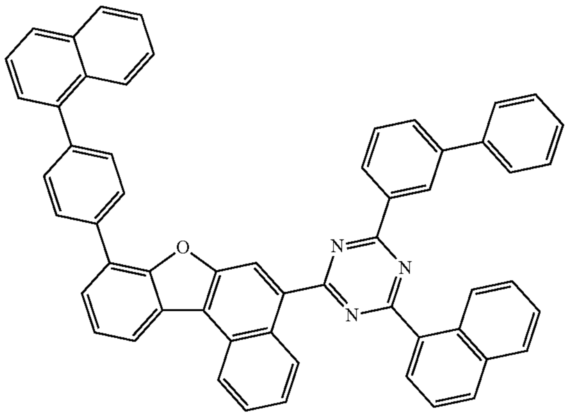
F461
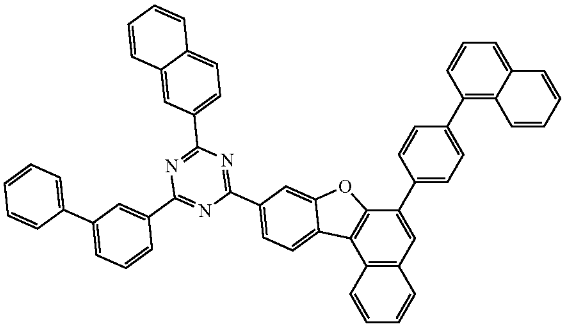
F462
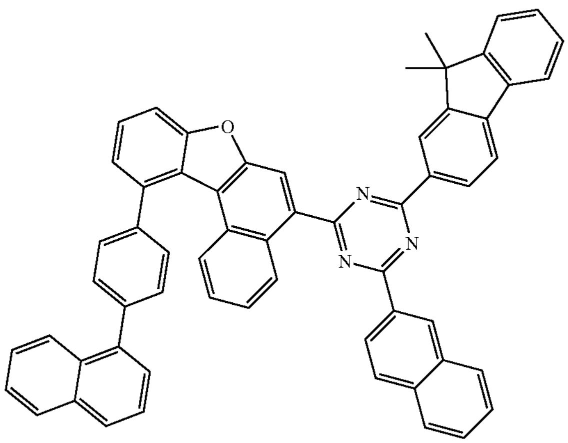
F463
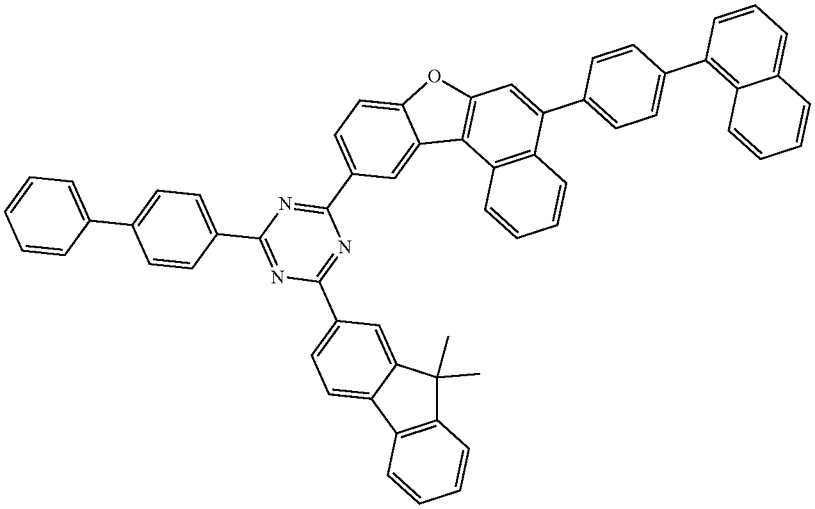

-continued
F464
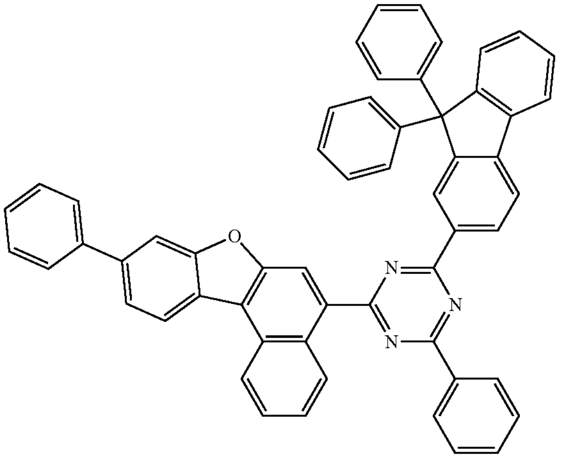
F465
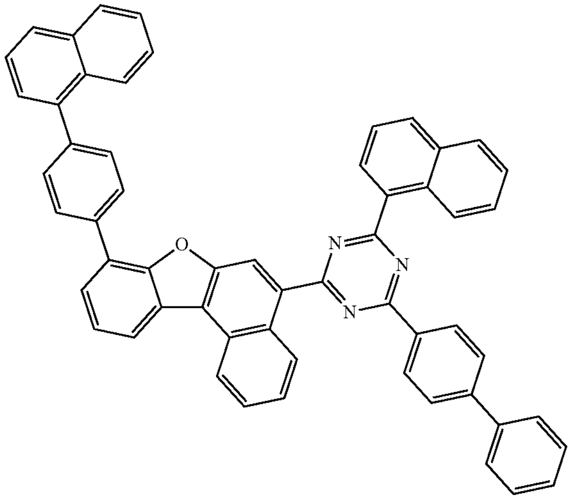
F466
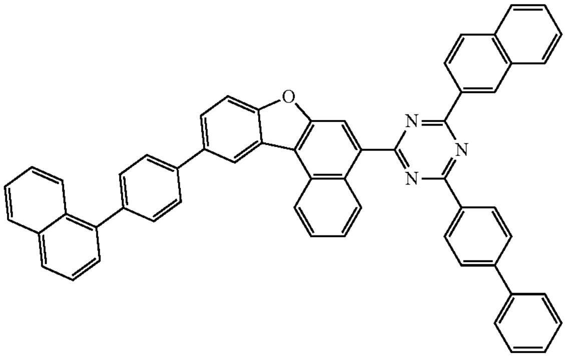
F467
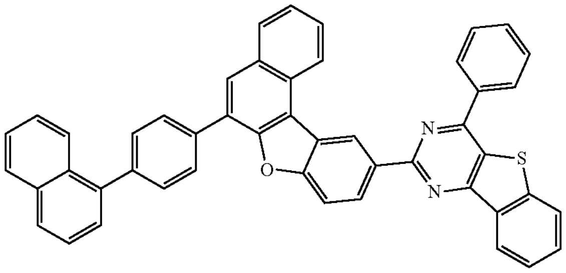
F468
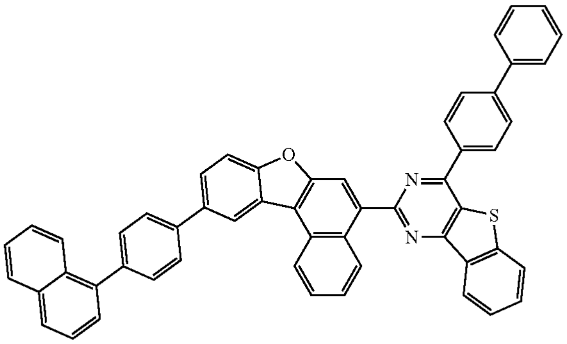
F469
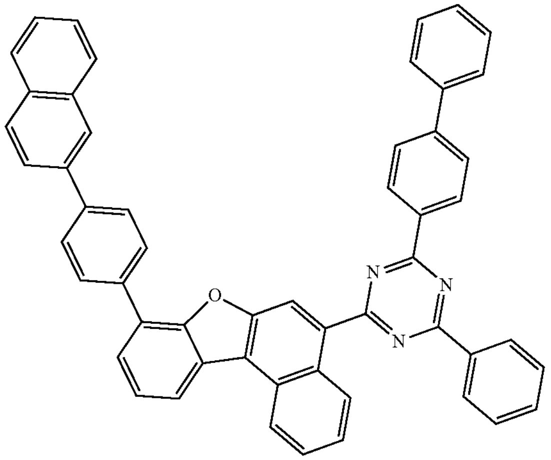

-continued
F470
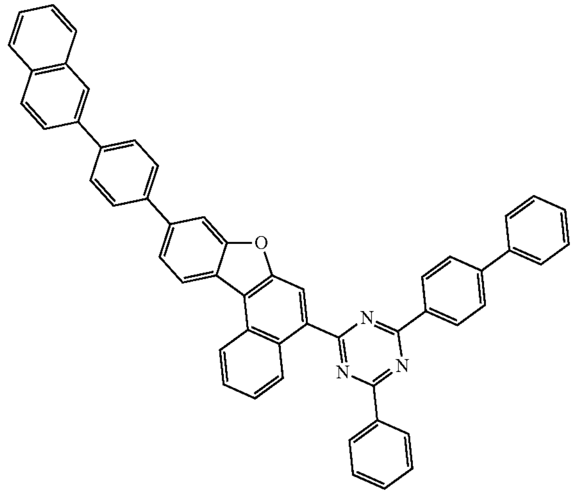
F471
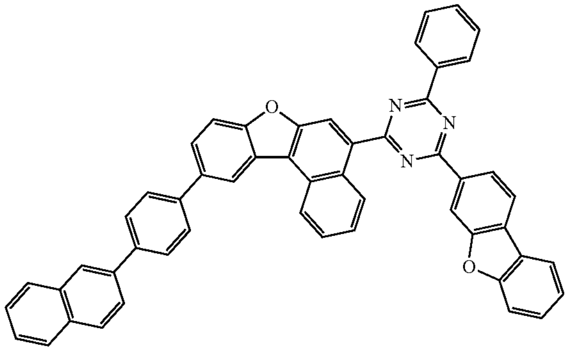
F472
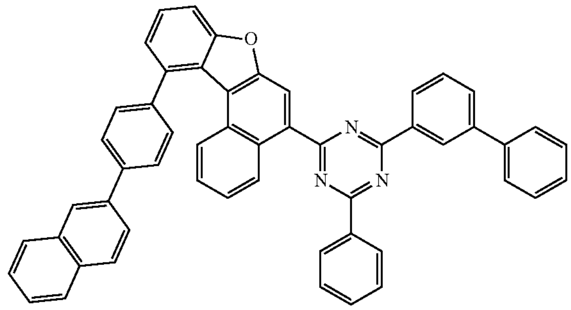
F473
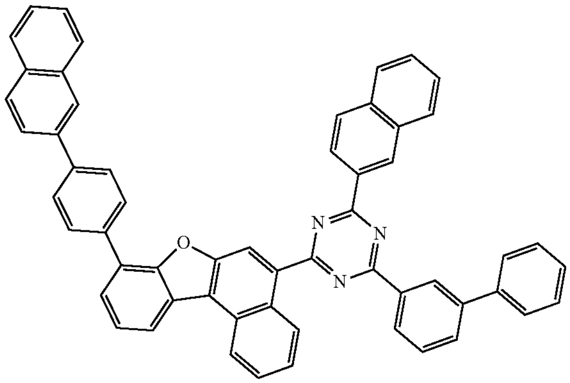
F474
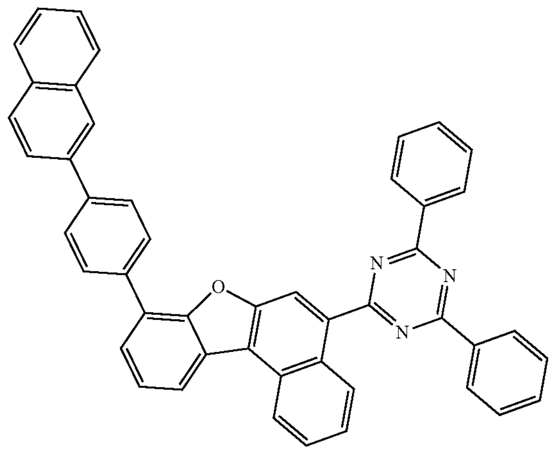
F475
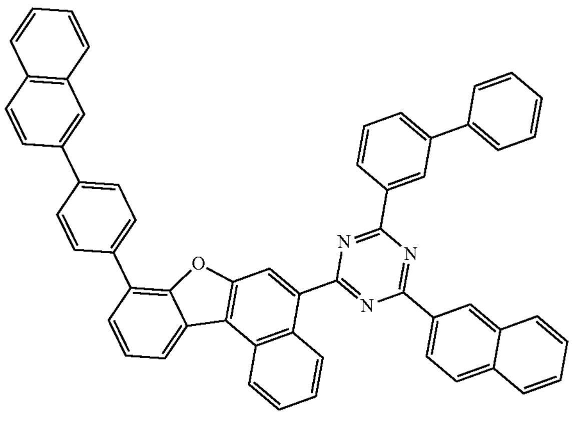

-continued
F476
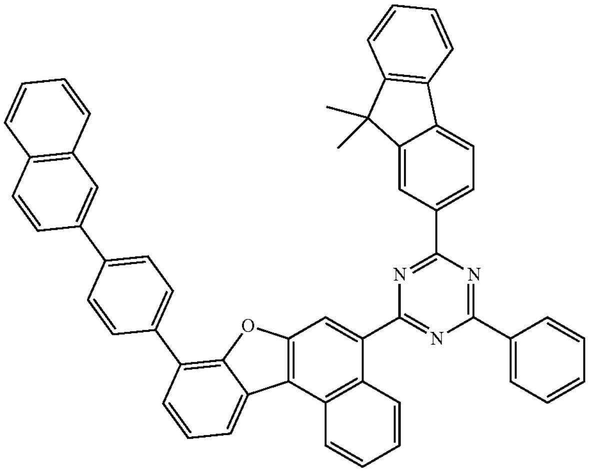
F477
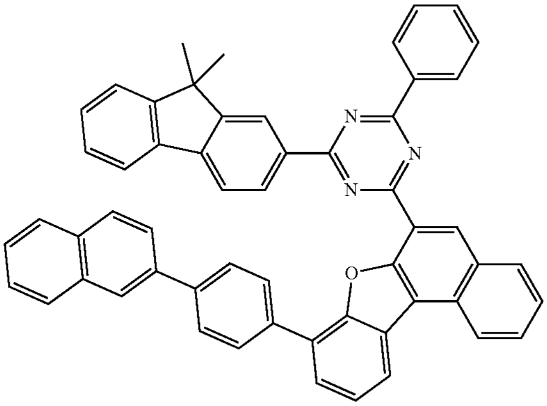
F478
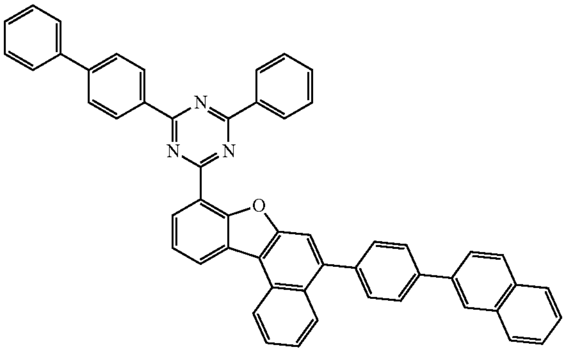
F479
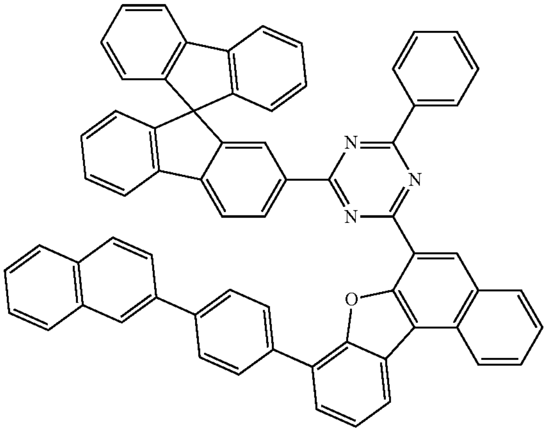
F480
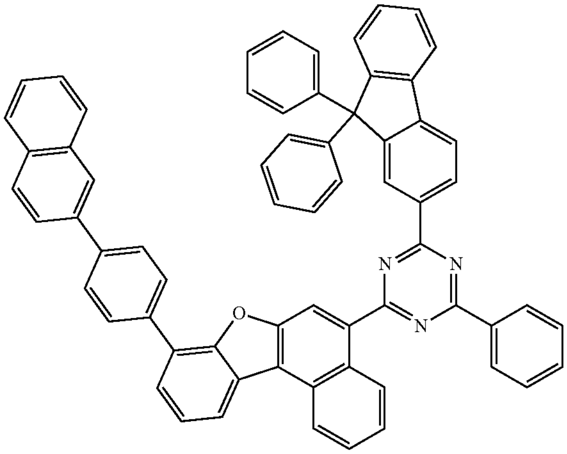
F481
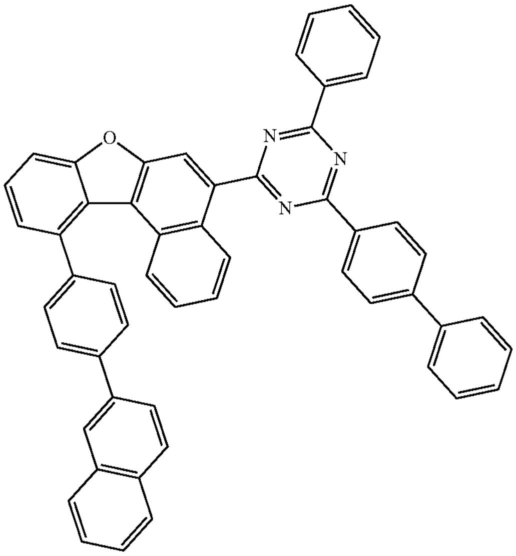

-continued
F482
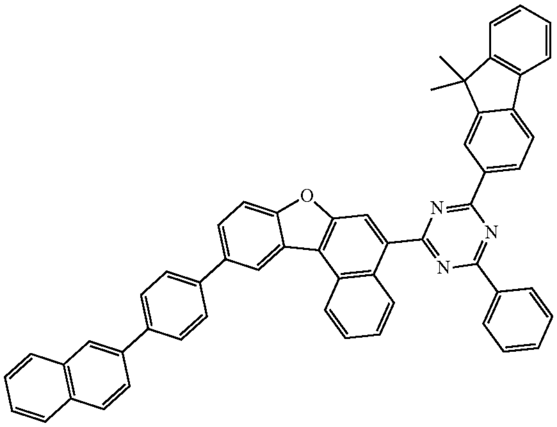
F483
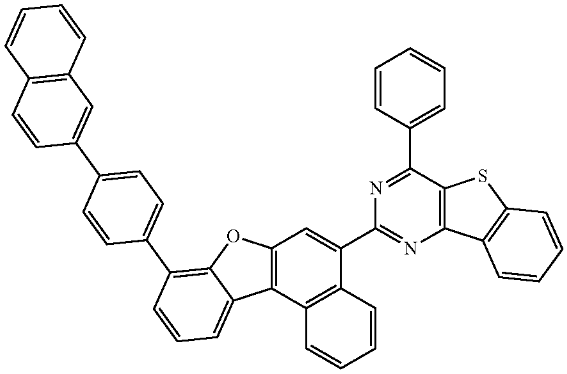
F484
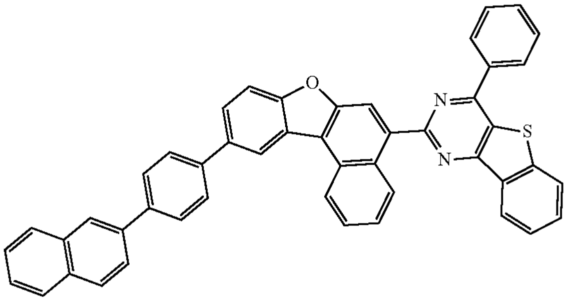
F485
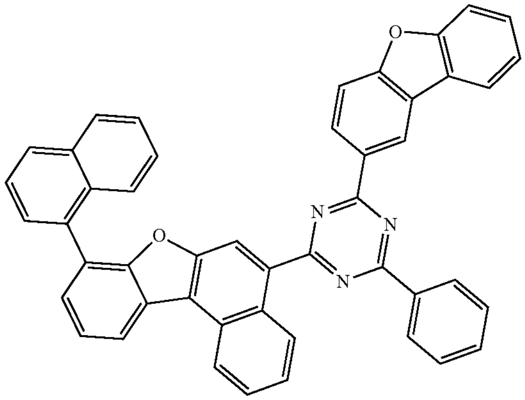
F486
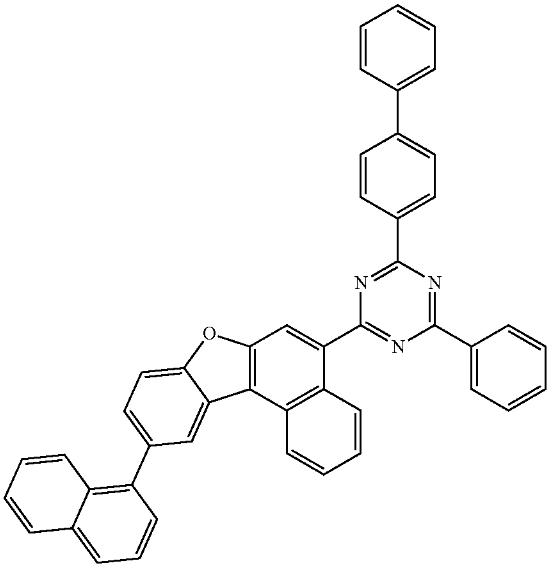
F487
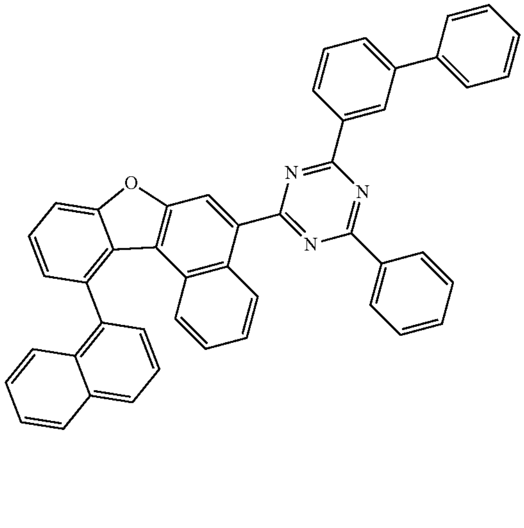

-continued
F488
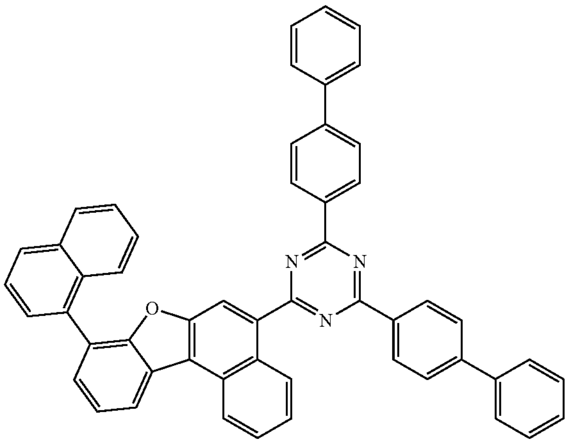
F489
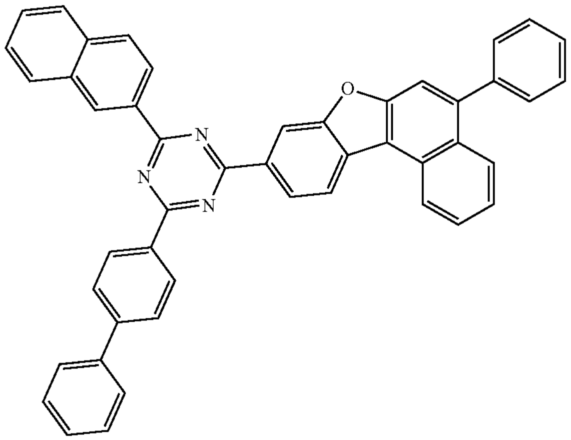
F490
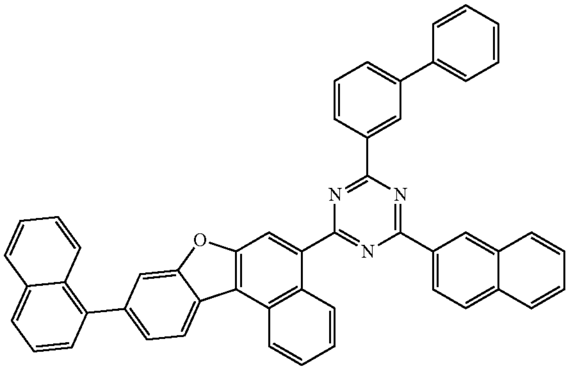
F491
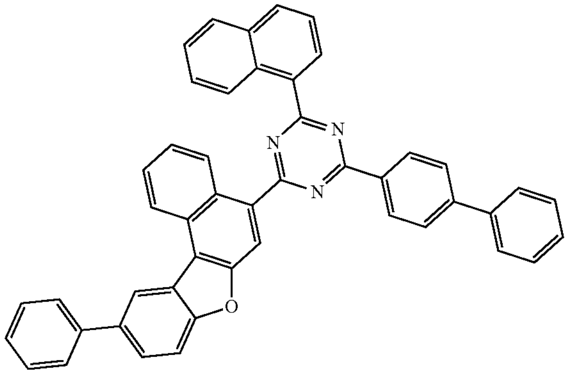
F492
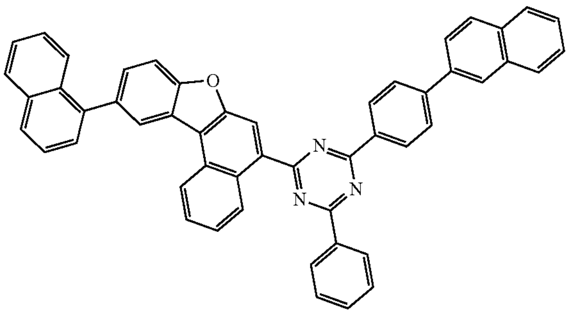
F493
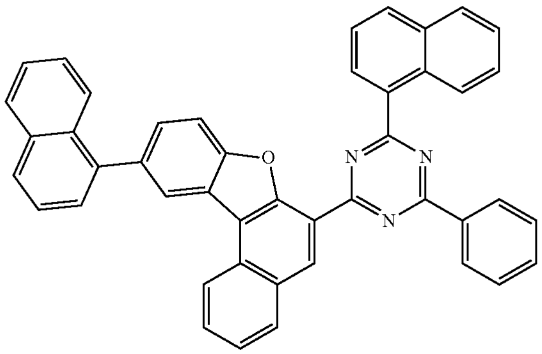

-continued
F494
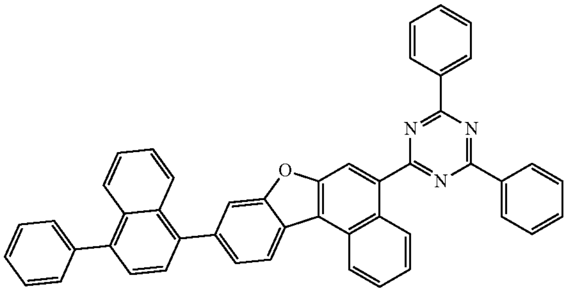
F495
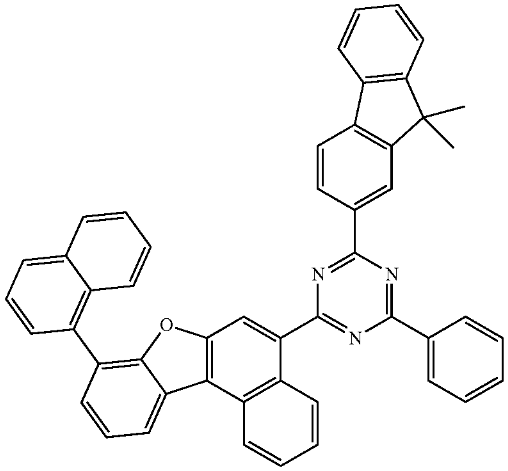
F496
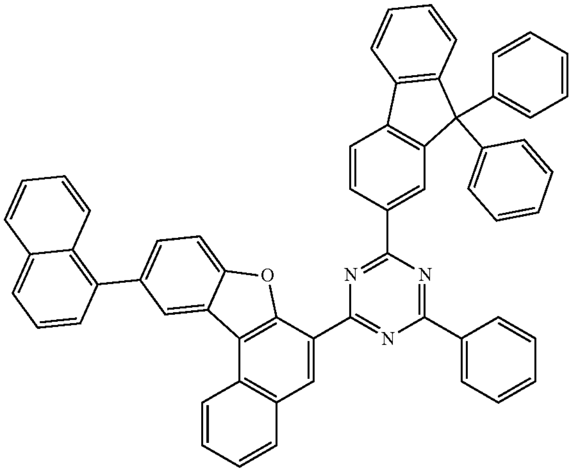
F497
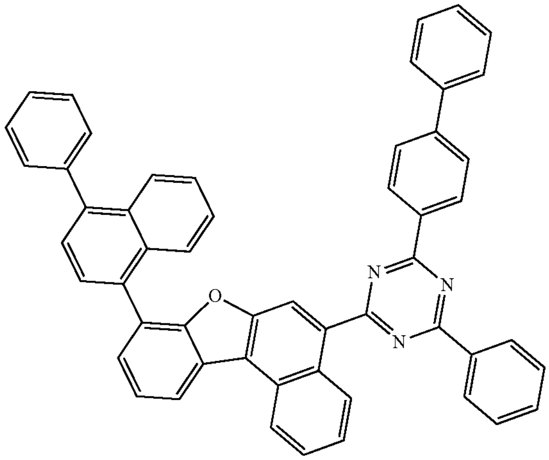
F498
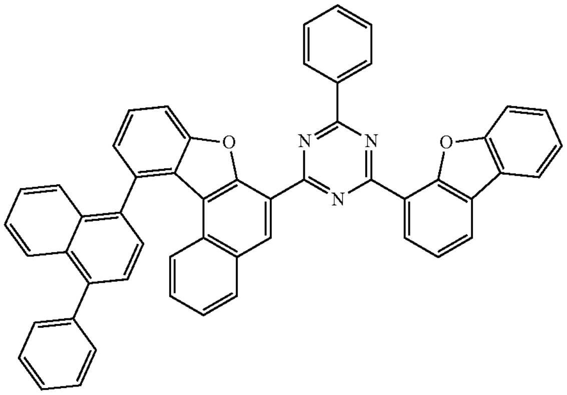
F499
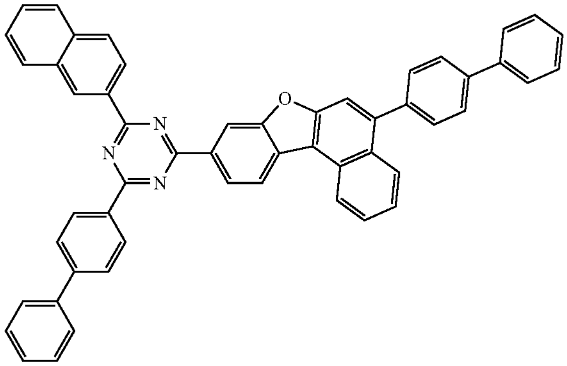

-continued
F500
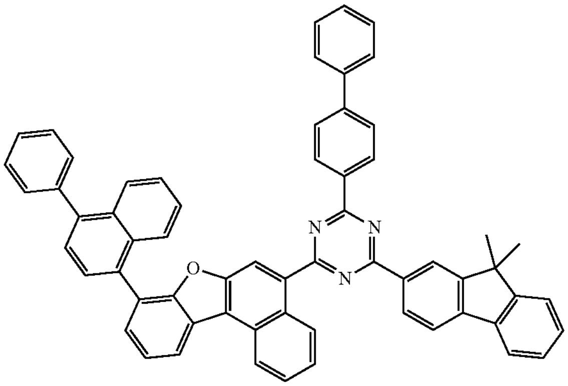
F501
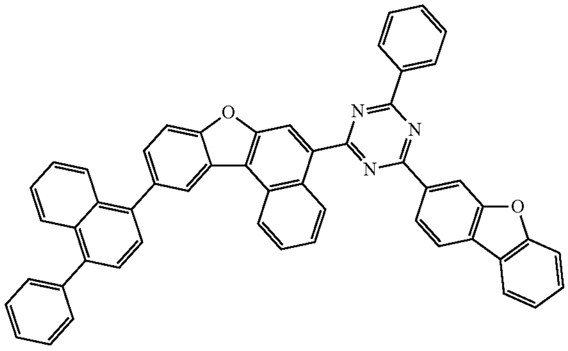
F502
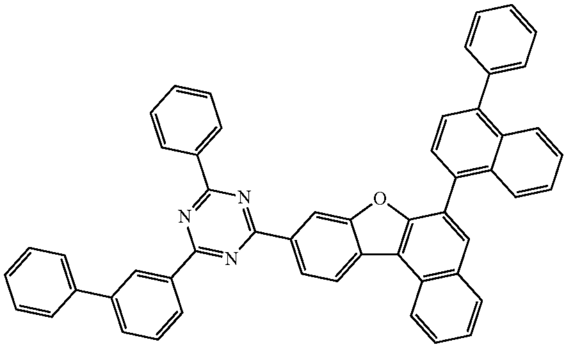
F503
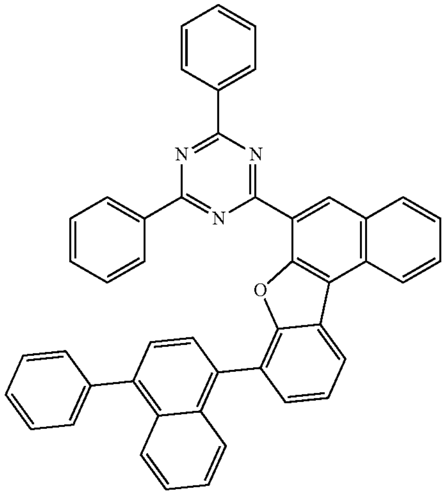
F504
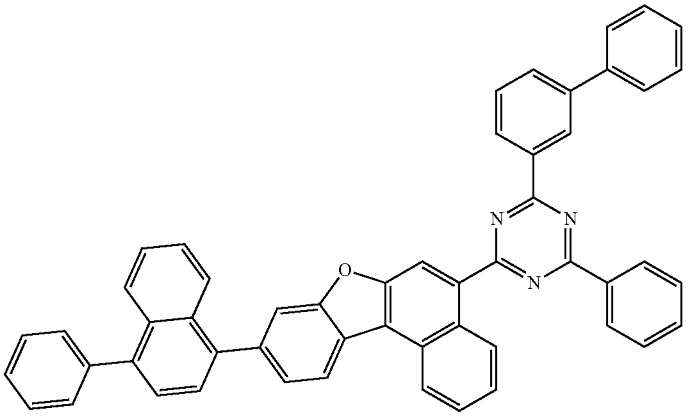

-continued
F505
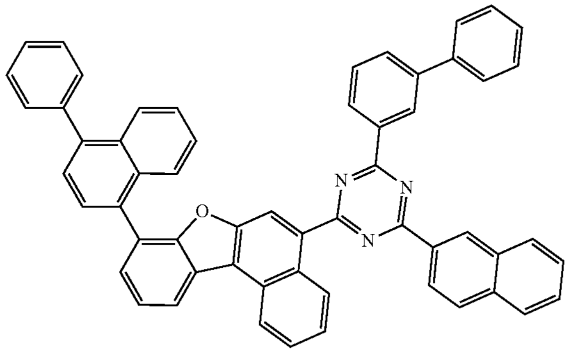
F506
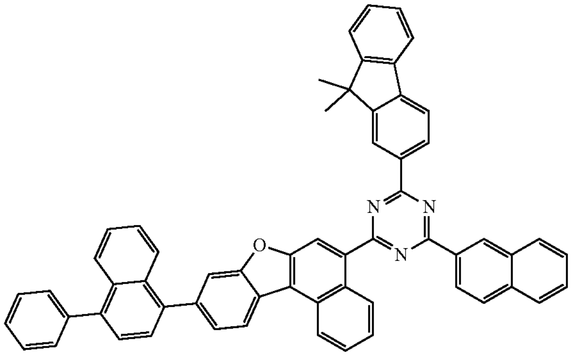
F507
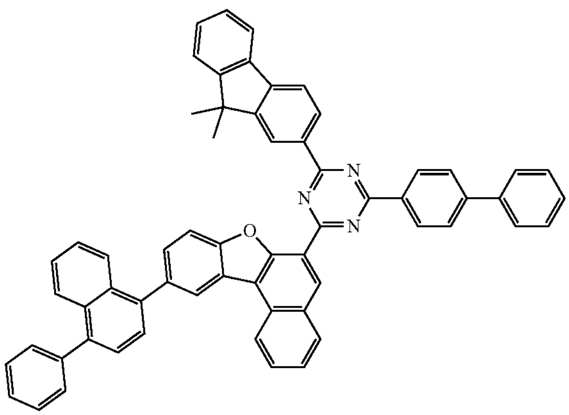
F508
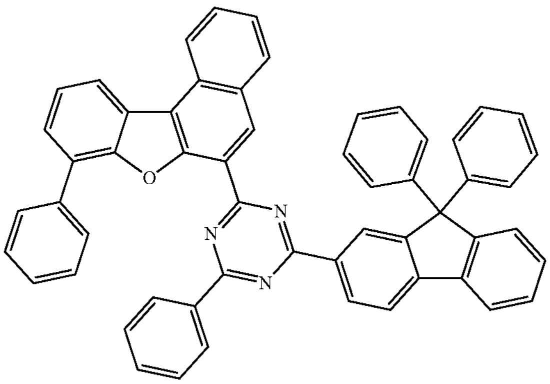
F509
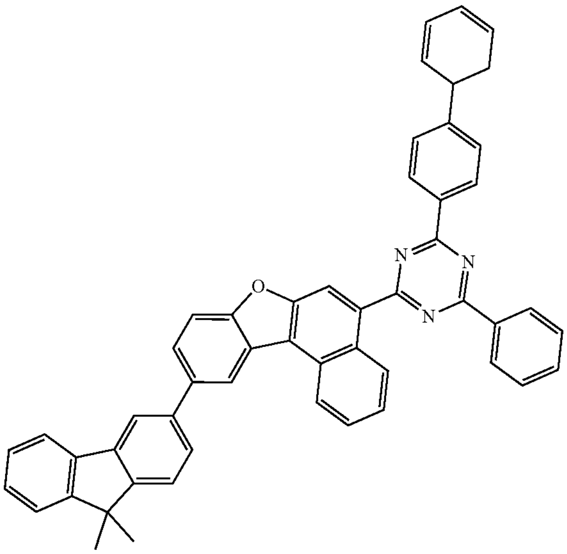
F510
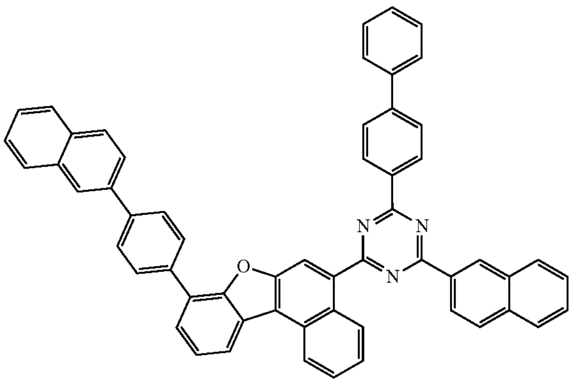
F511
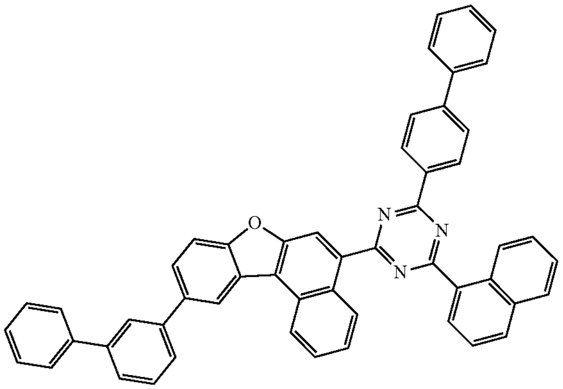

-continued
F512
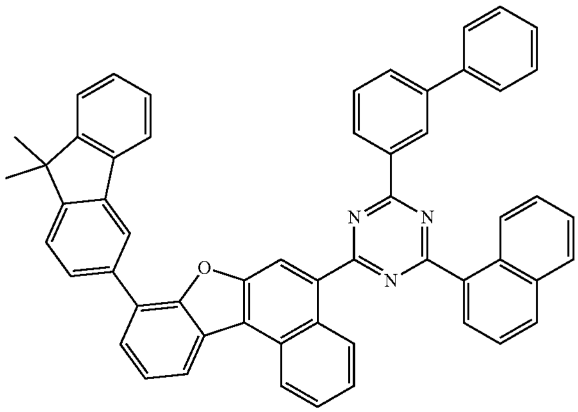
F513
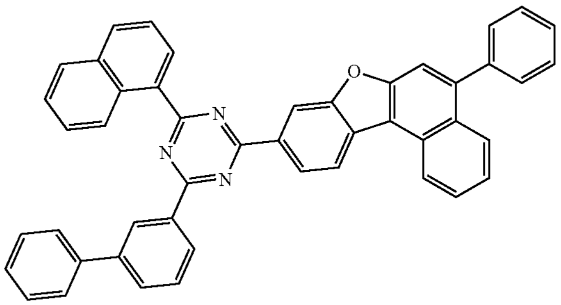
F514
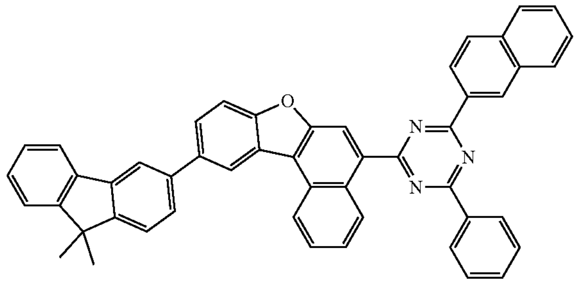
F515
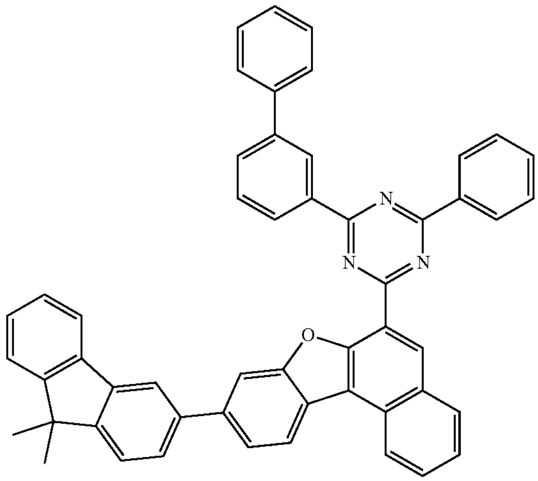
-continued
F516
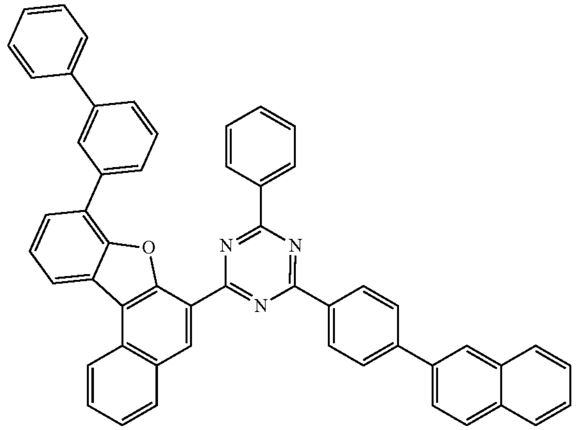
F517
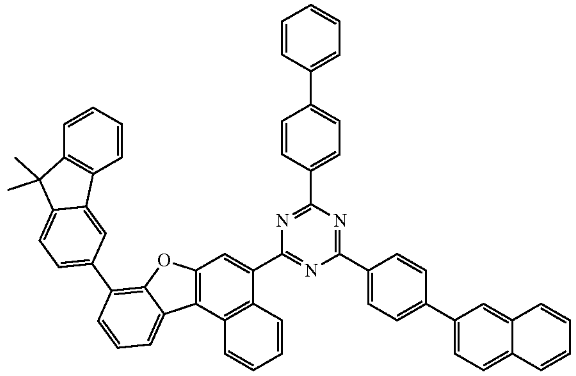
F518
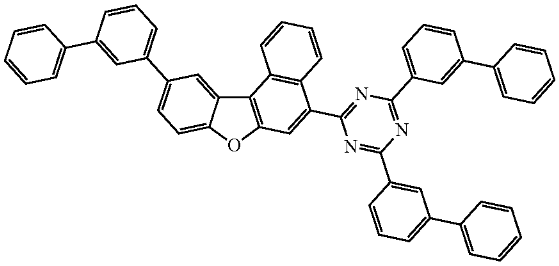

-continued
F519
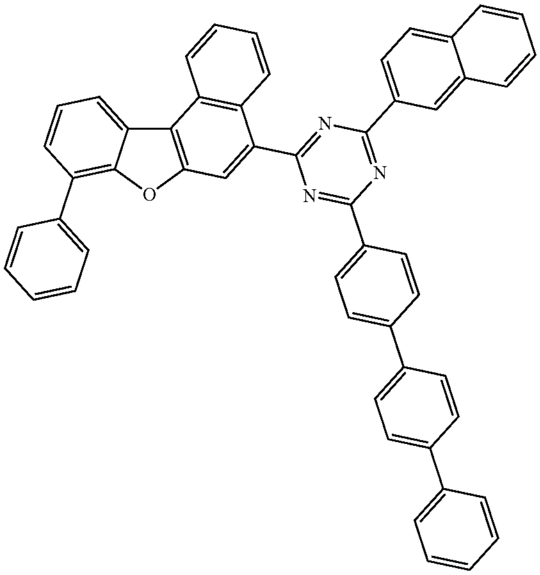
F520
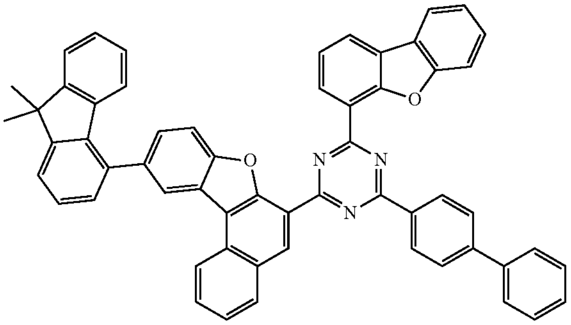
F521
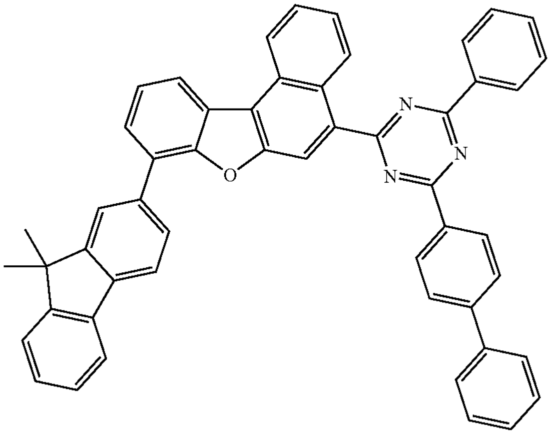
F522
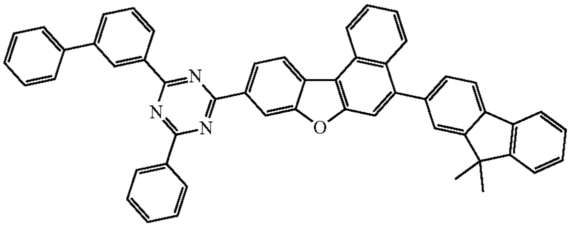
-continued
F523
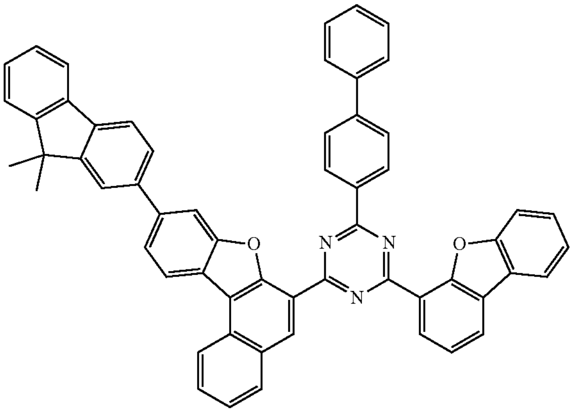
F524
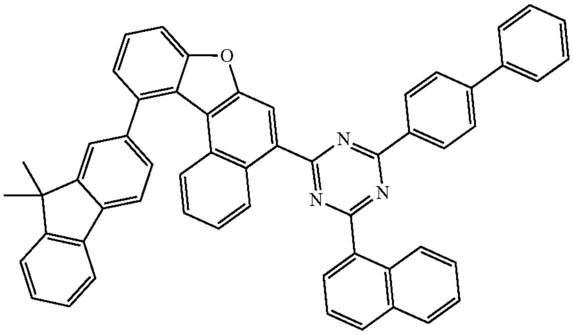
F525
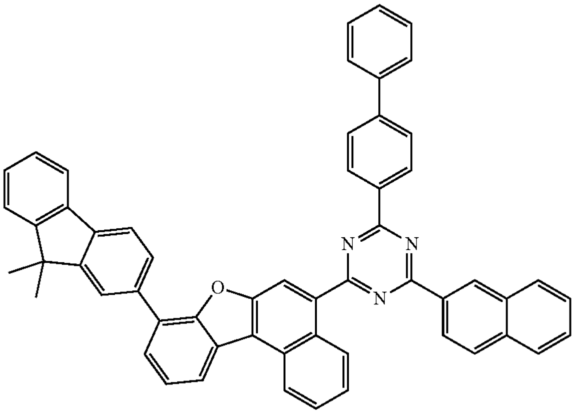
F526
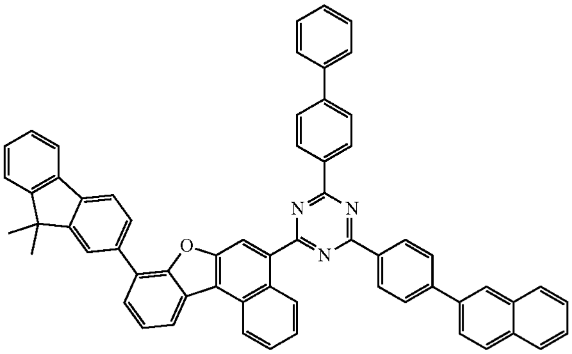

-continued
F527
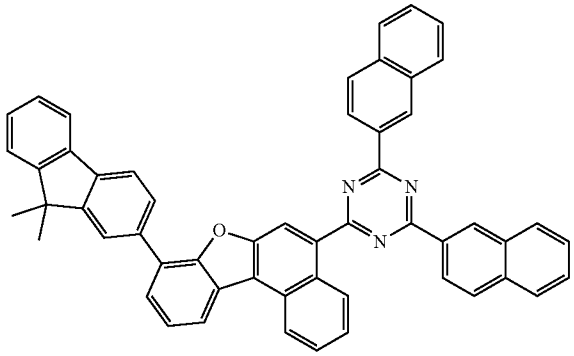
F528
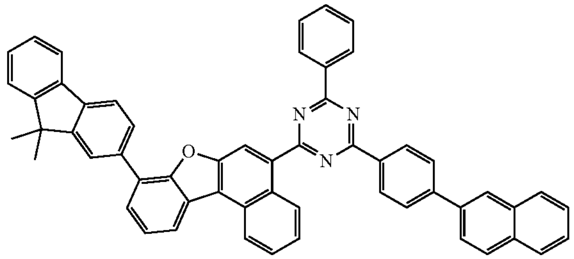
F529
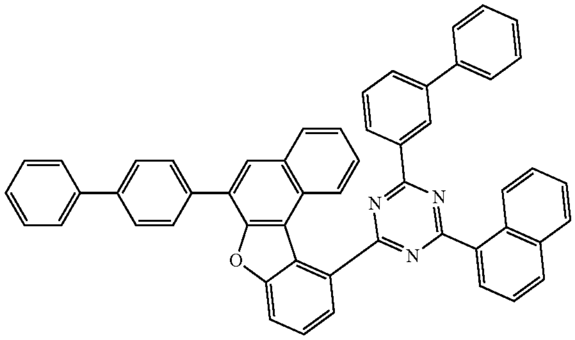
F530
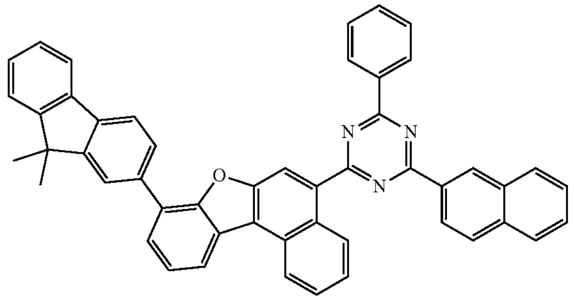
-continued
F531
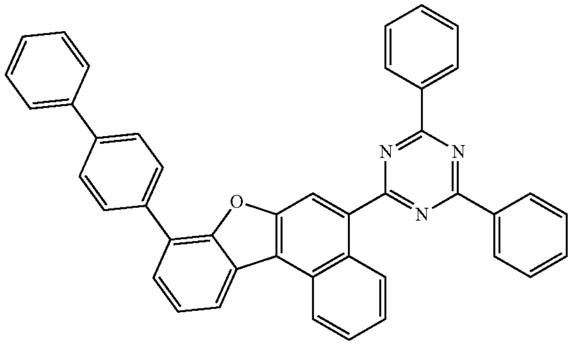
F532
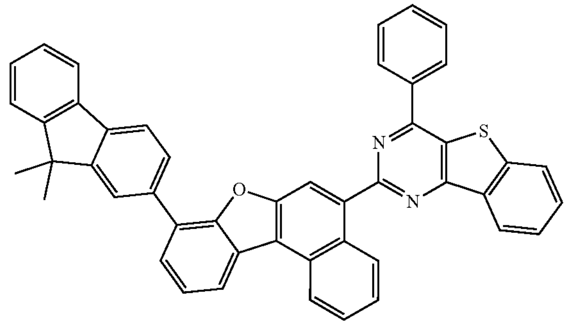
F533
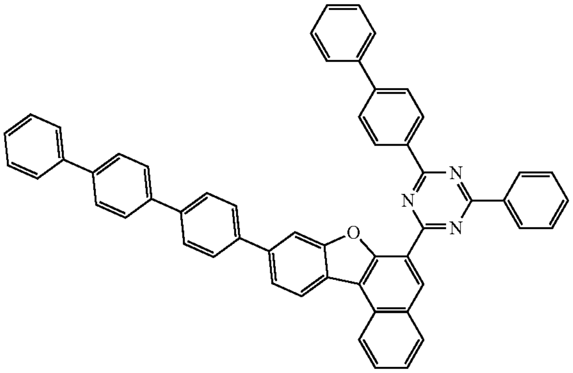
F534
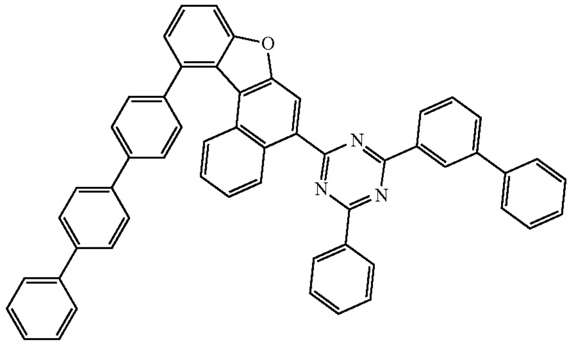

-continued
F535
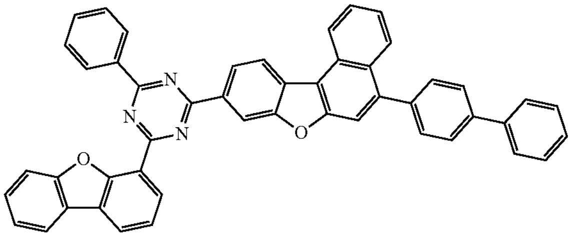
F536
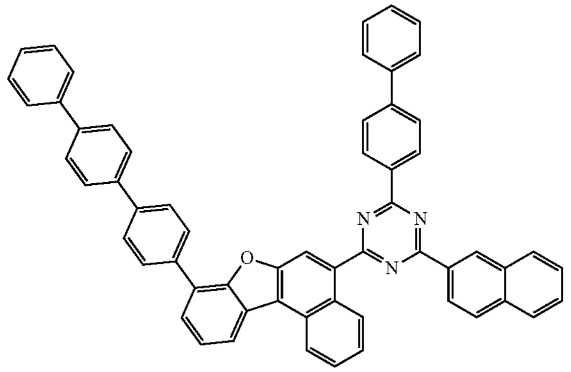
F537
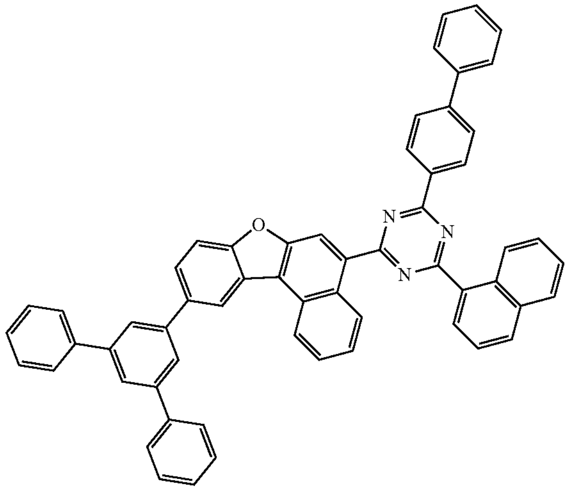
-continued
F538
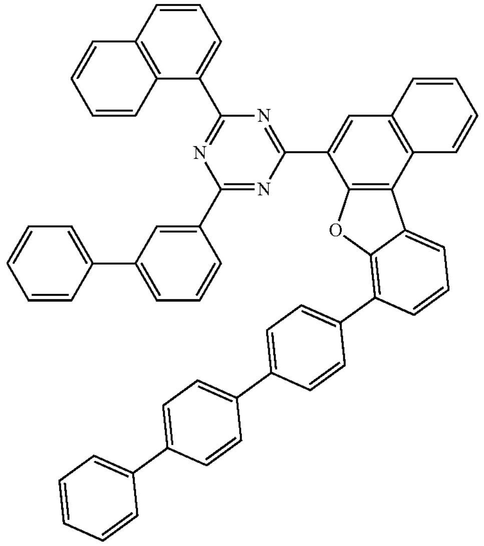
F539
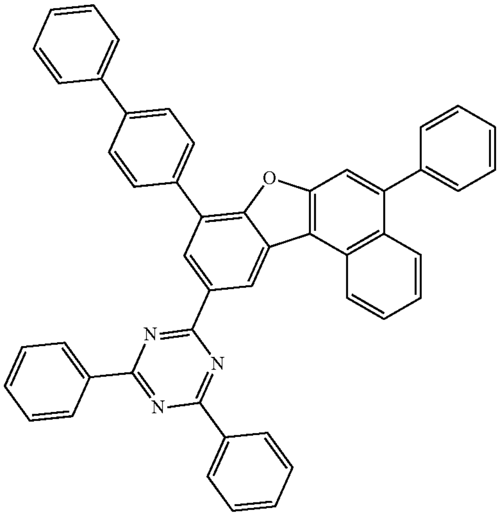
F540
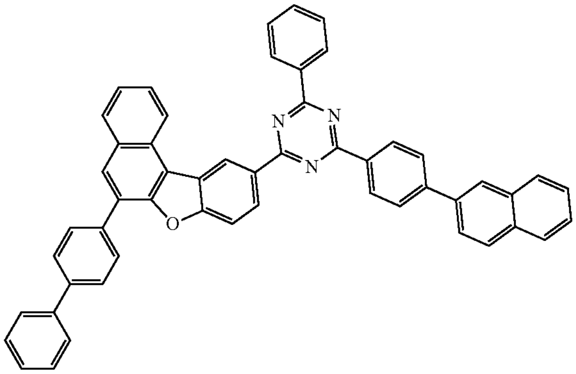

-continued
F541
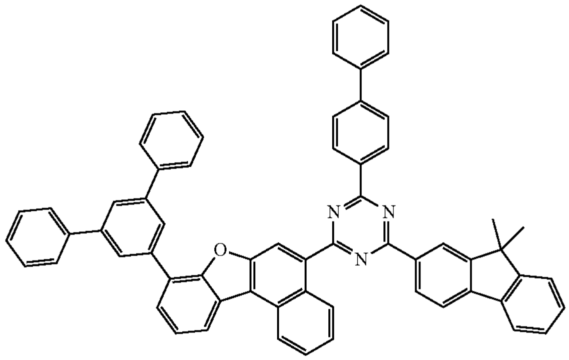
F542
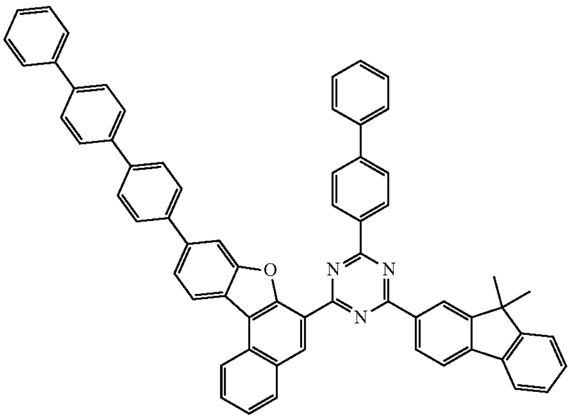
F543
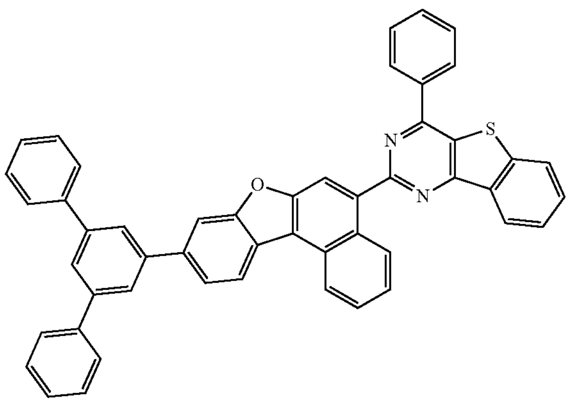
-continued
F544
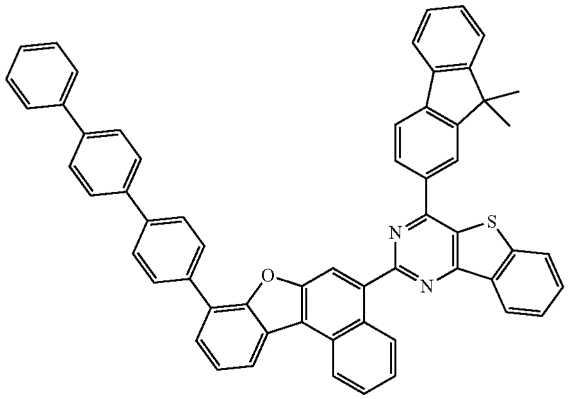
F545
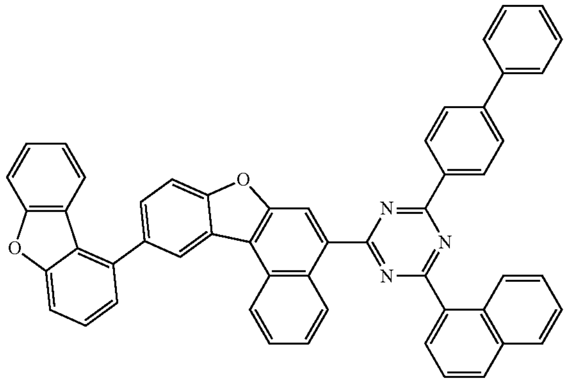
F546
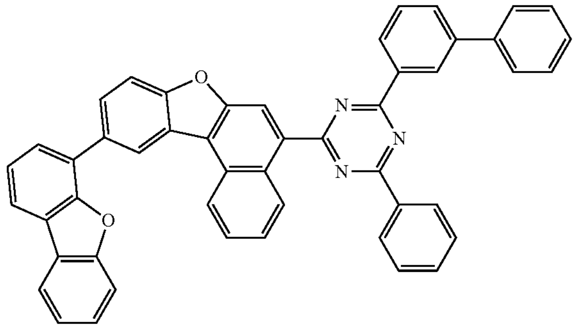
F547
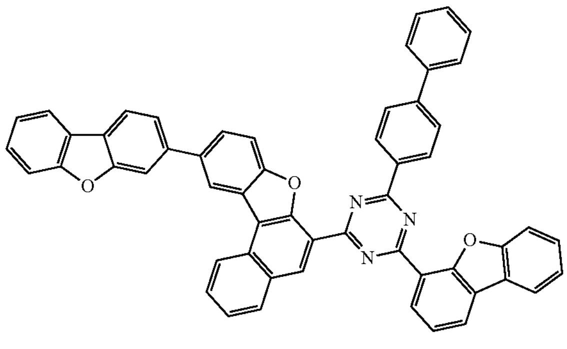

-continued
F548
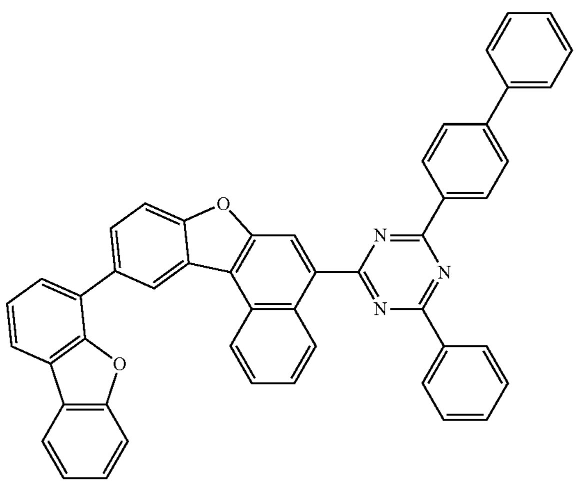
F549
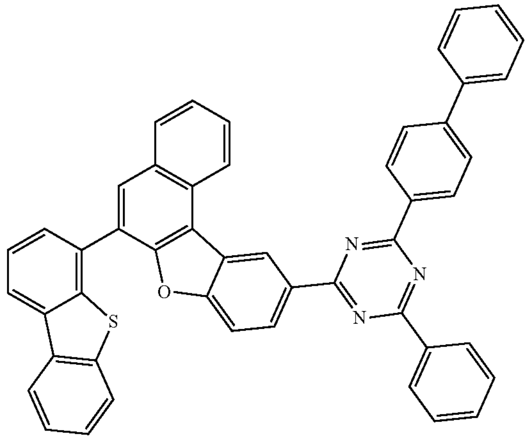
F550
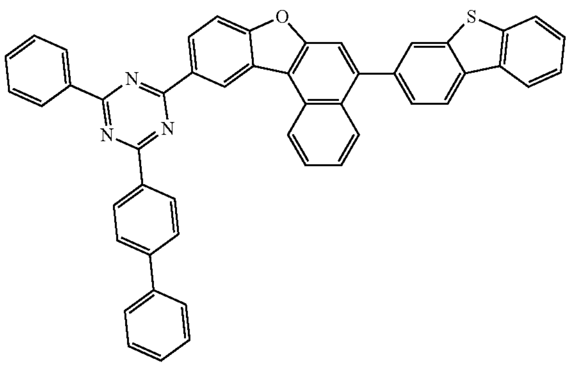
-continued
F551
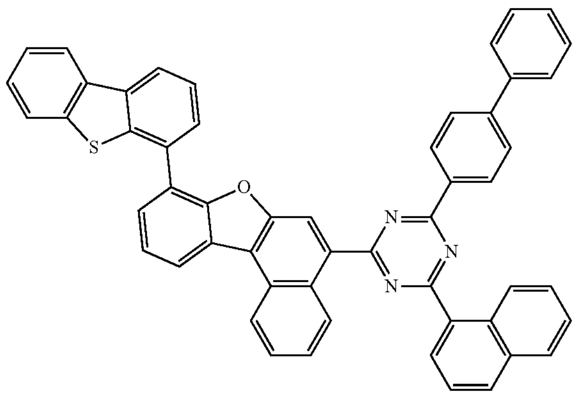
F552
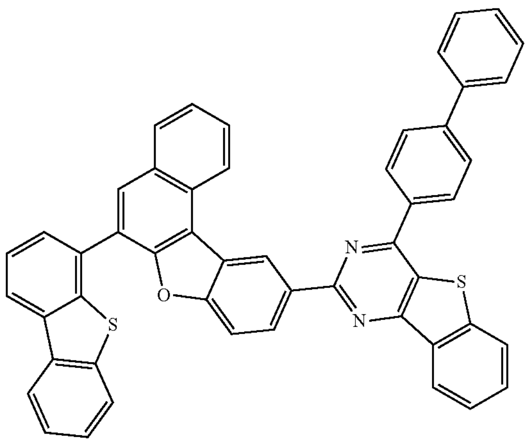
F553
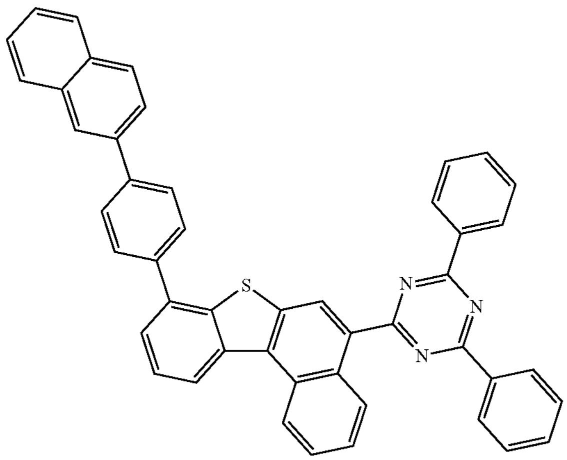

-continued
F554
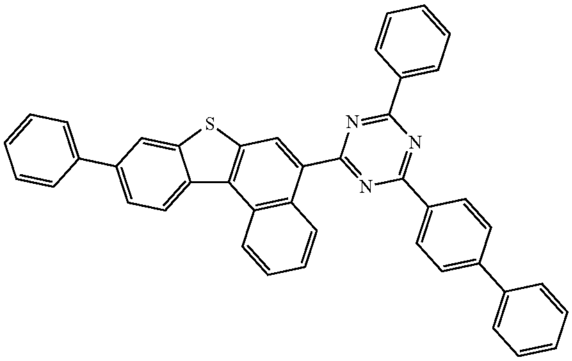
F555
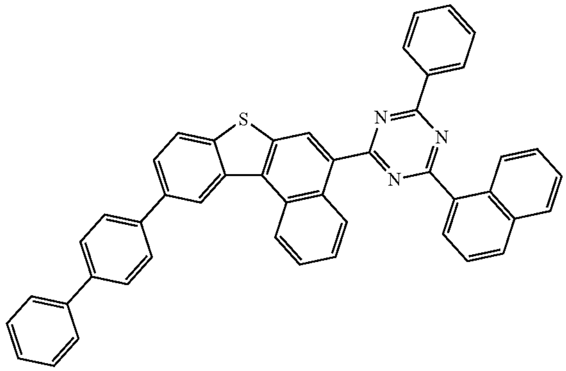
F556
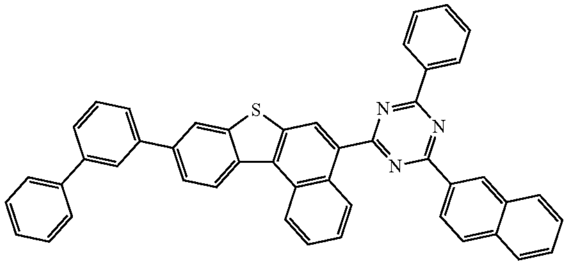
F557
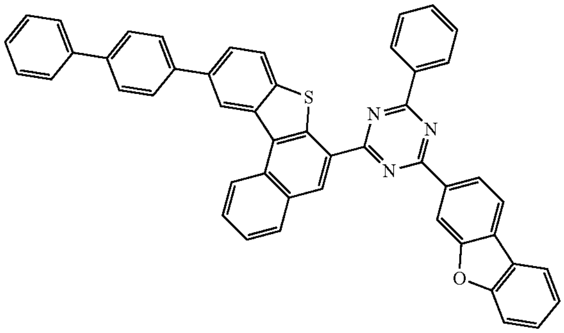
-continued
F558
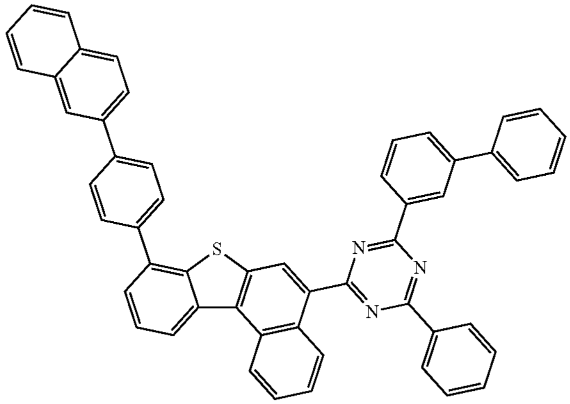
F559
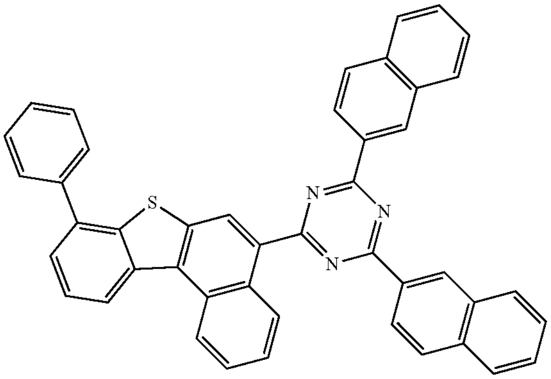
F560
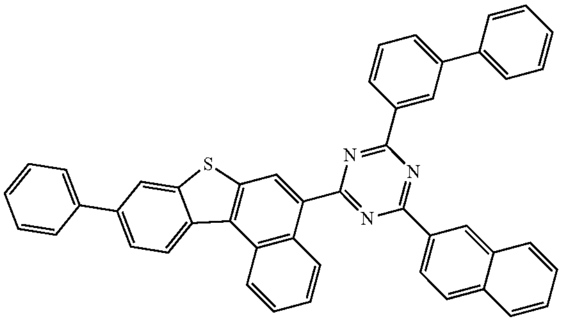

-continued
F561
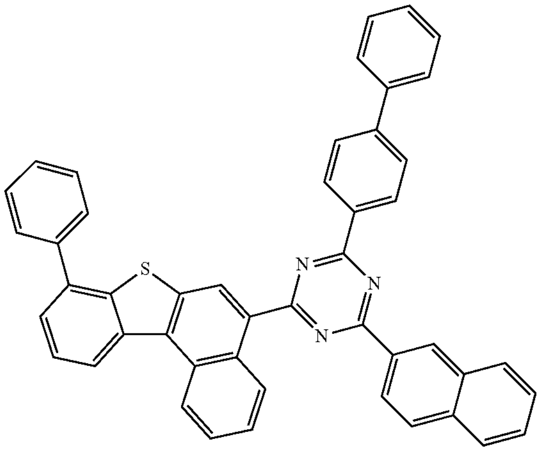
F562
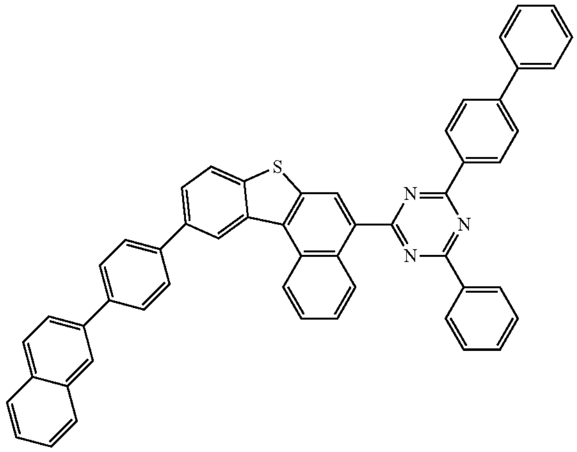
F563
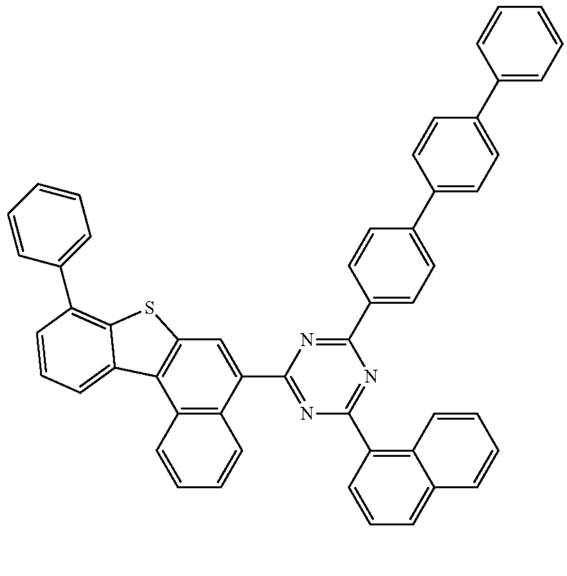
F564
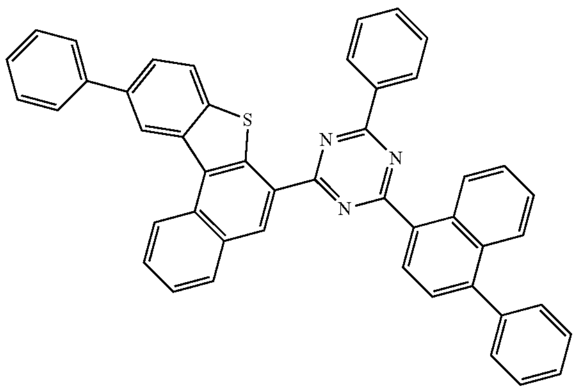
F565
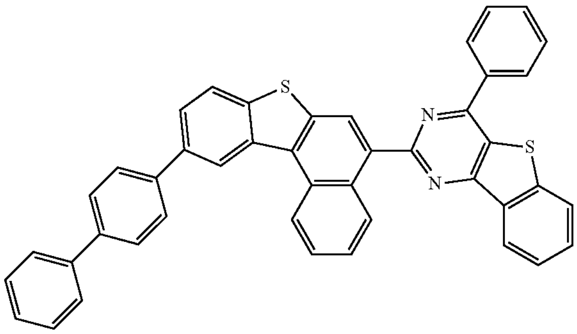
F566
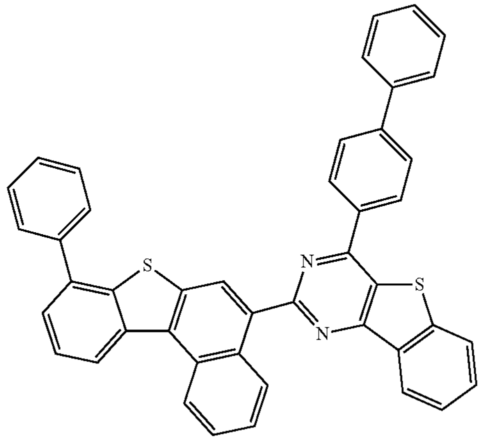
F567
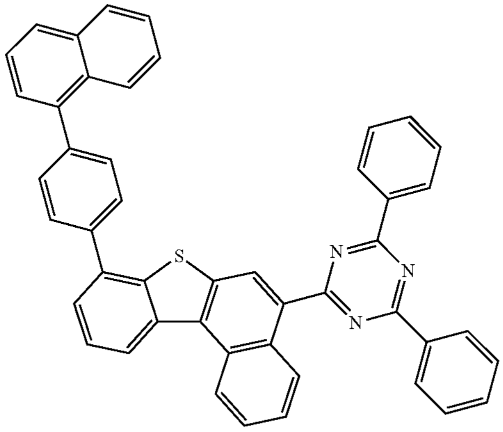

-continued
F568
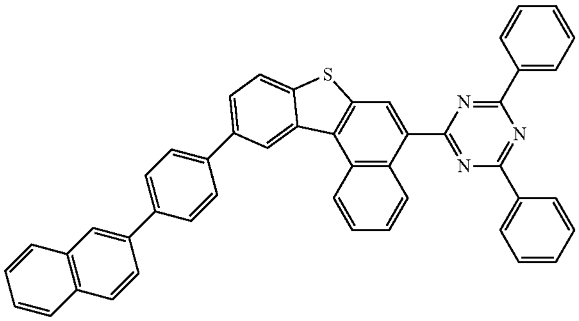
F569
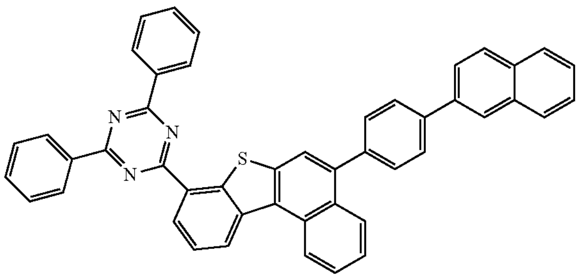
F570
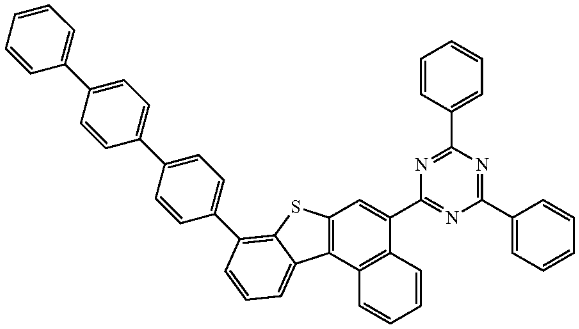
F571
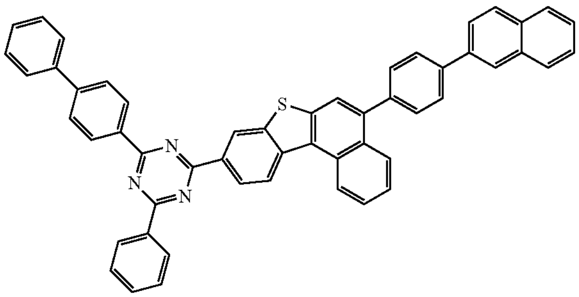
-continued
F572
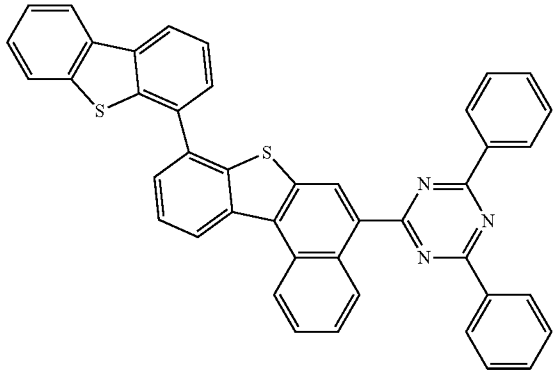
F573
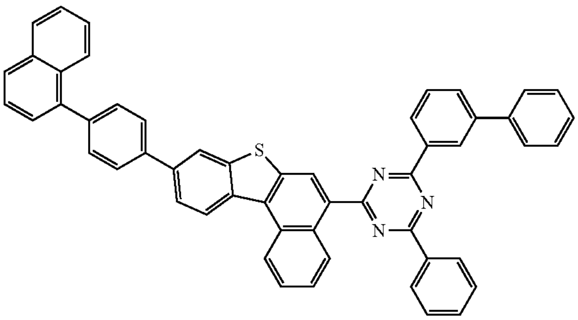
F574
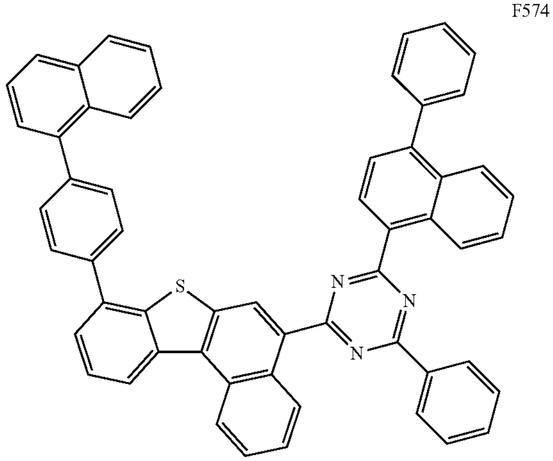
F575
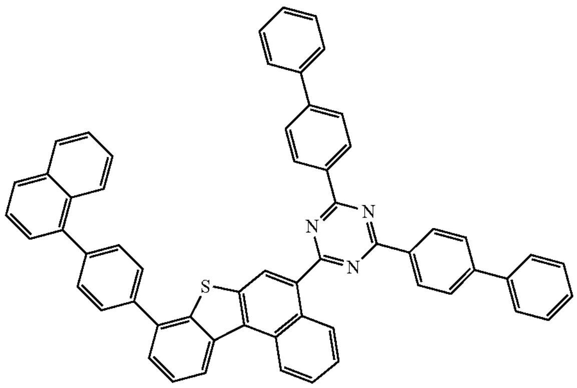

-continued
F576
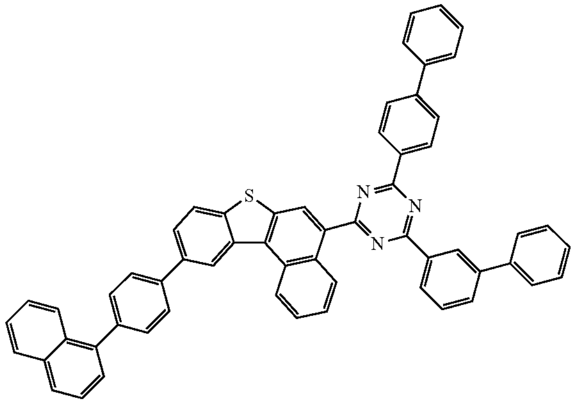
F577
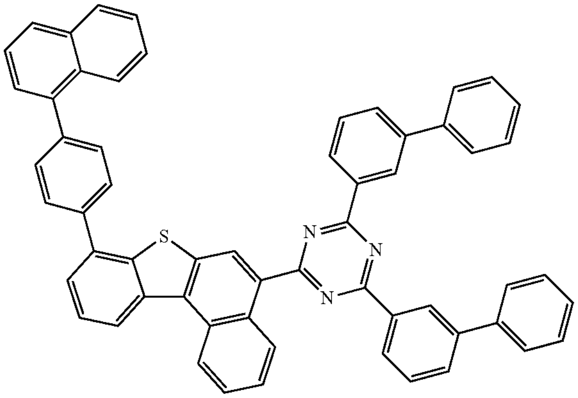
F578
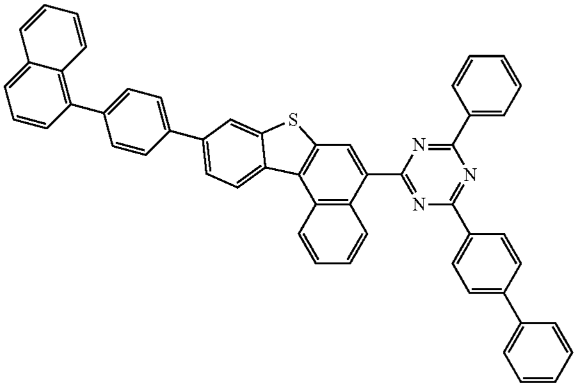
-continued
F579
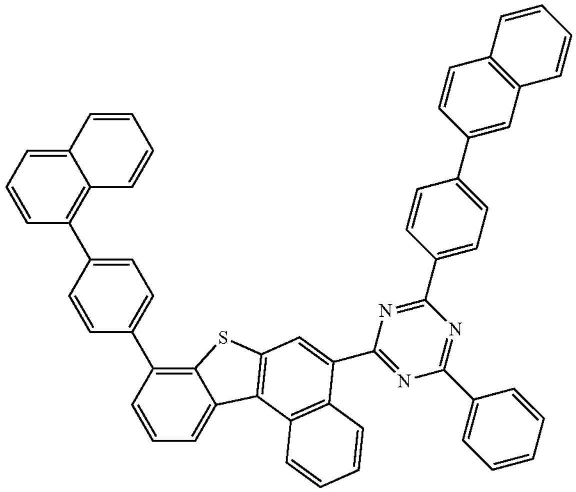
F580
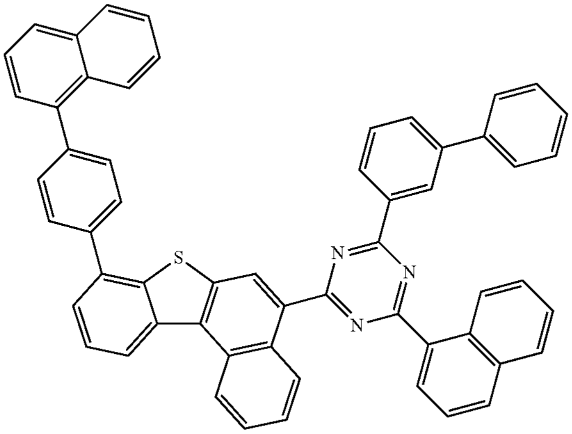
F581
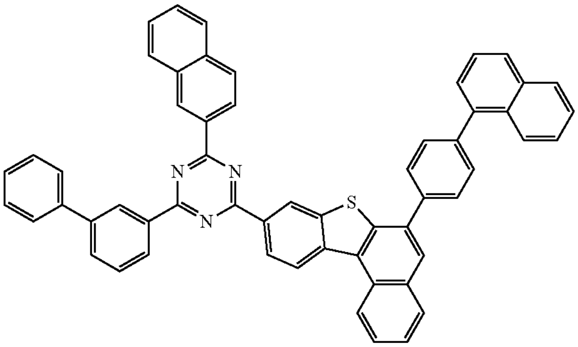

-continued
F582
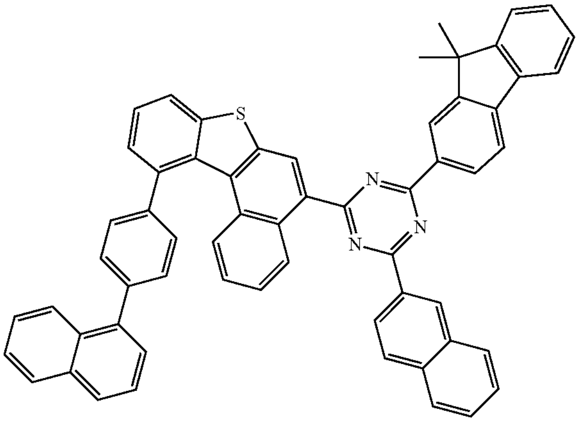
F583
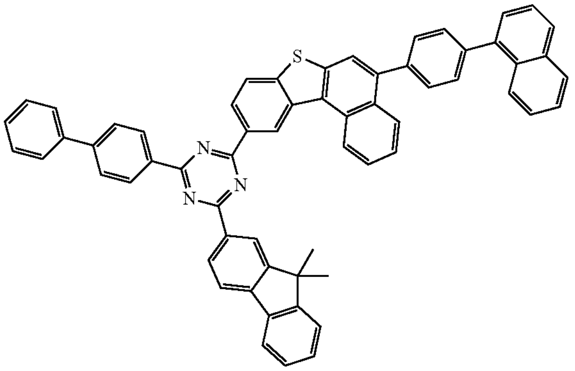
F584
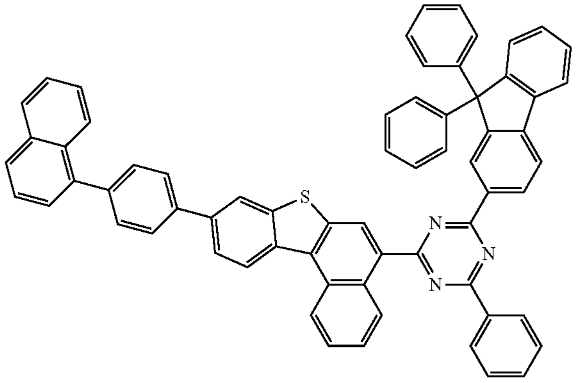
-continued
F585
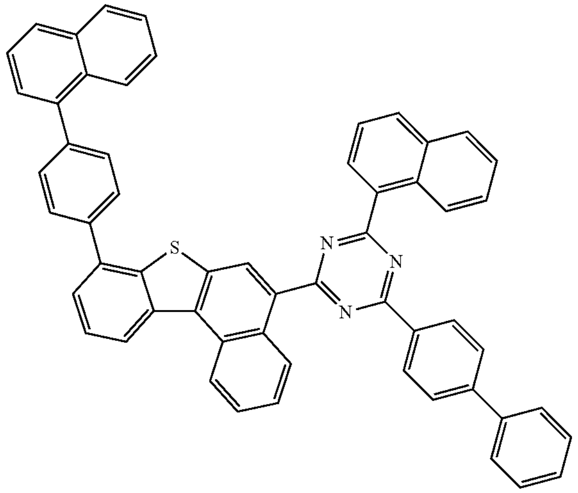
F586
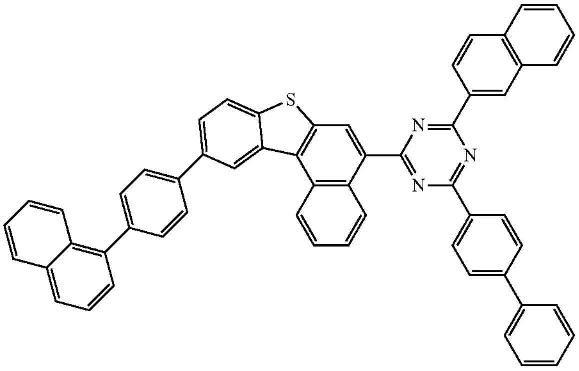
F587
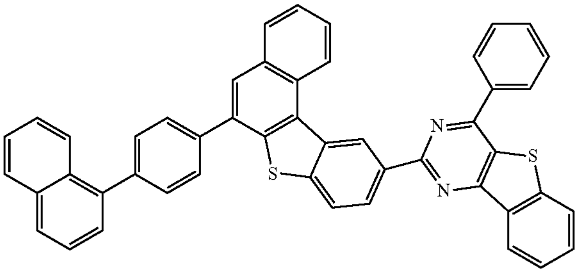
F588
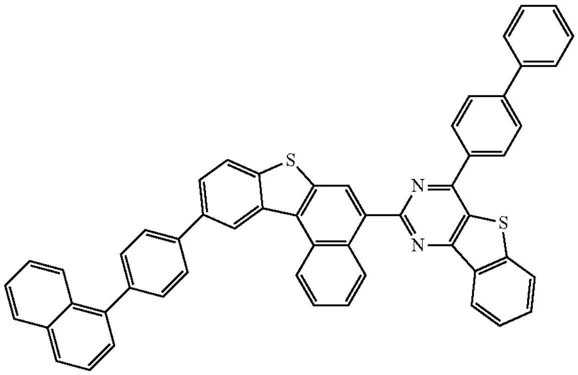

-continued
F589
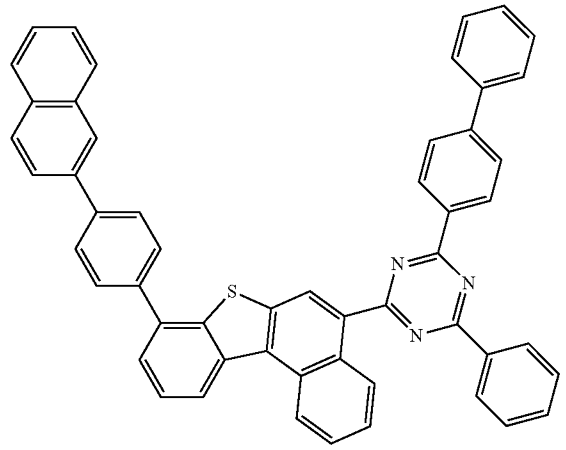
F590
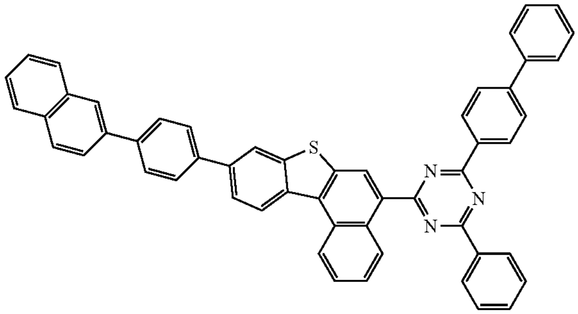
F591
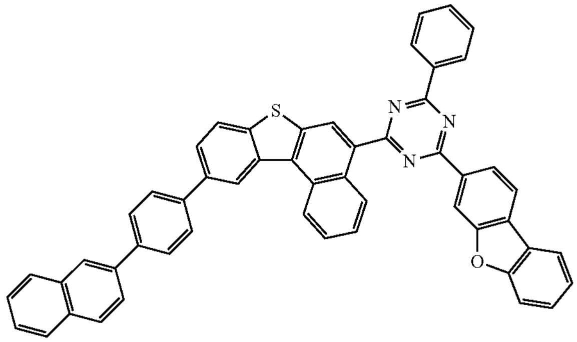
F592
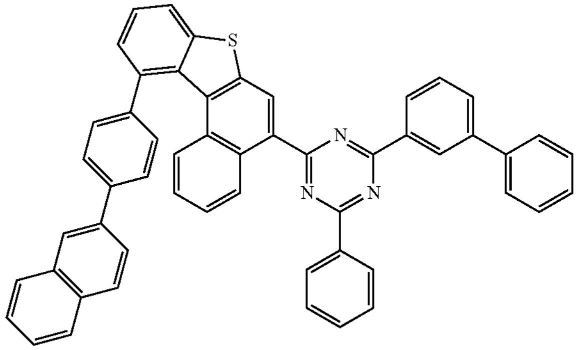
-continued
F593
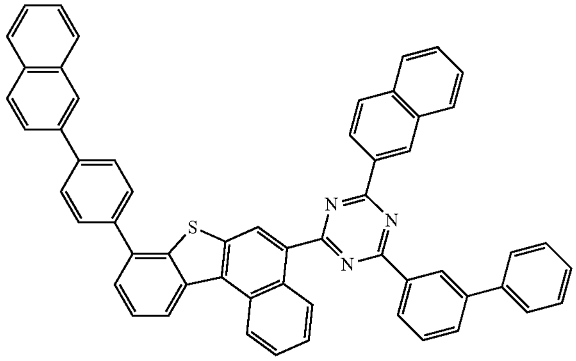
F594
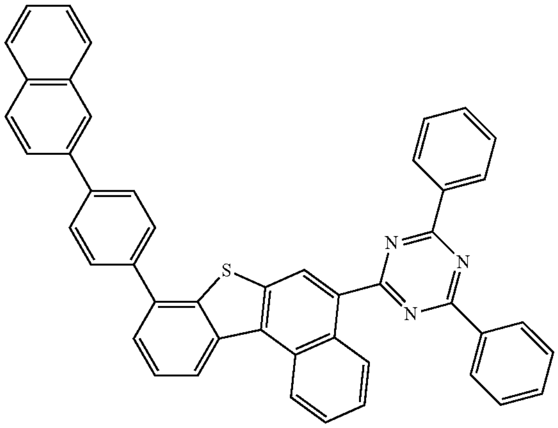
F595
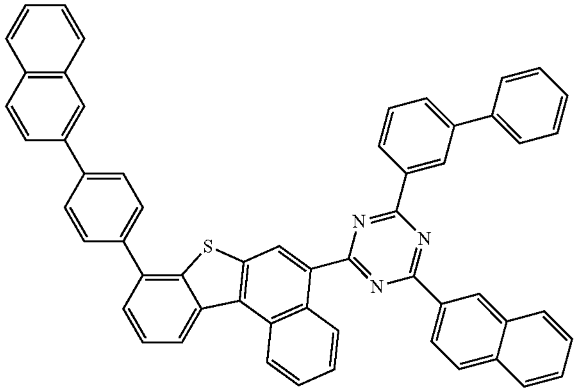

-continued
F596
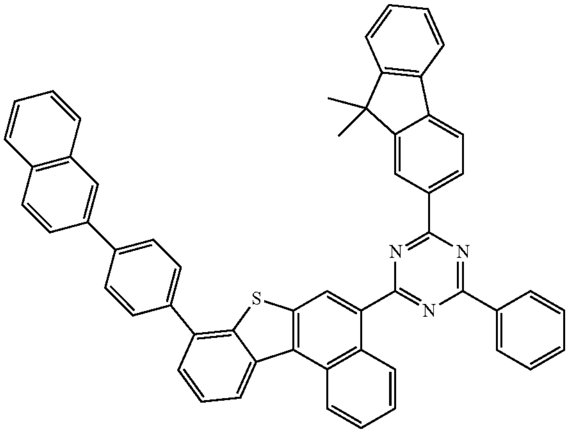
F597
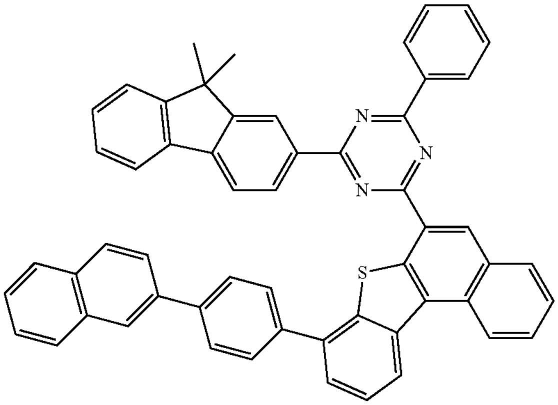
F598
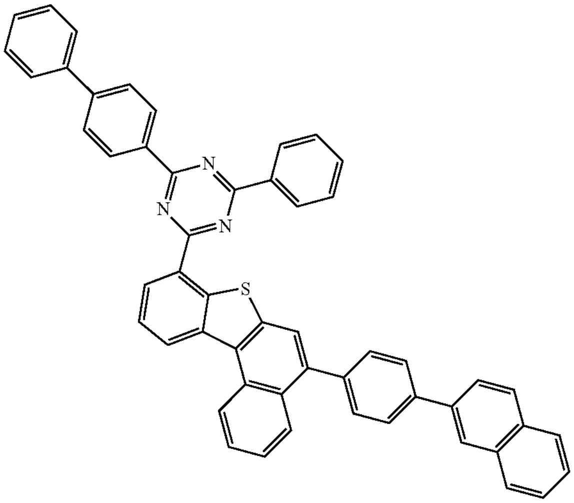
-continued
F599
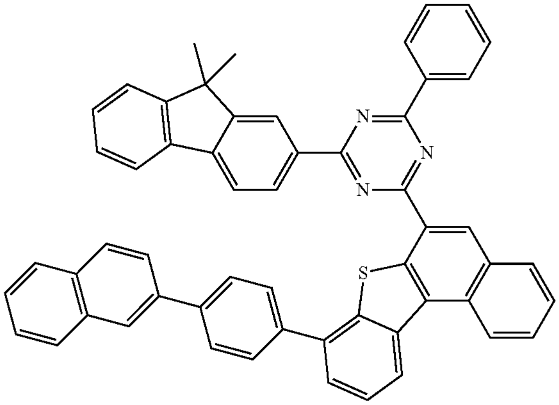
F600
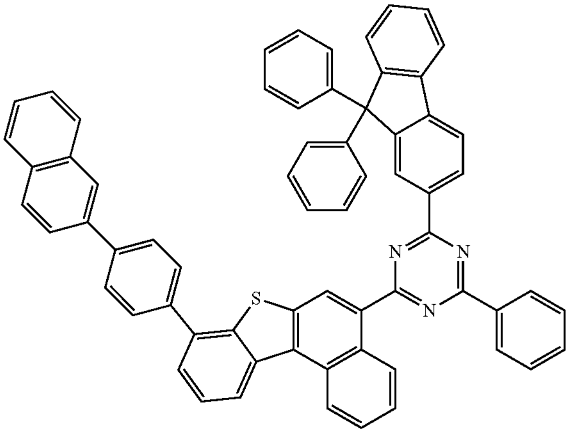
F601
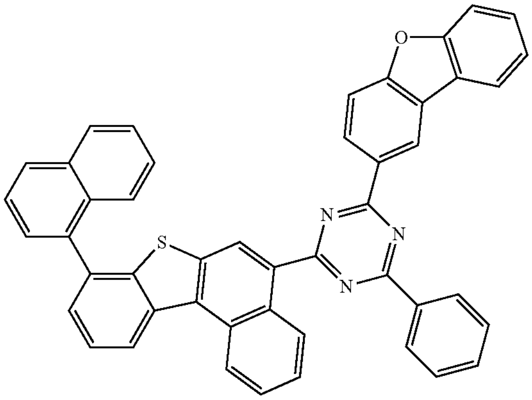

-continued
F602
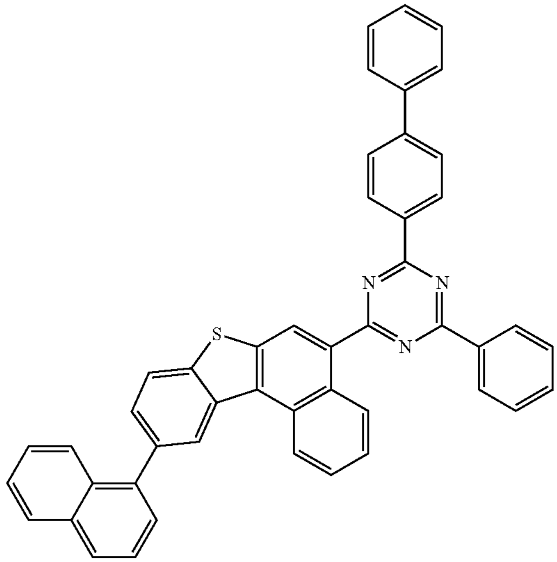
F603
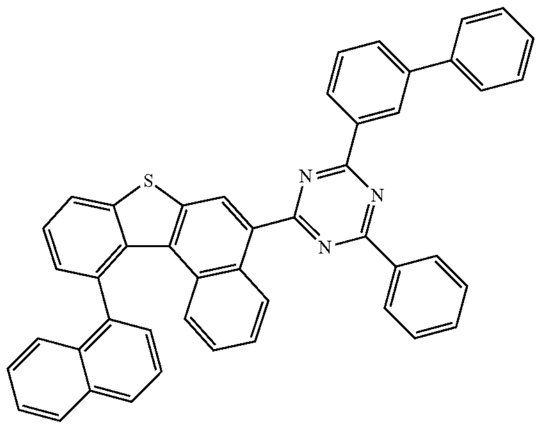
F604
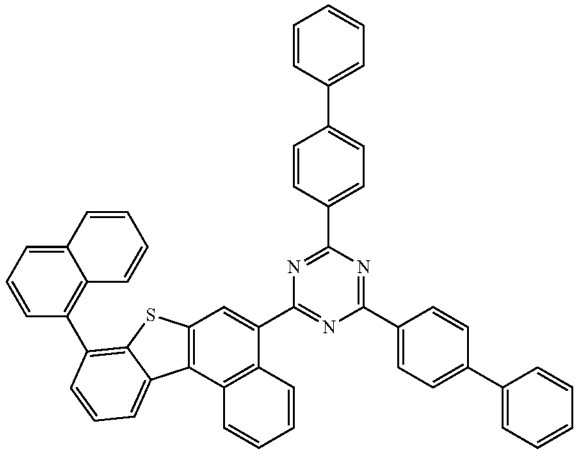
-continued
F605
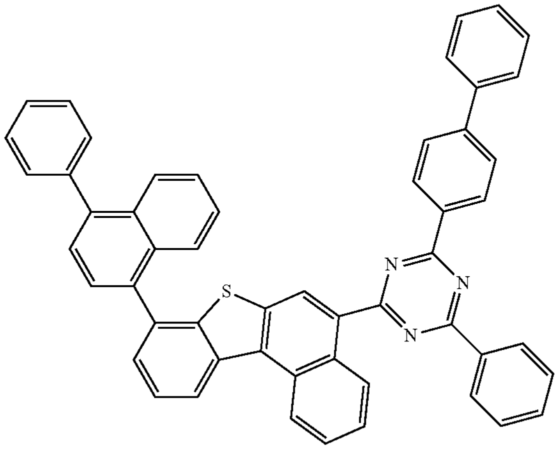
F606
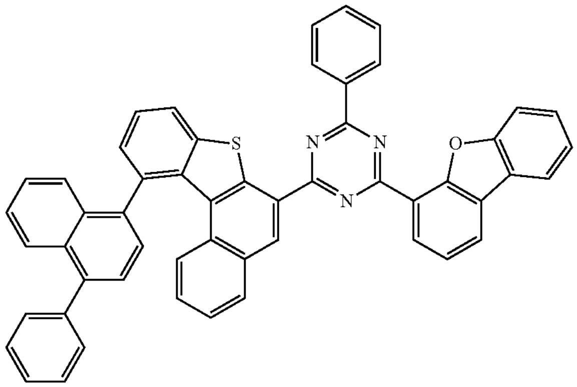
F607
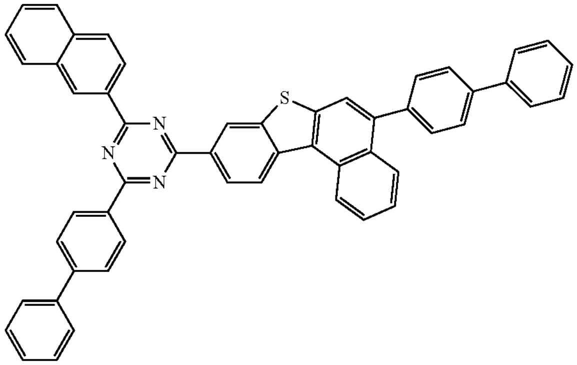

F608
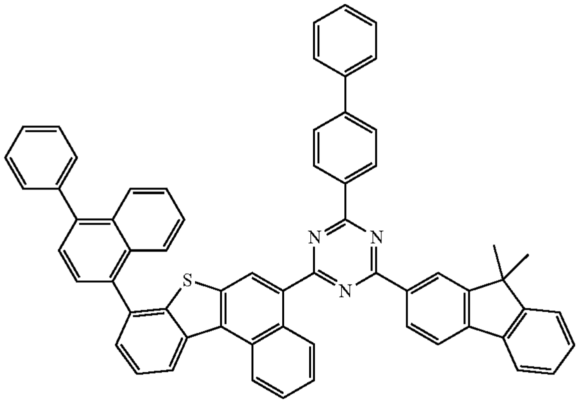
F609
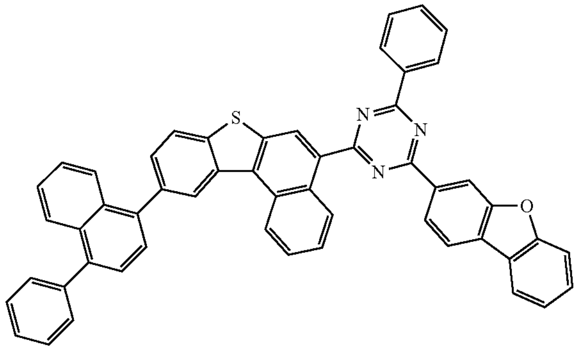
F610
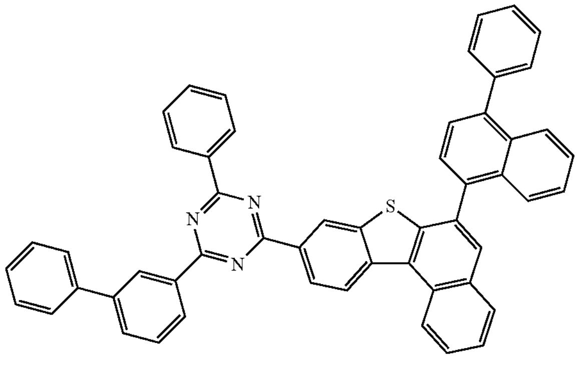
F611
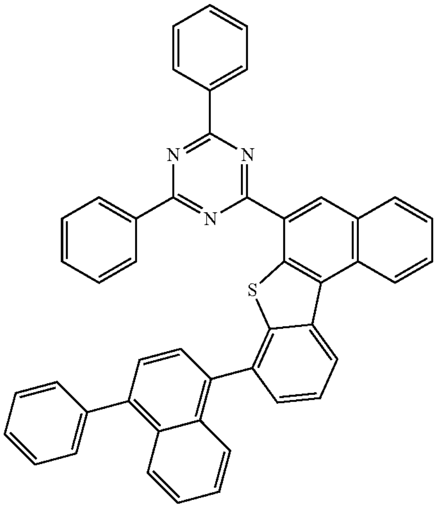
F612
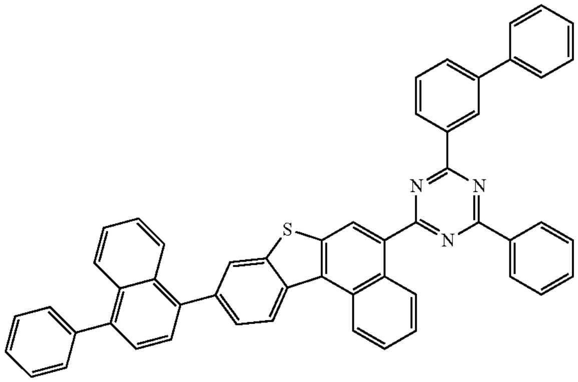
F613
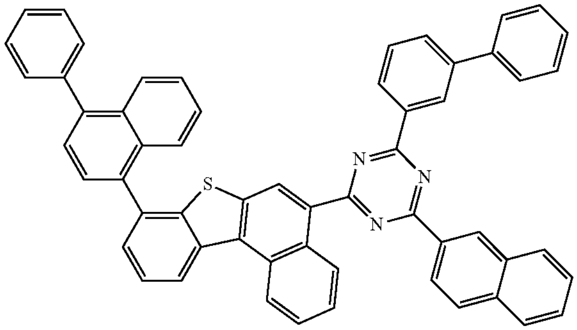

F614
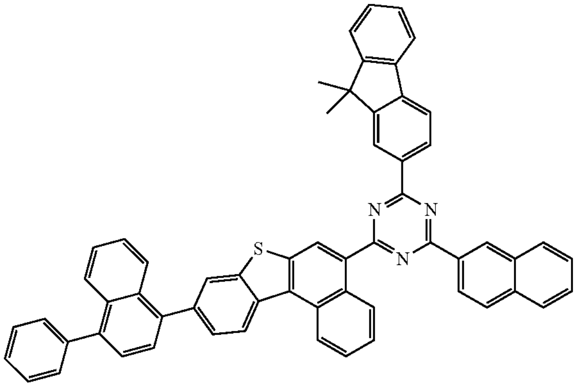
F615
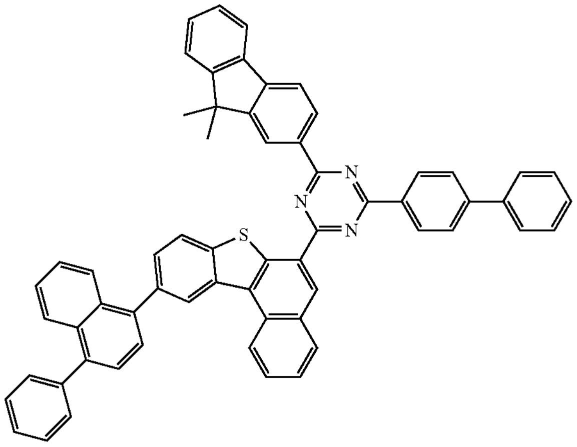
F616
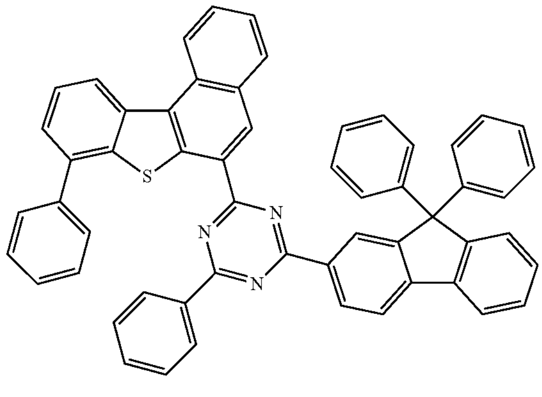
F617
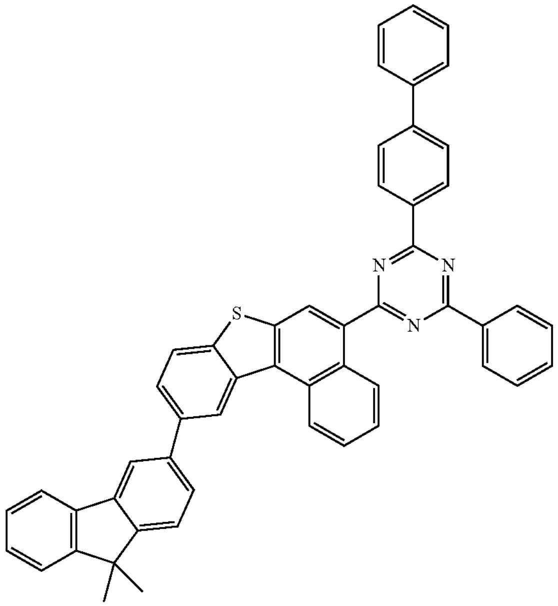
F618
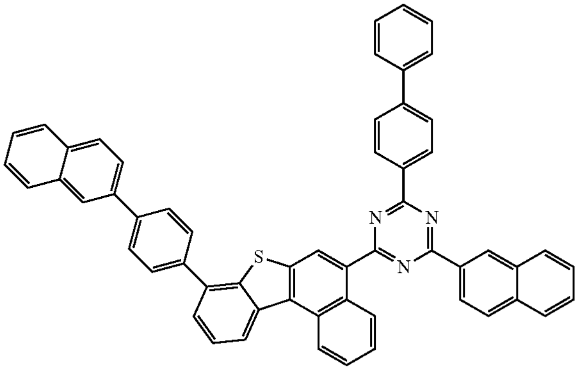
F619
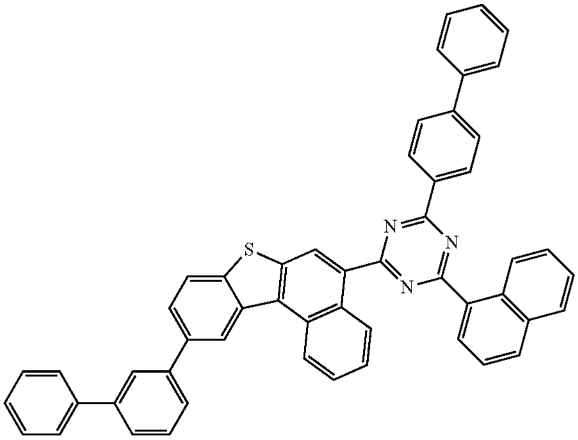

F620
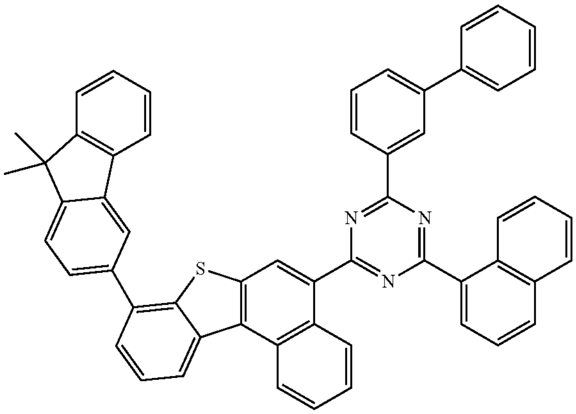
F621
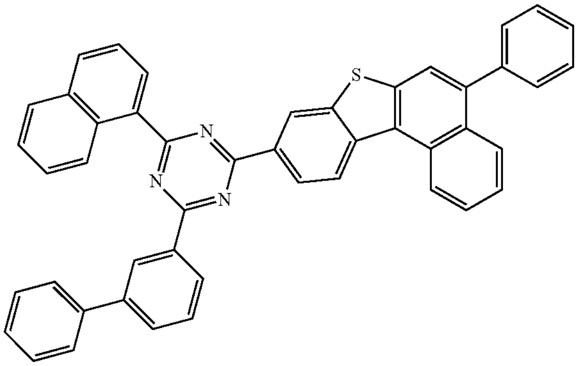
F622
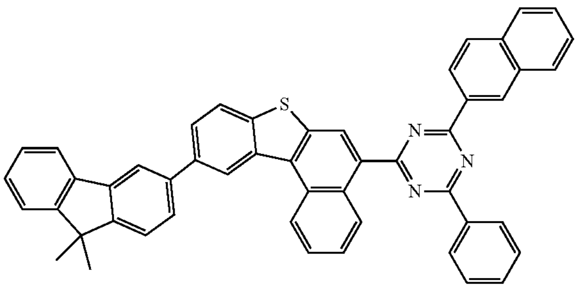
F623
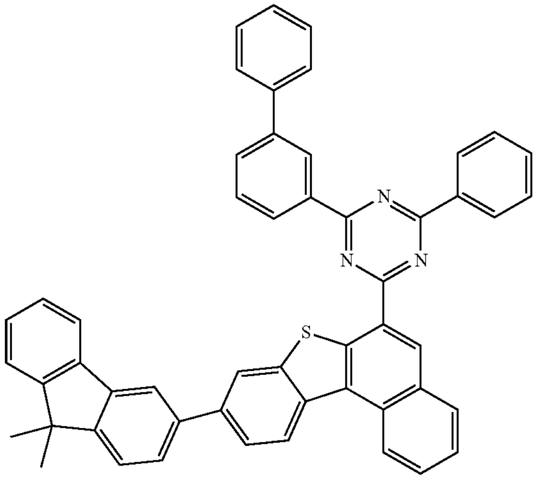
F624
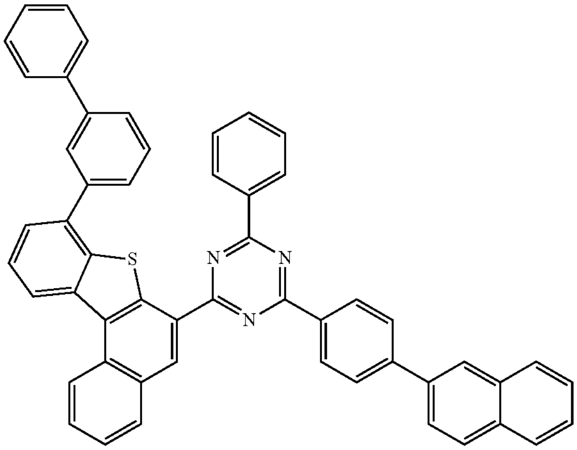
F625
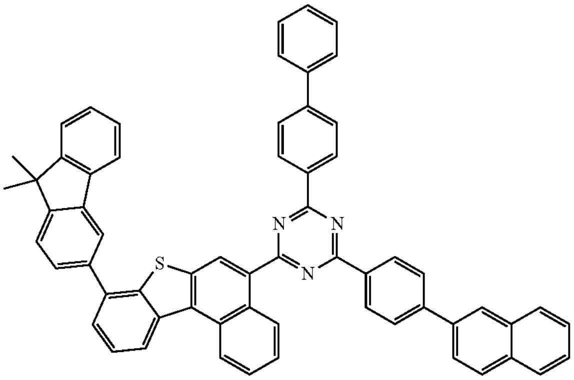
F626
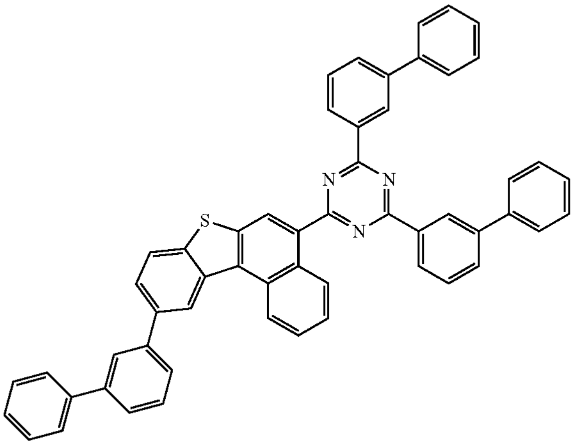

-continued
F627
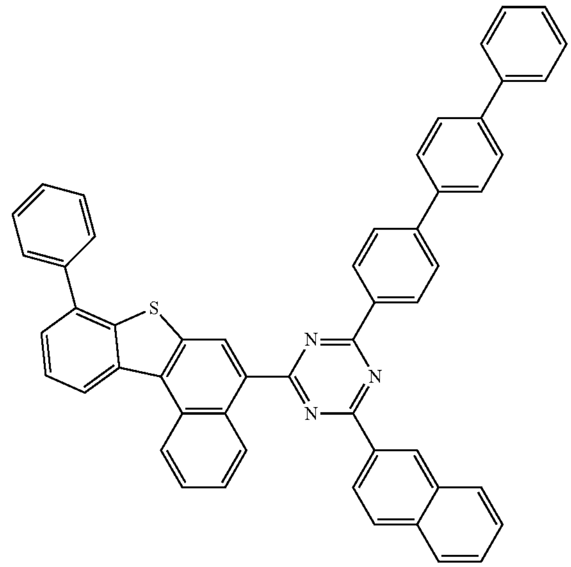
F628
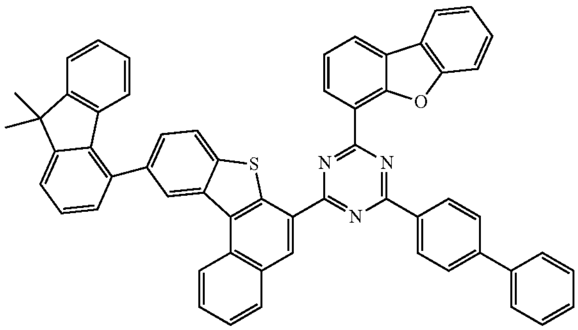
F629
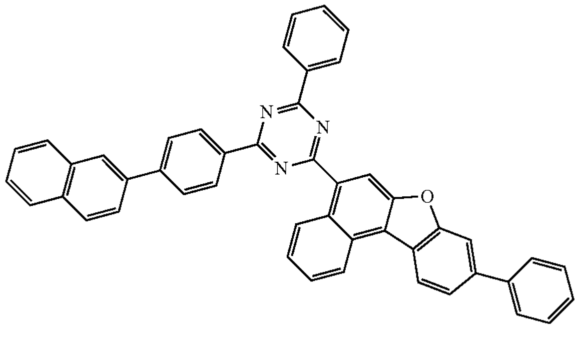
-continued
F630
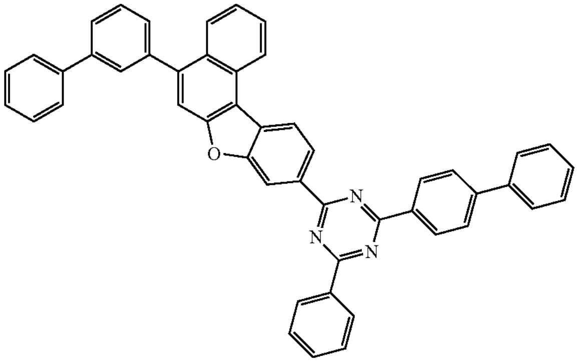
F631
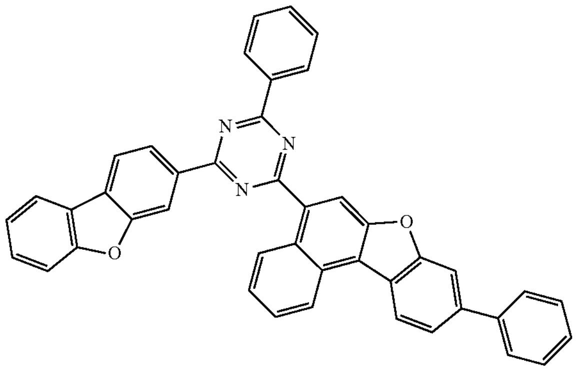
F632
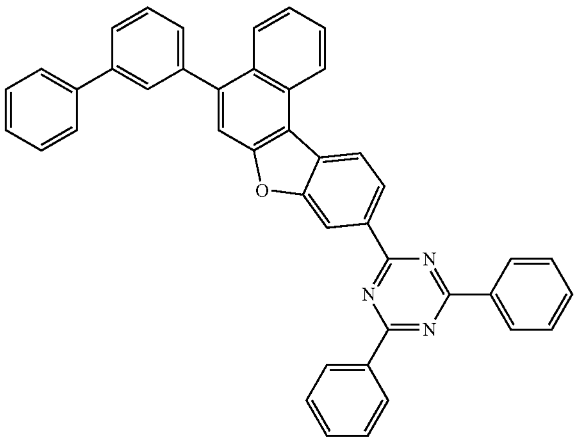
F633
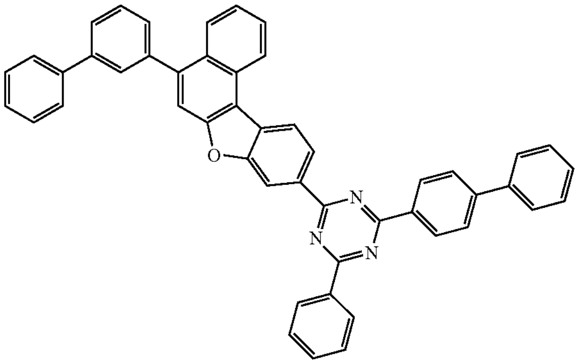

-continued
F634
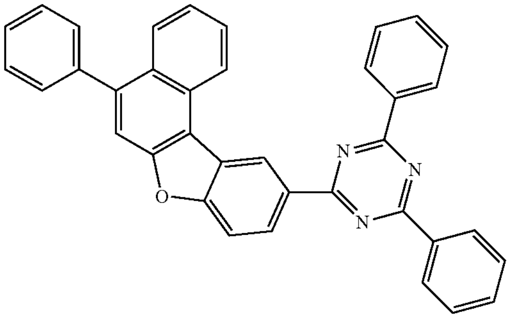
F635
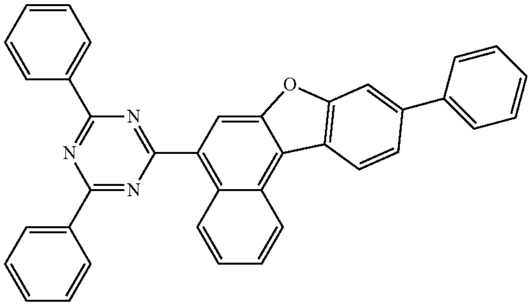
F636
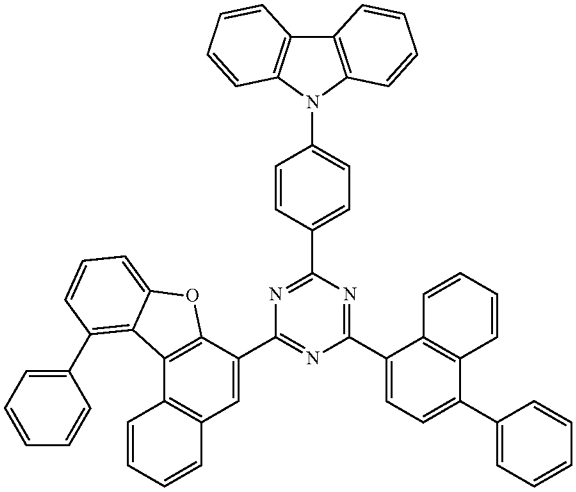
-continued
F637
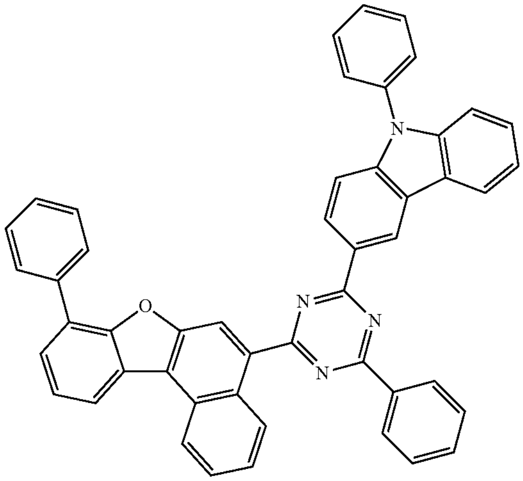
F638
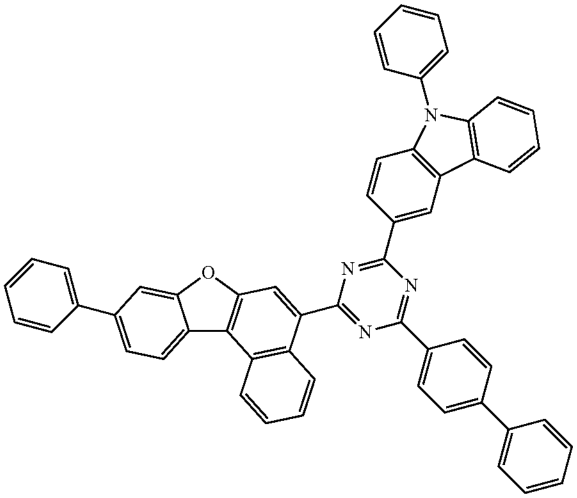
F639
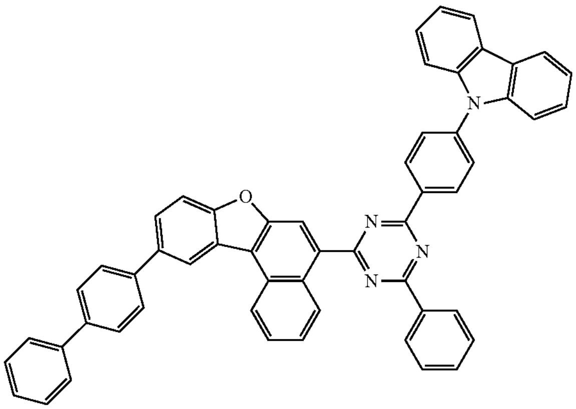

-continued
F640
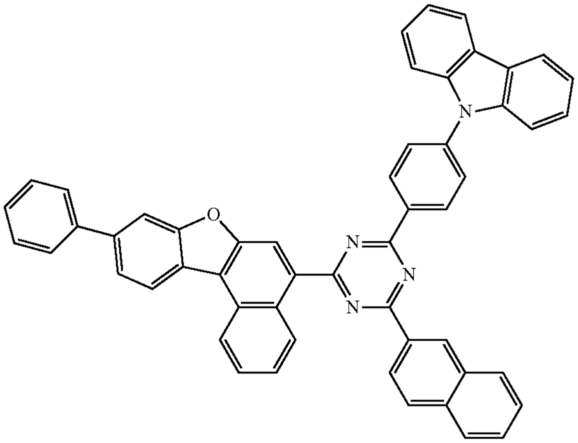
F641
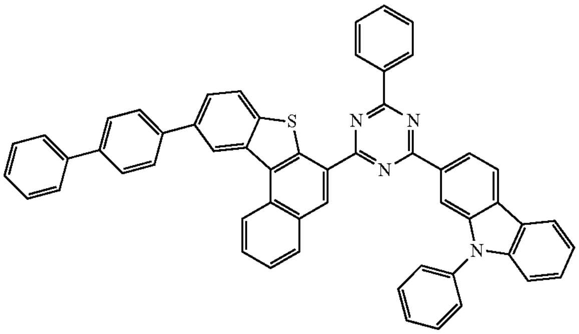
F642
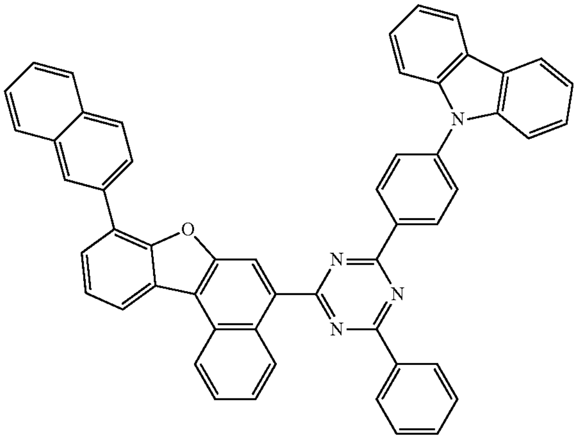
-continued
F643
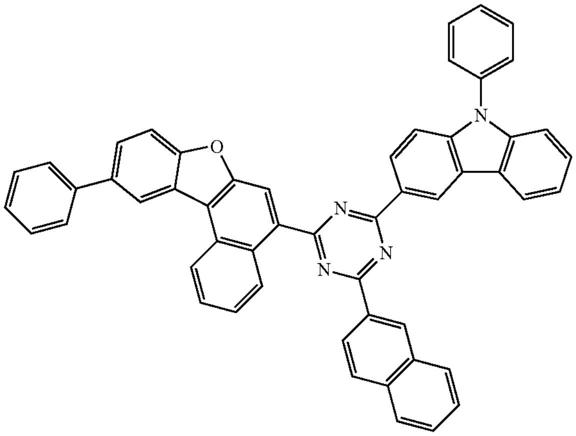
F644
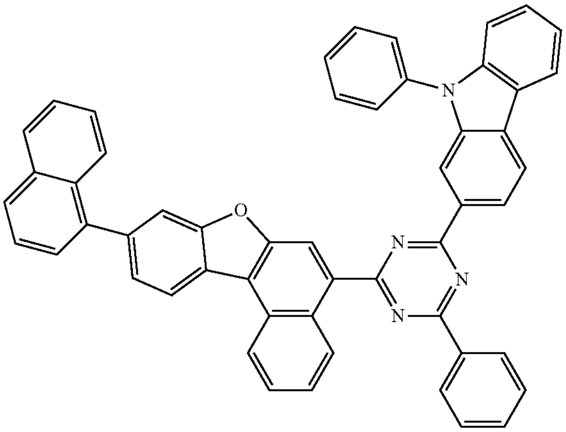
F645
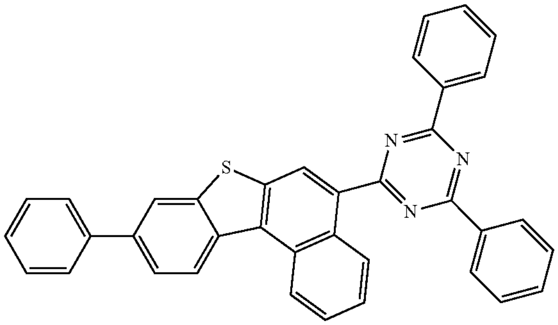
F646
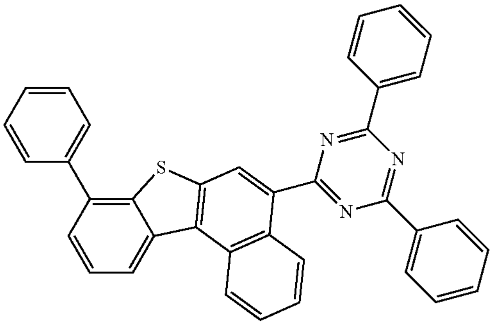

-continued

F647

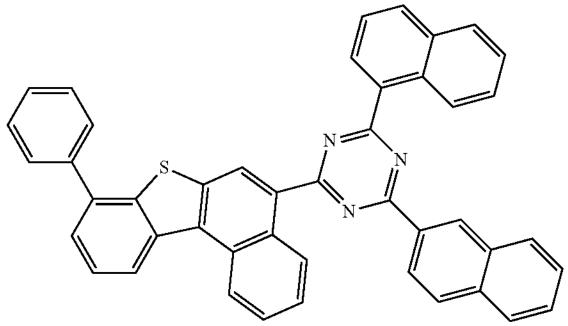

F648

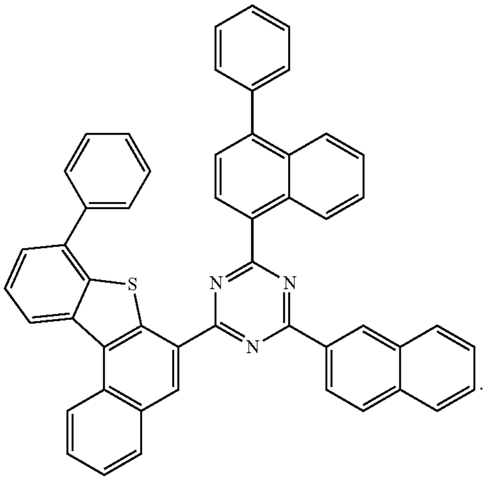

4. An organic light emitting device comprising:

a first electrode;

a second electrode; and one or more organic material layers provided between the first electrode and the second electrode, wherein one or more layers of the organic material layers include one or more types of the multicyclic compound of claim 1.

5. The organic light emitting device of claim 4, wherein the organic material layer includes two types of the multicyclic compound.

6. The organic light emitting device of claim 4, wherein the organic material layer further includes a compound represented by the following Chemical Formula 4:

[Chemical Formula 4]

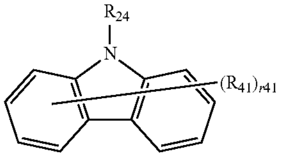

in Chemical Formula 4, $R_{24}$ is a substituted or unsubstituted aryl group;

$R_{41}$ is hydrogen; deuterium; a substituted or unsubstituted alkyl group; a substituted or unsubstituted amine group; a substituted or unsubstituted aryl group; or a substituted or unsubstituted heteroaryl group, or groups adjacent to each other bond to form a substituted or unsubstituted ring;

r41 is an integer of 1 to 8; and when r41 is an integer of 2 or greater, substituents in the parentheses are the same as or different from each other.

7. The organic light emitting device of claim 6, wherein Chemical Formula 4 is represented by the following Chemical Formula 4-1 or Chemical Formula 4-2:

[Chemical Formula 4-1]

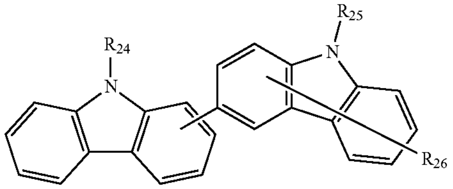

[Chemical Formula 4-2]

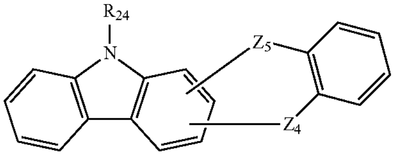

in Chemical Formulae 4-1 and 4-2, $R_{24}$ has the same definition as in Chemical Formula 4;

$Z_4$ and $Z_5$ are each independently a direct bond; $NR_{27}$; or $CR_{28}R_{29}$;

$R_{25}$ is a substituted or unsubstituted aryl group; and $R_{26}$ to $R_{29}$ are each independently hydrogen; deuterium; a substituted or unsubstituted alkyl group; a substituted or unsubstituted aryl group; or a substituted or unsubstituted heteroaryl group.

8. The organic light emitting device of claim 6, wherein Chemical Formula 4 is represented by any one of the following compounds:

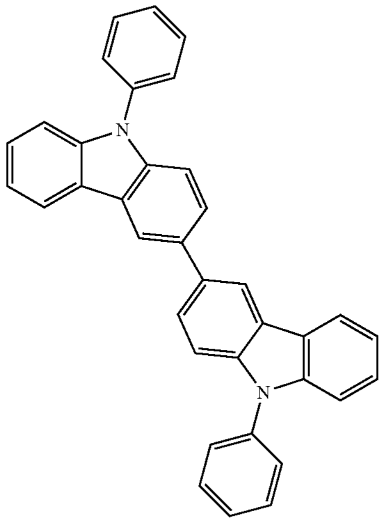

-continued
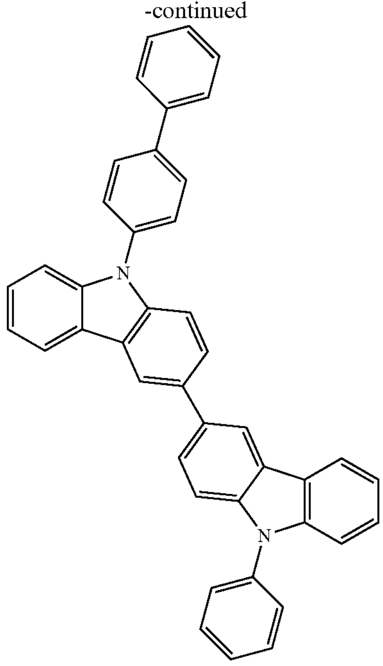
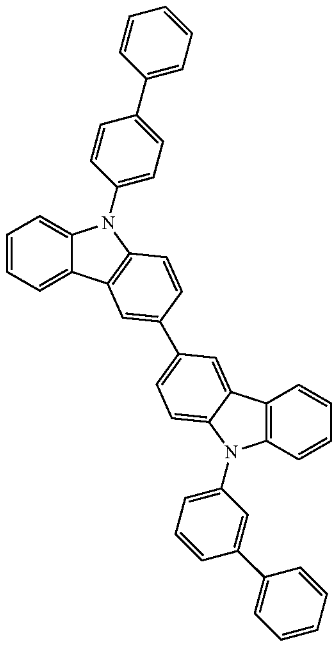
-continued
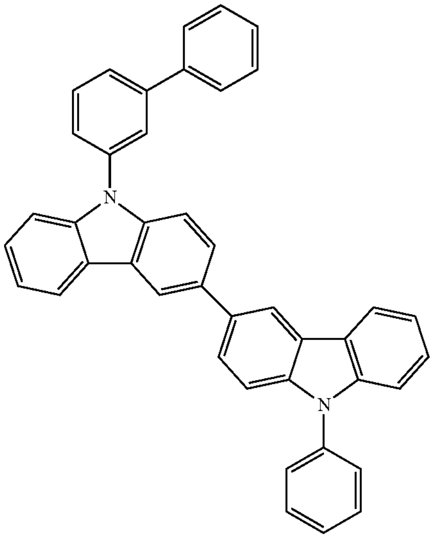
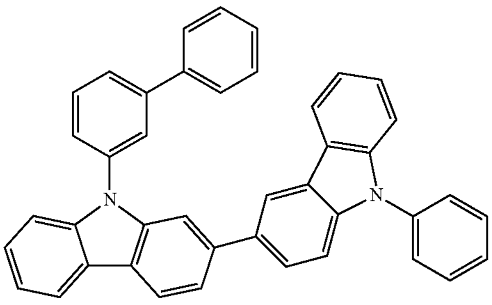
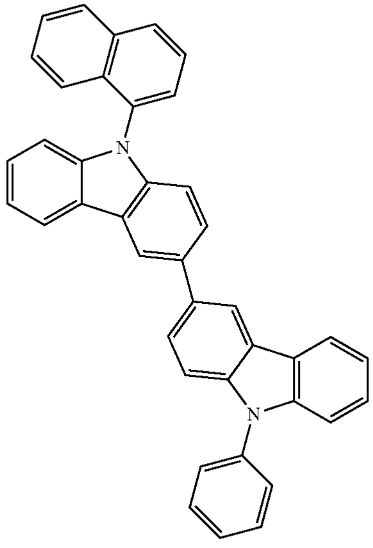

-continued
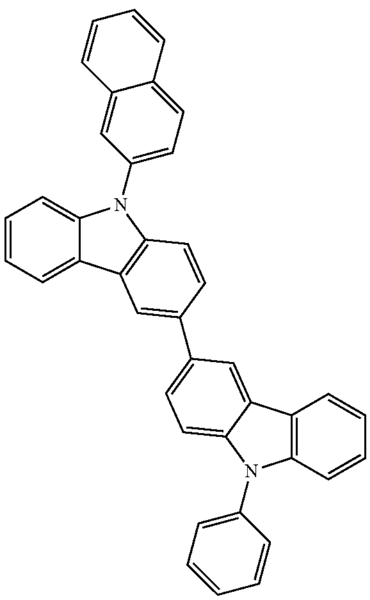
-continued
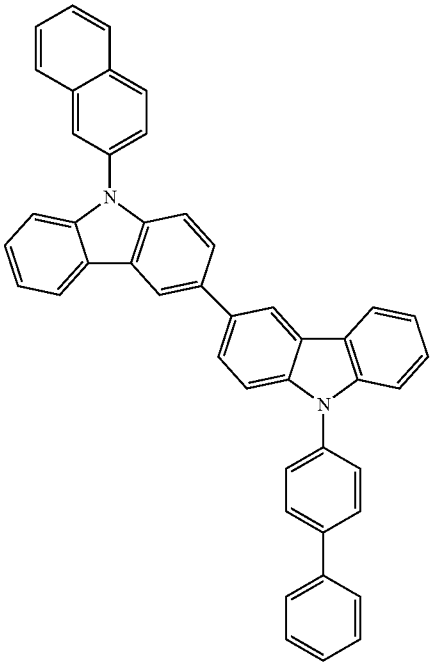
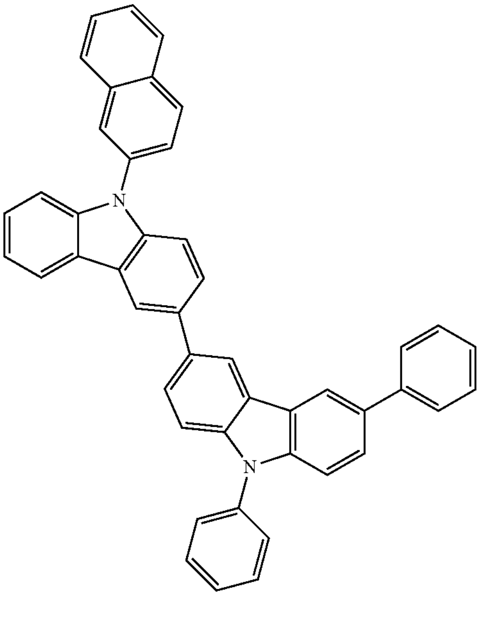
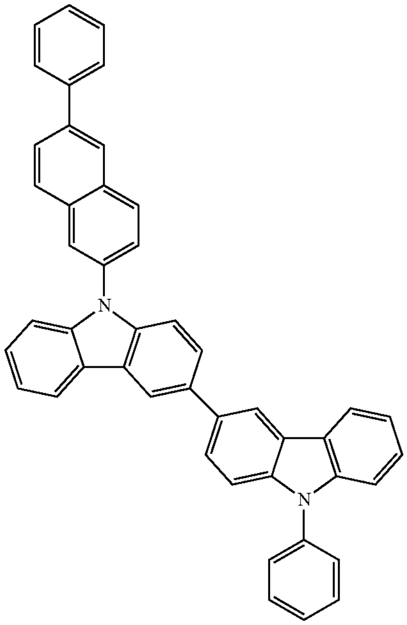

-continued
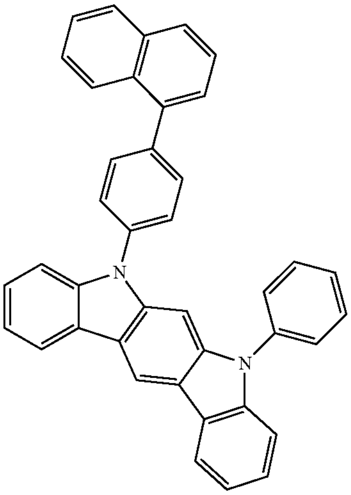
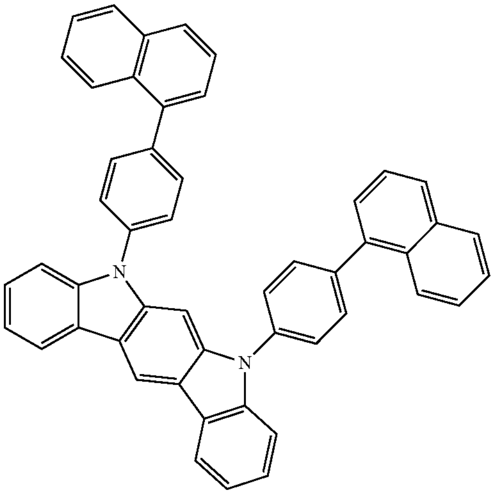
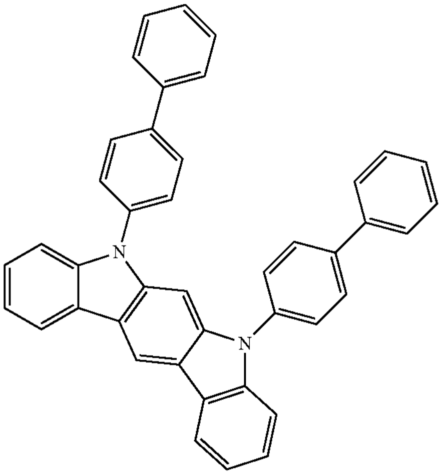
-continued
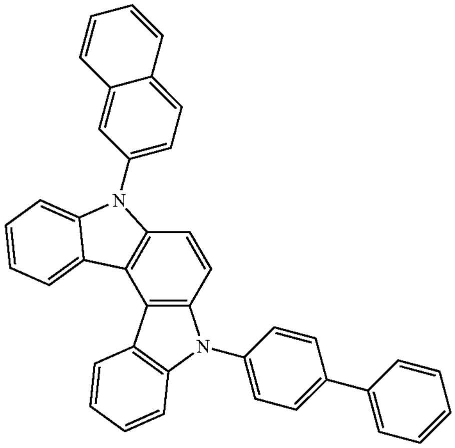
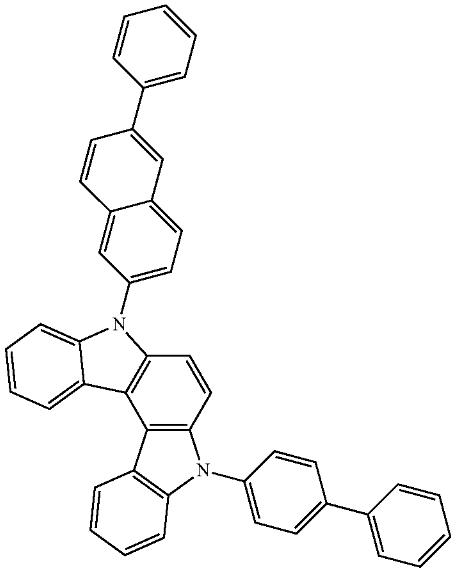
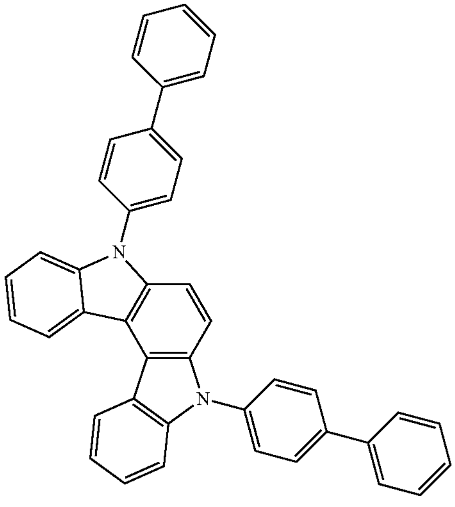

-continued

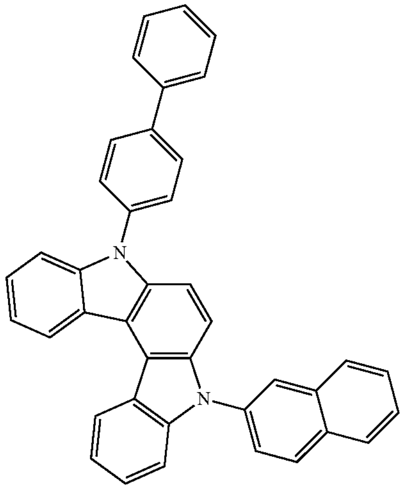

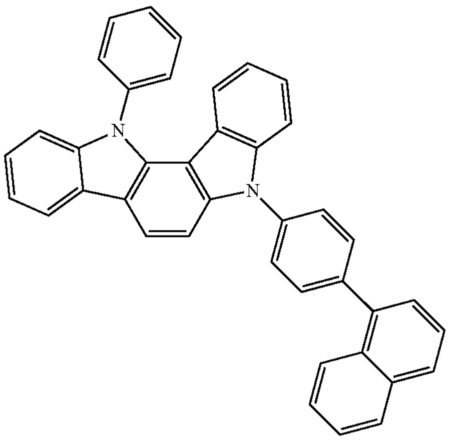

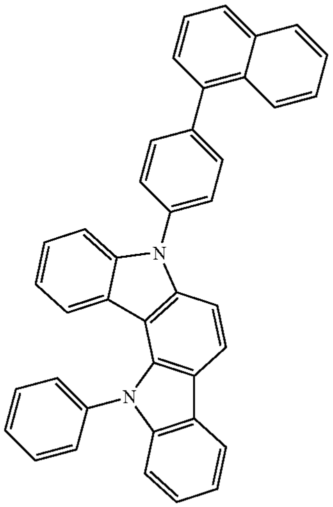

-continued

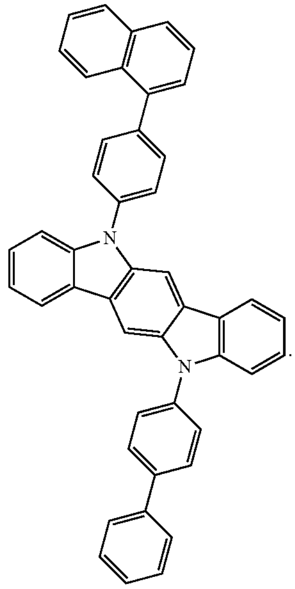

.

9. The organic light emitting device of claim 4, wherein the organic material layer further includes a compound represented by the following Chemical Formula 5:

[Chemical Formula 5]

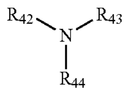

in Chemical Formula 5, $R_{42}$ to $R_{44}$ are each independently a substituted or unsubstituted aryl group; or a substituted or unsubstituted heteroaryl group.

10. The organic light emitting device of claim 9, wherein Chemical Formula 5 is represented by one of the following compounds:

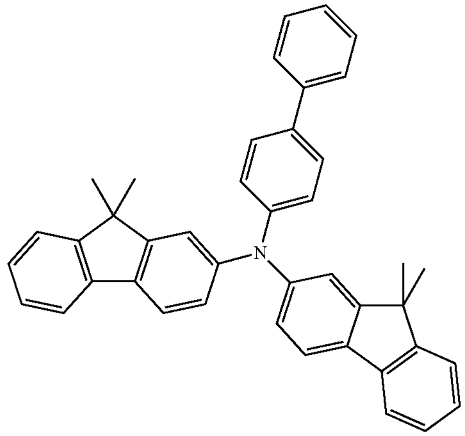

-continued
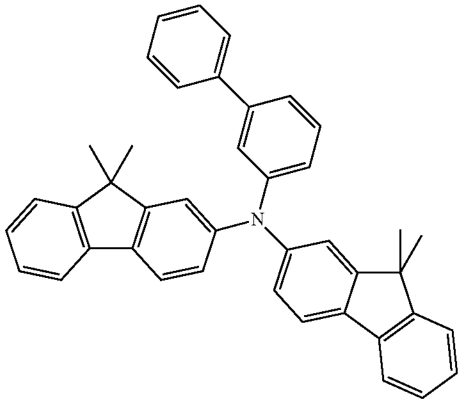
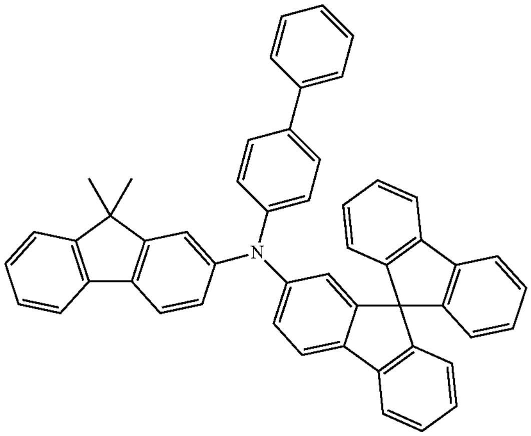
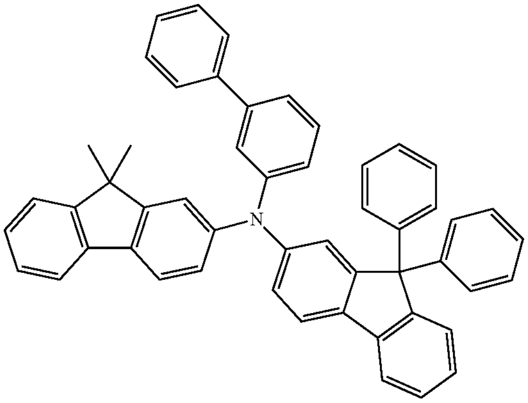
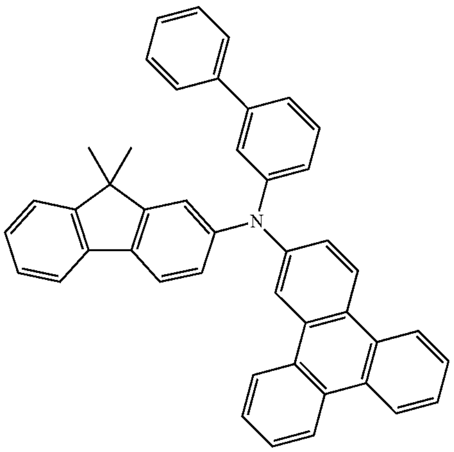
-continued
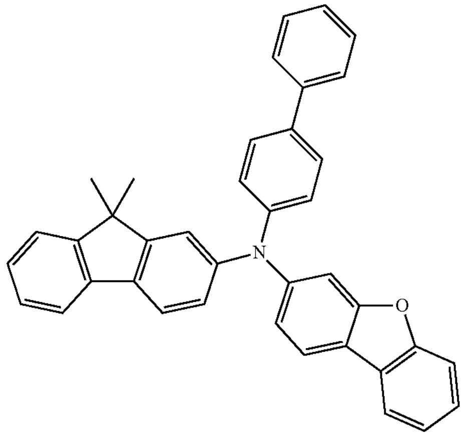
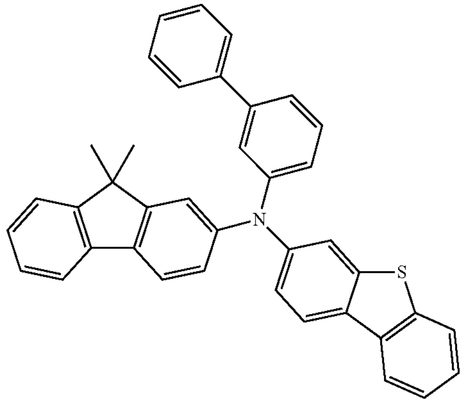
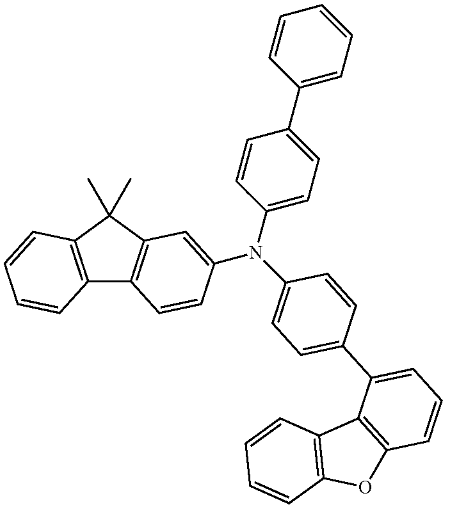

-continued

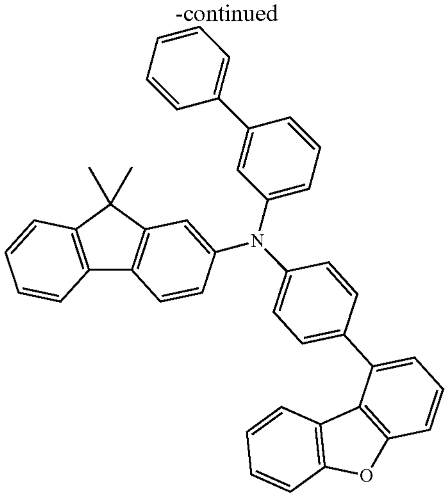

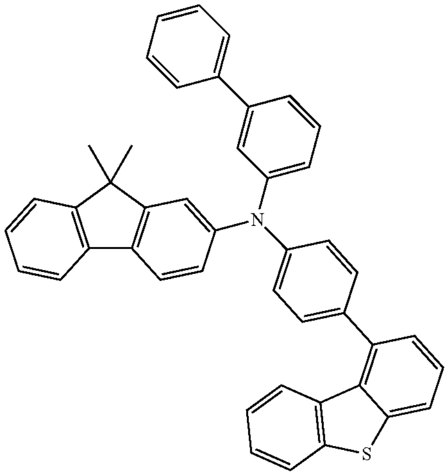

-continued

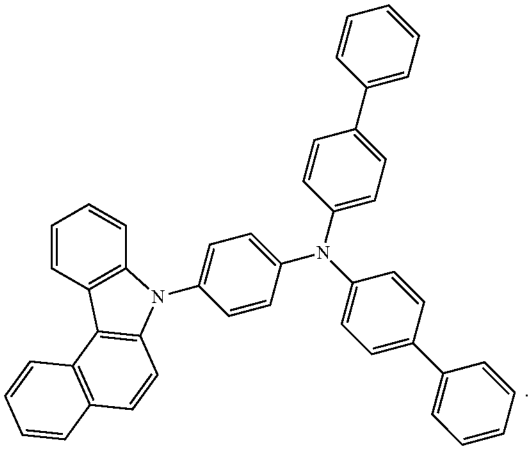

11. The organic light emitting device of claim 4, wherein the organic material layer includes a light emitting layer, and the light emitting layer includes one or more types of the multicyclic compound.

12. The organic light emitting device of claim 11, wherein the light emitting layer includes a host, and the host includes one or more types of the multicyclic compound.

13. The organic light emitting device of claim 4, further comprising one, two or more layers selected from the group consisting of a light emitting layer, a hole injection layer, a hole transfer layer, an electron injection layer, an electron transfer layer, an electron blocking layer and a hole blocking layer.

* * * * *